United States Patent
Cherf et al.

(10) Patent No.: US 11,643,446 B2
(45) Date of Patent: May 9, 2023

(54) PROGRANULIN VARIANTS

(71) Applicant: Denali Therapeutics Inc., South San Francisco, CA (US)

(72) Inventors: Gerald Maxwell Cherf, South San Francisco, CA (US); Gunasekaran Kannan, South San Francisco, CA (US); Katrina W. Lexa, South San Francisco, CA (US); Ray L. Y. Low, South San Francisco, CA (US); Rachel Prorok, South San Francisco, CA (US); Ankita Srivastava, South San Francisco, CA (US)

(73) Assignee: Denali Therapeutics Inc., South San Francisco, CA (US)

( * ) Notice: Subject to any disclaimer, the term of this patent is extended or adjusted under 35 U.S.C. 154(b) by 0 days.

(21) Appl. No.: 17/697,771

(22) Filed: Mar. 17, 2022

(65) Prior Publication Data

US 2022/0213155 A1    Jul. 7, 2022

Related U.S. Application Data

(63) Continuation of application No. PCT/US2020/066831, filed on Dec. 23, 2020.

(60) Provisional application No. 63/091,819, filed on Oct. 14, 2020, provisional application No. 62/953,099, filed on Dec. 23, 2019.

(51) Int. Cl.

| | | |
|---|---|---|
| *C07K 14/47* | (2006.01) | |
| *A61P 25/28* | (2006.01) | |
| *C07K 14/475* | (2006.01) | |
| *A61K 38/00* | (2006.01) | |

(52) U.S. Cl.
CPC .............. *C07K 14/47* (2013.01); *A61P 25/28* (2018.01); *C07K 14/475* (2013.01); *A61K 38/00* (2013.01); *C07K 2319/30* (2013.01)

(58) Field of Classification Search
CPC .......................... C07K 14/475; C07K 2319/30
See application file for complete search history.

(56) References Cited

U.S. PATENT DOCUMENTS

| | | |
|---|---|---|
| 7,928,068 B2 | 4/2011 | Liu |
| 8,536,128 B2 | 9/2013 | Liu |
| 9,611,323 B2 | 4/2017 | Dennis et al. |
| 9,708,406 B2 | 7/2017 | Zhang et al. |
| 10,808,036 B2 | 10/2020 | Zhang et al. |
| 10,870,837 B2 | 12/2020 | Henry et al. |
| 11,124,567 B2 | 9/2021 | Dennis et al. |
| 2002/0115824 A1 | 8/2002 | Engler et al. |
| 2004/0110938 A1 | 6/2004 | Parekh et al. |
| 2005/0106658 A1 | 5/2005 | Defrees et al. |
| 2005/0123962 A1 | 6/2005 | Gan et al. |
| 2010/0093979 A1 | 4/2010 | Lazar |
| 2012/0276125 A1 | 11/2012 | Ast et al. |
| 2014/0066599 A2 | 3/2014 | Blein et al. |
| 2014/0079689 A1 | 3/2014 | Elliott et al. |
| 2014/0212423 A1 | 7/2014 | Hanzatian et al. |
| 2014/0348754 A1 | 11/2014 | Wiley et al. |
| 2015/0110791 A1 | 4/2015 | Zhang et al. |
| 2015/0307628 A1 | 10/2015 | Kim et al. |
| 2015/0329636 A1 | 11/2015 | Dennis et al. |
| 2016/0008485 A1 | 1/2016 | Marquette et al. |
| 2016/0168213 A1 | 6/2016 | Xiong et al. |
| 2016/0168247 A1 | 6/2016 | Van Den Brink et al. |
| 2016/0271269 A1 | 9/2016 | Moghimi et al. |
| 2017/0226189 A1 | 8/2017 | Peters et al. |
| 2018/0222952 A1 | 8/2018 | Liu et al. |
| 2018/0222992 A1 | 8/2018 | Duerr et al. |
| 2018/0237496 A1 | 8/2018 | Chen et al. |
| 2020/0216522 A1 | 7/2020 | Chen et al. |
| 2020/0223935 A1 | 7/2020 | Chen et al. |
| 2020/0289627 A1 | 9/2020 | Dennis et al. |
| 2020/0369746 A1 | 11/2020 | Chen et al. |
| 2021/0070881 A1 | 3/2021 | Dennis et al. |
| 2021/0087288 A1 | 3/2021 | Zhang et al. |
| 2021/0130485 A1 | 5/2021 | Dennis et al. |
| 2021/0188925 A1 | 6/2021 | Cherf et al. |
| 2021/0198640 A1 | 7/2021 | Astarita et al. |
| 2021/0214438 A1 | 7/2021 | Dennis et al. |
| 2021/0284702 A1 | 9/2021 | Di Paolo et al. |
| 2021/0396772 A1 | 12/2021 | Astarita et al. |
| 2022/0002436 A1 | 1/2022 | Dennis et al. |
| 2022/0017634 A1 | 1/2022 | Kannan et al. |
| 2022/0025065 A1 | 1/2022 | Arguello et al. |

(Continued)

FOREIGN PATENT DOCUMENTS

| | | | |
|---|---|---|---|
| CN | 105273087 A | * | 1/2016 |
| EP | 2842969 A1 | | 3/2015 |

(Continued)

OTHER PUBLICATIONS

Peppel et al. A tumor necrosis factor (TNF) receptor-IgG heavy chain chimeric protein as a bivalent antagonist of TNF activity. J Exp Med. Dec. 1, 1991;174(6):1483-9.*
U.S. Appl. No. 16/543,332, US-2020-0223935.
U.S. Appl. No. 16/543,367, US-2020-0216522.
U.S. Appl. No. 16/782,669, US-2020-0369746.
U.S. Appl. No. 16/782,984, US-2020-0289627.
U.S. Appl. No. 16/867,942, US-2021-0070881.
U.S. Appl. No. 16/921,506, US-2021-0130485.
U.S. Appl. No. 17/102,138, US-2021-0198640.
U.S. Appl. No. 17/478,587, unpublished.
U.S. Appl. No. 17/174,231, US-2022-0017634.
U.S. Appl. No. 17/178,595, US-2022-0002436.
U.S. Appl. No. 17/253,391, US-2021-0284702.

(Continued)

*Primary Examiner* — Gregory S Emch
(74) *Attorney, Agent, or Firm* — Kilpatrick Townsend & Stockton LLP

(57) ABSTRACT

Provided herein are progranulin variants and fusion proteins that comprise a progranulin variant and an Fc polypeptide. Methods of using such proteins to treat progranulin-associated disorders (e.g., a neurodegenerative disease, such as frontotemporal dementia (FTD)) are also provided herein.

50 Claims, 26 Drawing Sheets

Specification includes a Sequence Listing.

(56) References Cited

U.S. PATENT DOCUMENTS

| | | | |
|---|---|---|---|
| 2022/0177576 A1 | 6/2022 | Dennis et al. | |
| 2022/0220172 A1 | 7/2022 | Cherf et al. | |

FOREIGN PATENT DOCUMENTS

| | | |
|---|---|---|
| EP | 2687223 B1 | 7/2017 |
| EP | 3315606 A1 | 5/2018 |
| EP | 3560958 A1 | 10/2019 |
| WO | 2005/077981 A2 | 8/2005 |
| WO | 2006/072620 A1 | 7/2006 |
| WO | 2007/146046 A2 | 12/2007 |
| WO | 2008/019187 A2 | 2/2008 |
| WO | 2008/094687 A2 | 8/2008 |
| WO | 2009/010045 A1 | 1/2009 |
| WO | 2009/089635 A1 | 7/2009 |
| WO | 2010/022175 A1 | 2/2010 |
| WO | 2010/120374 A2 | 10/2010 |
| WO | 2012/065248 A1 | 5/2012 |
| WO | 2012/075037 A1 | 6/2012 |
| WO | 2012/106587 A1 | 8/2012 |
| WO | 2014/033074 A1 | 3/2014 |
| WO | 2014/189973 A2 | 11/2014 |
| WO | 2015/119989 A1 | 8/2015 |
| WO | 2016/077840 A2 | 5/2016 |
| WO | 2016/079081 A1 | 5/2016 |
| WO | 2016/081640 A1 | 5/2016 |
| WO | 2016/081643 A1 | 5/2016 |
| WO | 2016/207091 A1 | 12/2016 |
| WO | 2016/207240 A1 | 12/2016 |
| WO | 2017/024137 A1 | 2/2017 |
| WO | 2017/049004 A1 | 3/2017 |
| WO | 2018/013775 A2 | 1/2018 |
| WO | 2019/203555 A1 | 10/2019 |
| WO | 2020/206320 A1 | 10/2020 |
| WO | 2021/158986 A1 | 8/2021 |
| WO | 2022/081765 A1 | 4/2022 |
| WO | 2022/082178 A2 | 4/2022 |

OTHER PUBLICATIONS

U.S. Appl. No. 17/284,764, US-2021-0396772.
U.S. Appl. No. 17/159,038, US-2021-0188925.
U.S. Appl. No. 17/698,456, unpublished.
Extended European Search Report for EP Application No. 19849330.6, dated Jul. 8, 2022, 15 pages.
Extended European Search Report received for EP Appl. No. 18843180.3, dated Jun. 4, 2021, 11 pages.
Baker et al. 2006. "Mutations in progranulin cause tau-negative frontotemporal dementia linked to chromosome 17." Nature vol. 442:916-919.
Cruts et al. 2006. "Null mutations in progranulin cause ubiquitin-positive frontotemporal dementia linked to chromosome 17q21." Nature vol. 442, pp. 920-924.
De Tommaso et al. 2016. "Pain in Neurodegenerative Disease: Current Knowledge and Future Perspectives." Behav Neurol 2016, Article ID7576292, pp. 1-14. doi:10.1155/2016/7576292.
Feng et al. 2010. "Granulin epithelin precursor: a bone morphogenic protein 2-inducible growth factor that activates Erk1/2 signaling and JunB transcription factor in chondrogenesis." FASEB J. vol. 24, Issue 6, pp. 1879-1892.
Gironi et al. 2016. "Multiple Sclerosis and Neurodegenerative Diseases." Immune Rebalancing: The Future of Immunosuppression. Elsevier Inc., pp. 63-84.
Ha et al. 2016. "Immunoglobulin Fc Heterodimer Platform Technology: From Design to Applications in Therapeutic Antibodies and Proteins", Frontiers in Immunology, vol. 7, pp. 1-16. DOI: 10.3389/fimmu.2016.00394.
He et al. 2003. "Progranulin is a mediator of the wound response." Nature Medicine vol. 9, Issue 2, pp. 225-229.
Hultqvist et al. 2017. "Bivalent Brain Shuttle Increases Antibody Uptake by Monovalent Binding to the Transferrin Receptor" Theranostics, vol. 7, Issue 2, pp. 308-318. DOI: 10.7150/thno.17155.
Klein et al. 2006. "Parkin is protective for substantia nigra dopamine neurons in a tau gene transfer neurodegeneration model." Neurosci Lett vol. 401(1-2), pp. 130-135.
Liu et al. 2017. "Fc Engineering for Developing Therapeutic Bispecific Antibodies and Novel Scaffolds" Frontiers in Immunology, vol. 8, Article 38, pp. 1-15. DOI: 10.3389/fimmu.2017.00038.
Lo Bianco et al. 2004. "Lentiviral vector delivery of parkin prevents dopaminergic degeneration in an α-synuclein rat model of Parkinson's disease." PNAS, vol. 101, Issue 50, pp. 17510-17515.
Lobner et al. 2016. "Engineered IgG1-Fc—one fragment to bind them all" Immunological Reviews, vol. 270, pp. 113-131. DOI: 10.1111/imr.12385.
Niewoehner et al. 2014. "Increased Brain Penetration and Potency of a Therapeutic Antibody Using a Monovalent Molecular Shuttle," Neuron, vol. 81, pp. 49-60. DOI: 10.1016/J.NEURON.2013.10.061.
Pardridge, William M, 2015. "Blood-brain barrier drug delivery of IgG fusion proteins with a transferrin receptor monoclonal antibody" Expert Opinion on Drug Delivery, Informa Healthcare UK, vol. 12, Issue 2, pp. 207-222.
Park et al. 2016. "The Highly Evolvable Antibody Fc Domain" Trends in Biotechnology, vol. 34, Issue 11, pp. 895-908.
Sleegers et al., "Progranulin Modifies Onset Age and Survival in Amyotrophic Lateral Sclerosis", Neurology, Mar. 20, 2007, vol. 68, No. 12, Suppl. 1, p. A202.
Snowden et al. 2006. "Progranulin gene mutations associated with frontotemporal dementia and progressive non-fluent aphasia." Brain vol. 129, Issue 11, pp. 3091-3102.
Syrovaya et al. 2014. "Amino Acids Through the Eyes of Chemists, Pharmacists, Biologists, vol. 1." Shchedra sadiba plus, pp. 1-228. (Machine Translation Provided).
Tang et al. 2011. "The growth factor progranulin binds to TNF receptors and is therapeutic against inflammatory arthritis in mice." Science vol. 332, Issue 6028, pp. 478-484.
Van Damme et al. 2008. "Progranulin functions as a neurotrophic factor to regulate neurite outgrowth and enhance neuronal survival." J Cell Biol vol. 181, No. 1, pp. 37-41.
Weber et al. 2018. "Brain Shuttle Antibody for Alzheimer's Disease with Attenuated Peripheral Effector Function due to an Inverted Binding Mode" Cell Reports, vol. 22, pp. 149-162. DOI: 10.1016/j.celrep.2017.12.019.
Wozniak-Knopp et al. 2010. "Introducing antigen-binding sites in structural loops of immunoglobulin constant domains: Fc fragments with engineered HER2/neu-binding sites and antibody properties" Protein Engineering, Design and Selection, vol. 23, Issue 4, pp. 289-297.
Yang et al. 2016. "Bispecific Antibodies as a Development Platform for New Concepts and Treatment Strategies" International Journal of Molecular Sciences, vol. 18, pp. 1-21. DOI: 10.3390/ijms18010048.
Ying et al. 2014. "Engineered Fc based antibody domains and fragments as novel scaffolds", Elsevier, Biochimica et Biophysica Acta (BBA)—Proteins and Proteomics, vol. 1844, pp. 1977-1982. DOI: 10.1016/J.BBAPAP.2014.04.018.
Ying et al. 2015. "Engineered antibody domains with significantly increased transcytosis and half-life in macaques mediated by FcRn" Mabs, vol. 7, Issue 5, pp. 922-930. DOI: 10.1080/19420862.2015.1067353.
Yu et al., "Boosting Brain Uptake of a Therapeutic Antibody by Reducing Its Affinity for a Transcytosis Target", Science Translational Medicine, vol. 3, No. 84, May 25, 2011, pp. 1-9.
Yu et al. 2014. "Therapeutic bispecific antibodies cross the blood-brain barrier in nonhuman primates." Science Translational Medicine, vol. 6, Issue 261, pp. 1-10. DOI: 10.1126/scitranslmed.3009835.
Zhang et al. 2007. "Progranulin mediates caspase-dependent cleavage of TAR DNA binding protein-43." J Neurosci. vol. 27, Issue 39, pp. 10530-10534.
Zhao et al. 2018. "Methods for Expression and Purification of Biologically Active Recombinant Progranulin": In: Bateman A., Bennett H., Cheung S. (eds) Progranulin. Methods in Molecular Biology, vol. 1806, Chapter 3, Humana Press, New York, NY, pp. 3549. https://doi.org/10.1007/978-1-4939-8559-3_3.

(56) References Cited

OTHER PUBLICATIONS

Zheng et al. 2011. "C-Terminus of Progranulin Interacts with the Beta-Propeller Region of Sortilin to Regulate Progranulin Trafficking." PLoS ONE vol. 6, Issue 6, pp. 1-8. e21023.
UniProtKB—L5KTN6 (L5KTN6_PTEAL), granulin protein (*Pteropus alecto*), 1 page.
UniProtKB—H3AMW7 (H3AMW7_LATCH), uncharacterized protein (*Latimeria chalumnae*), 2012, 5 pages.
UniProtKB—Q0IHZ2 (Q0IHZ2_XENTR), GRN protein (*Xenopus tropicalis*), 1 page.
Database Geneseq [Online] Feb. 3, 2011: "Immunostimulatory fusion protein production related protein SEQ ID 6", XP002779799, retrieved from EBI accession No. GSP:AYM52804. Database accession No. AYM52804 sequence, 2 pages.
Database NCBI [Online] Sep. 25, 2018, "Predicted: Piliocolobus tephrosceles granulin precursor (GRN), transcript variant X2, mRNA", XM_026447642.1, 2 pages.
Database NCBI [Online] Sep. 25, 2018, "granulins [Piliocolobus tephrosceles]", XP_026303427.1, 2 pages.
Database NCBI [Online] Dec. 30, 2019, "progranulin [Piliocolobus tephrosceles]", XP_026303427.1, 2 pages.
International Search Report and Written Opinion mailed for International Application No. PCT/US2020/066831 dated Dec. 23, 2020, 13 pages.
Clarke et al. "Single Domain Shark Antibody Targeting the Transferrin Receptor 1 Delivers a TrkB Agonist Antibody Across the Blood Brain Barrier to Provide Full Neuroprotection in a Mouse Model of Parkinson's Disease", Available online at https://www.biorxiv.org/content/10.1101/2020.03.12.987313v3.full.pdf, Jun. 5, 2021, 25 pages.
UniProtKB—P23088 (HVCM_HETFR), Ig Heavy Chain C Region, Membrane-Bound Form, 1991, 6 pages.
Kariolis et al. "Brain delivery of therapeutic proteins using an Fc fragment blood-brain barrier transport vehicle in mice and monkeys", Science Translational Medicine, May 27, 2020, vol. 12, No. 545, pp. 1-13.
Marri et al., "Human Biochemistry", Moscow "Mir", 1993, v. 1, 3 pages.
Brinkmann et al., "The making of bispecific antibodies", MABS, 2017, vol. 9, No. 2, pp. 182-212.
U.S. Appl. No. 17/797,644, unpublished.
U.S. Appl. No. 17/855,543, unpublished.
Bateman et al., "Re-engineering progranulin as an Alzheimer's and FTD disease-modifying therapeutic", The Weston Brain Institute (extract), 2016, 2 pages. Accessed at https://westonfoundation.ca/weston-brain-institute/ on Sep. 10, 2021.
Butler et al., "Multi-Granulin Domain Peptides Bind to Pro-Cathepsin D and Stimulate Its Enzymatic Activity More Effectively Than Progranulin in Vitro", Biochemistry, 2019, vol. 58, No. 23, pp. 2670-2674.
Chitramuthu et al., "Progranulin modulates zebrafish motoneuron development in vivo and rescues truncation defects associated with knockdown of Survival motor neuron 1", *Molecular Neurodegeneration*, 2010, vol. 5, No. 41, 13 pages.
Chitramuthu et al., "Neurotrophic effects of progranulin in vivo in reversing motor neuron defects caused by over or under expression of TDP-43 or FUS", *PLoS ONE*, 2017, vol. 12, No. 3, e0174784, 21 pages.
Goedert et al., "Frontotemporal lobar degeneration through loss of progranulin function", *Brain*, 2006, vol. 129, pp. 2808-2010.
Logan et al., "Rescue of a lysosomal storage disorder caused by Grn loss of function with a brain penetrant progranulin biologic", *Cell*, 2021, vol. 184, 1-18, 44 pages.
Nelson et al., "Limbic-predominant age-related TDP-43 encephalopathy (LATE): consensus working group report." *Brain*, 2019, vol. 142, No. 6, pp. 1503-1527.
Schymick et al. "Progranulin mutations and amyotrophic lateral sclerosis or amyotrophic lateral sclerosis-frontotemporal dementia phenotypes", J. *Neurol. Neurosurg. Psychiatry*, 2007, vol. 78, No. 7, pp. 754-756.
Simon et al., "Lysosomal functions of progranulin and implications for treatment of frontotemporal dementia", *Trends in Cell Biology*, 2022, ISSN 0962-8924, https://doi.org/10.1016/j.tcb.2022.09.006 (published online Oct. 13, 2022), 17 pages.
Vossel et al., "New approaches to the treatment of frontotemporal lobar degeneration", *Curr. Opin. Neurol.*, 2008, vol. 21, No. 6, pp. 708-716.
Zhou et al., "Progranulin deficiency leads to reduced glucocerebrosidase activity", *PLoS ONE*, 2019, vol. 14, No. 7, e0212382, 17 pages.
Bhattacharya et al., "Impact of genetic variation on three dimensional structure and function of proteins", *PLoS ONE*, 2017, vol. 12, No. 3, e0171355, 22 pages.
Davies et al., "Structural determinants of unique properties of human IgG4-Fc", *Journal of Molecular Biology*, 2014, vol. 426, pp. 630-644.
Fenton et al., "Rheostat positions: A new classification of protein positions Yelevant to pharmacogenomics", *Medicinal Chemistry Research*, 2020, vol. 29, pp. 1133-1146.
Guo et al., "Protein tolerance to random amino acid change", *PNAS*, 2004, vol. 101, No. 25, pp. 9205-9210.
Lee et al., "Receptor mediated uptake of peptides that bind the human transferrin receptor," Eur. J. Biochem., 268:2004-2012, 2001.

* cited by examiner

FIG. 2

| Fusion Protein | Buffer | DSF Tm1 | DSF TON |
|---|---|---|---|
| Fusion 1 | 20mM Sodium Phosphate, 6% sucrose, pH6.5 | 69.32 (0.26) | 63.19 (0.45) |
| Fusion 2 | 20mM Sodium Phosphate, 6% sucrose, pH6.5 | 69.57 (0.27) | 62.61 (0.52) |

20mM Sodium Phosphate, 6% sucrose, pH6.5

Rescue of Gcase activity phenotype (2 weeks post treatment)

SEQUENCE LISTING

<160> NUMBER OF SEQ ID NOS: 143

<210> SEQ ID NO 1
<211> LENGTH: 593
<212> TYPE: PRT
<213> ORGANISM: Homo sapiens

<400> SEQUENCE: 1

Met Trp Thr Leu Val Ser Trp Val Ala Leu Thr Ala Gly Leu Val Ala
1               5                   10                  15

Gly Thr Arg Cys Pro Asp Gly Gln Phe Cys Pro Val Ala Cys Cys Leu
            20                  25                  30

Asp Pro Gly Gly Ala Ser Tyr Ser Cys Cys Arg Pro Leu Leu Asp Lys
        35                  40                  45

Trp Pro Thr Thr Leu Ser Arg His Leu Gly Gly Pro Cys Gln Val Asp
    50                  55                  60

Ala His Cys Ser Ala Gly His Ser Cys Ile Phe Thr Val Ser Gly Thr
65                  70                  75                  80

Ser Ser Cys Cys Pro Phe Pro Glu Ala Val Ala Cys Gly Asp Gly His
                85                  90                  95

His Cys Cys Pro Arg Gly Phe His Cys Ser Ala Asp Gly Arg Ser Cys
            100                 105                 110

Phe Gln Arg Ser Gly Asn Asn Ser Val Gly Ala Ile Gln Cys Pro Asp
        115                 120                 125

Ser Gln Phe Glu Cys Pro Asp Phe Ser Thr Cys Cys Val Met Val Asp
    130                 135                 140

Gly Ser Trp Gly Cys Cys Pro Met Pro Gln Ala Ser Cys Cys Glu Asp
145                 150                 155                 160

Arg Val His Cys Cys Pro His Gly Ala Phe Cys Asp Leu Val His Thr
                165                 170                 175

Arg Cys Ile Thr Pro Thr Gly Thr His Pro Leu Ala Lys Lys Leu Pro
            180                 185                 190

```
Ala Gln Arg Thr Asn Arg Ala Val Ala Leu Ser Ser Val Met Cys
            195                 200                 205

Pro Asp Ala Arg Ser Arg Cys Pro Asp Gly Ser Thr Cys Cys Glu Leu
        210                 215                 220

Pro Ser Gly Lys Tyr Gly Cys Cys Pro Met Pro Asn Ala Thr Cys Cys
225                 230                 235                 240

Ser Asp His Leu His Cys Cys Pro Gln Asp Thr Val Cys Asp Leu Ile
                245                 250                 255

Gln Ser Lys Cys Leu Ser Lys Glu Asn Ala Thr Thr Asp Leu Leu Thr
            260                 265                 270

Lys Leu Pro Ala His Thr Val Gly Asp Val Lys Cys Asp Met Glu Val
            275                 280                 285

Ser Cys Pro Asp Gly Tyr Thr Cys Cys Arg Leu Gln Ser Gly Ala Trp
        290                 295                 300

Gly Cys Cys Pro Phe Thr Gln Ala Val Cys Cys Glu Asp His Ile His
305                 310                 315                 320

Cys Cys Pro Ala Gly Phe Thr Cys Asp Thr Gln Lys Gly Thr Cys Glu
                325                 330                 335

Gln Gly Pro His Gln Val Pro Trp Met Glu Lys Ala Pro Ala His Leu
            340                 345                 350

Ser Leu Pro Asp Pro Gln Ala Leu Lys Arg Asp Val Pro Cys Asp Asn
            355                 360                 365

Val Ser Ser Cys Pro Ser Ser Asp Thr Cys Cys Gln Leu Thr Ser Gly
        370                 375                 380

Glu Trp Gly Cys Cys Pro Ile Pro Glu Ala Val Cys Cys Ser Asp His
385                 390                 395                 400

Gln His Cys Cys Pro Gln Gly Tyr Thr Cys Val Ala Glu Gly Gln Cys
                405                 410                 415

Gln Arg Gly Ser Glu Ile Val Ala Gly Leu Glu Lys Met Pro Ala Arg
            420                 425                 430

Arg Ala Ser Leu Ser His Pro Arg Asp Ile Gly Cys Asp Gln His Thr
            435                 440                 445

Ser Cys Pro Val Gly Gln Thr Cys Cys Pro Ser Leu Gly Gly Ser Trp
        450                 455                 460

Ala Cys Cys Gln Leu Pro His Ala Val Cys Cys Glu Asp Arg Gln His
465                 470                 475                 480

Cys Cys Pro Ala Gly Tyr Thr Cys Asn Val Lys Ala Arg Ser Cys Glu
                485                 490                 495

Lys Glu Val Val Ser Ala Gln Pro Ala Thr Phe Leu Ala Arg Ser Pro
            500                 505                 510

His Val Gly Val Lys Asp Val Glu Cys Gly Glu Gly His Phe Cys His
            515                 520                 525

Asp Asn Gln Thr Cys Cys Arg Asp Asn Arg Gln Gly Trp Ala Cys Cys
            530                 535                 540

Pro Tyr Arg Gln Gly Val Cys Cys Ala Asp Arg His Cys Cys Pro
545                 550                 555                 560

Ala Gly Phe Arg Cys Ala Ala Arg Gly Thr Lys Cys Leu Arg Arg Glu
                565                 570                 575

Ala Pro Arg Trp Asp Ala Pro Leu Arg Asp Pro Ala Leu Arg Gln Leu
            580                 585                 590

Leu
```

```
<210> SEQ ID NO 2
<211> LENGTH: 576
<212> TYPE: PRT
<213> ORGANISM: Homo sapiens

<400> SEQUENCE: 2

Thr Arg Cys Pro Asp Gly Gln Phe Cys Pro Val Ala Cys Cys Leu Asp
1               5                   10                  15

Pro Gly Gly Ala Ser Tyr Ser Cys Cys Arg Pro Leu Leu Asp Lys Trp
            20                  25                  30

Pro Thr Thr Leu Ser Arg His Leu Gly Gly Pro Cys Gln Val Asp Ala
        35                  40                  45

His Cys Ser Ala Gly His Ser Cys Ile Phe Thr Val Ser Gly Thr Ser
    50                  55                  60

Ser Cys Cys Pro Phe Pro Glu Ala Val Ala Cys Gly Asp Gly His His
65                  70                  75                  80

Cys Cys Pro Arg Gly Phe His Cys Ser Ala Asp Gly Arg Ser Cys Phe
                85                  90                  95

Gln Arg Ser Gly Asn Asn Ser Val Gly Ala Ile Gln Cys Pro Asp Ser
            100                 105                 110

Gln Phe Glu Cys Pro Asp Phe Ser Thr Cys Cys Val Met Val Asp Gly
        115                 120                 125

Ser Trp Gly Cys Cys Pro Met Pro Gln Ala Ser Cys Cys Glu Asp Arg
    130                 135                 140

Val His Cys Cys Pro His Gly Ala Phe Cys Asp Leu Val His Thr Arg
145                 150                 155                 160

Cys Ile Thr Pro Thr Gly Thr His Pro Leu Ala Lys Lys Leu Pro Ala
                165                 170                 175

Gln Arg Thr Asn Arg Ala Val Ala Leu Ser Ser Ser Val Met Cys Pro
            180                 185                 190

Asp Ala Arg Ser Arg Cys Pro Asp Gly Ser Thr Cys Cys Glu Leu Pro
        195                 200                 205

Ser Gly Lys Tyr Gly Cys Cys Pro Met Pro Asn Ala Thr Cys Cys Ser
    210                 215                 220

Asp His Leu His Cys Cys Pro Gln Asp Thr Val Cys Asp Leu Ile Gln
225                 230                 235                 240

Ser Lys Cys Leu Ser Lys Glu Asn Ala Thr Thr Asp Leu Leu Thr Lys
                245                 250                 255

Leu Pro Ala His Thr Val Gly Asp Val Lys Cys Asp Met Glu Val Ser
            260                 265                 270

Cys Pro Asp Gly Tyr Thr Cys Cys Arg Leu Gln Ser Gly Ala Trp Gly
        275                 280                 285

Cys Cys Pro Phe Thr Gln Ala Val Cys Cys Glu Asp His Ile His Cys
    290                 295                 300

Cys Pro Ala Gly Phe Thr Cys Asp Thr Gln Lys Gly Thr Cys Glu Gln
305                 310                 315                 320

Gly Pro His Gln Val Pro Trp Met Glu Lys Ala Pro Ala His Leu Ser
                325                 330                 335

Leu Pro Asp Pro Gln Ala Leu Lys Arg Asp Val Pro Cys Asp Asn Val
            340                 345                 350

Ser Ser Cys Pro Ser Ser Asp Thr Cys Cys Gln Leu Thr Ser Gly Glu
        355                 360                 365

Trp Gly Cys Cys Pro Ile Pro Glu Ala Val Cys Cys Ser Asp His Gln
    370                 375                 380
```

-continued

```
His Cys Cys Pro Gln Gly Tyr Thr Cys Val Ala Glu Gly Gln Cys Gln
385                 390                 395                 400

Arg Gly Ser Glu Ile Val Ala Gly Leu Glu Lys Met Pro Ala Arg Arg
            405                 410                 415

Ala Ser Leu Ser His Pro Arg Asp Ile Gly Cys Asp Gln His Thr Ser
            420                 425                 430

Cys Pro Val Gly Gln Thr Cys Cys Pro Ser Leu Gly Gly Ser Trp Ala
            435                 440                 445

Cys Cys Gln Leu Pro His Ala Val Cys Cys Glu Asp Arg Gln His Cys
        450                 455                 460

Cys Pro Ala Gly Tyr Thr Cys Asn Val Lys Ala Arg Ser Cys Glu Lys
465                 470                 475                 480

Glu Val Val Ser Ala Gln Pro Ala Thr Phe Leu Ala Arg Ser Pro His
                485                 490                 495

Val Gly Val Lys Asp Val Glu Cys Gly Glu Gly His Phe Cys His Asp
            500                 505                 510

Asn Gln Thr Cys Cys Arg Asp Asn Arg Gln Gly Trp Ala Cys Cys Pro
            515                 520                 525

Tyr Arg Gln Gly Val Cys Cys Ala Asp Arg Arg His Cys Cys Pro Ala
530                 535                 540

Gly Phe Arg Cys Ala Ala Arg Gly Thr Lys Cys Leu Arg Arg Glu Ala
545                 550                 555                 560

Pro Arg Trp Asp Ala Pro Leu Arg Asp Pro Ala Leu Arg Gln Leu Leu
                565                 570                 575
```

```
<210> SEQ ID NO 3
<211> LENGTH: 576
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (574)..(576)
<223> OTHER INFORMATION: Any amino acid
<220> FEATURE:
<221> NAME/KEY: source
<223> OTHER INFORMATION: /note="See specification as filed for detailed
      description of substitutions and preferred embodiments"

<400> SEQUENCE: 3

Thr Arg Cys Pro Asp Gly Gln Phe Cys Pro Val Ala Cys Cys Leu Asp
1               5                   10                  15

Pro Gly Gly Ala Ser Tyr Ser Cys Cys Arg Pro Leu Leu Asp Lys Trp
            20                  25                  30

Pro Thr Thr Leu Ser Arg His Leu Gly Gly Pro Cys Gln Val Asp Ala
            35                  40                  45

His Cys Ser Ala Gly His Ser Cys Ile Phe Thr Val Ser Gly Thr Ser
        50                  55                  60

Ser Cys Cys Pro Phe Pro Glu Ala Val Ala Cys Gly Asp Gly His His
65                  70                  75                  80

Cys Cys Pro Arg Gly Phe His Cys Ser Ala Asp Gly Arg Ser Cys Phe
                85                  90                  95

Gln Arg Ser Gly Asn Asn Ser Val Gly Ala Ile Gln Cys Pro Asp Ser
            100                 105                 110

Gln Phe Glu Cys Pro Asp Phe Ser Thr Cys Cys Val Met Val Asp Gly
            115                 120                 125
```

-continued

```
Ser Trp Gly Cys Cys Pro Met Pro Gln Ala Ser Cys Cys Glu Asp Arg
    130                 135                 140
Val His Cys Cys Pro His Gly Ala Phe Cys Asp Leu Val His Thr Arg
145                 150                 155                 160
Cys Ile Thr Pro Thr Gly Thr His Pro Leu Ala Lys Lys Leu Pro Ala
                165                 170                 175
Gln Arg Thr Asn Arg Ala Val Ala Leu Ser Ser Val Met Cys Pro
            180                 185                 190
Asp Ala Arg Ser Arg Cys Pro Asp Gly Ser Thr Cys Cys Glu Leu Pro
        195                 200                 205
Ser Gly Lys Tyr Gly Cys Cys Pro Met Pro Asn Ala Thr Cys Cys Ser
    210                 215                 220
Asp His Leu His Cys Cys Pro Gln Asp Thr Val Cys Asp Leu Ile Gln
225                 230                 235                 240
Ser Lys Cys Leu Ser Lys Glu Asn Ala Thr Thr Asp Leu Leu Thr Lys
                245                 250                 255
Leu Pro Ala His Thr Val Gly Asp Val Lys Cys Asp Met Glu Val Ser
            260                 265                 270
Cys Pro Asp Gly Tyr Thr Cys Cys Arg Leu Gln Ser Gly Ala Trp Gly
        275                 280                 285
Cys Cys Pro Phe Thr Gln Ala Val Cys Cys Glu Asp His Ile His Cys
    290                 295                 300
Cys Pro Ala Gly Phe Thr Cys Asp Thr Gln Lys Gly Thr Cys Glu Gln
305                 310                 315                 320
Gly Pro His Gln Val Pro Trp Met Glu Lys Ala Pro Ala His Leu Ser
                325                 330                 335
Leu Pro Asp Pro Gln Ala Leu Lys Arg Asp Val Pro Cys Asp Asn Val
            340                 345                 350
Ser Ser Cys Pro Ser Ser Asp Thr Cys Cys Gln Leu Thr Ser Gly Glu
        355                 360                 365
Trp Gly Cys Cys Pro Ile Pro Glu Ala Val Cys Cys Ser Asp His Gln
    370                 375                 380
His Cys Cys Pro Gln Gly Tyr Thr Cys Val Ala Glu Gly Gln Cys Gln
385                 390                 395                 400
Arg Gly Ser Glu Ile Val Ala Gly Leu Glu Lys Met Pro Ala Arg Arg
                405                 410                 415
Ala Ser Leu Ser His Pro Arg Asp Ile Gly Cys Asp Gln His Thr Ser
            420                 425                 430
Cys Pro Val Gly Gln Thr Cys Cys Pro Ser Leu Gly Gly Ser Trp Ala
        435                 440                 445
Cys Cys Gln Leu Pro His Ala Val Cys Cys Glu Asp Arg Gln His Cys
    450                 455                 460
Cys Pro Ala Gly Tyr Thr Cys Asn Val Lys Ala Arg Ser Cys Glu Lys
465                 470                 475                 480
Glu Val Val Ser Ala Gln Pro Ala Thr Phe Leu Ala Arg Ser Pro His
                485                 490                 495
Val Gly Val Lys Asp Val Glu Cys Gly Glu Gly His Phe Cys His Asp
            500                 505                 510
Asn Gln Thr Cys Cys Arg Asp Asn Arg Gln Gly Trp Ala Cys Cys Pro
        515                 520                 525
Tyr Arg Gln Gly Val Cys Cys Ala Asp Arg Arg His Cys Cys Pro Ala
    530                 535                 540
```

```
Gly Phe Arg Cys Ala Ala Arg Gly Thr Lys Cys Leu Arg Arg Glu Ala
545                 550                 555                 560

Pro Arg Trp Asp Ala Pro Leu Arg Asp Pro Ala Leu Arg Xaa Xaa Xaa
            565                 570                 575

<210> SEQ ID NO 4
<211> LENGTH: 576
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 4

Thr Arg Cys Pro Asp Gly Gln Phe Cys Pro Val Ala Cys Cys Leu Asp
1               5                   10                  15

Pro Gly Gly Ala Ser Tyr Ser Cys Cys Arg Pro Leu Leu Asp Lys Trp
            20                  25                  30

Pro Thr Thr Leu Ser Arg His Leu Gly Pro Cys Gln Val Asp Ala
        35                  40                  45

His Cys Ser Ala Gly His Ser Cys Ile Phe Thr Val Ser Gly Thr Ser
50                  55                  60

Ser Cys Cys Pro Phe Pro Glu Ala Val Ala Cys Gly Asp Gly His His
65                  70                  75                  80

Cys Cys Pro Arg Gly Phe His Cys Ser Ala Asp Gly Arg Ser Cys Phe
                85                  90                  95

Gln Arg Ser Gly Asn Asn Ser Val Gly Ala Ile Gln Cys Pro Asp Ser
            100                 105                 110

Gln Phe Glu Cys Pro Asp Phe Ser Thr Cys Cys Val Met Val Asp Gly
        115                 120                 125

Ser Trp Gly Cys Cys Pro Met Pro Gln Ala Ser Cys Cys Glu Asp Arg
130                 135                 140

Val His Cys Cys Pro His Gly Ala Phe Cys Asp Leu Val His Thr Arg
145                 150                 155                 160

Cys Ile Thr Pro Thr Gly Thr His Pro Leu Ala Lys Lys Leu Pro Ala
                165                 170                 175

Gln Arg Thr Asn Arg Ala Val Ala Leu Ser Ser Ser Val Met Cys Pro
            180                 185                 190

Asp Ala Arg Ser Arg Cys Pro Asp Gly Ser Thr Cys Cys Glu Leu Pro
        195                 200                 205

Ser Gly Lys Tyr Gly Cys Cys Pro Met Pro Asn Ala Thr Cys Cys Ser
210                 215                 220

Asp His Leu His Cys Cys Pro Gln Asp Thr Val Cys Asp Leu Ile Gln
225                 230                 235                 240

Ser Lys Cys Leu Ser Lys Glu Asn Ala Thr Thr Asp Leu Leu Thr Lys
                245                 250                 255

Leu Pro Ala His Thr Val Gly Asp Val Lys Cys Asp Met Glu Val Ser
            260                 265                 270

Cys Pro Asp Gly Tyr Thr Cys Cys Arg Leu Gln Ser Gly Ala Trp Gly
        275                 280                 285

Cys Cys Pro Phe Thr Gln Ala Val Cys Cys Glu Asp His Ile His Cys
290                 295                 300

Cys Pro Ala Gly Phe Thr Cys Asp Thr Gln Lys Gly Thr Cys Glu Gln
305                 310                 315                 320
```

Gly Pro His Gln Val Pro Trp Met Glu Lys Ala Pro Ala His Leu Ser
            325                 330                 335

Leu Pro Asp Pro Gln Ala Leu Lys Arg Asp Val Pro Cys Asp Asn Val
            340                 345                 350

Ser Ser Cys Pro Ser Ser Asp Thr Cys Cys Gln Leu Thr Ser Gly Glu
            355                 360                 365

Trp Gly Cys Cys Pro Ile Pro Glu Ala Val Cys Cys Ser Asp His Gln
        370                 375                 380

His Cys Cys Pro Gln Gly Tyr Thr Cys Val Ala Glu Gly Gln Cys Gln
385                 390                 395                 400

Arg Gly Ser Glu Ile Val Ala Gly Leu Glu Lys Met Pro Ala Arg Arg
            405                 410                 415

Ala Ser Leu Ser His Pro Arg Asp Ile Gly Cys Asp Gln His Thr Ser
            420                 425                 430

Cys Pro Val Gly Gln Thr Cys Cys Pro Ser Leu Gly Gly Ser Trp Ala
            435                 440                 445

Cys Cys Gln Leu Pro His Ala Val Cys Cys Glu Asp Arg Gln His Cys
        450                 455                 460

Cys Pro Ala Gly Tyr Thr Cys Asn Val Lys Ala Arg Ser Cys Glu Lys
465                 470                 475                 480

Glu Val Val Ser Ala Gln Pro Ala Thr Phe Leu Ala Arg Ser Pro His
            485                 490                 495

Val Gly Val Lys Asp Val Glu Cys Gly Glu Gly His Phe Cys His Asp
            500                 505                 510

Asn Gln Thr Cys Cys Arg Asp Asn Arg Gln Gly Trp Ala Cys Cys Pro
            515                 520                 525

Tyr Arg Gln Gly Val Cys Cys Ala Asp Arg Arg His Cys Cys Pro Ala
            530                 535                 540

Gly Phe Arg Cys Ala Ala Arg Gly Thr Lys Cys Leu Arg Arg Glu Ala
545                 550                 555                 560

Pro Arg Trp Asp Ala Pro Leu Arg Asp Pro Ala Leu Arg Pro His Leu
            565                 570                 575

<210> SEQ ID NO 5
<211> LENGTH: 576
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 5

Thr Arg Cys Pro Asp Gly Gln Phe Cys Pro Val Ala Cys Cys Leu Asp
1               5                   10                  15

Pro Gly Gly Ala Ser Tyr Ser Cys Cys Arg Pro Leu Leu Asp Lys Trp
            20                  25                  30

Pro Thr Thr Leu Ser Arg His Leu Gly Gly Pro Cys Gln Val Asp Ala
            35                  40                  45

His Cys Ser Ala Gly His Ser Cys Ile Phe Thr Val Ser Gly Thr Ser
        50                  55                  60

Ser Cys Cys Pro Phe Pro Glu Ala Val Ala Cys Gly Asp Gly His His
65                  70                  75                  80

Cys Cys Pro Arg Gly Phe His Cys Ser Ala Asp Gly Arg Ser Cys Phe
            85                  90                  95

```
Gln Arg Ser Gly Asn Asn Ser Val Gly Ala Ile Gln Cys Pro Asp Ser
            100                 105                 110

Gln Phe Glu Cys Pro Asp Phe Ser Thr Cys Cys Val Met Val Asp Gly
        115                 120                 125

Ser Trp Gly Cys Cys Pro Met Pro Gln Ala Ser Cys Cys Glu Asp Arg
    130                 135                 140

Val His Cys Cys Pro His Gly Ala Phe Cys Asp Leu Val His Thr Arg
145                 150                 155                 160

Cys Ile Thr Pro Thr Gly Thr His Pro Leu Ala Lys Lys Leu Pro Ala
                165                 170                 175

Gln Arg Thr Asn Arg Ala Val Ala Leu Ser Ser Ser Val Met Cys Pro
            180                 185                 190

Asp Ala Arg Ser Arg Cys Pro Asp Gly Ser Thr Cys Cys Glu Leu Pro
        195                 200                 205

Ser Gly Lys Tyr Gly Cys Cys Pro Met Pro Asn Ala Thr Cys Cys Ser
    210                 215                 220

Asp His Leu His Cys Cys Pro Gln Asp Thr Val Cys Asp Leu Ile Gln
225                 230                 235                 240

Ser Lys Cys Leu Ser Lys Glu Asn Ala Thr Thr Asp Leu Leu Thr Lys
                245                 250                 255

Leu Pro Ala His Thr Val Gly Asp Val Lys Cys Asp Met Glu Val Ser
            260                 265                 270

Cys Pro Asp Gly Tyr Thr Cys Cys Arg Leu Gln Ser Gly Ala Trp Gly
        275                 280                 285

Cys Cys Pro Phe Thr Gln Ala Val Cys Cys Glu Asp His Ile His Cys
    290                 295                 300

Cys Pro Ala Gly Phe Thr Cys Asp Thr Gln Lys Gly Thr Cys Glu Gln
305                 310                 315                 320

Gly Pro His Gln Val Pro Trp Met Glu Lys Ala Pro Ala His Leu Ser
                325                 330                 335

Leu Pro Asp Pro Gln Ala Leu Lys Arg Asp Val Pro Cys Asp Asn Val
            340                 345                 350

Ser Ser Cys Pro Ser Ser Asp Thr Cys Cys Gln Leu Thr Ser Gly Glu
        355                 360                 365

Trp Gly Cys Cys Pro Ile Pro Glu Ala Val Cys Cys Ser Asp His Gln
    370                 375                 380

His Cys Cys Pro Gln Gly Tyr Thr Cys Val Ala Glu Gly Gln Cys Gln
385                 390                 395                 400

Arg Gly Ser Glu Ile Val Ala Gly Leu Glu Lys Met Pro Ala Arg Arg
                405                 410                 415

Ala Ser Leu Ser His Pro Arg Asp Ile Gly Cys Asp Gln His Thr Ser
            420                 425                 430

Cys Pro Val Gly Gln Thr Cys Cys Pro Ser Leu Gly Gly Ser Trp Ala
        435                 440                 445

Cys Cys Gln Leu Pro His Ala Val Cys Cys Glu Asp Arg Gln His Cys
    450                 455                 460

Cys Pro Ala Gly Tyr Thr Cys Asn Val Lys Ala Arg Ser Cys Glu Lys
465                 470                 475                 480

Glu Val Val Ser Ala Gln Pro Ala Thr Phe Leu Ala Arg Ser Pro His
                485                 490                 495

Val Gly Val Lys Asp Val Glu Cys Gly Glu Gly His Phe Cys His Asp
            500                 505                 510
```

Asn Gln Thr Cys Cys Arg Asp Asn Arg Gln Gly Trp Ala Cys Cys Pro
            515                 520                 525

Tyr Arg Gln Gly Val Cys Cys Ala Asp Arg Arg His Cys Cys Pro Ala
        530                 535                 540

Gly Phe Arg Cys Ala Ala Arg Gly Thr Lys Cys Leu Arg Arg Glu Ala
545                 550                 555                 560

Pro Arg Trp Asp Ala Pro Leu Arg Asp Pro Ala Leu Arg Pro Lys Leu
            565                 570                 575

<210> SEQ ID NO 6
<211> LENGTH: 576
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6

Thr Arg Cys Pro Asp Gly Gln Phe Cys Pro Val Ala Cys Cys Leu Asp
1               5                   10                  15

Pro Gly Gly Ala Ser Tyr Ser Cys Cys Arg Pro Leu Leu Asp Lys Trp
            20                  25                  30

Pro Thr Thr Leu Ser Arg His Leu Gly Gly Pro Cys Gln Val Asp Ala
        35                  40                  45

His Cys Ser Ala Gly His Ser Cys Ile Phe Thr Val Ser Gly Thr Ser
    50                  55                  60

Ser Cys Cys Pro Phe Pro Glu Ala Val Ala Cys Gly Asp Gly His His
65                  70                  75                  80

Cys Cys Pro Arg Gly Phe His Cys Ser Ala Asp Gly Arg Ser Cys Phe
            85                  90                  95

Gln Arg Ser Gly Asn Asn Ser Val Gly Ala Ile Gln Cys Pro Asp Ser
            100                 105                 110

Gln Phe Glu Cys Pro Asp Phe Ser Thr Cys Cys Val Met Val Asp Gly
        115                 120                 125

Ser Trp Gly Cys Cys Pro Met Pro Gln Ala Ser Cys Cys Glu Asp Arg
    130                 135                 140

Val His Cys Cys Pro His Gly Ala Phe Cys Asp Leu Val His Thr Arg
145                 150                 155                 160

Cys Ile Thr Pro Thr Gly Thr His Pro Leu Ala Lys Lys Leu Pro Ala
            165                 170                 175

Gln Arg Thr Asn Arg Ala Val Ala Leu Ser Ser Val Met Cys Pro
            180                 185                 190

Asp Ala Arg Ser Arg Cys Pro Asp Gly Ser Thr Cys Cys Glu Leu Pro
            195                 200                 205

Ser Gly Lys Tyr Gly Cys Cys Pro Met Pro Asn Ala Thr Cys Cys Ser
    210                 215                 220

Asp His Leu His Cys Cys Pro Gln Asp Thr Val Cys Asp Leu Ile Gln
225                 230                 235                 240

Ser Lys Cys Leu Ser Lys Glu Asn Ala Thr Thr Asp Leu Leu Thr Lys
            245                 250                 255

Leu Pro Ala His Thr Val Gly Asp Val Lys Cys Asp Met Glu Val Ser
            260                 265                 270

Cys Pro Asp Gly Tyr Thr Cys Cys Arg Leu Gln Ser Gly Ala Trp Gly
        275                 280                 285

```
Cys Cys Pro Phe Thr Gln Ala Val Cys Cys Glu Asp His Ile His Cys
            290                 295                 300

Cys Pro Ala Gly Phe Thr Cys Asp Thr Gln Lys Gly Thr Cys Glu Gln
305                 310                 315                 320

Gly Pro His Gln Val Pro Trp Met Glu Lys Ala Pro Ala His Leu Ser
                325                 330                 335

Leu Pro Asp Pro Gln Ala Leu Lys Arg Asp Val Pro Cys Asp Asn Val
            340                 345                 350

Ser Ser Cys Pro Ser Ser Asp Thr Cys Cys Gln Leu Thr Ser Gly Glu
        355                 360                 365

Trp Gly Cys Cys Pro Ile Pro Glu Ala Val Cys Cys Ser Asp His Gln
    370                 375                 380

His Cys Cys Pro Gln Gly Tyr Thr Cys Val Ala Glu Gly Gln Cys Gln
385                 390                 395                 400

Arg Gly Ser Glu Ile Val Ala Gly Leu Glu Lys Met Pro Ala Arg Arg
                405                 410                 415

Ala Ser Leu Ser His Pro Arg Asp Ile Gly Cys Asp Gln His Thr Ser
            420                 425                 430

Cys Pro Val Gly Gln Thr Cys Cys Pro Ser Leu Gly Gly Ser Trp Ala
        435                 440                 445

Cys Cys Gln Leu Pro His Ala Val Cys Cys Glu Asp Arg Gln His Cys
    450                 455                 460

Cys Pro Ala Gly Tyr Thr Cys Asn Val Lys Ala Arg Ser Cys Glu Lys
465                 470                 475                 480

Glu Val Val Ser Ala Gln Pro Ala Thr Phe Leu Ala Arg Ser Pro His
                485                 490                 495

Val Gly Val Lys Asp Val Glu Cys Gly Glu Gly His Phe Cys His Asp
            500                 505                 510

Asn Gln Thr Cys Cys Arg Asp Asn Arg Gln Gly Trp Ala Cys Cys Pro
        515                 520                 525

Tyr Arg Gln Gly Val Cys Cys Ala Asp Arg Arg His Cys Cys Pro Ala
    530                 535                 540

Gly Phe Arg Cys Ala Ala Arg Gly Thr Lys Cys Leu Arg Arg Glu Ala
545                 550                 555                 560

Pro Arg Trp Asp Ala Pro Leu Arg Asp Pro Ala Leu Arg Pro Asp Leu
                565                 570                 575

<210> SEQ ID NO 7
<211> LENGTH: 576
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7

Thr Arg Cys Pro Asp Gly Gln Phe Cys Pro Val Ala Cys Cys Leu Asp
1               5                   10                  15

Pro Gly Gly Ala Ser Tyr Ser Cys Cys Arg Pro Leu Leu Asp Lys Trp
                20                  25                  30

Pro Thr Thr Leu Ser Arg His Leu Gly Gly Pro Cys Gln Val Asp Ala
            35                  40                  45

His Cys Ser Ala Gly His Ser Cys Ile Phe Thr Val Ser Gly Thr Ser
        50                  55                  60
```

-continued

```
Ser Cys Cys Pro Phe Pro Glu Ala Val Ala Cys Gly Asp Gly His His
 65                  70                  75                  80

Cys Cys Pro Arg Gly Phe His Cys Ser Ala Asp Gly Arg Ser Cys Phe
                 85                  90                  95

Gln Arg Ser Gly Asn Asn Ser Val Gly Ala Ile Gln Cys Pro Asp Ser
            100                 105                 110

Gln Phe Glu Cys Pro Asp Phe Ser Thr Cys Cys Val Met Val Asp Gly
        115                 120                 125

Ser Trp Gly Cys Cys Pro Met Pro Gln Ala Ser Cys Cys Glu Asp Arg
    130                 135                 140

Val His Cys Cys Pro His Gly Ala Phe Cys Asp Leu Val His Thr Arg
145                 150                 155                 160

Cys Ile Thr Pro Thr Gly Thr His Pro Leu Ala Lys Lys Leu Pro Ala
                165                 170                 175

Gln Arg Thr Asn Arg Ala Val Ala Leu Ser Ser Ser Val Met Cys Pro
            180                 185                 190

Asp Ala Arg Ser Arg Cys Pro Asp Gly Ser Thr Cys Cys Glu Leu Pro
        195                 200                 205

Ser Gly Lys Tyr Gly Cys Cys Pro Met Pro Asn Ala Thr Cys Cys Ser
    210                 215                 220

Asp His Leu His Cys Cys Pro Gln Asp Thr Val Cys Asp Leu Ile Gln
225                 230                 235                 240

Ser Lys Cys Leu Ser Lys Glu Asn Ala Thr Thr Asp Leu Leu Thr Lys
                245                 250                 255

Leu Pro Ala His Thr Val Gly Asp Val Lys Cys Asp Met Glu Val Ser
            260                 265                 270

Cys Pro Asp Gly Tyr Thr Cys Cys Arg Leu Gln Ser Gly Ala Trp Gly
        275                 280                 285

Cys Cys Pro Phe Thr Gln Ala Val Cys Cys Glu Asp His Ile His Cys
    290                 295                 300

Cys Pro Ala Gly Phe Thr Cys Asp Thr Gln Lys Gly Thr Cys Glu Gln
305                 310                 315                 320

Gly Pro His Gln Val Pro Trp Met Glu Lys Ala Pro Ala His Leu Ser
                325                 330                 335

Leu Pro Asp Pro Gln Ala Leu Lys Arg Asp Val Pro Cys Asp Asn Val
            340                 345                 350

Ser Ser Cys Pro Ser Ser Asp Thr Cys Cys Gln Leu Thr Ser Gly Glu
        355                 360                 365

Trp Gly Cys Cys Pro Ile Pro Glu Ala Val Cys Cys Ser Asp His Gln
    370                 375                 380

His Cys Cys Pro Gln Gly Tyr Thr Cys Val Ala Glu Gly Gln Cys Gln
385                 390                 395                 400

Arg Gly Ser Glu Ile Val Ala Gly Leu Glu Lys Met Pro Ala Arg Arg
                405                 410                 415

Ala Ser Leu Ser His Pro Arg Asp Ile Gly Cys Asp Gln His Thr Ser
            420                 425                 430

Cys Pro Val Gly Gln Thr Cys Cys Pro Ser Leu Gly Gly Ser Trp Ala
        435                 440                 445

Cys Cys Gln Leu Pro His Ala Val Cys Cys Glu Asp Arg Gln His Cys
    450                 455                 460

Cys Pro Ala Gly Tyr Thr Cys Asn Val Lys Ala Arg Ser Cys Glu Lys
465                 470                 475                 480
```

-continued

Glu Val Val Ser Ala Gln Pro Ala Thr Phe Leu Ala Arg Ser Pro His
            485                 490                 495

Val Gly Val Lys Asp Val Glu Cys Gly Glu Gly His Phe Cys His Asp
            500                 505                 510

Asn Gln Thr Cys Cys Arg Asp Asn Arg Gln Gly Trp Ala Cys Cys Pro
            515                 520                 525

Tyr Arg Gln Gly Val Cys Cys Ala Asp Arg Arg His Cys Cys Pro Ala
            530                 535                 540

Gly Phe Arg Cys Ala Ala Arg Gly Thr Lys Cys Leu Arg Arg Glu Ala
545                 550                 555                 560

Pro Arg Trp Asp Ala Pro Leu Arg Asp Pro Ala Leu Arg Pro Glu Leu
            565                 570                 575

<210> SEQ ID NO 8
<211> LENGTH: 576
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 8

Thr Arg Cys Pro Asp Gly Gln Phe Cys Pro Val Ala Cys Cys Leu Asp
1               5                   10                  15

Pro Gly Gly Ala Ser Tyr Ser Cys Cys Arg Pro Leu Leu Asp Lys Trp
            20                  25                  30

Pro Thr Thr Leu Ser Arg His Leu Gly Gly Pro Cys Gln Val Asp Ala
            35                  40                  45

His Cys Ser Ala Gly His Ser Cys Ile Phe Thr Val Ser Gly Thr Ser
        50                  55                  60

Ser Cys Cys Pro Phe Pro Glu Ala Val Ala Cys Gly Asp Gly His His
65                  70                  75                  80

Cys Cys Pro Arg Gly Phe His Cys Ser Ala Asp Gly Arg Ser Cys Phe
            85                  90                  95

Gln Arg Ser Gly Asn Asn Ser Val Gly Ala Ile Gln Cys Pro Asp Ser
            100                 105                 110

Gln Phe Glu Cys Pro Asp Phe Ser Thr Cys Cys Val Met Val Asp Gly
        115                 120                 125

Ser Trp Gly Cys Cys Pro Met Pro Gln Ala Ser Cys Cys Glu Asp Arg
130                 135                 140

Val His Cys Cys Pro His Gly Ala Phe Cys Asp Leu Val His Thr Arg
145                 150                 155                 160

Cys Ile Thr Pro Thr Gly Thr His Pro Leu Ala Lys Lys Leu Pro Ala
            165                 170                 175

Gln Arg Thr Asn Arg Ala Val Ala Leu Ser Ser Ser Val Met Cys Pro
            180                 185                 190

Asp Ala Arg Ser Arg Cys Pro Asp Gly Ser Thr Cys Cys Glu Leu Pro
        195                 200                 205

Ser Gly Lys Tyr Gly Cys Cys Pro Met Pro Asn Ala Thr Cys Cys Ser
        210                 215                 220

Asp His Leu His Cys Cys Pro Gln Asp Thr Val Cys Asp Leu Ile Gln
225                 230                 235                 240

Ser Lys Cys Leu Ser Lys Glu Asn Ala Thr Thr Asp Leu Leu Thr Lys
            245                 250                 255

```
Leu Pro Ala His Thr Val Gly Asp Val Lys Cys Asp Met Glu Val Ser
            260                 265                 270

Cys Pro Asp Gly Tyr Thr Cys Arg Leu Gln Ser Gly Ala Trp Gly
            275                 280             285

Cys Cys Pro Phe Thr Gln Ala Val Cys Cys Asp His Ile His Cys
            290                 295                 300

Cys Pro Ala Gly Phe Thr Cys Asp Thr Gln Lys Gly Thr Cys Glu Gln
305                 310                 315                 320

Gly Pro His Gln Val Pro Trp Met Glu Lys Ala Pro Ala His Leu Ser
            325                 330                 335

Leu Pro Asp Pro Gln Ala Leu Lys Arg Asp Val Pro Cys Asp Asn Val
            340                 345                 350

Ser Ser Cys Pro Ser Ser Asp Thr Cys Cys Gln Leu Thr Ser Gly Glu
            355                 360                 365

Trp Gly Cys Cys Pro Ile Pro Glu Ala Val Cys Cys Ser Asp His Gln
            370                 375                 380

His Cys Cys Pro Gln Gly Tyr Thr Cys Val Ala Glu Gly Gln Cys Gln
385                 390                 395                 400

Arg Gly Ser Glu Ile Val Ala Gly Leu Glu Lys Met Pro Ala Arg Arg
            405                 410                 415

Ala Ser Leu Ser His Pro Arg Asp Ile Gly Cys Asp Gln His Thr Ser
            420                 425                 430

Cys Pro Val Gly Gln Thr Cys Cys Pro Ser Leu Gly Gly Ser Trp Ala
            435                 440                 445

Cys Cys Gln Leu Pro His Ala Val Cys Cys Glu Asp Arg Gln His Cys
            450                 455                 460

Cys Pro Ala Gly Tyr Thr Cys Asn Val Lys Ala Arg Ser Cys Glu Lys
465                 470                 475                 480

Glu Val Val Ser Ala Gln Pro Ala Thr Phe Leu Ala Arg Ser Pro His
            485                 490                 495

Val Gly Val Lys Asp Val Glu Cys Gly Glu Gly His Phe Cys His Asp
            500                 505                 510

Asn Gln Thr Cys Cys Arg Asp Asn Arg Gln Gly Trp Ala Cys Cys Pro
            515                 520                 525

Tyr Arg Gln Gly Val Cys Cys Ala Asp Arg Arg His Cys Cys Pro Ala
            530                 535                 540

Gly Phe Arg Cys Ala Ala Arg Gly Thr Lys Cys Leu Arg Arg Glu Ala
545                 550                 555                 560

Pro Arg Trp Asp Ala Pro Leu Arg Asp Pro Ala Leu Arg Pro Ser Leu
            565                 570                 575
```

<210> SEQ ID NO 9
<211> LENGTH: 576
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 9

```
Thr Arg Cys Pro Asp Gly Gln Phe Cys Pro Val Ala Cys Cys Leu Asp
1               5                   10                  15

Pro Gly Gly Ala Ser Tyr Ser Cys Cys Arg Pro Leu Leu Asp Lys Trp
            20                  25                  30
```

```
Pro Thr Thr Leu Ser Arg His Leu Gly Gly Pro Cys Gln Val Asp Ala
        35                  40                  45

His Cys Ser Ala Gly His Ser Cys Ile Phe Thr Val Ser Gly Thr Ser
 50                  55                  60

Ser Cys Cys Pro Phe Pro Glu Ala Val Ala Cys Gly Asp Gly His His
 65              70                  75                      80

Cys Cys Pro Arg Gly Phe His Cys Ser Ala Asp Gly Arg Ser Cys Phe
                85                  90                  95

Gln Arg Ser Gly Asn Asn Ser Val Gly Ala Ile Gln Cys Pro Asp Ser
                100                 105                 110

Gln Phe Glu Cys Pro Asp Phe Ser Thr Cys Cys Val Met Val Asp Gly
            115                 120                 125

Ser Trp Gly Cys Cys Pro Met Pro Gln Ala Ser Cys Cys Glu Asp Arg
        130                 135                 140

Val His Cys Cys Pro His Gly Ala Phe Cys Asp Leu Val His Thr Arg
145                 150                 155                 160

Cys Ile Thr Pro Thr Gly Thr His Pro Leu Ala Lys Lys Leu Pro Ala
                165                 170                 175

Gln Arg Thr Asn Arg Ala Val Ala Leu Ser Ser Val Met Cys Pro
            180                 185                 190

Asp Ala Arg Ser Arg Cys Pro Asp Gly Ser Thr Cys Cys Glu Leu Pro
        195                 200                 205

Ser Gly Lys Tyr Gly Cys Cys Pro Met Pro Asn Ala Thr Cys Cys Ser
        210                 215                 220

Asp His Leu His Cys Cys Pro Gln Asp Thr Val Cys Asp Leu Ile Gln
225                 230                 235                 240

Ser Lys Cys Leu Ser Lys Glu Asn Ala Thr Thr Asp Leu Leu Thr Lys
                245                 250                 255

Leu Pro Ala His Thr Val Gly Asp Val Lys Cys Asp Met Glu Val Ser
                260                 265                 270

Cys Pro Asp Gly Tyr Thr Cys Cys Arg Leu Gln Ser Gly Ala Trp Gly
        275                 280                 285

Cys Cys Pro Phe Thr Gln Ala Val Cys Cys Glu Asp His Ile His Cys
        290                 295                 300

Cys Pro Ala Gly Phe Thr Cys Asp Thr Gln Lys Gly Thr Cys Glu Gln
305                 310                 315                 320

Gly Pro His Gln Val Pro Trp Met Glu Lys Ala Pro Ala His Leu Ser
                325                 330                 335

Leu Pro Asp Pro Gln Ala Leu Lys Arg Asp Val Pro Cys Asp Asn Val
            340                 345                 350

Ser Ser Cys Pro Ser Ser Asp Thr Cys Cys Gln Leu Thr Ser Gly Glu
            355                 360                 365

Trp Gly Cys Cys Pro Ile Pro Glu Ala Val Cys Cys Ser Asp His Gln
        370                 375                 380

His Cys Cys Pro Gln Gly Tyr Thr Cys Val Ala Glu Gly Gln Cys Gln
385                 390                 395                 400

Arg Gly Ser Glu Ile Val Ala Gly Leu Glu Lys Met Pro Ala Arg Arg
                405                 410                 415

Ala Ser Leu Ser His Pro Arg Asp Ile Gly Cys Asp Gln His Thr Ser
            420                 425                 430

Cys Pro Val Gly Gln Thr Cys Cys Pro Ser Leu Gly Gly Ser Trp Ala
        435                 440                 445
```

```
Cys Cys Gln Leu Pro His Ala Val Cys Cys Glu Asp Arg Gln His Cys
    450                 455                 460

Cys Pro Ala Gly Tyr Thr Cys Asn Val Lys Ala Arg Ser Cys Glu Lys
465                 470                 475                 480

Glu Val Val Ser Ala Gln Pro Ala Thr Phe Leu Ala Arg Ser Pro His
                485                 490                 495

Val Gly Val Lys Asp Val Glu Cys Gly Glu Gly His Phe Cys His Asp
                500                 505                 510

Asn Gln Thr Cys Cys Arg Asp Asn Arg Gln Gly Trp Ala Cys Cys Pro
            515                 520                 525

Tyr Arg Gln Gly Val Cys Cys Ala Asp Arg Arg His Cys Cys Pro Ala
            530                 535                 540

Gly Phe Arg Cys Ala Ala Arg Gly Thr Lys Cys Leu Arg Arg Glu Ala
545                 550                 555                 560

Pro Arg Trp Asp Ala Pro Leu Arg Asp Pro Ala Leu Arg Pro Thr Leu
                565                 570                 575

<210> SEQ ID NO 10
<211> LENGTH: 576
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

Thr Arg Cys Pro Asp Gly Gln Phe Cys Pro Val Ala Cys Cys Leu Asp
1               5                   10                  15

Pro Gly Gly Ala Ser Tyr Ser Cys Cys Arg Pro Leu Leu Asp Lys Trp
                20                  25                  30

Pro Thr Thr Leu Ser Arg His Leu Gly Gly Pro Cys Gln Val Asp Ala
            35                  40                  45

His Cys Ser Ala Gly His Ser Cys Ile Phe Thr Val Ser Gly Thr Ser
        50                  55                  60

Ser Cys Cys Pro Phe Pro Glu Ala Val Ala Cys Gly Asp Gly His His
65                  70                  75                  80

Cys Cys Pro Arg Gly Phe His Cys Ser Ala Asp Gly Arg Ser Cys Phe
                85                  90                  95

Gln Arg Ser Gly Asn Asn Ser Val Gly Ala Ile Gln Cys Pro Asp Ser
                100                 105                 110

Gln Phe Glu Cys Pro Asp Phe Ser Thr Cys Cys Val Met Val Asp Gly
            115                 120                 125

Ser Trp Gly Cys Cys Pro Met Pro Gln Ala Ser Cys Cys Glu Asp Arg
        130                 135                 140

Val His Cys Cys Pro His Gly Ala Phe Cys Asp Leu Val His Thr Arg
145                 150                 155                 160

Cys Ile Thr Pro Thr Gly Thr His Pro Leu Ala Lys Lys Leu Pro Ala
                165                 170                 175

Gln Arg Thr Asn Arg Ala Val Ala Leu Ser Ser Ser Val Met Cys Pro
                180                 185                 190

Asp Ala Arg Ser Arg Cys Pro Asp Gly Ser Thr Cys Cys Glu Leu Pro
            195                 200                 205

Ser Gly Lys Tyr Gly Cys Cys Pro Met Pro Asn Ala Thr Cys Cys Ser
        210                 215                 220
```

-continued

```
Asp His Leu His Cys Cys Pro Gln Asp Thr Val Cys Asp Leu Ile Gln
225                 230                 235                 240

Ser Lys Cys Leu Ser Lys Glu Asn Ala Thr Thr Asp Leu Leu Thr Lys
            245                 250                 255

Leu Pro Ala His Thr Val Gly Asp Val Lys Cys Asp Met Glu Val Ser
                260                 265                 270

Cys Pro Asp Gly Tyr Thr Cys Cys Arg Leu Gln Ser Gly Ala Trp Gly
            275                 280                 285

Cys Cys Pro Phe Thr Gln Ala Val Cys Cys Glu Asp His Ile His Cys
        290                 295                 300

Cys Pro Ala Gly Phe Thr Cys Asp Thr Gln Lys Gly Thr Cys Glu Gln
305                 310                 315                 320

Gly Pro His Gln Val Pro Trp Met Glu Lys Ala Pro Ala His Leu Ser
                325                 330                 335

Leu Pro Asp Pro Gln Ala Leu Lys Arg Asp Val Pro Cys Asp Asn Val
            340                 345                 350

Ser Ser Cys Pro Ser Ser Asp Thr Cys Cys Gln Leu Thr Ser Gly Glu
        355                 360                 365

Trp Gly Cys Cys Pro Ile Pro Glu Ala Val Cys Cys Ser Asp His Gln
    370                 375                 380

His Cys Cys Pro Gln Gly Tyr Thr Cys Val Ala Glu Gly Gln Cys Gln
385                 390                 395                 400

Arg Gly Ser Glu Ile Val Ala Gly Leu Glu Lys Met Pro Ala Arg Arg
                405                 410                 415

Ala Ser Leu Ser His Pro Arg Asp Ile Gly Cys Asp Gln His Thr Ser
            420                 425                 430

Cys Pro Val Gly Gln Thr Cys Cys Pro Ser Leu Gly Gly Ser Trp Ala
        435                 440                 445

Cys Cys Gln Leu Pro His Ala Val Cys Cys Glu Asp Arg Gln His Cys
450                 455                 460

Cys Pro Ala Gly Tyr Thr Cys Asn Val Lys Ala Arg Ser Cys Glu Lys
465                 470                 475                 480

Glu Val Val Ser Ala Gln Pro Ala Thr Phe Leu Ala Arg Ser Pro His
            485                 490                 495

Val Gly Val Lys Asp Val Glu Cys Gly Glu Gly His Phe Cys His Asp
        500                 505                 510

Asn Gln Thr Cys Cys Arg Asp Asn Arg Gln Gly Trp Ala Cys Cys Pro
    515                 520                 525

Tyr Arg Gln Gly Val Cys Cys Ala Asp Arg Arg His Cys Cys Pro Ala
            530                 535                 540

Gly Phe Arg Cys Ala Ala Arg Gly Thr Lys Cys Leu Arg Arg Glu Ala
545                 550                 555                 560

Pro Arg Trp Asp Ala Pro Leu Arg Asp Pro Ala Leu Arg Pro Asn Leu
                565                 570                 575
```

<210> SEQ ID NO 11
<211> LENGTH: 576
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 11

```
Thr Arg Cys Pro Asp Gly Gln Phe Cys Pro Val Ala Cys Cys Leu Asp
1               5                   10                  15

Pro Gly Gly Ala Ser Tyr Ser Cys Cys Arg Pro Leu Leu Asp Lys Trp
            20                  25                  30

Pro Thr Thr Leu Ser Arg His Leu Gly Gly Pro Cys Gln Val Asp Ala
        35                  40                  45

His Cys Ser Ala Gly His Ser Cys Ile Phe Thr Val Ser Gly Thr Ser
    50                  55                  60

Ser Cys Cys Pro Phe Pro Glu Ala Val Ala Cys Gly Asp Gly His His
65                  70                  75                  80

Cys Cys Pro Arg Gly Phe His Cys Ser Ala Asp Gly Arg Ser Cys Phe
                85                  90                  95

Gln Arg Ser Gly Asn Asn Ser Val Gly Ala Ile Gln Cys Pro Asp Ser
            100                 105                 110

Gln Phe Glu Cys Pro Asp Phe Ser Thr Cys Cys Val Met Val Asp Gly
        115                 120                 125

Ser Trp Gly Cys Cys Pro Met Pro Gln Ala Ser Cys Cys Glu Asp Arg
130                 135                 140

Val His Cys Cys Pro His Gly Ala Phe Cys Asp Leu Val His Thr Arg
145                 150                 155                 160

Cys Ile Thr Pro Thr Gly Thr His Pro Leu Ala Lys Lys Leu Pro Ala
                165                 170                 175

Gln Arg Thr Asn Arg Ala Val Ala Leu Ser Ser Ser Val Met Cys Pro
            180                 185                 190

Asp Ala Arg Ser Arg Cys Pro Asp Gly Ser Thr Cys Cys Glu Leu Pro
        195                 200                 205

Ser Gly Lys Tyr Gly Cys Cys Pro Met Pro Asn Ala Thr Cys Cys Ser
210                 215                 220

Asp His Leu His Cys Cys Pro Gln Asp Thr Val Cys Asp Leu Ile Gln
225                 230                 235                 240

Ser Lys Cys Leu Ser Lys Glu Asn Ala Thr Thr Asp Leu Leu Thr Lys
                245                 250                 255

Leu Pro Ala His Thr Val Gly Asp Val Lys Cys Asp Met Glu Val Ser
            260                 265                 270

Cys Pro Asp Gly Tyr Thr Cys Cys Arg Leu Gln Ser Gly Ala Trp Gly
        275                 280                 285

Cys Cys Pro Phe Thr Gln Ala Val Cys Cys Glu Asp His Ile His Cys
290                 295                 300

Cys Pro Ala Gly Phe Thr Cys Asp Thr Gln Lys Gly Thr Cys Glu Gln
305                 310                 315                 320

Gly Pro His Gln Val Pro Trp Met Glu Lys Ala Pro Ala His Leu Ser
                325                 330                 335

Leu Pro Asp Pro Gln Ala Leu Lys Arg Asp Val Pro Cys Asp Asn Val
            340                 345                 350

Ser Ser Cys Pro Ser Ser Asp Thr Cys Cys Gln Leu Thr Ser Gly Glu
        355                 360                 365

Trp Gly Cys Cys Pro Ile Pro Glu Ala Val Cys Cys Ser Asp His Gln
370                 375                 380

His Cys Cys Pro Gln Gly Tyr Thr Cys Val Ala Glu Gly Gln Cys Gln
385                 390                 395                 400
```

-continued

```
Arg Gly Ser Glu Ile Val Ala Gly Leu Glu Lys Met Pro Ala Arg Arg
                405                 410                 415

Ala Ser Leu Ser His Pro Arg Asp Ile Gly Cys Asp Gln His Thr Ser
            420                 425                 430

Cys Pro Val Gly Gln Thr Cys Cys Pro Ser Leu Gly Gly Ser Trp Ala
        435                 440                 445

Cys Cys Gln Leu Pro His Ala Val Cys Cys Glu Asp Arg Gln His Cys
    450                 455                 460

Cys Pro Ala Gly Tyr Thr Cys Asn Val Lys Ala Arg Ser Cys Glu Lys
465                 470                 475                 480

Glu Val Val Ser Ala Gln Pro Ala Thr Phe Leu Ala Arg Ser Pro His
                485                 490                 495

Val Gly Val Lys Asp Val Glu Cys Gly Glu Gly His Phe Cys His Asp
            500                 505                 510

Asn Gln Thr Cys Cys Arg Asp Asn Arg Gln Gly Trp Ala Cys Cys Pro
        515                 520                 525

Tyr Arg Gln Gly Val Cys Cys Ala Asp Arg Arg His Cys Cys Pro Ala
    530                 535                 540

Gly Phe Arg Cys Ala Ala Arg Gly Thr Lys Cys Leu Arg Arg Glu Ala
545                 550                 555                 560

Pro Arg Trp Asp Ala Pro Leu Arg Asp Pro Ala Leu Arg Pro Gln Leu
                565                 570                 575
```

<210> SEQ ID NO 12
<211> LENGTH: 576
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 12

```
Thr Arg Cys Pro Asp Gly Gln Phe Cys Pro Val Ala Cys Cys Leu Asp
1               5                   10                  15

Pro Gly Gly Ala Ser Tyr Ser Cys Cys Arg Pro Leu Leu Asp Lys Trp
            20                  25                  30

Pro Thr Thr Leu Ser Arg His Leu Gly Gly Pro Cys Gln Val Asp Ala
        35                  40                  45

His Cys Ser Ala Gly His Ser Cys Ile Phe Thr Val Ser Gly Thr Ser
    50                  55                  60

Ser Cys Cys Pro Phe Pro Glu Ala Val Ala Cys Gly Asp Gly His His
65                  70                  75                  80

Cys Cys Pro Arg Gly Phe His Cys Ser Ala Asp Gly Arg Ser Cys Phe
                85                  90                  95

Gln Arg Ser Gly Asn Asn Ser Val Gly Ala Ile Gln Cys Pro Asp Ser
            100                 105                 110

Gln Phe Glu Cys Pro Asp Phe Ser Thr Cys Cys Val Met Val Asp Gly
        115                 120                 125

Ser Trp Gly Cys Cys Pro Met Pro Gln Ala Ser Cys Cys Glu Asp Arg
    130                 135                 140

Val His Cys Cys Pro His Gly Ala Phe Cys Asp Leu Val His Thr Arg
145                 150                 155                 160

Cys Ile Thr Pro Thr Gly Thr His Pro Leu Ala Lys Lys Leu Pro Ala
                165                 170                 175
```

```
Gln Arg Thr Asn Arg Ala Val Ala Leu Ser Ser Ser Val Met Cys Pro
                180                 185                 190

Asp Ala Arg Ser Arg Cys Pro Asp Gly Ser Thr Cys Cys Glu Leu Pro
            195                 200                 205

Ser Gly Lys Tyr Gly Cys Cys Pro Met Pro Asn Ala Thr Cys Cys Ser
        210                 215                 220

Asp His Leu His Cys Cys Pro Gln Asp Thr Val Cys Asp Leu Ile Gln
225                 230                 235                 240

Ser Lys Cys Leu Ser Lys Glu Asn Ala Thr Thr Asp Leu Leu Thr Lys
                245                 250                 255

Leu Pro Ala His Thr Val Gly Asp Val Lys Cys Asp Met Glu Val Ser
            260                 265                 270

Cys Pro Asp Gly Tyr Thr Cys Cys Arg Leu Gln Ser Gly Ala Trp Gly
        275                 280                 285

Cys Cys Pro Phe Thr Gln Ala Val Cys Cys Glu Asp His Ile His Cys
        290                 295                 300

Cys Pro Ala Gly Phe Thr Cys Asp Thr Gln Lys Gly Thr Cys Glu Gln
305                 310                 315                 320

Gly Pro His Gln Val Pro Trp Met Glu Lys Ala Pro Ala His Leu Ser
                325                 330                 335

Leu Pro Asp Pro Gln Ala Leu Lys Arg Asp Val Pro Cys Asp Asn Val
            340                 345                 350

Ser Ser Cys Pro Ser Ser Asp Thr Cys Cys Gln Leu Thr Ser Gly Glu
        355                 360                 365

Trp Gly Cys Cys Pro Ile Pro Glu Ala Val Cys Cys Ser Asp His Gln
370                 375                 380

His Cys Cys Pro Gln Gly Tyr Thr Cys Val Ala Glu Gly Gln Cys Gln
385                 390                 395                 400

Arg Gly Ser Glu Ile Val Ala Gly Leu Glu Lys Met Pro Ala Arg Arg
                405                 410                 415

Ala Ser Leu Ser His Pro Arg Asp Ile Gly Cys Asp Gln His Thr Ser
            420                 425                 430

Cys Pro Val Gly Gln Thr Cys Cys Pro Ser Leu Gly Gly Ser Trp Ala
        435                 440                 445

Cys Cys Gln Leu Pro His Ala Val Cys Cys Glu Asp Arg Gln His Cys
        450                 455                 460

Cys Pro Ala Gly Tyr Thr Cys Asn Val Lys Ala Arg Ser Cys Glu Lys
465                 470                 475                 480

Glu Val Val Ser Ala Gln Pro Ala Thr Phe Leu Ala Arg Ser Pro His
                485                 490                 495

Val Gly Val Lys Asp Val Glu Cys Gly Glu Gly His Phe Cys His Asp
            500                 505                 510

Asn Gln Thr Cys Cys Arg Asp Asn Arg Gln Gly Trp Ala Cys Cys Pro
        515                 520                 525

Tyr Arg Gln Gly Val Cys Cys Ala Asp Arg Arg His Cys Cys Pro Ala
        530                 535                 540

Gly Phe Arg Cys Ala Ala Arg Gly Thr Lys Cys Leu Arg Arg Glu Ala
545                 550                 555                 560

Pro Arg Trp Asp Ala Pro Leu Arg Asp Pro Ala Leu Arg Pro Gly Leu
                565                 570                 575

<210> SEQ ID NO 13
<211> LENGTH: 576
<212> TYPE: PRT
```

<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 13

```
Thr Arg Cys Pro Asp Gly Gln Phe Cys Pro Val Ala Cys Cys Leu Asp
1               5                   10                  15

Pro Gly Gly Ala Ser Tyr Ser Cys Cys Arg Pro Leu Leu Asp Lys Trp
            20                  25                  30

Pro Thr Thr Leu Ser Arg His Leu Gly Gly Pro Cys Gln Val Asp Ala
            35                  40                  45

His Cys Ser Ala Gly His Ser Cys Ile Phe Thr Val Ser Gly Thr Ser
50                  55                  60

Ser Cys Cys Pro Phe Pro Glu Ala Val Ala Cys Gly Asp Gly His His
65                  70                  75                  80

Cys Cys Pro Arg Gly Phe His Cys Ser Ala Asp Gly Arg Ser Cys Phe
                85                  90                  95

Gln Arg Ser Gly Asn Asn Ser Val Gly Ala Ile Gln Cys Pro Asp Ser
            100                 105                 110

Gln Phe Glu Cys Pro Asp Phe Ser Thr Cys Cys Val Met Val Asp Gly
            115                 120                 125

Ser Trp Gly Cys Cys Pro Met Pro Gln Ala Ser Cys Cys Glu Asp Arg
130                 135                 140

Val His Cys Cys Pro His Gly Ala Phe Cys Asp Leu Val His Thr Arg
145                 150                 155                 160

Cys Ile Thr Pro Thr Gly Thr His Pro Leu Ala Lys Lys Leu Pro Ala
                165                 170                 175

Gln Arg Thr Asn Arg Ala Val Ala Leu Ser Ser Val Met Cys Pro
            180                 185                 190

Asp Ala Arg Ser Arg Cys Pro Asp Gly Ser Thr Cys Cys Glu Leu Pro
            195                 200                 205

Ser Gly Lys Tyr Gly Cys Cys Pro Met Pro Asn Ala Thr Cys Cys Ser
210                 215                 220

Asp His Leu His Cys Cys Pro Gln Asp Thr Val Cys Asp Leu Ile Gln
225                 230                 235                 240

Ser Lys Cys Leu Ser Lys Glu Asn Ala Thr Thr Asp Leu Leu Thr Lys
                245                 250                 255

Leu Pro Ala His Thr Val Gly Asp Val Lys Cys Asp Met Glu Val Ser
            260                 265                 270

Cys Pro Asp Gly Tyr Thr Cys Cys Arg Leu Gln Ser Gly Ala Trp Gly
            275                 280                 285

Cys Cys Pro Phe Thr Gln Ala Val Cys Cys Glu Asp His Ile His Cys
290                 295                 300

Cys Pro Ala Gly Phe Thr Cys Asp Thr Gln Lys Gly Thr Cys Glu Gln
305                 310                 315                 320

Gly Pro His Gln Val Pro Trp Met Glu Lys Ala Pro Ala His Leu Ser
                325                 330                 335

Leu Pro Asp Pro Gln Ala Leu Lys Arg Asp Val Pro Cys Asp Asn Val
            340                 345                 350

Ser Ser Cys Pro Ser Ser Asp Thr Cys Cys Gln Leu Thr Ser Gly Glu
            355                 360                 365

Trp Gly Cys Cys Pro Ile Pro Glu Ala Val Cys Cys Ser Asp His Gln
370                 375                 380
```

-continued

```
His Cys Cys Pro Gln Gly Tyr Thr Cys Val Ala Glu Gly Gln Cys Gln
385                 390                 395                 400

Arg Gly Ser Glu Ile Val Ala Gly Leu Glu Lys Met Pro Ala Arg Arg
            405                 410                 415

Ala Ser Leu Ser His Pro Arg Asp Ile Gly Cys Asp Gln His Thr Ser
            420                 425                 430

Cys Pro Val Gly Gln Thr Cys Cys Pro Ser Leu Gly Gly Ser Trp Ala
            435                 440                 445

Cys Cys Gln Leu Pro His Ala Val Cys Cys Glu Asp Arg Gln His Cys
            450                 455                 460

Cys Pro Ala Gly Tyr Thr Cys Asn Val Lys Ala Arg Ser Cys Glu Lys
465                 470                 475                 480

Glu Val Val Ser Ala Gln Pro Ala Thr Phe Leu Ala Arg Ser Pro His
                485                 490                 495

Val Gly Val Lys Asp Val Glu Cys Gly Glu Gly His Phe Cys His Asp
            500                 505                 510

Asn Gln Thr Cys Cys Arg Asp Asn Arg Gln Gly Trp Ala Cys Cys Pro
            515                 520                 525

Tyr Arg Gln Gly Val Cys Cys Ala Asp Arg Arg His Cys Cys Pro Ala
530                 535                 540

Gly Phe Arg Cys Ala Ala Arg Gly Thr Lys Cys Leu Arg Arg Glu Ala
545                 550                 555                 560

Pro Arg Trp Asp Ala Pro Leu Arg Asp Pro Ala Leu Arg Pro Leu
                565                 570                 575
```

<210> SEQ ID NO 14
<211> LENGTH: 576
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 14

```
Thr Arg Cys Pro Asp Gly Gln Phe Cys Pro Val Ala Cys Cys Leu Asp
1               5                   10                  15

Pro Gly Gly Ala Ser Tyr Ser Cys Cys Arg Pro Leu Leu Asp Lys Trp
            20                  25                  30

Pro Thr Thr Leu Ser Arg His Leu Gly Gly Pro Cys Gln Val Asp Ala
            35                  40                  45

His Cys Ser Ala Gly His Ser Cys Ile Phe Thr Val Ser Gly Thr Ser
        50                  55                  60

Ser Cys Cys Pro Phe Pro Glu Ala Val Ala Cys Gly Asp Gly His His
65                  70                  75                  80

Cys Cys Pro Arg Gly Phe His Cys Ser Ala Asp Gly Arg Ser Cys Phe
                85                  90                  95

Gln Arg Ser Gly Asn Asn Ser Val Gly Ala Ile Gln Cys Pro Asp Ser
            100                 105                 110

Gln Phe Glu Cys Pro Asp Phe Ser Thr Cys Cys Val Met Val Asp Gly
            115                 120                 125

Ser Trp Gly Cys Cys Pro Met Pro Gln Ala Ser Cys Cys Glu Asp Arg
        130                 135                 140

Val His Cys Cys Pro His Gly Ala Phe Cys Asp Leu Val His Thr Arg
145                 150                 155                 160
```

-continued

```
Cys Ile Thr Pro Thr Gly Thr His Pro Leu Ala Lys Lys Leu Pro Ala
            165                 170                 175
Gln Arg Thr Asn Arg Ala Val Ala Leu Ser Ser Val Met Cys Pro
        180                 185                 190
Asp Ala Arg Ser Arg Cys Pro Asp Gly Ser Thr Cys Cys Glu Leu Pro
            195                 200                 205
Ser Gly Lys Tyr Gly Cys Cys Pro Met Pro Asn Ala Thr Cys Cys Ser
        210                 215                 220
Asp His Leu His Cys Cys Pro Gln Asp Thr Val Cys Asp Leu Ile Gln
225                 230                 235                 240
Ser Lys Cys Leu Ser Lys Glu Asn Ala Thr Thr Asp Leu Leu Thr Lys
            245                 250                 255
Leu Pro Ala His Thr Val Gly Asp Val Lys Cys Asp Met Glu Val Ser
            260                 265                 270
Cys Pro Asp Gly Tyr Thr Cys Cys Arg Leu Gln Ser Gly Ala Trp Gly
        275                 280                 285
Cys Cys Pro Phe Thr Gln Ala Val Cys Cys Glu Asp His Ile His Cys
290                 295                 300
Cys Pro Ala Gly Phe Thr Cys Asp Thr Gln Lys Gly Thr Cys Glu Gln
305                 310                 315                 320
Gly Pro His Gln Val Pro Trp Met Glu Lys Ala Pro Ala His Leu Ser
            325                 330                 335
Leu Pro Asp Pro Gln Ala Leu Lys Arg Asp Val Pro Cys Asp Asn Val
            340                 345                 350
Ser Ser Cys Pro Ser Ser Asp Thr Cys Cys Gln Leu Thr Ser Gly Glu
        355                 360                 365
Trp Gly Cys Cys Pro Ile Pro Glu Ala Val Cys Cys Ser Asp His Gln
        370                 375                 380
His Cys Cys Pro Gln Gly Tyr Thr Cys Val Ala Glu Gly Gln Cys Gln
385                 390                 395                 400
Arg Gly Ser Glu Ile Val Ala Gly Leu Glu Lys Met Pro Ala Arg Arg
            405                 410                 415
Ala Ser Leu Ser His Pro Arg Asp Ile Gly Cys Asp Gln His Thr Ser
            420                 425                 430
Cys Pro Val Gly Gln Thr Cys Cys Pro Ser Leu Gly Gly Ser Trp Ala
        435                 440                 445
Cys Cys Gln Leu Pro His Ala Val Cys Cys Glu Asp Arg Gln His Cys
        450                 455                 460
Cys Pro Ala Gly Tyr Thr Cys Asn Val Lys Ala Arg Ser Cys Glu Lys
465                 470                 475                 480
Glu Val Val Ser Ala Gln Pro Ala Thr Phe Leu Ala Arg Ser Pro His
            485                 490                 495
Val Gly Val Lys Asp Val Glu Cys Gly Glu Gly His Phe Cys His Asp
            500                 505                 510
Asn Gln Thr Cys Cys Arg Asp Asn Arg Gln Gly Trp Ala Cys Cys Pro
        515                 520                 525
Tyr Arg Gln Gly Val Cys Cys Ala Asp Arg Arg His Cys Cys Pro Ala
        530                 535                 540
Gly Phe Arg Cys Ala Ala Arg Gly Thr Lys Cys Leu Arg Arg Glu Ala
545                 550                 555                 560
Pro Arg Trp Asp Ala Pro Leu Arg Asp Pro Ala Leu Arg Pro Ala Leu
            565                 570                 575
```

-continued

```
<210> SEQ ID NO 15
<211> LENGTH: 576
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15
```

Thr Arg Cys Pro Asp Gly Gln Phe Cys Pro Val Ala Cys Cys Leu Asp
1               5                   10                  15

Pro Gly Gly Ala Ser Tyr Ser Cys Cys Arg Pro Leu Leu Asp Lys Trp
                20                  25                  30

Pro Thr Thr Leu Ser Arg His Leu Gly Gly Pro Cys Gln Val Asp Ala
            35                  40                  45

His Cys Ser Ala Gly His Ser Cys Ile Phe Thr Val Ser Gly Thr Ser
50                  55                  60

Ser Cys Cys Pro Phe Pro Glu Ala Val Ala Cys Gly Asp Gly His His
65                  70                  75                  80

Cys Cys Pro Arg Gly Phe His Cys Ser Ala Asp Gly Arg Ser Cys Phe
                85                  90                  95

Gln Arg Ser Gly Asn Asn Ser Val Gly Ala Ile Gln Cys Pro Asp Ser
                100                 105                 110

Gln Phe Glu Cys Pro Asp Phe Ser Thr Cys Cys Val Met Val Asp Gly
            115                 120                 125

Ser Trp Gly Cys Cys Pro Met Pro Gln Ala Ser Cys Cys Glu Asp Arg
            130                 135                 140

Val His Cys Cys Pro His Gly Ala Phe Cys Asp Leu Val His Thr Arg
145                 150                 155                 160

Cys Ile Thr Pro Thr Gly Thr His Pro Leu Ala Lys Lys Leu Pro Ala
                165                 170                 175

Gln Arg Thr Asn Arg Ala Val Ala Leu Ser Ser Ser Val Met Cys Pro
                180                 185                 190

Asp Ala Arg Ser Arg Cys Pro Asp Gly Ser Thr Cys Cys Glu Leu Pro
            195                 200                 205

Ser Gly Lys Tyr Gly Cys Cys Pro Met Pro Asn Ala Thr Cys Cys Ser
            210                 215                 220

Asp His Leu His Cys Cys Pro Gln Asp Thr Val Cys Asp Leu Ile Gln
225                 230                 235                 240

Ser Lys Cys Leu Ser Lys Glu Asn Ala Thr Thr Asp Leu Leu Thr Lys
                245                 250                 255

Leu Pro Ala His Thr Val Gly Asp Val Lys Cys Asp Met Glu Val Ser
                260                 265                 270

Cys Pro Asp Gly Tyr Thr Cys Cys Arg Leu Gln Ser Gly Ala Trp Gly
            275                 280                 285

Cys Cys Pro Phe Thr Gln Ala Val Cys Cys Glu Asp His Ile His Cys
            290                 295                 300

Cys Pro Ala Gly Phe Thr Cys Asp Thr Gln Lys Gly Thr Cys Glu Gln
305                 310                 315                 320

Gly Pro His Gln Val Pro Trp Met Glu Lys Ala Pro Ala His Leu Ser
                325                 330                 335

Leu Pro Asp Pro Gln Ala Leu Lys Arg Asp Val Pro Cys Asp Asn Val
                340                 345                 350

Ser Ser Cys Pro Ser Ser Asp Thr Cys Cys Gln Leu Thr Ser Gly Glu
            355                 360                 365

Trp Gly Cys Cys Pro Ile Pro Glu Ala Val Cys Cys Ser Asp His Gln
      370                 375                 380

His Cys Cys Pro Gln Gly Tyr Thr Cys Val Ala Glu Gly Gln Cys Gln
385                 390                 395                 400

Arg Gly Ser Glu Ile Val Ala Gly Leu Glu Lys Met Pro Ala Arg Arg
                405                 410                 415

Ala Ser Leu Ser His Pro Arg Asp Ile Gly Cys Asp Gln His Thr Ser
                420                 425                 430

Cys Pro Val Gly Gln Thr Cys Cys Pro Ser Leu Gly Gly Ser Trp Ala
            435                 440                 445

Cys Cys Gln Leu Pro His Ala Val Cys Cys Glu Asp Arg Gln His Cys
        450                 455                 460

Cys Pro Ala Gly Tyr Thr Cys Asn Val Lys Ala Arg Ser Cys Glu Lys
465                 470                 475                 480

Glu Val Val Ser Ala Gln Pro Ala Thr Phe Leu Ala Arg Ser Pro His
                485                 490                 495

Val Gly Val Lys Asp Val Glu Cys Gly Glu Gly His Phe Cys His Asp
                500                 505                 510

Asn Gln Thr Cys Cys Arg Asp Asn Arg Gln Gly Trp Ala Cys Cys Pro
            515                 520                 525

Tyr Arg Gln Gly Val Cys Cys Ala Asp Arg Arg His Cys Cys Pro Ala
        530                 535                 540

Gly Phe Arg Cys Ala Ala Arg Gly Thr Lys Cys Leu Arg Arg Glu Ala
545                 550                 555                 560

Pro Arg Trp Asp Ala Pro Leu Arg Asp Pro Ala Leu Arg Pro Tyr Leu
                565                 570                 575

<210> SEQ ID NO 16
<211> LENGTH: 576
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16

Thr Arg Cys Pro Asp Gly Gln Phe Cys Pro Val Ala Cys Cys Leu Asp
1               5                   10                  15

Pro Gly Gly Ala Ser Tyr Ser Cys Cys Arg Pro Leu Leu Asp Lys Trp
                20                  25                  30

Pro Thr Thr Leu Ser Arg His Leu Gly Gly Pro Cys Gln Val Asp Ala
            35                  40                  45

His Cys Ser Ala Gly His Ser Cys Ile Phe Thr Val Ser Gly Thr Ser
        50                  55                  60

Ser Cys Cys Pro Phe Pro Glu Ala Val Ala Cys Gly Asp Gly His His
65                  70                  75                  80

Cys Cys Pro Arg Gly Phe His Cys Ser Ala Asp Gly Arg Ser Cys Phe
                85                  90                  95

Gln Arg Ser Gly Asn Asn Ser Val Gly Ala Ile Gln Cys Pro Asp Ser
                100                 105                 110

Gln Phe Glu Cys Pro Asp Phe Ser Thr Cys Cys Val Met Val Asp Gly
            115                 120                 125

Ser Trp Gly Cys Cys Pro Met Pro Gln Ala Ser Cys Cys Glu Asp Arg
        130                 135                 140

```
Val His Cys Cys Pro His Gly Ala Phe Cys Asp Leu Val His Thr Arg
145                 150                 155                 160

Cys Ile Thr Pro Thr Gly Thr His Pro Leu Ala Lys Lys Leu Pro Ala
                165                 170                 175

Gln Arg Thr Asn Arg Ala Val Ala Leu Ser Ser Val Met Cys Pro
            180                 185                 190

Asp Ala Arg Ser Arg Cys Pro Asp Gly Ser Thr Cys Cys Glu Leu Pro
            195                 200                 205

Ser Gly Lys Tyr Gly Cys Cys Pro Met Pro Asn Ala Thr Cys Cys Ser
210                 215                 220

Asp His Leu His Cys Cys Pro Gln Asp Thr Val Cys Asp Leu Ile Gln
225                 230                 235                 240

Ser Lys Cys Leu Ser Lys Glu Asn Ala Thr Thr Asp Leu Leu Thr Lys
                245                 250                 255

Leu Pro Ala His Thr Val Gly Asp Val Lys Cys Asp Met Glu Val Ser
                260                 265                 270

Cys Pro Asp Gly Tyr Thr Cys Cys Arg Leu Gln Ser Gly Ala Trp Gly
        275                 280                 285

Cys Cys Pro Phe Thr Gln Ala Val Cys Cys Glu Asp His Ile His Cys
        290                 295                 300

Cys Pro Ala Gly Phe Thr Cys Asp Thr Gln Lys Gly Thr Cys Glu Gln
305                 310                 315                 320

Gly Pro His Gln Val Pro Trp Met Glu Lys Ala Pro Ala His Leu Ser
                325                 330                 335

Leu Pro Asp Pro Gln Ala Leu Lys Arg Asp Val Pro Cys Asp Asn Val
                340                 345                 350

Ser Ser Cys Pro Ser Ser Asp Thr Cys Cys Gln Leu Thr Ser Gly Glu
            355                 360                 365

Trp Gly Cys Cys Pro Ile Pro Glu Ala Val Cys Cys Ser Asp His Gln
        370                 375                 380

His Cys Cys Pro Gln Gly Tyr Thr Cys Val Ala Glu Gly Gln Cys Gln
385                 390                 395                 400

Arg Gly Ser Glu Ile Val Ala Gly Leu Glu Lys Met Pro Ala Arg Arg
                405                 410                 415

Ala Ser Leu Ser His Pro Arg Asp Ile Gly Cys Asp Gln His Thr Ser
            420                 425                 430

Cys Pro Val Gly Gln Thr Cys Cys Pro Ser Leu Gly Gly Ser Trp Ala
        435                 440                 445

Cys Cys Gln Leu Pro His Ala Val Cys Cys Glu Asp Arg Gln His Cys
450                 455                 460

Cys Pro Ala Gly Tyr Thr Cys Asn Val Lys Ala Arg Ser Cys Glu Lys
465                 470                 475                 480

Glu Val Val Ser Ala Gln Pro Ala Thr Phe Leu Ala Arg Ser Pro His
                485                 490                 495

Val Gly Val Lys Asp Val Glu Cys Gly Glu Gly His Phe Cys His Asp
                500                 505                 510

Asn Gln Thr Cys Cys Arg Asp Asn Arg Gln Gly Trp Ala Cys Cys Pro
            515                 520                 525

Tyr Arg Gln Gly Val Cys Cys Ala Asp Arg Arg His Cys Cys Pro Ala
            530                 535                 540

Gly Phe Arg Cys Ala Ala Arg Gly Thr Lys Cys Leu Arg Arg Glu Ala
545                 550                 555                 560
```

```
Pro Arg Trp Asp Ala Pro Leu Arg Asp Pro Ala Leu Arg Pro Val Leu
                565                 570                 575

<210> SEQ ID NO 17
<211> LENGTH: 576
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 17

Thr Arg Cys Pro Asp Gly Gln Phe Cys Pro Val Ala Cys Cys Leu Asp
1               5                   10                  15

Pro Gly Gly Ala Ser Tyr Ser Cys Cys Arg Pro Leu Leu Asp Lys Trp
                20                  25                  30

Pro Thr Thr Leu Ser Arg His Leu Gly Gly Pro Cys Gln Val Asp Ala
            35                  40                  45

His Cys Ser Ala Gly His Ser Cys Ile Phe Thr Val Ser Gly Thr Ser
    50                  55                  60

Ser Cys Cys Pro Phe Pro Glu Ala Val Ala Cys Gly Asp Gly His His
65                  70                  75                  80

Cys Cys Pro Arg Gly Phe His Cys Ser Ala Asp Gly Arg Ser Cys Phe
                85                  90                  95

Gln Arg Ser Gly Asn Asn Ser Val Gly Ala Ile Gln Cys Pro Asp Ser
                100                 105                 110

Gln Phe Glu Cys Pro Asp Phe Ser Thr Cys Cys Val Met Val Asp Gly
            115                 120                 125

Ser Trp Gly Cys Cys Pro Met Pro Gln Ala Ser Cys Cys Glu Asp Arg
    130                 135                 140

Val His Cys Cys Pro His Gly Ala Phe Cys Asp Leu Val His Thr Arg
145                 150                 155                 160

Cys Ile Thr Pro Thr Gly Thr His Pro Leu Ala Lys Lys Leu Pro Ala
                165                 170                 175

Gln Arg Thr Asn Arg Ala Val Ala Leu Ser Ser Ser Val Met Cys Pro
                180                 185                 190

Asp Ala Arg Ser Arg Cys Pro Asp Gly Ser Thr Cys Cys Glu Leu Pro
            195                 200                 205

Ser Gly Lys Tyr Gly Cys Cys Pro Met Pro Asn Ala Thr Cys Cys Ser
    210                 215                 220

Asp His Leu His Cys Cys Pro Gln Asp Thr Val Cys Asp Leu Ile Gln
225                 230                 235                 240

Ser Lys Cys Leu Ser Lys Glu Asn Ala Thr Thr Asp Leu Leu Thr Lys
                245                 250                 255

Leu Pro Ala His Thr Val Gly Asp Val Lys Cys Asp Met Glu Val Ser
                260                 265                 270

Cys Pro Asp Gly Tyr Thr Cys Cys Arg Leu Gln Ser Gly Ala Trp Gly
            275                 280                 285

Cys Cys Pro Phe Thr Gln Ala Val Cys Cys Glu Asp His Ile His Cys
    290                 295                 300

Cys Pro Ala Gly Phe Thr Cys Asp Thr Gln Lys Gly Thr Cys Glu Gln
305                 310                 315                 320

Gly Pro His Gln Val Pro Trp Met Glu Lys Ala Pro Ala His Leu Ser
                325                 330                 335
```

Leu Pro Asp Pro Gln Ala Leu Lys Arg Asp Val Pro Cys Asp Asn Val
                340                 345                 350

Ser Ser Cys Pro Ser Ser Asp Thr Cys Cys Gln Leu Thr Ser Gly Glu
        355                 360                 365

Trp Gly Cys Cys Pro Ile Pro Glu Ala Val Cys Cys Ser Asp His Gln
    370                 375                 380

His Cys Cys Pro Gln Gly Tyr Thr Cys Val Ala Glu Gly Gln Cys Gln
385                 390                 395                 400

Arg Gly Ser Glu Ile Val Ala Gly Leu Glu Lys Met Pro Ala Arg Arg
                405                 410                 415

Ala Ser Leu Ser His Pro Arg Asp Ile Gly Cys Asp Gln His Thr Ser
            420                 425                 430

Cys Pro Val Gly Gln Thr Cys Cys Pro Ser Leu Gly Gly Ser Trp Ala
        435                 440                 445

Cys Cys Gln Leu Pro His Ala Val Cys Cys Glu Asp Arg Gln His Cys
    450                 455                 460

Cys Pro Ala Gly Tyr Thr Cys Asn Val Lys Ala Arg Ser Cys Glu Lys
465                 470                 475                 480

Glu Val Val Ser Ala Gln Pro Ala Thr Phe Leu Ala Arg Ser Pro His
                485                 490                 495

Val Gly Val Lys Asp Val Glu Cys Gly Glu Gly His Phe Cys His Asp
            500                 505                 510

Asn Gln Thr Cys Cys Arg Asp Asn Arg Gln Gly Trp Ala Cys Cys Pro
        515                 520                 525

Tyr Arg Gln Gly Val Cys Cys Ala Asp Arg Arg His Cys Cys Pro Ala
    530                 535                 540

Gly Phe Arg Cys Ala Ala Arg Gly Thr Lys Cys Leu Arg Arg Glu Ala
545                 550                 555                 560

Pro Arg Trp Asp Ala Pro Leu Arg Asp Pro Ala Leu Arg Pro Ile Leu
                565                 570                 575

<210> SEQ ID NO 18
<211> LENGTH: 576
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 18

Thr Arg Cys Pro Asp Gly Gln Phe Cys Pro Val Ala Cys Cys Leu Asp
1               5                   10                  15

Pro Gly Gly Ala Ser Tyr Ser Cys Cys Arg Pro Leu Leu Asp Lys Trp
                20                  25                  30

Pro Thr Thr Leu Ser Arg His Leu Gly Gly Pro Cys Gln Val Asp Ala
            35                  40                  45

His Cys Ser Ala Gly His Ser Cys Ile Phe Thr Val Ser Gly Thr Ser
        50                  55                  60

Ser Cys Cys Pro Phe Pro Glu Ala Val Ala Cys Gly Asp Gly His His
65                  70                  75                  80

Cys Cys Pro Arg Gly Phe His Cys Ser Ala Asp Gly Arg Ser Cys Phe
                85                  90                  95

Gln Arg Ser Gly Asn Asn Ser Val Gly Ala Ile Gln Cys Pro Asp Ser
            100                 105                 110

```
Gln Phe Glu Cys Pro Asp Phe Ser Thr Cys Cys Val Met Val Asp Gly
            115                 120                 125

Ser Trp Gly Cys Cys Pro Met Pro Gln Ala Ser Cys Cys Glu Asp Arg
        130                 135                 140

Val His Cys Cys Pro His Gly Ala Phe Cys Asp Leu Val His Thr Arg
145                 150                 155                 160

Cys Ile Thr Pro Thr Gly Thr His Pro Leu Ala Lys Lys Leu Pro Ala
                165                 170                 175

Gln Arg Thr Asn Arg Ala Val Ala Leu Ser Ser Val Met Cys Pro
            180                 185                 190

Asp Ala Arg Ser Arg Cys Pro Asp Gly Ser Thr Cys Cys Glu Leu Pro
                195                 200                 205

Ser Gly Lys Tyr Gly Cys Cys Pro Met Pro Asn Ala Thr Cys Cys Ser
        210                 215                 220

Asp His Leu His Cys Cys Pro Gln Asp Thr Val Cys Asp Leu Ile Gln
225                 230                 235                 240

Ser Lys Cys Leu Ser Lys Glu Asn Ala Thr Thr Asp Leu Leu Thr Lys
                245                 250                 255

Leu Pro Ala His Thr Val Gly Asp Val Lys Cys Asp Met Glu Val Ser
            260                 265                 270

Cys Pro Asp Gly Tyr Thr Cys Cys Arg Leu Gln Ser Gly Ala Trp Gly
        275                 280                 285

Cys Cys Pro Phe Thr Gln Ala Val Cys Cys Glu Asp His Ile His Cys
        290                 295                 300

Cys Pro Ala Gly Phe Thr Cys Asp Thr Gln Lys Gly Thr Cys Glu Gln
305                 310                 315                 320

Gly Pro His Gln Val Pro Trp Met Glu Lys Ala Pro Ala His Leu Ser
                325                 330                 335

Leu Pro Asp Pro Gln Ala Leu Lys Arg Asp Val Pro Cys Asp Asn Val
            340                 345                 350

Ser Ser Cys Pro Ser Ser Asp Thr Cys Cys Gln Leu Thr Ser Gly Glu
        355                 360                 365

Trp Gly Cys Cys Pro Ile Pro Glu Ala Val Cys Cys Ser Asp His Gln
        370                 375                 380

His Cys Cys Pro Gln Gly Tyr Thr Cys Val Ala Glu Gly Gln Cys Gln
385                 390                 395                 400

Arg Gly Ser Glu Ile Val Ala Gly Leu Glu Lys Met Pro Ala Arg Arg
            405                 410                 415

Ala Ser Leu Ser His Pro Arg Asp Ile Gly Cys Asp Gln His Thr Ser
        420                 425                 430

Cys Pro Val Gly Gln Thr Cys Cys Pro Ser Leu Gly Gly Ser Trp Ala
        435                 440                 445

Cys Cys Gln Leu Pro His Ala Val Cys Cys Glu Asp Arg Gln His Cys
450                 455                 460

Cys Pro Ala Gly Tyr Thr Cys Asn Val Lys Ala Arg Ser Cys Glu Lys
465                 470                 475                 480

Glu Val Val Ser Ala Gln Pro Ala Thr Phe Leu Ala Arg Ser Pro His
            485                 490                 495

Val Gly Val Lys Asp Val Glu Cys Gly Glu Gly His Phe Cys His Asp
        500                 505                 510

Asn Gln Thr Cys Cys Arg Asp Asn Arg Gln Gly Trp Ala Cys Cys Pro
        515                 520                 525
```

```
Tyr Arg Gln Gly Val Cys Cys Ala Asp Arg Arg His Cys Cys Pro Ala
            530                 535                 540

Gly Phe Arg Cys Ala Ala Arg Gly Thr Lys Cys Leu Arg Arg Glu Ala
545                 550                 555                 560

Pro Arg Trp Asp Ala Pro Leu Arg Asp Pro Ala Leu Arg Pro Phe Leu
                565                 570                 575

<210> SEQ ID NO 19
<211> LENGTH: 576
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 19

Thr Arg Cys Pro Asp Gly Gln Phe Cys Pro Val Ala Cys Cys Leu Asp
1               5                   10                  15

Pro Gly Gly Ala Ser Tyr Ser Cys Cys Arg Pro Leu Leu Asp Lys Trp
            20                  25                  30

Pro Thr Thr Leu Ser Arg His Leu Gly Gly Pro Cys Gln Val Asp Ala
        35                  40                  45

His Cys Ser Ala Gly His Ser Cys Ile Phe Thr Val Ser Gly Thr Ser
    50                  55                  60

Ser Cys Cys Pro Phe Pro Glu Ala Val Ala Cys Gly Asp Gly His His
65                  70                  75                  80

Cys Cys Pro Arg Gly Phe His Cys Ser Ala Asp Gly Arg Ser Cys Phe
                85                  90                  95

Gln Arg Ser Gly Asn Asn Ser Val Gly Ala Ile Gln Cys Pro Asp Ser
            100                 105                 110

Gln Phe Glu Cys Pro Asp Phe Ser Thr Cys Cys Val Met Val Asp Gly
        115                 120                 125

Ser Trp Gly Cys Cys Pro Met Pro Gln Ala Ser Cys Cys Glu Asp Arg
    130                 135                 140

Val His Cys Cys Pro His Gly Ala Phe Cys Asp Leu Val His Thr Arg
145                 150                 155                 160

Cys Ile Thr Pro Thr Gly Thr His Pro Leu Ala Lys Lys Leu Pro Ala
                165                 170                 175

Gln Arg Thr Asn Arg Ala Val Ala Leu Ser Ser Val Met Cys Pro
            180                 185                 190

Asp Ala Arg Ser Arg Cys Pro Asp Gly Ser Thr Cys Cys Glu Leu Pro
        195                 200                 205

Ser Gly Lys Tyr Gly Cys Cys Pro Met Pro Asn Ala Thr Cys Cys Ser
    210                 215                 220

Asp His Leu His Cys Cys Pro Gln Asp Thr Val Cys Asp Leu Ile Gln
225                 230                 235                 240

Ser Lys Cys Leu Ser Lys Glu Asn Ala Thr Thr Asp Leu Leu Thr Lys
                245                 250                 255

Leu Pro Ala His Thr Val Gly Asp Val Lys Cys Asp Met Glu Val Ser
            260                 265                 270

Cys Pro Asp Gly Tyr Thr Cys Cys Arg Leu Gln Ser Gly Ala Trp Gly
        275                 280                 285

Cys Cys Pro Phe Thr Gln Ala Val Cys Cys Glu Asp His Ile His Cys
    290                 295                 300
```

```
Cys Pro Ala Gly Phe Thr Cys Asp Thr Gln Lys Gly Thr Cys Glu Gln
305                 310                 315                 320

Gly Pro His Gln Val Pro Trp Met Glu Lys Ala Pro Ala His Leu Ser
            325                 330                 335

Leu Pro Asp Pro Gln Ala Leu Lys Arg Asp Val Pro Cys Asp Asn Val
        340                 345                 350

Ser Ser Cys Pro Ser Ser Asp Thr Cys Cys Gln Leu Thr Ser Gly Glu
            355                 360                 365

Trp Gly Cys Cys Pro Ile Pro Glu Ala Val Cys Cys Ser Asp His Gln
        370                 375                 380

His Cys Cys Pro Gln Gly Tyr Thr Cys Val Ala Glu Gly Gln Cys Gln
385                 390                 395                 400

Arg Gly Ser Glu Ile Val Ala Gly Leu Glu Lys Met Pro Ala Arg Arg
            405                 410                 415

Ala Ser Leu Ser His Pro Arg Asp Ile Gly Cys Asp Gln His Thr Ser
        420                 425                 430

Cys Pro Val Gly Gln Thr Cys Cys Pro Ser Leu Gly Gly Ser Trp Ala
            435                 440                 445

Cys Cys Gln Leu Pro His Ala Val Cys Cys Glu Asp Arg Gln His Cys
        450                 455                 460

Cys Pro Ala Gly Tyr Thr Cys Asn Val Lys Ala Arg Ser Cys Glu Lys
465                 470                 475                 480

Glu Val Val Ser Ala Gln Pro Ala Thr Phe Leu Ala Arg Ser Pro His
            485                 490                 495

Val Gly Val Lys Asp Val Glu Cys Gly Glu Gly His Phe Cys His Asp
        500                 505                 510

Asn Gln Thr Cys Cys Arg Asp Asn Arg Gln Gly Trp Ala Cys Cys Pro
        515                 520                 525

Tyr Arg Gln Gly Val Cys Cys Ala Asp Arg Arg His Cys Cys Pro Ala
        530                 535                 540

Gly Phe Arg Cys Ala Ala Arg Gly Thr Lys Cys Leu Arg Arg Glu Ala
545                 550                 555                 560

Pro Arg Trp Asp Ala Pro Leu Arg Asp Pro Ala Leu Arg Gln Arg Leu
            565                 570                 575
```

<210> SEQ ID NO 20
<211> LENGTH: 576
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 20

```
Thr Arg Cys Pro Asp Gly Gln Phe Cys Pro Val Ala Cys Cys Leu Asp
1               5                   10                  15

Pro Gly Gly Ala Ser Tyr Ser Cys Cys Arg Pro Leu Leu Asp Lys Trp
            20                  25                  30

Pro Thr Thr Leu Ser Arg His Leu Gly Gly Pro Cys Gln Val Asp Ala
        35                  40                  45

His Cys Ser Ala Gly His Ser Cys Ile Phe Thr Val Ser Gly Thr Ser
    50                  55                  60

Ser Cys Cys Pro Phe Pro Glu Ala Val Ala Cys Gly Asp Gly His His
65                  70                  75                  80
```

```
Cys Cys Pro Arg Gly Phe His Cys Ser Ala Asp Gly Arg Ser Cys Phe
            85                  90                  95

Gln Arg Ser Gly Asn Asn Ser Val Gly Ala Ile Gln Cys Pro Asp Ser
        100                 105                 110

Gln Phe Glu Cys Pro Asp Phe Ser Thr Cys Cys Val Met Val Asp Gly
    115                 120                 125

Ser Trp Gly Cys Cys Pro Met Pro Gln Ala Ser Cys Cys Glu Asp Arg
130                 135                 140

Val His Cys Cys Pro His Gly Ala Phe Cys Asp Leu Val His Thr Arg
145                 150                 155                 160

Cys Ile Thr Pro Thr Gly Thr His Pro Leu Ala Lys Lys Leu Pro Ala
                165                 170                 175

Gln Arg Thr Asn Arg Ala Val Ala Leu Ser Ser Ser Val Met Cys Pro
            180                 185                 190

Asp Ala Arg Ser Arg Cys Pro Asp Gly Ser Thr Cys Cys Glu Leu Pro
        195                 200                 205

Ser Gly Lys Tyr Gly Cys Cys Pro Met Pro Asn Ala Thr Cys Cys Ser
    210                 215                 220

Asp His Leu His Cys Cys Pro Gln Asp Thr Val Cys Asp Leu Ile Gln
225                 230                 235                 240

Ser Lys Cys Leu Ser Lys Glu Asn Ala Thr Thr Asp Leu Leu Thr Lys
                245                 250                 255

Leu Pro Ala His Thr Val Gly Asp Val Lys Cys Asp Met Glu Val Ser
            260                 265                 270

Cys Pro Asp Gly Tyr Thr Cys Cys Arg Leu Gln Ser Gly Ala Trp Gly
        275                 280                 285

Cys Cys Pro Phe Thr Gln Ala Val Cys Cys Glu Asp His Ile His Cys
    290                 295                 300

Cys Pro Ala Gly Phe Thr Cys Asp Thr Gln Lys Gly Thr Cys Glu Gln
305                 310                 315                 320

Gly Pro His Gln Val Pro Trp Met Glu Lys Ala Pro Ala His Leu Ser
                325                 330                 335

Leu Pro Asp Pro Gln Ala Leu Lys Arg Asp Val Pro Cys Asp Asn Val
            340                 345                 350

Ser Ser Cys Pro Ser Ser Asp Thr Cys Cys Gln Leu Thr Ser Gly Glu
        355                 360                 365

Trp Gly Cys Cys Pro Ile Pro Glu Ala Val Cys Cys Ser Asp His Gln
    370                 375                 380

His Cys Cys Pro Gln Gly Tyr Thr Cys Val Ala Glu Gly Gln Cys Gln
385                 390                 395                 400

Arg Gly Ser Glu Ile Val Ala Gly Leu Glu Lys Met Pro Ala Arg Arg
                405                 410                 415

Ala Ser Leu Ser His Pro Arg Asp Ile Gly Cys Asp Gln His Thr Ser
            420                 425                 430

Cys Pro Val Gly Gln Thr Cys Cys Pro Ser Leu Gly Gly Ser Trp Ala
        435                 440                 445

Cys Cys Gln Leu Pro His Ala Val Cys Cys Glu Asp Arg Gln His Cys
    450                 455                 460

Cys Pro Ala Gly Tyr Thr Cys Asn Val Lys Ala Arg Ser Cys Glu Lys
465                 470                 475                 480

Glu Val Val Ser Ala Gln Pro Ala Thr Phe Leu Ala Arg Ser Pro His
                485                 490                 495
```

```
Val Gly Val Lys Asp Val Glu Cys Gly Glu Gly His Phe Cys His Asp
            500                 505                 510

Asn Gln Thr Cys Cys Arg Asp Asn Arg Gln Gly Trp Ala Cys Cys Pro
            515                 520                 525

Tyr Arg Gln Gly Val Cys Cys Ala Asp Arg Arg His Cys Cys Pro Ala
            530                 535                 540

Gly Phe Arg Cys Ala Ala Arg Gly Thr Lys Cys Leu Arg Arg Glu Ala
545                 550                 555                 560

Pro Arg Trp Asp Ala Pro Leu Arg Asp Pro Ala Leu Arg Gln His Leu
            565                 570                 575

<210> SEQ ID NO 21
<211> LENGTH: 576
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 21

Thr Arg Cys Pro Asp Gly Gln Phe Cys Pro Val Ala Cys Cys Leu Asp
1               5                   10                  15

Pro Gly Gly Ala Ser Tyr Ser Cys Cys Arg Pro Leu Leu Asp Lys Trp
            20                  25                  30

Pro Thr Thr Leu Ser Arg His Leu Gly Gly Pro Cys Gln Val Asp Ala
            35                  40                  45

His Cys Ser Ala Gly His Ser Cys Ile Phe Thr Val Ser Gly Thr Ser
    50                  55                  60

Ser Cys Cys Pro Phe Pro Glu Ala Val Ala Cys Gly Asp Gly His His
65                  70                  75                  80

Cys Cys Pro Arg Gly Phe His Cys Ser Ala Asp Gly Arg Ser Cys Phe
                85                  90                  95

Gln Arg Ser Gly Asn Asn Ser Val Gly Ala Ile Gln Cys Pro Asp Ser
            100                 105                 110

Gln Phe Glu Cys Pro Asp Phe Ser Thr Cys Cys Val Met Val Asp Gly
            115                 120                 125

Ser Trp Gly Cys Cys Pro Met Pro Gln Ala Ser Cys Cys Glu Asp Arg
        130                 135                 140

Val His Cys Cys Pro His Gly Ala Phe Cys Asp Leu Val His Thr Arg
145                 150                 155                 160

Cys Ile Thr Pro Thr Gly Thr His Pro Leu Ala Lys Lys Leu Pro Ala
                165                 170                 175

Gln Arg Thr Asn Arg Ala Val Ala Leu Ser Ser Ser Val Met Cys Pro
            180                 185                 190

Asp Ala Arg Ser Arg Cys Pro Asp Gly Ser Thr Cys Cys Glu Leu Pro
            195                 200                 205

Ser Gly Lys Tyr Gly Cys Cys Pro Met Pro Asn Ala Thr Cys Cys Ser
        210                 215                 220

Asp His Leu His Cys Cys Pro Gln Asp Thr Val Cys Asp Leu Ile Gln
225                 230                 235                 240

Ser Lys Cys Leu Ser Lys Glu Asn Ala Thr Thr Asp Leu Leu Thr Lys
                245                 250                 255

Leu Pro Ala His Thr Val Gly Asp Val Lys Cys Asp Met Glu Val Ser
            260                 265                 270
```

-continued

```
Cys Pro Asp Gly Tyr Thr Cys Arg Leu Gln Ser Gly Ala Trp Gly
            275                 280                 285

Cys Cys Pro Phe Thr Gln Ala Val Cys Glu Asp His Ile His Cys
    290                 295                 300

Cys Pro Ala Gly Phe Thr Cys Asp Thr Gln Lys Gly Thr Cys Glu Gln
305                 310                 315                 320

Gly Pro His Gln Val Pro Trp Met Glu Lys Ala Pro Ala His Leu Ser
                325                 330                 335

Leu Pro Asp Pro Gln Ala Leu Lys Arg Asp Val Pro Cys Asp Asn Val
            340                 345                 350

Ser Ser Cys Pro Ser Ser Asp Thr Cys Cys Gln Leu Thr Ser Gly Glu
            355                 360                 365

Trp Gly Cys Cys Pro Ile Pro Glu Ala Val Cys Cys Ser Asp His Gln
        370                 375                 380

His Cys Cys Pro Gln Gly Tyr Thr Cys Val Ala Glu Gly Gln Cys Gln
385                 390                 395                 400

Arg Gly Ser Glu Ile Val Ala Gly Leu Glu Lys Met Pro Ala Arg Arg
                405                 410                 415

Ala Ser Leu Ser His Pro Arg Asp Ile Gly Cys Asp Gln His Thr Ser
            420                 425                 430

Cys Pro Val Gly Gln Thr Cys Cys Pro Ser Leu Gly Gly Ser Trp Ala
            435                 440                 445

Cys Cys Gln Leu Pro His Ala Val Cys Cys Glu Asp Arg Gln His Cys
    450                 455                 460

Cys Pro Ala Gly Tyr Thr Cys Asn Val Lys Ala Arg Ser Cys Glu Lys
465                 470                 475                 480

Glu Val Val Ser Ala Gln Pro Ala Thr Phe Leu Ala Arg Ser Pro His
                485                 490                 495

Val Gly Val Lys Asp Val Glu Cys Gly Glu Gly His Phe Cys His Asp
            500                 505                 510

Asn Gln Thr Cys Cys Arg Asp Asn Arg Gln Gly Trp Ala Cys Cys Pro
            515                 520                 525

Tyr Arg Gln Gly Val Cys Cys Ala Asp Arg Arg His Cys Cys Pro Ala
            530                 535                 540

Gly Phe Arg Cys Ala Ala Arg Gly Thr Lys Cys Leu Arg Arg Glu Ala
545                 550                 555                 560

Pro Arg Trp Asp Ala Pro Leu Arg Asp Pro Ala Leu Arg Gln Lys Leu
                565                 570                 575
```

<210> SEQ ID NO 22
<211> LENGTH: 576
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 22

```
Thr Arg Cys Pro Asp Gly Gln Phe Cys Pro Val Ala Cys Cys Leu Asp
1               5                   10                  15

Pro Gly Gly Ala Ser Tyr Ser Cys Cys Arg Pro Leu Leu Asp Lys Trp
            20                  25                  30

Pro Thr Thr Leu Ser Arg His Leu Gly Gly Pro Cys Gln Val Asp Ala
        35                  40                  45
```

```
His Cys Ser Ala Gly His Ser Cys Ile Phe Thr Val Ser Gly Thr Ser
 50                  55                  60

Ser Cys Cys Pro Phe Pro Glu Ala Val Ala Cys Gly Asp Gly His His
 65                  70                  75                  80

Cys Cys Pro Arg Gly Phe His Cys Ser Ala Asp Gly Arg Ser Cys Phe
                 85                  90                  95

Gln Arg Ser Gly Asn Asn Ser Val Gly Ala Ile Gln Cys Pro Asp Ser
                100                 105                 110

Gln Phe Glu Cys Pro Asp Phe Ser Thr Cys Cys Val Met Val Asp Gly
            115                 120                 125

Ser Trp Gly Cys Cys Pro Met Pro Gln Ala Ser Cys Cys Glu Asp Arg
    130                 135                 140

Val His Cys Cys Pro His Gly Ala Phe Cys Asp Leu Val His Thr Arg
145                 150                 155                 160

Cys Ile Thr Pro Thr Gly Thr His Pro Leu Ala Lys Lys Leu Pro Ala
                165                 170                 175

Gln Arg Thr Asn Arg Ala Val Ala Leu Ser Ser Ser Val Met Cys Pro
            180                 185                 190

Asp Ala Arg Ser Arg Cys Pro Asp Gly Ser Thr Cys Cys Glu Leu Pro
        195                 200                 205

Ser Gly Lys Tyr Gly Cys Cys Pro Met Pro Asn Ala Thr Cys Cys Ser
    210                 215                 220

Asp His Leu His Cys Cys Pro Gln Asp Thr Val Cys Asp Leu Ile Gln
225                 230                 235                 240

Ser Lys Cys Leu Ser Lys Glu Asn Ala Thr Thr Asp Leu Leu Thr Lys
                245                 250                 255

Leu Pro Ala His Thr Val Gly Asp Val Lys Cys Asp Met Glu Val Ser
            260                 265                 270

Cys Pro Asp Gly Tyr Thr Cys Cys Arg Leu Gln Ser Gly Ala Trp Gly
        275                 280                 285

Cys Cys Pro Phe Thr Gln Ala Val Cys Cys Glu Asp His Ile His Cys
    290                 295                 300

Cys Pro Ala Gly Phe Thr Cys Asp Thr Gln Lys Gly Thr Cys Glu Gln
305                 310                 315                 320

Gly Pro His Gln Val Pro Trp Met Glu Lys Ala Pro Ala His Leu Ser
                325                 330                 335

Leu Pro Asp Pro Gln Ala Leu Lys Arg Asp Val Pro Cys Asp Asn Val
            340                 345                 350

Ser Ser Cys Pro Ser Ser Asp Thr Cys Cys Gln Leu Thr Ser Gly Glu
        355                 360                 365

Trp Gly Cys Cys Pro Ile Pro Glu Ala Val Cys Cys Ser Asp His Gln
    370                 375                 380

His Cys Cys Pro Gln Gly Tyr Thr Cys Val Ala Glu Gly Gln Cys Gln
385                 390                 395                 400

Arg Gly Ser Glu Ile Val Ala Gly Leu Glu Lys Met Pro Ala Arg Arg
                405                 410                 415

Ala Ser Leu Ser His Pro Arg Asp Ile Gly Cys Asp Gln His Thr Ser
            420                 425                 430

Cys Pro Val Gly Gln Thr Cys Cys Pro Ser Leu Gly Gly Ser Trp Ala
        435                 440                 445

Cys Cys Gln Leu Pro His Ala Val Cys Cys Glu Asp Arg Gln His Cys
    450                 455                 460
```

```
Cys Pro Ala Gly Tyr Thr Cys Asn Val Lys Ala Arg Ser Cys Glu Lys
465                 470                 475                 480

Glu Val Val Ser Ala Gln Pro Ala Thr Phe Leu Ala Arg Ser Pro His
                485                 490                 495

Val Gly Val Lys Asp Val Glu Cys Gly Glu Gly His Phe Cys His Asp
            500                 505                 510

Asn Gln Thr Cys Cys Arg Asp Asn Arg Gln Gly Trp Ala Cys Cys Pro
        515                 520                 525

Tyr Arg Gln Gly Val Cys Cys Ala Asp Arg Arg His Cys Cys Pro Ala
    530                 535                 540

Gly Phe Arg Cys Ala Ala Arg Gly Thr Lys Cys Leu Arg Arg Glu Ala
545                 550                 555                 560

Pro Arg Trp Asp Ala Pro Leu Arg Asp Pro Ala Leu Arg Gln Asp Leu
                565                 570                 575

<210> SEQ ID NO 23
<211> LENGTH: 576
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 23

Thr Arg Cys Pro Asp Gly Gln Phe Cys Pro Val Ala Cys Cys Leu Asp
1               5                   10                  15

Pro Gly Gly Ala Ser Tyr Ser Cys Cys Arg Pro Leu Leu Asp Lys Trp
            20                  25                  30

Pro Thr Thr Leu Ser Arg His Leu Gly Gly Pro Cys Gln Val Asp Ala
        35                  40                  45

His Cys Ser Ala Gly His Ser Cys Ile Phe Thr Val Ser Gly Thr Ser
    50                  55                  60

Ser Cys Cys Pro Phe Pro Glu Ala Val Ala Cys Gly Asp Gly His His
65                  70                  75                  80

Cys Cys Pro Arg Gly Phe His Cys Ser Ala Asp Gly Arg Ser Cys Phe
                85                  90                  95

Gln Arg Ser Gly Asn Asn Ser Val Gly Ala Ile Gln Cys Pro Asp Ser
            100                 105                 110

Gln Phe Glu Cys Pro Asp Phe Ser Thr Cys Cys Val Met Val Asp Gly
        115                 120                 125

Ser Trp Gly Cys Cys Pro Met Pro Gln Ala Ser Cys Cys Glu Asp Arg
    130                 135                 140

Val His Cys Cys Pro His Gly Ala Phe Cys Asp Leu Val His Thr Arg
145                 150                 155                 160

Cys Ile Thr Pro Thr Gly Thr His Pro Leu Ala Lys Lys Leu Pro Ala
                165                 170                 175

Gln Arg Thr Asn Arg Ala Val Ala Leu Ser Ser Ser Val Met Cys Pro
            180                 185                 190

Asp Ala Arg Ser Arg Cys Pro Asp Gly Ser Thr Cys Cys Glu Leu Pro
        195                 200                 205

Ser Gly Lys Tyr Gly Cys Cys Pro Met Pro Asn Ala Thr Cys Cys Ser
    210                 215                 220

Asp His Leu His Cys Cys Pro Gln Asp Thr Val Cys Asp Leu Ile Gln
225                 230                 235                 240
```

```
Ser Lys Cys Leu Ser Lys Glu Asn Ala Thr Thr Asp Leu Leu Thr Lys
            245                 250                 255

Leu Pro Ala His Thr Val Gly Asp Val Lys Cys Asp Met Glu Val Ser
            260                 265                 270

Cys Pro Asp Gly Tyr Thr Cys Arg Leu Gln Ser Gly Ala Trp Gly
            275                 280                 285

Cys Cys Pro Phe Thr Gln Ala Val Cys Cys Glu Asp His Ile His Cys
            290                 295                 300

Cys Pro Ala Gly Phe Thr Cys Asp Thr Gln Lys Gly Thr Cys Glu Gln
305                 310                 315                 320

Gly Pro His Gln Val Pro Trp Met Glu Lys Ala Pro Ala His Leu Ser
            325                 330                 335

Leu Pro Asp Pro Gln Ala Leu Lys Arg Asp Val Pro Cys Asp Asn Val
            340                 345                 350

Ser Ser Cys Pro Ser Ser Asp Thr Cys Cys Gln Leu Thr Ser Gly Glu
            355                 360                 365

Trp Gly Cys Cys Pro Ile Pro Glu Ala Val Cys Cys Ser Asp His Gln
            370                 375                 380

His Cys Cys Pro Gln Gly Tyr Thr Cys Val Ala Glu Gly Gln Cys Gln
385                 390                 395                 400

Arg Gly Ser Glu Ile Val Ala Gly Leu Glu Lys Met Pro Ala Arg Arg
            405                 410                 415

Ala Ser Leu Ser His Pro Arg Asp Ile Gly Cys Asp Gln His Thr Ser
            420                 425                 430

Cys Pro Val Gly Gln Thr Cys Cys Pro Ser Leu Gly Gly Ser Trp Ala
            435                 440                 445

Cys Cys Gln Leu Pro His Ala Val Cys Cys Glu Asp Arg Gln His Cys
            450                 455                 460

Cys Pro Ala Gly Tyr Thr Cys Asn Val Lys Ala Arg Ser Cys Glu Lys
465                 470                 475                 480

Glu Val Val Ser Ala Gln Pro Ala Thr Phe Leu Ala Arg Ser Pro His
            485                 490                 495

Val Gly Val Lys Asp Val Glu Cys Gly Glu Gly His Phe Cys His Asp
            500                 505                 510

Asn Gln Thr Cys Cys Arg Asp Asn Arg Gln Gly Trp Ala Cys Cys Pro
            515                 520                 525

Tyr Arg Gln Gly Val Cys Cys Ala Asp Arg Arg His Cys Cys Pro Ala
            530                 535                 540

Gly Phe Arg Cys Ala Ala Arg Gly Thr Lys Cys Leu Arg Arg Glu Ala
545                 550                 555                 560

Pro Arg Trp Asp Ala Pro Leu Arg Asp Pro Ala Leu Arg Gln Glu Leu
            565                 570                 575
```

<210> SEQ ID NO 24
<211> LENGTH: 576
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 24

```
Thr Arg Cys Pro Asp Gly Gln Phe Cys Pro Val Ala Cys Cys Leu Asp
1               5                   10                  15
```

```
Pro Gly Gly Ala Ser Tyr Ser Cys Cys Arg Pro Leu Leu Asp Lys Trp
            20                  25                  30

Pro Thr Thr Leu Ser Arg His Leu Gly Gly Pro Cys Gln Val Asp Ala
        35                  40                  45

His Cys Ser Ala Gly His Ser Cys Ile Phe Thr Val Ser Gly Thr Ser
50                  55                  60

Ser Cys Cys Pro Phe Pro Glu Ala Val Ala Cys Gly Asp Gly His His
65                  70                  75                  80

Cys Cys Pro Arg Gly Phe His Cys Ser Ala Asp Gly Arg Ser Cys Phe
                85                  90                  95

Gln Arg Ser Gly Asn Asn Ser Val Gly Ala Ile Gln Cys Pro Asp Ser
                100                 105                 110

Gln Phe Glu Cys Pro Asp Phe Ser Thr Cys Cys Val Met Val Asp Gly
        115                 120                 125

Ser Trp Gly Cys Cys Pro Met Pro Gln Ala Ser Cys Cys Glu Asp Arg
        130                 135                 140

Val His Cys Cys Pro His Gly Ala Phe Cys Asp Leu Val His Thr Arg
145                 150                 155                 160

Cys Ile Thr Pro Thr Gly Thr His Pro Leu Ala Lys Lys Leu Pro Ala
                165                 170                 175

Gln Arg Thr Asn Arg Ala Val Ala Leu Ser Ser Val Met Cys Pro
                180                 185                 190

Asp Ala Arg Ser Arg Cys Pro Asp Gly Ser Thr Cys Cys Glu Leu Pro
        195                 200                 205

Ser Gly Lys Tyr Gly Cys Cys Pro Met Pro Asn Ala Thr Cys Cys Ser
        210                 215                 220

Asp His Leu His Cys Cys Pro Gln Asp Thr Val Cys Asp Leu Ile Gln
225                 230                 235                 240

Ser Lys Cys Leu Ser Lys Glu Asn Ala Thr Thr Asp Leu Leu Thr Lys
                245                 250                 255

Leu Pro Ala His Thr Val Gly Asp Val Lys Cys Asp Met Glu Val Ser
                260                 265                 270

Cys Pro Asp Gly Tyr Thr Cys Cys Arg Leu Gln Ser Gly Ala Trp Gly
        275                 280                 285

Cys Cys Pro Phe Thr Gln Ala Val Cys Cys Glu Asp His Ile His Cys
        290                 295                 300

Cys Pro Ala Gly Phe Thr Cys Asp Thr Gln Lys Gly Thr Cys Glu Gln
305                 310                 315                 320

Gly Pro His Gln Val Pro Trp Met Glu Lys Ala Pro Ala His Leu Ser
                325                 330                 335

Leu Pro Asp Pro Gln Ala Leu Lys Arg Asp Val Pro Cys Asp Asn Val
        340                 345                 350

Ser Ser Cys Pro Ser Ser Asp Thr Cys Cys Gln Leu Thr Ser Gly Glu
        355                 360                 365

Trp Gly Cys Cys Pro Ile Pro Glu Ala Val Cys Cys Ser Asp His Gln
        370                 375                 380

His Cys Cys Pro Gln Gly Tyr Thr Cys Val Ala Glu Gly Gln Cys Gln
385                 390                 395                 400

Arg Gly Ser Glu Ile Val Ala Gly Leu Glu Lys Met Pro Ala Arg Arg
                405                 410                 415

Ala Ser Leu Ser His Pro Arg Asp Ile Gly Cys Asp Gln His Thr Ser
                420                 425                 430
```

-continued

```
Cys Pro Val Gly Gln Thr Cys Pro Ser Leu Gly Gly Ser Trp Ala
            435                 440                 445

Cys Cys Gln Leu Pro His Ala Val Cys Cys Glu Asp Arg Gln His Cys
        450                 455                 460

Cys Pro Ala Gly Tyr Thr Cys Asn Val Lys Ala Arg Ser Cys Glu Lys
465                 470                 475                 480

Glu Val Val Ser Ala Gln Pro Ala Thr Phe Leu Ala Arg Ser Pro His
                485                 490                 495

Val Gly Val Lys Asp Val Glu Cys Gly Glu Gly His Phe Cys His Asp
                500                 505                 510

Asn Gln Thr Cys Cys Arg Asp Asn Arg Gln Gly Trp Ala Cys Cys Pro
                515                 520                 525

Tyr Arg Gln Gly Val Cys Cys Ala Asp Arg Arg His Cys Cys Pro Ala
                530                 535                 540

Gly Phe Arg Cys Ala Ala Arg Gly Thr Lys Cys Leu Arg Arg Glu Ala
545                 550                 555                 560

Pro Arg Trp Asp Ala Pro Leu Arg Asp Pro Ala Leu Arg Gln Asn Leu
                565                 570                 575
```

<210> SEQ ID NO 25
<211> LENGTH: 576
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 25

```
Thr Arg Cys Pro Asp Gly Gln Phe Cys Pro Val Ala Cys Cys Leu Asp
1               5                   10                  15

Pro Gly Gly Ala Ser Tyr Ser Cys Cys Arg Pro Leu Leu Asp Lys Trp
                20                  25                  30

Pro Thr Thr Leu Ser Arg His Leu Gly Gly Pro Cys Gln Val Asp Ala
                35                  40                  45

His Cys Ser Ala Gly His Ser Cys Ile Phe Thr Val Ser Gly Thr Ser
            50                  55                  60

Ser Cys Cys Pro Phe Pro Glu Ala Val Ala Cys Gly Asp Gly His His
65              70                  75                  80

Cys Cys Pro Arg Gly Phe His Cys Ser Ala Asp Gly Arg Ser Cys Phe
                85                  90                  95

Gln Arg Ser Gly Asn Asn Ser Val Gly Ala Ile Gln Cys Pro Asp Ser
                100                 105                 110

Gln Phe Glu Cys Pro Asp Phe Ser Thr Cys Cys Val Met Val Asp Gly
            115                 120                 125

Ser Trp Gly Cys Cys Pro Met Pro Gln Ala Ser Cys Cys Glu Asp Arg
130                 135                 140

Val His Cys Cys Pro His Gly Ala Phe Cys Asp Leu Val His Thr Arg
145                 150                 155                 160

Cys Ile Thr Pro Thr Gly Thr His Pro Leu Ala Lys Lys Leu Pro Ala
                165                 170                 175

Gln Arg Thr Asn Arg Ala Val Ala Leu Ser Ser Ser Val Met Cys Pro
                180                 185                 190

Asp Ala Arg Ser Arg Cys Pro Asp Gly Ser Thr Cys Cys Glu Leu Pro
                195                 200                 205
```

Ser Gly Lys Tyr Gly Cys Cys Pro Met Pro Asn Ala Thr Cys Cys Ser
210                 215                 220

Asp His Leu His Cys Cys Pro Gln Asp Thr Val Cys Asp Leu Ile Gln
225                 230                 235                 240

Ser Lys Cys Leu Ser Lys Glu Asn Ala Thr Thr Asp Leu Leu Thr Lys
            245                 250                 255

Leu Pro Ala His Thr Val Gly Asp Val Lys Cys Asp Met Glu Val Ser
                260                 265                 270

Cys Pro Asp Gly Tyr Thr Cys Cys Arg Leu Gln Ser Gly Ala Trp Gly
            275                 280                 285

Cys Cys Pro Phe Thr Gln Ala Val Cys Cys Glu Asp His Ile His Cys
290                 295                 300

Cys Pro Ala Gly Phe Thr Cys Asp Thr Gln Lys Gly Thr Cys Glu Gln
305                 310                 315                 320

Gly Pro His Gln Val Pro Trp Met Glu Lys Ala Pro Ala His Leu Ser
                325                 330                 335

Leu Pro Asp Pro Gln Ala Leu Lys Arg Asp Val Pro Cys Asp Asn Val
            340                 345                 350

Ser Ser Cys Pro Ser Ser Asp Thr Cys Cys Gln Leu Thr Ser Gly Glu
            355                 360                 365

Trp Gly Cys Cys Pro Ile Pro Glu Ala Val Cys Cys Ser Asp His Gln
    370                 375                 380

His Cys Cys Pro Gln Gly Tyr Thr Cys Val Ala Glu Gly Gln Cys Gln
385                 390                 395                 400

Arg Gly Ser Glu Ile Val Ala Gly Leu Glu Lys Met Pro Ala Arg Arg
                405                 410                 415

Ala Ser Leu Ser His Pro Arg Asp Ile Gly Cys Asp Gln His Thr Ser
            420                 425                 430

Cys Pro Val Gly Gln Thr Cys Cys Pro Ser Leu Gly Gly Ser Trp Ala
            435                 440                 445

Cys Cys Gln Leu Pro His Ala Val Cys Cys Glu Asp Arg Gln His Cys
    450                 455                 460

Cys Pro Ala Gly Tyr Thr Cys Asn Val Lys Ala Arg Ser Cys Glu Lys
465                 470                 475                 480

Glu Val Val Ser Ala Gln Pro Ala Thr Phe Leu Ala Arg Ser Pro His
                485                 490                 495

Val Gly Val Lys Asp Val Glu Cys Gly Glu Gly His Phe Cys His Asp
            500                 505                 510

Asn Gln Thr Cys Cys Arg Asp Asn Arg Gln Gly Trp Ala Cys Cys Pro
            515                 520                 525

Tyr Arg Gln Gly Val Cys Cys Ala Asp Arg Arg His Cys Cys Pro Ala
530                 535                 540

Gly Phe Arg Cys Ala Ala Arg Gly Thr Lys Cys Leu Arg Arg Glu Ala
545                 550                 555                 560

Pro Arg Trp Asp Ala Pro Leu Arg Asp Pro Ala Leu Arg Gln Pro Leu
                565                 570                 575

<210> SEQ ID NO 26
<211> LENGTH: 576
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 26

```
Thr Arg Cys Pro Asp Gly Gln Phe Cys Pro Val Ala Cys Cys Leu Asp
1               5                   10                  15

Pro Gly Gly Ala Ser Tyr Ser Cys Cys Arg Pro Leu Leu Asp Lys Trp
            20                  25                  30

Pro Thr Thr Leu Ser Arg His Leu Gly Gly Pro Cys Gln Val Asp Ala
        35                  40                  45

His Cys Ser Ala Gly His Ser Cys Ile Phe Thr Val Ser Gly Thr Ser
    50                  55                  60

Ser Cys Cys Pro Phe Pro Glu Ala Val Ala Cys Gly Asp Gly His His
65              70                  75                  80

Cys Cys Pro Arg Gly Phe His Cys Ser Ala Asp Gly Arg Ser Cys Phe
                85                  90                  95

Gln Arg Ser Gly Asn Asn Ser Val Gly Ala Ile Gln Cys Pro Asp Ser
            100                 105                 110

Gln Phe Glu Cys Pro Asp Phe Ser Thr Cys Cys Val Met Val Asp Gly
        115                 120                 125

Ser Trp Gly Cys Cys Pro Met Pro Gln Ala Ser Cys Cys Glu Asp Arg
    130                 135                 140

Val His Cys Cys Pro His Gly Ala Phe Cys Asp Leu Val His Thr Arg
145                 150                 155                 160

Cys Ile Thr Pro Thr Gly Thr His Pro Leu Ala Lys Lys Leu Pro Ala
                165                 170                 175

Gln Arg Thr Asn Arg Ala Val Ala Leu Ser Ser Ser Val Met Cys Pro
            180                 185                 190

Asp Ala Arg Ser Arg Cys Pro Asp Gly Ser Thr Cys Cys Glu Leu Pro
        195                 200                 205

Ser Gly Lys Tyr Gly Cys Cys Pro Met Pro Asn Ala Thr Cys Cys Ser
    210                 215                 220

Asp His Leu His Cys Cys Pro Gln Asp Thr Val Cys Asp Leu Ile Gln
225                 230                 235                 240

Ser Lys Cys Leu Ser Lys Glu Asn Ala Thr Thr Asp Leu Leu Thr Lys
                245                 250                 255

Leu Pro Ala His Thr Val Gly Asp Val Lys Cys Asp Met Glu Val Ser
            260                 265                 270

Cys Pro Asp Gly Tyr Thr Cys Cys Arg Leu Gln Ser Gly Ala Trp Gly
        275                 280                 285

Cys Cys Pro Phe Thr Gln Ala Val Cys Cys Glu Asp His Ile His Cys
    290                 295                 300

Cys Pro Ala Gly Phe Thr Cys Asp Thr Gln Lys Gly Thr Cys Glu Gln
305                 310                 315                 320

Gly Pro His Gln Val Pro Trp Met Glu Lys Ala Pro Ala His Leu Ser
                325                 330                 335

Leu Pro Asp Pro Gln Ala Leu Lys Arg Asp Val Pro Cys Asp Asn Val
            340                 345                 350

Ser Ser Cys Pro Ser Ser Asp Thr Cys Cys Gln Leu Thr Ser Gly Glu
        355                 360                 365

Trp Gly Cys Cys Pro Ile Pro Glu Ala Val Cys Cys Ser Asp His Gln
    370                 375                 380

His Cys Cys Pro Gln Gly Tyr Thr Cys Val Ala Glu Gly Gln Cys Gln
385                 390                 395                 400

Arg Gly Ser Glu Ile Val Ala Gly Leu Glu Lys Met Pro Ala Arg Arg
                405                 410                 415
```

```
Ala Ser Leu Ser His Pro Arg Asp Ile Gly Cys Asp Gln His Thr Ser
            420                 425                 430

Cys Pro Val Gly Gln Thr Cys Cys Pro Ser Leu Gly Gly Ser Trp Ala
            435                 440                 445

Cys Cys Gln Leu Pro His Ala Val Cys Glu Asp Arg Gln His Cys
            450                 455                 460

Cys Pro Ala Gly Tyr Thr Cys Asn Val Lys Ala Arg Ser Cys Glu Lys
465                 470                 475                 480

Glu Val Val Ser Ala Gln Pro Ala Thr Phe Leu Ala Arg Ser Pro His
                    485                 490                 495

Val Gly Val Lys Asp Val Glu Cys Gly Glu Gly His Phe Cys His Asp
            500                 505                 510

Asn Gln Thr Cys Cys Arg Asp Asn Arg Gln Gly Trp Ala Cys Cys Pro
            515                 520                 525

Tyr Arg Gln Gly Val Cys Cys Ala Asp Arg Arg His Cys Cys Pro Ala
530                 535                 540

Gly Phe Arg Cys Ala Ala Arg Gly Thr Lys Cys Leu Arg Arg Glu Ala
545                 550                 555                 560

Pro Arg Trp Asp Ala Pro Leu Arg Asp Pro Ala Leu Arg Gln Tyr Leu
            565                 570                 575
```

<210> SEQ ID NO 27
<211> LENGTH: 576
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 27

```
Thr Arg Cys Pro Asp Gly Gln Phe Cys Pro Val Ala Cys Cys Leu Asp
1               5                   10                  15

Pro Gly Gly Ala Ser Tyr Ser Cys Cys Arg Pro Leu Leu Asp Lys Trp
                20                  25                  30

Pro Thr Thr Leu Ser Arg His Leu Gly Gly Pro Cys Gln Val Asp Ala
            35                  40                  45

His Cys Ser Ala Gly His Ser Cys Ile Phe Thr Val Ser Gly Thr Ser
        50                  55                  60

Ser Cys Cys Pro Phe Pro Glu Ala Val Ala Cys Gly Asp Gly His His
65                  70                  75                  80

Cys Cys Pro Arg Gly Phe His Cys Ser Ala Asp Gly Arg Ser Cys Phe
                85                  90                  95

Gln Arg Ser Gly Asn Asn Ser Val Gly Ala Ile Gln Cys Pro Asp Ser
            100                 105                 110

Gln Phe Glu Cys Pro Asp Phe Ser Thr Cys Cys Val Met Val Asp Gly
        115                 120                 125

Ser Trp Gly Cys Cys Pro Met Pro Gln Ala Ser Cys Cys Glu Asp Arg
130                 135                 140

Val His Cys Cys Pro His Gly Ala Phe Cys Asp Leu Val His Thr Arg
145                 150                 155                 160

Cys Ile Thr Pro Thr Gly Thr His Pro Leu Ala Lys Lys Leu Pro Ala
                165                 170                 175

Gln Arg Thr Asn Arg Ala Val Ala Leu Ser Ser Ser Val Met Cys Pro
            180                 185                 190
```

```
Asp Ala Arg Ser Arg Cys Pro Asp Gly Ser Thr Cys Cys Glu Leu Pro
        195                 200                 205
Ser Gly Lys Tyr Gly Cys Cys Pro Met Pro Asn Ala Thr Cys Cys Ser
    210                 215                 220
Asp His Leu His Cys Cys Pro Gln Asp Thr Val Cys Asp Leu Ile Gln
225                 230                 235                 240
Ser Lys Cys Leu Ser Lys Glu Asn Ala Thr Thr Asp Leu Leu Thr Lys
            245                 250                 255
Leu Pro Ala His Thr Val Gly Asp Val Lys Cys Asp Met Glu Val Ser
                260                 265                 270
Cys Pro Asp Gly Tyr Thr Cys Arg Leu Gln Ser Gly Ala Trp Gly
            275                 280                 285
Cys Cys Pro Phe Thr Gln Ala Val Cys Cys Glu Asp His Ile His Cys
        290                 295                 300
Cys Pro Ala Gly Phe Thr Cys Asp Thr Gln Lys Gly Thr Cys Glu Gln
305                 310                 315                 320
Gly Pro His Gln Val Pro Trp Met Glu Lys Ala Pro Ala His Leu Ser
                325                 330                 335
Leu Pro Asp Pro Gln Ala Leu Lys Arg Asp Val Pro Cys Asp Asn Val
                340                 345                 350
Ser Ser Cys Pro Ser Ser Asp Thr Cys Cys Gln Leu Thr Ser Gly Glu
        355                 360                 365
Trp Gly Cys Cys Pro Ile Pro Glu Ala Val Cys Cys Ser Asp His Gln
        370                 375                 380
His Cys Cys Pro Gln Gly Tyr Thr Cys Val Ala Glu Gly Gln Cys Gln
385                 390                 395                 400
Arg Gly Ser Glu Ile Val Ala Gly Leu Glu Lys Met Pro Ala Arg Arg
                405                 410                 415
Ala Ser Leu Ser His Pro Arg Asp Ile Gly Cys Asp Gln His Thr Ser
                420                 425                 430
Cys Pro Val Gly Gln Thr Cys Cys Pro Ser Leu Gly Gly Ser Trp Ala
            435                 440                 445
Cys Cys Gln Leu Pro His Ala Val Cys Cys Glu Asp Arg Gln His Cys
        450                 455                 460
Cys Pro Ala Gly Tyr Thr Cys Asn Val Lys Ala Arg Ser Cys Glu Lys
465                 470                 475                 480
Glu Val Val Ser Ala Gln Pro Ala Thr Phe Leu Ala Arg Ser Pro His
                485                 490                 495
Val Gly Val Lys Asp Val Glu Cys Gly Glu Gly His Phe Cys His Asp
            500                 505                 510
Asn Gln Thr Cys Cys Arg Asp Asn Arg Gln Gly Trp Ala Cys Cys Pro
        515                 520                 525
Tyr Arg Gln Gly Val Cys Cys Ala Asp Arg Arg His Cys Cys Pro Ala
530                 535                 540
Gly Phe Arg Cys Ala Ala Arg Gly Thr Lys Cys Leu Arg Arg Glu Ala
545                 550                 555                 560
Pro Arg Trp Asp Ala Pro Leu Arg Asp Pro Ala Leu Arg Gln Gln Leu
                565                 570                 575
```

<210> SEQ ID NO 28
<211> LENGTH: 576
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 28

```
Thr Arg Cys Pro Asp Gly Gln Phe Cys Pro Val Ala Cys Cys Leu Asp
1               5                   10                  15

Pro Gly Gly Ala Ser Tyr Ser Cys Cys Arg Pro Leu Leu Asp Lys Trp
            20                  25                  30

Pro Thr Thr Leu Ser Arg His Leu Gly Gly Pro Cys Gln Val Asp Ala
        35                  40                  45

His Cys Ser Ala Gly His Ser Cys Ile Phe Thr Val Ser Gly Thr Ser
    50                  55                  60

Ser Cys Cys Pro Phe Pro Glu Ala Val Ala Cys Gly Asp Gly His His
65                  70                  75                  80

Cys Cys Pro Arg Gly Phe His Cys Ser Ala Asp Gly Arg Ser Cys Phe
                85                  90                  95

Gln Arg Ser Gly Asn Asn Ser Val Gly Ala Ile Gln Cys Pro Asp Ser
            100                 105                 110

Gln Phe Glu Cys Pro Asp Phe Ser Thr Cys Cys Val Met Val Asp Gly
        115                 120                 125

Ser Trp Gly Cys Cys Pro Met Pro Gln Ala Ser Cys Cys Glu Asp Arg
    130                 135                 140

Val His Cys Cys Pro His Gly Ala Phe Cys Asp Leu Val His Thr Arg
145                 150                 155                 160

Cys Ile Thr Pro Thr Gly Thr His Pro Leu Ala Lys Lys Leu Pro Ala
                165                 170                 175

Gln Arg Thr Asn Arg Ala Val Ala Leu Ser Ser Val Met Cys Pro
            180                 185                 190

Asp Ala Arg Ser Arg Cys Pro Asp Gly Ser Thr Cys Cys Glu Leu Pro
            195                 200                 205

Ser Gly Lys Tyr Gly Cys Cys Pro Met Pro Asn Ala Thr Cys Cys Ser
    210                 215                 220

Asp His Leu His Cys Cys Pro Gln Asp Thr Val Cys Asp Leu Ile Gln
225                 230                 235                 240

Ser Lys Cys Leu Ser Lys Glu Asn Ala Thr Thr Asp Leu Leu Thr Lys
                245                 250                 255

Leu Pro Ala His Thr Val Gly Asp Val Lys Cys Asp Met Glu Val Ser
            260                 265                 270

Cys Pro Asp Gly Tyr Thr Cys Cys Arg Leu Gln Ser Gly Ala Trp Gly
        275                 280                 285

Cys Cys Pro Phe Thr Gln Ala Val Cys Cys Glu Asp His Ile His Cys
    290                 295                 300

Cys Pro Ala Gly Phe Thr Cys Asp Thr Gln Lys Gly Thr Cys Glu Gln
305                 310                 315                 320

Gly Pro His Gln Val Pro Trp Met Glu Lys Ala Pro Ala His Leu Ser
                325                 330                 335

Leu Pro Asp Pro Gln Ala Leu Lys Arg Asp Val Pro Cys Asp Asn Val
            340                 345                 350

Ser Ser Cys Pro Ser Ser Asp Thr Cys Cys Gln Leu Thr Ser Gly Glu
        355                 360                 365

Trp Gly Cys Cys Pro Ile Pro Glu Ala Val Cys Cys Ser Asp His Gln
    370                 375                 380

His Cys Cys Pro Gln Gly Tyr Thr Cys Val Ala Glu Gly Gln Cys Gln
385                 390                 395                 400
```

```
Arg Gly Ser Glu Ile Val Ala Gly Leu Glu Lys Met Pro Ala Arg Arg
                405                 410                 415

Ala Ser Leu Ser His Pro Arg Asp Ile Gly Cys Asp Gln His Thr Ser
            420                 425                 430

Cys Pro Val Gly Gln Thr Cys Cys Pro Ser Leu Gly Gly Ser Trp Ala
        435                 440                 445

Cys Cys Gln Leu Pro His Ala Val Cys Cys Glu Asp Arg Gln His Cys
    450                 455                 460

Cys Pro Ala Gly Tyr Thr Cys Asn Val Lys Ala Arg Ser Cys Glu Lys
465                 470                 475                 480

Glu Val Val Ser Ala Gln Pro Ala Thr Phe Leu Ala Arg Ser Pro His
                485                 490                 495

Val Gly Val Lys Asp Val Glu Cys Gly Glu Gly His Phe Cys His Asp
            500                 505                 510

Asn Gln Thr Cys Cys Arg Asp Asn Arg Gln Gly Trp Ala Cys Cys Pro
        515                 520                 525

Tyr Arg Gln Gly Val Cys Cys Ala Asp Arg Arg His Cys Cys Pro Ala
    530                 535                 540

Gly Phe Arg Cys Ala Ala Arg Gly Thr Lys Cys Leu Arg Arg Glu Ala
545                 550                 555                 560

Pro Arg Trp Asp Ala Pro Leu Arg Asp Pro Ala Leu Arg Val Val Leu
                565                 570                 575
```

<210> SEQ ID NO 29
<211> LENGTH: 576
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 29

```
Thr Arg Cys Pro Asp Gly Gln Phe Cys Pro Val Ala Cys Cys Leu Asp
1               5                   10                  15

Pro Gly Gly Ala Ser Tyr Ser Cys Cys Arg Pro Leu Leu Asp Lys Trp
            20                  25                  30

Pro Thr Thr Leu Ser Arg His Leu Gly Gly Pro Cys Gln Val Asp Ala
        35                  40                  45

His Cys Ser Ala Gly His Ser Cys Ile Phe Thr Val Ser Gly Thr Ser
    50                  55                  60

Ser Cys Cys Pro Phe Pro Glu Ala Val Ala Cys Gly Asp Gly His His
65                  70                  75                  80

Cys Cys Pro Arg Gly Phe His Cys Ser Ala Asp Gly Arg Ser Cys Phe
                85                  90                  95

Gln Arg Ser Gly Asn Asn Ser Val Gly Ala Ile Gln Cys Pro Asp Ser
            100                 105                 110

Gln Phe Glu Cys Pro Asp Phe Ser Thr Cys Cys Val Met Val Asp Gly
        115                 120                 125

Ser Trp Gly Cys Cys Pro Met Pro Gln Ala Ser Cys Cys Glu Asp Arg
    130                 135                 140

Val His Cys Cys Pro His Gly Ala Phe Cys Asp Leu Val His Thr Arg
145                 150                 155                 160

Cys Ile Thr Pro Thr Gly Thr His Pro Leu Ala Lys Lys Leu Pro Ala
                165                 170                 175
```

-continued

Gln Arg Thr Asn Arg Ala Val Ala Leu Ser Ser Val Met Cys Pro
                180                 185                 190

Asp Ala Arg Ser Arg Cys Pro Asp Gly Ser Thr Cys Cys Glu Leu Pro
            195                 200                 205

Ser Gly Lys Tyr Gly Cys Cys Pro Met Pro Asn Ala Thr Cys Cys Ser
        210                 215                 220

Asp His Leu His Cys Cys Pro Gln Asp Thr Val Cys Asp Leu Ile Gln
225                 230                 235                 240

Ser Lys Cys Leu Ser Lys Glu Asn Ala Thr Thr Asp Leu Leu Thr Lys
                245                 250                 255

Leu Pro Ala His Thr Val Gly Asp Val Lys Cys Asp Met Glu Val Ser
            260                 265                 270

Cys Pro Asp Gly Tyr Thr Cys Cys Arg Leu Gln Ser Gly Ala Trp Gly
        275                 280                 285

Cys Cys Pro Phe Thr Gln Ala Val Cys Cys Glu Asp His Ile His Cys
290                 295                 300

Cys Pro Ala Gly Phe Thr Cys Asp Thr Gln Lys Gly Thr Cys Glu Gln
305                 310                 315                 320

Gly Pro His Gln Val Pro Trp Met Glu Lys Ala Pro Ala His Leu Ser
                325                 330                 335

Leu Pro Asp Pro Gln Ala Leu Lys Arg Asp Val Pro Cys Asp Asn Val
            340                 345                 350

Ser Ser Cys Pro Ser Ser Asp Thr Cys Cys Gln Leu Thr Ser Gly Glu
        355                 360                 365

Trp Gly Cys Cys Pro Ile Pro Glu Ala Val Cys Cys Ser Asp His Gln
370                 375                 380

His Cys Cys Pro Gln Gly Tyr Thr Cys Val Ala Glu Gly Gln Cys Gln
385                 390                 395                 400

Arg Gly Ser Glu Ile Val Ala Gly Leu Glu Lys Met Pro Ala Arg Arg
                405                 410                 415

Ala Ser Leu Ser His Pro Arg Asp Ile Gly Cys Asp Gln His Thr Ser
            420                 425                 430

Cys Pro Val Gly Gln Thr Cys Cys Pro Ser Leu Gly Gly Ser Trp Ala
        435                 440                 445

Cys Cys Gln Leu Pro His Ala Val Cys Cys Glu Asp Arg Gln His Cys
450                 455                 460

Cys Pro Ala Gly Tyr Thr Cys Asn Val Lys Ala Arg Ser Cys Glu Lys
465                 470                 475                 480

Glu Val Val Ser Ala Gln Pro Ala Thr Phe Leu Ala Arg Ser Pro His
                485                 490                 495

Val Gly Val Lys Asp Val Glu Cys Gly Glu Gly His Phe Cys His Asp
            500                 505                 510

Asn Gln Thr Cys Cys Arg Asp Asn Arg Gln Gly Trp Ala Cys Cys Pro
        515                 520                 525

Tyr Arg Gln Gly Val Cys Cys Ala Asp Arg Arg His Cys Cys Pro Ala
530                 535                 540

Gly Phe Arg Cys Ala Ala Arg Gly Thr Lys Cys Leu Arg Arg Glu Ala
545                 550                 555                 560

Pro Arg Trp Asp Ala Pro Leu Arg Asp Pro Ala Leu Arg Val Thr Leu
                565                 570                 575

<210> SEQ ID NO 30
<211> LENGTH: 576
<212> TYPE: PRT

<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 30

```
Thr Arg Cys Pro Asp Gly Gln Phe Cys Pro Val Ala Cys Cys Leu Asp
1               5                   10                  15

Pro Gly Gly Ala Ser Tyr Ser Cys Cys Arg Pro Leu Leu Asp Lys Trp
            20                  25                  30

Pro Thr Thr Leu Ser Arg His Leu Gly Gly Pro Cys Gln Val Asp Ala
        35                  40                  45

His Cys Ser Ala Gly His Ser Cys Ile Phe Thr Val Ser Gly Thr Ser
    50                  55                  60

Ser Cys Cys Pro Phe Pro Glu Ala Val Ala Cys Gly Asp Gly His His
65                  70                  75                  80

Cys Cys Pro Arg Gly Phe His Cys Ser Ala Asp Gly Arg Ser Cys Phe
                85                  90                  95

Gln Arg Ser Gly Asn Asn Ser Val Gly Ala Ile Gln Cys Pro Asp Ser
            100                 105                 110

Gln Phe Glu Cys Pro Asp Phe Ser Thr Cys Cys Val Met Val Asp Gly
        115                 120                 125

Ser Trp Gly Cys Cys Pro Met Pro Gln Ala Ser Cys Cys Glu Asp Arg
    130                 135                 140

Val His Cys Cys Pro His Gly Ala Phe Cys Asp Leu Val His Thr Arg
145                 150                 155                 160

Cys Ile Thr Pro Thr Gly Thr His Pro Leu Ala Lys Lys Leu Pro Ala
                165                 170                 175

Gln Arg Thr Asn Arg Ala Val Ala Leu Ser Ser Val Met Cys Pro
            180                 185                 190

Asp Ala Arg Ser Arg Cys Pro Asp Gly Ser Thr Cys Cys Glu Leu Pro
        195                 200                 205

Ser Gly Lys Tyr Gly Cys Cys Pro Met Pro Asn Ala Thr Cys Cys Ser
    210                 215                 220

Asp His Leu His Cys Cys Pro Gln Asp Thr Val Cys Asp Leu Ile Gln
225                 230                 235                 240

Ser Lys Cys Leu Ser Lys Glu Asn Ala Thr Thr Asp Leu Leu Thr Lys
                245                 250                 255

Leu Pro Ala His Thr Val Gly Asp Val Lys Cys Asp Met Glu Val Ser
            260                 265                 270

Cys Pro Asp Gly Tyr Thr Cys Cys Arg Leu Gln Ser Gly Ala Trp Gly
        275                 280                 285

Cys Cys Pro Phe Thr Gln Ala Val Cys Cys Glu Asp His Ile His Cys
    290                 295                 300

Cys Pro Ala Gly Phe Thr Cys Asp Thr Gln Lys Gly Thr Cys Glu Gln
305                 310                 315                 320

Gly Pro His Gln Val Pro Trp Met Glu Lys Ala Pro Ala His Leu Ser
                325                 330                 335

Leu Pro Asp Pro Gln Ala Leu Lys Arg Asp Val Pro Cys Asp Asn Val
            340                 345                 350

Ser Ser Cys Pro Ser Ser Asp Thr Cys Cys Gln Leu Thr Ser Gly Glu
        355                 360                 365

Trp Gly Cys Cys Pro Ile Pro Glu Ala Val Cys Cys Ser Asp His Gln
    370                 375                 380
```

-continued

His Cys Cys Pro Gln Gly Tyr Thr Cys Val Ala Glu Gly Gln Cys Gln
385                 390                 395                 400

Arg Gly Ser Glu Ile Val Ala Gly Leu Glu Lys Met Pro Ala Arg Arg
            405                 410                 415

Ala Ser Leu Ser His Pro Arg Asp Ile Gly Cys Asp Gln His Thr Ser
            420                 425                 430

Cys Pro Val Gly Gln Thr Cys Cys Pro Ser Leu Gly Gly Ser Trp Ala
            435                 440                 445

Cys Cys Gln Leu Pro His Ala Val Cys Cys Glu Asp Arg Gln His Cys
            450                 455                 460

Cys Pro Ala Gly Tyr Thr Cys Asn Val Lys Ala Arg Ser Cys Glu Lys
465                 470                 475                 480

Glu Val Val Ser Ala Gln Pro Ala Thr Phe Leu Ala Arg Ser Pro His
            485                 490                 495

Val Gly Val Lys Asp Val Glu Cys Gly Glu Gly His Phe Cys His Asp
            500                 505                 510

Asn Gln Thr Cys Cys Arg Asp Asn Arg Gln Gly Trp Ala Cys Cys Pro
            515                 520                 525

Tyr Arg Gln Gly Val Cys Cys Ala Asp Arg Arg His Cys Cys Pro Ala
530                 535                 540

Gly Phe Arg Cys Ala Ala Arg Gly Thr Lys Cys Leu Arg Arg Glu Ala
545                 550                 555                 560

Pro Arg Trp Asp Ala Pro Leu Arg Asp Pro Ala Leu Arg Arg Ile Leu
            565                 570                 575

<210> SEQ ID NO 31
<211> LENGTH: 576
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 31

Thr Arg Cys Pro Asp Gly Gln Phe Cys Pro Val Ala Cys Cys Leu Asp
1               5                   10                  15

Pro Gly Gly Ala Ser Tyr Ser Cys Cys Arg Pro Leu Leu Asp Lys Trp
            20                  25                  30

Pro Thr Thr Leu Ser Arg His Leu Gly Gly Pro Cys Gln Val Asp Ala
            35                  40                  45

His Cys Ser Ala Gly His Ser Cys Ile Phe Thr Val Ser Gly Thr Ser
            50                  55                  60

Ser Cys Cys Pro Phe Pro Glu Ala Val Ala Cys Gly Asp Gly His His
65                  70                  75                  80

Cys Cys Pro Arg Gly Phe His Cys Ser Ala Asp Gly Arg Ser Cys Phe
            85                  90                  95

Gln Arg Ser Gly Asn Asn Ser Val Gly Ala Ile Gln Cys Pro Asp Ser
            100                 105                 110

Gln Phe Glu Cys Pro Asp Phe Ser Thr Cys Cys Val Met Val Asp Gly
            115                 120                 125

Ser Trp Gly Cys Cys Pro Met Pro Gln Ala Ser Cys Cys Glu Asp Arg
            130                 135                 140

Val His Cys Cys Pro His Gly Ala Phe Cys Asp Leu Val His Thr Arg
145                 150                 155                 160

-continued

```
Cys Ile Thr Pro Thr Gly Thr His Pro Leu Ala Lys Lys Leu Pro Ala
            165                 170                 175
Gln Arg Thr Asn Arg Ala Val Ala Leu Ser Ser Val Met Cys Pro
        180                 185                 190
Asp Ala Arg Ser Arg Cys Pro Asp Gly Ser Thr Cys Cys Glu Leu Pro
            195                 200                 205
Ser Gly Lys Tyr Gly Cys Cys Pro Met Pro Asn Ala Thr Cys Cys Ser
        210                 215                 220
Asp His Leu His Cys Cys Pro Gln Asp Thr Val Cys Asp Leu Ile Gln
225                 230                 235                 240
Ser Lys Cys Leu Ser Lys Glu Asn Ala Thr Thr Asp Leu Leu Thr Lys
            245                 250                 255
Leu Pro Ala His Thr Val Gly Asp Val Lys Cys Asp Met Glu Val Ser
            260                 265                 270
Cys Pro Asp Gly Tyr Thr Cys Cys Arg Leu Gln Ser Gly Ala Trp Gly
        275                 280                 285
Cys Cys Pro Phe Thr Gln Ala Val Cys Cys Glu Asp His Ile His Cys
        290                 295                 300
Cys Pro Ala Gly Phe Thr Cys Asp Thr Gln Lys Gly Thr Cys Glu Gln
305                 310                 315                 320
Gly Pro His Gln Val Pro Trp Met Glu Lys Ala Pro Ala His Leu Ser
            325                 330                 335
Leu Pro Asp Pro Gln Ala Leu Lys Arg Asp Val Pro Cys Asp Asn Val
            340                 345                 350
Ser Ser Cys Pro Ser Ser Asp Thr Cys Cys Gln Leu Thr Ser Gly Glu
        355                 360                 365
Trp Gly Cys Cys Pro Ile Pro Glu Ala Val Cys Cys Ser Asp His Gln
        370                 375                 380
His Cys Cys Pro Gln Gly Tyr Thr Cys Val Ala Glu Gly Gln Cys Gln
385                 390                 395                 400
Arg Gly Ser Glu Ile Val Ala Gly Leu Glu Lys Met Pro Ala Arg Arg
            405                 410                 415
Ala Ser Leu Ser His Pro Arg Asp Ile Gly Cys Asp Gln His Thr Ser
        420                 425                 430
Cys Pro Val Gly Gln Thr Cys Cys Pro Ser Leu Gly Gly Ser Trp Ala
        435                 440                 445
Cys Cys Gln Leu Pro His Ala Val Cys Cys Glu Asp Arg Gln His Cys
        450                 455                 460
Cys Pro Ala Gly Tyr Thr Cys Asn Val Lys Ala Arg Ser Cys Glu Lys
465                 470                 475                 480
Glu Val Val Ser Ala Gln Pro Ala Thr Phe Leu Ala Arg Ser Pro His
            485                 490                 495
Val Gly Val Lys Asp Val Glu Cys Gly Glu Gly His Phe Cys His Asp
            500                 505                 510
Asn Gln Thr Cys Cys Arg Asp Asn Arg Gln Gly Trp Ala Cys Cys Pro
        515                 520                 525
Tyr Arg Gln Gly Val Cys Cys Ala Asp Arg Arg His Cys Cys Pro Ala
        530                 535                 540
Gly Phe Arg Cys Ala Ala Arg Gly Thr Lys Cys Leu Arg Arg Glu Ala
545                 550                 555                 560
Pro Arg Trp Asp Ala Pro Leu Arg Asp Pro Ala Leu Arg His Ile Leu
            565                 570                 575
```

```
<210> SEQ ID NO 32
<211> LENGTH: 576
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 32
```

Thr Arg Cys Pro Asp Gly Gln Phe Cys Pro Val Ala Cys Cys Leu Asp
1               5                   10                  15

Pro Gly Gly Ala Ser Tyr Ser Cys Cys Arg Pro Leu Leu Asp Lys Trp
                20                  25                  30

Pro Thr Thr Leu Ser Arg His Leu Gly Gly Pro Cys Gln Val Asp Ala
            35                  40                  45

His Cys Ser Ala Gly His Ser Cys Ile Phe Thr Val Ser Gly Thr Ser
    50                  55                  60

Ser Cys Cys Pro Phe Pro Glu Ala Val Ala Cys Gly Asp Gly His His
65                  70                  75                  80

Cys Cys Pro Arg Gly Phe His Cys Ser Ala Asp Gly Arg Ser Cys Phe
                85                  90                  95

Gln Arg Ser Gly Asn Asn Ser Val Gly Ala Ile Gln Cys Pro Asp Ser
                100                 105                 110

Gln Phe Glu Cys Pro Asp Phe Ser Thr Cys Cys Val Met Val Asp Gly
            115                 120                 125

Ser Trp Gly Cys Cys Pro Met Pro Gln Ala Ser Cys Cys Glu Asp Arg
            130                 135                 140

Val His Cys Cys Pro His Gly Ala Phe Cys Asp Leu Val His Thr Arg
145                 150                 155                 160

Cys Ile Thr Pro Thr Gly Thr His Pro Leu Ala Lys Lys Leu Pro Ala
                165                 170                 175

Gln Arg Thr Asn Arg Ala Val Ala Leu Ser Ser Ser Val Met Cys Pro
            180                 185                 190

Asp Ala Arg Ser Arg Cys Pro Asp Gly Ser Thr Cys Cys Glu Leu Pro
            195                 200                 205

Ser Gly Lys Tyr Gly Cys Cys Pro Met Pro Asn Ala Thr Cys Cys Ser
            210                 215                 220

Asp His Leu His Cys Cys Pro Gln Asp Thr Val Cys Asp Leu Ile Gln
225                 230                 235                 240

Ser Lys Cys Leu Ser Lys Glu Asn Ala Thr Thr Asp Leu Leu Thr Lys
                245                 250                 255

Leu Pro Ala His Thr Val Gly Asp Val Lys Cys Asp Met Glu Val Ser
            260                 265                 270

Cys Pro Asp Gly Tyr Thr Cys Cys Arg Leu Gln Ser Gly Ala Trp Gly
            275                 280                 285

Cys Cys Pro Phe Thr Gln Ala Val Cys Cys Glu Asp His Ile His Cys
            290                 295                 300

Cys Pro Ala Gly Phe Thr Cys Asp Thr Gln Lys Gly Thr Cys Glu Gln
305                 310                 315                 320

Gly Pro His Gln Val Pro Trp Met Glu Lys Ala Pro Ala His Leu Ser
                325                 330                 335

Leu Pro Asp Pro Gln Ala Leu Lys Arg Asp Val Pro Cys Asp Asn Val
            340                 345                 350

Ser Ser Cys Pro Ser Ser Asp Thr Cys Cys Gln Leu Thr Ser Gly Glu
            355                 360                 365

-continued

Trp Gly Cys Cys Pro Ile Pro Glu Ala Val Cys Cys Ser Asp His Gln
        370                 375                 380

His Cys Cys Pro Gln Gly Tyr Thr Cys Val Ala Glu Gly Gln Cys Gln
385                 390                 395                 400

Arg Gly Ser Glu Ile Val Ala Gly Leu Glu Lys Met Pro Ala Arg Arg
                405                 410                 415

Ala Ser Leu Ser His Pro Arg Asp Ile Gly Cys Asp Gln His Thr Ser
                420                 425                 430

Cys Pro Val Gly Gln Thr Cys Cys Pro Ser Leu Gly Gly Ser Trp Ala
            435                 440                 445

Cys Cys Gln Leu Pro His Ala Val Cys Cys Glu Asp Arg Gln His Cys
        450                 455                 460

Cys Pro Ala Gly Tyr Thr Cys Asn Val Lys Ala Arg Ser Cys Glu Lys
465                 470                 475                 480

Glu Val Val Ser Ala Gln Pro Ala Thr Phe Leu Ala Arg Ser Pro His
                485                 490                 495

Val Gly Val Lys Asp Val Glu Cys Gly Glu Gly His Phe Cys His Asp
                500                 505                 510

Asn Gln Thr Cys Cys Arg Asp Asn Arg Gln Gly Trp Ala Cys Cys Pro
            515                 520                 525

Tyr Arg Gln Gly Val Cys Cys Ala Asp Arg Arg His Cys Cys Pro Ala
        530                 535                 540

Gly Phe Arg Cys Ala Ala Arg Gly Thr Lys Cys Leu Arg Arg Glu Ala
545                 550                 555                 560

Pro Arg Trp Asp Ala Pro Leu Arg Asp Pro Ala Leu Arg Lys Ile Leu
                565                 570                 575

<210> SEQ ID NO 33
<211> LENGTH: 576
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 33

Thr Arg Cys Pro Asp Gly Gln Phe Cys Pro Val Ala Cys Cys Leu Asp
1               5                   10                  15

Pro Gly Gly Ala Ser Tyr Ser Cys Cys Arg Pro Leu Leu Asp Lys Trp
                20                  25                  30

Pro Thr Thr Leu Ser Arg His Leu Gly Gly Pro Cys Gln Val Asp Ala
            35                  40                  45

His Cys Ser Ala Gly His Ser Cys Ile Phe Thr Val Ser Gly Thr Ser
        50                  55                  60

Ser Cys Cys Pro Phe Pro Glu Ala Val Ala Cys Gly Asp Gly His His
65                  70                  75                  80

Cys Cys Pro Arg Gly Phe His Cys Ser Ala Asp Gly Arg Ser Cys Phe
                85                  90                  95

Gln Arg Ser Gly Asn Asn Ser Val Gly Ala Ile Gln Cys Pro Asp Ser
                100                 105                 110

Gln Phe Glu Cys Pro Asp Phe Ser Thr Cys Cys Val Met Val Asp Gly
            115                 120                 125

Ser Trp Gly Cys Cys Pro Met Pro Gln Ala Ser Cys Cys Glu Asp Arg
        130                 135                 140

-continued

```
Val His Cys Cys Pro His Gly Ala Phe Cys Asp Leu Val His Thr Arg
145                 150                 155                 160

Cys Ile Thr Pro Thr Gly Thr His Pro Leu Ala Lys Lys Leu Pro Ala
            165                 170                 175

Gln Arg Thr Asn Arg Ala Val Ala Leu Ser Ser Val Met Cys Pro
        180                 185                 190

Asp Ala Arg Ser Arg Cys Pro Asp Gly Ser Thr Cys Cys Glu Leu Pro
        195                 200                 205

Ser Gly Lys Tyr Gly Cys Cys Pro Met Pro Asn Ala Thr Cys Cys Ser
        210                 215                 220

Asp His Leu His Cys Cys Pro Gln Asp Thr Val Cys Asp Leu Ile Gln
225                 230                 235                 240

Ser Lys Cys Leu Ser Lys Glu Asn Ala Thr Thr Asp Leu Leu Thr Lys
            245                 250                 255

Leu Pro Ala His Thr Val Gly Asp Val Lys Cys Asp Met Glu Val Ser
            260                 265                 270

Cys Pro Asp Gly Tyr Thr Cys Cys Arg Leu Gln Ser Gly Ala Trp Gly
        275                 280                 285

Cys Cys Pro Phe Thr Gln Ala Val Cys Cys Glu Asp His Ile His Cys
        290                 295                 300

Cys Pro Ala Gly Phe Thr Cys Asp Thr Gln Lys Gly Thr Cys Glu Gln
305                 310                 315                 320

Gly Pro His Gln Val Pro Trp Met Glu Lys Ala Pro Ala His Leu Ser
            325                 330                 335

Leu Pro Asp Pro Gln Ala Leu Lys Arg Asp Val Pro Cys Asp Asn Val
            340                 345                 350

Ser Ser Cys Pro Ser Ser Asp Thr Cys Cys Gln Leu Thr Ser Gly Glu
        355                 360                 365

Trp Gly Cys Cys Pro Ile Pro Glu Ala Val Cys Cys Ser Asp His Gln
        370                 375                 380

His Cys Cys Pro Gln Gly Tyr Thr Cys Val Ala Glu Gly Gln Cys Gln
385                 390                 395                 400

Arg Gly Ser Glu Ile Val Ala Gly Leu Glu Lys Met Pro Ala Arg Arg
            405                 410                 415

Ala Ser Leu Ser His Pro Arg Asp Ile Gly Cys Asp Gln His Thr Ser
            420                 425                 430

Cys Pro Val Gly Gln Thr Cys Cys Pro Ser Leu Gly Gly Ser Trp Ala
        435                 440                 445

Cys Cys Gln Leu Pro His Ala Val Cys Cys Glu Asp Arg Gln His Cys
450                 455                 460

Cys Pro Ala Gly Tyr Thr Cys Asn Val Lys Ala Arg Ser Cys Glu Lys
465                 470                 475                 480

Glu Val Val Ser Ala Gln Pro Ala Thr Phe Leu Ala Arg Ser Pro His
            485                 490                 495

Val Gly Val Lys Asp Val Glu Cys Gly Glu Gly His Phe Cys His Asp
            500                 505                 510

Asn Gln Thr Cys Cys Arg Asp Asn Arg Gln Gly Trp Ala Cys Cys Pro
        515                 520                 525

Tyr Arg Gln Gly Val Cys Cys Ala Asp Arg Arg His Cys Cys Pro Ala
        530                 535                 540

Gly Phe Arg Cys Ala Ala Arg Gly Thr Lys Cys Leu Arg Arg Glu Ala
545                 550                 555                 560
```

Pro Arg Trp Asp Ala Pro Leu Arg Asp Pro Ala Leu Arg Glu Ile Leu
                565                 570                 575

<210> SEQ ID NO 34
<211> LENGTH: 576
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 34

Thr Arg Cys Pro Asp Gly Gln Phe Cys Pro Val Ala Cys Cys Leu Asp
1               5                   10                  15

Pro Gly Gly Ala Ser Tyr Ser Cys Cys Arg Pro Leu Leu Asp Lys Trp
                20                  25                  30

Pro Thr Thr Leu Ser Arg His Leu Gly Gly Pro Cys Gln Val Asp Ala
            35                  40                  45

His Cys Ser Ala Gly His Ser Cys Ile Phe Thr Val Ser Gly Thr Ser
    50                  55                  60

Ser Cys Cys Pro Phe Pro Glu Ala Val Ala Cys Gly Asp Gly His His
65                  70                  75                  80

Cys Cys Pro Arg Gly Phe His Cys Ser Ala Asp Gly Arg Ser Cys Phe
                85                  90                  95

Gln Arg Ser Gly Asn Asn Ser Val Gly Ala Ile Gln Cys Pro Asp Ser
                100                 105                 110

Gln Phe Glu Cys Pro Asp Phe Ser Thr Cys Cys Val Met Val Asp Gly
            115                 120                 125

Ser Trp Gly Cys Cys Pro Met Pro Gln Ala Ser Cys Cys Glu Asp Arg
    130                 135                 140

Val His Cys Cys Pro His Gly Ala Phe Cys Asp Leu Val His Thr Arg
145                 150                 155                 160

Cys Ile Thr Pro Thr Gly Thr His Pro Leu Ala Lys Lys Leu Pro Ala
                165                 170                 175

Gln Arg Thr Asn Arg Ala Val Ala Leu Ser Ser Ser Val Met Cys Pro
            180                 185                 190

Asp Ala Arg Ser Arg Cys Pro Asp Gly Ser Thr Cys Cys Glu Leu Pro
    195                 200                 205

Ser Gly Lys Tyr Gly Cys Cys Pro Met Pro Asn Ala Thr Cys Cys Ser
    210                 215                 220

Asp His Leu His Cys Cys Pro Gln Asp Thr Val Cys Asp Leu Ile Gln
225                 230                 235                 240

Ser Lys Cys Leu Ser Lys Glu Asn Ala Thr Thr Asp Leu Leu Thr Lys
                245                 250                 255

Leu Pro Ala His Thr Val Gly Asp Val Lys Cys Asp Met Glu Val Ser
            260                 265                 270

Cys Pro Asp Gly Tyr Thr Cys Cys Arg Leu Gln Ser Gly Ala Trp Gly
            275                 280                 285

Cys Cys Pro Phe Thr Gln Ala Val Cys Cys Glu Asp His Ile His Cys
    290                 295                 300

Cys Pro Ala Gly Phe Thr Cys Asp Thr Gln Lys Gly Thr Cys Glu Gln
305                 310                 315                 320

Gly Pro His Gln Val Pro Trp Met Glu Lys Ala Pro Ala His Leu Ser
                325                 330                 335

Leu Pro Asp Pro Gln Ala Leu Lys Arg Asp Val Pro Cys Asp Asn Val
                340                 345                 350

Ser Ser Cys Pro Ser Ser Asp Thr Cys Cys Gln Leu Thr Ser Gly Glu
            355                 360                 365

Trp Gly Cys Cys Pro Ile Pro Glu Ala Val Cys Cys Ser Asp His Gln
        370                 375                 380

His Cys Cys Pro Gln Gly Tyr Thr Cys Val Ala Glu Gly Gln Cys Gln
385                 390                 395                 400

Arg Gly Ser Glu Ile Val Ala Gly Leu Glu Lys Met Pro Ala Arg Arg
                405                 410                 415

Ala Ser Leu Ser His Pro Arg Asp Ile Gly Cys Asp Gln His Thr Ser
            420                 425                 430

Cys Pro Val Gly Gln Thr Cys Cys Pro Ser Leu Gly Gly Ser Trp Ala
        435                 440                 445

Cys Cys Gln Leu Pro His Ala Val Cys Cys Glu Asp Arg Gln His Cys
        450                 455                 460

Cys Pro Ala Gly Tyr Thr Cys Asn Val Lys Ala Arg Ser Cys Glu Lys
465                 470                 475                 480

Glu Val Val Ser Ala Gln Pro Ala Thr Phe Leu Ala Arg Ser Pro His
                485                 490                 495

Val Gly Val Lys Asp Val Glu Cys Gly Glu Gly His Phe Cys His Asp
            500                 505                 510

Asn Gln Thr Cys Cys Arg Asp Asn Arg Gln Gly Trp Ala Cys Cys Pro
            515                 520                 525

Tyr Arg Gln Gly Val Cys Cys Ala Asp Arg Arg His Cys Cys Pro Ala
530                 535                 540

Gly Phe Arg Cys Ala Ala Arg Gly Thr Lys Cys Leu Arg Arg Glu Ala
545                 550                 555                 560

Pro Arg Trp Asp Ala Pro Leu Arg Asp Pro Ala Leu Arg Arg Phe Leu
                565                 570                 575

<210> SEQ ID NO 35
<211> LENGTH: 576
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 35

Thr Arg Cys Pro Asp Gly Gln Phe Cys Pro Val Ala Cys Cys Leu Asp
1               5                   10                  15

Pro Gly Gly Ala Ser Tyr Ser Cys Cys Arg Pro Leu Leu Asp Lys Trp
                20                  25                  30

Pro Thr Thr Leu Ser Arg His Leu Gly Gly Pro Cys Gln Val Asp Ala
            35                  40                  45

His Cys Ser Ala Gly His Ser Cys Ile Phe Thr Val Ser Gly Thr Ser
        50                  55                  60

Ser Cys Cys Pro Phe Pro Glu Ala Val Ala Cys Gly Asp Gly His His
65                  70                  75                  80

Cys Cys Pro Arg Gly Phe His Cys Ser Ala Asp Gly Arg Ser Cys Phe
                85                  90                  95

Gln Arg Ser Gly Asn Asn Ser Val Gly Ala Ile Gln Cys Pro Asp Ser
            100                 105                 110

```
Gln Phe Glu Cys Pro Asp Phe Ser Thr Cys Cys Val Met Val Asp Gly
            115                 120                 125

Ser Trp Gly Cys Cys Pro Met Pro Gln Ala Ser Cys Cys Glu Asp Arg
        130                 135                 140

Val His Cys Cys Pro His Gly Ala Phe Cys Asp Leu Val His Thr Arg
145                 150                 155                 160

Cys Ile Thr Pro Thr Gly Thr His Pro Leu Ala Lys Lys Leu Pro Ala
                165                 170                 175

Gln Arg Thr Asn Arg Ala Val Ala Leu Ser Ser Val Met Cys Pro
            180                 185                 190

Asp Ala Arg Ser Arg Cys Pro Asp Gly Ser Thr Cys Cys Glu Leu Pro
                195                 200                 205

Ser Gly Lys Tyr Gly Cys Cys Pro Met Pro Asn Ala Thr Cys Cys Ser
        210                 215                 220

Asp His Leu His Cys Cys Pro Gln Asp Thr Val Cys Asp Leu Ile Gln
225                 230                 235                 240

Ser Lys Cys Leu Ser Lys Glu Asn Ala Thr Thr Asp Leu Leu Thr Lys
                245                 250                 255

Leu Pro Ala His Thr Val Gly Asp Val Lys Cys Asp Met Glu Val Ser
                260                 265                 270

Cys Pro Asp Gly Tyr Thr Cys Cys Arg Leu Gln Ser Gly Ala Trp Gly
        275                 280                 285

Cys Cys Pro Phe Thr Gln Ala Val Cys Cys Glu Asp His Ile His Cys
        290                 295                 300

Cys Pro Ala Gly Phe Thr Cys Asp Thr Gln Lys Gly Thr Cys Glu Gln
305                 310                 315                 320

Gly Pro His Gln Val Pro Trp Met Glu Lys Ala Pro Ala His Leu Ser
                325                 330                 335

Leu Pro Asp Pro Gln Ala Leu Lys Arg Asp Val Pro Cys Asp Asn Val
                340                 345                 350

Ser Ser Cys Pro Ser Ser Asp Thr Cys Cys Gln Leu Thr Ser Gly Glu
            355                 360                 365

Trp Gly Cys Cys Pro Ile Pro Glu Ala Val Cys Cys Ser Asp His Gln
        370                 375                 380

His Cys Cys Pro Gln Gly Tyr Thr Cys Val Ala Glu Gly Gln Cys Gln
385                 390                 395                 400

Arg Gly Ser Glu Ile Val Ala Gly Leu Glu Lys Met Pro Ala Arg Arg
                405                 410                 415

Ala Ser Leu Ser His Pro Arg Asp Ile Gly Cys Asp Gln His Thr Ser
            420                 425                 430

Cys Pro Val Gly Gln Thr Cys Cys Pro Ser Leu Gly Gly Ser Trp Ala
        435                 440                 445

Cys Cys Gln Leu Pro His Ala Val Cys Cys Glu Asp Arg Gln His Cys
        450                 455                 460

Cys Pro Ala Gly Tyr Thr Cys Asn Val Lys Ala Arg Ser Cys Glu Lys
465                 470                 475                 480

Glu Val Val Ser Ala Gln Pro Ala Thr Phe Leu Ala Arg Ser Pro His
            485                 490                 495

Val Gly Val Lys Asp Val Glu Cys Gly Glu Gly His Phe Cys His Asp
                500                 505                 510

Asn Gln Thr Cys Cys Arg Asp Asn Arg Gln Gly Trp Ala Cys Cys Pro
            515                 520                 525
```

-continued

```
Tyr Arg Gln Gly Val Cys Cys Ala Asp Arg Arg His Cys Cys Pro Ala
            530                 535                 540

Gly Phe Arg Cys Ala Ala Arg Gly Thr Lys Cys Leu Arg Arg Glu Ala
545                 550                 555                 560

Pro Arg Trp Asp Ala Pro Leu Arg Asp Pro Ala Leu Arg His Phe Leu
            565                 570                 575
```

<210> SEQ ID NO 36
<211> LENGTH: 576
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 36

```
Thr Arg Cys Pro Asp Gly Gln Phe Cys Pro Val Ala Cys Cys Leu Asp
1               5                   10                  15

Pro Gly Gly Ala Ser Tyr Ser Cys Cys Arg Pro Leu Leu Asp Lys Trp
            20                  25                  30

Pro Thr Thr Leu Ser Arg His Leu Gly Gly Pro Cys Gln Val Asp Ala
        35                  40                  45

His Cys Ser Ala Gly His Ser Cys Ile Phe Thr Val Ser Gly Thr Ser
50                  55                  60

Ser Cys Cys Pro Phe Pro Glu Ala Val Ala Cys Gly Asp Gly His His
65                  70                  75                  80

Cys Cys Pro Arg Gly Phe His Cys Ser Ala Asp Gly Arg Ser Cys Phe
                85                  90                  95

Gln Arg Ser Gly Asn Asn Ser Val Gly Ala Ile Gln Cys Pro Asp Ser
            100                 105                 110

Gln Phe Glu Cys Pro Asp Phe Ser Thr Cys Cys Val Met Val Asp Gly
        115                 120                 125

Ser Trp Gly Cys Cys Pro Met Pro Gln Ala Ser Cys Cys Glu Asp Arg
130                 135                 140

Val His Cys Cys Pro His Gly Ala Phe Cys Asp Leu Val His Thr Arg
145                 150                 155                 160

Cys Ile Thr Pro Thr Gly Thr His Pro Leu Ala Lys Lys Leu Pro Ala
                165                 170                 175

Gln Arg Thr Asn Arg Ala Val Ala Leu Ser Ser Ser Val Met Cys Pro
            180                 185                 190

Asp Ala Arg Ser Arg Cys Pro Asp Gly Ser Thr Cys Cys Glu Leu Pro
        195                 200                 205

Ser Gly Lys Tyr Gly Cys Cys Pro Met Pro Asn Ala Thr Cys Cys Ser
210                 215                 220

Asp His Leu His Cys Cys Pro Gln Asp Thr Val Cys Asp Leu Ile Gln
225                 230                 235                 240

Ser Lys Cys Leu Ser Lys Glu Asn Ala Thr Thr Asp Leu Leu Thr Lys
                245                 250                 255

Leu Pro Ala His Thr Val Gly Asp Val Lys Cys Asp Met Glu Val Ser
            260                 265                 270

Cys Pro Asp Gly Tyr Thr Cys Cys Arg Leu Gln Ser Gly Ala Trp Gly
        275                 280                 285

Cys Cys Pro Phe Thr Gln Ala Val Cys Cys Glu Asp His Ile His Cys
290                 295                 300
```

Cys Pro Ala Gly Phe Thr Cys Asp Thr Gln Lys Gly Thr Cys Glu Gln
305                 310                 315                 320

Gly Pro His Gln Val Pro Trp Met Glu Lys Ala Pro Ala His Leu Ser
            325                 330                 335

Leu Pro Asp Pro Gln Ala Leu Lys Arg Asp Val Pro Cys Asp Asn Val
            340                 345                 350

Ser Ser Cys Pro Ser Ser Asp Thr Cys Cys Gln Leu Thr Ser Gly Glu
                355                 360                 365

Trp Gly Cys Cys Pro Ile Pro Glu Ala Val Cys Cys Ser Asp His Gln
            370                 375                 380

His Cys Cys Pro Gln Gly Tyr Thr Cys Val Ala Glu Gly Gln Cys Gln
385                 390                 395                 400

Arg Gly Ser Glu Ile Val Ala Gly Leu Glu Lys Met Pro Ala Arg Arg
                405                 410                 415

Ala Ser Leu Ser His Pro Arg Asp Ile Gly Cys Asp Gln His Thr Ser
            420                 425                 430

Cys Pro Val Gly Gln Thr Cys Cys Pro Ser Leu Gly Gly Ser Trp Ala
                435                 440                 445

Cys Cys Gln Leu Pro His Ala Val Cys Cys Glu Asp Arg Gln His Cys
450                 455                 460

Cys Pro Ala Gly Tyr Thr Cys Asn Val Lys Ala Arg Ser Cys Glu Lys
465                 470                 475                 480

Glu Val Val Ser Ala Gln Pro Ala Thr Phe Leu Ala Arg Ser Pro His
                485                 490                 495

Val Gly Val Lys Asp Val Glu Cys Gly Glu Gly His Phe Cys His Asp
            500                 505                 510

Asn Gln Thr Cys Cys Arg Asp Asn Arg Gln Gly Trp Ala Cys Cys Pro
            515                 520                 525

Tyr Arg Gln Gly Val Cys Cys Ala Asp Arg Arg His Cys Cys Pro Ala
            530                 535                 540

Gly Phe Arg Cys Ala Ala Arg Gly Thr Lys Cys Leu Arg Arg Glu Ala
545                 550                 555                 560

Pro Arg Trp Asp Ala Pro Leu Arg Asp Pro Ala Leu Arg Lys Phe Leu
            565                 570                 575

<210> SEQ ID NO 37
<211> LENGTH: 576
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 37

Thr Arg Cys Pro Asp Gly Gln Phe Cys Pro Val Ala Cys Cys Leu Asp
1               5                   10                  15

Pro Gly Gly Ala Ser Tyr Ser Cys Cys Arg Pro Leu Leu Asp Lys Trp
            20                  25                  30

Pro Thr Thr Leu Ser Arg His Leu Gly Gly Pro Cys Gln Val Asp Ala
            35                  40                  45

His Cys Ser Ala Gly His Ser Cys Ile Phe Thr Val Ser Gly Thr Ser
        50                  55                  60

Ser Cys Cys Pro Phe Pro Glu Ala Val Ala Cys Gly Asp Gly His His
65                  70                  75                  80

```
Cys Cys Pro Arg Gly Phe His Cys Ser Ala Asp Gly Arg Ser Cys Phe
            85                  90                  95

Gln Arg Ser Gly Asn Asn Ser Val Gly Ala Ile Gln Cys Pro Asp Ser
        100                 105                 110

Gln Phe Glu Cys Pro Asp Phe Ser Thr Cys Cys Val Met Val Asp Gly
        115                 120                 125

Ser Trp Gly Cys Cys Pro Met Pro Gln Ala Ser Cys Cys Glu Asp Arg
130                 135                 140

Val His Cys Cys Pro His Gly Ala Phe Cys Asp Leu Val His Thr Arg
145                 150                 155                 160

Cys Ile Thr Pro Thr Gly Thr His Pro Leu Ala Lys Lys Leu Pro Ala
                165                 170                 175

Gln Arg Thr Asn Arg Ala Val Ala Leu Ser Ser Ser Val Met Cys Pro
        180                 185                 190

Asp Ala Arg Ser Arg Cys Pro Asp Gly Ser Thr Cys Cys Glu Leu Pro
        195                 200                 205

Ser Gly Lys Tyr Gly Cys Cys Pro Met Pro Asn Ala Thr Cys Cys Ser
        210                 215                 220

Asp His Leu His Cys Cys Pro Gln Asp Thr Val Cys Asp Leu Ile Gln
225                 230                 235                 240

Ser Lys Cys Leu Ser Lys Glu Asn Ala Thr Thr Asp Leu Leu Thr Lys
                245                 250                 255

Leu Pro Ala His Thr Val Gly Asp Val Lys Cys Asp Met Glu Val Ser
                260                 265                 270

Cys Pro Asp Gly Tyr Thr Cys Cys Arg Leu Gln Ser Gly Ala Trp Gly
        275                 280                 285

Cys Cys Pro Phe Thr Gln Ala Val Cys Cys Glu Asp His Ile His Cys
        290                 295                 300

Cys Pro Ala Gly Phe Thr Cys Asp Thr Gln Lys Gly Thr Cys Glu Gln
305                 310                 315                 320

Gly Pro His Gln Val Pro Trp Met Glu Lys Ala Pro Ala His Leu Ser
                325                 330                 335

Leu Pro Asp Pro Gln Ala Leu Lys Arg Asp Val Pro Cys Asp Asn Val
                340                 345                 350

Ser Ser Cys Pro Ser Ser Asp Thr Cys Cys Gln Leu Thr Ser Gly Glu
        355                 360                 365

Trp Gly Cys Cys Pro Ile Pro Glu Ala Val Cys Cys Ser Asp His Gln
        370                 375                 380

His Cys Cys Pro Gln Gly Tyr Thr Cys Val Ala Glu Gly Gln Cys Gln
385                 390                 395                 400

Arg Gly Ser Glu Ile Val Ala Gly Leu Glu Lys Met Pro Ala Arg Arg
                405                 410                 415

Ala Ser Leu Ser His Pro Arg Asp Ile Gly Cys Asp Gln His Thr Ser
                420                 425                 430

Cys Pro Val Gly Gln Thr Cys Cys Pro Ser Leu Gly Gly Ser Trp Ala
        435                 440                 445

Cys Cys Gln Leu Pro His Ala Val Cys Cys Glu Asp Arg Gln His Cys
        450                 455                 460

Cys Pro Ala Gly Tyr Thr Cys Asn Val Lys Ala Arg Ser Cys Glu Lys
465                 470                 475                 480

Glu Val Val Ser Ala Gln Pro Ala Thr Phe Leu Ala Arg Ser Pro His
                485                 490                 495
```

Val Gly Val Lys Asp Val Glu Cys Gly Glu Gly His Phe Cys His Asp
            500                 505                 510

Asn Gln Thr Cys Cys Arg Asp Asn Arg Gln Gly Trp Ala Cys Cys Pro
            515                 520                 525

Tyr Arg Gln Gly Val Cys Cys Ala Asp Arg Arg His Cys Cys Pro Ala
            530                 535                 540

Gly Phe Arg Cys Ala Ala Arg Gly Thr Lys Cys Leu Arg Arg Glu Ala
545                 550                 555                 560

Pro Arg Trp Asp Ala Pro Leu Arg Asp Pro Ala Leu Arg Asp Phe Leu
            565                 570                 575

<210> SEQ ID NO 38
<211> LENGTH: 576
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 38

Thr Arg Cys Pro Asp Gly Gln Phe Cys Pro Val Ala Cys Cys Leu Asp
1               5                   10                  15

Pro Gly Gly Ala Ser Tyr Ser Cys Cys Arg Pro Leu Leu Asp Lys Trp
            20                  25                  30

Pro Thr Thr Leu Ser Arg His Leu Gly Gly Pro Cys Gln Val Asp Ala
            35                  40                  45

His Cys Ser Ala Gly His Ser Cys Ile Phe Thr Val Ser Gly Thr Ser
    50                  55                  60

Ser Cys Cys Pro Phe Pro Glu Ala Val Ala Cys Gly Asp Gly His His
65                  70                  75                  80

Cys Cys Pro Arg Gly Phe His Cys Ser Ala Asp Gly Arg Ser Cys Phe
                85                  90                  95

Gln Arg Ser Gly Asn Asn Ser Val Gly Ala Ile Gln Cys Pro Asp Ser
            100                 105                 110

Gln Phe Glu Cys Pro Asp Phe Ser Thr Cys Cys Val Met Val Asp Gly
            115                 120                 125

Ser Trp Gly Cys Cys Pro Met Pro Gln Ala Ser Cys Cys Glu Asp Arg
    130                 135                 140

Val His Cys Cys Pro His Gly Ala Phe Cys Asp Leu Val His Thr Arg
145                 150                 155                 160

Cys Ile Thr Pro Thr Gly Thr His Pro Leu Ala Lys Lys Leu Pro Ala
                165                 170                 175

Gln Arg Thr Asn Arg Ala Val Ala Leu Ser Ser Ser Val Met Cys Pro
            180                 185                 190

Asp Ala Arg Ser Arg Cys Pro Asp Gly Ser Thr Cys Cys Glu Leu Pro
            195                 200                 205

Ser Gly Lys Tyr Gly Cys Cys Pro Met Pro Asn Ala Thr Cys Cys Ser
    210                 215                 220

Asp His Leu His Cys Cys Pro Gln Asp Thr Val Cys Asp Leu Ile Gln
225                 230                 235                 240

Ser Lys Cys Leu Ser Lys Glu Asn Ala Thr Thr Asp Leu Leu Thr Lys
                245                 250                 255

Leu Pro Ala His Thr Val Gly Asp Val Lys Cys Asp Met Glu Val Ser
            260                 265                 270

Cys Pro Asp Gly Tyr Thr Cys Arg Leu Gln Ser Gly Ala Trp Gly
                275                 280                 285

Cys Cys Pro Phe Thr Gln Ala Val Cys Glu Asp His Ile His Cys
        290                 295                 300

Cys Pro Ala Gly Phe Thr Cys Asp Thr Gln Lys Gly Thr Cys Glu Gln
305                 310                 315                 320

Gly Pro His Gln Val Pro Trp Met Glu Lys Ala Pro Ala His Leu Ser
                325                 330                 335

Leu Pro Asp Pro Gln Ala Leu Lys Arg Asp Val Pro Cys Asp Asn Val
                340                 345                 350

Ser Ser Cys Pro Ser Ser Asp Thr Cys Cys Gln Leu Thr Ser Gly Glu
                355                 360                 365

Trp Gly Cys Cys Pro Ile Pro Glu Ala Val Cys Cys Ser Asp His Gln
        370                 375                 380

His Cys Cys Pro Gln Gly Tyr Thr Cys Val Ala Glu Gly Gln Cys Gln
385                 390                 395                 400

Arg Gly Ser Glu Ile Val Ala Gly Leu Glu Lys Met Pro Ala Arg Arg
                405                 410                 415

Ala Ser Leu Ser His Pro Arg Asp Ile Gly Cys Asp Gln His Thr Ser
                420                 425                 430

Cys Pro Val Gly Gln Thr Cys Cys Pro Ser Leu Gly Gly Ser Trp Ala
        435                 440                 445

Cys Cys Gln Leu Pro His Ala Val Cys Cys Glu Asp Arg Gln His Cys
        450                 455                 460

Cys Pro Ala Gly Tyr Thr Cys Asn Val Lys Ala Arg Ser Cys Glu Lys
465                 470                 475                 480

Glu Val Val Ser Ala Gln Pro Ala Thr Phe Leu Ala Arg Ser Pro His
                485                 490                 495

Val Gly Val Lys Asp Val Glu Cys Gly Glu Gly His Phe Cys His Asp
                500                 505                 510

Asn Gln Thr Cys Cys Arg Asp Asn Arg Gln Gly Trp Ala Cys Cys Pro
                515                 520                 525

Tyr Arg Gln Gly Val Cys Cys Ala Asp Arg Arg His Cys Cys Pro Ala
                530                 535                 540

Gly Phe Arg Cys Ala Ala Arg Gly Thr Lys Cys Leu Arg Arg Glu Ala
545                 550                 555                 560

Pro Arg Trp Asp Ala Pro Leu Arg Asp Pro Ala Leu Arg Glu Phe Leu
                565                 570                 575

<210> SEQ ID NO 39
<211> LENGTH: 576
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 39

Thr Arg Cys Pro Asp Gly Gln Phe Cys Pro Val Ala Cys Cys Leu Asp
1               5                   10                  15

Pro Gly Gly Ala Ser Tyr Ser Cys Cys Arg Pro Leu Leu Asp Lys Trp
                20                  25                  30

Pro Thr Thr Leu Ser Arg His Leu Gly Gly Pro Cys Gln Val Asp Ala
                35                  40                  45

-continued

```
His Cys Ser Ala Gly His Ser Cys Ile Phe Thr Val Ser Gly Thr Ser
 50                  55                  60

Ser Cys Cys Pro Phe Pro Glu Ala Val Ala Cys Gly Asp Gly His His
 65                  70                  75                  80

Cys Cys Pro Arg Gly Phe His Cys Ser Ala Asp Gly Arg Ser Cys Phe
                 85                  90                  95

Gln Arg Ser Gly Asn Asn Ser Val Gly Ala Ile Gln Cys Pro Asp Ser
            100                 105                 110

Gln Phe Glu Cys Pro Asp Phe Ser Thr Cys Cys Val Met Val Asp Gly
        115                 120                 125

Ser Trp Gly Cys Cys Pro Met Pro Gln Ala Ser Cys Cys Glu Asp Arg
    130                 135                 140

Val His Cys Cys Pro His Gly Ala Phe Cys Asp Leu Val His Thr Arg
145                 150                 155                 160

Cys Ile Thr Pro Thr Gly Thr His Pro Leu Ala Lys Lys Leu Pro Ala
                165                 170                 175

Gln Arg Thr Asn Arg Ala Val Ala Leu Ser Ser Ser Val Met Cys Pro
            180                 185                 190

Asp Ala Arg Ser Arg Cys Pro Asp Gly Ser Thr Cys Cys Glu Leu Pro
        195                 200                 205

Ser Gly Lys Tyr Gly Cys Cys Pro Met Pro Asn Ala Thr Cys Cys Ser
    210                 215                 220

Asp His Leu His Cys Cys Pro Gln Asp Thr Val Cys Asp Leu Ile Gln
225                 230                 235                 240

Ser Lys Cys Leu Ser Lys Glu Asn Ala Thr Thr Asp Leu Leu Thr Lys
                245                 250                 255

Leu Pro Ala His Thr Val Gly Asp Val Lys Cys Asp Met Glu Val Ser
            260                 265                 270

Cys Pro Asp Gly Tyr Thr Cys Cys Arg Leu Gln Ser Gly Ala Trp Gly
        275                 280                 285

Cys Cys Pro Phe Thr Gln Ala Val Cys Cys Glu Asp His Ile His Cys
    290                 295                 300

Cys Pro Ala Gly Phe Thr Cys Asp Thr Gln Lys Gly Thr Cys Glu Gln
305                 310                 315                 320

Gly Pro His Gln Val Pro Trp Met Glu Lys Ala Pro Ala His Leu Ser
                325                 330                 335

Leu Pro Asp Pro Gln Ala Leu Lys Arg Asp Val Pro Cys Asp Asn Val
            340                 345                 350

Ser Ser Cys Pro Ser Ser Asp Thr Cys Cys Gln Leu Thr Ser Gly Glu
        355                 360                 365

Trp Gly Cys Cys Pro Ile Pro Glu Ala Val Cys Cys Ser Asp His Gln
    370                 375                 380

His Cys Cys Pro Gln Gly Tyr Thr Cys Val Ala Glu Gly Gln Cys Gln
385                 390                 395                 400

Arg Gly Ser Glu Ile Val Ala Gly Leu Glu Lys Met Pro Ala Arg Arg
                405                 410                 415

Ala Ser Leu Ser His Pro Arg Asp Ile Gly Cys Asp Gln His Thr Ser
            420                 425                 430

Cys Pro Val Gly Gln Thr Cys Cys Pro Ser Leu Gly Gly Ser Trp Ala
        435                 440                 445

Cys Cys Gln Leu Pro His Ala Val Cys Cys Glu Asp Arg Gln His Cys
    450                 455                 460
```

```
Cys Pro Ala Gly Tyr Thr Cys Asn Val Lys Ala Arg Ser Cys Glu Lys
465                 470                 475                 480

Glu Val Val Ser Ala Gln Pro Ala Thr Phe Leu Ala Arg Ser Pro His
            485                 490                 495

Val Gly Val Lys Asp Val Glu Cys Gly Glu Gly His Phe Cys His Asp
            500                 505                 510

Asn Gln Thr Cys Cys Arg Asp Asn Arg Gln Gly Trp Ala Cys Cys Pro
            515                 520                 525

Tyr Arg Gln Gly Val Cys Cys Ala Asp Arg Arg His Cys Cys Pro Ala
            530                 535                 540

Gly Phe Arg Cys Ala Ala Arg Gly Thr Lys Cys Leu Arg Arg Glu Ala
545                 550                 555                 560

Pro Arg Trp Asp Ala Pro Leu Arg Asp Pro Ala Leu Arg Ser Phe Leu
            565                 570                 575
```

<210> SEQ ID NO 40
<211> LENGTH: 576
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 40

```
Thr Arg Cys Pro Asp Gly Gln Phe Cys Pro Val Ala Cys Cys Leu Asp
1               5                   10                  15

Pro Gly Gly Ala Ser Tyr Ser Cys Cys Arg Pro Leu Leu Asp Lys Trp
            20                  25                  30

Pro Thr Thr Leu Ser Arg His Leu Gly Gly Pro Cys Gln Val Asp Ala
            35                  40                  45

His Cys Ser Ala Gly His Ser Cys Ile Phe Thr Val Ser Gly Thr Ser
        50                  55                  60

Ser Cys Cys Pro Phe Pro Glu Ala Val Ala Cys Gly Asp Gly His His
65              70                  75                  80

Cys Cys Pro Arg Gly Phe His Cys Ser Ala Asp Gly Arg Ser Cys Phe
                85                  90                  95

Gln Arg Ser Gly Asn Asn Ser Val Gly Ala Ile Gln Cys Pro Asp Ser
            100                 105                 110

Gln Phe Glu Cys Pro Asp Phe Ser Thr Cys Cys Val Met Val Asp Gly
        115                 120                 125

Ser Trp Gly Cys Cys Pro Met Pro Gln Ala Ser Cys Cys Glu Asp Arg
130                 135                 140

Val His Cys Cys Pro His Gly Ala Phe Cys Asp Leu Val His Thr Arg
145                 150                 155                 160

Cys Ile Thr Pro Thr Gly Thr His Pro Leu Ala Lys Lys Leu Pro Ala
                165                 170                 175

Gln Arg Thr Asn Arg Ala Val Ala Leu Ser Ser Ser Val Met Cys Pro
            180                 185                 190

Asp Ala Arg Ser Arg Cys Pro Asp Gly Ser Thr Cys Cys Glu Leu Pro
        195                 200                 205

Ser Gly Lys Tyr Gly Cys Cys Pro Met Pro Asn Ala Thr Cys Cys Ser
    210                 215                 220

Asp His Leu His Cys Cys Pro Gln Asp Thr Val Cys Asp Leu Ile Gln
225                 230                 235                 240
```

Ser Lys Cys Leu Ser Lys Glu Asn Ala Thr Thr Asp Leu Leu Thr Lys
            245                 250                 255

Leu Pro Ala His Thr Val Gly Asp Val Lys Cys Asp Met Glu Val Ser
            260                 265                 270

Cys Pro Asp Gly Tyr Thr Cys Cys Arg Leu Gln Ser Gly Ala Trp Gly
            275                 280                 285

Cys Cys Pro Phe Thr Gln Ala Val Cys Cys Glu Asp His Ile His Cys
            290                 295                 300

Cys Pro Ala Gly Phe Thr Cys Asp Thr Gln Lys Gly Thr Cys Glu Gln
305                 310                 315                 320

Gly Pro His Gln Val Pro Trp Met Glu Lys Ala Pro Ala His Leu Ser
            325                 330                 335

Leu Pro Asp Pro Gln Ala Leu Lys Arg Asp Val Pro Cys Asp Asn Val
            340                 345                 350

Ser Ser Cys Pro Ser Ser Asp Thr Cys Cys Gln Leu Thr Ser Gly Glu
            355                 360                 365

Trp Gly Cys Cys Pro Ile Pro Glu Ala Val Cys Cys Ser Asp His Gln
            370                 375                 380

His Cys Cys Pro Gln Gly Tyr Thr Cys Val Ala Glu Gly Gln Cys Gln
385                 390                 395                 400

Arg Gly Ser Glu Ile Val Ala Gly Leu Glu Lys Met Pro Ala Arg Arg
            405                 410                 415

Ala Ser Leu Ser His Pro Arg Asp Ile Gly Cys Asp Gln His Thr Ser
            420                 425                 430

Cys Pro Val Gly Gln Thr Cys Cys Pro Ser Leu Gly Gly Ser Trp Ala
            435                 440                 445

Cys Cys Gln Leu Pro His Ala Val Cys Cys Glu Asp Arg Gln His Cys
            450                 455                 460

Cys Pro Ala Gly Tyr Thr Cys Asn Val Lys Ala Arg Ser Cys Glu Lys
465                 470                 475                 480

Glu Val Val Ser Ala Gln Pro Ala Thr Phe Leu Ala Arg Ser Pro His
            485                 490                 495

Val Gly Val Lys Asp Val Glu Cys Gly Glu Gly His Phe Cys His Asp
            500                 505                 510

Asn Gln Thr Cys Cys Arg Asp Asn Arg Gln Gly Trp Ala Cys Cys Pro
            515                 520                 525

Tyr Arg Gln Gly Val Cys Cys Ala Asp Arg Arg His Cys Cys Pro Ala
            530                 535                 540

Gly Phe Arg Cys Ala Ala Arg Gly Thr Lys Cys Leu Arg Arg Glu Ala
545                 550                 555                 560

Pro Arg Trp Asp Ala Pro Leu Arg Asp Pro Ala Leu Arg Thr Phe Leu
            565                 570                 575

<210> SEQ ID NO 41
<211> LENGTH: 576
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 41

Thr Arg Cys Pro Asp Gly Gln Phe Cys Pro Val Ala Cys Cys Leu Asp
1               5                   10                  15

```
Pro Gly Gly Ala Ser Tyr Ser Cys Cys Arg Pro Leu Leu Asp Lys Trp
            20                  25                  30

Pro Thr Thr Leu Ser Arg His Leu Gly Gly Pro Cys Gln Val Asp Ala
            35                  40                  45

His Cys Ser Ala Gly His Ser Cys Ile Phe Thr Val Ser Gly Thr Ser
 50                      55                  60

Ser Cys Cys Pro Phe Pro Glu Ala Val Ala Cys Gly Asp Gly His His
 65              70                  75                      80

Cys Cys Pro Arg Gly Phe His Cys Ser Ala Asp Gly Arg Ser Cys Phe
                85                  90                  95

Gln Arg Ser Gly Asn Asn Ser Val Gly Ala Ile Gln Cys Pro Asp Ser
            100                 105                 110

Gln Phe Glu Cys Pro Asp Phe Ser Thr Cys Cys Val Met Val Asp Gly
            115                 120                 125

Ser Trp Gly Cys Cys Pro Met Pro Gln Ala Ser Cys Cys Glu Asp Arg
            130                 135                 140

Val His Cys Cys Pro His Gly Ala Phe Cys Asp Leu Val His Thr Arg
145                 150                 155                 160

Cys Ile Thr Pro Thr Gly Thr His Pro Leu Ala Lys Lys Leu Pro Ala
                165                 170                 175

Gln Arg Thr Asn Arg Ala Val Ala Leu Ser Ser Val Met Cys Pro
            180                 185                 190

Asp Ala Arg Ser Arg Cys Pro Asp Gly Ser Thr Cys Cys Glu Leu Pro
            195                 200                 205

Ser Gly Lys Tyr Gly Cys Cys Pro Met Pro Asn Ala Thr Cys Cys Ser
    210                 215                 220

Asp His Leu His Cys Cys Pro Gln Asp Thr Val Cys Asp Leu Ile Gln
225                 230                 235                 240

Ser Lys Cys Leu Ser Lys Glu Asn Ala Thr Thr Asp Leu Leu Thr Lys
                245                 250                 255

Leu Pro Ala His Thr Val Gly Asp Val Lys Cys Asp Met Glu Val Ser
                260                 265                 270

Cys Pro Asp Gly Tyr Thr Cys Cys Arg Leu Gln Ser Gly Ala Trp Gly
                275                 280                 285

Cys Cys Pro Phe Thr Gln Ala Val Cys Cys Glu Asp His Ile His Cys
        290                 295                 300

Cys Pro Ala Gly Phe Thr Cys Asp Thr Gln Lys Gly Thr Cys Glu Gln
305                 310                 315                 320

Gly Pro His Gln Val Pro Trp Met Glu Lys Ala Pro Ala His Leu Ser
                325                 330                 335

Leu Pro Asp Pro Gln Ala Leu Lys Arg Asp Val Pro Cys Asp Asn Val
            340                 345                 350

Ser Ser Cys Pro Ser Ser Asp Thr Cys Cys Gln Leu Thr Ser Gly Glu
            355                 360                 365

Trp Gly Cys Cys Pro Ile Pro Glu Ala Val Cys Cys Ser Asp His Gln
        370                 375                 380

His Cys Cys Pro Gln Gly Tyr Thr Cys Val Ala Glu Gly Gln Cys Gln
385                 390                 395                 400

Arg Gly Ser Glu Ile Val Ala Gly Leu Glu Lys Met Pro Ala Arg Arg
            405                 410                 415

Ala Ser Leu Ser His Pro Arg Asp Ile Gly Cys Asp Gln His Thr Ser
            420                 425                 430
```

-continued

```
Cys Pro Val Gly Gln Thr Cys Pro Ser Leu Gly Gly Ser Trp Ala
        435                 440                 445

Cys Cys Gln Leu Pro His Ala Val Cys Cys Glu Asp Arg Gln His Cys
    450                 455                 460

Cys Pro Ala Gly Tyr Thr Cys Asn Val Lys Ala Arg Ser Cys Glu Lys
465                 470                 475                 480

Glu Val Val Ser Ala Gln Pro Ala Thr Phe Leu Ala Arg Ser Pro His
                485                 490                 495

Val Gly Val Lys Asp Val Glu Cys Gly Glu Gly His Phe Cys His Asp
                500                 505                 510

Asn Gln Thr Cys Cys Arg Asp Asn Arg Gln Gly Trp Ala Cys Cys Pro
            515                 520                 525

Tyr Arg Gln Gly Val Cys Cys Ala Asp Arg Arg His Cys Cys Pro Ala
        530                 535                 540

Gly Phe Arg Cys Ala Ala Arg Gly Thr Lys Cys Leu Arg Arg Glu Ala
545                 550                 555                 560

Pro Arg Trp Asp Ala Pro Leu Arg Asp Pro Ala Leu Arg Asn Phe Leu
                565                 570                 575
```

<210> SEQ ID NO 42
<211> LENGTH: 576
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 42

```
Thr Arg Cys Pro Asp Gly Gln Phe Cys Pro Val Ala Cys Cys Leu Asp
1               5                   10                  15

Pro Gly Gly Ala Ser Tyr Ser Cys Cys Arg Pro Leu Leu Asp Lys Trp
                20                  25                  30

Pro Thr Thr Leu Ser Arg His Leu Gly Gly Pro Cys Gln Val Asp Ala
            35                  40                  45

His Cys Ser Ala Gly His Ser Cys Ile Phe Thr Val Ser Gly Thr Ser
        50                  55                  60

Ser Cys Cys Pro Phe Pro Glu Ala Val Ala Cys Gly Asp Gly His His
65                  70                  75                  80

Cys Cys Pro Arg Gly Phe His Cys Ser Ala Asp Gly Arg Ser Cys Phe
                85                  90                  95

Gln Arg Ser Gly Asn Asn Ser Val Gly Ala Ile Gln Cys Pro Asp Ser
                100                 105                 110

Gln Phe Glu Cys Pro Asp Phe Ser Thr Cys Cys Val Met Val Asp Gly
            115                 120                 125

Ser Trp Gly Cys Cys Pro Met Pro Gln Ala Ser Cys Cys Glu Asp Arg
        130                 135                 140

Val His Cys Cys Pro His Gly Ala Phe Cys Asp Leu Val His Thr Arg
145                 150                 155                 160

Cys Ile Thr Pro Thr Gly Thr His Pro Leu Ala Lys Lys Leu Pro Ala
                165                 170                 175

Gln Arg Thr Asn Arg Ala Val Ala Leu Ser Ser Ser Val Met Cys Pro
            180                 185                 190

Asp Ala Arg Ser Arg Cys Pro Asp Gly Ser Thr Cys Cys Glu Leu Pro
        195                 200                 205
```

-continued

```
Ser Gly Lys Tyr Gly Cys Cys Pro Met Pro Asn Ala Thr Cys Cys Ser
210                 215                 220
Asp His Leu His Cys Cys Pro Gln Asp Thr Val Cys Asp Leu Ile Gln
225                 230                 235                 240
Ser Lys Cys Leu Ser Lys Glu Asn Ala Thr Thr Asp Leu Leu Thr Lys
            245                 250                 255
Leu Pro Ala His Thr Val Gly Asp Val Lys Cys Asp Met Glu Val Ser
            260                 265                 270
Cys Pro Asp Gly Tyr Thr Cys Cys Arg Leu Gln Ser Gly Ala Trp Gly
            275                 280                 285
Cys Cys Pro Phe Thr Gln Ala Val Cys Cys Glu Asp His Ile His Cys
290                 295                 300
Cys Pro Ala Gly Phe Thr Cys Asp Thr Gln Lys Gly Thr Cys Glu Gln
305                 310                 315                 320
Gly Pro His Gln Val Pro Trp Met Glu Lys Ala Pro Ala His Leu Ser
            325                 330                 335
Leu Pro Asp Pro Gln Ala Leu Lys Arg Asp Val Pro Cys Asp Asn Val
            340                 345                 350
Ser Ser Cys Pro Ser Ser Asp Thr Cys Cys Gln Leu Thr Ser Gly Glu
355                 360                 365
Trp Gly Cys Cys Pro Ile Pro Glu Ala Val Cys Cys Ser Asp His Gln
370                 375                 380
His Cys Cys Pro Gln Gly Tyr Thr Cys Val Ala Glu Gly Gln Cys Gln
385                 390                 395                 400
Arg Gly Ser Glu Ile Val Ala Gly Leu Glu Lys Met Pro Ala Arg Arg
            405                 410                 415
Ala Ser Leu Ser His Pro Arg Asp Ile Gly Cys Asp Gln His Thr Ser
            420                 425                 430
Cys Pro Val Gly Gln Thr Cys Cys Pro Ser Leu Gly Gly Ser Trp Ala
            435                 440                 445
Cys Cys Gln Leu Pro His Ala Val Cys Cys Glu Asp Arg Gln His Cys
450                 455                 460
Cys Pro Ala Gly Tyr Thr Cys Asn Val Lys Ala Arg Ser Cys Glu Lys
465                 470                 475                 480
Glu Val Val Ser Ala Gln Pro Ala Thr Phe Leu Ala Arg Ser Pro His
            485                 490                 495
Val Gly Val Lys Asp Val Glu Cys Gly Glu Gly His Phe Cys His Asp
            500                 505                 510
Asn Gln Thr Cys Cys Arg Asp Asn Arg Gln Gly Trp Ala Cys Cys Pro
            515                 520                 525
Tyr Arg Gln Gly Val Cys Cys Ala Asp Arg Arg His Cys Cys Pro Ala
530                 535                 540
Gly Phe Arg Cys Ala Ala Arg Gly Thr Lys Cys Leu Arg Arg Glu Ala
545                 550                 555                 560
Pro Arg Trp Asp Ala Pro Leu Arg Asp Pro Ala Leu Arg Gln Phe Leu
            565                 570                 575
```

<210> SEQ ID NO 43
<211> LENGTH: 576
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 43

```
Thr Arg Cys Pro Asp Gly Gln Phe Cys Pro Val Ala Cys Cys Leu Asp
1               5                   10                  15
Pro Gly Gly Ala Ser Tyr Ser Cys Cys Arg Pro Leu Leu Asp Lys Trp
            20                  25                  30
Pro Thr Thr Leu Ser Arg His Leu Gly Gly Pro Cys Gln Val Asp Ala
        35                  40                  45
His Cys Ser Ala Gly His Ser Cys Ile Phe Thr Val Ser Gly Thr Ser
    50                  55                  60
Ser Cys Cys Pro Phe Pro Glu Ala Val Ala Cys Gly Asp Gly His His
65                  70                  75                  80
Cys Cys Pro Arg Gly Phe His Cys Ser Ala Asp Gly Arg Ser Cys Phe
                85                  90                  95
Gln Arg Ser Gly Asn Asn Ser Val Gly Ala Ile Gln Cys Pro Asp Ser
            100                 105                 110
Gln Phe Glu Cys Pro Asp Phe Ser Thr Cys Cys Val Met Val Asp Gly
        115                 120                 125
Ser Trp Gly Cys Cys Pro Met Pro Gln Ala Ser Cys Cys Glu Asp Arg
    130                 135                 140
Val His Cys Cys Pro His Gly Ala Phe Cys Asp Leu Val His Thr Arg
145                 150                 155                 160
Cys Ile Thr Pro Thr Gly Thr His Pro Leu Ala Lys Lys Leu Pro Ala
                165                 170                 175
Gln Arg Thr Asn Arg Ala Val Ala Leu Ser Ser Val Met Cys Pro
            180                 185                 190
Asp Ala Arg Ser Arg Cys Pro Asp Gly Ser Thr Cys Cys Glu Leu Pro
        195                 200                 205
Ser Gly Lys Tyr Gly Cys Cys Pro Met Pro Asn Ala Thr Cys Cys Ser
    210                 215                 220
Asp His Leu His Cys Cys Pro Gln Asp Thr Val Cys Asp Leu Ile Gln
225                 230                 235                 240
Ser Lys Cys Leu Ser Lys Glu Asn Ala Thr Thr Asp Leu Leu Thr Lys
                245                 250                 255
Leu Pro Ala His Thr Val Gly Asp Val Lys Cys Asp Met Glu Val Ser
            260                 265                 270
Cys Pro Asp Gly Tyr Thr Cys Cys Arg Leu Gln Ser Gly Ala Trp Gly
        275                 280                 285
Cys Cys Pro Phe Thr Gln Ala Val Cys Cys Glu Asp His Ile His Cys
    290                 295                 300
Cys Pro Ala Gly Phe Thr Cys Asp Thr Gln Lys Gly Thr Cys Glu Gln
305                 310                 315                 320
Gly Pro His Gln Val Pro Trp Met Glu Lys Ala Pro Ala His Leu Ser
                325                 330                 335
Leu Pro Asp Pro Gln Ala Leu Lys Arg Asp Val Pro Cys Asp Asn Val
            340                 345                 350
Ser Ser Cys Pro Ser Ser Asp Thr Cys Cys Gln Leu Thr Ser Gly Glu
        355                 360                 365
Trp Gly Cys Cys Pro Ile Pro Glu Ala Val Cys Cys Ser Asp His Gln
    370                 375                 380
His Cys Cys Pro Gln Gly Tyr Thr Cys Val Ala Glu Gly Gln Cys Gln
385                 390                 395                 400
Arg Gly Ser Glu Ile Val Ala Gly Leu Glu Lys Met Pro Ala Arg Arg
                405                 410                 415
```

```
Ala Ser Leu Ser His Pro Arg Asp Ile Gly Cys Asp Gln His Thr Ser
            420                 425                 430

Cys Pro Val Gly Gln Thr Cys Cys Pro Ser Leu Gly Gly Ser Trp Ala
            435                 440                 445

Cys Cys Gln Leu Pro His Ala Val Cys Glu Asp Arg Gln His Cys
            450                 455                 460

Cys Pro Ala Gly Tyr Thr Cys Asn Val Lys Ala Arg Ser Cys Glu Lys
465                 470                 475                 480

Glu Val Val Ser Ala Gln Pro Ala Thr Phe Leu Ala Arg Ser Pro His
                485                 490                 495

Val Gly Val Lys Asp Val Glu Cys Gly Glu Gly His Phe Cys His Asp
            500                 505                 510

Asn Gln Thr Cys Cys Arg Asp Asn Arg Gln Gly Trp Ala Cys Cys Pro
            515                 520                 525

Tyr Arg Gln Gly Val Cys Cys Ala Asp Arg Arg His Cys Cys Pro Ala
            530                 535                 540

Gly Phe Arg Cys Ala Ala Arg Gly Thr Lys Cys Leu Arg Arg Glu Ala
545                 550                 555                 560

Pro Arg Trp Asp Ala Pro Leu Arg Asp Pro Ala Leu Arg Leu Phe Leu
            565                 570                 575

<210> SEQ ID NO 44
<211> LENGTH: 576
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 44

Thr Arg Cys Pro Asp Gly Gln Phe Cys Pro Val Ala Cys Cys Leu Asp
1               5                   10                  15

Pro Gly Gly Ala Ser Tyr Ser Cys Cys Arg Pro Leu Leu Asp Lys Trp
            20                  25                  30

Pro Thr Thr Leu Ser Arg His Leu Gly Gly Pro Cys Gln Val Asp Ala
            35                  40                  45

His Cys Ser Ala Gly His Ser Cys Ile Phe Thr Val Ser Gly Thr Ser
            50                  55                  60

Ser Cys Cys Pro Phe Pro Glu Ala Val Ala Cys Gly Asp Gly His His
65                  70                  75                  80

Cys Cys Pro Arg Gly Phe His Cys Ser Ala Asp Gly Arg Ser Cys Phe
                85                  90                  95

Gln Arg Ser Gly Asn Asn Ser Val Gly Ala Ile Gln Cys Pro Asp Ser
            100                 105                 110

Gln Phe Glu Cys Pro Asp Phe Ser Thr Cys Cys Val Met Val Asp Gly
            115                 120                 125

Ser Trp Gly Cys Cys Pro Met Pro Gln Ala Ser Cys Cys Glu Asp Arg
            130                 135                 140

Val His Cys Cys Pro His Gly Ala Phe Cys Asp Leu Val His Thr Arg
145                 150                 155                 160

Cys Ile Thr Pro Thr Gly Thr His Pro Leu Ala Lys Lys Leu Pro Ala
                165                 170                 175

Gln Arg Thr Asn Arg Ala Val Ala Leu Ser Ser Ser Val Met Cys Pro
            180                 185                 190
```

```
Asp Ala Arg Ser Arg Cys Pro Asp Gly Ser Thr Cys Cys Glu Leu Pro
            195                 200                 205
Ser Gly Lys Tyr Gly Cys Cys Pro Met Pro Asn Ala Thr Cys Cys Ser
210                 215                 220
Asp His Leu His Cys Cys Pro Gln Asp Thr Val Cys Asp Leu Ile Gln
225                 230                 235                 240
Ser Lys Cys Leu Ser Lys Glu Asn Ala Thr Thr Asp Leu Leu Thr Lys
            245                 250                 255
Leu Pro Ala His Thr Val Gly Asp Val Lys Cys Asp Met Glu Val Ser
            260                 265                 270
Cys Pro Asp Gly Tyr Thr Cys Cys Arg Leu Gln Ser Gly Ala Trp Gly
            275                 280                 285
Cys Cys Pro Phe Thr Gln Ala Val Cys Cys Glu Asp His Ile His Cys
290                 295                 300
Cys Pro Ala Gly Phe Thr Cys Asp Thr Gln Lys Gly Thr Cys Glu Gln
305                 310                 315                 320
Gly Pro His Gln Val Pro Trp Met Glu Lys Ala Pro Ala His Leu Ser
            325                 330                 335
Leu Pro Asp Pro Gln Ala Leu Lys Arg Asp Val Pro Cys Asp Asn Val
            340                 345                 350
Ser Ser Cys Pro Ser Ser Asp Thr Cys Cys Gln Leu Thr Ser Gly Glu
            355                 360                 365
Trp Gly Cys Cys Pro Ile Pro Glu Ala Val Cys Cys Ser Asp His Gln
370                 375                 380
His Cys Cys Pro Gln Gly Tyr Thr Cys Val Ala Glu Gly Gln Cys Gln
385                 390                 395                 400
Arg Gly Ser Glu Ile Val Ala Gly Leu Glu Lys Met Pro Ala Arg Arg
            405                 410                 415
Ala Ser Leu Ser His Pro Arg Asp Ile Gly Cys Asp Gln His Thr Ser
            420                 425                 430
Cys Pro Val Gly Gln Thr Cys Cys Pro Ser Leu Gly Gly Ser Trp Ala
            435                 440                 445
Cys Cys Gln Leu Pro His Ala Val Cys Cys Glu Asp Arg Gln His Cys
450                 455                 460
Cys Pro Ala Gly Tyr Thr Cys Asn Val Lys Ala Arg Ser Cys Glu Lys
465                 470                 475                 480
Glu Val Val Ser Ala Gln Pro Ala Thr Phe Leu Ala Arg Ser Pro His
            485                 490                 495
Val Gly Val Lys Asp Val Glu Cys Gly Glu Gly His Phe Cys His Asp
            500                 505                 510
Asn Gln Thr Cys Cys Arg Asp Asn Arg Gln Gly Trp Ala Cys Cys Pro
            515                 520                 525
Tyr Arg Gln Gly Val Cys Cys Ala Asp Arg Arg His Cys Cys Pro Ala
530                 535                 540
Gly Phe Arg Cys Ala Ala Arg Gly Thr Lys Cys Leu Arg Arg Glu Ala
545                 550                 555                 560
Pro Arg Trp Asp Ala Pro Leu Arg Asp Pro Ala Leu Arg Phe Phe Leu
            565                 570                 575
```

<210> SEQ ID NO 45
<211> LENGTH: 576
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic polypeptide"

<400> SEQUENCE: 45

Thr Arg Cys Pro Asp Gly Gln Phe Cys Pro Val Ala Cys Cys Leu Asp
1               5                   10                  15

Pro Gly Gly Ala Ser Tyr Ser Cys Cys Arg Pro Leu Leu Asp Lys Trp
            20                  25                  30

Pro Thr Thr Leu Ser Arg His Leu Gly Gly Pro Cys Gln Val Asp Ala
        35                  40                  45

His Cys Ser Ala Gly His Ser Cys Ile Phe Thr Val Ser Gly Thr Ser
    50                  55                  60

Ser Cys Cys Pro Phe Pro Glu Ala Val Ala Cys Gly Asp Gly His His
65                  70                  75                  80

Cys Cys Pro Arg Gly Phe His Cys Ser Ala Asp Gly Arg Ser Cys Phe
                85                  90                  95

Gln Arg Ser Gly Asn Asn Ser Val Gly Ala Ile Gln Cys Pro Asp Ser
            100                 105                 110

Gln Phe Glu Cys Pro Asp Phe Ser Thr Cys Cys Val Met Val Asp Gly
        115                 120                 125

Ser Trp Gly Cys Cys Pro Met Pro Gln Ala Ser Cys Cys Glu Asp Arg
    130                 135                 140

Val His Cys Cys Pro His Gly Ala Phe Cys Asp Leu Val His Thr Arg
145                 150                 155                 160

Cys Ile Thr Pro Thr Gly Thr His Pro Leu Ala Lys Lys Leu Pro Ala
                165                 170                 175

Gln Arg Thr Asn Arg Ala Val Ala Leu Ser Ser Val Met Cys Pro
            180                 185                 190

Asp Ala Arg Ser Arg Cys Pro Asp Gly Ser Thr Cys Cys Glu Leu Pro
                195                 200                 205

Ser Gly Lys Tyr Gly Cys Cys Pro Met Pro Asn Ala Thr Cys Cys Ser
    210                 215                 220

Asp His Leu His Cys Cys Pro Gln Asp Thr Val Cys Asp Leu Ile Gln
225                 230                 235                 240

Ser Lys Cys Leu Ser Lys Glu Asn Ala Thr Thr Asp Leu Leu Thr Lys
                245                 250                 255

Leu Pro Ala His Thr Val Gly Asp Val Lys Cys Asp Met Glu Val Ser
                260                 265                 270

Cys Pro Asp Gly Tyr Thr Cys Cys Arg Leu Gln Ser Gly Ala Trp Gly
        275                 280                 285

Cys Cys Pro Phe Thr Gln Ala Val Cys Cys Glu Asp His Ile His Cys
    290                 295                 300

Cys Pro Ala Gly Phe Thr Cys Asp Thr Gln Lys Gly Thr Cys Glu Gln
305                 310                 315                 320

Gly Pro His Gln Val Pro Trp Met Glu Lys Ala Pro Ala His Leu Ser
                325                 330                 335

Leu Pro Asp Pro Gln Ala Leu Lys Arg Asp Val Pro Cys Asp Asn Val
            340                 345                 350

Ser Ser Cys Pro Ser Ser Asp Thr Cys Cys Gln Leu Thr Ser Gly Glu
        355                 360                 365

Trp Gly Cys Cys Pro Ile Pro Glu Ala Val Cys Cys Ser Asp His Gln
    370                 375                 380

His Cys Cys Pro Gln Gly Tyr Thr Cys Val Ala Glu Gly Gln Cys Gln
385                 390                 395                 400

```
Arg Gly Ser Glu Ile Val Ala Gly Leu Glu Lys Met Pro Ala Arg Arg
            405                 410                 415

Ala Ser Leu Ser His Pro Arg Asp Ile Gly Cys Asp Gln His Thr Ser
            420                 425                 430

Cys Pro Val Gly Gln Thr Cys Cys Pro Ser Leu Gly Gly Ser Trp Ala
            435                 440                 445

Cys Cys Gln Leu Pro His Ala Val Cys Cys Glu Asp Arg Gln His Cys
            450                 455                 460

Cys Pro Ala Gly Tyr Thr Cys Asn Val Lys Ala Arg Ser Cys Glu Lys
465                 470                 475                 480

Glu Val Val Ser Ala Gln Pro Ala Thr Phe Leu Ala Arg Ser Pro His
            485                 490                 495

Val Gly Val Lys Asp Val Glu Cys Gly Glu Gly His Phe Cys His Asp
            500                 505                 510

Asn Gln Thr Cys Cys Arg Asp Asn Arg Gln Gly Trp Ala Cys Cys Pro
            515                 520                 525

Tyr Arg Gln Gly Val Cys Cys Ala Asp Arg Arg His Cys Cys Pro Ala
            530                 535                 540

Gly Phe Arg Cys Ala Ala Arg Gly Thr Lys Cys Leu Arg Arg Glu Ala
545                 550                 555                 560

Pro Arg Trp Asp Ala Pro Leu Arg Asp Pro Ala Leu Arg Tyr Phe Leu
            565                 570                 575

<210> SEQ ID NO 46
<211> LENGTH: 576
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 46

Thr Arg Cys Pro Asp Gly Gln Phe Cys Pro Val Ala Cys Cys Leu Asp
1               5                   10                  15

Pro Gly Gly Ala Ser Tyr Ser Cys Cys Arg Pro Leu Leu Asp Lys Trp
            20                  25                  30

Pro Thr Thr Leu Ser Arg His Leu Gly Gly Pro Cys Gln Val Asp Ala
            35                  40                  45

His Cys Ser Ala Gly His Ser Cys Ile Phe Thr Val Ser Gly Thr Ser
        50                  55                  60

Ser Cys Cys Pro Phe Pro Glu Ala Val Ala Cys Gly Asp Gly His His
65                  70                  75                  80

Cys Cys Pro Arg Gly Phe His Cys Ser Ala Asp Gly Arg Ser Cys Phe
            85                  90                  95

Gln Arg Ser Gly Asn Asn Ser Val Gly Ala Ile Gln Cys Pro Asp Ser
            100                 105                 110

Gln Phe Glu Cys Pro Asp Phe Ser Thr Cys Cys Val Met Val Asp Gly
            115                 120                 125

Ser Trp Gly Cys Cys Pro Met Pro Gln Ala Ser Cys Cys Glu Asp Arg
        130                 135                 140

Val His Cys Cys Pro His Gly Ala Phe Cys Asp Leu Val His Thr Arg
145                 150                 155                 160

Cys Ile Thr Pro Thr Gly Thr His Pro Leu Ala Lys Lys Leu Pro Ala
            165                 170                 175
```

-continued

Gln Arg Thr Asn Arg Ala Val Ala Leu Ser Ser Val Met Cys Pro
                180                 185                 190

Asp Ala Arg Ser Arg Cys Pro Asp Gly Ser Thr Cys Cys Glu Leu Pro
            195                 200                 205

Ser Gly Lys Tyr Gly Cys Cys Pro Met Pro Asn Ala Thr Cys Cys Ser
        210                 215                 220

Asp His Leu His Cys Cys Pro Gln Asp Thr Val Cys Asp Leu Ile Gln
225                 230                 235                 240

Ser Lys Cys Leu Ser Lys Glu Asn Ala Thr Thr Asp Leu Leu Thr Lys
                245                 250                 255

Leu Pro Ala His Thr Val Gly Asp Val Lys Cys Asp Met Glu Val Ser
            260                 265                 270

Cys Pro Asp Gly Tyr Thr Cys Cys Arg Leu Gln Ser Gly Ala Trp Gly
        275                 280                 285

Cys Cys Pro Phe Thr Gln Ala Val Cys Cys Glu Asp His Ile His Cys
        290                 295                 300

Cys Pro Ala Gly Phe Thr Cys Asp Thr Gln Lys Gly Thr Cys Glu Gln
305                 310                 315                 320

Gly Pro His Gln Val Pro Trp Met Glu Lys Ala Pro Ala His Leu Ser
                325                 330                 335

Leu Pro Asp Pro Gln Ala Leu Lys Arg Asp Val Pro Cys Asp Asn Val
            340                 345                 350

Ser Ser Cys Pro Ser Ser Asp Thr Cys Cys Gln Leu Thr Ser Gly Glu
        355                 360                 365

Trp Gly Cys Cys Pro Ile Pro Glu Ala Val Cys Cys Ser Asp His Gln
370                 375                 380

His Cys Cys Pro Gln Gly Tyr Thr Cys Val Ala Glu Gly Gln Cys Gln
385                 390                 395                 400

Arg Gly Ser Glu Ile Val Ala Gly Leu Glu Lys Met Pro Ala Arg Arg
                405                 410                 415

Ala Ser Leu Ser His Pro Arg Asp Ile Gly Cys Asp Gln His Thr Ser
            420                 425                 430

Cys Pro Val Gly Gln Thr Cys Cys Pro Ser Leu Gly Gly Ser Trp Ala
        435                 440                 445

Cys Cys Gln Leu Pro His Ala Val Cys Cys Glu Asp Arg Gln His Cys
450                 455                 460

Cys Pro Ala Gly Tyr Thr Cys Asn Val Lys Ala Arg Ser Cys Glu Lys
465                 470                 475                 480

Glu Val Val Ser Ala Gln Pro Ala Thr Phe Leu Ala Arg Ser Pro His
                485                 490                 495

Val Gly Val Lys Asp Val Glu Cys Gly Glu Gly His Phe Cys His Asp
            500                 505                 510

Asn Gln Thr Cys Cys Arg Asp Asn Arg Gln Gly Trp Ala Cys Cys Pro
        515                 520                 525

Tyr Arg Gln Gly Val Cys Cys Ala Asp Arg Arg His Cys Cys Pro Ala
530                 535                 540

Gly Phe Arg Cys Ala Ala Arg Gly Thr Lys Cys Leu Arg Arg Glu Ala
545                 550                 555                 560

Pro Arg Trp Asp Ala Pro Leu Arg Asp Pro Ala Leu Arg Arg Gln Leu
                565                 570                 575

<210> SEQ ID NO 47
<211> LENGTH: 576
<212> TYPE: PRT

<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 47

```
Thr Arg Cys Pro Asp Gly Gln Phe Cys Pro Val Ala Cys Cys Leu Asp
1               5                   10                  15

Pro Gly Gly Ala Ser Tyr Ser Cys Cys Arg Pro Leu Leu Asp Lys Trp
            20                  25                  30

Pro Thr Thr Leu Ser Arg His Leu Gly Gly Pro Cys Gln Val Asp Ala
        35                  40                  45

His Cys Ser Ala Gly His Ser Cys Ile Phe Thr Val Ser Gly Thr Ser
    50                  55                  60

Ser Cys Cys Pro Phe Pro Glu Ala Val Ala Cys Gly Asp Gly His His
65                  70                  75                  80

Cys Cys Pro Arg Gly Phe His Cys Ser Ala Asp Gly Arg Ser Cys Phe
                85                  90                  95

Gln Arg Ser Gly Asn Asn Ser Val Gly Ala Ile Gln Cys Pro Asp Ser
            100                 105                 110

Gln Phe Glu Cys Pro Asp Phe Ser Thr Cys Cys Val Met Val Asp Gly
        115                 120                 125

Ser Trp Gly Cys Cys Pro Met Pro Gln Ala Ser Cys Cys Glu Asp Arg
    130                 135                 140

Val His Cys Cys Pro His Gly Ala Phe Cys Asp Leu Val His Thr Arg
145                 150                 155                 160

Cys Ile Thr Pro Thr Gly Thr His Pro Leu Ala Lys Lys Leu Pro Ala
                165                 170                 175

Gln Arg Thr Asn Arg Ala Val Ala Leu Ser Ser Ser Val Met Cys Pro
            180                 185                 190

Asp Ala Arg Ser Arg Cys Pro Asp Gly Ser Thr Cys Cys Glu Leu Pro
        195                 200                 205

Ser Gly Lys Tyr Gly Cys Cys Pro Met Pro Asn Ala Thr Cys Cys Ser
    210                 215                 220

Asp His Leu His Cys Cys Pro Gln Asp Thr Val Cys Asp Leu Ile Gln
225                 230                 235                 240

Ser Lys Cys Leu Ser Lys Glu Asn Ala Thr Thr Asp Leu Leu Thr Lys
                245                 250                 255

Leu Pro Ala His Thr Val Gly Asp Val Lys Cys Asp Met Glu Val Ser
            260                 265                 270

Cys Pro Asp Gly Tyr Thr Cys Cys Arg Leu Gln Ser Gly Ala Trp Gly
        275                 280                 285

Cys Cys Pro Phe Thr Gln Ala Val Cys Cys Glu Asp His Ile His Cys
    290                 295                 300

Cys Pro Ala Gly Phe Thr Cys Asp Thr Gln Lys Gly Thr Cys Glu Gln
305                 310                 315                 320

Gly Pro His Gln Val Pro Trp Met Glu Lys Ala Pro Ala His Leu Ser
                325                 330                 335

Leu Pro Asp Pro Gln Ala Leu Lys Arg Asp Val Pro Cys Asp Asn Val
            340                 345                 350

Ser Ser Cys Pro Ser Ser Asp Thr Cys Cys Gln Leu Thr Ser Gly Glu
        355                 360                 365

Trp Gly Cys Cys Pro Ile Pro Glu Ala Val Cys Cys Ser Asp His Gln
    370                 375                 380
```

His Cys Cys Pro Gln Gly Tyr Thr Cys Val Ala Glu Gly Gln Cys Gln
385                 390                 395                 400

Arg Gly Ser Glu Ile Val Ala Gly Leu Glu Lys Met Pro Ala Arg Arg
            405                 410                 415

Ala Ser Leu Ser His Pro Arg Asp Ile Gly Cys Asp Gln His Thr Ser
            420                 425                 430

Cys Pro Val Gly Gln Thr Cys Cys Pro Ser Leu Gly Gly Ser Trp Ala
            435                 440                 445

Cys Cys Gln Leu Pro His Ala Val Cys Cys Glu Asp Arg Gln His Cys
            450                 455                 460

Cys Pro Ala Gly Tyr Thr Cys Asn Val Lys Ala Arg Ser Cys Glu Lys
465                 470                 475                 480

Glu Val Val Ser Ala Gln Pro Ala Thr Phe Leu Ala Arg Ser Pro His
            485                 490                 495

Val Gly Val Lys Asp Val Glu Cys Gly Glu Gly His Phe Cys His Asp
            500                 505                 510

Asn Gln Thr Cys Cys Arg Asp Asn Arg Gln Gly Trp Ala Cys Cys Pro
            515                 520                 525

Tyr Arg Gln Gly Val Cys Cys Ala Asp Arg Arg His Cys Cys Pro Ala
530                 535                 540

Gly Phe Arg Cys Ala Ala Arg Gly Thr Lys Cys Leu Arg Arg Glu Ala
545                 550                 555                 560

Pro Arg Trp Asp Ala Pro Leu Arg Asp Pro Ala Leu Arg His Gln Leu
            565                 570                 575

<210> SEQ ID NO 48
<211> LENGTH: 576
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 48

Thr Arg Cys Pro Asp Gly Gln Phe Cys Pro Val Ala Cys Cys Leu Asp
1               5                   10                  15

Pro Gly Gly Ala Ser Tyr Ser Cys Cys Arg Pro Leu Leu Asp Lys Trp
            20                  25                  30

Pro Thr Thr Leu Ser Arg His Leu Gly Gly Pro Cys Gln Val Asp Ala
            35                  40                  45

His Cys Ser Ala Gly His Ser Cys Ile Phe Thr Val Ser Gly Thr Ser
        50                  55                  60

Ser Cys Cys Pro Phe Pro Glu Ala Val Ala Cys Gly Asp Gly His His
65                  70                  75                  80

Cys Cys Pro Arg Gly Phe His Cys Ser Ala Asp Gly Arg Ser Cys Phe
            85                  90                  95

Gln Arg Ser Gly Asn Asn Ser Val Gly Ala Ile Gln Cys Pro Asp Ser
            100                 105                 110

Gln Phe Glu Cys Pro Asp Phe Ser Thr Cys Cys Val Met Val Asp Gly
            115                 120                 125

Ser Trp Gly Cys Cys Pro Met Pro Gln Ala Ser Cys Cys Glu Asp Arg
        130                 135                 140

Val His Cys Cys Pro His Gly Ala Phe Cys Asp Leu Val His Thr Arg
145                 150                 155                 160

```
Cys Ile Thr Pro Thr Gly Thr His Pro Leu Ala Lys Lys Leu Pro Ala
                165                 170                 175
Gln Arg Thr Asn Arg Ala Val Ala Leu Ser Ser Val Met Cys Pro
            180                 185                 190
Asp Ala Arg Ser Arg Cys Pro Asp Gly Ser Thr Cys Cys Glu Leu Pro
            195                 200                 205
Ser Gly Lys Tyr Gly Cys Cys Pro Met Pro Asn Ala Thr Cys Cys Ser
        210                 215                 220
Asp His Leu His Cys Cys Pro Gln Asp Thr Val Cys Asp Leu Ile Gln
225                 230                 235                 240
Ser Lys Cys Leu Ser Lys Glu Asn Ala Thr Thr Asp Leu Leu Thr Lys
                245                 250                 255
Leu Pro Ala His Thr Val Gly Asp Val Lys Cys Asp Met Glu Val Ser
                260                 265                 270
Cys Pro Asp Gly Tyr Thr Cys Arg Leu Gln Ser Gly Ala Trp Gly
                275                 280                 285
Cys Cys Pro Phe Thr Gln Ala Val Cys Cys Glu Asp His Ile His Cys
        290                 295                 300
Cys Pro Ala Gly Phe Thr Cys Asp Thr Gln Lys Gly Thr Cys Glu Gln
305                 310                 315                 320
Gly Pro His Gln Val Pro Trp Met Glu Lys Ala Pro Ala His Leu Ser
                325                 330                 335
Leu Pro Asp Pro Gln Ala Leu Lys Arg Asp Val Pro Cys Asp Asn Val
                340                 345                 350
Ser Ser Cys Pro Ser Ser Asp Thr Cys Cys Gln Leu Thr Ser Gly Glu
                355                 360                 365
Trp Gly Cys Cys Pro Ile Pro Glu Ala Val Cys Cys Ser Asp His Gln
        370                 375                 380
His Cys Cys Pro Gln Gly Tyr Thr Cys Val Ala Glu Gly Gln Cys Gln
385                 390                 395                 400
Arg Gly Ser Glu Ile Val Ala Gly Leu Glu Lys Met Pro Ala Arg Arg
                405                 410                 415
Ala Ser Leu Ser His Pro Arg Asp Ile Gly Cys Asp Gln His Thr Ser
                420                 425                 430
Cys Pro Val Gly Gln Thr Cys Cys Pro Ser Leu Gly Gly Ser Trp Ala
        435                 440                 445
Cys Cys Gln Leu Pro His Ala Val Cys Cys Glu Asp Arg Gln His Cys
        450                 455                 460
Cys Pro Ala Gly Tyr Thr Cys Asn Val Lys Ala Arg Ser Cys Glu Lys
465                 470                 475                 480
Glu Val Val Ser Ala Gln Pro Ala Thr Phe Leu Ala Arg Ser Pro His
                485                 490                 495
Val Gly Val Lys Asp Val Glu Cys Gly Glu Gly His Phe Cys His Asp
                500                 505                 510
Asn Gln Thr Cys Cys Arg Asp Asn Arg Gln Gly Trp Ala Cys Cys Pro
        515                 520                 525
Tyr Arg Gln Gly Val Cys Cys Ala Asp Arg Arg His Cys Cys Pro Ala
        530                 535                 540
Gly Phe Arg Cys Ala Ala Arg Gly Thr Lys Cys Leu Arg Arg Glu Ala
545                 550                 555                 560
Pro Arg Trp Asp Ala Pro Leu Arg Asp Pro Ala Leu Arg Lys Gln Leu
                565                 570                 575
```

-continued

```
<210> SEQ ID NO 49
<211> LENGTH: 576
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 49
```

Thr Arg Cys Pro Asp Gly Gln Phe Cys Pro Val Ala Cys Cys Leu Asp
1               5                   10                  15

Pro Gly Gly Ala Ser Tyr Ser Cys Cys Arg Pro Leu Leu Asp Lys Trp
            20                  25                  30

Pro Thr Thr Leu Ser Arg His Leu Gly Gly Pro Cys Gln Val Asp Ala
        35                  40                  45

His Cys Ser Ala Gly His Ser Cys Ile Phe Thr Val Ser Gly Thr Ser
    50                  55                  60

Ser Cys Cys Pro Phe Pro Glu Ala Val Ala Cys Gly Asp Gly His His
65                  70                  75                  80

Cys Cys Pro Arg Gly Phe His Cys Ser Ala Asp Gly Arg Ser Cys Phe
                85                  90                  95

Gln Arg Ser Gly Asn Asn Ser Val Gly Ala Ile Gln Cys Pro Asp Ser
            100                 105                 110

Gln Phe Glu Cys Pro Asp Phe Ser Thr Cys Cys Val Met Val Asp Gly
        115                 120                 125

Ser Trp Gly Cys Cys Pro Met Pro Gln Ala Ser Cys Cys Glu Asp Arg
    130                 135                 140

Val His Cys Cys Pro His Gly Ala Phe Cys Asp Leu Val His Thr Arg
145                 150                 155                 160

Cys Ile Thr Pro Thr Gly Thr His Pro Leu Ala Lys Lys Leu Pro Ala
                165                 170                 175

Gln Arg Thr Asn Arg Ala Val Ala Leu Ser Ser Ser Val Met Cys Pro
            180                 185                 190

Asp Ala Arg Ser Arg Cys Pro Asp Gly Ser Thr Cys Cys Glu Leu Pro
        195                 200                 205

Ser Gly Lys Tyr Gly Cys Cys Pro Met Pro Asn Ala Thr Cys Cys Ser
    210                 215                 220

Asp His Leu His Cys Cys Pro Gln Asp Thr Val Cys Asp Leu Ile Gln
225                 230                 235                 240

Ser Lys Cys Leu Ser Lys Glu Asn Ala Thr Thr Asp Leu Leu Thr Lys
                245                 250                 255

Leu Pro Ala His Thr Val Gly Asp Val Lys Cys Asp Met Glu Val Ser
            260                 265                 270

Cys Pro Asp Gly Tyr Thr Cys Cys Arg Leu Gln Ser Gly Ala Trp Gly
        275                 280                 285

Cys Cys Pro Phe Thr Gln Ala Val Cys Cys Glu Asp His Ile His Cys
    290                 295                 300

Cys Pro Ala Gly Phe Thr Cys Asp Thr Gln Lys Gly Thr Cys Glu Gln
305                 310                 315                 320

Gly Pro His Gln Val Pro Trp Met Glu Lys Ala Pro Ala His Leu Ser
                325                 330                 335

Leu Pro Asp Pro Gln Ala Leu Lys Arg Asp Val Pro Cys Asp Asn Val
            340                 345                 350

Ser Ser Cys Pro Ser Ser Asp Thr Cys Cys Gln Leu Thr Ser Gly Glu
        355                 360                 365

Trp Gly Cys Cys Pro Ile Pro Glu Ala Val Cys Cys Ser Asp His Gln
            370                 375                 380

His Cys Cys Pro Gln Gly Tyr Thr Cys Val Ala Glu Gly Gln Cys Gln
385                 390                 395                 400

Arg Gly Ser Glu Ile Val Ala Gly Leu Glu Lys Met Pro Ala Arg Arg
                405                 410                 415

Ala Ser Leu Ser His Pro Arg Asp Ile Gly Cys Asp Gln His Thr Ser
                420                 425                 430

Cys Pro Val Gly Gln Thr Cys Cys Pro Ser Leu Gly Gly Ser Trp Ala
            435                 440                 445

Cys Cys Gln Leu Pro His Ala Val Cys Cys Glu Asp Arg Gln His Cys
450                 455                 460

Cys Pro Ala Gly Tyr Thr Cys Asn Val Lys Ala Arg Ser Cys Glu Lys
465                 470                 475                 480

Glu Val Val Ser Ala Gln Pro Ala Thr Phe Leu Ala Arg Ser Pro His
                485                 490                 495

Val Gly Val Lys Asp Val Glu Cys Gly Glu Gly His Phe Cys His Asp
                500                 505                 510

Asn Gln Thr Cys Cys Arg Asp Asn Arg Gln Gly Trp Ala Cys Cys Pro
            515                 520                 525

Tyr Arg Gln Gly Val Cys Cys Ala Asp Arg Arg His Cys Cys Pro Ala
530                 535                 540

Gly Phe Arg Cys Ala Ala Arg Gly Thr Lys Cys Leu Arg Arg Glu Ala
545                 550                 555                 560

Pro Arg Trp Asp Ala Pro Leu Arg Asp Pro Ala Leu Arg Asp Gln Leu
                565                 570                 575

<210> SEQ ID NO 50
<211> LENGTH: 576
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 50

Thr Arg Cys Pro Asp Gly Gln Phe Cys Pro Val Ala Cys Cys Leu Asp
1               5                   10                  15

Pro Gly Gly Ala Ser Tyr Ser Cys Cys Arg Pro Leu Leu Asp Lys Trp
                20                  25                  30

Pro Thr Thr Leu Ser Arg His Leu Gly Gly Pro Cys Gln Val Asp Ala
            35                  40                  45

His Cys Ser Ala Gly His Ser Cys Ile Phe Thr Val Ser Gly Thr Ser
50                  55                  60

Ser Cys Cys Pro Phe Pro Glu Ala Val Ala Cys Gly Asp Gly His His
65                  70                  75                  80

Cys Cys Pro Arg Gly Phe His Cys Ser Ala Asp Gly Arg Ser Cys Phe
                85                  90                  95

Gln Arg Ser Gly Asn Asn Ser Val Gly Ala Ile Gln Cys Pro Asp Ser
                100                 105                 110

Gln Phe Glu Cys Pro Asp Phe Ser Thr Cys Cys Val Met Val Asp Gly
            115                 120                 125

Ser Trp Gly Cys Cys Pro Met Pro Gln Ala Ser Cys Cys Glu Asp Arg
            130                 135                 140

```
Val His Cys Cys Pro His Gly Ala Phe Cys Asp Leu Val His Thr Arg
145                 150                 155                 160

Cys Ile Thr Pro Thr Gly Thr His Pro Leu Ala Lys Lys Leu Pro Ala
                165                 170                 175

Gln Arg Thr Asn Arg Ala Val Ala Leu Ser Ser Val Met Cys Pro
            180                 185                 190

Asp Ala Arg Ser Arg Cys Pro Asp Gly Ser Thr Cys Cys Glu Leu Pro
            195                 200                 205

Ser Gly Lys Tyr Gly Cys Cys Pro Met Pro Asn Ala Thr Cys Cys Ser
    210                 215                 220

Asp His Leu His Cys Cys Pro Gln Asp Thr Val Cys Asp Leu Ile Gln
225                 230                 235                 240

Ser Lys Cys Leu Ser Lys Glu Asn Ala Thr Thr Asp Leu Leu Thr Lys
                245                 250                 255

Leu Pro Ala His Thr Val Gly Asp Val Lys Cys Asp Met Glu Val Ser
                260                 265                 270

Cys Pro Asp Gly Tyr Thr Cys Cys Arg Leu Gln Ser Gly Ala Trp Gly
        275                 280                 285

Cys Cys Pro Phe Thr Gln Ala Val Cys Cys Glu Asp His Ile His Cys
        290                 295                 300

Cys Pro Ala Gly Phe Thr Cys Asp Thr Gln Lys Gly Thr Cys Glu Gln
305                 310                 315                 320

Gly Pro His Gln Val Pro Trp Met Glu Lys Ala Pro Ala His Leu Ser
                325                 330                 335

Leu Pro Asp Pro Gln Ala Leu Lys Arg Asp Val Pro Cys Asp Asn Val
                340                 345                 350

Ser Ser Cys Pro Ser Ser Asp Thr Cys Cys Gln Leu Thr Ser Gly Glu
        355                 360                 365

Trp Gly Cys Cys Pro Ile Pro Glu Ala Val Cys Cys Ser Asp His Gln
    370                 375                 380

His Cys Cys Pro Gln Gly Tyr Thr Cys Val Ala Glu Gly Gln Cys Gln
385                 390                 395                 400

Arg Gly Ser Glu Ile Val Ala Gly Leu Glu Lys Met Pro Ala Arg Arg
                405                 410                 415

Ala Ser Leu Ser His Pro Arg Asp Ile Gly Cys Asp Gln His Thr Ser
                420                 425                 430

Cys Pro Val Gly Gln Thr Cys Cys Pro Ser Leu Gly Gly Ser Trp Ala
        435                 440                 445

Cys Cys Gln Leu Pro His Ala Val Cys Cys Glu Asp Arg Gln His Cys
    450                 455                 460

Cys Pro Ala Gly Tyr Thr Cys Asn Val Lys Ala Arg Ser Cys Glu Lys
465                 470                 475                 480

Glu Val Val Ser Ala Gln Pro Ala Thr Phe Leu Ala Arg Ser Pro His
                485                 490                 495

Val Gly Val Lys Asp Val Glu Cys Gly Glu Gly His Phe Cys His Asp
                500                 505                 510

Asn Gln Thr Cys Cys Arg Asp Asn Arg Gln Gly Trp Ala Cys Cys Pro
            515                 520                 525

Tyr Arg Gln Gly Val Cys Cys Ala Asp Arg Arg His Cys Cys Pro Ala
        530                 535                 540

Gly Phe Arg Cys Ala Ala Arg Gly Thr Lys Cys Leu Arg Arg Glu Ala
545                 550                 555                 560
```

Pro Arg Trp Asp Ala Pro Leu Arg Asp Pro Ala Leu Arg Glu Gln Leu
             565                 570                 575

<210> SEQ ID NO 51
<211> LENGTH: 576
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 51

Thr Arg Cys Pro Asp Gly Gln Phe Cys Pro Val Ala Cys Cys Leu Asp
1               5                   10                  15

Pro Gly Gly Ala Ser Tyr Ser Cys Cys Arg Pro Leu Leu Asp Lys Trp
            20                  25                  30

Pro Thr Thr Leu Ser Arg His Leu Gly Gly Pro Cys Gln Val Asp Ala
        35                  40                  45

His Cys Ser Ala Gly His Ser Cys Ile Phe Thr Val Ser Gly Thr Ser
    50                  55                  60

Ser Cys Cys Pro Phe Pro Glu Ala Val Ala Cys Gly Asp Gly His His
65                  70                  75                  80

Cys Cys Pro Arg Gly Phe His Cys Ser Ala Asp Gly Arg Ser Cys Phe
                85                  90                  95

Gln Arg Ser Gly Asn Asn Ser Val Gly Ala Ile Gln Cys Pro Asp Ser
            100                 105                 110

Gln Phe Glu Cys Pro Asp Phe Ser Thr Cys Cys Val Met Val Asp Gly
        115                 120                 125

Ser Trp Gly Cys Cys Pro Met Pro Gln Ala Ser Cys Cys Glu Asp Arg
    130                 135                 140

Val His Cys Cys Pro His Gly Ala Phe Cys Asp Leu Val His Thr Arg
145                 150                 155                 160

Cys Ile Thr Pro Thr Gly Thr His Pro Leu Ala Lys Lys Leu Pro Ala
                165                 170                 175

Gln Arg Thr Asn Arg Ala Val Ala Leu Ser Ser Ser Val Met Cys Pro
            180                 185                 190

Asp Ala Arg Ser Arg Cys Pro Asp Gly Ser Thr Cys Cys Glu Leu Pro
        195                 200                 205

Ser Gly Lys Tyr Gly Cys Cys Pro Met Pro Asn Ala Thr Cys Cys Ser
    210                 215                 220

Asp His Leu His Cys Cys Pro Gln Asp Thr Val Cys Asp Leu Ile Gln
225                 230                 235                 240

Ser Lys Cys Leu Ser Lys Glu Asn Ala Thr Thr Asp Leu Leu Thr Lys
                245                 250                 255

Leu Pro Ala His Thr Val Gly Asp Val Lys Cys Asp Met Glu Val Ser
            260                 265                 270

Cys Pro Asp Gly Tyr Thr Cys Cys Arg Leu Gln Ser Gly Ala Trp Gly
        275                 280                 285

Cys Cys Pro Phe Thr Gln Ala Val Cys Cys Glu Asp His Ile His Cys
    290                 295                 300

Cys Pro Ala Gly Phe Thr Cys Asp Thr Gln Lys Gly Thr Cys Glu Gln
305                 310                 315                 320

Gly Pro His Gln Val Pro Trp Met Glu Lys Ala Pro Ala His Leu Ser
                325                 330                 335

```
Leu Pro Asp Pro Gln Ala Leu Lys Arg Asp Val Pro Cys Asp Asn Val
            340                 345                 350

Ser Ser Cys Pro Ser Ser Asp Thr Cys Cys Gln Leu Thr Ser Gly Glu
        355                 360                 365

Trp Gly Cys Cys Pro Ile Pro Glu Ala Val Cys Cys Ser Asp His Gln
    370                 375                 380

His Cys Cys Pro Gln Gly Tyr Thr Cys Val Ala Glu Gly Gln Cys Gln
385                 390                 395                 400

Arg Gly Ser Glu Ile Val Ala Gly Leu Glu Lys Met Pro Ala Arg Arg
                405                 410                 415

Ala Ser Leu Ser His Pro Arg Asp Ile Gly Cys Asp Gln His Thr Ser
            420                 425                 430

Cys Pro Val Gly Gln Thr Cys Cys Pro Ser Leu Gly Gly Ser Trp Ala
        435                 440                 445

Cys Cys Gln Leu Pro His Ala Val Cys Cys Glu Asp Arg Gln His Cys
    450                 455                 460

Cys Pro Ala Gly Tyr Thr Cys Asn Val Lys Ala Arg Ser Cys Glu Lys
465                 470                 475                 480

Glu Val Val Ser Ala Gln Pro Ala Thr Phe Leu Ala Arg Ser Pro His
                485                 490                 495

Val Gly Val Lys Asp Val Glu Cys Gly Glu Gly His Phe Cys His Asp
            500                 505                 510

Asn Gln Thr Cys Cys Arg Asp Asn Arg Gln Gly Trp Ala Cys Cys Pro
        515                 520                 525

Tyr Arg Gln Gly Val Cys Cys Ala Asp Arg Arg His Cys Cys Pro Ala
    530                 535                 540

Gly Phe Arg Cys Ala Ala Arg Gly Thr Lys Cys Leu Arg Arg Glu Ala
545                 550                 555                 560

Pro Arg Trp Asp Ala Pro Leu Arg Asp Pro Ala Leu Arg Asn Gln Leu
                565                 570                 575

<210> SEQ ID NO 52
<211> LENGTH: 576
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 52

Thr Arg Cys Pro Asp Gly Gln Phe Cys Pro Val Ala Cys Cys Leu Asp
1               5                   10                  15

Pro Gly Gly Ala Ser Tyr Ser Cys Cys Arg Pro Leu Leu Asp Lys Trp
                20                  25                  30

Pro Thr Thr Leu Ser Arg His Leu Gly Gly Pro Cys Gln Val Asp Ala
            35                  40                  45

His Cys Ser Ala Gly His Ser Cys Ile Phe Thr Val Ser Gly Thr Ser
        50                  55                  60

Ser Cys Cys Pro Phe Pro Glu Ala Val Ala Cys Gly Asp Gly His His
65                  70                  75                  80

Cys Cys Pro Arg Gly Phe His Cys Ser Ala Asp Gly Arg Ser Cys Phe
                85                  90                  95

Gln Arg Ser Gly Asn Asn Ser Val Gly Ala Ile Gln Cys Pro Asp Ser
            100                 105                 110
```

-continued

```
Gln Phe Glu Cys Pro Asp Phe Ser Thr Cys Cys Val Met Val Asp Gly
            115                 120                 125

Ser Trp Gly Cys Cys Pro Met Pro Gln Ala Ser Cys Cys Glu Asp Arg
    130                 135                 140

Val His Cys Cys Pro His Gly Ala Phe Cys Asp Leu Val His Thr Arg
145                 150                 155                 160

Cys Ile Thr Pro Thr Gly Thr His Pro Leu Ala Lys Lys Leu Pro Ala
                165                 170                 175

Gln Arg Thr Asn Arg Ala Val Ala Leu Ser Ser Val Met Cys Pro
            180                 185                 190

Asp Ala Arg Ser Arg Cys Pro Asp Gly Ser Thr Cys Cys Glu Leu Pro
                195                 200                 205

Ser Gly Lys Tyr Gly Cys Cys Pro Met Pro Asn Ala Thr Cys Cys Ser
    210                 215                 220

Asp His Leu His Cys Cys Pro Gln Asp Thr Val Cys Asp Leu Ile Gln
225                 230                 235                 240

Ser Lys Cys Leu Ser Lys Glu Asn Ala Thr Thr Asp Leu Leu Thr Lys
                245                 250                 255

Leu Pro Ala His Thr Val Gly Asp Val Lys Cys Asp Met Glu Val Ser
            260                 265                 270

Cys Pro Asp Gly Tyr Thr Cys Cys Arg Leu Gln Ser Gly Ala Trp Gly
    275                 280                 285

Cys Cys Pro Phe Thr Gln Ala Val Cys Cys Glu Asp His Ile His Cys
    290                 295                 300

Cys Pro Ala Gly Phe Thr Cys Asp Thr Gln Lys Gly Thr Cys Glu Gln
305                 310                 315                 320

Gly Pro His Gln Val Pro Trp Met Glu Lys Ala Pro Ala His Leu Ser
                325                 330                 335

Leu Pro Asp Pro Gln Ala Leu Lys Arg Asp Val Pro Cys Asp Asn Val
            340                 345                 350

Ser Ser Cys Pro Ser Ser Asp Thr Cys Cys Gln Leu Thr Ser Gly Glu
    355                 360                 365

Trp Gly Cys Cys Pro Ile Pro Glu Ala Val Cys Cys Ser Asp His Gln
    370                 375                 380

His Cys Cys Pro Gln Gly Tyr Thr Cys Val Ala Glu Gly Gln Cys Gln
385                 390                 395                 400

Arg Gly Ser Glu Ile Val Ala Gly Leu Glu Lys Met Pro Ala Arg Arg
                405                 410                 415

Ala Ser Leu Ser His Pro Arg Asp Ile Gly Cys Asp Gln His Thr Ser
            420                 425                 430

Cys Pro Val Gly Gln Thr Cys Cys Pro Ser Leu Gly Gly Ser Trp Ala
    435                 440                 445

Cys Cys Gln Leu Pro His Ala Val Cys Cys Glu Asp Arg Gln His Cys
    450                 455                 460

Cys Pro Ala Gly Tyr Thr Cys Asn Val Lys Ala Arg Ser Cys Glu Lys
465                 470                 475                 480

Glu Val Val Ser Ala Gln Pro Ala Thr Phe Leu Ala Arg Ser Pro His
                485                 490                 495

Val Gly Val Lys Asp Val Glu Cys Gly Glu Gly His Phe Cys His Asp
            500                 505                 510

Asn Gln Thr Cys Cys Arg Asp Asn Arg Gln Gly Trp Ala Cys Cys Pro
            515                 520                 525
```

```
Tyr Arg Gln Gly Val Cys Cys Ala Asp Arg Arg His Cys Cys Pro Ala
            530                 535                 540

Gly Phe Arg Cys Ala Ala Arg Gly Thr Lys Cys Leu Arg Arg Glu Ala
545                 550                 555                 560

Pro Arg Trp Asp Ala Pro Leu Arg Asp Pro Ala Leu Arg Leu Gln Leu
                565                 570                 575
```

<210> SEQ ID NO 53
<211> LENGTH: 576
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 53

```
Thr Arg Cys Pro Asp Gly Gln Phe Cys Pro Val Ala Cys Cys Leu Asp
1               5                   10                  15

Pro Gly Gly Ala Ser Tyr Ser Cys Cys Arg Pro Leu Leu Asp Lys Trp
            20                  25                  30

Pro Thr Thr Leu Ser Arg His Leu Gly Gly Pro Cys Gln Val Asp Ala
        35                  40                  45

His Cys Ser Ala Gly His Ser Cys Ile Phe Thr Val Ser Gly Thr Ser
 50                  55                  60

Ser Cys Cys Pro Phe Pro Glu Ala Val Ala Cys Gly Asp Gly His His
65                  70                  75                  80

Cys Cys Pro Arg Gly Phe His Cys Ser Ala Asp Gly Arg Ser Cys Phe
                85                  90                  95

Gln Arg Ser Gly Asn Asn Ser Val Gly Ala Ile Gln Cys Pro Asp Ser
            100                 105                 110

Gln Phe Glu Cys Pro Asp Phe Ser Thr Cys Cys Val Met Val Asp Gly
        115                 120                 125

Ser Trp Gly Cys Cys Pro Met Pro Gln Ala Ser Cys Cys Glu Asp Arg
130                 135                 140

Val His Cys Cys Pro His Gly Ala Phe Cys Asp Leu Val His Thr Arg
145                 150                 155                 160

Cys Ile Thr Pro Thr Gly Thr His Pro Leu Ala Lys Lys Leu Pro Ala
                165                 170                 175

Gln Arg Thr Asn Arg Ala Val Ala Leu Ser Ser Ser Val Met Cys Pro
            180                 185                 190

Asp Ala Arg Ser Arg Cys Pro Asp Gly Ser Thr Cys Cys Glu Leu Pro
        195                 200                 205

Ser Gly Lys Tyr Gly Cys Cys Pro Met Pro Asn Ala Thr Cys Cys Ser
210                 215                 220

Asp His Leu His Cys Cys Pro Gln Asp Thr Val Cys Asp Leu Ile Gln
225                 230                 235                 240

Ser Lys Cys Leu Ser Lys Glu Asn Ala Thr Thr Asp Leu Leu Thr Lys
                245                 250                 255

Leu Pro Ala His Thr Val Gly Asp Val Lys Cys Asp Met Glu Val Ser
            260                 265                 270

Cys Pro Asp Gly Tyr Thr Cys Cys Arg Leu Gln Ser Gly Ala Trp Gly
        275                 280                 285

Cys Cys Pro Phe Thr Gln Ala Val Cys Cys Glu Asp His Ile His Cys
290                 295                 300
```

```
Cys Pro Ala Gly Phe Thr Cys Asp Thr Gln Lys Gly Thr Cys Glu Gln
305                 310                 315                 320

Gly Pro His Gln Val Pro Trp Met Glu Lys Ala Pro Ala His Leu Ser
                325                 330                 335

Leu Pro Asp Pro Gln Ala Leu Lys Arg Asp Val Pro Cys Asp Asn Val
            340                 345                 350

Ser Ser Cys Pro Ser Ser Asp Thr Cys Cys Gln Leu Thr Ser Gly Glu
        355                 360                 365

Trp Gly Cys Cys Pro Ile Pro Glu Ala Val Cys Cys Ser Asp His Gln
    370                 375                 380

His Cys Cys Pro Gln Gly Tyr Thr Cys Val Ala Glu Gly Gln Cys Gln
385                 390                 395                 400

Arg Gly Ser Glu Ile Val Ala Gly Leu Glu Lys Met Pro Ala Arg Arg
                405                 410                 415

Ala Ser Leu Ser His Pro Arg Asp Ile Gly Cys Asp Gln His Thr Ser
            420                 425                 430

Cys Pro Val Gly Gln Thr Cys Cys Pro Ser Leu Gly Gly Ser Trp Ala
        435                 440                 445

Cys Cys Gln Leu Pro His Ala Val Cys Cys Glu Asp Arg Gln His Cys
450                 455                 460

Cys Pro Ala Gly Tyr Thr Cys Asn Val Lys Ala Arg Ser Cys Glu Lys
465                 470                 475                 480

Glu Val Val Ser Ala Gln Pro Ala Thr Phe Leu Ala Arg Ser Pro His
                485                 490                 495

Val Gly Val Lys Asp Val Glu Cys Gly Glu Gly His Phe Cys His Asp
            500                 505                 510

Asn Gln Thr Cys Cys Arg Asp Asn Arg Gln Gly Trp Ala Cys Cys Pro
        515                 520                 525

Tyr Arg Gln Gly Val Cys Cys Ala Asp Arg Arg His Cys Cys Pro Ala
    530                 535                 540

Gly Phe Arg Cys Ala Ala Arg Gly Thr Lys Cys Leu Arg Arg Glu Ala
545                 550                 555                 560

Pro Arg Trp Asp Ala Pro Leu Arg Asp Pro Ala Leu Arg Phe Gln Leu
                565                 570                 575

<210> SEQ ID NO 54
<211> LENGTH: 576
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 54

Thr Arg Cys Pro Asp Gly Gln Phe Cys Pro Val Ala Cys Cys Leu Asp
1               5                   10                  15

Pro Gly Gly Ala Ser Tyr Ser Cys Cys Arg Pro Leu Leu Asp Lys Trp
                20                  25                  30

Pro Thr Thr Leu Ser Arg His Leu Gly Gly Pro Cys Gln Val Asp Ala
            35                  40                  45

His Cys Ser Ala Gly His Ser Cys Ile Phe Thr Val Ser Gly Thr Ser
        50                  55                  60

Ser Cys Cys Pro Phe Pro Glu Ala Val Ala Cys Gly Asp Gly His His
65                  70                  75                  80
```

-continued

```
Cys Cys Pro Arg Gly Phe His Cys Ser Ala Asp Gly Arg Ser Cys Phe
            85                  90                  95
Gln Arg Ser Gly Asn Asn Ser Val Gly Ala Ile Gln Cys Pro Asp Ser
        100                 105                 110
Gln Phe Glu Cys Pro Asp Phe Ser Thr Cys Cys Val Met Val Asp Gly
        115                 120                 125
Ser Trp Gly Cys Cys Pro Met Pro Gln Ala Ser Cys Cys Glu Asp Arg
        130                 135                 140
Val His Cys Cys Pro His Gly Ala Phe Cys Asp Leu Val His Thr Arg
145                 150                 155                 160
Cys Ile Thr Pro Thr Gly Thr His Pro Leu Ala Lys Lys Leu Pro Ala
                165                 170                 175
Gln Arg Thr Asn Arg Ala Val Ala Leu Ser Ser Ser Val Met Cys Pro
            180                 185                 190
Asp Ala Arg Ser Arg Cys Pro Asp Gly Ser Thr Cys Cys Glu Leu Pro
        195                 200                 205
Ser Gly Lys Tyr Gly Cys Cys Pro Met Pro Asn Ala Thr Cys Cys Ser
        210                 215                 220
Asp His Leu His Cys Cys Pro Gln Asp Thr Val Cys Asp Leu Ile Gln
225                 230                 235                 240
Ser Lys Cys Leu Ser Lys Glu Asn Ala Thr Thr Asp Leu Leu Thr Lys
                245                 250                 255
Leu Pro Ala His Thr Val Gly Asp Val Lys Cys Asp Met Glu Val Ser
            260                 265                 270
Cys Pro Asp Gly Tyr Thr Cys Cys Arg Leu Gln Ser Gly Ala Trp Gly
        275                 280                 285
Cys Cys Pro Phe Thr Gln Ala Val Cys Cys Glu Asp His Ile His Cys
        290                 295                 300
Cys Pro Ala Gly Phe Thr Cys Asp Thr Gln Lys Gly Thr Cys Glu Gln
305                 310                 315                 320
Gly Pro His Gln Val Pro Trp Met Glu Lys Ala Pro Ala His Leu Ser
                325                 330                 335
Leu Pro Asp Pro Gln Ala Leu Lys Arg Asp Val Pro Cys Asp Asn Val
            340                 345                 350
Ser Ser Cys Pro Ser Ser Asp Thr Cys Cys Gln Leu Thr Ser Gly Glu
        355                 360                 365
Trp Gly Cys Cys Pro Ile Pro Glu Ala Val Cys Cys Ser Asp His Gln
        370                 375                 380
His Cys Cys Pro Gln Gly Tyr Thr Cys Val Ala Glu Gly Gln Cys Gln
385                 390                 395                 400
Arg Gly Ser Glu Ile Val Ala Gly Leu Glu Lys Met Pro Ala Arg Arg
                405                 410                 415
Ala Ser Leu Ser His Pro Arg Asp Ile Gly Cys Asp Gln His Thr Ser
            420                 425                 430
Cys Pro Val Gly Gln Thr Cys Cys Pro Ser Leu Gly Gly Ser Trp Ala
        435                 440                 445
Cys Cys Gln Leu Pro His Ala Val Cys Cys Glu Asp Arg Gln His Cys
        450                 455                 460
Cys Pro Ala Gly Tyr Thr Cys Asn Val Lys Ala Arg Ser Cys Glu Lys
465                 470                 475                 480
Glu Val Val Ser Ala Gln Pro Ala Thr Phe Leu Ala Arg Ser Pro His
                485                 490                 495
```

```
Val Gly Val Lys Asp Val Glu Cys Gly Glu Gly His Phe Cys His Asp
            500                 505                 510

Asn Gln Thr Cys Cys Arg Asp Asn Arg Gln Gly Trp Ala Cys Cys Pro
            515                 520                 525

Tyr Arg Gln Gly Val Cys Cys Ala Asp Arg Arg His Cys Cys Pro Ala
            530                 535                 540

Gly Phe Arg Cys Ala Ala Arg Gly Thr Lys Cys Leu Arg Arg Glu Ala
545                 550                 555                 560

Pro Arg Trp Asp Ala Pro Leu Arg Asp Pro Ala Leu Arg Tyr Gln Leu
                565                 570                 575

<210> SEQ ID NO 55
<211> LENGTH: 581
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (577)..(577)
<223> OTHER INFORMATION: /replace=" "
<220> FEATURE:
<221> NAME/KEY: VARIANT
<222> LOCATION: (578)..(578)
<223> OTHER INFORMATION: /replace=" "
<220> FEATURE:
<221> NAME/KEY: SITE
<222> LOCATION: (1)..(581)
<223> OTHER INFORMATION: /note="Variant residues given in the sequence
      have no preference with respect to those in the annotations
      for variant positions"

<400> SEQUENCE: 55

Thr Arg Cys Pro Asp Gly Gln Phe Cys Pro Val Ala Cys Cys Leu Asp
1               5                   10                  15

Pro Gly Gly Ala Ser Tyr Ser Cys Cys Arg Pro Leu Leu Asp Lys Trp
            20                  25                  30

Pro Thr Thr Leu Ser Arg His Leu Gly Gly Pro Cys Gln Val Asp Ala
            35                  40                  45

His Cys Ser Ala Gly His Ser Cys Ile Phe Thr Val Ser Gly Thr Ser
        50                  55                  60

Ser Cys Cys Pro Phe Pro Glu Ala Val Ala Cys Gly Asp Gly His His
65                  70                  75                  80

Cys Cys Pro Arg Gly Phe His Cys Ser Ala Asp Gly Arg Ser Cys Phe
                85                  90                  95

Gln Arg Ser Gly Asn Asn Ser Val Gly Ala Ile Gln Cys Pro Asp Ser
            100                 105                 110

Gln Phe Glu Cys Pro Asp Phe Ser Thr Cys Cys Val Met Val Asp Gly
            115                 120                 125

Ser Trp Gly Cys Cys Pro Met Pro Gln Ala Ser Cys Cys Glu Asp Arg
        130                 135                 140

Val His Cys Cys Pro His Gly Ala Phe Cys Asp Leu Val His Thr Arg
145                 150                 155                 160

Cys Ile Thr Pro Thr Gly Thr His Pro Leu Ala Lys Lys Leu Pro Ala
                165                 170                 175

Gln Arg Thr Asn Arg Ala Val Ala Leu Ser Ser Ser Val Met Cys Pro
            180                 185                 190
```

```
Asp Ala Arg Ser Arg Cys Pro Asp Gly Ser Thr Cys Cys Glu Leu Pro
        195                 200                 205

Ser Gly Lys Tyr Gly Cys Cys Pro Met Pro Asn Ala Thr Cys Cys Ser
    210                 215                 220

Asp His Leu His Cys Cys Pro Gln Asp Thr Val Cys Asp Leu Ile Gln
225                 230                 235                 240

Ser Lys Cys Leu Ser Lys Glu Asn Ala Thr Thr Asp Leu Leu Thr Lys
                245                 250                 255

Leu Pro Ala His Thr Val Gly Asp Val Lys Cys Asp Met Glu Val Ser
            260                 265                 270

Cys Pro Asp Gly Tyr Thr Cys Cys Arg Leu Gln Ser Gly Ala Trp Gly
        275                 280                 285

Cys Cys Pro Phe Thr Gln Ala Val Cys Cys Glu Asp His Ile His Cys
    290                 295                 300

Cys Pro Ala Gly Phe Thr Cys Asp Thr Gln Lys Gly Thr Cys Glu Gln
305                 310                 315                 320

Gly Pro His Gln Val Pro Trp Met Glu Lys Ala Pro Ala His Leu Ser
                325                 330                 335

Leu Pro Asp Pro Gln Ala Leu Lys Arg Asp Val Pro Cys Asp Asn Val
            340                 345                 350

Ser Ser Cys Pro Ser Ser Asp Thr Cys Cys Gln Leu Thr Ser Gly Glu
        355                 360                 365

Trp Gly Cys Cys Pro Ile Pro Glu Ala Val Cys Cys Ser Asp His Gln
    370                 375                 380

His Cys Cys Pro Gln Gly Tyr Thr Cys Val Ala Glu Gly Gln Cys Gln
385                 390                 395                 400

Arg Gly Ser Glu Ile Val Ala Gly Leu Glu Lys Met Pro Ala Arg Arg
                405                 410                 415

Ala Ser Leu Ser His Pro Arg Asp Ile Gly Cys Asp Gln His Thr Ser
            420                 425                 430

Cys Pro Val Gly Gln Thr Cys Cys Pro Ser Leu Gly Gly Ser Trp Ala
        435                 440                 445

Cys Cys Gln Leu Pro His Ala Val Cys Cys Glu Asp Arg Gln His Cys
    450                 455                 460

Cys Pro Ala Gly Tyr Thr Cys Asn Val Lys Ala Arg Ser Cys Glu Lys
465                 470                 475                 480

Glu Val Val Ser Ala Gln Pro Ala Thr Phe Leu Ala Arg Ser Pro His
                485                 490                 495

Val Gly Val Lys Asp Val Glu Cys Gly Glu Gly His Phe Cys His Asp
            500                 505                 510

Asn Gln Thr Cys Cys Arg Asp Asn Arg Gln Gly Trp Ala Cys Cys Pro
        515                 520                 525

Tyr Arg Gln Gly Val Cys Cys Ala Asp Arg Arg His Cys Cys Pro Ala
    530                 535                 540

Gly Phe Arg Cys Ala Ala Arg Gly Thr Lys Cys Leu Arg Arg Glu Ala
545                 550                 555                 560

Pro Arg Trp Asp Ala Pro Leu Arg Asp Pro Ala Leu Arg Gln Leu Leu
                565                 570                 575

Leu Arg Gln Leu Leu
            580

<210> SEQ ID NO 56
<211> LENGTH: 579
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 56

Thr Arg Cys Pro Asp Gly Gln Phe Cys Pro Val Ala Cys Cys Leu Asp
1               5                   10                  15

Pro Gly Gly Ala Ser Tyr Ser Cys Cys Arg Pro Leu Leu Asp Lys Trp
            20                  25                  30

Pro Thr Thr Leu Ser Arg His Leu Gly Gly Pro Cys Gln Val Asp Ala
        35                  40                  45

His Cys Ser Ala Gly His Ser Cys Ile Phe Thr Val Ser Gly Thr Ser
    50                  55                  60

Ser Cys Cys Pro Phe Pro Glu Ala Val Ala Cys Gly Asp Gly His His
65                  70                  75                  80

Cys Cys Pro Arg Gly Phe His Cys Ser Ala Asp Gly Arg Ser Cys Phe
                85                  90                  95

Gln Arg Ser Gly Asn Asn Ser Val Gly Ala Ile Gln Cys Pro Asp Ser
            100                 105                 110

Gln Phe Glu Cys Pro Asp Phe Ser Thr Cys Cys Val Met Val Asp Gly
        115                 120                 125

Ser Trp Gly Cys Cys Pro Met Pro Gln Ala Ser Cys Cys Glu Asp Arg
    130                 135                 140

Val His Cys Cys Pro His Gly Ala Phe Cys Asp Leu Val His Thr Arg
145                 150                 155                 160

Cys Ile Thr Pro Thr Gly Thr His Pro Leu Ala Lys Lys Leu Pro Ala
                165                 170                 175

Gln Arg Thr Asn Arg Ala Val Ala Leu Ser Ser Ser Val Met Cys Pro
            180                 185                 190

Asp Ala Arg Ser Arg Cys Pro Asp Gly Ser Thr Cys Cys Glu Leu Pro
        195                 200                 205

Ser Gly Lys Tyr Gly Cys Cys Pro Met Pro Asn Ala Thr Cys Cys Ser
    210                 215                 220

Asp His Leu His Cys Cys Pro Gln Asp Thr Val Cys Asp Leu Ile Gln
225                 230                 235                 240

Ser Lys Cys Leu Ser Lys Glu Asn Ala Thr Thr Asp Leu Leu Thr Lys
                245                 250                 255

Leu Pro Ala His Thr Val Gly Asp Val Lys Cys Asp Met Glu Val Ser
            260                 265                 270

Cys Pro Asp Gly Tyr Thr Cys Cys Arg Leu Gln Ser Gly Ala Trp Gly
        275                 280                 285

Cys Cys Pro Phe Thr Gln Ala Val Cys Cys Glu Asp His Ile His Cys
    290                 295                 300

Cys Pro Ala Gly Phe Thr Cys Asp Thr Gln Lys Gly Thr Cys Glu Gln
305                 310                 315                 320

Gly Pro His Gln Val Pro Trp Met Glu Lys Ala Pro Ala His Leu Ser
                325                 330                 335

Leu Pro Asp Pro Gln Ala Leu Lys Arg Asp Val Pro Cys Asp Asn Val
            340                 345                 350

Ser Ser Cys Pro Ser Ser Asp Thr Cys Cys Gln Leu Thr Ser Gly Glu
        355                 360                 365
```

Trp Gly Cys Cys Pro Ile Pro Glu Ala Val Cys Cys Ser Asp His Gln
    370             375             380

His Cys Cys Pro Gln Gly Tyr Thr Cys Val Ala Glu Gly Gln Cys Gln
385             390             395             400

Arg Gly Ser Glu Ile Val Ala Gly Leu Glu Lys Met Pro Ala Arg Arg
            405             410             415

Ala Ser Leu Ser His Pro Arg Asp Ile Gly Cys Asp Gln His Thr Ser
            420             425             430

Cys Pro Val Gly Gln Thr Cys Cys Pro Ser Leu Gly Gly Ser Trp Ala
        435             440             445

Cys Cys Gln Leu Pro His Ala Val Cys Cys Glu Asp Arg Gln His Cys
    450             455             460

Cys Pro Ala Gly Tyr Thr Cys Asn Val Lys Ala Arg Ser Cys Glu Lys
465             470             475             480

Glu Val Val Ser Ala Gln Pro Ala Thr Phe Leu Ala Arg Ser Pro His
            485             490             495

Val Gly Val Lys Asp Val Glu Cys Gly Glu Gly His Phe Cys His Asp
            500             505             510

Asn Gln Thr Cys Cys Arg Asp Asn Arg Gln Gly Trp Ala Cys Cys Pro
        515             520             525

Tyr Arg Gln Gly Val Cys Cys Ala Asp Arg Arg His Cys Cys Pro Ala
    530             535             540

Gly Phe Arg Cys Ala Ala Arg Gly Thr Lys Cys Leu Arg Arg Glu Ala
545             550             555             560

Pro Arg Trp Asp Ala Pro Leu Arg Asp Pro Ala Leu Arg Gln Leu Leu
            565             570             575

Gln Leu Leu

<210> SEQ ID NO 57
<211> LENGTH: 581
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 57

Thr Arg Cys Pro Asp Gly Gln Phe Cys Pro Val Ala Cys Cys Leu Asp
1               5               10              15

Pro Gly Gly Ala Ser Tyr Ser Cys Cys Arg Pro Leu Leu Asp Lys Trp
            20              25              30

Pro Thr Thr Leu Ser Arg His Leu Gly Gly Pro Cys Gln Val Asp Ala
            35              40              45

His Cys Ser Ala Gly His Ser Cys Ile Phe Thr Val Ser Gly Thr Ser
        50              55              60

Ser Cys Cys Pro Phe Pro Glu Ala Val Ala Cys Gly Asp Gly His His
65              70              75              80

Cys Cys Pro Arg Gly Phe His Cys Ser Ala Asp Gly Arg Ser Cys Phe
            85              90              95

Gln Arg Ser Gly Asn Asn Ser Val Gly Ala Ile Gln Cys Pro Asp Ser
            100             105             110

Gln Phe Glu Cys Pro Asp Phe Ser Thr Cys Cys Val Met Val Asp Gly
            115             120             125

```
Ser Trp Gly Cys Cys Pro Met Pro Gln Ala Ser Cys Cys Glu Asp Arg
130                 135                 140

Val His Cys Cys Pro His Gly Ala Phe Cys Asp Leu Val His Thr Arg
145                 150                 155                 160

Cys Ile Thr Pro Thr Gly Thr His Pro Leu Ala Lys Lys Leu Pro Ala
            165                 170                 175

Gln Arg Thr Asn Arg Ala Val Ala Leu Ser Ser Val Met Cys Pro
                180                 185                 190

Asp Ala Arg Ser Arg Cys Pro Asp Gly Ser Thr Cys Cys Glu Leu Pro
            195                 200                 205

Ser Gly Lys Tyr Gly Cys Cys Pro Met Pro Asn Ala Thr Cys Cys Ser
210                 215                 220

Asp His Leu His Cys Cys Pro Gln Asp Thr Val Cys Asp Leu Ile Gln
225                 230                 235                 240

Ser Lys Cys Leu Ser Lys Glu Asn Ala Thr Thr Asp Leu Leu Thr Lys
                245                 250                 255

Leu Pro Ala His Thr Val Gly Asp Val Lys Cys Asp Met Glu Val Ser
                260                 265                 270

Cys Pro Asp Gly Tyr Thr Cys Cys Arg Leu Gln Ser Gly Ala Trp Gly
        275                 280                 285

Cys Cys Pro Phe Thr Gln Ala Val Cys Cys Glu Asp His Ile His Cys
        290                 295                 300

Cys Pro Ala Gly Phe Thr Cys Asp Thr Gln Lys Gly Thr Cys Glu Gln
305                 310                 315                 320

Gly Pro His Gln Val Pro Trp Met Glu Lys Ala Pro Ala His Leu Ser
                325                 330                 335

Leu Pro Asp Pro Gln Ala Leu Lys Arg Asp Val Pro Cys Asp Asn Val
                340                 345                 350

Ser Ser Cys Pro Ser Ser Asp Thr Cys Cys Gln Leu Thr Ser Gly Glu
        355                 360                 365

Trp Gly Cys Cys Pro Ile Pro Glu Ala Val Cys Cys Ser Asp His Gln
        370                 375                 380

His Cys Cys Pro Gln Gly Tyr Thr Cys Val Ala Glu Gly Gln Cys Gln
385                 390                 395                 400

Arg Gly Ser Glu Ile Val Ala Gly Leu Glu Lys Met Pro Ala Arg Arg
                405                 410                 415

Ala Ser Leu Ser His Pro Arg Asp Ile Gly Cys Asp Gln His Thr Ser
                420                 425                 430

Cys Pro Val Gly Gln Thr Cys Cys Pro Ser Leu Gly Gly Ser Trp Ala
        435                 440                 445

Cys Cys Gln Leu Pro His Ala Val Cys Cys Glu Asp Arg Gln His Cys
450                 455                 460

Cys Pro Ala Gly Tyr Thr Cys Asn Val Lys Ala Arg Ser Cys Glu Lys
465                 470                 475                 480

Glu Val Val Ser Ala Gln Pro Ala Thr Phe Leu Ala Arg Ser Pro His
                485                 490                 495

Val Gly Val Lys Asp Val Glu Cys Gly Glu Gly His Phe Cys His Asp
            500                 505                 510

Asn Gln Thr Cys Cys Arg Asp Asn Arg Gln Gly Trp Ala Cys Cys Pro
        515                 520                 525

Tyr Arg Gln Gly Val Cys Cys Ala Asp Arg Arg His Cys Cys Pro Ala
530                 535                 540
```

```
Gly Phe Arg Cys Ala Ala Arg Gly Thr Lys Cys Leu Arg Arg Glu Ala
545                 550                 555                 560

Pro Arg Trp Asp Ala Pro Leu Arg Asp Pro Ala Leu Arg Gln Leu Leu
                565                 570                 575

Leu Arg Gln Leu Leu
            580

<210> SEQ ID NO 58
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 58

Leu Arg Gln Leu Leu
1               5

<210> SEQ ID NO 59
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 59

Gln Leu Leu Gln Leu Leu
1               5

<210> SEQ ID NO 60
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 60

Gln Leu Leu Leu Arg Gln Leu Leu
1               5

<210> SEQ ID NO 61
<211> LENGTH: 217
<212> TYPE: PRT
<213> ORGANISM: Homo sapiens

<400> SEQUENCE: 61

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
                20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
        50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95
```

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
            115                 120                 125

Thr Lys Asn Gln Val Ser Leu Thr Cys Leu Val Lys Gly Phe Tyr Pro
            130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
            195                 200                 205

Lys Ser Leu Ser Leu Ser Pro Gly Lys
            210                 215

<210> SEQ ID NO 62
<211> LENGTH: 110
<212> TYPE: PRT
<213> ORGANISM: Homo sapiens

<400> SEQUENCE: 62

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110

<210> SEQ ID NO 63
<211> LENGTH: 107
<212> TYPE: PRT
<213> ORGANISM: Homo sapiens

<400> SEQUENCE: 63

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

```
Thr Gln Lys Ser Leu Ser Leu Ser Pro Gly Lys
        100                 105
```

<210> SEQ ID NO 64
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 64

```
Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215
```

<210> SEQ ID NO 65
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 65

```
Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45
```

```
Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
            115                 120                 125

Thr Lys Asn Gln Val Ser Leu Trp Cys Leu Val Lys Gly Phe Tyr Pro
130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
            195                 200                 205

Lys Ser Leu Ser Leu Ser Pro Gly Lys
            210                 215
```

<210> SEQ ID NO 66
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 66

```
Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
            115                 120                 125

Thr Lys Asn Gln Val Ser Leu Ser Cys Ala Val Lys Gly Phe Tyr Pro
130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175
```

Val Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 67
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 67

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Ser Cys Ala Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Val Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 68
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 68

Ala Pro Glu Leu Leu Gly Gly Pro Ser Val Phe Leu Phe Pro Pro Lys
1               5                   10                  15

```
Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Tyr Gly Thr Glu Trp Ala Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Thr Lys Glu Glu Trp Gln Gln Gly Phe Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 69
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 69

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Trp Cys Leu Val Lys Gly Phe Tyr Pro
    130                 135                 140
```

Ser Asp Ile Ala Val Glu Trp Glu Ser Tyr Gly Thr Glu Trp Ala Asn
145                 150                 155                 160

Tyr Lys Thr Thr Pro Pro Val Leu Asp Ser Asp Gly Ser Phe Phe Leu
            165                 170                 175

Tyr Ser Lys Leu Thr Val Thr Lys Glu Glu Trp Gln Gln Gly Phe Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 70
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 70

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Tyr Gly Thr Glu Trp Ala Asn
145                 150                 155                 160

Tyr Lys Thr Thr Pro Pro Val Leu Asp Ser Asp Gly Ser Phe Phe Leu
            165                 170                 175

Tyr Ser Lys Leu Thr Val Thr Lys Glu Glu Trp Gln Gln Gly Phe Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 71
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 71

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Ser Cys Ala Val Lys Gly Phe Tyr Pro
    130                 135                 140

Ser Asp Ile Ala Val Glu Trp Glu Ser Tyr Gly Thr Glu Trp Ala Asn
145                 150                 155                 160

Tyr Lys Thr Thr Pro Pro Val Leu Asp Ser Asp Gly Ser Phe Phe Leu
                165                 170                 175

Val Ser Lys Leu Thr Val Thr Lys Glu Glu Trp Gln Gln Gly Phe Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 72
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 72

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

```
Pro Arg Glu Pro Gln Val Tyr Thr Leu Pro Pro Ser Arg Asp Glu Leu
        115                 120                 125

Thr Lys Asn Gln Val Ser Leu Ser Cys Ala Val Lys Gly Phe Tyr Pro
        130                 135                 140

Ser Asp Ile Ala Val Glu Trp Glu Ser Tyr Gly Thr Glu Trp Ala Asn
145                 150                 155                 160

Tyr Lys Thr Thr Pro Pro Val Leu Asp Ser Asp Gly Ser Phe Phe Leu
                165                 170                 175

Val Ser Lys Leu Thr Val Thr Lys Glu Glu Trp Gln Gln Gly Phe Val
                180                 185                 190

Phe Ser Cys Ser Val Met His Glu Ala Leu His Asn His Tyr Thr Gln
                195                 200                 205

Lys Ser Leu Ser Leu Ser Pro Gly Lys
        210                 215

<210> SEQ ID NO 73
<211> LENGTH: 227
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 73

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
        50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
130                 135                 140

Leu Thr Cys Leu Val Lys Gly Phe Tyr Pro Ser Asp Ile Ala Val Glu
145                 150                 155                 160

Trp Glu Ser Tyr Gly Thr Glu Trp Ala Asn Tyr Lys Thr Thr Pro Pro
                165                 170                 175

Val Leu Asp Ser Asp Gly Ser Phe Phe Leu Tyr Ser Lys Leu Thr Val
                180                 185                 190

Thr Lys Glu Glu Trp Gln Gln Gly Phe Val Phe Ser Cys Ser Val Met
            195                 200                 205

His Glu Ala Leu His Asn His Tyr Thr Gln Lys Ser Leu Ser Leu Ser
        210                 215                 220

Pro Gly Lys
225
```

```
<210> SEQ ID NO 74
<211> LENGTH: 227
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 74

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Tyr Gly Thr Glu Trp Ala Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Thr Lys Glu Glu Trp Gln Gln Gly Phe Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 75
<211> LENGTH: 227
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 75

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45
```

Glu Asp Pro Glu Val Lys Phe Asn Trp Tyr Val Asp Gly Val Glu Val
        50                      55                      60

His Asn Ala Lys Thr Lys Pro Arg Glu Glu Gln Tyr Asn Ser Thr Tyr
 65                      70                      75                      80

Arg Val Val Ser Val Leu Thr Val Leu His Gln Asp Trp Leu Asn Gly
                        85                      90                      95

Lys Glu Tyr Lys Cys Lys Val Ser Asn Lys Ala Leu Pro Ala Pro Ile
                100                     105                     110

Glu Lys Thr Ile Ser Lys Ala Lys Gly Gln Pro Arg Glu Pro Gln Val
                115                     120                     125

Tyr Thr Leu Pro Pro Ser Arg Asp Glu Leu Thr Lys Asn Gln Val Ser
                130                     135                     140

Leu Trp Cys Leu Val Lys Gly Phe Tyr Pro Ser Asp Ile Ala Val Glu
145                     150                     155                     160

Trp Glu Ser Tyr Gly Thr Glu Trp Ala Asn Tyr Lys Thr Thr Pro Pro
                        165                     170                     175

Val Leu Asp Ser Asp Gly Ser Phe Phe Leu Tyr Ser Lys Leu Thr Val
                180                     185                     190

Thr Lys Glu Glu Trp Gln Gln Gly Phe Val Phe Ser Cys Ser Val Met
                195                     200                     205

His Glu Ala Leu His Asn His Tyr Thr Gln Lys Ser Leu Ser Leu Ser
                210                     215                     220

Pro Gly Lys
225

<210> SEQ ID NO 76
<211> LENGTH: 227
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 76

Asp Lys Thr His Thr Cys Pro Pro Cys Pro Ala Pro Glu Leu Leu Gly
  1               5                      10                      15

Gly Pro Ser Val Phe Leu Phe Pro Pro Lys Pro Lys Asp Thr Leu Met
                20                      25                      30

Ile Ser Arg Thr Pro Glu Val Thr Cys Val Val Val Asp Val Ser His
                35                      40                      45

Glu Asp Pro Glu Val Lys Phe Asn Trp Tyr Val Asp Gly Val Glu Val
        50                      55                      60

His Asn Ala Lys Thr Lys Pro Arg Glu Glu Gln Tyr Asn Ser Thr Tyr
 65                      70                      75                      80

Arg Val Val Ser Val Leu Thr Val Leu His Gln Asp Trp Leu Asn Gly
                        85                      90                      95

Lys Glu Tyr Lys Cys Lys Val Ser Asn Lys Ala Leu Pro Ala Pro Ile
                100                     105                     110

Glu Lys Thr Ile Ser Lys Ala Lys Gly Gln Pro Arg Glu Pro Gln Val
                115                     120                     125

Tyr Thr Leu Pro Pro Ser Arg Asp Glu Leu Thr Lys Asn Gln Val Ser
                130                     135                     140

Leu Ser Cys Ala Val Lys Gly Phe Tyr Pro Ser Asp Ile Ala Val Glu
145                     150                     155                     160

```
Trp Glu Ser Tyr Gly Thr Glu Trp Ala Asn Tyr Lys Thr Thr Pro Pro
                165                 170                 175

Val Leu Asp Ser Asp Gly Ser Phe Phe Leu Val Ser Lys Leu Thr Val
            180                 185                 190

Thr Lys Glu Glu Trp Gln Gln Gly Phe Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 77
<211> LENGTH: 227
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 77

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
130                 135                 140

Leu Ser Cys Ala Val Lys Gly Phe Tyr Pro Ser Asp Ile Ala Val Glu
145                 150                 155                 160

Trp Glu Ser Tyr Gly Thr Glu Trp Ala Asn Tyr Lys Thr Thr Pro Pro
                165                 170                 175

Val Leu Asp Ser Asp Gly Ser Phe Phe Leu Val Ser Lys Leu Thr Val
            180                 185                 190

Thr Lys Glu Glu Trp Gln Gln Gly Phe Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 78
<211> LENGTH: 217
<212> TYPE: PRT
<213> ORGANISM: Artificial Sequence
<220> FEATURE:
<221> NAME/KEY: source
```

<223> OTHER INFORMATION: /note="Description of Artificial Sequence:
      Synthetic polypeptide"

<400> SEQUENCE: 78

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Leu Trp Glu Ser Tyr Gly Thr Glu Trp Ser Ser
145                 150                 155                 160

Tyr Lys Thr Thr Pro Pro Val Leu Asp Ser Asp Gly Ser Phe Phe Leu
                165                 170                 175

Tyr Ser Lys Leu Thr Val Thr Lys Glu Glu Trp Gln Gln Gly Phe Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 79
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 79

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

```
Pro Arg Glu Pro Gln Val Tyr Thr Leu Pro Pro Ser Arg Asp Glu Leu
        115                 120                 125

Thr Lys Asn Gln Val Ser Leu Trp Cys Leu Val Lys Gly Phe Tyr Pro
        130                 135                 140

Ser Asp Ile Ala Val Leu Trp Glu Ser Tyr Gly Thr Glu Trp Ser Ser
145                 150                 155                 160

Tyr Lys Thr Thr Pro Pro Val Leu Asp Ser Asp Gly Ser Phe Phe Leu
                165                 170                 175

Tyr Ser Lys Leu Thr Val Thr Lys Glu Glu Trp Gln Gln Gly Phe Val
                180                 185                 190

Phe Ser Cys Ser Val Met His Glu Ala Leu His Asn His Tyr Thr Gln
        195                 200                 205

Lys Ser Leu Ser Leu Ser Pro Gly Lys
        210                 215

<210> SEQ ID NO 80
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 80

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Trp Cys Leu Val Lys Gly Phe Tyr Pro
        130                 135                 140

Ser Asp Ile Ala Val Leu Trp Glu Ser Tyr Gly Thr Glu Trp Ser Ser
145                 150                 155                 160

Tyr Lys Thr Thr Pro Pro Val Leu Asp Ser Asp Gly Ser Phe Phe Leu
                165                 170                 175

Tyr Ser Lys Leu Thr Val Thr Lys Glu Glu Trp Gln Gln Gly Phe Val
                180                 185                 190

Phe Ser Cys Ser Val Met His Glu Ala Leu His Asn His Tyr Thr Gln
        195                 200                 205

Lys Ser Leu Ser Leu Ser Pro Gly Lys
        210                 215

<210> SEQ ID NO 81
<211> LENGTH: 217
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 81

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Ser Cys Ala Val Lys Gly Phe Tyr Pro
    130                 135                 140

Ser Asp Ile Ala Val Leu Trp Glu Ser Tyr Gly Thr Glu Trp Ser Ser
145                 150                 155                 160

Tyr Lys Thr Thr Pro Pro Val Leu Asp Ser Asp Gly Ser Phe Phe Leu
                165                 170                 175

Val Ser Lys Leu Thr Val Thr Lys Glu Glu Trp Gln Gln Gly Phe Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 82
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 82

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80
```

```
Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Ser Cys Ala Val Lys Gly Phe Tyr Pro
    130                 135                 140

Ser Asp Ile Ala Val Leu Trp Glu Ser Tyr Gly Thr Glu Trp Ser Ser
145                 150                 155                 160

Tyr Lys Thr Thr Pro Pro Val Leu Asp Ser Asp Gly Ser Phe Phe Leu
                165                 170                 175

Val Ser Lys Leu Thr Val Thr Lys Glu Glu Trp Gln Gln Gly Phe Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215
```

<210> SEQ ID NO 83
<211> LENGTH: 227
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 83

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Leu
145                 150                 155                 160

Trp Glu Ser Tyr Gly Thr Glu Trp Ser Ser Tyr Lys Thr Thr Pro Pro
                165                 170                 175

Val Leu Asp Ser Asp Gly Ser Phe Phe Leu Tyr Ser Lys Leu Thr Val
            180                 185                 190

Thr Lys Glu Glu Trp Gln Gln Gly Phe Val Phe Ser Cys Ser Val Met
        195                 200                 205
```

His Glu Ala Leu His Asn His Tyr Thr Gln Lys Ser Leu Ser Leu Ser
210                 215                 220

Pro Gly Lys
225

<210> SEQ ID NO 84
<211> LENGTH: 227
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 84

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Trp Cys Leu Val Lys Gly Phe Tyr Pro Ser Asp Ile Ala Val Leu
145                 150                 155                 160

Trp Glu Ser Tyr Gly Thr Glu Trp Ser Ser Tyr Lys Thr Thr Pro Pro
                165                 170                 175

Val Leu Asp Ser Asp Gly Ser Phe Phe Leu Tyr Ser Lys Leu Thr Val
            180                 185                 190

Thr Lys Glu Glu Trp Gln Gln Gly Phe Val Phe Ser Cys Ser Val Met
        195                 200                 205

His Glu Ala Leu His Asn His Tyr Thr Gln Lys Ser Leu Ser Leu Ser
210                 215                 220

Pro Gly Lys
225

<210> SEQ ID NO 85
<211> LENGTH: 227
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 85

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
130                 135                 140

Leu Trp Cys Leu Val Lys Gly Phe Tyr Pro Ser Asp Ile Ala Val Leu
145                 150                 155                 160

Trp Glu Ser Tyr Gly Thr Glu Trp Ser Ser Tyr Lys Thr Thr Pro Pro
                165                 170                 175

Val Leu Asp Ser Asp Gly Ser Phe Phe Leu Tyr Ser Lys Leu Thr Val
            180                 185                 190

Thr Lys Glu Glu Trp Gln Gln Gly Phe Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 86
<211> LENGTH: 227
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 86

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

```
Tyr Thr Leu Pro Pro Ser Arg Asp Glu Leu Thr Lys Asn Gln Val Ser
    130                 135                 140

Leu Ser Cys Ala Val Lys Gly Phe Tyr Pro Ser Asp Ile Ala Val Leu
145                 150                 155                 160

Trp Glu Ser Tyr Gly Thr Glu Trp Ser Ser Tyr Lys Thr Thr Pro Pro
                165                 170                 175

Val Leu Asp Ser Asp Gly Ser Phe Phe Leu Val Ser Lys Leu Thr Val
                180                 185                 190

Thr Lys Glu Glu Trp Gln Gln Gly Phe Val Phe Ser Cys Ser Val Met
                195                 200                 205

His Glu Ala Leu His Asn His Tyr Thr Gln Lys Ser Leu Ser Leu Ser
            210                 215                 220

Pro Gly Lys
225

<210> SEQ ID NO 87
<211> LENGTH: 227
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 87

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
        50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Ser Cys Ala Val Lys Gly Phe Tyr Pro Ser Asp Ile Ala Val Leu
145                 150                 155                 160

Trp Glu Ser Tyr Gly Thr Glu Trp Ser Ser Tyr Lys Thr Thr Pro Pro
                165                 170                 175

Val Leu Asp Ser Asp Gly Ser Phe Phe Leu Val Ser Lys Leu Thr Val
                180                 185                 190

Thr Lys Glu Glu Trp Gln Gln Gly Phe Val Phe Ser Cys Ser Val Met
                195                 200                 205

His Glu Ala Leu His Asn His Tyr Thr Gln Lys Ser Leu Ser Leu Ser
            210                 215                 220

Pro Gly Lys
225
```

```
<210> SEQ ID NO 88
<211> LENGTH: 15
<212> TYPE: PRT
<213> ORGANISM: Homo sapiens

<400> SEQUENCE: 88

Glu Pro Lys Ser Cys Asp Lys Thr His Thr Cys Pro Pro Cys Pro
1               5                   10                  15

<210> SEQ ID NO 89
<211> LENGTH: 10
<212> TYPE: PRT
<213> ORGANISM: Homo sapiens

<400> SEQUENCE: 89

Asp Lys Thr His Thr Cys Pro Pro Cys Pro
1               5                   10

<210> SEQ ID NO 90
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 90

Gly Gly Gly Gly Ser
1               5

<210> SEQ ID NO 91
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 91

Gly Gly Gly Gly Ser Gly Gly Gly Gly Ser
1               5                   10

<210> SEQ ID NO 92
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 92

Gly Gly Ser Gly
1

<210> SEQ ID NO 93
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

-continued

```
<400> SEQUENCE: 93

Ser Gly Gly Gly
1

<210> SEQ ID NO 94
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 94

Lys Glu Ser Gly Ser Val Ser Ser Glu Gln Leu Ala Gln Phe Arg Ser
1               5                   10                  15

Leu Asp

<210> SEQ ID NO 95
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 95

Glu Gly Lys Ser Ser Gly Ser Gly Ser Glu Ser Lys Ser Thr
1               5                   10

<210> SEQ ID NO 96
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 96

Gly Ser Ala Gly Ser Ala Ala Gly Ser Gly Glu Phe
1               5                   10

<210> SEQ ID NO 97
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 97

Ala Glu Ala Ala Ala Lys Ala
1               5

<210> SEQ ID NO 98
<211> LENGTH: 813
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

<400> SEQUENCE: 98

```
Asp Lys Thr His Thr Cys Pro Pro Cys Pro Ala Pro Glu Ala Ala Gly
1               5                   10                  15
Gly Pro Ser Val Phe Leu Phe Pro Pro Lys Pro Lys Asp Thr Leu Met
            20                  25                  30
Ile Ser Arg Thr Pro Glu Val Thr Cys Val Val Val Asp Val Ser His
        35                  40                  45
Glu Asp Pro Glu Val Lys Phe Asn Trp Tyr Val Asp Gly Val Glu Val
    50                  55                  60
His Asn Ala Lys Thr Lys Pro Arg Glu Glu Gln Tyr Asn Ser Thr Tyr
65                  70                  75                  80
Arg Val Val Ser Val Leu Thr Val Leu His Gln Asp Trp Leu Asn Gly
                85                  90                  95
Lys Glu Tyr Lys Cys Lys Val Ser Asn Lys Ala Leu Pro Ala Pro Ile
            100                 105                 110
Glu Lys Thr Ile Ser Lys Ala Lys Gly Gln Pro Arg Glu Pro Gln Val
        115                 120                 125
Tyr Thr Leu Pro Pro Ser Arg Asp Glu Leu Thr Lys Asn Gln Val Ser
    130                 135                 140
Leu Ser Cys Ala Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                165                 170                 175
Val Leu Asp Ser Asp Gly Ser Phe Phe Leu Val Ser Lys Leu Thr Val
            180                 185                 190
Asp Lys Ser Arg Trp Gln Gln Gly Asn Val Phe Ser Cys Ser Val Met
        195                 200                 205
His Glu Ala Leu His Asn His Tyr Thr Gln Lys Ser Leu Ser Leu Ser
    210                 215                 220
Pro Gly Lys Gly Gly Gly Gly Ser Gly Gly Gly Gly Ser Thr Arg Cys
225                 230                 235                 240
Pro Asp Gly Gln Phe Cys Pro Val Ala Cys Cys Leu Asp Pro Gly Gly
                245                 250                 255
Ala Ser Tyr Ser Cys Cys Arg Pro Leu Leu Asp Lys Trp Pro Thr Thr
            260                 265                 270
Leu Ser Arg His Leu Gly Gly Pro Cys Gln Val Asp Ala His Cys Ser
        275                 280                 285
Ala Gly His Ser Cys Ile Phe Thr Val Ser Gly Thr Ser Ser Cys Cys
    290                 295                 300
Pro Phe Pro Glu Ala Val Ala Cys Gly Asp Gly His His Cys Cys Pro
305                 310                 315                 320
Arg Gly Phe His Cys Ser Ala Asp Gly Arg Ser Cys Phe Gln Arg Ser
                325                 330                 335
Gly Asn Asn Ser Val Gly Ala Ile Gln Cys Pro Asp Ser Gln Phe Glu
            340                 345                 350
Cys Pro Asp Phe Ser Thr Cys Cys Val Met Val Asp Gly Ser Trp Gly
        355                 360                 365
Cys Cys Pro Met Pro Gln Ala Ser Cys Cys Glu Asp Arg Val His Cys
    370                 375                 380
Cys Pro His Gly Ala Phe Cys Asp Leu Val His Thr Arg Cys Ile Thr
385                 390                 395                 400
```

-continued

```
Pro Thr Gly Thr His Pro Leu Ala Lys Lys Leu Pro Ala Gln Arg Thr
            405                 410                 415
Asn Arg Ala Val Ala Leu Ser Ser Val Met Cys Pro Asp Ala Arg
        420                 425                 430
Ser Arg Cys Pro Asp Gly Ser Thr Cys Cys Glu Leu Pro Ser Gly Lys
            435                 440                 445
Tyr Gly Cys Cys Pro Met Pro Asn Ala Thr Cys Cys Ser Asp His Leu
    450                 455                 460
His Cys Cys Pro Gln Asp Thr Val Cys Asp Leu Ile Gln Ser Lys Cys
465                 470                 475                 480
Leu Ser Lys Glu Asn Ala Thr Thr Asp Leu Leu Thr Lys Leu Pro Ala
            485                 490                 495
His Thr Val Gly Asp Val Lys Cys Asp Met Glu Val Ser Cys Pro Asp
            500                 505                 510
Gly Tyr Thr Cys Cys Arg Leu Gln Ser Gly Ala Trp Gly Cys Cys Pro
            515                 520                 525
Phe Thr Gln Ala Val Cys Cys Glu Asp His Ile His Cys Cys Pro Ala
530                 535                 540
Gly Phe Thr Cys Asp Thr Gln Lys Gly Thr Cys Glu Gln Gly Pro His
545                 550                 555                 560
Gln Val Pro Trp Met Glu Lys Ala Pro Ala His Leu Ser Leu Pro Asp
            565                 570                 575
Pro Gln Ala Leu Lys Arg Asp Val Pro Cys Asp Asn Val Ser Ser Cys
            580                 585                 590
Pro Ser Ser Asp Thr Cys Cys Gln Leu Thr Ser Gly Glu Trp Gly Cys
            595                 600                 605
Cys Pro Ile Pro Glu Ala Val Cys Cys Ser Asp His Gln His Cys Cys
            610                 615                 620
Pro Gln Gly Tyr Thr Cys Val Ala Glu Gly Gln Cys Gln Arg Gly Ser
625                 630                 635                 640
Glu Ile Val Ala Gly Leu Glu Lys Met Pro Ala Arg Arg Ala Ser Leu
            645                 650                 655
Ser His Pro Arg Asp Ile Gly Cys Asp Gln His Thr Ser Cys Pro Val
            660                 665                 670
Gly Gln Thr Cys Cys Pro Ser Leu Gly Gly Ser Trp Ala Cys Cys Gln
            675                 680                 685
Leu Pro His Ala Val Cys Cys Glu Asp Arg Gln His Cys Cys Pro Ala
            690                 695                 700
Gly Tyr Thr Cys Asn Val Lys Ala Arg Ser Cys Glu Lys Glu Val Val
705                 710                 715                 720
Ser Ala Gln Pro Ala Thr Phe Leu Ala Arg Ser Pro His Val Gly Val
            725                 730                 735
Lys Asp Val Glu Cys Gly Glu Gly His Phe Cys His Asp Asn Gln Thr
            740                 745                 750
Cys Cys Arg Asp Asn Arg Gln Gly Trp Ala Cys Cys Pro Tyr Arg Gln
            755                 760                 765
Gly Val Cys Cys Ala Asp Arg Arg His Cys Cys Pro Ala Gly Phe Arg
    770                 775                 780
Cys Ala Ala Arg Gly Thr Lys Cys Leu Arg Arg Glu Ala Pro Arg Trp
785                 790                 795                 800
Asp Ala Pro Leu Arg Asp Pro Ala Leu Arg Pro Ile Leu
            805                 810
```

```
<210> SEQ ID NO 99
<211> LENGTH: 813
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 99

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Gly Gly Gly Ser Gly Gly Gly Ser Thr Arg Cys
225                 230                 235                 240

Pro Asp Gly Gln Phe Cys Pro Val Ala Cys Cys Leu Asp Pro Gly Gly
                245                 250                 255

Ala Ser Tyr Ser Cys Cys Arg Pro Leu Leu Asp Lys Trp Pro Thr Thr
            260                 265                 270

Leu Ser Arg His Leu Gly Gly Pro Cys Gln Val Asp Ala His Cys Ser
        275                 280                 285

Ala Gly His Ser Cys Ile Phe Thr Val Ser Gly Thr Ser Ser Cys Cys
    290                 295                 300

Pro Phe Pro Glu Ala Val Ala Cys Gly Asp Gly His Cys Cys Pro
305                 310                 315                 320

Arg Gly Phe His Cys Ser Ala Asp Gly Arg Ser Cys Phe Gln Arg Ser
                325                 330                 335

Gly Asn Asn Ser Val Gly Ala Ile Gln Cys Pro Asp Ser Gln Phe Glu
            340                 345                 350
```

```
Cys Pro Asp Phe Ser Thr Cys Cys Val Met Val Asp Gly Ser Trp Gly
            355                 360                 365

Cys Cys Pro Met Pro Gln Ala Ser Cys Cys Glu Asp Arg Val His Cys
    370                 375                 380

Cys Pro His Gly Ala Phe Cys Asp Leu Val His Thr Arg Cys Ile Thr
385                 390                 395                 400

Pro Thr Gly Thr His Pro Leu Ala Lys Lys Leu Pro Ala Gln Arg Thr
                405                 410                 415

Asn Arg Ala Val Ala Leu Ser Ser Val Met Cys Pro Asp Ala Arg
                420                 425                 430

Ser Arg Cys Pro Asp Gly Ser Thr Cys Cys Glu Leu Pro Ser Gly Lys
        435                 440                 445

Tyr Gly Cys Cys Pro Met Pro Asn Ala Thr Cys Cys Ser Asp His Leu
    450                 455                 460

His Cys Cys Pro Gln Asp Thr Val Cys Asp Leu Ile Gln Ser Lys Cys
465                 470                 475                 480

Leu Ser Lys Glu Asn Ala Thr Thr Asp Leu Leu Thr Lys Leu Pro Ala
                485                 490                 495

His Thr Val Gly Asp Val Lys Cys Asp Met Glu Val Ser Cys Pro Asp
                500                 505                 510

Gly Tyr Thr Cys Cys Arg Leu Gln Ser Gly Ala Trp Gly Cys Cys Pro
        515                 520                 525

Phe Thr Gln Ala Val Cys Cys Glu Asp His Ile His Cys Cys Pro Ala
    530                 535                 540

Gly Phe Thr Cys Asp Thr Gln Lys Gly Thr Cys Glu Gln Gly Pro His
545                 550                 555                 560

Gln Val Pro Trp Met Glu Lys Ala Pro Ala His Leu Ser Leu Pro Asp
                565                 570                 575

Pro Gln Ala Leu Lys Arg Asp Val Pro Cys Asp Asn Val Ser Ser Cys
            580                 585                 590

Pro Ser Ser Asp Thr Cys Cys Gln Leu Thr Ser Gly Glu Trp Gly Cys
        595                 600                 605

Cys Pro Ile Pro Glu Ala Val Cys Cys Ser Asp His Gln His Cys Cys
    610                 615                 620

Pro Gln Gly Tyr Thr Cys Val Ala Glu Gly Gln Cys Gln Arg Gly Ser
625                 630                 635                 640

Glu Ile Val Ala Gly Leu Glu Lys Met Pro Ala Arg Arg Ala Ser Leu
                645                 650                 655

Ser His Pro Arg Asp Ile Gly Cys Asp Gln His Thr Ser Cys Pro Val
            660                 665                 670

Gly Gln Thr Cys Cys Pro Ser Leu Gly Gly Ser Trp Ala Cys Cys Gln
        675                 680                 685

Leu Pro His Ala Val Cys Cys Glu Asp Arg Gln His Cys Cys Pro Ala
    690                 695                 700

Gly Tyr Thr Cys Asn Val Lys Ala Arg Ser Cys Glu Lys Glu Val Val
705                 710                 715                 720

Ser Ala Gln Pro Ala Thr Phe Leu Ala Arg Ser Pro His Val Gly Val
                725                 730                 735

Lys Asp Val Glu Cys Gly Glu Gly His Phe Cys His Asp Asn Gln Thr
            740                 745                 750

Cys Cys Arg Asp Asn Arg Gln Gly Trp Ala Cys Cys Pro Tyr Arg Gln
        755                 760                 765
```

-continued

```
Gly Val Cys Cys Ala Asp Arg Arg His Cys Cys Pro Ala Gly Phe Arg
770                 775                 780
Cys Ala Ala Arg Gly Thr Lys Cys Leu Arg Arg Glu Ala Pro Arg Trp
785                 790                 795                 800
Asp Ala Pro Leu Arg Asp Pro Ala Leu Arg Pro Phe Leu
                805                 810

<210> SEQ ID NO 100
<211> LENGTH: 813
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 100

Asp Lys Thr His Thr Cys Pro Pro Cys Pro Ala Pro Glu Ala Ala Gly
1               5                   10                  15
Gly Pro Ser Val Phe Leu Phe Pro Pro Lys Pro Lys Asp Thr Leu Met
                20                  25                  30
Ile Ser Arg Thr Pro Glu Val Thr Cys Val Val Val Asp Val Ser His
            35                  40                  45
Glu Asp Pro Glu Val Lys Phe Asn Trp Tyr Val Asp Gly Val Glu Val
50                  55                  60
His Asn Ala Lys Thr Lys Pro Arg Glu Glu Gln Tyr Asn Ser Thr Tyr
65                  70                  75                  80
Arg Val Val Ser Val Leu Thr Val Leu His Gln Asp Trp Leu Asn Gly
                85                  90                  95
Lys Glu Tyr Lys Cys Lys Val Ser Asn Lys Ala Leu Pro Ala Pro Ile
            100                 105                 110
Glu Lys Thr Ile Ser Lys Ala Lys Gly Gln Pro Arg Glu Pro Gln Val
        115                 120                 125
Tyr Thr Leu Pro Pro Ser Arg Asp Glu Leu Thr Lys Asn Gln Val Ser
130                 135                 140
Leu Ser Cys Ala Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                165                 170                 175
Val Leu Asp Ser Asp Gly Ser Phe Phe Leu Val Ser Lys Leu Thr Val
            180                 185                 190
Asp Lys Ser Arg Trp Gln Gln Gly Asn Val Phe Ser Cys Ser Val Met
        195                 200                 205
His Glu Ala Leu His Asn His Tyr Thr Gln Lys Ser Leu Ser Leu Ser
    210                 215                 220
Pro Gly Lys Gly Gly Gly Gly Ser Gly Gly Gly Ser Thr Arg Cys
225                 230                 235                 240
Pro Asp Gly Gln Phe Cys Pro Val Ala Cys Cys Leu Asp Pro Gly Gly
                245                 250                 255
Ala Ser Tyr Ser Cys Cys Arg Pro Leu Leu Asp Lys Trp Pro Thr Thr
            260                 265                 270
Leu Ser Arg His Leu Gly Gly Pro Cys Gln Val Asp Ala His Cys Ser
        275                 280                 285
Ala Gly His Ser Cys Ile Phe Thr Val Ser Gly Thr Ser Cys Cys
    290                 295                 300
```

```
Pro Phe Pro Glu Ala Val Ala Cys Gly Asp Gly His His Cys Cys Pro
305                 310                 315                 320

Arg Gly Phe His Cys Ser Ala Asp Gly Arg Ser Cys Phe Gln Arg Ser
            325                 330                 335

Gly Asn Asn Ser Val Gly Ala Ile Gln Cys Pro Asp Ser Gln Phe Glu
            340                 345                 350

Cys Pro Asp Phe Ser Thr Cys Cys Val Met Val Asp Gly Ser Trp Gly
            355                 360                 365

Cys Cys Pro Met Pro Gln Ala Ser Cys Cys Glu Asp Arg Val His Cys
    370                 375                 380

Cys Pro His Gly Ala Phe Cys Asp Leu Val His Thr Arg Cys Ile Thr
385                 390                 395                 400

Pro Thr Gly Thr His Pro Leu Ala Lys Lys Leu Pro Ala Gln Arg Thr
                405                 410                 415

Asn Arg Ala Val Ala Leu Ser Ser Val Met Cys Pro Asp Ala Arg
                420                 425                 430

Ser Arg Cys Pro Asp Gly Ser Thr Cys Cys Glu Leu Pro Ser Gly Lys
        435                 440                 445

Tyr Gly Cys Cys Pro Met Pro Asn Ala Thr Cys Cys Ser Asp His Leu
    450                 455                 460

His Cys Cys Pro Gln Asp Thr Val Cys Asp Leu Ile Gln Ser Lys Cys
465                 470                 475                 480

Leu Ser Lys Glu Asn Ala Thr Thr Asp Leu Leu Thr Lys Leu Pro Ala
                485                 490                 495

His Thr Val Gly Asp Val Lys Cys Asp Met Glu Val Ser Cys Pro Asp
            500                 505                 510

Gly Tyr Thr Cys Cys Arg Leu Gln Ser Gly Ala Trp Gly Cys Cys Pro
        515                 520                 525

Phe Thr Gln Ala Val Cys Cys Glu Asp His Ile His Cys Cys Pro Ala
    530                 535                 540

Gly Phe Thr Cys Asp Thr Gln Lys Gly Thr Cys Glu Gln Gly Pro His
545                 550                 555                 560

Gln Val Pro Trp Met Glu Lys Ala Pro Ala His Leu Ser Leu Pro Asp
                565                 570                 575

Pro Gln Ala Leu Lys Arg Asp Val Pro Cys Asp Asn Val Ser Ser Cys
        580                 585                 590

Pro Ser Ser Asp Thr Cys Cys Gln Leu Thr Ser Gly Glu Trp Gly Cys
    595                 600                 605

Cys Pro Ile Pro Glu Ala Val Cys Cys Ser Asp His Gln His Cys Cys
    610                 615                 620

Pro Gln Gly Tyr Thr Cys Val Ala Glu Gly Gln Cys Gln Arg Gly Ser
625                 630                 635                 640

Glu Ile Val Ala Gly Leu Glu Lys Met Pro Ala Arg Arg Ala Ser Leu
                645                 650                 655

Ser His Pro Arg Asp Ile Gly Cys Asp Gln His Thr Ser Cys Pro Val
            660                 665                 670

Gly Gln Thr Cys Cys Pro Ser Leu Gly Gly Ser Trp Ala Cys Cys Gln
        675                 680                 685

Leu Pro His Ala Val Cys Cys Glu Asp Arg Gln His Cys Cys Pro Ala
    690                 695                 700

Gly Tyr Thr Cys Asn Val Lys Ala Arg Ser Cys Glu Lys Glu Val Val
705                 710                 715                 720
```

```
Ser Ala Gln Pro Ala Thr Phe Leu Ala Arg Ser Pro His Val Gly Val
            725                 730                 735

Lys Asp Val Glu Cys Gly Glu Gly His Phe Cys His Asn Gln Thr
        740                 745                 750

Cys Cys Arg Asp Asn Arg Gln Gly Trp Ala Cys Cys Pro Tyr Arg Gln
        755                 760                 765

Gly Val Cys Cys Ala Asp Arg Arg His Cys Cys Pro Ala Gly Phe Arg
        770                 775                 780

Cys Ala Ala Arg Gly Thr Lys Cys Leu Arg Arg Glu Ala Pro Arg Trp
785                 790                 795                 800

Asp Ala Pro Leu Arg Asp Pro Ala Leu Arg Gln Gln Leu
            805                 810

<210> SEQ ID NO 101
<211> LENGTH: 813
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 101

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Gly Gly Gly Gly Ser Gly Gly Gly Ser Thr Arg Cys
225                 230                 235                 240

Pro Asp Gly Gln Phe Cys Pro Val Ala Cys Cys Leu Asp Pro Gly Gly
                245                 250                 255
```

-continued

```
Ala Ser Tyr Ser Cys Cys Arg Pro Leu Leu Asp Lys Trp Pro Thr Thr
            260                 265                 270

Leu Ser Arg His Leu Gly Gly Pro Cys Gln Val Asp Ala His Cys Ser
        275                 280                 285

Ala Gly His Ser Cys Ile Phe Thr Val Ser Gly Thr Ser Ser Cys Cys
    290                 295                 300

Pro Phe Pro Glu Ala Val Ala Cys Gly Asp Gly His His Cys Cys Pro
305                 310                 315                 320

Arg Gly Phe His Cys Ser Ala Asp Gly Arg Ser Cys Phe Gln Arg Ser
                325                 330                 335

Gly Asn Asn Ser Val Gly Ala Ile Gln Cys Pro Asp Ser Gln Phe Glu
            340                 345                 350

Cys Pro Asp Phe Ser Thr Cys Cys Val Met Val Asp Gly Ser Trp Gly
        355                 360                 365

Cys Cys Pro Met Pro Gln Ala Ser Cys Cys Glu Asp Arg Val His Cys
    370                 375                 380

Cys Pro His Gly Ala Phe Cys Asp Leu Val His Thr Arg Cys Ile Thr
385                 390                 395                 400

Pro Thr Gly Thr His Pro Leu Ala Lys Lys Leu Pro Ala Gln Arg Thr
                405                 410                 415

Asn Arg Ala Val Ala Leu Ser Ser Val Met Cys Pro Asp Ala Arg
            420                 425                 430

Ser Arg Cys Pro Asp Gly Ser Thr Cys Cys Glu Leu Pro Ser Gly Lys
        435                 440                 445

Tyr Gly Cys Cys Pro Met Pro Asn Ala Thr Cys Cys Ser Asp His Leu
    450                 455                 460

His Cys Cys Pro Gln Asp Thr Val Cys Asp Leu Ile Gln Ser Lys Cys
465                 470                 475                 480

Leu Ser Lys Glu Asn Ala Thr Thr Asp Leu Leu Thr Lys Leu Pro Ala
                485                 490                 495

His Thr Val Gly Asp Val Lys Cys Asp Met Glu Val Ser Cys Pro Asp
            500                 505                 510

Gly Tyr Thr Cys Cys Arg Leu Gln Ser Gly Ala Trp Gly Cys Cys Pro
        515                 520                 525

Phe Thr Gln Ala Val Cys Cys Glu Asp His Ile His Cys Cys Pro Ala
    530                 535                 540

Gly Phe Thr Cys Asp Thr Gln Lys Gly Thr Cys Glu Gln Gly Pro His
545                 550                 555                 560

Gln Val Pro Trp Met Glu Lys Ala Pro Ala His Leu Ser Leu Pro Asp
                565                 570                 575

Pro Gln Ala Leu Lys Arg Asp Val Pro Cys Asp Asn Val Ser Ser Cys
            580                 585                 590

Pro Ser Ser Asp Thr Cys Cys Gln Leu Thr Ser Gly Glu Trp Gly Cys
        595                 600                 605

Cys Pro Ile Pro Glu Ala Val Cys Cys Ser Asp His Gln His Cys Cys
    610                 615                 620

Pro Gln Gly Tyr Thr Cys Val Ala Glu Gly Gln Cys Gln Arg Gly Ser
625                 630                 635                 640

Glu Ile Val Ala Gly Leu Glu Lys Met Pro Ala Arg Arg Ala Ser Leu
                645                 650                 655

Ser His Pro Arg Asp Ile Gly Cys Asp Gln His Thr Ser Cys Pro Val
            660                 665                 670
```

```
Gly Gln Thr Cys Cys Pro Ser Leu Gly Gly Ser Trp Ala Cys Cys Gln
            675                 680                 685

Leu Pro His Ala Val Cys Cys Glu Asp Arg Gln His Cys Cys Pro Ala
        690                 695                 700

Gly Tyr Thr Cys Asn Val Lys Ala Arg Ser Cys Glu Lys Glu Val Val
705                 710                 715                 720

Ser Ala Gln Pro Ala Thr Phe Leu Ala Arg Ser Pro His Val Gly Val
            725                 730                 735

Lys Asp Val Glu Cys Gly Glu Gly His Phe Cys His Asp Asn Gln Thr
        740                 745                 750

Cys Cys Arg Asp Asn Arg Gln Gly Trp Ala Cys Cys Pro Tyr Arg Gln
    755                 760                 765

Gly Val Cys Cys Ala Asp Arg Arg His Cys Cys Pro Ala Gly Phe Arg
770                 775                 780

Cys Ala Ala Arg Gly Thr Lys Cys Leu Arg Arg Glu Ala Pro Arg Trp
785                 790                 795                 800

Asp Ala Pro Leu Arg Asp Pro Ala Leu Arg Val Val Leu
            805                 810

<210> SEQ ID NO 102
<211> LENGTH: 813
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 102

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205
```

-continued

```
His Glu Ala Leu His Asn His Tyr Thr Gln Lys Ser Leu Ser Leu Ser
    210                 215                 220
Pro Gly Lys Gly Gly Gly Ser Gly Gly Gly Ser Thr Arg Cys
225                 230                 235                 240
Pro Asp Gly Gln Phe Cys Pro Val Ala Cys Cys Leu Asp Pro Gly Gly
                    245                 250                 255
Ala Ser Tyr Ser Cys Cys Arg Pro Leu Leu Asp Lys Trp Pro Thr Thr
                260                 265                 270
Leu Ser Arg His Leu Gly Gly Pro Cys Gln Val Asp Ala His Cys Ser
            275                 280                 285
Ala Gly His Ser Cys Ile Phe Thr Val Ser Gly Thr Ser Ser Cys Cys
        290                 295                 300
Pro Phe Pro Glu Ala Val Ala Cys Gly Asp Gly His His Cys Cys Pro
305                 310                 315                 320
Arg Gly Phe His Cys Ser Ala Asp Gly Arg Ser Cys Phe Gln Arg Ser
                325                 330                 335
Gly Asn Asn Ser Val Gly Ala Ile Gln Cys Pro Asp Ser Gln Phe Glu
                340                 345                 350
Cys Pro Asp Phe Ser Thr Cys Cys Val Met Val Asp Gly Ser Trp Gly
                355                 360                 365
Cys Cys Pro Met Pro Gln Ala Ser Cys Cys Glu Asp Arg Val His Cys
370                 375                 380
Cys Pro His Gly Ala Phe Cys Asp Leu Val His Thr Arg Cys Ile Thr
385                 390                 395                 400
Pro Thr Gly Thr His Pro Leu Ala Lys Lys Leu Pro Ala Gln Arg Thr
                405                 410                 415
Asn Arg Ala Val Ala Leu Ser Ser Ser Val Met Cys Pro Asp Ala Arg
                420                 425                 430
Ser Arg Cys Pro Asp Gly Ser Thr Cys Cys Glu Leu Pro Ser Gly Lys
            435                 440                 445
Tyr Gly Cys Cys Pro Met Pro Asn Ala Thr Cys Cys Ser Asp His Leu
        450                 455                 460
His Cys Cys Pro Gln Asp Thr Val Cys Asp Leu Ile Gln Ser Lys Cys
465                 470                 475                 480
Leu Ser Lys Glu Asn Ala Thr Thr Asp Leu Leu Thr Lys Leu Pro Ala
                485                 490                 495
His Thr Val Gly Asp Val Lys Cys Asp Met Glu Val Ser Cys Pro Asp
                500                 505                 510
Gly Tyr Thr Cys Cys Arg Leu Gln Ser Gly Ala Trp Gly Cys Cys Pro
            515                 520                 525
Phe Thr Gln Ala Val Cys Cys Glu Asp His Ile His Cys Cys Pro Ala
        530                 535                 540
Gly Phe Thr Cys Asp Thr Gln Lys Gly Thr Cys Glu Gln Gly Pro His
545                 550                 555                 560
Gln Val Pro Trp Met Glu Lys Ala Pro Ala His Leu Ser Leu Pro Asp
                565                 570                 575
Pro Gln Ala Leu Lys Arg Asp Val Pro Cys Asp Asn Val Ser Ser Cys
                580                 585                 590
Pro Ser Ser Asp Thr Cys Cys Gln Leu Thr Ser Gly Glu Trp Gly Cys
            595                 600                 605
Cys Pro Ile Pro Glu Ala Val Cys Cys Ser Asp His Gln His Cys Cys
        610                 615                 620
```

Pro Gln Gly Tyr Thr Cys Val Ala Glu Gly Gln Cys Gln Arg Gly Ser
625                 630                 635                 640

Glu Ile Val Ala Gly Leu Glu Lys Met Pro Ala Arg Arg Ala Ser Leu
            645                 650                 655

Ser His Pro Arg Asp Ile Gly Cys Asp Gln His Thr Ser Cys Pro Val
        660                 665                 670

Gly Gln Thr Cys Cys Pro Ser Leu Gly Gly Ser Trp Ala Cys Cys Gln
    675                 680                 685

Leu Pro His Ala Val Cys Cys Glu Asp Arg Gln His Cys Cys Pro Ala
690                 695                 700

Gly Tyr Thr Cys Asn Val Lys Ala Arg Ser Cys Glu Lys Glu Val Val
705                 710                 715                 720

Ser Ala Gln Pro Ala Thr Phe Leu Ala Arg Ser Pro His Val Gly Val
            725                 730                 735

Lys Asp Val Glu Cys Gly Glu Gly His Phe Cys His Asp Asn Gln Thr
        740                 745                 750

Cys Cys Arg Asp Asn Arg Gln Gly Trp Ala Cys Cys Pro Tyr Arg Gln
    755                 760                 765

Gly Val Cys Cys Ala Asp Arg Arg His Cys Cys Pro Ala Gly Phe Arg
    770                 775                 780

Cys Ala Ala Arg Gly Thr Lys Cys Leu Arg Arg Glu Ala Pro Arg Trp
785                 790                 795                 800

Asp Ala Pro Leu Arg Asp Pro Ala Leu Arg Val Thr Leu
            805                 810

<210> SEQ ID NO 103
<211> LENGTH: 813
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 103

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160

```
Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Gly Gly Gly Gly Ser Gly Gly Gly Ser Thr Arg Cys
225                 230                 235                 240

Pro Asp Gly Gln Phe Cys Pro Val Ala Cys Cys Leu Asp Pro Gly Gly
                245                 250                 255

Ala Ser Tyr Ser Cys Cys Arg Pro Leu Leu Asp Lys Trp Pro Thr Thr
            260                 265                 270

Leu Ser Arg His Leu Gly Gly Pro Cys Gln Val Asp Ala His Cys Ser
        275                 280                 285

Ala Gly His Ser Cys Ile Phe Thr Val Ser Gly Thr Ser Ser Cys Cys
    290                 295                 300

Pro Phe Pro Glu Ala Val Ala Cys Gly Asp Gly His His Cys Cys Pro
305                 310                 315                 320

Arg Gly Phe His Cys Ser Ala Asp Gly Arg Ser Cys Phe Gln Arg Ser
                325                 330                 335

Gly Asn Asn Ser Val Gly Ala Ile Gln Cys Pro Asp Ser Gln Phe Glu
            340                 345                 350

Cys Pro Asp Phe Ser Thr Cys Cys Val Met Val Asp Gly Ser Trp Gly
        355                 360                 365

Cys Cys Pro Met Pro Gln Ala Ser Cys Cys Glu Asp Arg Val His Cys
370                 375                 380

Cys Pro His Gly Ala Phe Cys Asp Leu Val His Thr Arg Cys Ile Thr
385                 390                 395                 400

Pro Thr Gly Thr His Pro Leu Ala Lys Lys Leu Pro Ala Gln Arg Thr
                405                 410                 415

Asn Arg Ala Val Ala Leu Ser Ser Ser Val Met Cys Pro Asp Ala Arg
            420                 425                 430

Ser Arg Cys Pro Asp Gly Ser Thr Cys Cys Glu Leu Pro Ser Gly Lys
        435                 440                 445

Tyr Gly Cys Cys Pro Met Pro Asn Ala Thr Cys Cys Ser Asp His Leu
450                 455                 460

His Cys Cys Pro Gln Asp Thr Val Cys Asp Leu Ile Gln Ser Lys Cys
465                 470                 475                 480

Leu Ser Lys Glu Asn Ala Thr Thr Asp Leu Leu Thr Lys Leu Pro Ala
                485                 490                 495

His Thr Val Gly Asp Val Lys Cys Asp Met Glu Val Ser Cys Pro Asp
            500                 505                 510

Gly Tyr Thr Cys Cys Arg Leu Gln Ser Gly Ala Trp Gly Cys Cys Pro
        515                 520                 525

Phe Thr Gln Ala Val Cys Cys Glu Asp His Ile His Cys Cys Pro Ala
530                 535                 540

Gly Phe Thr Cys Asp Thr Gln Lys Gly Thr Cys Glu Gln Gly Pro His
545                 550                 555                 560

Gln Val Pro Trp Met Glu Lys Ala Pro Ala His Leu Ser Leu Pro Asp
                565                 570                 575
```

```
Pro Gln Ala Leu Lys Arg Asp Val Pro Cys Asp Asn Val Ser Ser Cys
                580                 585                 590

Pro Ser Ser Asp Thr Cys Cys Gln Leu Thr Ser Gly Glu Trp Gly Cys
            595                 600                 605

Cys Pro Ile Pro Glu Ala Val Cys Cys Ser Asp His Gln His Cys Cys
        610                 615                 620

Pro Gln Gly Tyr Thr Cys Val Ala Glu Gly Gln Cys Gln Arg Gly Ser
625                 630                 635                 640

Glu Ile Val Ala Gly Leu Glu Lys Met Pro Ala Arg Arg Ala Ser Leu
                645                 650                 655

Ser His Pro Arg Asp Ile Gly Cys Asp Gln His Thr Ser Cys Pro Val
            660                 665                 670

Gly Gln Thr Cys Cys Pro Ser Leu Gly Gly Ser Trp Ala Cys Cys Gln
        675                 680                 685

Leu Pro His Ala Val Cys Cys Glu Asp Arg Gln His Cys Cys Pro Ala
690                 695                 700

Gly Tyr Thr Cys Asn Val Lys Ala Arg Ser Cys Glu Lys Glu Val Val
705                 710                 715                 720

Ser Ala Gln Pro Ala Thr Phe Leu Ala Arg Ser Pro His Val Gly Val
                725                 730                 735

Lys Asp Val Glu Cys Gly Glu Gly His Phe Cys His Asp Asn Gln Thr
            740                 745                 750

Cys Cys Arg Asp Asn Arg Gln Gly Trp Ala Cys Cys Pro Tyr Arg Gln
        755                 760                 765

Gly Val Cys Cys Ala Asp Arg Arg His Cys Cys Pro Ala Gly Phe Arg
770                 775                 780

Cys Ala Ala Arg Gly Thr Lys Cys Leu Arg Arg Glu Ala Pro Arg Trp
785                 790                 795                 800

Asp Ala Pro Leu Arg Asp Pro Ala Leu Arg Pro Ile Leu
                805                 810

<210> SEQ ID NO 104
<211> LENGTH: 813
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 104

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
        50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110
```

```
Glu Lys Thr Ile Ser Lys Ala Lys Gly Gln Pro Arg Glu Pro Gln Val
            115                 120                 125

Tyr Thr Leu Pro Pro Ser Arg Asp Glu Leu Thr Lys Asn Gln Val Ser
        130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
            210                 215                 220

Pro Gly Lys Gly Gly Gly Gly Ser Gly Gly Gly Gly Ser Thr Arg Cys
225                 230                 235                 240

Pro Asp Gly Gln Phe Cys Pro Val Ala Cys Cys Leu Asp Pro Gly Gly
                245                 250                 255

Ala Ser Tyr Ser Cys Cys Arg Pro Leu Leu Asp Lys Trp Pro Thr Thr
            260                 265                 270

Leu Ser Arg His Leu Gly Gly Pro Cys Gln Val Asp Ala His Cys Ser
        275                 280                 285

Ala Gly His Ser Cys Ile Phe Thr Val Ser Gly Thr Ser Ser Cys Cys
        290                 295                 300

Pro Phe Pro Glu Ala Val Ala Cys Gly Asp Gly His His Cys Cys Pro
305                 310                 315                 320

Arg Gly Phe His Cys Ser Ala Asp Gly Arg Ser Cys Phe Gln Arg Ser
                325                 330                 335

Gly Asn Asn Ser Val Gly Ala Ile Gln Cys Pro Asp Ser Gln Phe Glu
            340                 345                 350

Cys Pro Asp Phe Ser Thr Cys Cys Val Met Val Asp Gly Ser Trp Gly
        355                 360                 365

Cys Cys Pro Met Pro Gln Ala Ser Cys Cys Glu Asp Arg Val His Cys
        370                 375                 380

Cys Pro His Gly Ala Phe Cys Asp Leu Val His Thr Arg Cys Ile Thr
385                 390                 395                 400

Pro Thr Gly Thr His Pro Leu Ala Lys Lys Leu Pro Ala Gln Arg Thr
                405                 410                 415

Asn Arg Ala Val Ala Leu Ser Ser Val Met Cys Pro Asp Ala Arg
            420                 425                 430

Ser Arg Cys Pro Asp Gly Ser Thr Cys Cys Glu Leu Pro Ser Gly Lys
        435                 440                 445

Tyr Gly Cys Cys Pro Met Pro Asn Ala Thr Cys Cys Ser Asp His Leu
    450                 455                 460

His Cys Cys Pro Gln Asp Thr Val Cys Asp Leu Ile Gln Ser Lys Cys
465                 470                 475                 480

Leu Ser Lys Glu Asn Ala Thr Thr Asp Leu Leu Thr Lys Leu Pro Ala
                485                 490                 495

His Thr Val Gly Asp Val Lys Cys Asp Met Glu Val Ser Cys Pro Asp
            500                 505                 510

Gly Tyr Thr Cys Cys Arg Leu Gln Ser Gly Ala Trp Gly Cys Cys Pro
        515                 520                 525
```

Phe Thr Gln Ala Val Cys Cys Glu Asp His Ile His Cys Cys Pro Ala
        530                 535                 540

Gly Phe Thr Cys Asp Thr Gln Lys Gly Thr Cys Glu Gln Gly Pro His
545                 550                 555                 560

Gln Val Pro Trp Met Glu Lys Ala Pro Ala His Leu Ser Leu Pro Asp
                565                 570                 575

Pro Gln Ala Leu Lys Arg Asp Val Pro Cys Asp Asn Val Ser Ser Cys
            580                 585                 590

Pro Ser Ser Asp Thr Cys Cys Gln Leu Thr Ser Gly Glu Trp Gly Cys
        595                 600                 605

Cys Pro Ile Pro Glu Ala Val Cys Cys Ser Asp His Gln His Cys Cys
610                 615                 620

Pro Gln Gly Tyr Thr Cys Val Ala Glu Gly Gln Cys Gln Arg Gly Ser
625                 630                 635                 640

Glu Ile Val Ala Gly Leu Glu Lys Met Pro Ala Arg Arg Ala Ser Leu
                645                 650                 655

Ser His Pro Arg Asp Ile Gly Cys Asp Gln His Thr Ser Cys Pro Val
            660                 665                 670

Gly Gln Thr Cys Cys Pro Ser Leu Gly Gly Ser Trp Ala Cys Cys Gln
        675                 680                 685

Leu Pro His Ala Val Cys Cys Glu Asp Arg Gln His Cys Cys Pro Ala
690                 695                 700

Gly Tyr Thr Cys Asn Val Lys Ala Arg Ser Cys Glu Lys Glu Val Val
705                 710                 715                 720

Ser Ala Gln Pro Ala Thr Phe Leu Ala Arg Ser Pro His Val Gly Val
                725                 730                 735

Lys Asp Val Glu Cys Gly Glu Gly His Phe Cys His Asp Asn Gln Thr
            740                 745                 750

Cys Cys Arg Asp Asn Arg Gln Gly Trp Ala Cys Pro Tyr Arg Gln
        755                 760                 765

Gly Val Cys Cys Ala Asp Arg Arg His Cys Cys Pro Ala Gly Phe Arg
770                 775                 780

Cys Ala Ala Arg Gly Thr Lys Cys Leu Arg Arg Glu Ala Pro Arg Trp
785                 790                 795                 800

Asp Ala Pro Leu Arg Asp Pro Ala Leu Arg Pro Phe Leu
                805                 810

<210> SEQ ID NO 105
<211> LENGTH: 813
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 105

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
50                  55                  60

-continued

His Asn Ala Lys Thr Lys Pro Arg Glu Glu Gln Tyr Asn Ser Thr Tyr
65              70              75              80

Arg Val Val Ser Val Leu Thr Val Leu His Gln Asp Trp Leu Asn Gly
            85              90              95

Lys Glu Tyr Lys Cys Lys Val Ser Asn Lys Ala Leu Pro Ala Pro Ile
        100             105             110

Glu Lys Thr Ile Ser Lys Ala Lys Gly Gln Pro Arg Glu Pro Gln Val
    115             120             125

Tyr Thr Leu Pro Pro Ser Arg Asp Glu Leu Thr Lys Asn Gln Val Ser
130             135             140

Leu Trp Cys Leu Val Lys Gly Phe Tyr Pro Ser Asp Ile Ala Val Glu
145             150             155             160

Trp Glu Ser Asn Gly Gln Pro Glu Asn Asn Tyr Lys Thr Thr Pro Pro
            165             170             175

Val Leu Asp Ser Asp Gly Ser Phe Phe Leu Tyr Ser Lys Leu Thr Val
        180             185             190

Asp Lys Ser Arg Trp Gln Gln Gly Asn Val Phe Ser Cys Ser Val Met
    195             200             205

His Glu Ala Leu His Asn His Tyr Thr Gln Lys Ser Leu Ser Leu Ser
210             215             220

Pro Gly Lys Gly Gly Gly Gly Ser Gly Gly Gly Ser Thr Arg Cys
225             230             235             240

Pro Asp Gly Gln Phe Cys Pro Val Ala Cys Cys Leu Asp Pro Gly Gly
            245             250             255

Ala Ser Tyr Ser Cys Cys Arg Pro Leu Leu Asp Lys Trp Pro Thr Thr
        260             265             270

Leu Ser Arg His Leu Gly Gly Pro Cys Gln Val Asp Ala His Cys Ser
    275             280             285

Ala Gly His Ser Cys Ile Phe Thr Val Ser Gly Thr Ser Ser Cys Cys
290             295             300

Pro Phe Pro Glu Ala Val Ala Cys Gly Asp Gly His His Cys Cys Pro
305             310             315             320

Arg Gly Phe His Cys Ser Ala Asp Gly Arg Ser Cys Phe Gln Arg Ser
            325             330             335

Gly Asn Asn Ser Val Gly Ala Ile Gln Cys Pro Asp Ser Gln Phe Glu
        340             345             350

Cys Pro Asp Phe Ser Thr Cys Cys Val Met Val Asp Gly Ser Trp Gly
    355             360             365

Cys Cys Pro Met Pro Gln Ala Ser Cys Cys Glu Asp Arg Val His Cys
370             375             380

Cys Pro His Gly Ala Phe Cys Asp Leu Val His Thr Arg Cys Ile Thr
385             390             395             400

Pro Thr Gly Thr His Pro Leu Ala Lys Lys Leu Pro Ala Gln Arg Thr
            405             410             415

Asn Arg Ala Val Ala Leu Ser Ser Ser Val Met Cys Pro Asp Ala Arg
        420             425             430

Ser Arg Cys Pro Asp Gly Ser Thr Cys Cys Glu Leu Pro Ser Gly Lys
    435             440             445

Tyr Gly Cys Cys Pro Met Pro Asn Ala Thr Cys Cys Ser Asp His Leu
450             455             460

His Cys Cys Pro Gln Asp Thr Val Cys Asp Leu Ile Gln Ser Lys Cys
465             470             475             480

```
Leu Ser Lys Glu Asn Ala Thr Thr Asp Leu Leu Thr Lys Leu Pro Ala
            485                 490                 495

His Thr Val Gly Asp Val Lys Cys Asp Met Glu Val Ser Cys Pro Asp
        500                 505                 510

Gly Tyr Thr Cys Cys Arg Leu Gln Ser Gly Ala Trp Gly Cys Cys Pro
            515                 520                 525

Phe Thr Gln Ala Val Cys Cys Glu Asp His Ile His Cys Cys Pro Ala
        530                 535                 540

Gly Phe Thr Cys Asp Thr Gln Lys Gly Thr Cys Glu Gln Gly Pro His
545                 550                 555                 560

Gln Val Pro Trp Met Glu Lys Ala Pro Ala His Leu Ser Leu Pro Asp
                565                 570                 575

Pro Gln Ala Leu Lys Arg Asp Val Pro Cys Asp Asn Val Ser Ser Cys
            580                 585                 590

Pro Ser Ser Asp Thr Cys Cys Gln Leu Thr Ser Gly Glu Trp Gly Cys
        595                 600                 605

Cys Pro Ile Pro Glu Ala Val Cys Cys Ser Asp His Gln His Cys Cys
        610                 615                 620

Pro Gln Gly Tyr Thr Cys Val Ala Glu Gly Gln Cys Gln Arg Gly Ser
625                 630                 635                 640

Glu Ile Val Ala Gly Leu Glu Lys Met Pro Ala Arg Arg Ala Ser Leu
                645                 650                 655

Ser His Pro Arg Asp Ile Gly Cys Asp Gln His Thr Ser Cys Pro Val
            660                 665                 670

Gly Gln Thr Cys Cys Pro Ser Leu Gly Gly Ser Trp Ala Cys Cys Gln
        675                 680                 685

Leu Pro His Ala Val Cys Cys Glu Asp Arg Gln His Cys Cys Pro Ala
        690                 695                 700

Gly Tyr Thr Cys Asn Val Lys Ala Arg Ser Cys Glu Lys Glu Val Val
705                 710                 715                 720

Ser Ala Gln Pro Ala Thr Phe Leu Ala Arg Ser Pro His Val Gly Val
                725                 730                 735

Lys Asp Val Glu Cys Gly Glu Gly His Phe Cys His Asp Asn Gln Thr
            740                 745                 750

Cys Cys Arg Asp Asn Arg Gln Gly Trp Ala Cys Cys Pro Tyr Arg Gln
        755                 760                 765

Gly Val Cys Cys Ala Asp Arg Arg His Cys Cys Pro Ala Gly Phe Arg
        770                 775                 780

Cys Ala Ala Arg Gly Thr Lys Cys Leu Arg Arg Glu Ala Pro Arg Trp
785                 790                 795                 800

Asp Ala Pro Leu Arg Asp Pro Ala Leu Arg Gln Gln Leu
                805                 810

<210> SEQ ID NO 106
<211> LENGTH: 813
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 106

Asp Lys Thr His Thr Cys Pro Pro Cys Pro Ala Pro Glu Ala Ala Gly
1               5                   10                  15
```

-continued

```
Gly Pro Ser Val Phe Leu Phe Pro Pro Lys Pro Lys Asp Thr Leu Met
             20                  25                  30
Ile Ser Arg Thr Pro Glu Val Thr Cys Val Val Val Asp Val Ser His
         35                  40                  45
Glu Asp Pro Glu Val Lys Phe Asn Trp Tyr Val Asp Gly Val Glu Val
 50                  55                  60
His Asn Ala Lys Thr Lys Pro Arg Glu Glu Gln Tyr Asn Ser Thr Tyr
 65                  70                  75                  80
Arg Val Val Ser Val Leu Thr Val Leu His Gln Asp Trp Leu Asn Gly
                 85                  90                  95
Lys Glu Tyr Lys Cys Lys Val Ser Asn Lys Ala Leu Pro Ala Pro Ile
             100                 105                 110
Glu Lys Thr Ile Ser Lys Ala Lys Gly Gln Pro Arg Glu Pro Gln Val
         115                 120                 125
Tyr Thr Leu Pro Pro Ser Arg Asp Glu Leu Thr Lys Asn Gln Val Ser
130                 135                 140
Leu Trp Cys Leu Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                 165                 170                 175
Val Leu Asp Ser Asp Gly Ser Phe Phe Leu Tyr Ser Lys Leu Thr Val
             180                 185                 190
Asp Lys Ser Arg Trp Gln Gln Gly Asn Val Phe Ser Cys Ser Val Met
         195                 200                 205
His Glu Ala Leu His Asn His Tyr Thr Gln Lys Ser Leu Ser Leu Ser
         210                 215                 220
Pro Gly Lys Gly Gly Gly Gly Ser Gly Gly Gly Gly Ser Thr Arg Cys
225                 230                 235                 240
Pro Asp Gly Gln Phe Cys Pro Val Ala Cys Cys Leu Asp Pro Gly Gly
                 245                 250                 255
Ala Ser Tyr Ser Cys Cys Arg Pro Leu Leu Asp Lys Trp Pro Thr Thr
             260                 265                 270
Leu Ser Arg His Leu Gly Gly Pro Cys Gln Val Asp Ala His Cys Ser
         275                 280                 285
Ala Gly His Ser Cys Ile Phe Thr Val Ser Gly Thr Ser Ser Cys Cys
     290                 295                 300
Pro Phe Pro Glu Ala Val Ala Cys Gly Asp Gly His His Cys Cys Pro
305                 310                 315                 320
Arg Gly Phe His Cys Ser Ala Asp Gly Arg Ser Cys Phe Gln Arg Ser
                 325                 330                 335
Gly Asn Asn Ser Val Gly Ala Ile Gln Cys Pro Asp Ser Gln Phe Glu
             340                 345                 350
Cys Pro Asp Phe Ser Thr Cys Cys Val Met Val Asp Gly Ser Trp Gly
         355                 360                 365
Cys Cys Pro Met Pro Gln Ala Ser Cys Cys Glu Asp Arg Val His Cys
     370                 375                 380
Cys Pro His Gly Ala Phe Cys Asp Leu Val His Thr Arg Cys Ile Thr
385                 390                 395                 400
Pro Thr Gly Thr His Pro Leu Ala Lys Lys Leu Pro Ala Gln Arg Thr
                 405                 410                 415
Asn Arg Ala Val Ala Leu Ser Ser Val Met Cys Pro Asp Ala Arg
             420                 425                 430
```

-continued

```
Ser Arg Cys Pro Asp Gly Ser Thr Cys Cys Glu Leu Pro Ser Gly Lys
        435                 440                 445

Tyr Gly Cys Cys Pro Met Pro Asn Ala Thr Cys Cys Ser Asp His Leu
450                 455                 460

His Cys Cys Pro Gln Asp Thr Val Cys Asp Leu Ile Gln Ser Lys Cys
465                 470                 475                 480

Leu Ser Lys Glu Asn Ala Thr Thr Asp Leu Leu Thr Lys Leu Pro Ala
                485                 490                 495

His Thr Val Gly Asp Val Lys Cys Asp Met Glu Val Ser Cys Pro Asp
            500                 505                 510

Gly Tyr Thr Cys Cys Arg Leu Gln Ser Gly Ala Trp Gly Cys Cys Pro
        515                 520                 525

Phe Thr Gln Ala Val Cys Cys Glu Asp His Ile His Cys Cys Pro Ala
    530                 535                 540

Gly Phe Thr Cys Asp Thr Gln Lys Gly Thr Cys Glu Gln Gly Pro His
545                 550                 555                 560

Gln Val Pro Trp Met Glu Lys Ala Pro Ala His Leu Ser Leu Pro Asp
                565                 570                 575

Pro Gln Ala Leu Lys Arg Asp Val Pro Cys Asp Asn Val Ser Ser Cys
            580                 585                 590

Pro Ser Ser Asp Thr Cys Cys Gln Leu Thr Ser Gly Glu Trp Gly Cys
        595                 600                 605

Cys Pro Ile Pro Glu Ala Val Cys Cys Ser Asp His Gln His Cys Cys
    610                 615                 620

Pro Gln Gly Tyr Thr Cys Val Ala Glu Gly Gln Cys Gln Arg Gly Ser
625                 630                 635                 640

Glu Ile Val Ala Gly Leu Glu Lys Met Pro Ala Arg Arg Ala Ser Leu
                645                 650                 655

Ser His Pro Arg Asp Ile Gly Cys Asp Gln His Thr Ser Cys Pro Val
            660                 665                 670

Gly Gln Thr Cys Cys Pro Ser Leu Gly Gly Ser Trp Ala Cys Cys Gln
        675                 680                 685

Leu Pro His Ala Val Cys Cys Glu Asp Arg Gln His Cys Cys Pro Ala
    690                 695                 700

Gly Tyr Thr Cys Asn Val Lys Ala Arg Ser Cys Glu Lys Glu Val Val
705                 710                 715                 720

Ser Ala Gln Pro Ala Thr Phe Leu Ala Arg Ser Pro His Val Gly Val
                725                 730                 735

Lys Asp Val Glu Cys Gly Glu Gly His Phe Cys His Asp Asn Gln Thr
            740                 745                 750

Cys Cys Arg Asp Asn Arg Gln Gly Trp Ala Cys Cys Pro Tyr Arg Gln
        755                 760                 765

Gly Val Cys Cys Ala Asp Arg Arg His Cys Cys Pro Ala Gly Phe Arg
    770                 775                 780

Cys Ala Ala Arg Gly Thr Lys Cys Leu Arg Arg Glu Ala Pro Arg Trp
785                 790                 795                 800

Asp Ala Pro Leu Arg Asp Pro Ala Leu Arg Val Val Leu
                805                 810
```

<210> SEQ ID NO 107
<211> LENGTH: 813
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 107

```
Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Gly Gly Gly Gly Ser Gly Gly Gly Gly Ser Thr Arg Cys
225                 230                 235                 240

Pro Asp Gly Gln Phe Cys Pro Val Ala Cys Cys Leu Asp Pro Gly Gly
                245                 250                 255

Ala Ser Tyr Ser Cys Cys Arg Pro Leu Leu Asp Lys Trp Pro Thr Thr
            260                 265                 270

Leu Ser Arg His Leu Gly Gly Pro Cys Gln Val Asp Ala His Cys Ser
        275                 280                 285

Ala Gly His Ser Cys Ile Phe Thr Val Ser Gly Thr Ser Ser Cys Cys
    290                 295                 300

Pro Phe Pro Glu Ala Val Ala Cys Gly Asp Gly His His Cys Cys Pro
305                 310                 315                 320

Arg Gly Phe His Cys Ser Ala Asp Gly Arg Ser Cys Phe Gln Arg Ser
                325                 330                 335

Gly Asn Asn Ser Val Gly Ala Ile Gln Cys Pro Asp Ser Gln Phe Glu
            340                 345                 350

Cys Pro Asp Phe Ser Thr Cys Cys Val Met Val Asp Gly Ser Trp Gly
        355                 360                 365

Cys Cys Pro Met Pro Gln Ala Ser Cys Cys Glu Asp Arg Val His Cys
    370                 375                 380

Cys Pro His Gly Ala Phe Cys Asp Leu Val His Thr Arg Cys Ile Thr
385                 390                 395                 400
```

-continued

```
Pro Thr Gly Thr His Pro Leu Ala Lys Lys Leu Pro Ala Gln Arg Thr
                405                 410                 415
Asn Arg Ala Val Ala Leu Ser Ser Val Met Cys Pro Asp Ala Arg
            420                 425                 430
Ser Arg Cys Pro Asp Gly Ser Thr Cys Cys Glu Leu Pro Ser Gly Lys
        435                 440                 445
Tyr Gly Cys Cys Pro Met Pro Asn Ala Thr Cys Cys Ser Asp His Leu
    450                 455                 460
His Cys Cys Pro Gln Asp Thr Val Cys Asp Leu Ile Gln Ser Lys Cys
465                 470                 475                 480
Leu Ser Lys Glu Asn Ala Thr Thr Asp Leu Leu Thr Lys Leu Pro Ala
                485                 490                 495
His Thr Val Gly Asp Val Lys Cys Asp Met Glu Val Ser Cys Pro Asp
            500                 505                 510
Gly Tyr Thr Cys Cys Arg Leu Gln Ser Gly Ala Trp Gly Cys Cys Pro
        515                 520                 525
Phe Thr Gln Ala Val Cys Cys Glu Asp His Ile His Cys Cys Pro Ala
    530                 535                 540
Gly Phe Thr Cys Asp Thr Gln Lys Gly Thr Cys Glu Gln Gly Pro His
545                 550                 555                 560
Gln Val Pro Trp Met Glu Lys Ala Pro Ala His Leu Ser Leu Pro Asp
                565                 570                 575
Pro Gln Ala Leu Lys Arg Asp Val Pro Cys Asp Asn Val Ser Ser Cys
            580                 585                 590
Pro Ser Ser Asp Thr Cys Cys Gln Leu Thr Ser Gly Glu Trp Gly Cys
        595                 600                 605
Cys Pro Ile Pro Glu Ala Val Cys Cys Ser Asp His Gln His Cys Cys
    610                 615                 620
Pro Gln Gly Tyr Thr Cys Val Ala Glu Gly Gln Cys Gln Arg Gly Ser
625                 630                 635                 640
Glu Ile Val Ala Gly Leu Glu Lys Met Pro Ala Arg Arg Ala Ser Leu
                645                 650                 655
Ser His Pro Arg Asp Ile Gly Cys Asp Gln His Thr Ser Cys Pro Val
            660                 665                 670
Gly Gln Thr Cys Cys Pro Ser Leu Gly Gly Ser Trp Ala Cys Cys Gln
        675                 680                 685
Leu Pro His Ala Val Cys Cys Glu Asp Arg Gln His Cys Cys Pro Ala
    690                 695                 700
Gly Tyr Thr Cys Asn Val Lys Ala Arg Ser Cys Glu Lys Glu Val Val
705                 710                 715                 720
Ser Ala Gln Pro Ala Thr Phe Leu Ala Arg Ser Pro His Val Gly Val
                725                 730                 735
Lys Asp Val Glu Cys Gly Glu Gly His Phe Cys His Asp Asn Gln Thr
            740                 745                 750
Cys Cys Arg Asp Asn Arg Gln Gly Trp Ala Cys Cys Pro Tyr Arg Gln
        755                 760                 765
Gly Val Cys Cys Ala Asp Arg Arg His Cys Cys Pro Ala Gly Phe Arg
    770                 775                 780
Cys Ala Ala Arg Gly Thr Lys Cys Leu Arg Arg Glu Ala Pro Arg Trp
785                 790                 795                 800
Asp Ala Pro Leu Arg Asp Pro Ala Leu Arg Val Thr Leu
                805                 810
```

<210> SEQ ID NO 108
<211> LENGTH: 813
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 108

```
Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Gly Gly Gly Ser Gly Gly Gly Ser Thr Arg Cys
225                 230                 235                 240

Pro Asp Gly Gln Phe Cys Pro Val Ala Cys Cys Leu Asp Pro Gly Gly
                245                 250                 255

Ala Ser Tyr Ser Cys Cys Arg Pro Leu Leu Asp Lys Trp Pro Thr Thr
            260                 265                 270

Leu Ser Arg His Leu Gly Gly Pro Cys Gln Val Asp Ala His Cys Ser
        275                 280                 285

Ala Gly His Ser Cys Ile Phe Thr Val Ser Gly Thr Ser Ser Cys Cys
    290                 295                 300

Pro Phe Pro Glu Ala Val Ala Cys Gly Asp Gly His His Cys Cys Pro
305                 310                 315                 320

Arg Gly Phe His Cys Ser Ala Asp Gly Arg Ser Cys Phe Gln Arg Ser
                325                 330                 335

Gly Asn Asn Ser Val Gly Ala Ile Gln Cys Pro Asp Ser Gln Phe Glu
            340                 345                 350
```

```
Cys Pro Asp Phe Ser Thr Cys Cys Val Met Val Asp Gly Ser Trp Gly
            355                 360                 365

Cys Cys Pro Met Pro Gln Ala Ser Cys Cys Glu Asp Arg Val His Cys
        370                 375                 380

Cys Pro His Gly Ala Phe Cys Asp Leu Val His Thr Arg Cys Ile Thr
385                 390                 395                 400

Pro Thr Gly Thr His Pro Leu Ala Lys Lys Leu Pro Ala Gln Arg Thr
                405                 410                 415

Asn Arg Ala Val Ala Leu Ser Ser Val Met Cys Pro Asp Ala Arg
                420                 425                 430

Ser Arg Cys Pro Asp Gly Ser Thr Cys Cys Glu Leu Pro Ser Gly Lys
        435                 440                 445

Tyr Gly Cys Cys Pro Met Pro Asn Ala Thr Cys Cys Ser Asp His Leu
        450                 455                 460

His Cys Cys Pro Gln Asp Thr Val Cys Asp Leu Ile Gln Ser Lys Cys
465                 470                 475                 480

Leu Ser Lys Glu Asn Ala Thr Thr Asp Leu Leu Thr Lys Leu Pro Ala
                485                 490                 495

His Thr Val Gly Asp Val Lys Cys Asp Met Glu Val Ser Cys Pro Asp
                500                 505                 510

Gly Tyr Thr Cys Cys Arg Leu Gln Ser Gly Ala Trp Gly Cys Cys Pro
        515                 520                 525

Phe Thr Gln Ala Val Cys Cys Glu Asp His Ile His Cys Cys Pro Ala
        530                 535                 540

Gly Phe Thr Cys Asp Thr Gln Lys Gly Thr Cys Glu Gln Gly Pro His
545                 550                 555                 560

Gln Val Pro Trp Met Glu Lys Ala Pro Ala His Leu Ser Leu Pro Asp
                565                 570                 575

Pro Gln Ala Leu Lys Arg Asp Val Pro Cys Asp Asn Val Ser Ser Cys
            580                 585                 590

Pro Ser Ser Asp Thr Cys Cys Gln Leu Thr Ser Gly Glu Trp Gly Cys
        595                 600                 605

Cys Pro Ile Pro Glu Ala Val Cys Cys Ser Asp His Gln His Cys Cys
        610                 615                 620

Pro Gln Gly Tyr Thr Cys Val Ala Glu Gly Gln Cys Gln Arg Gly Ser
625                 630                 635                 640

Glu Ile Val Ala Gly Leu Glu Lys Met Pro Ala Arg Arg Ala Ser Leu
                645                 650                 655

Ser His Pro Arg Asp Ile Gly Cys Asp Gln His Thr Ser Cys Pro Val
                660                 665                 670

Gly Gln Thr Cys Cys Pro Ser Leu Gly Gly Ser Trp Ala Cys Cys Gln
            675                 680                 685

Leu Pro His Ala Val Cys Cys Glu Asp Arg Gln His Cys Cys Pro Ala
        690                 695                 700

Gly Tyr Thr Cys Asn Val Lys Ala Arg Ser Cys Glu Lys Glu Val Val
705                 710                 715                 720

Ser Ala Gln Pro Ala Thr Phe Leu Ala Arg Ser Pro His Val Gly Val
                725                 730                 735

Lys Asp Val Glu Cys Gly Glu Gly His Phe Cys His Asp Asn Gln Thr
            740                 745                 750

Cys Cys Arg Asp Asn Arg Gln Gly Trp Ala Cys Cys Pro Tyr Arg Gln
        755                 760                 765
```

```
Gly Val Cys Cys Ala Asp Arg Arg His Cys Cys Pro Ala Gly Phe Arg
    770                 775                 780

Cys Ala Ala Arg Gly Thr Lys Cys Leu Arg Arg Glu Ala Pro Arg Trp
785                 790                 795                 800

Asp Ala Pro Leu Arg Asp Pro Ala Leu Arg Gln Leu Leu
                805                 810

<210> SEQ ID NO 109
<211> LENGTH: 760
<212> TYPE: PRT
<213> ORGANISM: Homo sapiens

<400> SEQUENCE: 109

Met Met Asp Gln Ala Arg Ser Ala Phe Ser Asn Leu Phe Gly Gly Glu
1               5                   10                  15

Pro Leu Ser Tyr Thr Arg Phe Ser Leu Ala Arg Gln Val Asp Gly Asp
            20                  25                  30

Asn Ser His Val Glu Met Lys Leu Ala Val Asp Glu Glu Asn Ala
        35                  40                  45

Asp Asn Asn Thr Lys Ala Asn Val Thr Lys Pro Lys Arg Cys Ser Gly
    50                  55                  60

Ser Ile Cys Tyr Gly Thr Ile Ala Val Ile Val Phe Phe Leu Ile Gly
65                  70                  75                  80

Phe Met Ile Gly Tyr Leu Gly Tyr Cys Lys Gly Val Glu Pro Lys Thr
                85                  90                  95

Glu Cys Glu Arg Leu Ala Gly Thr Glu Ser Pro Val Arg Glu Glu Pro
            100                 105                 110

Gly Glu Asp Phe Pro Ala Ala Arg Arg Leu Tyr Trp Asp Asp Leu Lys
        115                 120                 125

Arg Lys Leu Ser Glu Lys Leu Asp Ser Thr Asp Phe Thr Gly Thr Ile
    130                 135                 140

Lys Leu Leu Asn Glu Asn Ser Tyr Val Pro Arg Glu Ala Gly Ser Gln
145                 150                 155                 160

Lys Asp Glu Asn Leu Ala Leu Tyr Val Glu Asn Gln Phe Arg Glu Phe
                165                 170                 175

Lys Leu Ser Lys Val Trp Arg Asp Gln His Phe Val Lys Ile Gln Val
            180                 185                 190

Lys Asp Ser Ala Gln Asn Ser Val Ile Ile Val Asp Lys Asn Gly Arg
        195                 200                 205

Leu Val Tyr Leu Val Glu Asn Pro Gly Gly Tyr Val Ala Tyr Ser Lys
    210                 215                 220

Ala Ala Thr Val Thr Gly Lys Leu Val His Ala Asn Phe Gly Thr Lys
225                 230                 235                 240

Lys Asp Phe Glu Asp Leu Tyr Thr Pro Val Asn Gly Ser Ile Val Ile
                245                 250                 255

Val Arg Ala Gly Lys Ile Thr Phe Ala Glu Lys Val Ala Asn Ala Glu
            260                 265                 270

Ser Leu Asn Ala Ile Gly Val Leu Ile Tyr Met Asp Gln Thr Lys Phe
        275                 280                 285

Pro Ile Val Asn Ala Glu Leu Ser Phe Phe Gly His Ala His Leu Gly
    290                 295                 300

Thr Gly Asp Pro Tyr Thr Pro Gly Phe Pro Ser Phe Asn His Thr Gln
305                 310                 315                 320

Phe Pro Pro Ser Arg Ser Ser Gly Leu Pro Asn Ile Pro Val Gln Thr
                325                 330                 335
```

-continued

```
Ile Ser Arg Ala Ala Glu Lys Leu Phe Gly Asn Met Glu Gly Asp
            340                 345                 350

Cys Pro Ser Asp Trp Lys Thr Asp Ser Thr Cys Arg Met Val Thr Ser
            355                 360                 365

Glu Ser Lys Asn Val Lys Leu Thr Val Ser Asn Val Leu Lys Glu Ile
            370                 375                 380

Lys Ile Leu Asn Ile Phe Gly Val Ile Lys Gly Phe Val Glu Pro Asp
385                 390                 395                 400

His Tyr Val Val Val Gly Ala Gln Arg Asp Ala Trp Gly Pro Gly Ala
                405                 410                 415

Ala Lys Ser Gly Val Gly Thr Ala Leu Leu Leu Lys Leu Ala Gln Met
            420                 425                 430

Phe Ser Asp Met Val Leu Lys Asp Gly Phe Gln Pro Ser Arg Ser Ile
            435                 440                 445

Ile Phe Ala Ser Trp Ser Ala Gly Asp Phe Gly Ser Val Gly Ala Thr
            450                 455                 460

Glu Trp Leu Glu Gly Tyr Leu Ser Ser Leu His Leu Lys Ala Phe Thr
465                 470                 475                 480

Tyr Ile Asn Leu Asp Lys Ala Val Leu Gly Thr Ser Asn Phe Lys Val
                485                 490                 495

Ser Ala Ser Pro Leu Leu Tyr Thr Leu Ile Glu Lys Thr Met Gln Asn
            500                 505                 510

Val Lys His Pro Val Thr Gly Gln Phe Leu Tyr Gln Asp Ser Asn Trp
            515                 520                 525

Ala Ser Lys Val Glu Lys Leu Thr Leu Asp Asn Ala Ala Phe Pro Phe
            530                 535                 540

Leu Ala Tyr Ser Gly Ile Pro Ala Val Ser Phe Cys Phe Cys Glu Asp
545                 550                 555                 560

Thr Asp Tyr Pro Tyr Leu Gly Thr Thr Met Asp Thr Tyr Lys Glu Leu
            565                 570                 575

Ile Glu Arg Ile Pro Glu Leu Asn Lys Val Ala Arg Ala Ala Ala Glu
            580                 585                 590

Val Ala Gly Gln Phe Val Ile Lys Leu Thr His Asp Val Glu Leu Asn
            595                 600                 605

Leu Asp Tyr Glu Arg Tyr Asn Ser Gln Leu Leu Ser Phe Val Arg Asp
            610                 615                 620

Leu Asn Gln Tyr Arg Ala Asp Ile Lys Glu Met Gly Leu Ser Leu Gln
625                 630                 635                 640

Trp Leu Tyr Ser Ala Arg Gly Asp Phe Phe Arg Ala Thr Ser Arg Leu
                645                 650                 655

Thr Thr Asp Phe Gly Asn Ala Glu Lys Thr Asp Arg Phe Val Met Lys
            660                 665                 670

Lys Leu Asn Asp Arg Val Met Arg Val Glu Tyr His Phe Leu Ser Pro
            675                 680                 685

Tyr Val Ser Pro Lys Glu Ser Pro Phe Arg His Val Phe Trp Gly Ser
            690                 695                 700

Gly Ser His Thr Leu Pro Ala Leu Leu Glu Asn Leu Lys Leu Arg Lys
705                 710                 715                 720

Gln Asn Asn Gly Ala Phe Asn Glu Thr Leu Phe Arg Asn Gln Leu Ala
                725                 730                 735

Leu Ala Thr Trp Thr Ile Gln Gly Ala Ala Asn Ala Leu Ser Gly Asp
            740                 745                 750
```

```
Val Trp Asp Ile Asp Asn Glu Phe
        755                 760
```

<210> SEQ ID NO 110
<211> LENGTH: 227
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 110

```
Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225
```

<210> SEQ ID NO 111
<211> LENGTH: 576
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 111

```
Thr Arg Cys Pro Asp Gly Gln Phe Cys Pro Val Ala Cys Cys Leu Asp
1               5                   10                  15

Pro Gly Gly Ala Ser Tyr Ser Cys Cys Arg Pro Leu Leu Asp Lys Trp
            20                  25                  30
```

```
Pro Thr Thr Leu Ser Arg His Leu Gly Gly Pro Cys Gln Val Asp Ala
        35                  40                  45

His Cys Ser Ala Gly His Ser Cys Ile Phe Thr Val Ser Gly Thr Ser
 50                  55                  60

Ser Cys Cys Pro Phe Pro Glu Ala Val Ala Cys Gly Asp Gly His His
 65              70                  75                      80

Cys Cys Pro Arg Gly Phe His Cys Ser Ala Asp Gly Arg Ser Cys Phe
                85                  90                  95

Gln Arg Ser Gly Asn Asn Ser Val Gly Ala Ile Gln Cys Pro Asp Ser
                100                 105                 110

Gln Phe Glu Cys Pro Asp Phe Ser Thr Cys Cys Val Met Val Asp Gly
            115                 120                 125

Ser Trp Gly Cys Cys Pro Met Pro Gln Ala Ser Cys Cys Glu Asp Arg
            130                 135                 140

Val His Cys Cys Pro His Gly Ala Phe Cys Asp Leu Val His Thr Arg
145                 150                 155                 160

Cys Ile Thr Pro Thr Gly Thr His Pro Leu Ala Lys Lys Leu Pro Ala
                165                 170                 175

Gln Arg Thr Asn Arg Ala Val Ala Leu Ser Ser Val Met Cys Pro
                180                 185                 190

Asp Ala Arg Ser Arg Cys Pro Asp Gly Ser Thr Cys Cys Glu Leu Pro
            195                 200                 205

Ser Gly Lys Tyr Gly Cys Cys Pro Met Pro Asn Ala Thr Cys Cys Ser
    210                 215                 220

Asp His Leu His Cys Cys Pro Gln Asp Thr Val Cys Asp Leu Ile Gln
225                 230                 235                 240

Ser Lys Cys Leu Ser Lys Glu Asn Ala Thr Thr Asp Leu Leu Thr Lys
                245                 250                 255

Leu Pro Ala His Thr Val Gly Asp Val Lys Cys Asp Met Glu Val Ser
                260                 265                 270

Cys Pro Asp Gly Tyr Thr Cys Cys Arg Leu Gln Ser Gly Ala Trp Gly
        275                 280                 285

Cys Cys Pro Phe Thr Gln Ala Val Cys Cys Glu Asp His Ile His Cys
        290                 295                 300

Cys Pro Ala Gly Phe Thr Cys Asp Thr Gln Lys Gly Thr Cys Glu Gln
305                 310                 315                 320

Gly Pro His Gln Val Pro Trp Met Glu Lys Ala Pro Ala His Leu Ser
                325                 330                 335

Leu Pro Asp Pro Gln Ala Leu Lys Arg Asp Val Pro Cys Asp Asn Val
            340                 345                 350

Ser Ser Cys Pro Ser Ser Asp Thr Cys Cys Gln Leu Thr Ser Gly Glu
        355                 360                 365

Trp Gly Cys Cys Pro Ile Pro Glu Ala Val Cys Cys Ser Asp His Gln
    370                 375                 380

His Cys Cys Pro Gln Gly Tyr Thr Cys Val Ala Glu Gly Gln Cys Gln
385                 390                 395                 400

Arg Gly Ser Glu Ile Val Ala Gly Leu Glu Lys Met Pro Ala Arg Arg
                405                 410                 415

Ala Ser Leu Ser His Pro Arg Asp Ile Gly Cys Asp Gln His Thr Ser
            420                 425                 430

Cys Pro Val Gly Gln Thr Cys Cys Pro Ser Leu Gly Gly Ser Trp Ala
        435                 440                 445
```

```
Cys Cys Gln Leu Pro His Ala Val Cys Cys Glu Asp Arg Gln His Cys
450                 455                 460
Cys Pro Ala Gly Tyr Thr Cys Asn Val Lys Ala Arg Ser Cys Glu Lys
465                 470                 475                 480
Glu Val Val Ser Ala Gln Pro Ala Thr Phe Leu Ala Arg Ser Pro His
                485                 490                 495
Val Gly Val Lys Asp Val Glu Cys Gly Glu Gly His Phe Cys His Asp
                500                 505                 510
Asn Gln Thr Cys Cys Arg Asp Asn Arg Gln Gly Trp Ala Cys Cys Pro
                515                 520                 525
Tyr Arg Gln Gly Val Cys Cys Ala Asp Arg Arg His Cys Cys Pro Ala
530                 535                 540
Gly Phe Arg Cys Ala Ala Arg Gly Thr Lys Cys Leu Arg Arg Glu Ala
545                 550                 555                 560
Pro Arg Trp Asp Ala Pro Leu Arg Asp Pro Ala Leu Arg Asn Ile Leu
                565                 570                 575

<210> SEQ ID NO 112
<211> LENGTH: 576
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 112

Thr Arg Cys Pro Asp Gly Gln Phe Cys Pro Val Ala Cys Cys Leu Asp
1               5                   10                  15
Pro Gly Gly Ala Ser Tyr Ser Cys Cys Arg Pro Leu Leu Asp Lys Trp
                20                  25                  30
Pro Thr Thr Leu Ser Arg His Leu Gly Gly Pro Cys Gln Val Asp Ala
                35                  40                  45
His Cys Ser Ala Gly His Ser Cys Ile Phe Thr Val Ser Gly Thr Ser
        50                  55                  60
Ser Cys Cys Pro Phe Pro Glu Ala Val Ala Cys Gly Asp Gly His His
65                  70                  75                  80
Cys Cys Pro Arg Gly Phe His Cys Ser Ala Asp Gly Arg Ser Cys Phe
                85                  90                  95
Gln Arg Ser Gly Asn Asn Ser Val Gly Ala Ile Gln Cys Pro Asp Ser
                100                 105                 110
Gln Phe Glu Cys Pro Asp Phe Ser Thr Cys Cys Val Met Val Asp Gly
                115                 120                 125
Ser Trp Gly Cys Cys Pro Met Pro Gln Ala Ser Cys Cys Glu Asp Arg
130                 135                 140
Val His Cys Cys Pro His Gly Ala Phe Cys Asp Leu Val His Thr Arg
145                 150                 155                 160
Cys Ile Thr Pro Thr Gly Thr His Pro Leu Ala Lys Lys Leu Pro Ala
                165                 170                 175
Gln Arg Thr Asn Arg Ala Val Ala Leu Ser Ser Ser Val Met Cys Pro
                180                 185                 190
Asp Ala Arg Ser Arg Cys Pro Asp Gly Ser Thr Cys Cys Glu Leu Pro
                195                 200                 205
Ser Gly Lys Tyr Gly Cys Cys Pro Met Pro Asn Ala Thr Cys Cys Ser
        210                 215                 220
```

```
Asp His Leu His Cys Cys Pro Gln Asp Thr Val Cys Asp Leu Ile Gln
225                 230                 235                 240

Ser Lys Cys Leu Ser Lys Glu Asn Ala Thr Thr Asp Leu Leu Thr Lys
                245                 250                 255

Leu Pro Ala His Thr Val Gly Asp Val Lys Cys Asp Met Glu Val Ser
            260                 265                 270

Cys Pro Asp Gly Tyr Thr Cys Cys Arg Leu Gln Ser Gly Ala Trp Gly
        275                 280                 285

Cys Cys Pro Phe Thr Gln Ala Val Cys Cys Glu Asp His Ile His Cys
    290                 295                 300

Cys Pro Ala Gly Phe Thr Cys Asp Thr Gln Lys Gly Thr Cys Glu Gln
305                 310                 315                 320

Gly Pro His Gln Val Pro Trp Met Glu Lys Ala Pro Ala His Leu Ser
                325                 330                 335

Leu Pro Asp Pro Gln Ala Leu Lys Arg Asp Val Pro Cys Asp Asn Val
            340                 345                 350

Ser Ser Cys Pro Ser Ser Asp Thr Cys Cys Gln Leu Thr Ser Gly Glu
        355                 360                 365

Trp Gly Cys Cys Pro Ile Pro Glu Ala Val Cys Cys Ser Asp His Gln
    370                 375                 380

His Cys Cys Pro Gln Gly Tyr Thr Cys Val Ala Glu Gly Gln Cys Gln
385                 390                 395                 400

Arg Gly Ser Glu Ile Val Ala Gly Leu Glu Lys Met Pro Ala Arg Arg
                405                 410                 415

Ala Ser Leu Ser His Pro Arg Asp Ile Gly Cys Asp Gln His Thr Ser
            420                 425                 430

Cys Pro Val Gly Gln Thr Cys Cys Pro Ser Leu Gly Gly Ser Trp Ala
        435                 440                 445

Cys Cys Gln Leu Pro His Ala Val Cys Cys Glu Asp Arg Gln His Cys
    450                 455                 460

Cys Pro Ala Gly Tyr Thr Cys Asn Val Lys Ala Arg Ser Cys Glu Lys
465                 470                 475                 480

Glu Val Val Ser Ala Gln Pro Ala Thr Phe Leu Ala Arg Ser Pro His
                485                 490                 495

Val Gly Val Lys Asp Val Glu Cys Gly Glu Gly His Phe Cys His Asp
            500                 505                 510

Asn Gln Thr Cys Cys Arg Asp Asn Arg Gln Gly Trp Ala Cys Cys Pro
        515                 520                 525

Tyr Arg Gln Gly Val Cys Cys Ala Asp Arg Arg His Cys Cys Pro Ala
    530                 535                 540

Gly Phe Arg Cys Ala Ala Arg Gly Thr Lys Cys Leu Arg Arg Glu Ala
545                 550                 555                 560

Pro Arg Trp Asp Ala Pro Leu Arg Asp Pro Ala Leu Arg Leu Leu Leu
                565                 570                 575

<210> SEQ ID NO 113
<211> LENGTH: 576
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

<400> SEQUENCE: 113

```
Thr Arg Cys Pro Asp Gly Gln Phe Cys Pro Val Ala Cys Cys Leu Asp
1               5                   10                  15

Pro Gly Gly Ala Ser Tyr Ser Cys Cys Arg Pro Leu Leu Asp Lys Trp
            20                  25                  30

Pro Thr Thr Leu Ser Arg His Leu Gly Gly Pro Cys Gln Val Asp Ala
            35                  40                  45

His Cys Ser Ala Gly His Ser Cys Ile Phe Thr Val Ser Gly Thr Ser
    50                  55                  60

Ser Cys Cys Pro Phe Pro Glu Ala Val Ala Cys Gly Asp Gly His His
65                  70                  75                  80

Cys Cys Pro Arg Gly Phe His Cys Ser Ala Asp Gly Arg Ser Cys Phe
                85                  90                  95

Gln Arg Ser Gly Asn Asn Ser Val Gly Ala Ile Gln Cys Pro Asp Ser
            100                 105                 110

Gln Phe Glu Cys Pro Asp Phe Ser Thr Cys Cys Val Met Val Asp Gly
        115                 120                 125

Ser Trp Gly Cys Cys Pro Met Pro Gln Ala Ser Cys Cys Glu Asp Arg
    130                 135                 140

Val His Cys Cys Pro His Gly Ala Phe Cys Asp Leu Val His Thr Arg
145                 150                 155                 160

Cys Ile Thr Pro Thr Gly Thr His Pro Leu Ala Lys Lys Leu Pro Ala
                165                 170                 175

Gln Arg Thr Asn Arg Ala Val Ala Leu Ser Ser Ser Val Met Cys Pro
            180                 185                 190

Asp Ala Arg Ser Arg Cys Pro Asp Gly Ser Thr Cys Cys Glu Leu Pro
        195                 200                 205

Ser Gly Lys Tyr Gly Cys Cys Pro Met Pro Asn Ala Thr Cys Cys Ser
    210                 215                 220

Asp His Leu His Cys Cys Pro Gln Asp Thr Val Cys Asp Leu Ile Gln
225                 230                 235                 240

Ser Lys Cys Leu Ser Lys Glu Asn Ala Thr Thr Asp Leu Leu Thr Lys
                245                 250                 255

Leu Pro Ala His Thr Val Gly Asp Val Lys Cys Asp Met Glu Val Ser
            260                 265                 270

Cys Pro Asp Gly Tyr Thr Cys Cys Arg Leu Gln Ser Gly Ala Trp Gly
        275                 280                 285

Cys Cys Pro Phe Thr Gln Ala Val Cys Cys Glu Asp His Ile His Cys
    290                 295                 300

Cys Pro Ala Gly Phe Thr Cys Asp Thr Gln Lys Gly Thr Cys Glu Gln
305                 310                 315                 320

Gly Pro His Gln Val Pro Trp Met Glu Lys Ala Pro Ala His Leu Ser
                325                 330                 335

Leu Pro Asp Pro Gln Ala Leu Lys Arg Asp Val Pro Cys Asp Asn Val
            340                 345                 350

Ser Ser Cys Pro Ser Ser Asp Thr Cys Cys Gln Leu Thr Ser Gly Glu
        355                 360                 365

Trp Gly Cys Cys Pro Ile Pro Glu Ala Val Cys Cys Ser Asp His Gln
    370                 375                 380

His Cys Cys Pro Gln Gly Tyr Thr Cys Val Ala Glu Gly Gln Cys Gln
385                 390                 395                 400
```

```
Arg Gly Ser Glu Ile Val Ala Gly Leu Glu Lys Met Pro Ala Arg Arg
                405                 410                 415

Ala Ser Leu Ser His Pro Arg Asp Ile Gly Cys Asp Gln His Thr Ser
            420                 425                 430

Cys Pro Val Gly Gln Thr Cys Cys Pro Ser Leu Gly Gly Ser Trp Ala
        435                 440                 445

Cys Cys Gln Leu Pro His Ala Val Cys Cys Glu Asp Arg Gln His Cys
    450                 455                 460

Cys Pro Ala Gly Tyr Thr Cys Asn Val Lys Ala Arg Ser Cys Glu Lys
465                 470                 475                 480

Glu Val Val Ser Ala Gln Pro Ala Thr Phe Leu Ala Arg Ser Pro His
                485                 490                 495

Val Gly Val Lys Asp Val Glu Cys Gly Glu Gly His Phe Cys His Asp
            500                 505                 510

Asn Gln Thr Cys Cys Arg Asp Asn Arg Gln Gly Trp Ala Cys Cys Pro
        515                 520                 525

Tyr Arg Gln Gly Val Cys Cys Ala Asp Arg Arg His Cys Cys Pro Ala
    530                 535                 540

Gly Phe Arg Cys Ala Ala Arg Gly Thr Lys Cys Leu Arg Arg Glu Ala
545                 550                 555                 560

Pro Arg Trp Asp Ala Pro Leu Arg Asp Pro Ala Leu Arg Pro Leu Leu
                565                 570                 575
```

<210> SEQ ID NO 114
<211> LENGTH: 576
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 114

```
Thr Arg Cys Pro Asp Gly Gln Phe Cys Pro Val Ala Cys Cys Leu Asp
1               5                   10                  15

Pro Gly Gly Ala Ser Tyr Ser Cys Cys Arg Pro Leu Leu Asp Lys Trp
                20                  25                  30

Pro Thr Thr Leu Ser Arg His Leu Gly Gly Pro Cys Gln Val Asp Ala
            35                  40                  45

His Cys Ser Ala Gly His Ser Cys Ile Phe Thr Val Ser Gly Thr Ser
        50                  55                  60

Ser Cys Cys Pro Phe Pro Glu Ala Val Ala Cys Gly Asp Gly His His
65                  70                  75                  80

Cys Cys Pro Arg Gly Phe His Cys Ser Ala Asp Gly Arg Ser Cys Phe
                85                  90                  95

Gln Arg Ser Gly Asn Asn Ser Val Gly Ala Ile Gln Cys Pro Asp Ser
            100                 105                 110

Gln Phe Glu Cys Pro Asp Phe Ser Thr Cys Cys Val Met Val Asp Gly
        115                 120                 125

Ser Trp Gly Cys Cys Pro Met Pro Gln Ala Ser Cys Cys Glu Asp Arg
    130                 135                 140

Val His Cys Cys Pro His Gly Ala Phe Cys Asp Leu Val His Thr Arg
145                 150                 155                 160

Cys Ile Thr Pro Thr Gly Thr His Pro Leu Ala Lys Lys Leu Pro Ala
                165                 170                 175
```

Gln Arg Thr Asn Arg Ala Val Ala Leu Ser Ser Ser Val Met Cys Pro
            180                 185                 190

Asp Ala Arg Ser Arg Cys Pro Asp Gly Ser Thr Cys Cys Glu Leu Pro
            195                 200                 205

Ser Gly Lys Tyr Gly Cys Cys Pro Met Pro Asn Ala Thr Cys Cys Ser
            210                 215                 220

Asp His Leu His Cys Cys Pro Gln Asp Thr Val Cys Asp Leu Ile Gln
225                 230                 235                 240

Ser Lys Cys Leu Ser Lys Glu Asn Ala Thr Thr Asp Leu Leu Thr Lys
            245                 250                 255

Leu Pro Ala His Thr Val Gly Asp Val Lys Cys Asp Met Glu Val Ser
            260                 265                 270

Cys Pro Asp Gly Tyr Thr Cys Cys Arg Leu Gln Ser Gly Ala Trp Gly
            275                 280                 285

Cys Cys Pro Phe Thr Gln Ala Val Cys Cys Glu Asp His Ile His Cys
            290                 295                 300

Cys Pro Ala Gly Phe Thr Cys Asp Thr Gln Lys Gly Thr Cys Glu Gln
305                 310                 315                 320

Gly Pro His Gln Val Pro Trp Met Glu Lys Ala Pro Ala His Leu Ser
            325                 330                 335

Leu Pro Asp Pro Gln Ala Leu Lys Arg Asp Val Pro Cys Asp Asn Val
            340                 345                 350

Ser Ser Cys Pro Ser Ser Asp Thr Cys Cys Gln Leu Thr Ser Gly Glu
            355                 360                 365

Trp Gly Cys Cys Pro Ile Pro Glu Ala Val Cys Cys Ser Asp His Gln
370                 375                 380

His Cys Cys Pro Gln Gly Tyr Thr Cys Val Ala Glu Gly Gln Cys Gln
385                 390                 395                 400

Arg Gly Ser Glu Ile Val Ala Gly Leu Glu Lys Met Pro Ala Arg Arg
            405                 410                 415

Ala Ser Leu Ser His Pro Arg Asp Ile Gly Cys Asp Gln His Thr Ser
            420                 425                 430

Cys Pro Val Gly Gln Thr Cys Cys Pro Ser Leu Gly Gly Ser Trp Ala
            435                 440                 445

Cys Cys Gln Leu Pro His Ala Val Cys Cys Glu Asp Arg Gln His Cys
450                 455                 460

Cys Pro Ala Gly Tyr Thr Cys Asn Val Lys Ala Arg Ser Cys Glu Lys
465                 470                 475                 480

Glu Val Val Ser Ala Gln Pro Ala Thr Phe Leu Ala Arg Ser Pro His
            485                 490                 495

Val Gly Val Lys Asp Val Glu Cys Gly Glu Gly His Phe Cys His Asp
            500                 505                 510

Asn Gln Thr Cys Cys Arg Asp Asn Arg Gln Gly Trp Ala Cys Cys Pro
            515                 520                 525

Tyr Arg Gln Gly Val Cys Cys Ala Asp Arg Arg His Cys Cys Pro Ala
            530                 535                 540

Gly Phe Arg Cys Ala Ala Arg Gly Thr Lys Cys Leu Arg Arg Glu Ala
545                 550                 555                 560

Pro Arg Trp Asp Ala Pro Leu Arg Asp Pro Ala Leu Arg Pro Arg Leu
            565                 570                 575

<210> SEQ ID NO 115
<211> LENGTH: 576
<212> TYPE: PRT

<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 115

```
Thr Arg Cys Pro Asp Gly Gln Phe Cys Pro Val Ala Cys Cys Leu Asp
1               5                   10                  15

Pro Gly Gly Ala Ser Tyr Ser Cys Cys Arg Pro Leu Leu Asp Lys Trp
            20                  25                  30

Pro Thr Thr Leu Ser Arg His Leu Gly Gly Pro Cys Gln Val Asp Ala
        35                  40                  45

His Cys Ser Ala Gly His Ser Cys Ile Phe Thr Val Ser Gly Thr Ser
    50                  55                  60

Ser Cys Cys Pro Phe Pro Glu Ala Val Ala Cys Gly Asp Gly His His
65                  70                  75                  80

Cys Cys Pro Arg Gly Phe His Cys Ser Ala Asp Gly Arg Ser Cys Phe
                85                  90                  95

Gln Arg Ser Gly Asn Asn Ser Val Gly Ala Ile Gln Cys Pro Asp Ser
            100                 105                 110

Gln Phe Glu Cys Pro Asp Phe Ser Thr Cys Cys Val Met Val Asp Gly
        115                 120                 125

Ser Trp Gly Cys Cys Pro Met Pro Gln Ala Ser Cys Cys Glu Asp Arg
130                 135                 140

Val His Cys Cys Pro His Gly Ala Phe Cys Asp Leu Val His Thr Arg
145                 150                 155                 160

Cys Ile Thr Pro Thr Gly Thr His Pro Leu Ala Lys Lys Leu Pro Ala
                165                 170                 175

Gln Arg Thr Asn Arg Ala Val Ala Leu Ser Ser Val Met Cys Pro
            180                 185                 190

Asp Ala Arg Ser Arg Cys Pro Asp Gly Ser Thr Cys Cys Glu Leu Pro
        195                 200                 205

Ser Gly Lys Tyr Gly Cys Cys Pro Met Pro Asn Ala Thr Cys Cys Ser
210                 215                 220

Asp His Leu His Cys Cys Pro Gln Asp Thr Val Cys Asp Leu Ile Gln
225                 230                 235                 240

Ser Lys Cys Leu Ser Lys Glu Asn Ala Thr Thr Asp Leu Leu Thr Lys
                245                 250                 255

Leu Pro Ala His Thr Val Gly Asp Val Lys Cys Asp Met Glu Val Ser
            260                 265                 270

Cys Pro Asp Gly Tyr Thr Cys Cys Arg Leu Gln Ser Gly Ala Trp Gly
        275                 280                 285

Cys Cys Pro Phe Thr Gln Ala Val Cys Cys Glu Asp His Ile His Cys
    290                 295                 300

Cys Pro Ala Gly Phe Thr Cys Asp Thr Gln Lys Gly Thr Cys Glu Gln
305                 310                 315                 320

Gly Pro His Gln Val Pro Trp Met Glu Lys Ala Pro Ala His Leu Ser
                325                 330                 335

Leu Pro Asp Pro Gln Ala Leu Lys Arg Asp Val Pro Cys Asp Asn Val
            340                 345                 350

Ser Ser Cys Pro Ser Ser Asp Thr Cys Cys Gln Leu Thr Ser Gly Glu
        355                 360                 365

Trp Gly Cys Cys Pro Ile Pro Glu Ala Val Cys Cys Ser Asp His Gln
    370                 375                 380
```

```
His Cys Cys Pro Gln Gly Tyr Thr Cys Val Ala Glu Gly Gln Cys Gln
385                 390                 395                 400

Arg Gly Ser Glu Ile Val Ala Gly Leu Glu Lys Met Pro Ala Arg Arg
            405                 410                 415

Ala Ser Leu Ser His Pro Arg Asp Ile Gly Cys Asp Gln His Thr Ser
            420                 425                 430

Cys Pro Val Gly Gln Thr Cys Cys Pro Ser Leu Gly Gly Ser Trp Ala
        435                 440                 445

Cys Cys Gln Leu Pro His Ala Val Cys Cys Glu Asp Arg Gln His Cys
        450                 455                 460

Cys Pro Ala Gly Tyr Thr Cys Asn Val Lys Ala Arg Ser Cys Glu Lys
465                 470                 475                 480

Glu Val Val Ser Ala Gln Pro Ala Thr Phe Leu Ala Arg Ser Pro His
            485                 490                 495

Val Gly Val Lys Asp Val Glu Cys Gly Glu Gly His Phe Cys His Asp
            500                 505                 510

Asn Gln Thr Cys Cys Arg Asp Asn Arg Gln Gly Trp Ala Cys Cys Pro
        515                 520                 525

Tyr Arg Gln Gly Val Cys Cys Ala Asp Arg Arg His Cys Cys Pro Ala
530                 535                 540

Gly Phe Arg Cys Ala Ala Arg Gly Thr Lys Cys Leu Arg Arg Glu Ala
545                 550                 555                 560

Pro Arg Trp Asp Ala Pro Leu Arg Asp Pro Ala Leu Arg Tyr Ile Leu
            565                 570                 575
```

<210> SEQ ID NO 116
<211> LENGTH: 576
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 116

```
Thr Arg Cys Pro Asp Gly Gln Phe Cys Pro Val Ala Cys Cys Leu Asp
1               5                   10                  15

Pro Gly Gly Ala Ser Tyr Ser Cys Cys Arg Pro Leu Leu Asp Lys Trp
            20                  25                  30

Pro Thr Thr Leu Ser Arg His Leu Gly Gly Pro Cys Gln Val Asp Ala
            35                  40                  45

His Cys Ser Ala Gly His Ser Cys Ile Phe Thr Val Ser Gly Thr Ser
        50                  55                  60

Ser Cys Cys Pro Phe Pro Glu Ala Val Ala Cys Gly Asp Gly His His
65                  70                  75                  80

Cys Cys Pro Arg Gly Phe His Cys Ser Ala Asp Gly Arg Ser Cys Phe
                85                  90                  95

Gln Arg Ser Gly Asn Asn Ser Val Gly Ala Ile Gln Cys Pro Asp Ser
            100                 105                 110

Gln Phe Glu Cys Pro Asp Phe Ser Thr Cys Cys Val Met Val Asp Gly
        115                 120                 125

Ser Trp Gly Cys Cys Pro Met Pro Gln Ala Ser Cys Cys Glu Asp Arg
    130                 135                 140

Val His Cys Cys Pro His Gly Ala Phe Cys Asp Leu Val His Thr Arg
145                 150                 155                 160
```

```
Cys Ile Thr Pro Thr Gly Thr His Pro Leu Ala Lys Lys Leu Pro Ala
            165                 170                 175

Gln Arg Thr Asn Arg Ala Val Ala Leu Ser Ser Val Met Cys Pro
        180                 185                 190

Asp Ala Arg Ser Arg Cys Pro Asp Gly Ser Thr Cys Cys Glu Leu Pro
        195                 200                 205

Ser Gly Lys Tyr Gly Cys Cys Pro Met Pro Asn Ala Thr Cys Cys Ser
        210                 215                 220

Asp His Leu His Cys Cys Pro Gln Asp Thr Val Cys Asp Leu Ile Gln
225                 230                 235                 240

Ser Lys Cys Leu Ser Lys Glu Asn Ala Thr Thr Asp Leu Leu Thr Lys
            245                 250                 255

Leu Pro Ala His Thr Val Gly Asp Val Lys Cys Asp Met Glu Val Ser
            260                 265                 270

Cys Pro Asp Gly Tyr Thr Cys Cys Arg Leu Gln Ser Gly Ala Trp Gly
        275                 280                 285

Cys Cys Pro Phe Thr Gln Ala Val Cys Cys Glu Asp His Ile His Cys
        290                 295                 300

Cys Pro Ala Gly Phe Thr Cys Asp Thr Gln Lys Gly Thr Cys Glu Gln
305                 310                 315                 320

Gly Pro His Gln Val Pro Trp Met Glu Lys Ala Pro Ala His Leu Ser
            325                 330                 335

Leu Pro Asp Pro Gln Ala Leu Lys Arg Asp Val Pro Cys Asp Asn Val
            340                 345                 350

Ser Ser Cys Pro Ser Ser Asp Thr Cys Cys Gln Leu Thr Ser Gly Glu
        355                 360                 365

Trp Gly Cys Cys Pro Ile Pro Glu Ala Val Cys Cys Ser Asp His Gln
        370                 375                 380

His Cys Cys Pro Gln Gly Tyr Thr Cys Val Ala Glu Gly Gln Cys Gln
385                 390                 395                 400

Arg Gly Ser Glu Ile Val Ala Gly Leu Glu Lys Met Pro Ala Arg Arg
            405                 410                 415

Ala Ser Leu Ser His Pro Arg Asp Ile Gly Cys Asp Gln His Thr Ser
            420                 425                 430

Cys Pro Val Gly Gln Thr Cys Cys Pro Ser Leu Gly Gly Ser Trp Ala
        435                 440                 445

Cys Cys Gln Leu Pro His Ala Val Cys Cys Glu Asp Arg Gln His Cys
        450                 455                 460

Cys Pro Ala Gly Tyr Thr Cys Asn Val Lys Ala Arg Ser Cys Glu Lys
465                 470                 475                 480

Glu Val Val Ser Ala Gln Pro Ala Thr Phe Leu Ala Arg Ser Pro His
            485                 490                 495

Val Gly Val Lys Asp Val Glu Cys Gly Glu Gly His Phe Cys His Asp
            500                 505                 510

Asn Gln Thr Cys Cys Arg Asp Asn Arg Gln Gly Trp Ala Cys Cys Pro
        515                 520                 525

Tyr Arg Gln Gly Val Cys Cys Ala Asp Arg His Cys Cys Pro Ala
        530                 535                 540

Gly Phe Arg Cys Ala Ala Arg Gly Thr Lys Cys Leu Arg Arg Glu Ala
545                 550                 555                 560

Pro Arg Trp Asp Ala Pro Leu Arg Asp Pro Ala Leu Arg Val Leu Leu
            565                 570                 575
```

```
<210> SEQ ID NO 117
<211> LENGTH: 576
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 117

Thr Arg Cys Pro Asp Gly Gln Phe Cys Pro Val Ala Cys Cys Leu Asp
1               5                   10                  15

Pro Gly Gly Ala Ser Tyr Ser Cys Cys Arg Pro Leu Leu Asp Lys Trp
                20                  25                  30

Pro Thr Thr Leu Ser Arg His Leu Gly Gly Pro Cys Gln Val Asp Ala
            35                  40                  45

His Cys Ser Ala Gly His Ser Cys Ile Phe Thr Val Ser Gly Thr Ser
    50                  55                  60

Ser Cys Cys Pro Phe Pro Glu Ala Val Ala Cys Gly Asp Gly His His
65              70                  75                  80

Cys Cys Pro Arg Gly Phe His Cys Ser Ala Asp Gly Arg Ser Cys Phe
                85                  90                  95

Gln Arg Ser Gly Asn Asn Ser Val Gly Ala Ile Gln Cys Pro Asp Ser
                100                 105                 110

Gln Phe Glu Cys Pro Asp Phe Ser Thr Cys Cys Val Met Val Asp Gly
            115                 120                 125

Ser Trp Gly Cys Cys Pro Met Pro Gln Ala Ser Cys Cys Glu Asp Arg
    130                 135                 140

Val His Cys Cys Pro His Gly Ala Phe Cys Asp Leu Val His Thr Arg
145                 150                 155                 160

Cys Ile Thr Pro Thr Gly Thr His Pro Leu Ala Lys Lys Leu Pro Ala
                165                 170                 175

Gln Arg Thr Asn Arg Ala Val Ala Leu Ser Ser Ser Val Met Cys Pro
                180                 185                 190

Asp Ala Arg Ser Arg Cys Pro Asp Gly Ser Thr Cys Cys Glu Leu Pro
            195                 200                 205

Ser Gly Lys Tyr Gly Cys Cys Pro Met Pro Asn Ala Thr Cys Cys Ser
    210                 215                 220

Asp His Leu His Cys Cys Pro Gln Asp Thr Val Cys Asp Leu Ile Gln
225                 230                 235                 240

Ser Lys Cys Leu Ser Lys Glu Asn Ala Thr Thr Asp Leu Leu Thr Lys
                245                 250                 255

Leu Pro Ala His Thr Val Gly Asp Val Lys Cys Asp Met Glu Val Ser
                260                 265                 270

Cys Pro Asp Gly Tyr Thr Cys Cys Arg Leu Gln Ser Gly Ala Trp Gly
            275                 280                 285

Cys Cys Pro Phe Thr Gln Ala Val Cys Cys Glu Asp His Ile His Cys
    290                 295                 300

Cys Pro Ala Gly Phe Thr Cys Asp Thr Gln Lys Gly Thr Cys Glu Gln
305                 310                 315                 320

Gly Pro His Gln Val Pro Trp Met Glu Lys Ala Pro Ala His Leu Ser
                325                 330                 335

Leu Pro Asp Pro Gln Ala Leu Lys Arg Asp Val Pro Cys Asp Asn Val
                340                 345                 350

Ser Ser Cys Pro Ser Ser Asp Thr Cys Cys Gln Leu Thr Ser Gly Glu
            355                 360                 365
```

```
Trp Gly Cys Cys Pro Ile Pro Glu Ala Val Cys Cys Ser Asp His Gln
        370                 375                 380

His Cys Cys Pro Gln Gly Tyr Thr Cys Val Ala Glu Gly Gln Cys Gln
385                 390                 395                 400

Arg Gly Ser Glu Ile Val Ala Gly Leu Glu Lys Met Pro Ala Arg Arg
            405                 410                 415

Ala Ser Leu Ser His Pro Arg Asp Ile Gly Cys Asp Gln His Thr Ser
            420                 425                 430

Cys Pro Val Gly Gln Thr Cys Cys Pro Ser Leu Gly Gly Ser Trp Ala
            435                 440                 445

Cys Cys Gln Leu Pro His Ala Val Cys Cys Glu Asp Arg Gln His Cys
        450                 455                 460

Cys Pro Ala Gly Tyr Thr Cys Asn Val Lys Ala Arg Ser Cys Glu Lys
465                 470                 475                 480

Glu Val Val Ser Ala Gln Pro Ala Thr Phe Leu Ala Arg Ser Pro His
            485                 490                 495

Val Gly Val Lys Asp Val Glu Cys Gly Glu Gly His Phe Cys His Asp
            500                 505                 510

Asn Gln Thr Cys Cys Arg Asp Asn Arg Gln Gly Trp Ala Cys Cys Pro
            515                 520                 525

Tyr Arg Gln Gly Val Cys Cys Ala Asp Arg Arg His Cys Cys Pro Ala
            530                 535                 540

Gly Phe Arg Cys Ala Ala Arg Gly Thr Lys Cys Leu Arg Arg Glu Ala
545                 550                 555                 560

Pro Arg Trp Asp Ala Pro Leu Arg Asp Pro Ala Leu Arg Val Ile Val
                565                 570                 575

<210> SEQ ID NO 118
<211> LENGTH: 576
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 118

Thr Arg Cys Pro Asp Gly Gln Phe Cys Pro Val Ala Cys Cys Leu Asp
1               5                   10                  15

Pro Gly Gly Ala Ser Tyr Ser Cys Cys Arg Pro Leu Leu Asp Lys Trp
            20                  25                  30

Pro Thr Thr Leu Ser Arg His Leu Gly Gly Pro Cys Gln Val Asp Ala
            35                  40                  45

His Cys Ser Ala Gly His Ser Cys Ile Phe Thr Val Ser Gly Thr Ser
        50                  55                  60

Ser Cys Cys Pro Phe Pro Glu Ala Val Ala Cys Gly Asp Gly His His
65                  70                  75                  80

Cys Cys Pro Arg Gly Phe His Cys Ser Ala Asp Gly Arg Ser Cys Phe
                85                  90                  95

Gln Arg Ser Gly Asn Asn Ser Val Gly Ala Ile Gln Cys Pro Asp Ser
            100                 105                 110

Gln Phe Glu Cys Pro Asp Phe Ser Thr Cys Cys Val Met Val Asp Gly
        115                 120                 125

Ser Trp Gly Cys Cys Pro Met Pro Gln Ala Ser Cys Cys Glu Asp Arg
        130                 135                 140
```

Val His Cys Cys Pro His Gly Ala Phe Cys Asp Leu Val His Thr Arg
145                 150                 155                 160

Cys Ile Thr Pro Thr Gly Thr His Pro Leu Ala Lys Lys Leu Pro Ala
            165                 170                 175

Gln Arg Thr Asn Arg Ala Val Ala Leu Ser Ser Val Met Cys Pro
        180                 185                 190

Asp Ala Arg Ser Arg Cys Pro Asp Gly Ser Thr Cys Cys Glu Leu Pro
            195                 200                 205

Ser Gly Lys Tyr Gly Cys Cys Pro Met Pro Asn Ala Thr Cys Cys Ser
    210                 215                 220

Asp His Leu His Cys Cys Pro Gln Asp Thr Val Cys Asp Leu Ile Gln
225                 230                 235                 240

Ser Lys Cys Leu Ser Lys Glu Asn Ala Thr Thr Asp Leu Leu Thr Lys
                245                 250                 255

Leu Pro Ala His Thr Val Gly Asp Val Lys Cys Asp Met Glu Val Ser
                260                 265                 270

Cys Pro Asp Gly Tyr Thr Cys Cys Arg Leu Gln Ser Gly Ala Trp Gly
        275                 280                 285

Cys Cys Pro Phe Thr Gln Ala Val Cys Cys Glu Asp His Ile His Cys
    290                 295                 300

Cys Pro Ala Gly Phe Thr Cys Asp Thr Gln Lys Gly Thr Cys Glu Gln
305                 310                 315                 320

Gly Pro His Gln Val Pro Trp Met Glu Lys Ala Pro Ala His Leu Ser
                325                 330                 335

Leu Pro Asp Pro Gln Ala Leu Lys Arg Asp Val Pro Cys Asp Asn Val
                340                 345                 350

Ser Ser Cys Pro Ser Ser Asp Thr Cys Cys Gln Leu Thr Ser Gly Glu
        355                 360                 365

Trp Gly Cys Cys Pro Ile Pro Glu Ala Val Cys Cys Ser Asp His Gln
    370                 375                 380

His Cys Cys Pro Gln Gly Tyr Thr Cys Val Ala Glu Gly Gln Cys Gln
385                 390                 395                 400

Arg Gly Ser Glu Ile Val Ala Gly Leu Glu Lys Met Pro Ala Arg Arg
                405                 410                 415

Ala Ser Leu Ser His Pro Arg Asp Ile Gly Cys Asp Gln His Thr Ser
                420                 425                 430

Cys Pro Val Gly Gln Thr Cys Cys Pro Ser Leu Gly Gly Ser Trp Ala
        435                 440                 445

Cys Cys Gln Leu Pro His Ala Val Cys Cys Glu Asp Arg Gln His Cys
    450                 455                 460

Cys Pro Ala Gly Tyr Thr Cys Asn Val Lys Ala Arg Ser Cys Glu Lys
465                 470                 475                 480

Glu Val Val Ser Ala Gln Pro Ala Thr Phe Leu Ala Arg Ser Pro His
                485                 490                 495

Val Gly Val Lys Asp Val Glu Cys Gly Glu Gly His Phe Cys His Asp
                500                 505                 510

Asn Gln Thr Cys Cys Arg Asp Asn Arg Gln Gly Trp Ala Cys Cys Pro
        515                 520                 525

Tyr Arg Gln Gly Val Cys Cys Ala Asp Arg Arg His Cys Cys Pro Ala
            530                 535                 540

Gly Phe Arg Cys Ala Ala Arg Gly Thr Lys Cys Leu Arg Arg Glu Ala
545                 550                 555                 560

```
Pro Arg Trp Asp Ala Pro Leu Arg Asp Pro Ala Leu Arg Phe Ile Leu
            565                 570                 575

<210> SEQ ID NO 119
<211> LENGTH: 576
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 119

Thr Arg Cys Pro Asp Gly Gln Phe Cys Pro Val Ala Cys Cys Leu Asp
1               5                   10                  15

Pro Gly Gly Ala Ser Tyr Ser Cys Cys Arg Pro Leu Leu Asp Lys Trp
                20                  25                  30

Pro Thr Thr Leu Ser Arg His Leu Gly Gly Pro Cys Gln Val Asp Ala
            35                  40                  45

His Cys Ser Ala Gly His Ser Cys Ile Phe Thr Val Ser Gly Thr Ser
    50                  55                  60

Ser Cys Cys Pro Phe Pro Glu Ala Val Ala Cys Gly Asp Gly His His
65                  70                  75                  80

Cys Cys Pro Arg Gly Phe His Cys Ser Ala Asp Gly Arg Ser Cys Phe
                85                  90                  95

Gln Arg Ser Gly Asn Asn Ser Val Gly Ala Ile Gln Cys Pro Asp Ser
                100                 105                 110

Gln Phe Glu Cys Pro Asp Phe Ser Thr Cys Cys Val Met Val Asp Gly
            115                 120                 125

Ser Trp Gly Cys Cys Pro Met Pro Gln Ala Ser Cys Cys Glu Asp Arg
            130                 135                 140

Val His Cys Cys Pro His Gly Ala Phe Cys Asp Leu Val His Thr Arg
145                 150                 155                 160

Cys Ile Thr Pro Thr Gly Thr His Pro Leu Ala Lys Lys Leu Pro Ala
                165                 170                 175

Gln Arg Thr Asn Arg Ala Val Ala Leu Ser Ser Ser Val Met Cys Pro
            180                 185                 190

Asp Ala Arg Ser Arg Cys Pro Asp Gly Ser Thr Cys Cys Glu Leu Pro
            195                 200                 205

Ser Gly Lys Tyr Gly Cys Cys Pro Met Pro Asn Ala Thr Cys Cys Ser
        210                 215                 220

Asp His Leu His Cys Cys Pro Gln Asp Thr Val Cys Asp Leu Ile Gln
225                 230                 235                 240

Ser Lys Cys Leu Ser Lys Glu Asn Ala Thr Thr Asp Leu Leu Thr Lys
                245                 250                 255

Leu Pro Ala His Thr Val Gly Asp Val Lys Cys Asp Met Glu Val Ser
            260                 265                 270

Cys Pro Asp Gly Tyr Thr Cys Cys Arg Leu Gln Ser Gly Ala Trp Gly
            275                 280                 285

Cys Cys Pro Phe Thr Gln Ala Val Cys Cys Glu Asp His Ile His Cys
        290                 295                 300

Cys Pro Ala Gly Phe Thr Cys Asp Thr Gln Lys Gly Thr Cys Glu Gln
305                 310                 315                 320

Gly Pro His Gln Val Pro Trp Met Glu Lys Ala Pro Ala His Leu Ser
                325                 330                 335
```

```
Leu Pro Asp Pro Gln Ala Leu Lys Arg Asp Val Pro Cys Asp Asn Val
            340                 345                 350

Ser Ser Cys Pro Ser Ser Asp Thr Cys Cys Gln Leu Thr Ser Gly Glu
        355                 360                 365

Trp Gly Cys Cys Pro Ile Pro Glu Ala Val Cys Cys Ser Asp His Gln
    370                 375                 380

His Cys Cys Pro Gln Gly Tyr Thr Cys Val Ala Glu Gly Gln Cys Gln
385                 390                 395                 400

Arg Gly Ser Glu Ile Val Ala Gly Leu Glu Lys Met Pro Ala Arg Arg
                405                 410                 415

Ala Ser Leu Ser His Pro Arg Asp Ile Gly Cys Asp Gln His Thr Ser
            420                 425                 430

Cys Pro Val Gly Gln Thr Cys Cys Pro Ser Leu Gly Gly Ser Trp Ala
        435                 440                 445

Cys Cys Gln Leu Pro His Ala Val Cys Cys Glu Asp Arg Gln His Cys
    450                 455                 460

Cys Pro Ala Gly Tyr Thr Cys Asn Val Lys Ala Arg Ser Cys Glu Lys
465                 470                 475                 480

Glu Val Val Ser Ala Gln Pro Ala Thr Phe Leu Ala Arg Ser Pro His
                485                 490                 495

Val Gly Val Lys Asp Val Glu Cys Gly Glu Gly His Phe Cys His Asp
            500                 505                 510

Asn Gln Thr Cys Cys Arg Asp Asn Arg Gln Gly Trp Ala Cys Cys Pro
        515                 520                 525

Tyr Arg Gln Gly Val Cys Cys Ala Asp Arg Arg His Cys Cys Pro Ala
    530                 535                 540

Gly Phe Arg Cys Ala Ala Arg Gly Thr Lys Cys Leu Arg Arg Glu Ala
545                 550                 555                 560

Pro Arg Trp Asp Ala Pro Leu Arg Asp Pro Ala Leu Arg Met Leu Leu
                565                 570                 575

<210> SEQ ID NO 120
<211> LENGTH: 577
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 120

Thr Arg Cys Pro Asp Gly Gln Phe Cys Pro Val Ala Cys Cys Leu Asp
1               5                   10                  15

Pro Gly Gly Ala Ser Tyr Ser Cys Cys Arg Pro Leu Leu Asp Lys Trp
                20                  25                  30

Pro Thr Thr Leu Ser Arg His Leu Gly Gly Pro Cys Gln Val Asp Ala
            35                  40                  45

His Cys Ser Ala Gly His Ser Cys Ile Phe Thr Val Ser Gly Thr Ser
        50                  55                  60

Ser Cys Cys Pro Phe Pro Glu Ala Val Ala Cys Gly Asp Gly His His
65                  70                  75                  80

Cys Cys Pro Arg Gly Phe His Cys Ser Ala Asp Gly Arg Ser Cys Phe
                85                  90                  95

Gln Arg Ser Gly Asn Asn Ser Val Gly Ala Ile Gln Cys Pro Asp Ser
            100                 105                 110
```

```
Gln Phe Glu Cys Pro Asp Phe Ser Thr Cys Cys Val Met Val Asp Gly
            115                 120                 125

Ser Trp Gly Cys Cys Pro Met Pro Gln Ala Ser Cys Cys Glu Asp Arg
    130                 135                 140

Val His Cys Cys Pro His Gly Ala Phe Cys Asp Leu Val His Thr Arg
145                 150                 155                 160

Cys Ile Thr Pro Thr Gly Thr His Pro Leu Ala Lys Lys Leu Pro Ala
                165                 170                 175

Gln Arg Thr Asn Arg Ala Val Ala Leu Ser Ser Val Met Cys Pro
            180                 185                 190

Asp Ala Arg Ser Arg Cys Pro Asp Gly Ser Thr Cys Cys Glu Leu Pro
                195                 200                 205

Ser Gly Lys Tyr Gly Cys Cys Pro Met Pro Asn Ala Thr Cys Cys Ser
    210                 215                 220

Asp His Leu His Cys Cys Pro Gln Asp Thr Val Cys Asp Leu Ile Gln
225                 230                 235                 240

Ser Lys Cys Leu Ser Lys Glu Asn Ala Thr Thr Asp Leu Leu Thr Lys
                245                 250                 255

Leu Pro Ala His Thr Val Gly Asp Val Lys Cys Asp Met Glu Val Ser
            260                 265                 270

Cys Pro Asp Gly Tyr Thr Cys Cys Arg Leu Gln Ser Gly Ala Trp Gly
    275                 280                 285

Cys Cys Pro Phe Thr Gln Ala Val Cys Cys Glu Asp His Ile His Cys
    290                 295                 300

Cys Pro Ala Gly Phe Thr Cys Asp Thr Gln Lys Gly Thr Cys Glu Gln
305                 310                 315                 320

Gly Pro His Gln Val Pro Trp Met Glu Lys Ala Pro Ala His Leu Ser
            325                 330                 335

Leu Pro Asp Pro Gln Ala Leu Lys Arg Asp Val Pro Cys Asp Asn Val
            340                 345                 350

Ser Ser Cys Pro Ser Ser Asp Thr Cys Cys Gln Leu Thr Ser Gly Glu
    355                 360                 365

Trp Gly Cys Cys Pro Ile Pro Glu Ala Val Cys Cys Ser Asp His Gln
    370                 375                 380

His Cys Cys Pro Gln Gly Tyr Thr Cys Val Ala Glu Gly Gln Cys Gln
385                 390                 395                 400

Arg Gly Ser Glu Ile Val Ala Gly Leu Glu Lys Met Pro Ala Arg Arg
            405                 410                 415

Ala Ser Leu Ser His Pro Arg Asp Ile Gly Cys Asp Gln His Thr Ser
            420                 425                 430

Cys Pro Val Gly Gln Thr Cys Cys Pro Ser Leu Gly Gly Ser Trp Ala
    435                 440                 445

Cys Cys Gln Leu Pro His Ala Val Cys Cys Glu Asp Arg Gln His Cys
    450                 455                 460

Cys Pro Ala Gly Tyr Thr Cys Asn Val Lys Ala Arg Ser Cys Glu Lys
465                 470                 475                 480

Glu Val Val Ser Ala Gln Pro Ala Thr Phe Leu Ala Arg Ser Pro His
            485                 490                 495

Val Gly Val Lys Asp Val Glu Cys Gly Glu Gly His Phe Cys His Asp
            500                 505                 510

Asn Gln Thr Cys Cys Arg Asp Asn Arg Gln Gly Trp Ala Cys Cys Pro
    515                 520                 525
```

```
Tyr Arg Gln Gly Val Cys Cys Ala Asp Arg Arg His Cys Cys Pro Ala
            530                 535                 540

Gly Phe Arg Cys Ala Ala Arg Gly Thr Lys Cys Leu Arg Arg Glu Ala
545                 550                 555                 560

Pro Arg Trp Asp Ala Pro Leu Arg Asp Pro Ala Leu Arg Gln Leu Leu
                565                 570                 575

Gly

<210> SEQ ID NO 121
<211> LENGTH: 578
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 121

Thr Arg Cys Pro Asp Gly Gln Phe Cys Pro Val Ala Cys Cys Leu Asp
1               5                   10                  15

Pro Gly Gly Ala Ser Tyr Ser Cys Cys Arg Pro Leu Leu Asp Lys Trp
            20                  25                  30

Pro Thr Thr Leu Ser Arg His Leu Gly Gly Pro Cys Gln Val Asp Ala
        35                  40                  45

His Cys Ser Ala Gly His Ser Cys Ile Phe Thr Val Ser Gly Thr Ser
    50                  55                  60

Ser Cys Cys Pro Phe Pro Glu Ala Val Ala Cys Gly Asp Gly His His
65                  70                  75                  80

Cys Cys Pro Arg Gly Phe His Cys Ser Ala Asp Gly Arg Ser Cys Phe
                85                  90                  95

Gln Arg Ser Gly Asn Asn Ser Val Gly Ala Ile Gln Cys Pro Asp Ser
            100                 105                 110

Gln Phe Glu Cys Pro Asp Phe Ser Thr Cys Cys Val Met Val Asp Gly
        115                 120                 125

Ser Trp Gly Cys Cys Pro Met Pro Gln Ala Ser Cys Cys Glu Asp Arg
    130                 135                 140

Val His Cys Cys Pro His Gly Ala Phe Cys Asp Leu Val His Thr Arg
145                 150                 155                 160

Cys Ile Thr Pro Thr Gly Thr His Pro Leu Ala Lys Lys Leu Pro Ala
                165                 170                 175

Gln Arg Thr Asn Arg Ala Val Ala Leu Ser Ser Ser Val Met Cys Pro
            180                 185                 190

Asp Ala Arg Ser Arg Cys Pro Asp Gly Ser Thr Cys Cys Glu Leu Pro
        195                 200                 205

Ser Gly Lys Tyr Gly Cys Cys Pro Met Pro Asn Ala Thr Cys Cys Ser
    210                 215                 220

Asp His Leu His Cys Cys Pro Gln Asp Thr Val Cys Asp Leu Ile Gln
225                 230                 235                 240

Ser Lys Cys Leu Ser Lys Glu Asn Ala Thr Thr Asp Leu Leu Thr Lys
                245                 250                 255

Leu Pro Ala His Thr Val Gly Asp Val Lys Cys Asp Met Glu Val Ser
            260                 265                 270

Cys Pro Asp Gly Tyr Thr Cys Cys Arg Leu Gln Ser Gly Ala Trp Gly
        275                 280                 285

Cys Cys Pro Phe Thr Gln Ala Val Cys Cys Glu Asp His Ile His Cys
    290                 295                 300
```

```
Cys Pro Ala Gly Phe Thr Cys Asp Thr Gln Lys Gly Thr Cys Glu Gln
305                 310                 315                 320

Gly Pro His Gln Val Pro Trp Met Glu Lys Ala Pro Ala His Leu Ser
                325                 330                 335

Leu Pro Asp Pro Gln Ala Leu Lys Arg Asp Val Pro Cys Asp Asn Val
            340                 345                 350

Ser Ser Cys Pro Ser Ser Asp Thr Cys Cys Gln Leu Thr Ser Gly Glu
        355                 360                 365

Trp Gly Cys Cys Pro Ile Pro Glu Ala Val Cys Cys Ser Asp His Gln
    370                 375                 380

His Cys Cys Pro Gln Gly Tyr Thr Cys Val Ala Glu Gly Gln Cys Gln
385                 390                 395                 400

Arg Gly Ser Glu Ile Val Ala Gly Leu Glu Lys Met Pro Ala Arg Arg
                405                 410                 415

Ala Ser Leu Ser His Pro Arg Asp Ile Gly Cys Asp Gln His Thr Ser
            420                 425                 430

Cys Pro Val Gly Gln Thr Cys Cys Pro Ser Leu Gly Gly Ser Trp Ala
        435                 440                 445

Cys Cys Gln Leu Pro His Ala Val Cys Cys Glu Asp Arg Gln His Cys
    450                 455                 460

Cys Pro Ala Gly Tyr Thr Cys Asn Val Lys Ala Arg Ser Cys Glu Lys
465                 470                 475                 480

Glu Val Val Ser Ala Gln Pro Ala Thr Phe Leu Ala Arg Ser Pro His
                485                 490                 495

Val Gly Val Lys Asp Val Glu Cys Gly Glu Gly His Phe Cys His Asp
            500                 505                 510

Asn Gln Thr Cys Cys Arg Asp Asn Arg Gln Gly Trp Ala Cys Cys Pro
        515                 520                 525

Tyr Arg Gln Gly Val Cys Cys Ala Asp Arg Arg His Cys Cys Pro Ala
    530                 535                 540

Gly Phe Arg Cys Ala Ala Arg Gly Thr Lys Cys Leu Arg Arg Glu Ala
545                 550                 555                 560

Pro Arg Trp Asp Ala Pro Leu Arg Asp Pro Ala Leu Arg Gln Leu Leu
                565                 570                 575

Gly Lys

<210> SEQ ID NO 122
<211> LENGTH: 227
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 122

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60
```

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
             85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 123
<211> LENGTH: 813
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 123

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
             85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

```
Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Gly Gly Gly Ser Gly Gly Gly Ser Thr Arg Cys
225             230                 235                 240

Pro Asp Gly Gln Phe Cys Pro Val Ala Cys Cys Leu Asp Pro Gly Gly
                245                 250                 255

Ala Ser Tyr Ser Cys Cys Arg Pro Leu Leu Asp Lys Trp Pro Thr Thr
        260                 265                 270

Leu Ser Arg His Leu Gly Gly Pro Cys Gln Val Asp Ala His Cys Ser
    275                 280                 285

Ala Gly His Ser Cys Ile Phe Thr Val Ser Gly Thr Ser Ser Cys Cys
    290                 295                 300

Pro Phe Pro Glu Ala Val Ala Cys Gly Asp Gly His Cys Cys Pro
305             310                 315                 320

Arg Gly Phe His Cys Ser Ala Asp Gly Arg Ser Cys Phe Gln Arg Ser
                325                 330                 335

Gly Asn Asn Ser Val Gly Ala Ile Gln Cys Pro Asp Ser Gln Phe Glu
            340                 345                 350

Cys Pro Asp Phe Ser Thr Cys Cys Val Met Val Asp Gly Ser Trp Gly
        355                 360                 365

Cys Cys Pro Met Pro Gln Ala Ser Cys Cys Glu Asp Arg Val His Cys
    370                 375                 380

Cys Pro His Gly Ala Phe Cys Asp Leu Val His Thr Arg Cys Ile Thr
385             390                 395                 400

Pro Thr Gly Thr His Pro Leu Ala Lys Lys Leu Pro Ala Gln Arg Thr
            405                 410                 415

Asn Arg Ala Val Ala Leu Ser Ser Val Met Cys Pro Asp Ala Arg
        420                 425                 430

Ser Arg Cys Pro Asp Gly Ser Thr Cys Cys Glu Leu Pro Ser Gly Lys
    435                 440                 445

Tyr Gly Cys Cys Pro Met Pro Asn Ala Thr Cys Cys Ser Asp His Leu
    450                 455                 460

His Cys Cys Pro Gln Asp Thr Val Cys Asp Leu Ile Gln Ser Lys Cys
465             470                 475                 480

Leu Ser Lys Glu Asn Ala Thr Thr Asp Leu Leu Thr Lys Leu Pro Ala
            485                 490                 495

His Thr Val Gly Asp Val Lys Cys Asp Met Glu Val Ser Cys Pro Asp
                500                 505                 510

Gly Tyr Thr Cys Cys Arg Leu Gln Ser Gly Ala Trp Gly Cys Cys Pro
        515                 520                 525

Phe Thr Gln Ala Val Cys Cys Glu Asp His Ile His Cys Cys Pro Ala
    530                 535                 540

Gly Phe Thr Cys Asp Thr Gln Lys Gly Thr Cys Glu Gln Gly Pro His
545             550                 555                 560

Gln Val Pro Trp Met Glu Lys Ala Pro Ala His Leu Ser Leu Pro Asp
            565                 570                 575

Pro Gln Ala Leu Lys Arg Asp Val Pro Cys Asp Asn Val Ser Ser Cys
        580                 585                 590
```

-continued

```
Pro Ser Ser Asp Thr Cys Cys Gln Leu Thr Ser Gly Glu Trp Gly Cys
            595                 600                 605

Cys Pro Ile Pro Glu Ala Val Cys Cys Ser Asp His Gln His Cys Cys
        610                 615                 620

Pro Gln Gly Tyr Thr Cys Val Ala Glu Gly Gln Cys Gln Arg Gly Ser
625                 630                 635                 640

Glu Ile Val Ala Gly Leu Glu Lys Met Pro Ala Arg Arg Ala Ser Leu
                645                 650                 655

Ser His Pro Arg Asp Ile Gly Cys Asp Gln His Thr Ser Cys Pro Val
            660                 665                 670

Gly Gln Thr Cys Cys Pro Ser Leu Gly Gly Ser Trp Ala Cys Cys Gln
        675                 680                 685

Leu Pro His Ala Val Cys Cys Glu Asp Arg Gln His Cys Cys Pro Ala
        690                 695                 700

Gly Tyr Thr Cys Asn Val Lys Ala Arg Ser Cys Glu Lys Glu Val Val
705                 710                 715                 720

Ser Ala Gln Pro Ala Thr Phe Leu Ala Arg Ser Pro His Val Gly Val
                725                 730                 735

Lys Asp Val Glu Cys Gly Glu Gly His Phe Cys His Asp Asn Gln Thr
            740                 745                 750

Cys Cys Arg Asp Asn Arg Gln Gly Trp Ala Cys Cys Pro Tyr Arg Gln
        755                 760                 765

Gly Val Cys Cys Ala Asp Arg Arg His Cys Cys Pro Ala Gly Phe Arg
        770                 775                 780

Cys Ala Ala Arg Gly Thr Lys Cys Leu Arg Arg Glu Ala Pro Arg Trp
785                 790                 795                 800

Asp Ala Pro Leu Arg Asp Pro Ala Leu Arg Pro Pro Leu
                805                 810

<210> SEQ ID NO 124
<211> LENGTH: 813
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 124

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125
```

```
Tyr Thr Leu Pro Pro Ser Arg Asp Glu Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Gly Gly Gly Gly Ser Gly Gly Gly Gly Ser Thr Arg Cys
225                 230                 235                 240

Pro Asp Gly Gln Phe Cys Pro Val Ala Cys Cys Leu Asp Pro Gly Gly
                245                 250                 255

Ala Ser Tyr Ser Cys Cys Arg Pro Leu Leu Asp Lys Trp Pro Thr Thr
            260                 265                 270

Leu Ser Arg His Leu Gly Gly Pro Cys Gln Val Asp Ala His Cys Ser
        275                 280                 285

Ala Gly His Ser Cys Ile Phe Thr Val Ser Gly Thr Ser Ser Cys Cys
    290                 295                 300

Pro Phe Pro Glu Ala Val Ala Cys Gly Asp Gly His His Cys Cys Pro
305                 310                 315                 320

Arg Gly Phe His Cys Ser Ala Asp Gly Arg Ser Cys Phe Gln Arg Ser
                325                 330                 335

Gly Asn Asn Ser Val Gly Ala Ile Gln Cys Pro Asp Ser Gln Phe Glu
            340                 345                 350

Cys Pro Asp Phe Ser Thr Cys Cys Val Met Val Asp Gly Ser Trp Gly
        355                 360                 365

Cys Cys Pro Met Pro Gln Ala Ser Cys Cys Glu Asp Arg Val His Cys
    370                 375                 380

Cys Pro His Gly Ala Phe Cys Asp Leu Val His Thr Arg Cys Ile Thr
385                 390                 395                 400

Pro Thr Gly Thr His Pro Leu Ala Lys Lys Leu Pro Ala Gln Arg Thr
                405                 410                 415

Asn Arg Ala Val Ala Leu Ser Ser Val Met Cys Pro Asp Ala Arg
            420                 425                 430

Ser Arg Cys Pro Asp Gly Ser Thr Cys Cys Glu Leu Pro Ser Gly Lys
        435                 440                 445

Tyr Gly Cys Cys Pro Met Pro Asn Ala Thr Cys Cys Ser Asp His Leu
    450                 455                 460

His Cys Cys Pro Gln Asp Thr Val Cys Asp Leu Ile Gln Ser Lys Cys
465                 470                 475                 480

Leu Ser Lys Glu Asn Ala Thr Thr Asp Leu Leu Thr Lys Leu Pro Ala
                485                 490                 495

His Thr Val Gly Asp Val Lys Cys Asp Met Glu Val Ser Cys Pro Asp
            500                 505                 510

Gly Tyr Thr Cys Cys Arg Leu Gln Ser Gly Ala Trp Gly Cys Cys Pro
        515                 520                 525

Phe Thr Gln Ala Val Cys Cys Glu Asp His Ile His Cys Cys Pro Ala
    530                 535                 540
```

Gly Phe Thr Cys Asp Thr Gln Lys Gly Thr Cys Glu Gln Gly Pro His
545                 550                 555                 560

Gln Val Pro Trp Met Glu Lys Ala Pro Ala His Leu Ser Leu Pro Asp
                565                 570                 575

Pro Gln Ala Leu Lys Arg Asp Val Pro Cys Asp Asn Val Ser Ser Cys
            580                 585                 590

Pro Ser Ser Asp Thr Cys Cys Gln Leu Thr Ser Gly Glu Trp Gly Cys
        595                 600                 605

Cys Pro Ile Pro Glu Ala Val Cys Cys Ser Asp His Gln His Cys Cys
    610                 615                 620

Pro Gln Gly Tyr Thr Cys Val Ala Glu Gly Gln Cys Gln Arg Gly Ser
625                 630                 635                 640

Glu Ile Val Ala Gly Leu Glu Lys Met Pro Ala Arg Arg Ala Ser Leu
                645                 650                 655

Ser His Pro Arg Asp Ile Gly Cys Asp Gln His Thr Ser Cys Pro Val
            660                 665                 670

Gly Gln Thr Cys Cys Pro Ser Leu Gly Gly Ser Trp Ala Cys Cys Gln
        675                 680                 685

Leu Pro His Ala Val Cys Cys Glu Asp Arg Gln His Cys Cys Pro Ala
    690                 695                 700

Gly Tyr Thr Cys Asn Val Lys Ala Arg Ser Cys Glu Lys Glu Val Val
705                 710                 715                 720

Ser Ala Gln Pro Ala Thr Phe Leu Ala Arg Ser Pro His Val Gly Val
                725                 730                 735

Lys Asp Val Glu Cys Gly Glu Gly His Phe Cys His Asp Asn Gln Thr
            740                 745                 750

Cys Cys Arg Asp Asn Arg Gln Gly Trp Ala Cys Cys Pro Tyr Arg Gln
        755                 760                 765

Gly Val Cys Cys Ala Asp Arg Arg His Cys Cys Pro Ala Gly Phe Arg
    770                 775                 780

Cys Ala Ala Arg Gly Thr Lys Cys Leu Arg Arg Glu Ala Pro Arg Trp
785                 790                 795                 800

Asp Ala Pro Leu Arg Asp Pro Ala Leu Arg Pro Tyr Leu
                805                 810

<210> SEQ ID NO 125
<211> LENGTH: 813
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 125

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

-continued

```
Arg Val Val Ser Val Leu Thr Val Leu His Gln Asp Trp Leu Asn Gly
                 85                  90                  95
Lys Glu Tyr Lys Cys Lys Val Ser Asn Lys Ala Leu Pro Ala Pro Ile
            100                 105                 110
Glu Lys Thr Ile Ser Lys Ala Lys Gly Gln Pro Arg Glu Pro Gln Val
        115                 120                 125
Tyr Thr Leu Pro Pro Ser Arg Asp Glu Leu Thr Lys Asn Gln Val Ser
    130                 135                 140
Leu Ser Cys Ala Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                165                 170                 175
Val Leu Asp Ser Asp Gly Ser Phe Phe Leu Val Ser Lys Leu Thr Val
            180                 185                 190
Asp Lys Ser Arg Trp Gln Gln Gly Asn Val Phe Ser Cys Ser Val Met
        195                 200                 205
His Glu Ala Leu His Asn His Tyr Thr Gln Lys Ser Leu Ser Leu Ser
    210                 215                 220
Pro Gly Lys Gly Gly Gly Gly Ser Gly Gly Gly Gly Ser Thr Arg Cys
225                 230                 235                 240
Pro Asp Gly Gln Phe Cys Pro Val Ala Cys Cys Leu Asp Pro Gly Gly
                245                 250                 255
Ala Ser Tyr Ser Cys Cys Arg Pro Leu Leu Asp Lys Trp Pro Thr Thr
            260                 265                 270
Leu Ser Arg His Leu Gly Gly Pro Cys Gln Val Asp Ala His Cys Ser
    275                 280                 285
Ala Gly His Ser Cys Ile Phe Thr Val Ser Gly Thr Ser Ser Cys Cys
    290                 295                 300
Pro Phe Pro Glu Ala Val Ala Cys Gly Asp Gly His His Cys Cys Pro
305                 310                 315                 320
Arg Gly Phe His Cys Ser Ala Asp Gly Arg Ser Cys Phe Gln Arg Ser
                325                 330                 335
Gly Asn Asn Ser Val Gly Ala Ile Gln Cys Pro Asp Ser Gln Phe Glu
            340                 345                 350
Cys Pro Asp Phe Ser Thr Cys Cys Val Met Val Asp Gly Ser Trp Gly
        355                 360                 365
Cys Cys Pro Met Pro Gln Ala Ser Cys Cys Glu Asp Arg Val His Cys
    370                 375                 380
Cys Pro His Gly Ala Phe Cys Asp Leu Val His Thr Arg Cys Ile Thr
385                 390                 395                 400
Pro Thr Gly Thr His Pro Leu Ala Lys Lys Leu Pro Ala Gln Arg Thr
                405                 410                 415
Asn Arg Ala Val Ala Leu Ser Ser Ser Val Met Cys Pro Asp Ala Arg
            420                 425                 430
Ser Arg Cys Pro Asp Gly Ser Thr Cys Cys Glu Leu Pro Ser Gly Lys
        435                 440                 445
Tyr Gly Cys Cys Pro Met Pro Asn Ala Thr Cys Cys Ser Asp His Leu
    450                 455                 460
His Cys Cys Pro Gln Asp Thr Val Cys Asp Leu Ile Gln Ser Lys Cys
465                 470                 475                 480
Leu Ser Lys Glu Asn Ala Thr Thr Asp Leu Leu Thr Lys Leu Pro Ala
                485                 490                 495
```

His Thr Val Gly Asp Val Lys Cys Asp Met Glu Val Ser Cys Pro Asp
              500                 505                 510

Gly Tyr Thr Cys Cys Arg Leu Gln Ser Gly Ala Trp Gly Cys Cys Pro
          515                 520                 525

Phe Thr Gln Ala Val Cys Cys Glu Asp His Ile His Cys Cys Pro Ala
      530                 535                 540

Gly Phe Thr Cys Asp Thr Gln Lys Gly Thr Cys Glu Gln Gly Pro His
545                 550                 555                 560

Gln Val Pro Trp Met Glu Lys Ala Pro Ala His Leu Ser Leu Pro Asp
              565                 570                 575

Pro Gln Ala Leu Lys Arg Asp Val Pro Cys Asp Asn Val Ser Ser Cys
          580                 585                 590

Pro Ser Ser Asp Thr Cys Cys Gln Leu Thr Ser Gly Glu Trp Gly Cys
      595                 600                 605

Cys Pro Ile Pro Glu Ala Val Cys Cys Ser Asp His Gln His Cys Cys
    610                 615                 620

Pro Gln Gly Tyr Thr Cys Val Ala Glu Gly Gln Cys Gln Arg Gly Ser
625                 630                 635                 640

Glu Ile Val Ala Gly Leu Glu Lys Met Pro Ala Arg Arg Ala Ser Leu
              645                 650                 655

Ser His Pro Arg Asp Ile Gly Cys Asp Gln His Thr Ser Cys Pro Val
          660                 665                 670

Gly Gln Thr Cys Cys Pro Ser Leu Gly Gly Ser Trp Ala Cys Cys Gln
      675                 680                 685

Leu Pro His Ala Val Cys Cys Glu Asp Arg Gln His Cys Cys Pro Ala
    690                 695                 700

Gly Tyr Thr Cys Asn Val Lys Ala Arg Ser Cys Glu Lys Glu Val Val
705                 710                 715                 720

Ser Ala Gln Pro Ala Thr Phe Leu Ala Arg Ser Pro His Val Gly Val
              725                 730                 735

Lys Asp Val Glu Cys Gly Glu Gly His Phe Cys His Asp Asn Gln Thr
          740                 745                 750

Cys Cys Arg Asp Asn Arg Gln Gly Trp Ala Cys Cys Pro Tyr Arg Gln
      755                 760                 765

Gly Val Cys Cys Ala Asp Arg Arg His Cys Cys Pro Ala Gly Phe Arg
    770                 775                 780

Cys Ala Ala Arg Gly Thr Lys Cys Leu Arg Arg Glu Ala Pro Arg Trp
785                 790                 795                 800

Asp Ala Pro Leu Arg Asp Pro Ala Leu Arg Gln Arg Leu
              805                 810

<210> SEQ ID NO 126
<211> LENGTH: 813
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 126

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
              20                  25                  30

-continued

```
Ile Ser Arg Thr Pro Glu Val Thr Cys Val Val Val Asp Val Ser His
         35                  40                  45
Glu Asp Pro Glu Val Lys Phe Asn Trp Tyr Val Asp Gly Val Glu Val
 50                  55                  60
His Asn Ala Lys Thr Lys Pro Arg Glu Glu Gln Tyr Asn Ser Thr Tyr
 65                  70                  75                  80
Arg Val Val Ser Val Leu Thr Val Leu His Gln Asp Trp Leu Asn Gly
                 85                  90                  95
Lys Glu Tyr Lys Cys Lys Val Ser Asn Lys Ala Leu Pro Ala Pro Ile
            100                 105                 110
Glu Lys Thr Ile Ser Lys Ala Lys Gly Gln Pro Arg Glu Pro Gln Val
        115                 120                 125
Tyr Thr Leu Pro Pro Ser Arg Asp Glu Leu Thr Lys Asn Gln Val Ser
130                 135                 140
Leu Ser Cys Ala Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                165                 170                 175
Val Leu Asp Ser Asp Gly Ser Phe Phe Leu Val Ser Lys Leu Thr Val
            180                 185                 190
Asp Lys Ser Arg Trp Gln Gln Gly Asn Val Phe Ser Cys Ser Val Met
        195                 200                 205
His Glu Ala Leu His Asn His Tyr Thr Gln Lys Ser Leu Ser Leu Ser
210                 215                 220
Pro Gly Lys Gly Gly Gly Gly Ser Gly Gly Gly Gly Ser Thr Arg Cys
225                 230                 235                 240
Pro Asp Gly Gln Phe Cys Pro Val Ala Cys Cys Leu Asp Pro Gly Gly
                245                 250                 255
Ala Ser Tyr Ser Cys Cys Arg Pro Leu Leu Asp Lys Trp Pro Thr Thr
            260                 265                 270
Leu Ser Arg His Leu Gly Gly Pro Cys Gln Val Asp Ala His Cys Ser
        275                 280                 285
Ala Gly His Ser Cys Ile Phe Thr Val Ser Gly Thr Ser Ser Cys Cys
290                 295                 300
Pro Phe Pro Glu Ala Val Ala Cys Gly Asp Gly His His Cys Cys Pro
305                 310                 315                 320
Arg Gly Phe His Cys Ser Ala Asp Gly Arg Ser Cys Phe Gln Arg Ser
                325                 330                 335
Gly Asn Asn Ser Val Gly Ala Ile Gln Cys Pro Asp Ser Gln Phe Glu
            340                 345                 350
Cys Pro Asp Phe Ser Thr Cys Cys Val Met Val Asp Gly Ser Trp Gly
        355                 360                 365
Cys Cys Pro Met Pro Gln Ala Ser Cys Cys Glu Asp Arg Val His Cys
370                 375                 380
Cys Pro His Gly Ala Phe Cys Asp Leu Val His Thr Arg Cys Ile Thr
385                 390                 395                 400
Pro Thr Gly Thr His Pro Leu Ala Lys Lys Leu Pro Ala Gln Arg Thr
                405                 410                 415
Asn Arg Ala Val Ala Leu Ser Ser Val Met Cys Pro Asp Ala Arg
            420                 425                 430
Ser Arg Cys Pro Asp Gly Ser Thr Cys Cys Glu Leu Pro Ser Gly Lys
        435                 440                 445
```

```
Tyr Gly Cys Cys Pro Met Pro Asn Ala Thr Cys Cys Ser Asp His Leu
            450                 455                 460

His Cys Cys Pro Gln Asp Thr Val Cys Asp Leu Ile Gln Ser Lys Cys
465                 470                 475                 480

Leu Ser Lys Glu Asn Ala Thr Thr Asp Leu Leu Thr Lys Leu Pro Ala
                485                 490                 495

His Thr Val Gly Asp Val Lys Cys Asp Met Glu Val Ser Cys Pro Asp
            500                 505                 510

Gly Tyr Thr Cys Cys Arg Leu Gln Ser Gly Ala Trp Gly Cys Cys Pro
            515                 520                 525

Phe Thr Gln Ala Val Cys Cys Glu Asp His Ile His Cys Cys Pro Ala
            530                 535                 540

Gly Phe Thr Cys Asp Thr Gln Lys Gly Thr Cys Glu Gln Gly Pro His
545                 550                 555                 560

Gln Val Pro Trp Met Glu Lys Ala Pro Ala His Leu Ser Leu Pro Asp
                565                 570                 575

Pro Gln Ala Leu Lys Arg Asp Val Pro Cys Asp Asn Val Ser Ser Cys
            580                 585                 590

Pro Ser Ser Asp Thr Cys Cys Gln Leu Thr Ser Gly Glu Trp Gly Cys
            595                 600                 605

Cys Pro Ile Pro Glu Ala Val Cys Cys Ser Asp His Gln His Cys Cys
610                 615                 620

Pro Gln Gly Tyr Thr Cys Val Ala Glu Gly Gln Cys Gln Arg Gly Ser
625                 630                 635                 640

Glu Ile Val Ala Gly Leu Glu Lys Met Pro Ala Arg Arg Ala Ser Leu
                645                 650                 655

Ser His Pro Arg Asp Ile Gly Cys Asp Gln His Thr Ser Cys Pro Val
            660                 665                 670

Gly Gln Thr Cys Cys Pro Ser Leu Gly Gly Ser Trp Ala Cys Cys Gln
            675                 680                 685

Leu Pro His Ala Val Cys Cys Glu Asp Arg Gln His Cys Cys Pro Ala
690                 695                 700

Gly Tyr Thr Cys Asn Val Lys Ala Arg Ser Cys Glu Lys Glu Val Val
705                 710                 715                 720

Ser Ala Gln Pro Ala Thr Phe Leu Ala Arg Ser Pro His Val Gly Val
                725                 730                 735

Lys Asp Val Glu Cys Gly Glu Gly His Phe Cys His Asp Asn Gln Thr
            740                 745                 750

Cys Cys Arg Asp Asn Arg Gln Gly Trp Ala Cys Cys Pro Tyr Arg Gln
            755                 760                 765

Gly Val Cys Cys Ala Asp Arg Arg His Cys Cys Pro Ala Gly Phe Arg
770                 775                 780

Cys Ala Ala Arg Gly Thr Lys Cys Leu Arg Arg Glu Ala Pro Arg Trp
785                 790                 795                 800

Asp Ala Pro Leu Arg Asp Pro Ala Leu Arg Gln His Leu
                805                 810
```

<210> SEQ ID NO 127
<211> LENGTH: 576
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 127

```
Thr Arg Cys Pro Asp Gly Gln Phe Cys Pro Val Ala Cys Cys Leu Asp
1               5                   10                  15

Pro Gly Gly Ala Ser Tyr Ser Cys Cys Arg Pro Leu Leu Asp Lys Trp
            20                  25                  30

Pro Thr Thr Leu Ser Arg His Leu Gly Gly Pro Cys Gln Val Asp Ala
        35                  40                  45

His Cys Ser Ala Gly His Ser Cys Ile Phe Thr Val Ser Gly Thr Ser
    50                  55                  60

Ser Cys Cys Pro Phe Pro Glu Ala Val Ala Cys Gly Asp Gly His His
65              70                  75                  80

Cys Cys Pro Arg Gly Phe His Cys Ser Ala Asp Gly Arg Ser Cys Phe
            85                  90                  95

Gln Arg Ser Gly Asn Asn Ser Val Gly Ala Ile Gln Cys Pro Asp Ser
            100                 105                 110

Gln Phe Glu Cys Pro Asp Phe Ser Thr Cys Cys Val Met Val Asp Gly
        115                 120                 125

Ser Trp Gly Cys Cys Pro Met Pro Gln Ala Ser Cys Cys Glu Asp Arg
    130                 135                 140

Val His Cys Cys Pro His Gly Ala Phe Cys Asp Leu Val His Thr Arg
145             150                 155                 160

Cys Ile Thr Pro Thr Gly Thr His Pro Leu Ala Lys Lys Leu Pro Ala
            165                 170                 175

Gln Arg Thr Asn Arg Ala Val Ala Leu Ser Ser Val Met Cys Pro
            180                 185                 190

Asp Ala Arg Ser Arg Cys Pro Asp Gly Ser Thr Cys Cys Glu Leu Pro
            195                 200                 205

Ser Gly Lys Tyr Gly Cys Cys Pro Met Pro Asn Ala Thr Cys Cys Ser
    210                 215                 220

Asp His Leu His Cys Cys Pro Gln Asp Thr Val Cys Asp Leu Ile Gln
225             230                 235                 240

Ser Lys Cys Leu Ser Lys Glu Asn Ala Thr Thr Asp Leu Leu Thr Lys
            245                 250                 255

Leu Pro Ala His Thr Val Gly Asp Val Lys Cys Asp Met Glu Val Ser
            260                 265                 270

Cys Pro Asp Gly Tyr Thr Cys Cys Arg Leu Gln Ser Gly Ala Trp Gly
        275                 280                 285

Cys Cys Pro Phe Thr Gln Ala Val Cys Cys Glu Asp His Ile His Cys
    290                 295                 300

Cys Pro Ala Gly Phe Thr Cys Asp Thr Gln Lys Gly Thr Cys Glu Gln
305             310                 315                 320

Gly Pro His Gln Val Pro Trp Met Glu Lys Ala Pro Ala His Leu Ser
            325                 330                 335

Leu Pro Asp Pro Gln Ala Leu Lys Arg Asp Val Pro Cys Asp Asn Val
            340                 345                 350

Ser Ser Cys Pro Ser Ser Asp Thr Cys Cys Gln Leu Thr Ser Gly Glu
        355                 360                 365

Trp Gly Cys Cys Pro Ile Pro Glu Ala Val Cys Cys Ser Asp His Gln
    370                 375                 380

His Cys Cys Pro Gln Gly Tyr Thr Cys Val Ala Glu Gly Gln Cys Gln
385             390                 395                 400
```

```
Arg Gly Ser Glu Ile Val Ala Gly Leu Glu Lys Met Pro Ala Arg Arg
                405                 410                 415

Ala Ser Leu Ser His Pro Arg Asp Ile Gly Cys Asp Gln His Thr Ser
            420                 425                 430

Cys Pro Val Gly Gln Thr Cys Cys Pro Ser Leu Gly Gly Ser Trp Ala
        435                 440                 445

Cys Cys Gln Leu Pro His Ala Val Cys Cys Glu Asp Arg Gln His Cys
    450                 455                 460

Cys Pro Ala Gly Tyr Thr Cys Asn Val Lys Ala Arg Ser Cys Glu Lys
465                 470                 475                 480

Glu Val Val Ser Ala Gln Pro Ala Thr Phe Leu Ala Arg Ser Pro His
                485                 490                 495

Val Gly Val Lys Asp Val Glu Cys Gly Glu Gly His Phe Cys His Asp
            500                 505                 510

Asn Gln Thr Cys Cys Arg Asp Asn Arg Gln Gly Trp Ala Cys Cys Pro
        515                 520                 525

Tyr Arg Gln Gly Val Cys Cys Ala Asp Arg Arg His Cys Cys Pro Ala
    530                 535                 540

Gly Phe Arg Cys Ala Ala Arg Gly Thr Lys Cys Leu Arg Arg Glu Ala
545                 550                 555                 560

Pro Arg Trp Asp Ala Pro Leu Arg Asp Pro Ala Leu Arg Gln Leu Tyr
                565                 570                 575

<210> SEQ ID NO 128
<211> LENGTH: 576
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 128

Thr Arg Cys Pro Asp Gly Gln Phe Cys Pro Val Ala Cys Cys Leu Asp
1               5                   10                  15

Pro Gly Gly Ala Ser Tyr Ser Cys Cys Arg Pro Leu Leu Asp Lys Trp
            20                  25                  30

Pro Thr Thr Leu Ser Arg His Leu Gly Gly Pro Cys Gln Val Asp Ala
        35                  40                  45

His Cys Ser Ala Gly His Ser Cys Ile Phe Thr Val Ser Gly Thr Ser
    50                  55                  60

Ser Cys Cys Pro Phe Pro Glu Ala Val Ala Cys Gly Asp Gly His His
65                  70                  75                  80

Cys Cys Pro Arg Gly Phe His Cys Ser Ala Asp Gly Arg Ser Cys Phe
                85                  90                  95

Gln Arg Ser Gly Asn Asn Ser Val Gly Ala Ile Gln Cys Pro Asp Ser
            100                 105                 110

Gln Phe Glu Cys Pro Asp Phe Ser Thr Cys Cys Val Met Val Asp Gly
        115                 120                 125

Ser Trp Gly Cys Cys Pro Met Pro Gln Ala Ser Cys Cys Glu Asp Arg
    130                 135                 140

Val His Cys Cys Pro His Gly Ala Phe Cys Asp Leu Val His Thr Arg
145                 150                 155                 160

Cys Ile Thr Pro Thr Gly Thr His Pro Leu Ala Lys Lys Leu Pro Ala
                165                 170                 175
```

```
Gln Arg Thr Asn Arg Ala Val Ala Leu Ser Ser Val Met Cys Pro
                180                 185                 190

Asp Ala Arg Ser Arg Cys Pro Asp Gly Ser Thr Cys Cys Glu Leu Pro
            195                 200                 205

Ser Gly Lys Tyr Gly Cys Cys Pro Met Pro Asn Ala Thr Cys Cys Ser
        210                 215                 220

Asp His Leu His Cys Cys Pro Gln Asp Thr Val Cys Asp Leu Ile Gln
225                 230                 235                 240

Ser Lys Cys Leu Ser Lys Glu Asn Ala Thr Thr Asp Leu Leu Thr Lys
                245                 250                 255

Leu Pro Ala His Thr Val Gly Asp Val Lys Cys Asp Met Glu Val Ser
                260                 265                 270

Cys Pro Asp Gly Tyr Thr Cys Cys Arg Leu Gln Ser Gly Ala Trp Gly
            275                 280                 285

Cys Cys Pro Phe Thr Gln Ala Val Cys Cys Glu Asp His Ile His Cys
        290                 295                 300

Cys Pro Ala Gly Phe Thr Cys Asp Thr Gln Lys Gly Thr Cys Glu Gln
305                 310                 315                 320

Gly Pro His Gln Val Pro Trp Met Glu Lys Ala Pro Ala His Leu Ser
                325                 330                 335

Leu Pro Asp Pro Gln Ala Leu Lys Arg Asp Val Pro Cys Asp Asn Val
                340                 345                 350

Ser Ser Cys Pro Ser Ser Asp Thr Cys Cys Gln Leu Thr Ser Gly Glu
            355                 360                 365

Trp Gly Cys Cys Pro Ile Pro Glu Ala Val Cys Cys Ser Asp His Gln
        370                 375                 380

His Cys Cys Pro Gln Gly Tyr Thr Cys Val Ala Glu Gly Gln Cys Gln
385                 390                 395                 400

Arg Gly Ser Glu Ile Val Ala Gly Leu Glu Lys Met Pro Ala Arg Arg
                405                 410                 415

Ala Ser Leu Ser His Pro Arg Asp Ile Gly Cys Asp Gln His Thr Ser
                420                 425                 430

Cys Pro Val Gly Gln Thr Cys Cys Pro Ser Leu Gly Gly Ser Trp Ala
            435                 440                 445

Cys Cys Gln Leu Pro His Ala Val Cys Cys Glu Asp Arg Gln His Cys
450                 455                 460

Cys Pro Ala Gly Tyr Thr Cys Asn Val Lys Ala Arg Ser Cys Glu Lys
465                 470                 475                 480

Glu Val Val Ser Ala Gln Pro Ala Thr Phe Leu Ala Arg Ser Pro His
                485                 490                 495

Val Gly Val Lys Asp Val Glu Cys Gly Glu Gly His Phe Cys His Asp
                500                 505                 510

Asn Gln Thr Cys Cys Arg Asp Asn Arg Gln Gly Trp Ala Cys Cys Pro
            515                 520                 525

Tyr Arg Gln Gly Val Cys Cys Ala Asp Arg Arg His Cys Cys Pro Ala
        530                 535                 540

Gly Phe Arg Cys Ala Ala Arg Gly Thr Lys Cys Leu Arg Arg Glu Ala
545                 550                 555                 560

Pro Arg Trp Asp Ala Pro Leu Arg Asp Pro Ala Leu Arg Gln Leu Pro
                565                 570                 575
```

<210> SEQ ID NO 129
<211> LENGTH: 216
<212> TYPE: PRT

```
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 129

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Tyr Gly Thr Glu Trp Ala Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Thr Lys Glu Glu Trp Gln Gln Gly Phe Val
            180                 185                 190

Phe Ser Cys Ser Val Met His Glu Ala Leu His Asn His Tyr Thr Gln
        195                 200                 205

Lys Ser Leu Ser Leu Ser Pro Gly
    210                 215

<210> SEQ ID NO 130
<211> LENGTH: 226
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 130

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95
```

Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val
            115                 120                 125

Tyr Thr Leu Pro Pro Ser Arg Asp Glu Leu Thr Lys Asn Gln Val Ser
        130                 135                 140

Leu Trp Cys Leu Val Lys Gly Phe Tyr Pro Ser Asp Ile Ala Val Glu
145                 150                 155                 160

Trp Glu Ser Tyr Gly Thr Glu Trp Ala Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Thr Lys Glu Glu Trp Gln Gln Gly Phe Val Phe Ser Cys Ser Val Met
        195                 200                 205

His Glu Ala Leu His Asn His Tyr Thr Gln Lys Ser Leu Ser Leu Ser
            210                 215                 220

Pro Gly
225

<210> SEQ ID NO 131
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 131

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Trp Cys Leu Val Lys Gly Phe Tyr Pro
    130                 135                 140

Ser Asp Ile Ala Val Leu Trp Glu Ser Tyr Gly Thr Glu Trp Ser Ser
145                 150                 155                 160

Tyr Lys Thr Thr Pro Pro Val Leu Asp Ser Asp Gly Ser Phe Phe Leu
                165                 170                 175

Tyr Ser Lys Leu Thr Val Thr Lys Glu Glu Trp Gln Gln Gly Phe Val
            180                 185                 190

Phe Ser Cys Ser Val Met His Glu Ala Leu His Asn His Tyr Thr Gln
        195                 200                 205

```
Lys Ser Leu Ser Leu Ser Pro Gly
    210                 215
```

<210> SEQ ID NO 132
<211> LENGTH: 226
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 132

```
Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Trp Cys Leu Val Lys Gly Phe Tyr Pro Ser Asp Ile Ala Val Leu
145                 150                 155                 160

Trp Glu Ser Tyr Gly Thr Glu Trp Ser Ser Tyr Lys Thr Thr Pro Pro
                165                 170                 175

Val Leu Asp Ser Asp Gly Ser Phe Phe Leu Tyr Ser Lys Leu Thr Val
            180                 185                 190

Thr Lys Glu Glu Trp Gln Gln Gly Phe Val Phe Ser Cys Ser Val Met
        195                 200                 205

His Glu Ala Leu His Asn His Tyr Thr Gln Lys Ser Leu Ser Leu Ser
    210                 215                 220

Pro Gly
225
```

<210> SEQ ID NO 133
<211> LENGTH: 50
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: SITE
<222> LOCATION: (1)..(50)
<223> OTHER INFORMATION: /note="This sequence may encompass 1-10 'Gly
      Gly Gly Gly Ser' repeating units"

<400> SEQUENCE: 133

```
Gly Gly Gly Gly Ser Gly Gly Gly Gly Ser Gly Gly Gly Gly Ser Gly
1               5                   10                  15
```

Gly Gly Gly Ser Gly Gly Gly Ser Gly Gly Gly Ser Gly Gly
            20                  25                  30

Gly Gly Ser Gly Gly Gly Ser Gly Gly Gly Ser Gly Gly Gly
            35                  40                  45

Gly Ser
    50

<210> SEQ ID NO 134
<211> LENGTH: 40
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: SITE
<222> LOCATION: (1)..(40)
<223> OTHER INFORMATION: /note="This sequence may encompass 1-10 'Gly
      Gly Ser Gly' repeating units"

<400> SEQUENCE: 134

Gly Gly Ser Gly Gly Gly Ser Gly Gly Gly Ser Gly Gly Gly Ser Gly
1               5                   10                  15

Gly Gly Ser Gly Gly Gly Ser Gly Gly Gly Ser Gly Gly Gly Ser Gly
            20                  25                  30

Gly Gly Ser Gly Gly Gly Ser Gly
            35                  40

<210> SEQ ID NO 135
<211> LENGTH: 40
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: SITE
<222> LOCATION: (1)..(40)
<223> OTHER INFORMATION: /note="This sequence may encompass 1-10 'Ser
      Gly Gly Gly' repeating units"

<400> SEQUENCE: 135

Ser Gly Gly Gly Ser Gly Gly Gly Ser Gly Gly Gly Ser Gly Gly Gly
1               5                   10                  15

Ser Gly Gly Gly Ser Gly Gly Gly Ser Gly Gly Gly Ser Gly Gly Gly
            20                  25                  30

Ser Gly Gly Gly Ser Gly Gly Gly
            35                  40

<210> SEQ ID NO 136
<211> LENGTH: 27
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: SITE
<222> LOCATION: (2)..(26)
<223> OTHER INFORMATION: /note="This sequence may encompass 1-5 'Glu Ala
      Ala Ala Lys' repeating units"

<400> SEQUENCE: 136

Ala Glu Ala Ala Ala Lys Glu Ala Ala Lys Glu Ala Ala Ala Lys
1               5                   10                  15

Glu Ala Ala Ala Lys Glu Ala Ala Lys Ala
                20                  25

<210> SEQ ID NO 137
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(1)
<223> OTHER INFORMATION: /replace=" "
<220> FEATURE:
<221> NAME/KEY: VARIANT
<222> LOCATION: (2)..(2)
<223> OTHER INFORMATION: /replace=" "
<220> FEATURE:
<221> NAME/KEY: SITE
<222> LOCATION: (1)..(5)
<223> OTHER INFORMATION: /note="Variant residues given in the sequence
      have no preference with respect to those in the annotations
      for variant positions"

<400> SEQUENCE: 137

Leu Arg Gln Leu Leu
1               5

<210> SEQ ID NO 138
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: SITE
<222> LOCATION: (1)..(10)
<223> OTHER INFORMATION: /note="This sequence may encompass 1-10
      residues"

<400> SEQUENCE: 138

Gly Gly Gly Gly Gly Gly Gly Gly Gly Gly
1               5                   10

<210> SEQ ID NO 139
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: SITE
<222> LOCATION: (1)..(20)
<223> OTHER INFORMATION: /note="This sequence may encompass 1-10 'Gly
      Ser' repeating units"

<400> SEQUENCE: 139

Gly Ser Gly Ser Gly Ser Gly Ser Gly Ser Gly Ser Gly Ser Gly Ser
1               5                   10                  15

Gly Ser Gly Ser
            20

<210> SEQ ID NO 140
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: SITE
<222> LOCATION: (1)..(30)
<223> OTHER INFORMATION: /note="This sequence may encompass 1-10 'Gly
      Gly Ser' repeating units"

<400> SEQUENCE: 140

Gly Gly Ser Gly Gly Ser Gly Gly Ser Gly Gly Ser Gly Gly Ser Gly
1               5                   10                  15

Gly Ser Gly Gly Ser Gly Gly Ser Gly Gly Ser Gly Gly Ser
            20                  25                  30

<210> SEQ ID NO 141
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(1)
<223> OTHER INFORMATION: /replace="Lys" or "Glu"
<220> FEATURE:
<221> NAME/KEY: VARIANT
<222> LOCATION: (3)..(3)
<223> OTHER INFORMATION: /replace="Lys" or "Glu"
<220> FEATURE:
<221> NAME/KEY: VARIANT
<222> LOCATION: (5)..(5)
<223> OTHER INFORMATION: /replace="Lys" or "Glu"
<220> FEATURE:
<221> NAME/KEY: VARIANT
<222> LOCATION: (7)..(7)
<223> OTHER INFORMATION: /replace="Lys" or "Glu"
<220> FEATURE:
<221> NAME/KEY: VARIANT
<222> LOCATION: (9)..(9)
<223> OTHER INFORMATION: /replace="Lys" or "Glu"
<220> FEATURE:
<221> NAME/KEY: VARIANT
<222> LOCATION: (11)..(11)
<223> OTHER INFORMATION: /replace="Lys" or "Glu"
<220> FEATURE:
<221> NAME/KEY: VARIANT
<222> LOCATION: (13)..(13)
<223> OTHER INFORMATION: /replace="Lys" or "Glu"
<220> FEATURE:
<221> NAME/KEY: VARIANT
<222> LOCATION: (15)..(15)
<223> OTHER INFORMATION: /replace="Lys" or "Glu"
<220> FEATURE:
<221> NAME/KEY: VARIANT
<222> LOCATION: (17)..(17)
<223> OTHER INFORMATION: /replace="Lys" or "Glu"
<220> FEATURE:
<221> NAME/KEY: VARIANT

```
<222> LOCATION: (19)..(19)
<223> OTHER INFORMATION: /replace="Lys" or "Glu"
<220> FEATURE:
<221> NAME/KEY: SITE
<222> LOCATION: (1)..(20)
<223> OTHER INFORMATION: /note="Variant residues given in the sequence
      have no preference with respect to those in the annotations
      for variant positions"
<220> FEATURE:
<221> NAME/KEY: SITE
<222> LOCATION: (1)..(20)
<223> OTHER INFORMATION: /note="This sequence may encompass 1-10 'Ala
      Pro' repeating units"

<400> SEQUENCE: 141

Ala Pro Ala Pro Ala Pro Ala Pro Ala Pro Ala Pro Ala Pro Ala Pro
1               5                   10                  15

Ala Pro Ala Pro
            20

<210> SEQ ID NO 142
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 142

Gln Leu Leu Gly
1

<210> SEQ ID NO 143
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 143

Gln Leu Leu Gly Lys
1               5
```

US 11,643,446 B2

PROGRANULIN VARIANTS

CROSS-REFERENCE TO RELATED APPLICATIONS

The present application is a continuation of International Patent Application No. PCT/US2020/066831, filed on Dec. 23, 2020, which claims priority to U.S. Provisional Application No. 62/953,099, filed Dec. 23, 2019, and U.S. Provisional Application No. 63/091,819, filed Oct. 14, 2020, the disclosures of which are hereby incorporated by reference in their entirety for all purposes.

SEQUENCE LISTING

The instant application contains a Sequence Listing which has been submitted electronically in ASCII format and is hereby incorporated by reference in its entirety. Said ASCII copy, created on Dec. 14, 2020, is named 102342-003930US-1308905_SL.txt and is 543,801 bytes in size.

BACKGROUND

Frontotemporal dementia (FTD) is a progressive neurodegenerative disorder which accounts for 5-10% of all patients with dementia and $10^{-20}$% of patients with an onset of dementia before 65 years (Rademakers et al., *Nat Rev Neurol.* 8(8):423-34, 2012). While several genes have been linked to FTD, one of the most frequently mutated genes in FTD is GRN, which maps to human chromosome 17q21 and encodes the cysteine-rich protein progranulin (PGRN) (also known as proepithelin and acrogranin). Highly penetrant mutations in GRN were first reported in 2006 as a cause of autosomal dominant forms of familial FTD (Baker et al., *Nature.* 442(7105):916-9, 2006; Cruts et al., *Nature.* 2006 Aug. 24; 442(7105):920-4; Gass et al., *Hum Mol Genet.* 15(20):2988-3001, 2006). Recent estimates suggest that GRN mutations account for 5-20% of FTD patients with positive family history and 1-5% of sporadic cases (Rademakers et al., supra).

Following the identification of GRN mutations as a cause of FTD, reduced levels of progranulin and progranulin loss of function have been linked to multiple neurodegenerative diseases and disorders, including Alzheimer's Disease (AD), Parkinson's Disease (PD), amyotrophic lateral sclerosis (ALS), and neurodegenerative disorders caused by lysosomal storage disease (Petkau and Leavitt. 2014. *Trends Neurosci* 37(7):388-398). Accordingly, there is a need to develop therapies that can address disorders caused by loss of progranulin function or reduced levels of progranulin, or disorders for which increased levels of progranulin are beneficial.

SUMMARY

Provided herein are progranulin variants and fusion proteins comprising a progranulin or a variant thereof and methods of use such variants or fusion proteins for treating any disease where increased levels of progranulin are beneficial, including a neurodegenerative disease (e.g., FTD), atherosclerosis, a disorder associated with TDP-43, age-related macular degeneration (AMD), or a progranulin-associated disorder. The progranulin variants provided herein have modifications or additions to the C-terminus of a wild-type progranulin. As described herein, fusion proteins containing a progranulin variant are less susceptible to C-terminal cleavage in the progranulin portion of the protein, compared to fusion proteins containing the wild-type progranulin when the protein is recombinantly expressed and purified from Chinese Hamster Ovary (CHO) cells.

In one aspect, the disclosure features a progranulin variant comprising a sequence having at least 90% (e.g., at least 91%, 92%, 93%, 94%, 95%, 96%, 97%, 98%, or 99%) identity or 100% identity to SEQ ID NO:2 and a sequence defined by $X_1X_2X_3$ at the positions corresponding to residues 574 to 576 of SEQ ID NO:2, wherein $X_1$, $X_2$, and $X_3$ are each independently an amino acid and together are not QLL. In some embodiments, the progranulin variant has at least 95% (e.g., at least 96%, 97%, 98%, or 99%) identity or 100% identity to SEQ ID NO:2. In some embodiments, the progranulin variant has at least 98% identity (e.g., at least 99%) to SEQ ID NO:2. In some embodiments, the progranulin variant comprises a sequence having at least 95% (e.g., at least 96%, 97%, 98%, or 99%) identity or 100% identity to SEQ ID NO:2. In some embodiments, the progranulin variant comprises a sequence having at least 98% identity (e.g., at least 99%) to SEQ ID NO:2.

In some embodiments of this aspect, the progranulin variant comprises the sequence:

(SEQ ID NO: 3)
TRCPDGQFCPVACCLDPGGASYSCCRPLLDKWPTTLSRHLGGPCQVDAHC

SAGHSCIFTVSGTSSCCPFPEAVACGDGHHCCPRGFHCSADGRSCFQRSG

NNSVGAIQCPDSQFCPDFSTCCVMVDGSWGCCPMPQASCCEDRVHCCPHG

AFCDLVHTRCITPTGTHPLAKKLPAQRTNRAVALSSSVMCPDARSRCPDG

STCCELPSGKYGCCPMPNATCCSDHLHCCPQDTVCDLIQSKCLSKENATT

DLLTKLPAHTVGDVKCDMEVSCPDGYTCCRLQSGAWGCCPFTQAVCCEDH

IFICCPAGFTCDTQKGTCEQGPHQVPWMEKAPAHLSLPDPQALKRDVPCD

NVSSCPSSDTCCQLTSGEWGCCPIPEAVCCSDHQHCCPQGYTCVAEGQCQ

RGSEIVAGLEKMPARRASLSHPRDIGCDQHTSCPVGQTCCPSLGGSWACC

QLPHAVCCEDRQHCCPAGYTCNVKARSCEKEVVSAQPATFLARSPHVGVK

DVECGEGHFCHDNQTCCRDNRQGWACCPYRQGVCCADRRHCCPAGFRCAA

RGTKCLRREAPRWDAPLRDPALRX$_1$X$_2$X$_3$, in which $X_1X_2X_3$ together is not QLL.

In some embodiments, $X_1$ is R, H, K, D, E, S, T, N, Q, L, F, Y, P, or V. In some embodiments, $X_2$ is H, K, D, E, S, T, N, Q, G, P, A, Y, V, I, F, L, or R. In some embodiments, $X_3$ is L, Y, or P.

In some embodiments, $X_1X_2X_3$ is $X_1$IL, $X_1$FL, $X_1$QL, PX$_2$L, QX$_2$L, or VX$_2$L. In some embodiments, $X_1X_2X_3$ is $X_1X_2$L, and in some embodiments, $X_2$ in $X_1X_2$L is A, R, N, D, C, Q, E, G, H, I, K, M, F, P, S, T, W, Y, or V.

In particular embodiments, $X_1X_2X_3$ is PIL, PFL, QQL, VVL, or VTL. In particular embodiments, $X_1X_2X_3$ is PPL, PYL, QQL, QHL, or QRL.

In another aspect, the disclosure features a progranulin variant comprising a sequence having at least 90% (e.g., at least 91%, 92%, 93%, 94%, 95%, 96%, 97%, 98%, or 99%) identity or 100% identity to SEQ ID NO:2 and a sequence defined by $Y_1Y_2$QLL (SEQ ID NO:137) that is adjacent and C-terminal to the position corresponding to residue 576 of SEQ ID NO:2, wherein $Y_1$ is L or absent, and $Y_2$ is R or absent.

In some embodiments, the prograulin variant comprises the sequence:

(SEQ ID NO: 55)
TRCPDGQFCPVACCLDPGGASYSCCRPLLDKWPTTLSRHLGGPCQVDAHC

SAGHSCIFTVSGTSSCCPFPEAVACGDGHHCCPRGFHCSADGRSCFQRSG

NNSVGAIQCPDSQFECPDFSTCCVMVDGSWGCCPMPQASCCEDRVHCCPH

GAFCDLVHTRCITPTGTHPLAKKLPAQRTNRAVALSSSVMCPDARSRCPD

GSTCCELPSGKYGCCPMPNATCCSDHLHCCPQDTVCDLIQSKCLSKENAT

TDLLTKLPAHTVGDVKCDMEVSCPDGYTCCRLQSGAWGCCPFTQAVCCED

HIHCCPAGFTCDTQKGTCEQGPHQVPWMEKAPAHLSLPDPQALKRDVPCD

NVSSCPSSDTCCQLTSGEWGCCPIPEAVCCSDHQHCCPQGYTCVAEGQCQ

RGSEIVAGLEKMPARRASLSHPRDIGCDQHTSCPVGQTCCPSLGGSWACC

QLPHAVCCEDRQHCCPAGYTCNVKARSCEKEVVSAQPATFLARSPHVGVK

DVECGEGHFCHDNQTCCRDNRQGWACCPYRQGVCCADRRHCCPAGFRCAA

RGTKCLRREAPRWDAPLRDPALRQLLY$_1$Y$_2$QLL.

In some embodiments, Y$_1$ is L. In some embodiments, Y$_2$ is R. In some embodiments, Y$_1$ and Y$_2$ are both absent.

In another aspect, the disclosure features a polypeptide comprising a prograulin variant that comprises a sequence having at least 90% (e.g., at least 91%, 92%, 93%, 94%, 95%, 96%, 97%, 98%, or 99%) identity or 100% identity to SEQ ID NO:2 and a sequence defined by X$_1$X$_2$X$_3$ at the positions corresponding to residues 574 to 576 of SEQ ID NO:2, wherein X$_1$, X$_2$, and X$_3$ are each independently an amino acid and together are not QLL. In some embodiments, the prograulin variant in the polypeptide has at least 95% (e.g., at least 96%, 97%, 98%, or 99%) identity to SEQ ID NO:2. In some embodiments, the prograulin variant in the polypeptide comprises a sequence having at least 95% (e.g., at least 96%, 97%, 98%, or 99%) identity to SEQ ID NO:2.

In some embodiments of this aspect, the prograulin variant in the polypeptide comprises the sequence:

(SEQ ID NO: 3)
TRCPDGQFCPVACCLDPGGASYSCCRPLLDKWPTTLSRHLGGPCQVDAHC

SAGHSCIFTVSGTSSCCPFPEAVACGDMECCPRGFHCSADGRSCFQRSGN

NSVGAIQCPDSQFECPDFSTCCVMVDGSWGCCPMPQASCCEDRVHCCPHG

AFCDLVHTRCITPTGTHPLAKKLPAQRTNRAVALSSSVMCPDARSRCPDG

STCCELPSGKYGCCPMPNATCCSDHLHCCPQDTVCDLIQSKCLSKENATT

DLLTKLPAHTVGDVKCDMEVSCPDGYTCCRLQSGAWGCCPFTQAVCCEDH

IHCCPAGFTCDTQKGTCEQGPHQVPWMEKAPAHLSLPDPQALKRDVPCDN

VSSCPSSDTCCQLTSGEWGCCPIPEAVCCSDHQHCCPQGYTCVAEGQCQR

GSEIVAGLEKMPARRASLSHPRDIGCDQHTSCPVGQTCCPSLGGSWACCQ

LPHAVCCEDRQHCCPAGYTCNVKARSCEKEVVSAQPATFLARSPHVGVKD

VECGEGHFCHDNQTCCRDNRQGWACCPYRQGVCCADRRHCCPAGFRCAAR

GTKCLRREAPRWDAPLRDPALRX$_1$X$_2$X$_3$.

wherein X$_1$X$_2$X$_3$ is not QQL.

In some embodiments of this aspect, X$_1$ is R, H, K, D, E, S, T, N, Q, L, F, Y, P, or V. In some embodiments, X$_2$ is H, K, D, E, S, T, N, Q, G, P, A, Y, V, I, F, L, or R. In some embodiments, X$_3$ is L, Y, or P.

In some embodiments, X$_1$X$_2$X$_3$ is X$_1$IL. In certain embodiments, X$_1$ in X$_1$IL can be R, H, K, E, P, N, F, or Y (e.g., R, H, K, E, or P).

In some embodiments, X$_1$X$_2$X$_3$ is X$_1$FL. In certain embodiments, X$_1$ in X$_1$FL can be R, H, K, D, E, S, T, N, Q, L, F, Y, or P.

In some embodiments, X$_1$X$_2$X$_3$ is X$_1$QL. In certain embodiments, X$_1$ in X$_1$QL can be R, H, K, D, E, N, L, F, Y, or Q.

In some embodiments, X$_1$X$_2$X$_3$ is PX$_2$L. In certain embodiments, X$_2$ in PX$_2$L can be H, K, D, E, S, T, N, Q, G, P, A, Y, V, I, F, L, or R (e.g., H, K, D, E, S, T, N, Q, G, P, A, Y, V, I, or F).

In some embodiments, X$_1$X$_2$X$_3$ is QX$_2$L. In certain embodiments, X$_2$ in QX$_2$L can be R, H, K, D, E, N, P, Y, or Q.

In some embodiments, X$_1$X$_2$X$_3$ is VX$_2$L. In certain embodiments, X$_2$ in VX$_2$L can be V or T.

In some embodiments, X$_1$X$_2$X$_3$ is X$_1$X$_2$L. In certain embodiments, X$_2$ in X$_1$X$_2$L is A, R, N, D, C, Q, E, G, H, I, K, M, F, P, S, T, W, Y, or V.

In some embodiments, X$_1$X$_2$X$_3$ is PIL. In some embodiments, X$_1$X$_2$X$_3$ is PFL. In some embodiments, X$_1$X$_2$X$_3$ is QQL. In some embodiments, X$_1$X$_2$X$_3$ is VVL. In some embodiments, X$_1$X$_2$X$_3$ is VTL. In some embodiments, X$_1$X$_2$X$_3$ is PPL. In some embodiments, X$_1$X$_2$X$_3$ is PYL. In some embodiments, X$_1$X$_2$X$_3$ is QRL. In some embodiments, X$_1$X$_2$X$_3$ is QHL.

In another aspect, the disclosure features a polypeptide comprising a prograulin variant, wherein the prograulin variant comprises at least 90% (e.g., at least 91%, 92%, 93%, 94%, 95%, 96%, 97%, 98%, or 99%) identity or 100% identity to SEQ ID NO:2 and a sequence defined by Y$_1$Y$_2$QLL (SEQ ID NO:137) that is adjacent and C-terminal to the position corresponding to residue 576 of SEQ ID NO:2, wherein Y$_1$ is L or absent, and Y$_2$ is R or absent. In some embodiments, the polypeptide comprises a prograulin variant having the sequence:

(SEQ ID NO: 55)
TRCPDGQFCPVACCLDPGGASYSCCRPLLDKWPTTLSRHLGGPCQVDAHC

SAGHSCIFTVSGTSSCCPFPEAVACGDGHHCCPRGFHCSADGRSCFQRSG

NNSVGAIQCPDSQFECPDFSTCCVMVDGSWGCCPMPQASCCEDRVHCCPH

GAFCDLVHTRCITPTGTHPLAKKLPAQRTNRAVALSSSVMCPDARSRCPD

GSTCCELPSGKYGCCPMPNATCCSDHLHCCPQDTVCDLIQSKCLSKENAT

TDLLTKLPAHTVGDVKCDMEVSCPDGYTCCRLQSGAWGCCPFTQAVCCED

HIFICCPAGFTCDTQKGTCEQGPHQVPWMEKAPAHLSLPDPQALKRDVPC

DNVSSCPSSDTCCQLTSGEWGCCPIPEAVCCSDHQHCCPQGYTCVAEGQC

QRGSEIVAGLEKMPARRASLSHPRDIGCDQHTSCPVGQTCCPSLGGSWAC

CQLPHAVCCEDRQHCCPAGYTCNVKARSCEKEVVSAQPATFLARSPHVGV

KDVECGEGHFCHDNQTCCRDNRQGWACCPYRQGVCCADRRHCCPAGFRCA

ARGTKCLRREAPRWDAPLRDPALRQLLY$_1$Y$_2$QLL.

In some embodiments, Y$_1$ is L. In some embodiments, Y$_2$ is R. In some embodiments, Y$_1$ and Y$_2$ are both absent.

In some embodiments, a polypeptide described herein further comprises an Fc polypeptide that is linked to the prograulin variant. The N-terminus or C-terminus of the Fc polypeptide can be linked to the prograulin variant. In some embodiments, the Fc polypeptide is linked to the progranulin variant by a peptide bond or by a polypeptide linker. In some embodiments, the polypeptide linker is 1 to 50 (e.g., 1 to 45, 1 to 40, 1 to 35, 1 to 30, 1 to 25, 1 to 20, 1 to 15, 1 to 10, 1 to 5, 5 to 50, 10 to 50, 15 to 50, 20 to 50, 25 to 50, 30 to 50, 35 to 50, 40 to 50, 45 to 50, 1, 5, 10, 15, 20, 25, 30, 35, 40, or 45) amino acids in length. In some embodiments, the polypeptide linker is a flexible polypeptide linker, e.g., a glycine-rich linker. In certain embodiments, the glycine-rich linker is $G_4S$ (SEQ ID NO:90) or $(G_4S)_2$ (SEQ ID NO:91).

In certain embodiments, the Fc polypeptide comprises a sequence selected from the group consisting of SEQ ID NOS:64-67. In certain embodiments, the Fc polypeptide is a modified Fc polypeptide that specifically binds to a transferrin receptor (TfR; i.e., a TfR-binding Fc polypeptide). In some embodiments, the Fc polypeptide (e.g., a TfR-binding Fc polypeptide) comprises a sequence selected from the group consisting of SEQ ID NOS:68-87 and 129-132 (e.g., SEQ ID NOS:70, 75, 80, 85, and 129-132).

In particular embodiments, the Fc polypeptide (e.g., a TfR-binding Fc polypeptide) comprises a sequence selected from SEQ ID NOS:70, 75, 80, 85, and 129-132.

In another aspect, the disclosure features a fusion protein comprising: (a) a progranulin variant described herein; (b) a first Fc polypeptide that is linked to the progranulin variant of (a); and (c) a second Fc polypeptide that forms an Fc polypeptide dimer with the first Fc polypeptide. In some embodiments of this aspect, the second Fc polypeptide is also linked to a wild-type progranulin or a progranulin variant described herein (i.e., a second progranulin polypeptide). The progranulin variant linked to the first Fc polypeptide and the progranulin variant linked to the second Fc polypeptide can be the same or different.

In some embodiments, the first Fc polypeptide is linked to the progranulin variant by a peptide bond or by a polypeptide linker and/or the second Fc polypeptide is linked to the progranulin variant by a peptide bond or by a polypeptide linker. In some embodiments, the polypeptide linker is 1 to 50 (e.g., 1 to 45, 1 to 40, 1 to 35, 1 to 30, 1 to 25, 1 to 20, 1 to 15, 1 to 0, 1 to 5, 5 to 50, 10 to 50, 15 to 50, 20 to 50, 25 to 50, 30 to 50, 35 to 50, 40 to 50, 45 to 50, 1, 5, 10, 15, 20, 25, 30, 35, 40, or 45) amino acids in length. In some embodiments, the polypeptide linker is a flexible polypeptide linker, e.g., a glycine-rich linker. In certain embodiments, the glycine-rich linker is $G_4S$ (SEQ ID NO:90) or $(G_4S)_2$ (SEQ ID NO:91).

In some embodiments of this aspect, the C-terminus of the first Fc polypeptide is linked to the N-terminus of the progranulin, and/or the C-terminus of the second Fc polypeptide is linked to the N-terminus of the progranulin variant.

In some embodiments, the first Fc polypeptide or the second Fc polypeptide specifically binds to a transferrin receptor. In certain embodiments, the first Fc polypeptide or the second Fc polypeptide independently comprises a sequence selected from the group consisting of SEQ ID NOS:68-87 and 129-132. In certain embodiments, the first Fc polypeptide or the second Fc polypeptide independently comprises a sequence selected from SEQ ID NOS:70, 75, 80, 85, and 129-132.

In some embodiments, the first Fc polypeptide and the second Fc polypeptide each comprise modifications that promote heterodimerization. For example, the first Fc polypeptide comprises T366S, L368A, and Y407V substitutions and the second Fc polypeptide comprises a T366W substitution, according to EU numbering. In some embodiments, the first Fc polypeptide comprises a T366W substitution and the second Fc polypeptide comprises T366S, L368A, and Y407V substitutions, according to EU numbering.

In some embodiments, the first Fc polypeptide and/or the second Fc polypeptide independently comprises modifications that reduce effector function. In certain embodiments, the modifications that reduce effector function are L234A and L235A substitutions, according to EU numbering.

In some embodiments, the first Fc polypeptide comprises a sequence selected from the group consisting of SEQ ID NOS:64-67. In some embodiments, the second Fc polypeptide comprises a sequence selected from the group consisting of SEQ ID NOS:68-87 and 129-132 (e.g., SEQ ID NOS:70, 75, 80, 85, and 129-132).

In some embodiments of this aspect, the first Fc polypeptide comprises T366S, L368A, and Y407V substitutions and L234A and L235A substitutions, and the second Fc polypeptide comprises a T366W substitution and L234A and L235A substitutions, according to EU numbering. In some embodiments, the first Fc polypeptide comprises a T366W substitution and L234A and L235A substitutions, and the second Fc polypeptide comprises T366S, L368A, and Y407V substitutions and L234A and L235A substitutions, according to EU numbering.

In some embodiments of this aspect, a hinge region or a portion thereof is linked to the first Fc polypeptide and/or the second Fc polypeptide.

In some embodiments, the $K_D$ for sortilin binding of the fusion protein is less than about 100 nM (e.g., less than about 95 nM, 90 nM, 85 nM, 80 nM, 75 nM, 70 nM, 65 nM, 60 nM, 55 nM, 50 nM, 45 nM, or 40 nM). In some embodiments, the $K_D$ for sortilin binding of the fusion protein exhibits less than 10-fold decrease in sortilin binding relative to a fusion protein comprising SEQ ID NO:2 in the first polypeptide. In some embodiments, the $K_D$ for sortilin binding of the fusion protein exhibits less than 5-fold decrease in sortilin binding relative to a fusion protein comprising SEQ ID NO:2 in the first polypeptide.

In some embodiments, the EC50 for sortilin binding of the fusion protein is less than about 25 nM (e.g., less than about 20 nM, 15 nM, 10 nM, 5 nM, 4 nM, 3 nM, 2.5 nM, 2 nM, 1.5 nM, or 1 nM). In particular embodiments, the EC50 for sortilin binding of the fusion protein exhibits less than 10-fold decrease in sortilin binding relative to a fusion protein comprising SEQ ID NO:2 in the first polypeptide. In certain embodiments, the EC50 is measured by ELISA as described herein (e.g., as described in Example 4).

In some embodiments, the EC50 for sortilin binding of the fusion protein described herein exhibits less than 10-fold decrease in sortilin binding relative to a reference fusion protein, wherein the reference fusion protein comprises (i) a first polypeptide comprising SEQ ID NO:2 and (ii) a second Fc polypeptide that forms an Fc polypeptide dimer with the first Fc polypeptide.

In some embodiments, the EC50 for sortilin binding of the fusion protein exhibits less than 10-fold decrease in sortilin binding relative to a reference fusion protein, wherein the reference fusion protein comprises (i) a first polypeptide comprising SEQ ID NO:108 and (ii) a second Fc polypeptide that forms an Fc polypeptide dimer with the first Fc polypeptide.

In some embodiments, the reference fusion protein is produced in a HEK cell. In some embodiments, the reference fusion protein is purified substantially as described herein (e.g., as described in Example 1).

In some embodiments, the fusion protein is produced in a Chinese Hamster Ovary (CHO) cell. In particular embodiments, more than 50% (e.g., more than 55%, 60%, 65%, 70%, 75%, 80%, 85%, 90%, 95%, 97%, or 99%) of the fusion proteins are not cleaved at the C-terminus of the progranulin variant portion of the fusion protein. In some embodiments, the fusion proteins are purified from a cell culture medium containing the fusion protein-expressing cells by one or more methods selected from the group consisting of: protein A chromatography, ion exchange chromatography, hydrophobic interaction column chromatography, and dialysis. In some embodiments, the fusion protein is purified substantially as described herein (e.g., as described in Example 1).

In another aspect, the disclosure features a pharmaceutical composition comprising a progranulin variant or fusion protein described herein, and a pharmaceutically acceptable carrier.

In another aspect, the disclosure features a pharmaceutical composition comprising a plurality of a fusion protein described herein and a pharmaceutically acceptable carrier. In some embodiments, more than 50% (e.g., more than 55%, 60%, 65%, 70%, 75%, 80%, 85%, 90%, or 95%) of the plurality of the fusion protein comprises an intact C-terminus in the progranulin variant of the fusion protein.

In another aspect, the disclosure features a method of treating a subject having a neurodegenerative disease, atherosclerosis, a disorder associated with TDP-43, AMD, or a progranulin-associated disorder comprising administering a progranulin variant described herein, a fusion protein described herein, or a pharmaceutical composition described herein to the subject. In particular embodiments, the subject has a neurodegenerative disease.

In another aspect, the disclosure features a method of increasing the amount of a progranulin or a variant thereof in a subject, the method comprising administering a progranulin variant described herein, a fusion protein described herein, or a pharmaceutical composition described herein to the subject. In certain embodiments, the subject has a neurodegenerative disease, atherosclerosis, a disorder associated with TDP-43, AIMD, or a progranulin-associated disorder. In particular embodiments, the subject has a neurodegenerative disease.

In another aspect, the disclosure features a method of decreasing cathepsin D activity in a subject, the method comprising administering a progranulin variant described herein, a fusion protein described herein, or a pharmaceutical composition described herein to the subject. In certain embodiments, the subject has a neurodegenerative disease, atherosclerosis, a disorder associated with TDP-43, AMD, or a progranulin-associated disorder. In particular embodiments, the subject has a neurodegenerative disease.

In another aspect, the disclosure features a method of increasing lysosomal degradation or improving lysosomal function in a subject, the method comprising administering a progranulin variant described herein, a fusion protein described herein, or a pharmaceutical composition described herein to the subject. In certain embodiments, the subject has a neurodegenerative disease, atherosclerosis, a disorder associated with TDP-43, AMD, or a progranulin-associated disorder. In particular embodiments, the subject has a neurodegenerative disease.

In some embodiments of the methods described herein, the neurodegenerative disease is frontotemporal dementia (FTD), neuronal ceroid lipofuscinosis (NCL), Niemann-Pick disease type A (NPA), Niemann-Pick disease type B (NPB), Niemann-Pick disease type C (NPC), C9ORF72-associated amyotrophic lateral sclerosis (ALS)/FTD, sporadic ALS, Alzheimer's disease (AD), Gaucher's disease, or Parkinson's disease. In certain embodiments, the neurodegenerative disease is FTD.

Embodiments also relate to methods of treating FTD in a subject in need thereof, wherein the method comprises administering a progranulin variant or fusion protein described herein to the subject. In some embodiments, the FTD is C9ORF72-associated FTD.

In some embodiments of any of the foregoing methods, the subject has a mutation in a gene encoding the progranulin.

In another aspect, the disclosure features a polynucleotide comprising a nucleic acid sequence encoding a progranulin variant or polypeptide described herein. In another aspect, the disclosure features a vector comprising a polynucleotide described herein. In another aspect, the disclosure features a host cell comprising a polynucleotide or vector described herein. In some embodiments, the host cell further comprises a polynucleotide comprising a nucleic acid sequence encoding a second Fc polypeptide. In certain embodiments, the second Fc polypeptide has a sequence selected from any one of SEQ ID NOs: 61 and 64-87. In another aspect, the disclosure features a method for producing a polypeptide, comprising culturing a host cell under conditions in which the polypeptide encoded by a polynucleotide described herein is expressed.

In another aspect, provided is a method for evaluating a compound or monitoring a subject's response to a progranulin variant or a fusion protein described herein, or pharmaceutical composition or dosing regimen thereof, for treating a disease or disorder described herein, the method comprising: (a) measuring an abundance of one or more bis(monoacylglycero)phosphate (BMP) species and/or glucosylsphingosine (GlcSph) in a test sample from a subject having a progranulin-associated disorder, wherein the test sample or subject has been treated with the compound or pharmaceutical composition thereof (e.g., treated with a fusion protein described herein); (b) comparing the difference in abundance between the one or more BMP species and/or GlcSph measured in (a) and one or more reference values; and (c) determining from the comparison whether the compound, pharmaceutical composition, or dosing regimen thereof (e.g., a fusion protein described herein) improves one or more BMP species levels and/or GlcSph level for treating the disease or disorder.

In some embodiments, the methods provided herein further comprise treating another test sample or subject with another compound and selecting a candidate compound that improves the one or more BMP species levels and/or GlcSph level.

In some embodiments, the methods provided herein further comprise (d) maintaining or adjusting the amount or frequency of administration of the compound (e.g., a fusion protein described herein) to the test sample or subject; and (e) administering the compound to the test sample or to the subject.

In some embodiments, the methods provided herein further comprise administering to the subject a progranulin variant described herein for improving the one or more BMP species levels and/or GlcSph level for treating a progranulin-associated disorder. In some embodiments, at least one of the one or more signs or symptoms of a progranulin-associated disorder are ameliorated following treatment.

In some embodiments, treatment comprises administering a fusion protein described herein to the subject. In some embodiments, treatment comprises administering a library of compounds to a plurality of subjects or test samples.

In some embodiments, both the abundance of the one or more BMP species and the abundance of GlcSph can be measured from the same test sample from the subject. In other embodiments, two test samples (e.g., taken at the same time or at different times) can be taken from the subject, in which one test sample can be used to measure the abundance of the one or more BMP species, while the other test sample can be used to measure the abundance of GlcSph. The two test samples can be taken from the same fluid, cell, or tissue of the subject (e.g., whole blood, plasma, a cell, a tissue, serum, cerebrospinal fluid, interstitial fluid, sputum, urine, or lymph). In other embodiments, the two test samples can be taken from different fluids, cells, or tissues of the subject, e.g., one sample can be plasma, while the other sample can be brain tissue.

In some embodiments, the reference value is measured in a reference sample obtained from a reference subject or a population of reference subjects (e.g., an average value). In some embodiments, the reference value is the abundance of the one or more BMP species measured in a reference sample. In some embodiments, the reference value is the abundance of GlcSph measured in a reference sample. In some embodiments, the reference sample is the same type of cell, tissue, or fluid as the test sample. In some embodiments, at least two reference values from different types of cell, tissue, or fluid is measured.

In some embodiments, the reference sample is a healthy control. In some embodiments, the reference subject or population of reference subjects do not have a progranulin-associated disorder or a decreased level of progranulin. In particular embodiments, the reference subject or population of reference subjects do not have any signs or symptoms of such a disorder.

In some embodiments, BMP species levels are increased in bone marrow-derived macrophages (BMDMs) that are derived in vitro from bone marrow cells of a subject having, or at risk of having, a progranulin-associated disorder as compared to a healthy control or a control not related to a progranulin-associated disorder.

In some embodiments, BMP species levels are decreased in liver, brain, cerebrospinal fluid, plasma, or urine of a subject having, or at risk of having, a progranulin-associated disorder as compared to a healthy control or a control not related to a progranulin-associated disorder.

In some embodiments, the GlcSph level is increased in, e.g., whole blood, plasma, a cell, a tissue, serum, cerebrospinal fluid, interstitial fluid, sputum, urine, lymph, or a combination thereof of a subject having, or at risk of having, a progranulin-associated disorder as compared to a healthy control or a control not related to a progranulin-associated disorder. In particular embodiments, the increased GlcSph level can be found in the plasma of the subject.

In some embodiments, the GlcSph level is increased in the brain, for example, in the frontal lobe and/or temporal lobe of the brain, of a subject having, or at risk of having, a progranulin-associated disorder as compared to a healthy control or a control not related to a progranulin-associated disorder. In particular embodiments, the increased GlcSph level can be found in one or more regions of the frontal lobe, e.g., superior frontal gyrus, middle frontal gyrus, inferior frontal gyrus, and/or precentral gyrus.

In some embodiments, the GlcSph level is increased in a cell, such as a blood cell, a brain cell, a peripheral blood mononuclear cell (PBMC), a bone marrow-derived macrophage (BMDM), a retinal pigmented epithelial (RPE) cell, an erythrocyte, a leukocyte, a neural cell, a microglial cell, a cerebral cortex cell, a spinal cord cell, a bone marrow cell, a liver cell, a kidney cell, a splenic cell, a lung cell, an eye cell, a chorionic villus cell, a muscle cell, a skin cell, a fibroblast, a heart cell, a lymph node cell, or a combination thereof, of a subject having, or at risk of having, a progranulin-associated disorder as compared to a healthy control or a control not related to a progranulin-associated disorder. In some embodiments, the increased GlcSph level can be found in a blood cell. In some embodiments, the increased GlcSph level can be found in a brain cell.

In some embodiments, the GlcSph level is increased in a tissue, such as brain tissue, cerebral cortex tissue, spinal cord tissue, liver tissue, kidney tissue, muscle tissue, heart tissue, eye tissue, retinal tissue, a lymph node, bone marrow, skin tissue, blood vessel tissue, lung tissue, spleen tissue, valvular tissue, or a combination thereof, of a subject having, or at risk of having, a progranulin-associated disorder as compared to a healthy control or a control not related to a progranulin-associated disorder. In some embodiments, the increased GlcSph level can be found in brain tissue, such as brain tissue from the frontal lobe or temporal lobe of the subject's brain. In particular embodiments, the increased GlcSph level can be found in the superior frontal gyrus, middle frontal gyrus, inferior frontal gyrus, and/or precentral gyrus of the frontal lobe.

In further embodiments, the GlcSph level is increased in an endosome, a lysosome, an extracellular vesicle, an exosome, a microvesicle, or a combination thereof of a subject having, or at risk of having, a progranulin-associated disorder as compared to a healthy control or a control not related to a progranulin-associated disorder.

In some embodiments, the abundance of a BMP species and/or GlcSph in the test sample of a subject having, or at risk of having, a progranulin-associated disorder has at least about a 1.2-fold, 1.5-fold, or 2-fold difference compared to a reference value of a control such as a healthy control or a control not related to a progranulin-associated disorder. In other embodiments, the abundance of a BMP species and/or GlcSph in the test sample of a subject having, or at risk of having, a progranulin-associated disorder has about a 1.2-fold to about 5-fold (e.g., e.g., about 1.5-fold, 2-fold, 2.5-fold, 3-fold, 3.5-fold, 4-fold, 4.5-fold, or 5-fold) difference compared to a reference value of a control such as a healthy control or a control not related to a progranulin-associated disorder. In some embodiments, the difference compared to a reference value is about 2-fold to about 3-fold (e.g., about 2-fold, 2.1-fold, 2.2-fold, 2.3-fold, 2.4-fold, 2.5-fold, 2.6-fold, 2.7-fold, 2.8-fold, 2.9-fold, or 3-fold). In some embodiments, the subject has a disorder associated with a decreased level of progranulin and/or one or more signs or symptoms of a disorder associated with a decreased level of progranulin.

In some embodiments, the reference value is the BMP species value and/or GlcSph value prior to treatment. In some embodiments, the subject is treated for a decreased level of progranulin or a progranulin-associated disorder, and the test sample comprises one or more pre-treatment test samples that are obtained from the subject before treatment has started and one or more post-treatment test samples that are obtained from the subject after treatment has started. In some embodiments, the method further comprises determining that the subject is responding to the treatment when the abundance of at least one of the one or more BMP species and/or GlcSph post-treatment shows an improvement over the one or more BMP species and/or GlcSph pre-treatment relative to a healthy control.

In some embodiments, the methods comprise (a) measuring an abundance of one or more BMP species and/or GlcSph in a test sample obtained from a subject; (b) treating the test sample or subject with a compound, pharmaceutical composition, or dosing regimen thereof (e.g., treating the test sample or subject with a Fc dimer:PGRN fusion protein described herein); (c) measuring an abundance of one or more BMP species and/or GlcSph in a test sample obtained from the treated subject, and (d) comparing the abundance of the one or more BMP species and/or GlcSph measured in steps (a) and (c); and (e) determining whether the compound or a dosing regimen improves BMP levels and/or GlcSph level for treating a progranulin-associated disorder.

In some embodiments, two or more post-treatment test samples are obtained at different time points after treatment has started, and the method further comprises determining that the subject is responding to treatment when the abundance of at least one of the one or more BMP species measured in a post-treatment sample is a) lower in BMDMs or b) higher in liver, brain, cerebrospinal fluid, plasma, or urine than the abundance of the corresponding one or more BMP species measured in the pre-treatment sample. In some embodiments, the subject is determined to be responding to the treatment when the abundance of at least one of the one or more BMP species measured in a post-treatment sample is a) at least about 1.2-fold lower in BMDM or b) at least about 1.2-fold higher in liver, brain, cerebrospinal fluid, plasma, or urine than the abundance of the corresponding one or more BMP species measured in the pre-treatment sample.

In some embodiments, two or more post-treatment test samples are obtained at different time points after treatment has started, and the method further comprises determining that the subject is responding to treatment when the abundance of GlcSph measured in a post-treatment sample is lower in, e.g., whole blood, plasma, a cell, a tissue, serum, cerebrospinal fluid, interstitial fluid, sputum, urine, or lymph than the abundance of GlcSph measured in the pre-treatment sample. In some embodiments, the subject is determined to be responding to the treatment when the abundance of GlcSph measured in a post-treatment sample is at least about 1.2-fold (e.g., at least about 1.5-fold, 2-fold, 2.5-fold, 3-fold, 3.5-fold, 4-fold, 4.5-fold, 5-fold, 5.5-fold, 6-fold, 6.5-fold, 7-fold, 7.5-fold, 8-fold, 8.5-fold, 9-fold, 9.5-fold, or 10-fold) lower in, e.g., whole blood, plasma, a cell, a tissue, serum, cerebrospinal fluid, interstitial fluid, sputum, urine, or lymph than the abundance of GlcSph measured in the pre-treatment sample.

In some embodiments, the improved BMP species level and/or GlcSph level is an improvement over the BMP species level and/or GlcSph level prior to treatment relative to the reference value of a control such as a healthy control or a control not related to a progranulin-associated disorder. In some embodiments, the improved BMP species level and/or GlcSph level is closer in value to the control than the pre-treatment BMP species level and/or GlcSph level is to the control. In some embodiments, the improved BMP species level and/or GlcSph level has a difference compared to the control of less than 20%, 15%, 10%, or 5%. In some embodiments, the improved BMP species level and/or GlcSph level has a difference compared to a healthy control of less than 10% or 5%. In some embodiments, the improved BMP species level and/or GlcSph level has a difference compared to a healthy control of less than 5%.

In some embodiments, the method further comprises determining that the subject is responding to the treatment when the abundance of at least one of the one or more BMP species and/or GlcSph measured in at least one of the one or more post-treatment test samples is about the same as the corresponding reference value of a healthy control.

In some embodiments, the test or reference sample or one or more reference values comprises or relates to a cell, a tissue, whole blood, plasma, serum, cerebrospinal fluid, interstitial fluid, sputum, urine, feces, bronchioalveolar lavage fluid, lymph, semen, breast milk, amniotic fluid, or a combination thereof. In some embodiments, the cell is a peripheral blood mononuclear cell (PBMC), a BMDM, a retinal pigmented epithelial (RPE) cell, a blood cell, an erythrocyte, a leukocyte, a neural cell, a microglial cell, a brain cell, a cerebral cortex cell, a spinal cord cell, a bone marrow cell, a liver cell, a kidney cell, a splenic cell, a lung cell, an eye cell, a chorionic villus cell, a muscle cell, a skin cell, a fibroblast, a heart cell, a lymph node cell, or a combination thereof. In some embodiments, the cell is a cultured cell. In some embodiments, the cultured cell is a BMDM or an RPE cell.

In some embodiments, the tissue comprises brain tissue, cerebral cortex tissue, spinal cord tissue, liver tissue, kidney tissue, muscle tissue, heart tissue, eye tissue, retinal tissue, a lymph node, bone marrow, skin tissue, blood vessel tissue, lung tissue, spleen tissue, valvular tissue, or a combination thereof. In some embodiments, the test and/or reference sample is purified from a cell and/or a tissue and comprises an endosome, a lysosome, an extracellular vesicle, an exosome, a microvesicle, or a combination thereof.

In some embodiments, the one or more BMP species comprise two or more BMP species. In some embodiments, the one or more BMP species comprise BMP(16:0_18:1), BMP(16:0_18:2), BMP(18:0_18:0), BMP(18:0_18:1), BMP(18:1_18:1), BMP(16:0_20:3), BMP(18:1_20:2), BMP(18:0_20:4), BMP(16:0_22:5), BMP(20:4_20:4), BMP(22:6_22:6), BMP(20:4_20:5), BMP(18:2_18:2), BMP(16:0_20:4), BMP(18:0_18:2), BMP(18:0e_22:6), BMP(18:1e_20:4), BMP(18:3_22:5), BMP(20:4_22:6), BMP(18:0e_20:4), BMP(18:2_20:4), BMP(18:1_22:6), BMP(18:1_20:4), BMP(18:0_22:6), or a combination thereof.

In some embodiments, the one or more BMP species comprise BMP(18:1_18:1), BMP(18:0_20:4), BMP(20:4_20:4), BMP(22:6_22:6), BMP(20:4_22:6), BMP(18:1_22:6), BMP(18:1_20:4), BMP(18:0_22:6), BMP(18:3_22:5), or a combination thereof.

In some embodiments, the test sample comprises a cultured cell and the one or more BMP species comprise BMP(18:1_18:1). In some embodiments, the test sample comprises plasma, tissue, urine, cerebrospinal fluid (CSF), and/or brain or liver tissue, and the one or more BMP species comprise BMP(22:6_22:6). In some embodiments, the test sample comprises liver tissue and the one or more BMP species comprise BMP(22:6_22:6), BMP(18:3_22:5), or a combination thereof. In some embodiments, the test sample comprises CSF or urine and the one or more BMP species comprise BMP(22:6_22:6). In some embodiments, the test sample comprises microglia and the one or more BMP species comprise BMP(18:3_22:5).

In some embodiments, the abundance of the one or more BMP species and/or GlcSph is measured using liquid chromatography-tandem mass spectrometry (LC-MS/MS). In some embodiments, an internal BMP and/or GlcSph standard is used to measure the abundance of the one or more BMP species and/or GlcSph in step (a) and/or determine the corresponding reference value. In some embodiments, the internal BMP and/or GlcSph standard comprises a BMP species and/or GlcSph that is not naturally present in the subject and/or the reference subject or population of reference subjects. In some embodiments, the internal BMP standard comprises BMP(14:0_14:0). In some embodiments, the internal GlcSph standard comprises a deuterium-labeled GlcSph.

In some embodiments, the subject has, or is at risk of developing, a disorder related to progranulin expression, processing, glycosylation, cellular uptake, trafficking, and/or function. In some embodiments, the subject and/or the reference subject or population of reference subjects have a decreased level of progranulin and/or a disorder associated with a decreased level of progranulin, and the test sample has been contacted with a candidate compound (e.g., a Fc dimer:PGRN fusion protein described herein). In some embodiments, the subject and/or the reference subject or population of reference subjects have one or more signs or symptoms of the disorder associated with a decreased level of progranulin. In some embodiments, the subject and/or the reference subject or population of reference subjects have a mutation in a granulin (GRN) gene. In some embodiments, the mutation in the GRN gene decreases progranulin expression and/or activity. In some embodiments, the subject has, or is at risk of developing, atherosclerosis, Gaucher's disease (e.g., Gaucher's disease types 1, 2, or 3), or AMD. In some embodiments, the subject has, or is at risk of developing, a disorder associated with TDP-43 (e.g., AD or ALS).

In some embodiments, the subject and/or the reference subject is a human, a non-human primate, a rodent, a dog, or a pig.

In another aspect, the present disclosure provides a kit for monitoring a progranulin variant level in a subject. In some embodiments, the kit comprises a BMP and/or GlcSph standard for measuring the abundance of one or more BMP species and/or GlcSph in a test sample obtained from the subject and/or a reference sample obtained from a reference subject or a population of reference subjects. In some embodiments, the BMP and/or GlcSph standard comprises a BMP species and/or GlcSph that is not naturally present in the subject and/or reference subject. In some embodiments, the BMP standard comprises BMP(14:0_14:0). In some embodiments, the GlcSph standard is a deuterium-labeled GlcSph.

In some embodiments, the kit further comprises reagents for obtaining the sample from the subject and/or reference subject, processing the sample, measuring the abundance of the one or more BMP species, measuring the abundance of GlcSph, or a combination thereof. In some embodiments, the kit further comprises instructions for use.

BRIEF DESCRIPTION OF THE DRAWINGS

FIG. 2 shows a table demonstrating the thermal properties of exemplary fusion proteins as disclosed herein in different buffers.

DETAILED DESCRIPTION

I. Introduction

Figure 1A:
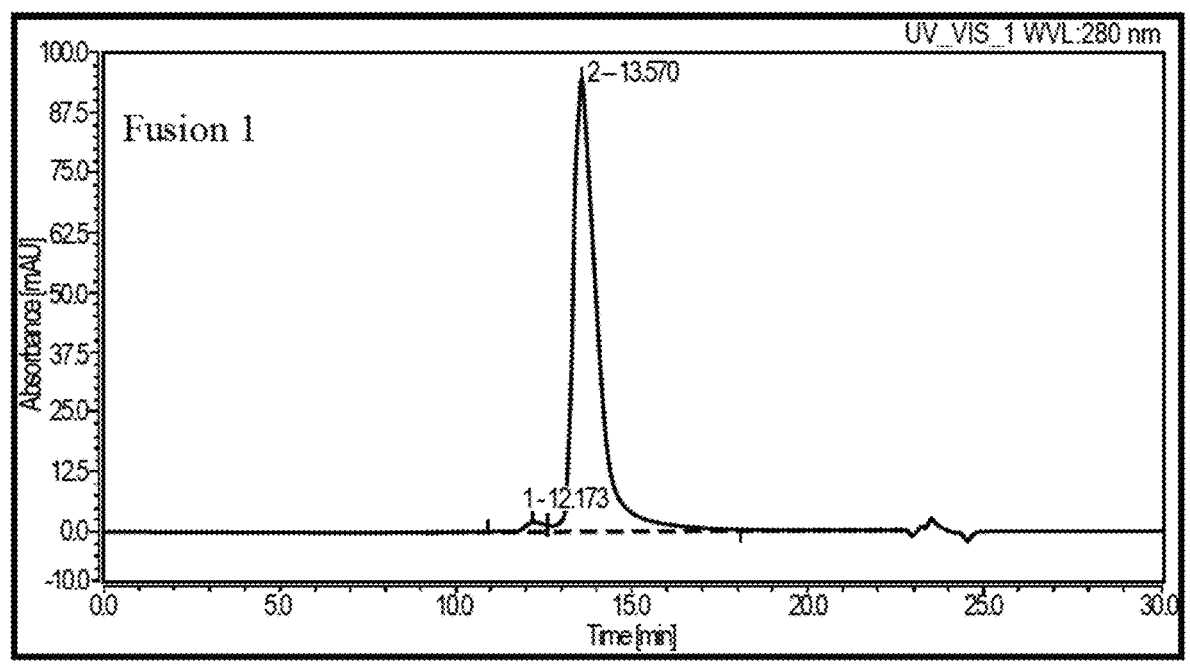
FIG. 1A and FIG. 1B show chromatography traces demonstrating that exemplary fusion proteins as disclosed herein were purified to greater than 98% purity.

Increasing levels of progranulin can be useful for treating a number of diseases in subjects, particularly where the subject has a reduced progranulin levels. We discovered that the C-terminus of wild-type progranulin is cleaved when expressed in CHO cells, which results in impaired sortilin binding. Sortilin binds directly to progranulin and is involved in uptake and trafficking of progranulin to cellular lysosomes. To reduce this cleavage, we developed progranulin variants that have amino acid modifications at the C-terminus, as well as fusion proteins that include one or more progranulin variants linked to an Fc polypeptide. Specifically, certain variants described herein have one or more amino acid substitutions in the QLL sequence at the C-terminus of the wild-type progranulin or have additional amino acids added to the C-terminus, as compared to wild-type progranulin, Importantly, these progranulin variants can maintain sortilin binding. The progranulin variants and the fusion proteins described herein are therefore suitable for treating such diseases, including neurodegenerative disease (e.g., FTD), atherosclerosis, a disorder associated with TDP-43, AMD, or a progranulin-associated disorder.

In addition to developing these progranulin variaints, we have also developed fusion proteins that contain a progranulin variant fused to an Fc molecule. In some cases, the fusion protein includes a dimeric Fc polypeptide, wherein at least one of the Fc polypeptide monomers is linked to the progranulin variant. The Fc polypeptides can increase progranulin levels and, in some cases, can be modified to confer additional functional properties onto the protein.

We have also developed fusion proteins that facilitate delivery of a progranulin or a variant thereof across the blood-brain barrier (BBB). These proteins comprise an Fc polypeptide and a modified Fc polypeptide that form a dimer, and a progranulin or a variant thereof linked to the Fc region and/or the modified Fc region. The modified Fc region can specifically bind to a BBB receptor such as TfR. When administered to a subject, the fusion protein binds to the TfR receptor, which is present on the endothelium forming the BBB. The fusion protein can be transcytosed across the BBB, thus increasing its concentration in the brain, compared, for example, to a Progranulin (PGRN) (also known as proepithelin and acrogranin) is a cysteine-rich protein encoded by the gene GRN, which maps to human chromosome 17q21. Progranulin is a lysosomal protein as well as a secreted protein consisting of seven and a half tandem repeats of conserved granulin peptides, each of which is about 60 amino acid long and can be released through cleavage by various extracellular proteases (e.g., elastase) and lysosomal proteases (e.g., cathepsin L) (Kao et al., *Nat Rev Neurosci.* 18(6):325-333, 2017). Generally, progranulin is believed to play both cell-autonomous and non-cell autonomous roles in the control of innate immunity as well as the function of lysosomes, where it regulates the activity and levels of various cathepsins and other hydrolases (Kao et al., supra). Progranulin also has a neurotrophic function and promotes neurite outgrowth and neuronal survival (Kao et al., supra).

II. Definitions

As used herein, the singular forms "a," "an," and "the" include plural referents unless the content clearly dictates otherwise. Thus, for example, reference to "a polypeptide" may include two or more such molecules, and the like.

As used herein, the terms "about" and "approximately," when used to modify an amount specified in a numeric value or range, indicate that the numeric value as well as reasonable deviations from the value known to the skilled person in the art, for example+20%, +10%, or +5%, are within the intended meaning of the recited value.

"Progranulin" or "PRGN" refers to a cysteine-rich, lysosomal protein encoded by the gene GRN. A progranulin may comprise a human progranulin sequence, e.g., the sequence of SEQ ID NO:1 or 2. A progranulin may comprise the sequence of SEQ ID NO:1, in which the first 17 amino acids indicate the signal peptide. A progranulin may be a mature progranulin in which the 17-amino acid signal peptide is cleaved. A mature progranulin may comprise the sequence of SEQ ID NO:2. A progranulin may include a sequence from a non-human species, e.g., mouse (accession no. NP_032201.2), rat (NP_058809.2 or NP_001139314.1), and chimpanzee (XP_016787144.1 or XP_016787145.1) in either a form that contains the signal peptide or in a mature form.

A "progranulin variant" or "PRGN variant" refers to a sequence variant of a wild-type progranulin. A progranulin variant can have similar or substantially the same functions as those of a wild-type progranulin, e.g., where the progranulin variant also binds sortilin or prosaposin, regulates the activity and levels of various lysosomal proteins (e.g., cathepsins), promotes neurite outgrowth and neuronal survival, and/or any other function described herein.

The term "progranulin-associated disorder" refers to any pathological condition relating to progranulin including expression, processing, glycosylation, cellular uptake, trafficking, and/or function. The term "disorder associated with a decreased level of progranulin" refers to any pathological condition that directly or indirectly results from a level of progranulin that is insufficient to enable (i.e., is too low to enable) normal physiological function within a cell, a tissue, and/or a subject, as well as a precursors to such a condition. For example, the progranulin-associated disorder can be caused by, or associated with, a mutation in the progranulin gene (GRN). In some embodiments, the progranulin-associated disorder is a neurodegenerative disease (e.g., FTD) or a lysosomal storage disorder.

The term "progranulin level" refers to the amount, concentration, and/or activity level of progranulin that is present, either in a subject or in a sample (e.g., a sample obtained from a subject). A progranulin level can refer to an absolute amount, concentration, and/or activity level of progranulin that is present, or can refer to a relative amount, concentration, and/or activity level. The term also refers to the amount or concentration of a progranulin and/or progranulin mRNA (e.g., expressed from a GRN gene) that is present.

The term "bone marrow-derived macrophage" or "BMDM" refers to a macrophage cell that is generated or derived in vitro from a mammalian bone marrow (e.g., a bone marrow obtained from a subject). As a non-limiting example, BMDMs can be generated by culturing undifferentiated bone marrow cells in the presence of a cytokine such as macrophage colony-stimulating factor (M-CSF).

A "transferrin receptor" or "TfR" as used in the context of this disclosure refers to transferrin receptor protein 1. The human transferrin receptor 1 polypeptide sequence is set forth in SEQ ID NO:109. Transferrin receptor protein 1 sequences from other species are also known (e.g., chimpanzee, accession number XP_003310238.1; rhesus monkey, NP_001244232.1; dog, NP_001003111.1; cattle, NP_001193506.1; mouse, NP_035768.1; rat, NP_073203.1; and chicken, NP_990587.1). The term "transferrin receptor" also encompasses allelic variants of exemplary reference sequences, e.g., human sequences, that are encoded by a gene at a transferrin receptor protein 1 chromosomal locus. Full-length transferrin receptor protein includes a short N-terminal intracellular region, a transmembrane region, and a large extracellular domain. The extracellular domain is characterized by three domains: a protease-like domain, a helical domain, and an apical domain.

As used herein, the term "Fc polypeptide" refers to the C-terminal region of a naturally occurring immunoglobulin heavy chain polypeptide that is characterized by an Ig fold as a structural domain. An Fc polypeptide contains constant region sequences including at least the CH2 domain and/or the CH3 domain and may contain at least part of the hinge region. In general, an Fc polypeptide does not contain a variable region.

A "modified Fc polypeptide" refers to an Fc polypeptide that has at least one mutation, e.g., a substitution, deletion, or insertion, as compared to a wild-type immunoglobulin heavy chain Fc polypeptide sequence, but retains the overall Ig fold or structure of the native Fc polypeptide.

As used herein, the term "Fc polypeptide dimer" refers to a dimer of two Fc polypeptides. In some embodiments, the two Fc polypeptides dimerize by the interaction between the two CH3 domains. If hinge regions or parts of the hinge regions are present in the two Fc polypeptides, one or more disulfide bonds can also form between the hinge regions of the two dimerizing Fc polypeptides.

A "modified Fc polypeptide dimer" refers to a dimer of two Fc polypeptides in which at least one Fc polypeptide is a modified Fc polypeptide that has at least one mutation, e.g., a substitution, deletion, or insertion, as compared to a wild-type immunoglobulin heavy chain Fc polypeptide sequence. For example, a modified Fc polypeptide dimer can be one that specifically binds TfR and has at least one modified Fc polypeptide having at least one mutation, e.g., a substitution, deletion, or insertion, as compared to a wild-type immunoglobulin heavy chain Fc polypeptide sequence.

The terms "CH3 domain" and "CH2 domain" as used herein refer to immunoglobulin constant region domain polypeptides. For purposes of this application, a CH3 domain polypeptide refers to the segment of amino acids from about position 341 to about position 447 as numbered according to the EU numbering scheme, and a CH2 domain polypeptide refers to the segment of amino acids from about position 231 to about position 340 as numbered according to the EU numbering scheme and does not include hinge region sequences. CH2 and CH3 domain polypeptides may also be numbered by the IMGT (ImMunoGeneTics) numbering scheme in which the CH2 domain numbering is 1-110 and the CH3 domain numbering is 1-107, according to the IMGT Scientific chart numbering (IMGT website). CH2 and CH3 domains are part of the Fc region of an immunoglobulin. An Fc region refers to the segment of amino acids from about position 231 to about position 447 as numbered according to the EU numbering scheme, but as used herein, can include at least a part of a hinge region of an antibody. An illustrative hinge region sequence is the human IgG1 hinge sequence EPKSCDKTHTCPPCP (SEQ ID NO:88).

The terms "wild-type," "native," and "naturally occurring" with respect to a CH3 or CH2 domain are used herein to refer to a domain that has a sequence that occurs in nature.

In the context of this disclosure, the term "mutant" with respect to a mutant polypeptide or mutant polynucleotide is used interchangeably with "variant." A variant with respect to a given wild-type CH3 or CH2 domain reference sequence can include naturally occurring allelic variants. A "non-naturally" occurring CH3 or CH2 domain refers to a variant or mutant domain that is not present in a cell in nature and that is produced by genetic modification, e.g., using genetic engineering technology or mutagenesis techniques, of a native CH3 domain or CH2 domain polynucleotide or polypeptide. A "variant" includes any domain comprising at least one amino acid mutation with respect to wild-type. Mutations may include substitutions, insertions, and deletions.

The term "amino acid" refers to naturally occurring and synthetic amino acids, as well as amino acid analogs and amino acid mimetics that function in a manner similar to the naturally occurring amino acids.

Naturally occurring amino acids are those encoded by the genetic code, as well as those amino acids that are later modified, e.g., hydroxyproline, γ-carboxyglutamate and O-phosphoserine. "Amino acid analogs" refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" refers to chemical compounds that have a structure that is different from the general chemical structure of an amino acid, but that function in a manner similar to a naturally occurring amino acid.

Naturally occurring α-amino acids include, without limitation, alanine (Ala), cysteine (Cys), aspartic acid (Asp), glutamic acid (Glu), phenylalanine (Phe), glycine (Gly), histidine (His), isoleucine (Ile), arginine (Arg), lysine (Lys), leucine (Leu), methionine (Met), asparagine (Asn), proline (Pro), glutamine (Gln), serine (Ser), threonine (Thr), valine (Val), tryptophan (Trp), tyrosine (Tyr), and combinations thereof. Stereoisomers of a naturally-occurring α-amino acids include, without limitation, D-alanine (D-Ala), D-cysteine (D-Cys), D-aspartic acid (D-Asp), D-glutamic acid (D-Glu), D-phenylalanine (D-Phe), D-histidine (D-His), D-isoleucine (D-Ile), D-arginine (D-Arg), D-lysine (D-Lys), D-leucine (D-Leu), D-methionine (D-Met), D-asparagine (D-Asn), D-proline (D-Pro), D-glutamine (D-Gln), D-serine (D-Ser), D-threonine (D-Thr), D-valine (D-Val), D-tryptophan (D-Trp), D-tyrosine (D-Tyr), and combinations thereof.

Amino acids may be referred to herein by either their commonly known three letter symbols or by the one-letter symbols recommended by the IUPAC-IUB Biochemical Nomenclature Commission.

The terms "polypeptide" and "peptide" are used interchangeably herein to refer to a polymer of amino acid residues in a single chain. The terms apply to amino acid polymers in which one or more amino acid residues is an artificial chemical mimetic of a corresponding naturally occurring amino acid, as well as to naturally occurring amino acid polymers and non-naturally occurring amino acid polymers. Amino acid polymers may comprise entirely L-amino acids, entirely D-amino acids, or a mixture of L and D amino acids.

The term "protein" as used herein refers to either a polypeptide or a dimer (i.e, two) or multimer (i.e., three or more) of single chain polypeptides. The single chain polypeptides of a protein may be joined by a covalent bond, e.g., a disulfide bond, or non-covalent interactions.

The term "conservative substitution," "conservative mutation," or "conservatively modified variant" refers to an alteration that results in the substitution of an amino acid with another amino acid that can be categorized as having a similar feature. Examples of categories of conservative amino acid groups defined in this manner can include: a "charged/polar group" including Glu (Glutamic acid or E), Asp (Aspartic acid or D), Asn (Asparagine or N), Gln (Glutamine or Q), Lys (Lysine or K), Arg (Arginine or R), and His (Histidine or H); an "aromatic group" including Phe (Phenylalanine or F), Tyr (Tyrosine or Y), Trp (Tryptophan or W), and (Histidine or H); and an "aliphatic group" including Gly (Glycine or G), Ala (Alanine or A), Val (Valine or V), Leu (Leucine or L), Ile (Isoleucine or I), Met (Methionine or M), Ser (Serine or S), Thr (Threonine or T), and Cys (Cysteine or C). Within each group, subgroups can also be identified. For example, the group of charged or polar amino acids can be sub-divided into sub-groups including: a "positively-charged sub-group" comprising Lys, Arg and His; a "negatively-charged sub-group" comprising Glu and Asp; and a "polar sub-group" comprising Asn and Gln. In another example, the aromatic or cyclic group can be sub-divided into sub-groups including: a "nitrogen ring sub-group" comprising Pro, His and Trp; and a "phenyl sub-group" comprising Phe and Tyr. In another further example, the aliphatic group can be sub-divided into sub-groups, e.g., an "aliphatic non-polar sub-group" comprising Val, Leu, Gly, and Ala; and an "aliphatic slightly-polar sub-group" comprising Met, Ser, Thr, and Cys. Examples of categories of conservative mutations include amino acid substitutions of amino acids within the sub-groups above, such as, but not limited to: Lys for Arg or vice versa, such that a positive charge can be maintained; Glu for Asp or vice versa, such that a negative charge can be maintained; Ser for Thr or vice versa, such that a free —OH can be maintained; and Gln for Asn or vice versa, such that a free —$NH_2$ can be maintained. In some embodiments, hydrophobic amino acids are substituted for naturally occurring hydrophobic amino acid, e.g., in the active site, to preserve hydrophobicity.

The terms "identical" or percent "identity," in the context of two or more polypeptide sequences, refer to two or more sequences or subsequences that are the same or have a specified percentage of amino acid residues, e.g., at least 85%, at least 90%, at least 95%, at least 96%, at least 97%, at least 98%, or at least 99% or greater, that are identical over a specified region when compared and aligned for maximum correspondence over a comparison window, or designated region as measured using a sequence comparison algorithm or by manual alignment and visual inspection.

For sequence comparison of polypeptides, typically one amino acid sequence acts as a reference sequence, to which a candidate sequence is compared. Alignment can be performed using various methods available to one of skill in the art, e.g., visual alignment or using publicly available software using known algorithms to achieve maximal alignment. Such programs include the BLAST programs, ALIGN, ALIGN-2 (Genentech, South San Francisco, Calif.) or Megalign (DNASTAR). The parameters employed for an alignment to achieve maximal alignment can be determined by one of skill in the art. For sequence comparison of polypeptide sequences for purposes of this application, the BLASTP algorithm standard protein BLAST for aligning two proteins sequence with the default parameters is used.

The terms "corresponding to," "determined with reference to," or "numbered with reference to" when used in the context of the identification of a given amino acid residue in a polypeptide sequence, refers to the position of the residue of a specified reference sequence when the given amino acid sequence is maximally aligned and compared to the reference sequence. Thus, for example, an amino acid residue in a modified Fc polypeptide "corresponds to" an amino acid in SEQ ID NO:61, when the residue aligns with the amino acid in SEQ ID NO:61 when optimally aligned to SEQ ID NO:61. The polypeptide that is aligned to the reference sequence need not be the same length as the reference sequence.

A "binding affinity" as used herein refers to the strength of the non-covalent interaction between two molecules, e.g., a single binding site on a polypeptide and a target, e.g., transferrin receptor, to which it binds. Thus, for example, the term may refer to 1:1 interactions between a polypeptide and its target, unless otherwise indicated or clear from context. Binding affinity may be quantified by measuring an equilibrium dissociation constant ($K_D$), which refers to the dissociation rate constant ($k_d$, time$^{-1}$) divided by the association rate constant (ka, time$^{-1}$ M$^{-1}$). $K_D$ can be determined by measurement of the kinetics of complex formation and dissociation, e.g., using Surface Plasmon Resonance (SPR) methods, e.g., a Biacore™ system; kinetic exclusion assays such as KinExA®; and BioLayer interferometry (e.g., using the ForteBio® Octet® platform). As used herein, "binding affinity" includes not only formal binding affinities, such as those reflecting 1:1 interactions between a polypeptide and its target, but also apparent affinities for which $K_D$'s are calculated that may reflect avid binding.

The phrase "specifically binds" or "selectively binds" to a target, e.g., transferrin receptor, when referring to a polypeptide comprising a transferrin receptor-binding modified Fc polypeptide as described herein, refers to a binding reaction whereby the polypeptide binds to the target with greater affinity, greater avidity, and/or greater duration than it binds to a structurally different target, e.g., a target not in the transferrin receptor family. In typical embodiments, the polypeptide has at least 5-fold, 10-fold, 25-fold, 50-fold, 100-fold, 1000-fold, 10,000-fold, or greater affinity for a transferrin receptor compared to an unrelated target when assayed under the same affinity assay conditions. The term "specific binding," "specifically binds to," or "is specific for" a particular target (e.g., TfR), as used herein, can be exhibited, for example, by a molecule having an equilibrium dissociation constant $K_D$ for the target to which it binds of, e.g., $10^{-4}$ M or smaller, e.g., $10^{-5}$ M, $10^{-6}$ M, $10^{-7}$ M, $10^{-1}$ M, $10^{-9}$ M, $10^{-10}$ M, $10^{-11}$ M, or $10^{-12}$ M. In some embodiments, a modified Fc polypeptide specifically binds to an epitope on a transferrin receptor that is conserved among species (e.g., structurally conserved among species), e.g., conserved between non-human primate and human species (e.g., structurally conserved between non-human primate and human species). In some embodiments, a polypeptide may bind exclusively to a human transferrin receptor.

The terms "treatment," "treating," and the like are used herein to generally mean obtaining a desired pharmacologic and/or physiologic effect. "Treating" or "treatment" may refer to any indicia of success in the treatment or amelioration of a disease, including neurodegenerative diseases (e.g., FTD, NCL, NPA, NPB, NPC, C9ORF72-associated ALS/FTD, sporadic ALS, AD, Gaucher's disease (e.g., Gaucher's disease types 1, 2, or 3), and Parkinson's disease), atherosclerosis, a disorder associated with TDP-43, AMD, and progranulin-associated disorders, including any objective or subjective parameter such as abatement, remission, improvement in patient survival, increase in survival time or rate, diminishing of symptoms or making the disorder more tolerable to the patient, slowing in the rate of degeneration or decline, or improving a patient's physical or mental well-being. The treatment or amelioration of symptoms can be based on objective or subjective parameters. The effect of treatment can be compared to an individual or pool of individuals not receiving the treatment, or to the same patient prior to treatment or at a different time during treatment.

The term "subject," "individual," and "patient," as used interchangeably herein, refer to a mammal, including but not limited to humans, non-human primates, rodents (e.g., rats, mice, and guinea pigs), rabbits, cows, pigs, horses, and other mammalian species. In one embodiment, the patient is a human.

The term "pharmaceutically acceptable excipient" refers to a non-active pharmaceutical ingredient that is biologically or pharmacologically compatible for use in humans or animals, such as but not limited to a buffer, carrier, or preservative.

As used herein, a "therapeutic amount" or "therapeutically effective amount" of an agent is an amount of the agent that treats symptoms of a disease in a subject.

The term "administer" refers to a method of delivering agents, compounds, or compositions to the desired site of biological action. These methods include, but are not limited to, topical delivery, parenteral delivery, intravenous delivery, intradermal delivery, intramuscular delivery, intrathecal delivery, colonic delivery, rectal delivery, or intraperitoneal delivery. In one embodiment, the polypeptides described herein are administered intravenously.

III. Progranulin Replacement Therapy

In some aspects, described herein are progranulin variants and fusion proteins comprising the same. The fusion proteins described herein comprise an Fc polypeptide dimer and a progranulin variant. In some embodiments, a fusion protein described herein further comprises a second progranulin or a variant thereof (e.g., a wild-type progranulin or a progranulin variant). An Fc polypeptide in the Fc polypeptide dimer may contain modifications (e.g., one or more modifications that promote heterodimerization) or may be a wild-type Fc polypeptide. In some embodiments, one or both Fc polypeptides in the Fc polypeptide dimer may contain modifications that result in binding to a BBB receptor, e.g., a TfR. One or both Fc polypeptides in the Fc polypeptide dimer may be a TfR-binding Fc polypeptide. A progranulin or a progranulin variant can be joined to the N-terminus or the C-terminus an Fc polypeptide (e.g., a wild-type Fc polypeptide or a TfR-binding Fc polypeptide). In some embodiments, a progranulin or a progranulin variant can be joined to an Fc polypeptide (e.g., a wild-type Fc polypeptide or a TfR-binding Fc polypeptide) either directly (e.g., via a peptide bond) or by way of a linker. In further embodiments, a hinge region or a portion thereof may be present at the N-terminus of an Fc polypeptide (e.g., a wild-type Fc polypeptide or a TfR-binding Fc polypeptide). If a hinge region or a portion thereof is present, the progranulain or the progranulin variant can be joined to N-terminus of the hinge region or the portion thereof either directly or by way of a linker.

The progranulin may be deficient in neurodegenerative diseases. The progranulin may be deficient in FTD, as well as in other diseases, such as Gaucher's disease and AD. A progranulin or a progranulin variant incorporated into the fusion protein may bind to sortilin or prosaposin (e.g., bind to sortilin).

In some embodiments, a progranulin or a progranulin variant that is present in a fusion protein described herein, retains at least 25% of its activity compared to its activity when not joined to an Fc polypeptide or a TfR-binding Fc polypeptide. In some embodiments, a progranulin or a progranulin variant that is present in a fusion protein described herein, retains at least 10%, or at least 15%, 20%, 25%, 30%, 35%, 40%, 45%, 50%, 55%, 60%, 65%, 70%, 75%, 80%, 85%, 90%, or 95% (e.g., at least 80%, 85%, 90%, or 95%) of its activity compared to its activity when not joined to an Fc polypeptide or a TfR-binding Fc polypeptide.

In some embodiments, fusion to an Fc polypeptide or to a TfR-binding Fc polypeptide does not decrease the expression and/or activity of the progranulin or the progranulin variant.

IV. Progranulin Variants

Provided herein are progranulin variants that have amino acid modifications or additions at the C-terminus of a wild-type progranulin. A progranulin variant is a functional variant of a wild-type progranulin that has at least 90% sequence identity (e.g., at least 91%, 92%, 93%, 94%, 95%, 96%, 97%, 98%, or 99% sequence identity) to a mature wild-type progranulin (e.g., SEQ ID NO:2) and amino acid modifications or additions at the C-terminus of the wild-type progranulin.

In some embodiments, a progranulin variant comprises modifications at the C-terminus of the wild-type progranulin, such that the last three amino acids at the C-terminus of the progranulin variant is not QLL. For example, a progranulin variant can have a sequence that is at least 90% (e.g., at least 91%, 92%, 93%, 94%, 95%, 96%, 97%, 98%, or 99%) identical to SEQ ID NO:2, wherein the positions corresponding to residues 574 to 576 of SEQ ID NO:2 have an amino acid sequence defined by $X_1X_2X_3$, and with the proviso that $X_1X_2X_3$ together is not QLL. In some embodiments, the progranulin variant has the sequence:

(SEQ ID NO: 3)
TRCPDGQFCPVACCLDPGGASYSCCRPLLDKWPTTLSRHLGGPCQVDAHC

SAGHSCIFTVSGTSSCCPFPEAVACGDMECCPRGFHCSADGRSCFQRSGN

NSVGAIQCPDSQFECPDFSTCCVMVDGSWGCCPMPQASCCEDRVHCCPHG

AFCDLVHTRCITPTGTHPLAKKLPAQRTNRAVALSSSVMCPDARSRCPDG

STCCELPSGKYGCCPMPNATCCSDHLHCCPQDTVCDLIQSKCLSKENATT

DLLTKLPAHTVGDVKCDMEVSCPDGYTCCRLQSGAWGCCPFTQAVCCEDH

IHCCPAGFTCDTQKGTCEQGPHQVPWMEKAPAHLSLPDPQALKRDVPCDN

VSSCPSSDTCCQLTSGEWGCCPIPEAVCCSDHQHCCPQGYTCVAEGQCQR

GSEIVAGLEKMPARRASLSHPRDIGCDQHTSCPVGQTCCPSLGGSWACCQ

LPHAVCCEDRQHCCPAGYTCNVKARSCEKEVVSAQPATFLARSPHVGVKD

VECGEGHFCHDNQTCCRDNRQGWACCPYRQGVCCADRRHCCPAGFRCAAR

GTKCLRREAPRWDAPLRDPALRX$_1$X$_2$X$_3$, wherein each of X$_1$, X$_2$, and X$_3$ is independently an amino acid, and X$_1$X$_2$X$_3$ together is not QLL. In certain embodiments, X$_1$ is R, H, K, D, E, S, T, N, Q, L, F, Y, P, or V. In certain embodiments, X$_2$ is H, K, D, E, S, T, N, Q, G, P, A, Y, V, I, F, L, or R. In certain embodiments, X$_3$ is L, Y, or P.

In some embodiments, X$_1$X$_2$X$_3$ is PX$_2$L. In certain embodiments, X$_2$ in PX$_2$L can be H, K, D, E, S, T, N, Q, G, P, A, Y, V, I, F, L, or R (e.g., H, K, D, E, S, T, N, Q, G, P, A, Y, V, I, or F). For example, a progranulin variant can have a sequence that has at least 90% (e.g., at least 91%, 92%, 93%, 94%, 95%, 96%, 97%, 98%, or 99%) identity or 100% identity to the sequence of any one of SEQ ID NOS:4-18, in which the progranulin variant has PHL, PKL, PDL, PEL, PSL, PTL, PNL, PQL, PGL, PPL, PAL, PYL, PVL, PIL, or PFL at the C-terminus. In particular, a progranulin variant can have a sequence that has at least 90% (e.g., at least 91%, 92%, 93%, 94%, 95%, 96%, 97%, 98%, or 99%) identity or 100% identity to the sequence of SEQ ID NO:13, in which the progranulin variant has PPL at the C-terminus. In some embodiments, a progranulin variant has the sequence of SEQ ID NO:13. In particular, a progranulin variant can have a sequence that has at least 90% (e.g., at least 91%, 92%, 93%, 94%, 95%, 96%, 97%, 98%, or 99%) identity or 100% identity to the sequence of SEQ ID NO:15, in which the progranulin variant has PYL at the C-terminus. In some embodiments, a progranulin variant has the sequence of SEQ ID NO:15. In particular, a progranulin variant can have a sequence that has at least 90% (e.g., at least 91%, 92%, 93%, 94%, 95%, 96%, 97%, 98%, or 99%) identity or 100% identity to the sequence of SEQ ID NO:17, in which the progranulin variant has PIL at the C-terminus. In some embodiments, a progranulin variant has the sequence of SEQ ID NO:17. In particular, a progranulin variant can have a sequence that has at least 90% (e.g., at least 91%, 92%, 93%, 94%, 95%, 96%, 97%, 98%, or 99%) identity or 100% identity to the sequence of SEQ ID NO:18, in which the progranulin variant has PFL at the C-terminus. In some embodiments, a progranulin variant has the sequence of SEQ ID NO:18.

In some embodiments, X$_1$X$_2$X$_3$ is QX$_2$L. In certain embodiments, X$_2$ in QX$_2$L can be R, H, K, D, E, N, P, Y, or Q. For example, a progranulin variant can have a sequence that has at least 90% (e.g., at least 91%, 92%, 93%, 94%, 95%, 96%, 97%, 98%, or 99%) identity or 100% identity to the sequence of any one of SEQ ID NOS:19-27, in which the progranulin variant has QRL, QHL, QKL, QDL, QEL, QNL, QPL, QYL, or QQL at the C-terminus. In particular, a progranulin variant can have a sequence that has at least 90% (e.g., at least 91%, 92%, 93%, 94%, 95%, 96%, 97%, 98%, or 99%) identity or 100% identity to the sequence of SEQ ID NO:19, in which the progranulin variant has QRL at the C-terminus. In some embodiments, a progranulin variant has the sequence of SEQ ID NO:19. In particular, a progranulin variant can have a sequence that has at least 90% (e.g., at least 91%, 92%, 93%, 94%, 95%, 96%, 97%, 98%, or 99%) identity or 100% identity to the sequence of SEQ ID NO:20, in which the progranulin variant has QHL at the C-terminus. In some embodiments, a progranulin variant has the sequence of SEQ ID NO:20. In particular, a progranulin variant can have a sequence that has at least 90% (e.g., at least 91%, 92%, 93%, 94%, 95%, 96%, 97%, 98%, or 99%) identity or 100% identity to the sequence of SEQ ID NO:27, in which the progranulin variant has QQL at the C-terminus. In some embodiments, a progranulin variant has the sequence of SEQ ID NO:27.

In some embodiments, X$_1$X$_2$X$_3$ is VX$_2$L. In certain embodiments, X$_2$ in VX$_2$L can be V or T. For example, a progranulin variant can have a sequence that has at least 90% (e.g., at least 91%, 92%, 93%, 94%, 95%, 96%, 97%, 98%, or 99%) identity or 100% identity to the sequence of any one of SEQ ID NOS:28 and 29, in which the progranulin variant has VVL or VTL at the C-terminus. In particular, a progranulin variant can have a sequence that has at least 90% (e.g., at least 91%, 92%, 93%, 94%, 95%, 96%, 97%, 98%, or 99%) identity or 100% identity to the sequence of SEQ ID NO:28, in which the progranulin variant has VVL at the C-terminus. In some embodiments, a progranulin variant has the sequence of SEQ ID NO:28. In particular, a progranulin variant can have a sequence that has at least 90% (e.g., at least 91%, 92%, 93%, 94%, 95%, 96%, 97%, 98%, or 99%) identity or 100% identity to the sequence of SEQ ID NO:29, in which the progranulin variant has VTL at the C-terminus. In some embodiments, a progranulin variant has the sequence of SEQ ID NO:29.

In some embodiments, X$_1$X$_2$X$_3$ is X$_1$IL. In certain embodiments, X$_1$ in X$_1$IL can be R, H, K, E, P, N, F, or Y (e.g., R, H, K, E, or P). For example, a progranulin variant can have a sequence that has at least 90% (e.g., at least 91%, 92%, 93%, 94%, 95%, 96%, 97%, 98%, or 99%) identity or 100% identity to the sequence of any one of SEQ ID NOS:30-33 and 17, in which the progranulin variant has RIL, HIL, KIL, EIL, or PIL at the C-terminus.

In some embodiments, X$_1$X$_2$X$_3$ is X$_1$FL. In certain embodiments, X$_1$ in X$_1$FL can be R, H, K, D, E, S, T, N, Q, L, F, Y, or P. For example, a progranulin variant can have a sequence that has at least 90% (e.g., at least 91%, 92%, 93%, 94%, 95%, 96%, 97%, 98%, or 99%) identity or 100% identity to the sequence of any one of SEQ ID NOS:34-45 and 18, in which the progranulin variant has RFL, HFL, KFL, DFL, EFL, SFL, TFL, NFL, QFL, LFL, FFL, YFL, or PFL at the C-terminus.

In some embodiments, X$_1$X$_2$X$_3$ is X$_1$QL. In certain embodiments, X$_1$ in X$_1$QL can be R, H, K, D, E, N, L, F, Y, or Q. For example, a progranulin variant can have a sequence that has at least 90% (e.g., at least 91%, 92%, 93%, 94%, 95%, 96%, 97%, 98%, or 99%) identity or 100% identity to the sequence of any one of SEQ ID NOS:46-54 and 27, in which the progranulin variant has RQL, HQL, KQL, DQL, EQL, NQL, LQL, FQL, YQL, or QQL at the C-terminus.

In further embodiments, X$_1$X$_2$X$_3$ is X$_1$X$_2$L, in which X$_2$ is A, R, N, D, C, Q, E, G, H, I, K, M, F, P, S, T, W, Y, or V.

In other embodiments, a progranulin variant comprises additional amino acids at the C-terminus compared to a wild-type progranulin. For example, a progranulin variant can comprise the amino acids QLL or LRQLL (SEQ ID NO:58) added to the C-terminus of a wild-type progranulin. For example, a progranulin variant can comprise a sequence having at least 90% (e.g., at least 91%, 92%, 93%, 94%, 95%, 96%, 97%, 98%, or 99%) identity or 100% identity to the sequence of SEQ ID NO:2 and a sequence defined by $Y_1Y_2$QLL (SEQ ID NO:137) that is adjacent and C-terminal to the position corresponding to residue 576 of SEQ ID NO:2, wherein $Y_1$ is L or absent, and $Y_2$ is R or absent. In some embodiments, the progranulin variant comprises the sequence:

(SEQ ID NO: 55)
TRCPDGQFCPVACCLDPGGASYSCCRPLLDKWPTTLSRHLGGPCQVDAH

CSAGHSCIFTVSGTSSCCPFPEAVACGDMECCPRGFHCSADGRSCFQRS

GNNSVGAIQCPDSQFECPDFSTCCVMVDGSWGCCPMPQASCCEDRVHCC

PHGAFCDLVHTRCITPTGTHPLAKKLPAQRTNRAVALSSSVMCPDARSR

CPDGSTCCELPSGKYGCCPMPNATCCSDHLHCCPQDTVCDLIQSKCLSK

ENATTDLLTKLPAHTVGDVKCDMEVSCPDGYTCCRLQSGAWGCCPFTQA

VCCEDHIHCCPAGFTCDTQKGTCEQGPHQVPWMEKAPAHLSLPDPQALK

RDVPCDNVSSCPSSDTCCQLTSGEWGCCPIPEAVCCSDHQHCCPQGYTC

VAEGQCQRGSEIVAGLEKMPARRASLSHPRDIGCDQHTSCPVGQTCCPS

LGGSWACCQLPHAVCCEDRQHCCPAGYTCNVKARSCEKEVVSAQPATFL

ARSPHVGVKDVECGEGHFCHDNQTCCRDNRQGWACCPYRQGVCCADRRH

CCPAGFRCAARGTKCLRREAPRWDAPLRDPALRQLLY$_1$Y$_2$QLL.

In some embodiments, a progranulin variant can have the sequence having at least 90% (e.g., at least 91%, 92%, 93%, 94%, 95%, 96%, 97%, 98%, or 99%) identity or 100% identity to the sequence of SEQ ID NO:56, in which the progranulin variant has the amino acids QLLQLL (SEQ ID NO:59) at the C-terminus. In particular embodiments, a progranulin variant has the sequence of SEQ ID NO:56. In some embodiments, a progranulin variant can have the sequence having at least 90% (e.g., at least 91%, 92%, 93%, 94%, 95%, 96%, 97%, 98%, or 99%) identity or 100% identity to the sequence of SEQ ID NO:57, in which the progranulin variant has the amino acids QLLLRQLL (SEQ ID NO:60) at the C-terminus. In particular embodiments, a progranulin variant has the sequence of SEQ ID NO:57.

A progranulin variant described herein (e.g., a progranulin variant having a sequence of any one of SEQ ID NOS:3-57, 111-121, 127, and 128 can be joined to the N-terminus or the C-terminus an Fc polypeptide (e.g., a wild-type Fc polypeptide or a modified Fc polypeptide). In some embodiments, the progranulin variant linked to the Fc polypeptide can have a sequence selected from any one of SEQ ID NOS:13, 15, 17, 18, 19, 20, and 27-29). In some embodiments, the progranulin variant can be joined to an Fc polypeptide (e.g., a wild-type Fc polypeptide or a modified Fc polypeptide) either directly (e.g., via a peptide bond) or by way of a linker. If a hinge region or a portion thereof is present at the N-terminus of an Fc polypeptide (e.g., a wild-type Fc polypeptide or a modified Fc polypeptide), the progranulin variant can be joined to N-terminus of the hinge region or the portion thereof either directly or by way of a linker.

Further, progranulin variants described herein can be produced from CHO cells. In particular embodiments, more than 50% (e.g., more than 55%, 60%, 65%, 70%, 75%, 80%, 85%, 90%, 95%, 97%, or 99%) of the progranulin variants produced are not truncated at the C-terminus (e.g., remain intact). In particular embodiments, more than 50% (e.g., more than 55%, 65%, 75%, 80%, 85%, 90%, 95%, 97%, or 99%) of the progranulin variants are able to bind sortilin with a $K_D$ value that is reduced by less than 10-fold (e.g., less than 9-fold, 8-fold, 7-fold, 6-fold, or 5-fold) relative to a wild-type progranulin (e.g., wild-type progranulin produced from HEK cells). The progranulin variants can be purified from a cell culture medium containing the progranulin variant-expressing cells by, e.g., a purification scheme comprising protein A chromatography, ion exchange chromatography, hydrophobic interaction column chromatography, and/or dialysis.

V. Fc Polypeptides and Modifications Thereof

In some aspects, fusion proteins described herein can comprise a progranulin variant and an Fc polypeptide dimer in which either one or both Fc polypeptides in the dimer contain amino acid modifications relative to a wild-type Fc polypeptide. In some embodiments, the amino acid modifications in an Fc polypeptide (e.g., a modified Fc polypeptide) can result in binding of the Fc polypeptide dimer to a BBB receptor (e.g., a TfR), promote heterodimerization of the two Fc polypeptides in the dimer, modulate effector function, extend serum half-life, influence glycosylation, and/or reduce immunogenicity in humans. In some embodiments, the Fc polypeptides present in the fusion protein independently have an amino acid sequence identity of at least about 85%, 90%, 95%, 96%, 97%, 98%, or 99% to a corresponding wild-type Fc polypeptide (e.g., a human IgG1, IgG2, IgG3, or IgG4 Fc polypeptide). Examples and descriptions of modified Fc polypeptides (e.g., TfR-binding Fc polypeptides) can be found, e.g., in International Patent Publication No. WO 2018/152326, which is incorporated herein by reference in its entirety.

Fc Polypeptide Modifications for BBB Receptor Binding

Provided herein are fusion proteins comprising a progranulin variant that are capable of being transported across the BBB. Such a protein comprises a modified Fc polypeptide that binds to a BBB receptor. BBB receptors are expressed on BBB endothelia, as well as other cell and tissue types. In some embodiments, the BBB receptor is a TfR.

Amino acid residues designated in various Fc modifications, including those introduced in a modified Fc polypeptide that binds to a BBB receptor, e.g., TfR, are numbered herein using EU index numbering. Any Fc polypeptide, e.g., an IgG1, IgG2, IgG3, or IgG4 Fc polypeptide, may have modifications, e.g., amino acid substitutions, in one or more positions as described herein. In some embodiments, the domain that is modified for BBB (e.g., TfR) receptor-binding activity is a human Ig CH3 domain, such as an IgG1 CH3 domain. The CH3 domain can be of any IgG subtype, i.e., from IgG1, IgG2, IgG3, or IgG4. In the context of IgG1 antibodies, a CH3 domain refers to the segment of amino acids from about position 341 to about position 447 as numbered according to the EU numbering scheme.

In some embodiments, a modified Fc polypeptide that specifically binds to TfR binds to the apical domain of TfR and may bind to TfR without blocking or otherwise inhibiting binding of transferrin to TfR. In some embodiments, binding of transferrin to TfR is not substantially inhibited. In some embodiments, binding of transferrin to TfR is inhibited by less than about 50% (e.g., less than about 45%, 40%, 35%, 30%, 25%, 20%, 15%, 10%, or 5%).

In some embodiments, a BBB (e.g., TfR) receptor-binding Fc polypeptide present in a fusion protein described herein comprises one or more at least one, two, or three substitutions; and in some embodiments, at least four, five, six, seven, eight, nine, or ten substitutions at amino acid positions comprising 266, 267, 268, 269, 270, 271, 295, 297, 298, and 299, according to the EU numbering scheme. In some embodiments, a BBB (e.g., TfR) receptor-binding Fc polypeptide present in a fusion protein described herein comprises at least one, two, or three substitutions; and in some embodiments, at least four, five, six, seven, eight, or nine substitutions at amino acid positions comprising 274, 276, 283, 285, 286, 287, 288, 289, and 290, according to the EU numbering scheme. In some embodiments, a BBB (e.g., TfR) receptor-binding Fc polypeptide present in a fusion protein described herein comprises at least one, two, or three substitutions; and in some embodiments, at least four, five, six, seven, eight, nine, or ten substitutions at amino acid positions comprising 268, 269, 270, 271, 272, 292, 293, 294, 296, and 300, according to the EU numbering scheme. In some embodiments, a BBB (e.g., TfR) receptor-binding Fc polypeptide present in a fusion protein described herein comprises at least one, two, or three substitutions; and in some embodiments, at least four, five, six, seven, eight, or nine substitutions at amino acid positions comprising 272, 274, 276, 322, 324, 326, 329, 330, and 331, according to the EU numbering scheme. In some embodiments, a BBB (e.g., TfR) receptor-binding Fc polypeptide present in a fusion protein described herein comprises at least one, two, or three substitutions; and in some embodiments, at least four, five, six, or seven substitutions at amino acid positions comprising 345, 346, 347, 349, 437, 438, 439, and 440, according to the EU numbering scheme.

In some embodiments, a BBB (e.g., TfR) receptor-binding Fc polypeptide present in a fusion protein described herein comprises at least one, two, or three substitutions; and in some embodiments, at least four, five, six, seven, eight, or nine substitutions at amino acid positions 384, 386, 387, 388, 389, 390, 413, 416, and 421, according to the EU numbering scheme. In some embodiments, the amino acid at position 388 and/or 421 is an aromatic amino acid, e.g., Trp, Phe, or Tyr. In some embodiments, the amino acid at position 388 is Trp. In some embodiments, the aromatic amino acid at position 421 is Trp or Phe. In additional embodiments, the BBB (e.g., TfR) receptor-binding Fc polypeptide further comprises one or more substitutions at positions comprising 391, 392, 414, 415, 424, and 426, according to the EU numbering scheme. In some embodiments, position 414 is Lys, Arg, Gly, or Pro; position 424 is Ser, Thr, Glu, or Lys; and/or position 426 is Ser, Trp, or Gly. In additional embodiments, the modified Fc polypeptide further comprises one, two, or three substitutions at positions comprising 414, 424, and 426, according to the EU numbering scheme. In some embodiments, position 414 is Lys, Arg, Gly, or Pro; position 424 is Ser, Thr, Glu, or Lys; and/or position 426 is Ser, Trp, or Gly.

In some embodiments, the BBB (e.g., TfR) receptor-binding Fc polypeptide has at least 90% (e.g., at least 91%, 92%, 93%, 94%, 95%, 96%, 97%, 98%, or 99%) identity or 100% identity to the sequence of SEQ ID NO:68 and in some embodiments has Glu at position 150, Tyr at position 154, Thr at position 156, Glu at position 157, Trp at position 158, Ala at position 159, Asn at position 160, Thr at position 183, Glu at position 185, Glu at position 186, and Phe at position 191, wherein each position is numbered with reference to SEQ ID NO:68. In particular embodiments, the BBB (e.g., TfR) receptor-binding Fc polypeptide has the sequence of SEQ ID NO:68. In some embodiments of the fusion proteins described herein, one of the two Fc polypeptides in the Fc polypeptide dimer can be a BBB (e.g., TfR) receptor-binding Fc polypeptide having the sequence of SEQ ID NO:68, while the other Fc polypeptide in the Fc polypeptide dimer can have the sequence of a wild-type Fc polypeptide (e.g., SEQ ID NO:61). In other embodiments of the fusion proteins described herein, both Fc polypeptides in the Fc polypeptide dimer can be a BBB (e.g., TfR) receptor-binding Fc polypeptide having the sequence of SEQ ID NO:68.

In some embodiments, the BBB (e.g., TfR) receptor-binding Fc polypeptide has at least 90% (e.g., at least 91%, 92%, 93%, 94%, 95%, 96%, 97%, 98%, or 99%) identity or 100% identity to the sequence of SEQ ID NO:78 and in some embodiments has Leu at position 150, Tyr at position 154, Thr at position 156, Glu at position 157, Trp at position 158, Ser at position 159, Ser at position 160, Thr at position 183, Glu at position 185, Glu at position 186, and Phe at position 191, wherein each position is number with reference to SEQ ID NO:78. In particular embodiments, the BBB (e.g., TfR) receptor-binding Fc polypeptide has the sequence of SEQ ID NO:78. In some embodiments of the fusion proteins described herein, one of the two Fc polypeptides in the Fc polypeptide dimer can be a BBB (e.g., TfR) receptor-binding Fc polypeptide having the sequence of SEQ ID NO:78, while the other Fc polypeptide in the Fc polypeptide dimer can have the sequence of a wild-type Fc polypeptide (e.g., SEQ ID NO:61). In other embodiments of the fusion proteins described herein, both Fc polypeptides in the Fc polypeptide dimer can be a BBB (e.g., TfR) receptor-binding Fc polypeptide having the sequence of SEQ ID NO:78.

Fc Polypeptide Modifications for Heterodimerization

In some embodiments, the Fc polypeptides present in the fusion protein include knob and hole mutations to promote heterodimer formation and hinder homodimer formation. Generally, the modifications introduce a protuberance ("knob") at the interface of a first polypeptide and a corresponding cavity ("hole") in the interface of a second polypeptide, such that the protuberance can be positioned in the cavity so as to promote heterodimer formation and thus hinder homodimer formation. Protuberances are constructed by replacing small amino acid side chains from the interface of the first polypeptide with larger side chains (e.g., tyrosine or tryptophan). Compensatory cavities of identical or similar size to the protuberances are created in the interface of the second polypeptide by replacing large amino acid side chains with smaller ones (e.g., alanine or threonine). In some embodiments, such additional mutations are at a position in the Fc polypeptide that does not have a negative effect on binding of the polypeptide to a BBB receptor, e.g., TfR.

In one illustrative embodiment of a knob and hole approach for dimerization, position 366 (numbered according to the EU numbering scheme) of one of the Fc polypeptides present in the fusion protein comprises a tryptophan in place of a native threonine. The other Fc polypeptide in the dimer has a valine at position 407 (numbered according to the EU numbering scheme) in place of the native tyrosine. The other Fc polypeptide may further comprise a substitution in which the native threonine at position 366 (numbered according to the EU numbering scheme) is substituted with a serine and a native leucine at position 368 (numbered according to the EU numbering scheme) is substituted with an alanine. Thus, one of the Fc polypeptides of a fusion protein described herein has the T366W knob mutation and the other Fc polypeptide has the Y407V mutation, which is typically accompanied by the T366S and L368A hole mutations.

In some embodiments, one or both Fc polypeptides present in a fusion protein described herein may also be engineered to contain other modifications for heterodimerization, e.g., electrostatic engineering of contact residues within a CH3-CH3 interface that are naturally charged or hydrophobic patch modifications.

For example, in some embodiments, a fusion protein described herein can contain an Fc polypeptide dimer that has one Fc polypeptide having the T366W knob mutation and at least 90% (e.g., at least 91%, 92%, 93%, 94%, 95%, 96%, 97%, 98%, or 99%) identity or 100% identity to the sequence of SEQ ID NO:64 and the other Fc polypeptide having the T366S, L368A, and Y407V hole mutations and at least 90% (e.g., at least 91%, 92%, 93%, 94%, 95%, 96%, 97%, 98%, or 99%) identity or 100% identity to the sequence of SEQ ID NO:66. In certain embodiments, one or both Fc polypeptides in the Fc polypeptide dimer can be a TfR-binding Fc polypeptide. In particular embodiments, a fusion protein described herein can contain an Fc polypeptide dimer that has (i) a first Fc polypeptide having at least 90% (e.g., at least 91%, 92%, 93%, 94%, 95%, 96%, 97%, 98%, or 99%) identity or 100% identity to the sequence of SEQ ID NO:66, wherein the sequence includes at positions numbered with reference to SEQ ID NO:66 Ser at position 136, Ala at position 138, and Val at position 177, and (ii) a second Fc polypeptide having at least 90% (e.g., at least 91%, 92%, 93%, 94%, 95%, 96%, 97%, 98%, or 99%) identity or 100% identity to the sequence of SEQ ID NO:69, wherein the sequence includes at positions numbered with reference to SEQ ID NO:69 Trp at position 136 and in some embodiments has Glu at position 150, Tyr at position 154, Thr at position 156, Glu at position 157, Trp at position 158, Ala at position 159, Asn at position 160, Thr at position 183, Glu at position 185, Glu at position 186, and Phe at position 191. In particular embodiments, a fusion protein described herein can contain an Fc polypeptide dimer that has (i) a first Fc polypeptide having at least 90% (e.g., at least 91%, 92%, 93%, 94%, 95%, 96%, 97%, 98%, or 99%) identity or 100% identity to the sequence of SEQ ID NO:66, wherein the sequence includes at positions numbered with reference to SEQ ID NO:66 Ser at position 136, Ala at position 138, and Val at position 177, and (ii) a second Fc polypeptide having at least 90% (e.g., at least 91%, 92%, 93%, 94%, 95%, 96%, 97%, 98%, or 99%) identity or 100% identity to the sequence of SEQ ID NO:79, wherein the sequence includes at positions numbered with reference to SEQ ID NO:79 Trp at position 136 and in some embodiments has Leu at position 150, Tyr at position 154, Thr at position 156, Glu at position 157, Trp at position 158, Ser at position 159, Ser at position 160, Thr at position 183, Glu at position 185, Glu at position 186, and Phe at position 191.

In particular embodiments, a fusion protein described herein can contain (i) a first Fc polypeptide having at least 90% (e.g., at least 91%, 92%, 93%, 94%, 95%, 96%, 97%, 98%, or 99%) identity or 100% identity to the sequence of SEQ ID NO:64, wherein the sequence includes at positions numbered with reference to SEQ ID NO:64 Trp at position 136, and (ii) a second Fc polypeptide having at least 90% (e.g., at least 91%, 92%, 93%, 94%, 95%, 96%, 97%, 98%, or 99%) identity or 100% identity to the sequence of SEQ ID NO:71, wherein the sequence includes at positions numbered with reference to SEQ ID NO:71 Ser at position 136, Ala at position 138, and Val at position 177 and in some embodiments has Glu at position 150, Tyr at position 154, Thr at position 156, Glu at position 157, Trp at position 158, Ala at position 159, Asn at position 160, Thr at position 183, Glu at position 185, Glu at position 186, and Phe at position 191. In particular embodiments, a fusion protein described herein can contain (i) a first Fc polypeptide dimer having at least 90% (e.g., at least 91%, 92%, 93%, 94%, 95%, 96%, 97%, 98%, or 99%) identity or 100% identity to the sequence of SEQ ID NO:64, wherein the sequence includes at positions numbered with reference to SEQ ID NO:64 Trp at position 136, and (ii) a second Fc polypeptide having at least 90% (e.g., at least 91%, 92%, 93%, 94%, 95%, 96%, 97%, 98%, or 99%) identity or 100% identity to the sequence of SEQ ID NO:81, wherein the sequence includes at positions numbered with reference to SEQ ID NO:81 Ser at position 136, Ala at position 138, and Val at position 177 and in some embodiments has Leu at position 150, Tyr at position 154, Thr at position 156, Glu at position 157, Trp at position 158, Ser at position 159, Ser at position 160, Thr at position 183, Glu at position 185, Glu at position 186, and Phe at position 191.

Fc Polypeptide Modifications for Modulating Effector Function

In some embodiments, one or both Fc polypeptides present in a fusion protein described herein may comprise modifications that reduce effector function, i.e., having a reduced ability to induce certain biological functions upon binding to an Fc receptor expressed on an effector cell that mediates the effector function. Examples of antibody effector functions include, but are not limited to, C1q binding and complement dependent cytotoxicity (CDC), Fc receptor binding, antibody-dependent cell-mediated cytotoxicity (ADCC), antibody-dependent cell-mediated phagocytosis (ADCP), down-regulation of cell surface receptors (e.g., B cell receptor), and B-cell activation. Effector functions may vary with the antibody class. For example, native human IgG1 and IgG3 antibodies can elicit ADCC and CDC activities upon binding to an appropriate Fc receptor present on an immune system cell; and native human IgG1, IgG2, IgG3, and IgG4 can elicit ADCP functions upon binding to the appropriate Fc receptor present on an immune cell.

In some embodiments, one or both Fc polypeptides present in a fusion protein described herein may comprise modifications that reduce or eliminate effector function. Illustrative Fc polypeptide mutations that reduce effector function include, but are not limited to, substitutions in a CH2 domain, e.g., at positions 234 and 235, according to the EU numbering scheme. For example, in some embodiments, one or both Fc polypeptides can comprise alanine residues at positions 234 and 235. Thus, one or both Fc polypeptides may have L234A and L235A (LALA) substitutions.

Additional Fc polypeptide mutations that modulate an effector function include, but are not limited to, the following: position 329 may have a mutation in which proline is substituted with a glycine or arginine or an amino acid residue large enough to destroy the Fc/Fcγ receptor interface that is formed between proline 329 of the Fc and tryptophan residues Trp 87 and Trp 110 of FcγRIII. Additional illustrative substitutions include S228P, E233P, L235E, N297A, N297D, and P331S, according to the EU numbering scheme. Multiple substitutions may also be present, e.g., L234A and L235A of a human IgG1 Fc region; L234A, L235A, and P329G of a human IgG1 Fc region; S228P and L235E of a human IgG4 Fc region; L234A and $G_{237}A$ of a human IgG1 Fc region; L234A, L235A, and $G_{237}A$ of a human IgG1 Fc region; V234A and $G_{237}A$ of a human IgG2 Fc region; L235A, $G_{237}A$, and E318A of a human IgG4 Fc region; and S228P and L236E of a human IgG4 Fc region, according to the EU numbering scheme. In some embodiments, one or both Fc polypeptides may have one or more amino acid substitutions that modulate ADCC, e.g., substitutions at positions 298, 333, and/or 334, according to the EU numbering scheme.

For example, in some embodiments, a fusion protein described herein can contain an Fc polypeptide dimer that has (i) a first Fc polypeptide having at least 90% (e.g., at least 91%, 92%, 93%, 94%, 95%, 96%, 97%, 98%, or 99%) identity or 100% identity to the sequence of SEQ ID NO:67, wherein the sequence includes at positions numbered with reference to SEQ ID NO:67 Ala at position 4, Ala at position 5, Ser at position 136, Ala at position 138, and Val at position 177, and (ii) a second Fc polypeptide having at least 90% (e.g., at least 91%, 92%, 93%, 94%, 95%, 96%, 97%, 98%, or 99%) identity or 100% identity to the sequence of SEQ ID NO:70, wherein the sequence includes at positions numbered with reference to SEQ ID NO:70 Ala at position 4, Ala at position 5, Trp at position 136 and in some embodiments has Glu at position 150, Tyr at position 154, Thr at position 156, Glu at position 157, Trp at position 158, Ala at position 159, Asn at position 160, Thr at position 183, Glu at position 185, Glu at position 186, and Phe at position 191. In some embodiments, a fusion protein described herein can contain an Fc polypeptide dimer that has (i) a first Fc polypeptide having at least 90% (e.g., at least 91%, 92%, 93%, 94%, 95%, 96%, 97%, 98%, or 99%) identity or 100% identity to the sequence of SEQ ID NO:67, wherein the sequence includes at positions numbered with reference to SEQ ID NO:67 Ala at position 4, Ala at position 5, Ser at position 136, Ala at position 138, and Val at position 177, and (ii) a second Fc polypeptide having at least 90% (e.g., at least 91%, 92%, 93%, 94%, 95%, 96%, 97%, 98%, or 99%) identity or 100% identity to the sequence of SEQ ID NO:80, wherein the sequence includes at positions numbered with reference to SEQ ID NO:80 Ala at position 4, Ala at position 5, Trp at position 136 and in some embodiments has Leu at position 150, Tyr at position 154, Thr at position 156, Glu at position 157, Trp at position 158, Ser at position 159, Ser at position 160, Thr at position 183, Glu at position 185, Glu at position 186, and Phe at position 191.

In some embodiments, a fusion protein described herein can contain an Fc polypeptide dimer that has (i) a first Fc polypeptide having at least 90% (e.g., at least 91%, 92%, 93%, 94%, 95%, 96%, 97%, 98%, or 99%) identity or 100% identity to the sequence of SEQ ID NO:65, wherein the sequence includes at positions numbered with reference to SEQ ID NO:65 Ala at position 4, Ala at position 5, and Trp at position 136 and (ii) a second Fc polypeptide having at least 90% (e.g., at least 91%, 92%, 93%, 94%, 95%, 96%, 97%, 98%, or 99%) identity or 100% identity to the sequence of SEQ ID NO:72, wherein the sequence includes at positions numbered with reference to SEQ ID NO:72 Ala at position 4, Ala at position 5, Ser at position 136, Ala at position 138, and Val at position 177 and in some embodiments has Glu at position 150, Tyr at position 154, Thr at position 156, Glu at position 157, Trp at position 158, Ala at position 159, Asn at position 160, Thr at position 183, Glu at position 185, Glu at position 186, and Phe at position 191. In some embodiments, a fusion protein described herein can contain an Fc polypeptide dimer that has (i) a first Fc polypeptide having at least 90% (e.g., at least 91%, 92%, 93%, 94%, 95%, 96%, 97%, 98%, or 99%) identity or 100% identity to the sequence of SEQ ID NO:65, wherein the sequence includes at positions numbered with reference to SEQ ID NO:65 Ala at position 4, Ala at position 5, and Trp at position 136, and (ii) a second Fc polypeptide having at least 90% (e.g., at least 91%, 92%, 93%, 94%, 95%, 96%, 97%, 98%, or 99%) identity or 100% identity to the sequence of SEQ ID NO:82, wherein the sequence includes at positions numbered with reference to SEQ ID NO:82 Ala at position 4, Ala at position 5, Ser at position 136, Ala at position 138, and Val at position 177 and in some embodiments has Leu at position 150, Tyr at position 154, Thr at position 156, Glu at position 157, Trp at position 158, Ser at position 159, Ser at position 160, Thr at position 183, Glu at position 185, Glu at position 186, and Phe at position 191.

Fc Polypeptide Modifications for Extending Serum Half-Life

In some embodiments, modifications to enhance serum half-life may be introduced. For example, in some embodiments, one or both Fc polypeptides present in a fusion protein described herein may comprise a tyrosine at position 252, a threonine at position 254, and a glutamic acid at position 256, as numbered according to the EU numbering scheme. Thus, one or both Fc polypeptides may have M252Y, S254T, and T256E substitutions. Alternatively, one or both Fc polypeptides may have M428L and N434S substitutions, as numbered according to the EU numbering scheme. Alternatively, one or both Fc polypeptides may have an N434S or N434A substitution.

In some embodiments, one or both of the Fc polypeptides can have its exposed C-terminal lysine removed (e.g., the Lys residue at position 447 of the Fc polypeptide, according to EU numbering). The C-terminal lysine residue is highly conserved in Fc domains and may be fully or partially removed by the cellular machinery during protein production. In some embodiments, removal of the C-terminal lysines in the Fc polypeptides can improve the stability of the fusion proteins.

In some embodiments, a hinge region (e.g., SEQ ID NO:88) or a portion thereof (e.g., SEQ ID NO:89) can be joined to an Fc polypeptide or a modified Fc polypeptide described herein. The hinge region can be from any immunoglobulin subclass or isotype. An illustrative immunoglobulin hinge is an IgG hinge region, such as an IgG1 hinge region, e.g., human IgG1 hinge amino acid sequence EPKSCDKTHTCPPCP (SEQ ID NO:88) or a portion thereof (e.g., DKTHTCPPCP; SEQ ID NO:89). In some embodiments, the hinge region is at the N-terminal region of the Fc polypeptide.

VI. Linkage Between Progranulins and Fc Polypeptides

In some embodiments, an Fc polypeptide is joined to the progranulin or the progranulin variant by a linker, e.g., a polypeptide linker. In some embodiments, the Fc polypeptide is joined to the progranulin or the progranulin variant by a peptide bond or by a polypeptide linker, e.g., is a fusion polypeptide. The polypeptide linker may be configured such that it allows for the rotation of the progranulin or the progranulin variant relative to the Fc polypeptide to which it is joined; and/or is resistant to digestion by proteases. Polypeptide linkers may contain natural amino acids, unnatural amino acids, or a combination thereof. In some embodiments, the polypeptide linker may be a flexible linker, e.g., containing amino acids such as Gly, Asn, Ser, Thr, Ala, and the like. Such linkers are designed using known parameters and may be of any length and contain any number of repeat units of any length (e.g., repeat units of Gly and Ser residues). For example, the linker may have repeats, such as two, three, four, five, or more $Gly_4$-Ser (SEQ ID NO:90) repeats or a single $Gly_4$-Ser (SEQ ID NO:90). In some embodiments, the polypeptide linker may include a protease cleavage site, e.g., that is cleavable by an enzyme present in the central nervous system. In some embodiments, if a hinge region (e.g., SEQ ID NO:88) or a portion thereof (e.g., SEQ ID NO:89) is joined to the N-terminus of the Fc polypeptide, the C-terminus of the progranulin or the variant thereof can be joined to the N-terminus of the hinge region or the portion thereof by a peptide bond or by a polypeptide linker (e.g., Gly$_4$-Ser (SEQ ID NO:90) repeats or a single Gly$_4$-Ser (SEQ ID NO:90)).

In some embodiments, the progranulin or the progranulin variant is joined to the N-terminus of the Fc polypeptide, e.g., by a Gly$_4$-Ser linker (SEQ ID NO:90) or a (Gly$_4$-Ser)$_2$ linker (SEQ ID NO:91). In some embodiments, the Fc polypeptide may comprise a hinge sequence or partial hinge sequence at the N-terminus that is joined to the linker or directly joined to the progranulin.

In some embodiments, the progranulin or the progranulin variant is joined to the C-terminus of the Fc polypeptide, e.g., by a Gly$_4$-Ser linker (SEQ ID NO:90) or a (Gly$_4$-Ser)$_2$ linker (SEQ ID NO:91). In some embodiments, the C-terminus of the Fc polypeptide is directly joined to the progranulin.

In some embodiments, the polypeptide linker between the Fc polypeptide and the progranulin or the progranulin variant can have 3-50, 3-25, 3-10, 3-5, 3, 5, 7, 10, 25, or 50 amino acids. Suitable polypeptide linkers are known in the art (e.g., as described in Chen et al. *Adv. Drug Deliv Rev.* 65(10):1357-1369, 2013), and include, for example, polypeptide linkers containing flexible amino acid residues such as glycine and serine. In certain embodiments, a polypeptide linker can be a polyglycine linker, e.g., (Gly)$_n$ (SEQ ID NO:138), in which n is an integer between 1 and 10. In certain embodiments, a polypeptide linker can contain motifs, e.g., multiple or repeating motifs, of (GS)$_n$ (SEQ ID NO: 139), (GGS)$_n$ (SEQ ID NO:140), (GGGGS)$_n$ (SEQ ID NO:133), (GGSG)$_n$ (SEQ ID NO:134), or (SGGG)$_n$ (SEQ ID NO:135), in which n is an integer between 1 and 10. In other embodiments, a polypeptide linker can also contain amino acids other than glycine and serine, e.g., KESGSVSSEQLAQFRSLD (SEQ ID NO:94), EGKSSGSGSESKST (SEQ ID NO:95), and GSAGSAAGSGEF (SEQ ID NO:96). In other embodiments, polypeptide linkers can also be rigid polypeptide linkers. In some embodiments, rigid polypeptide linkers can adopt an α-helical conformation, which can be stabilized by intra-segment hydrogen bonds and/or intra-segment salt bridges. Examples of rigid polypeptide linkers include, but are not limited to, A(EAAAK)$_n$A (SEQ ID NO:136), in which n is an integer between 1 and 5, and (XP)$_n$ (SEQ ID NO:141), in which X is Ala, Lys, or Glu, and n is an integer between 1 and 10, as described in Chen et al. *Adv. Drug Deliv Rev.* 65(10):1357-1369, 2013.

In some embodiments, the progranulin or the progranulin variant is joined to the Fc polypeptide by a chemical cross-linking agent. Such conjugates can be generated using well-known chemical cross-linking reagents and protocols. For example, there are a large number of chemical cross-linking agents that are known to those skilled in the art and useful for cross-linking the polypeptide with an agent of interest. For example, the cross-linking agents are heterobifunctional cross-linkers, which can be used to link molecules in a stepwise manner. Heterobifunctional cross-linkers provide the ability to design more specific coupling methods for conjugating proteins, thereby reducing the occurrences of unwanted side reactions such as homoprotein polymers. A wide variety of heterobifunctional cross-linkers are known in the art, including N-hydroxysuccinimide (NHS) or its water soluble analog N-hydroxysulfosuccinimide (sulfo-NHS), succinimidyl 4-(N-maleimidomethyl)cyclohexane-1-carboxylate (SMCC), m-maleimidobenzoyl-N-hydroxysuccinimide ester (MBS); N-succinimidyl (4-iodoacetyl) aminobenzoate (SIAB), succinimidyl 4-(p-maleimidophenyl)butyrate (SMPB), 1-ethyl-3-(3-dimethylaminopropyl)carbodiimide hydrochloride (EDC); 4-succinimidyloxycarbonyl-a-methyl-a-(2-pyridyldithio)-toluene (SMPT), N-succinimidyl 3-(2-pyridyldithio) propionate (SPDP), and succinimidyl 6-[3-(2-pyridyldithio) propionate]hexanoate (LC-SPDP). Those cross-linking agents having N-hydroxysuccinimide moieties can be obtained as the N-hydroxysulfosuccinimide analogs, which generally have greater water solubility. In addition, those cross-linking agents having disulfide bridges within the linking chain can be synthesized instead as the alkyl derivatives so as to reduce the amount of linker cleavage in vivo. In addition to the heterobifunctional cross-linkers, there exist a number of other cross-linking agents including homobifunctional and photoreactive cross-linkers. Disuccinimidyl subcrate (DSS), bismaleimidohexane (BMH) and dimethylpimelimidate.2HCl (DMP) are examples of useful homobifunctional cross-linking agents, and bis-[B-(4-azidosalicylamido)ethyl]disulfide (BASED) and N-succinimidyl-6(4'-azido-2'-nitrophenylamino)hexanoate (SANPAH) are examples of useful photoreactive cross-linkers.

VII. Illustrative Fusion Proteins

In some aspects, a fusion protein described herein comprises a first Fc polypeptide that is linked to a progranulin variant; and a second Fc polypeptide that forms an Fc polypeptide dimer with the first Fc polypeptide. In some embodiments, a fusion protein described herein further comprises a second progranulin or a variant thereof (e.g., a wild-type progranulin or a progranulin variant). In some embodiments, the first Fc polypeptide is a modified Fc polypeptide and/or the second Fc polypeptide is a modified Fc polypeptide. In some embodiments, the modified Fc polypeptide contains one or more modifications that promote its heterodimerization to the other Fc polypeptide. In some embodiments, the modified Fc polypeptide contains one or more modifications that reduce effector function. In some embodiments, the modified Fc polypeptide contains one or more modifications that extend serum half-life. In some embodiments, the modified Fc polypeptide contains one or more modifications that confer binding to a BBB receptor, e.g., a TfR.

In other aspects, a fusion protein described herein comprises a first polypeptide chain that comprises an Fc polypeptide, and a second polypeptide chain that comprises a modified Fc polypeptide that specifically binds to a BBB (e.g., TfR) receptor, e.g., a TfR-binding Fc polypeptide, which dimerizes with the Fc polypeptide in the first polypeptide chain to form an Fc polypeptide dimer. In some embodiments, a fusion protein comprises a progranulin variant, which can be joined to either the first or the second polypeptide chain. In certain embodiments, the progranulin variant is joined to the N-terminus or C-terminus of the first polypeptide chain by way of a polypeptide linker. In certain embodiments, the progranulin variant is joined to the N-terminus or C-terminus of the second polypeptide chain by way of a polypeptide linker.

In some embodiments, a fusion protein comprises two progranulin variants. In certain embodiments, the first progranulin variant is joined to the N-terminus of the first polypeptide chain and the second progranulin variant is joined to the N-terminus of the second polypeptide chain. In certain embodiments, the first progranulin variant is joined to the N-terminus of the first polypeptide chain and the second progranulin variant is joined to the C-terminus of the second polypeptide chain. In certain embodiments, the first progranulin variant is joined to the C-terminus of the first polypeptide chain and the second progranulin variant is joined to the N-terminus of the second polypeptide chain. In certain embodiments, the first progranulin variant is joined to the C-terminus of the first polypeptide chain and the second progranulin variant is joined to the C-terminus of the second polypeptide chain.

In some embodiments, a fusion protein comprises a progranulin variant and a wild-type progranulin. In certain embodiments, the progranulin variant is joined to the N-terminus of the first polypeptide chain and the wild-type progranulin is joined to the N-terminus of the second polypeptide chain. In certain embodiments, the progranulin variant is joined to the N-terminus of the first polypeptide chain and the wild-type progranulin is joined to the C-terminus of the second polypeptide chain. In certain embodiments, the progranulin variant is joined to the C-terminus of the first polypeptide chain and the wild-type progranulin is joined to the N-terminus of the second polypeptide chain. In certain embodiments, the progranulin variant is joined to the C-terminus of the first polypeptide chain and the wild-type progranulin is joined to the C-terminus of the second polypeptide chain. In certain embodiments, the wild-type progranulin is joined to the N-terminus of the first polypeptide chain and the progranulin variant is joined to the N-terminus of the second polypeptide chain. In certain embodiments, the wild-type progranulin is joined to the N-terminus of the first polypeptide chain and the progranulin variant is joined to the C-terminus of the second polypeptide chain. In certain embodiments, the wild-type progranulin is joined to the C-terminus of the first polypeptide chain and the progranulin variant is joined to the N-terminus of the second polypeptide chain. In certain embodiments, the wild-type progranulin is joined to the C-terminus of the first polypeptide chain and the progranulin variant is joined to the C-terminus of the second polypeptide chain.

In some embodiments, the $K_D$ for sortilin binding of a fusion protein described herein is less than about 100 nM (e.g., less than about 95 nM, 90 nM, 85 nM, 80 nM, 75 nM, 70 nM, 65 nM, 60 nM, 55 nM, 50 nM, 45 nM, or 40 nM). In some embodiments, the EC50 for sortilin binding of a fusion protein described herein is less than about 25 nM (e.g., less than about 20 nM, 15 nM, 10 nM, 5 nM, 4 nM, 3 nM, 2.5 nM, 2 nM, 1.5 nM, or 1 nM). In particular embodiments, the EC50 for sortilin binding of the fusion protein exhibits less than about 10-fold (e.g., less than about 9-fold, 8-fold, 7-fold, 6-fold, or 5-fold) decrease in sortilin binding relative to a fusion protein comprising SEQ ID NO:2 in the first polypeptide. In some embodiments, the EC50 for sortilin binding of the fusion protein exhibits less than about 10-fold (e.g., less than about 9-fold, 8-fold, 7-fold, 6-fold, or 5-fold) decrease in sortilin binding relative to a fusion protein comprising SEQ ID NO:108 in the first polypeptide. In certain embodiments, the EC50 is measured by ELISA. An exemplary method to measure EC50 for sortilin binding by ELISA is described herein.

In some embodiments, fusion proteins described herein are produced in CHO cells. In particular embodiments, more than 50% (e.g., more than 55%, 60%, 65%, 70%, 75%, 80%, 85%, 90%, 95%, 97%, or 99%) of the fusion proteins (e.g., the fusion proteins produced from CHO cells) are not cleaved at the C-terminus of the progranulin variant portion of the fusion protein.

In particular embodiments, a fusion protein described herein comprises: (a) a first polypeptide chain that comprises a progranulin variant joined to a modified Fc polypeptide comprising T366S, L368A, and Y407V (hole) substitutions and L234A and L235A (LALA) substitutions; and (b) a second polypeptide chain that comprises a modified Fc polypeptide that binds to TfR and comprises a T366W (knob) substitution and L234A and L235A (LALA) substitutions. The progranulin variant can include a sequence having at least 90% (e.g., at least 91%, 92%, 93%, 94%, 95%, 96%, 97%, 98%, or 99%) identity or 100% identity to a sequence of any one of SEQ ID NOS:4-54, 111-121, and 127-128, wherein positions 574-576 of the progranulin variant are as defined in SEQ ID NOS:4-54, 111-121, and 127-128. In some embodiments, the progranulin variant can include a sequence having at least 90% (e.g., at least 91%, 92%, 93%, 94%, 95%, 96%, 97%, 98%, or 99%) identity or 100% identity to SEQ ID NO:56, wherein positions 574-579 of the progranulin variant are as defined in SEQ ID NO:56. In some embodiments, the progranulin variant can include a sequence having at least 90% (e.g., at least 91%, 92%, 93%, 94%, 95%, 96%, 97%, 98%, or 99%) identity or 100% identity to SEQ ID NO:57, wherein positions 574-581 of the progranulin variant are as defined in SEQ ID NO:57. In some embodiments, the progranulin variant can be joined to the N-terminus or C-terminus (e.g., C-terminus) of the modified Fc polypeptide. In particular embodiments, a hinge region or a portion thereof is joined at the N-terminus of each of the modified Fc polypeptides in the first and second polypeptide chains. In particular embodiments, a polypeptide linker (e.g., GGGGS (SEQ ID NO:90) or GGGGSGGGGS (SEQ ID NO:91)) is present between the progranulin variant and the modified Fc polypeptide in the first polypeptide chain.

In some embodiments, a fusion protein described herein comprises (a) a first polypeptide chain comprising a progranulin variant and a modified Fc polypeptide, wherein the first polypeptide chain comprises a sequence that has at least 90% (e.g., at least 95%, 98%, or 99%) identity or 100% identity to the sequence of SEQ ID NO:98, wherein the sequence includes at positions numbered with reference to SEQ ID NO:98 Ala at position 14, Ala at position 15, Ser at position 146, Ala at position 148, Val at position 187, Pro at position 811, Ile at position 812, and Leu at position 813, and (b) a second polypeptide chain comprising a sequence that has at least 90% (e.g. at least 95%, 98%, or 99%) identity or 100% identity to the sequence of SEQ ID NO:75, wherein the sequence includes at positions numbered with reference to SEQ ID NO:75 Ala at position 14, Ala at position 15, Trp at position 146, Glu at position 160, Tyr at position 164, Thr at position 166, Glu at position 167, Trp at position 168, Ala at position 169, Asn at position 170, Thr at position 193, Glu at position 195, Glu at position 196, and Phe at position 201. In some embodiments, the first polypeptide chain comprises the sequence of SEQ ID NO:98, and the second polypeptide chain comprises the sequence of SEQ ID NO:75. In some embodiments, the first polypeptide chain comprises the sequence of SEQ ID NO:98, and the second polypeptide chain comprises the sequence of SEQ ID NO:130.

In some embodiments, a fusion protein described herein comprises (a) a first polypeptide chain comprising a progranulin variant and a modified Fc polypeptide, wherein the first polypeptide chain comprises a sequence that has at least 90% (e.g., at least 95%, 98%, or 99%) identity or 100% identity to the sequence of SEQ ID NO:99, wherein the sequence includes at positions numbered with reference to SEQ ID NO:99 Ala at position 14, Ala at position 15, Ser at position 146, Ala at position 148, Val at position 187, Pro at position 811, Phe at position 812, and Leu at position 813, and (b) a second polypeptide chain comprising a sequence that has at least 90% (e.g., at least 95%, 98%, or 99%) identity or 100% identity to the sequence of SEQ ID NO:75, wherein the sequence includes at positions numbered with reference to SEQ ID NO:75 Ala at position 14, Ala at position 15, Trp at position 146, Glu at position 160, Tyr at position 164, Thr at position 166, Glu at position 167, Trp at position 168, Ala at position 169, Asn at position 170, Thr at position 193, Glu at position 195, Glu at position 196, and Phe at position 201. In some embodiments, the first polypeptide chain comprises the sequence of SEQ ID NO:99, and the second polypeptide chain comprises the sequence of SEQ ID NO:75. In some embodiments, the first polypeptide chain comprises the sequence of SEQ ID NO: 99, and the second polypeptide chain comprises the sequence of SEQ ID NO:130.

In some embodiments, a fusion protein described herein comprises (a) a first polypeptide chain comprising a progranulin variant and a modified Fc polypeptide, wherein the first polypeptide chain comprises a sequence that has at least 90% (e.g., at least 95%, 98%, or 99%) identity or 100% identity to the sequence of SEQ ID NO:100, wherein the sequence includes at positions numbered with reference to SEQ ID NO:100 Ala at position 14, Ala at position 15, Ser at position 146, Ala at position 148, Val at position 187, Val at position 811, Gln at position 812, and Leu at position 813, and (b) a second polypeptide chain comprising a sequence that has at least 90% (e.g., at least 95%, 98%, or 99%) identity or 100% identity to the sequence of SEQ ID NO:75, wherein the sequence includes at positions numbered with reference to SEQ ID NO:75 Ala at position 14, Ala at position 15, Trp at position 146, Glu at position 160, Tyr at position 164, Thr at position 166, Glu at position 167, Trp at position 168, Ala at position 169, Asn at position 170, Thr at position 193, Glu at position 195, Glu at position 196, and Phe at position 201. In some embodiments, the first polypeptide chain comprises the sequence of SEQ ID NO:100, and the second polypeptide chain comprises the sequence of SEQ ID NO:75. In some embodiments, the first polypeptide chain comprises the sequence of SEQ ID NO:100, and the second polypeptide chain comprises the sequence of SEQ ID NO:130.

In some embodiments, a fusion protein described herein comprises (a) a first polypeptide chain comprising a progranulin variant and a modified Fc polypeptide, wherein the first polypeptide chain comprises a sequence that has at least 90% (e.g. at least 95%, 98%, or 99%) identity or 100% identity to the sequence of SEQ ID NO:101, wherein the sequence includes at positions numbered with reference to SEQ ID NO:101 Ala at position 14, Ala at position 15, Ser at position 146, Ala at position 148, Val at position 187, Val at position 811, Val at position 812, and Leu at position 813, and (b) a second polypeptide chain comprising a sequence that has at least 90% (e.g. at least 95%, 98%, or 99%) identity or 100% identity to the sequence of SEQ ID NO:75, wherein the sequence includes at positions numbered with reference to SEQ ID NO:75 Ala at position 14, Ala at position 15, Trp at position 146, Glu at position 160, Tyr at position 164, Thr at position 166, Glu at position 167, Trp at position 168, Ala at position 169, Asn at position 170, Thr at position 193, Glu at position 195, Glu at position 196, and Phe at position 201. In some embodiments, the first polypeptide chain comprises the sequence of SEQ ID NO:101, and the second polypeptide chain comprises the sequence of SEQ ID NO:75. In some embodiments, the first polypeptide chain comprises the sequence of SEQ ID NO:101, and the second polypeptide chain comprises the sequence of SEQ ID NO:130.

In some embodiments, a fusion protein described herein comprises (a) a first polypeptide chain comprising a progranulin variant and a modified Fc polypeptide, wherein the first polypeptide chain comprises a sequence that has at least 90% (e.g. at least 95%, 98%, or 99%) identity or 100% identity to the sequence of SEQ ID NO:102, wherein the sequence includes at positions numbered with reference to SEQ ID NO:102 Ala at position 14, Ala at position 15, Ser at position 146, Ala at position 148, Val at position 187, Val at position 811, Thr at position 812, and Leu at position 813, and (b) a second polypeptide chain comprising a sequence that has at least 90% (e.g. at least 95%, 98%, or 99%) identity or 100% identity to the sequence of SEQ ID NO:75, wherein the sequence includes at positions numbered with reference to SEQ ID NO:75 Ala at position 14, Ala at position 15, Trp at position 146, Glu at position 160, Tyr at position 164, Thr at position 166, Glu at position 167, Trp at position 168, Ala at position 169, Asn at position 170, Thr at position 193, Glu at position 195, Glu at position 196, and Phe at position 201. In some embodiments, the first polypeptide chain comprises the sequence of SEQ ID NO:102, and the second polypeptide chain comprises the sequence of SEQ ID NO:75. In some embodiments, the first polypeptide chain comprises the sequence of SEQ ID NO:102, and the second polypeptide chain comprises the sequence of SEQ ID NO:130.

In some embodiments, a fusion protein described herein comprises (a) a first polypeptide chain comprising a progranulin variant and a modified Fc polypeptide, wherein the first polypeptide chain comprises a sequence that has at least 90% (e.g., at least 95%, 98%, or 99%) identity to the sequence of SEQ ID NO:123, wherein the sequence includes at positions numbered with reference to SEQ ID NO:123 Ala at position 14, Ala at position 15, Ser at position 146, Ala at position 148, Val at position 187, Pro at position 811, Pro at position 812, and Leu at position 813, and (b) a second polypeptide chain comprising a sequence that has at least 90% (e.g., at least 95%, 98%, or 99%) identity or 100% identity to the sequence of SEQ ID NO:75, wherein the sequence includes at positions numbered with reference to SEQ ID NO:75 Ala at position 14, Ala at position 15, Trp at position 146, Glu at position 160, Tyr at position 164, Thr at position 166, Glu at position 167, Trp at position 168, Ala at position 169, Asn at position 170, Thr at position 193, Glu at position 195, Glu at position 196, and Phe at position 201. In some embodiments, the first polypeptide chain comprises the sequence of SEQ ID NO:123, and the second polypeptide chain comprises the sequence of SEQ ID NO:75. In some embodiments, the first polypeptide chain comprises the sequence of SEQ ID NO: 123, and the second polypeptide chain comprises the sequence of SEQ ID NO:130.

In some embodiments, a fusion protein described herein comprises (a) a first polypeptide chain comprising a progranulin variant and a modified Fc polypeptide, wherein the first polypeptide chain comprises a sequence that has at least 90% (e.g., at least 95%, 98%, or 99%) identity or 100% identity to the sequence of SEQ ID NO:124, wherein the sequence includes at positions numbered with reference to SEQ ID NO:124 Ala at position 14, Ala at position 15, Ser at position 146, Ala at position 148, Val at position 187, Pro at position 811, Tyr at position 812, and Leu at position 813, and (b) a second polypeptide chain comprising a sequence that has at least 90% (e.g., at least 95%, 98%, or 99%) identity or 100% identity to the sequence of SEQ ID NO:75, wherein the sequence includes at positions numbered with reference to SEQ ID NO:75 Ala at position 14, Ala at position 15, Trp at position 146, Glu at position 160, Tyr at position 164, Thr at position 166, Glu at position 167, Trp at position 168, Ala at position 169, Asn at position 170, Thr at position 193, Glu at position 195, Glu at position 196, and Phe at position 201. In some embodiments, the first polypeptide chain comprises the sequence of SEQ ID NO:124, and the second polypeptide chain comprises the sequence of SEQ ID NO:75. In some embodiments, the first polypeptide chain comprises the sequence of SEQ ID NO: 124, and the second polypeptide chain comprises the sequence of SEQ ID NO:130.

In some embodiments, a fusion protein described herein comprises (a) a first polypeptide chain comprising a progranulin variant and a modified Fc polypeptide, wherein the first polypeptide chain comprises a sequence that has at least 90% (e.g., at least 95%, 98%, or 99%) identity or 100% identity to the sequence of SEQ ID NO:125, wherein the sequence includes at positions numbered with reference to SEQ ID NO:125 Ala at position 14, Ala at position 15, Ser at position 146, Ala at position 148, Val at position 187, Gln at position 811, Arg at position 812, and Leu at position 813, and (b) a second polypeptide chain comprising a sequence that has at least 90% (e.g., at least 95%, 98%, or 99%) identity or 100% identity to the sequence of SEQ ID NO:75, wherein the sequence includes at positions numbered with reference to SEQ ID NO:75 Ala at position 14, Ala at position 15, Trp at position 146, Glu at position 160, Tyr at position 164, Thr at position 166, Glu at position 167, Trp at position 168, Ala at position 169, Asn at position 170, Thr at position 193, Glu at position 195, Glu at position 196, and Phe at position 201. In some embodiments, the first polypeptide chain comprises the sequence of SEQ ID NO:125, and the second polypeptide chain comprises the sequence of SEQ ID NO:75. In some embodiments, the first polypeptide chain comprises the sequence of SEQ ID NO: 125, and the second polypeptide chain comprises the sequence of SEQ ID NO:130.

In some embodiments, a fusion protein described herein comprises (a) a first polypeptide chain comprising a progranulin variant and a modified Fc polypeptide, wherein the first polypeptide chain comprises a sequence that has at least 90% (e.g., at least 95%, 98%, or 99%) identity or 100% identity to the sequence of SEQ ID NO:126, wherein the sequence includes at positions numbered with reference to SEQ ID NO:126 Ala at position 14, Ala at position 15, Ser at position 146, Ala at position 148, Val at position 187, Gln at position 811, His at position 812, and Leu at position 813, and (b) a second polypeptide chain comprising a sequence that has at least 90% (e.g., at least 95%, 98%, or 99%) identity or 100% identity to the sequence of SEQ ID NO:75, wherein the sequence includes at positions numbered with reference to SEQ ID NO:75 Ala at position 14, Ala at position 15, Trp at position 146, Glu at position 160, Tyr at position 164, Thr at position 166, Glu at position 167, Trp at position 168, Ala at position 169, Asn at position 170, Thr at position 193, Glu at position 195, Glu at position 196, and Phe at position 201. In some embodiments, the first polypeptide chain comprises the sequence of SEQ ID NO:126, and the second polypeptide chain comprises the sequence of SEQ ID NO:75. In some embodiments, the first polypeptide chain comprises the sequence of SEQ ID NO: 126, and the second polypeptide chain comprises the sequence of SEQ ID NO:130.

In some embodiments, a fusion protein described herein comprises (a) a first polypeptide chain comprising a progranulin variant and a modified Fc polypeptide, wherein the first polypeptide chain comprises a sequence that has at least 90% (e.g. at least 95%, 98%, or 99%) identity or 100% identity to the sequence of SEQ ID NO:98, wherein the sequence includes at positions numbered with reference to SEQ ID NO:98 Ala at position 14, Ala at position 15, Ser at position 146, Ala at position 148, Val at position 187, Pro at position 811, Ile at position 812, and Leu at position 813, and (b) a second polypeptide chain comprising a sequence that has at least 90% identity (e.g., at least 95%, 98%, or 99% identity) to the sequence of SEQ ID NO:85, wherein the sequence includes at positions numbered with reference to SEQ ID NO:85 Ala at position 14, Ala at position 15, Trp at position 146, Leu at position 160, Tyr at position 164, Thr at position 166, Glu at position 167, Trp at position 168, Ser at position 169, Ser at position 170, Thr at position 193, Glu at position 195, Glu at position 196, and Phe at position 201. In some embodiments, the first polypeptide chain comprises the sequence of SEQ ID NO:98, and the second polypeptide chain comprises the sequence of SEQ ID NO:85. In some embodiments, the first polypeptide chain comprises the sequence of SEQ ID NO:98, and the second polypeptide chain comprises the sequence of SEQ ID NO:132.

In some embodiments, a fusion protein described herein comprises (a) a first polypeptide chain comprising a progranulin variant and a modified Fc polypeptide, wherein the first polypeptide chain comprises a sequence that has at least 90% (e.g. at least 95%, 98%, or 99%) identity or 100% identity to the sequence of SEQ ID NO:99, wherein the sequence includes at positions numbered with reference to SEQ ID NO:99 Ala at position 14, Ala at position 15, Ser at position 146, Ala at position 148, Val at position 187, Pro at position 811, Phe at position 812, and Leu at position 813, and (b) a second polypeptide chain comprising a sequence that has at least 90% (e.g. at least 95%, 98%, or 99%) identity or 100% identity to the sequence of SEQ ID NO:85, wherein the sequence includes at positions numbered with reference to SEQ ID NO:85 Ala at position 14, Ala at position 15, Trp at position 146, Leu at position 160, Tyr at position 164, Thr at position 166, Glu at position 167, Trp at position 168, Ser at position 169, Ser at position 170, Thr at position 193, Glu at position 195, Glu at position 196, and Phe at position 201. In some embodiments, the first polypeptide chain comprises the sequence of SEQ ID NO:99, and the second polypeptide chain comprises the sequence of SEQ ID NO:85. In some embodiments, the first polypeptide chain comprises the sequence of SEQ ID NO:99, and the second polypeptide chain comprises the sequence of SEQ ID NO:132.

In some embodiments, a fusion protein described herein comprises (a) a first polypeptide chain comprising a progranulin variant and a modified Fc polypeptide, wherein the first polypeptide chain comprises a sequence that has at least 90% (e.g. at least 95%, 98%, or 99%) identity or 100% identity to the sequence of SEQ ID NO:100, wherein the sequence includes at positions numbered with reference to SEQ ID NO:100 Ala at position 14, Ala at position 15, Ser at position 146, Ala at position 148, Val at position 187, Gln at position 811, Gln at position 812, and Leu at position 813, and (b) a second polypeptide chain comprising a sequence that has at least 90% (e.g. at least 95%, 98%, or 99%) identity or 100% identity to the sequence of SEQ ID NO:85, wherein the sequence includes at positions numbered with reference to SEQ ID NO:85 Ala at position 14, Ala at position 15, Trp at position 146, Leu at position 160, Tyr at position 164, Thr at position 166, Glu at position 167, Trp at position 168, Ser at position 169, Ser at position 170, Thr at position 193, Glu at position 195, Glu at position 196, and Phe at position 201. In some embodiments, the first polypeptide chain comprises the sequence of SEQ ID NO:100, and the second polypeptide chain comprises the sequence of SEQ ID NO:85. In some embodiments, the first polypeptide chain comprises the sequence of SEQ ID NO:100, and the second polypeptide chain comprises the sequence of SEQ ID NO:132.

In some embodiments, a fusion protein described herein comprises (a) a first polypeptide chain comprising a progranulin variant and a modified Fc polypeptide, wherein the first polypeptide chain comprises a sequence that has at least 90% (e.g. at least 95%, 98%, or 99%) identity or 100% identity to the sequence of SEQ ID NO:101, wherein the sequence includes at positions numbered with reference to SEQ ID NO:101 Ala at position 14, Ala at position 15, Ser at position 146, Ala at position 148, Val at position 187, Val at position 811, Val at position 812, and Leu at position 813, and (b) a second polypeptide chain comprising a sequence that has at least 90% (e.g. at least 95%, 98%, or 99%) identity or 100% identity to the sequence of SEQ ID NO:85, wherein the sequence includes at positions numbered with reference to SEQ ID NO:85 Ala at position 14, Ala at position 15, Trp at position 146, Leu at position 160, Tyr at position 164, Thr at position 166, Glu at position 167, Trp at position 168, Ser at position 169, Ser at position 170, Thr at position 193, Glu at position 195, Glu at position 196, and Phe at position 201. In some embodiments, the first polypeptide chain comprises the sequence of SEQ ID NO:101, and the second polypeptide chain comprises the sequence of SEQ ID NO:85. In some embodiments, the first polypeptide chain comprises the sequence of SEQ ID NO:101, and the second polypeptide chain comprises the sequence of SEQ ID NO:132.

In some embodiments, a fusion protein described herein comprises (a) a first polypeptide chain comprising a progranulin variant and a modified Fc polypeptide, wherein the first polypeptide chain comprises a sequence that has at least 90% (e.g. at least 95%, 98%, or 99%) identity or 100% identity to the sequence of SEQ ID NO:102, wherein the sequence includes at positions numbered with reference to SEQ ID NO:102 Ala at position 14, Ala at position 15, Ser at position 146, Ala at position 148, Val at position 187, Val at position 811, Thr at position 812, and Leu at position 813, and (b) a second polypeptide chain comprising a sequence that has at least 90% (e.g. at least 95%, 98%, or 99%) identity or 100% identity to the sequence of SEQ ID NO:85, wherein the sequence includes at positions numbered with reference to SEQ ID NO:85 Ala at position 14, Ala at position 15, Trp at position 146, Leu at position 160, Tyr at position 164, Thr at position 166, Glu at position 167, Trp at position 168, Ser at position 169, Ser at position 170, Thr at position 193, Glu at position 195, Glu at position 196, and Phe at position 201. In some embodiments, the first polypeptide chain comprises the sequence of SEQ ID NO:102, and the second polypeptide chain comprises the sequence of SEQ ID NO:85. In some embodiments, the first polypeptide chain comprises the sequence of SEQ ID NO:102, and the second polypeptide chain comprises the sequence of SEQ ID NO:132.

In particular embodiments, a fusion protein described herein comprises: (a) a first polypeptide chain that comprises a modified Fc polypeptide that binds to TfR and comprises T366S, L368A, and Y407V (hole) substitutions and L234A and L235A (LALA) substitutions; and (b) a second polypeptide chain that comprises a progranulin variant joined to a modified Fc polypeptide comprising a T366W (knob) substitution and L234A and L235A (LALA) substitutions. The progranulin variant can have a sequence having at least 90% (e.g. at least 95%, 98%, or 99%) identity or 100% identity to a sequence of any one of SEQ ID NOS:3-57, 111-121, and 127-128. In some embodiments, the progranulin variant can be joined to the N-terminus or C-terminus (e.g., C-terminus) of the modified Fc polypeptide. In particular embodiments, a hinge region or a portion thereof is joined at the N-terminus of each of the modified Fc polypeptides in the first and second polypeptide chains. In particular embodiments, a polypeptide linker (e.g., GGGGS (SEQ ID NO:90) or GGGGSGGGGS (SEQ ID NO:91)) is present between the progranulin variant and the modified Fc polypeptide in the second polypeptide chain.

In some embodiments, a fusion protein described herein comprises (a) a first polypeptide chain comprising a sequence that has at least 90% (e.g. at least 95%, 98%, or 99%) identity or 100% identity to the sequence of SEQ ID NO:77, wherein the sequence includes at positions numbered with reference to SEQ ID NO:77 Ala at position 14, Ala at position 15, Ser at position 146, Ala at position 148, Glu at position 160, Tyr at position 164, Thr at position 166, Glu at position 167, Trp at position 168, Ala at position 169, Asn at position 170, Val at position 187, Thr at position 193, Glu at position 195, Glu at position 196, and Phe at position 201, and (b) a second polypeptide chain comprising a progranulin variant and a modified Fc polypeptide, wherein the second polypeptide chain comprises a sequence that has at least 90% (e.g. at least 95%, 98%, or 99%) identity or 100% identity to the sequence of SEQ ID NO:103, wherein the sequence includes at positions numbered with reference to SEQ ID NO:103 Ala at position 14, Ala at position 15, Trp at position 146, Pro at position 811, Ile at position 812, and Leu at position 813.

In some embodiments, a fusion protein described herein comprises (a) a first polypeptide chain comprising a sequence that has at least 90% (e.g. at least 95%, 98%, or 99%) identity or 100% identity to the sequence of SEQ ID NO:77, wherein the sequence includes at positions numbered with reference to SEQ ID NO:77 Ala at position 14, Ala at position 15, Ser at position 146, Ala at position 148, Glu at position 160, Tyr at position 164, Thr at position 166, Glu at position 167, Trp at position 168, Ala at position 169, Asn at position 170, Val at position 187, Thr at position 193, Glu at position 195, Glu at position 196, and Phe at position 201, and (b) a second polypeptide chain comprising a progranulin variant and a modified Fc polypeptide, wherein the second polypeptide chain comprises a sequence that has at least 90% (e.g. at least 95%, 98%, or 99%) identity or 100% identity to the sequence of SEQ ID NO:104, wherein the sequence includes at positions numbered with reference to SEQ ID NO:104 Ala at position 14, Ala at position 15, Trp at position 146, Pro at position 811, Phe at position 812, and Leu at position 813.

In some embodiments, a fusion protein described herein comprises (a) a first polypeptide chain comprising a sequence that has at least 90% (e.g. at least 95%, 98%, or 99%) identity or 100% identity to the sequence of SEQ ID NO:77, wherein the sequence includes at positions numbered with reference to SEQ ID NO:77 Ala at position 14, Ala at position 15, Ser at position 146, Ala at position 148, Glu at position 160, Tyr at position 164, Thr at position 166, Glu at position 167, Trp at position 168, Ala at position 169, Asn at position 170, Val at position 187, Thr at position 193, Glu at position 195, Glu at position 196, and Phe at position 201, and (b) a second polypeptide chain comprising a progranulin variant and a modified Fc polypeptide, wherein the second polypeptide chain comprises a sequence that has at least 90% (e.g. at least 95%, 98%, or 99%) identity or 100% identity to the sequence of SEQ ID NO:105, wherein the sequence includes at positions numbered with reference to SEQ ID NO:105 Ala at position 14, Ala at position 15, Trp at position 146, Gln at position 811, Gln at position 812, and Leu at position 813.

In some embodiments, a fusion protein described herein comprises (a) a first polypeptide chain comprising a sequence that has at least 90% (e.g. at least 95%, 98%, or 99%) identity or 100% identity to the sequence of SEQ ID NO:77, wherein the sequence includes at positions numbered with reference to SEQ ID NO:77 Ala at position 14, Ala at position 15, Ser at position 146, Ala at position 148, Glu at position 160, Tyr at position 164, Thr at position 166, Glu at position 167, Trp at position 168, Ala at position 169, Asn at position 170, Val at position 187, Thr at position 193, Glu at position 195, Glu at position 196, and Phe at position 201, and (b) a second polypeptide chain comprising a progranulin variant and a modified Fc polypeptide, wherein the second polypeptide chain comprises a sequence that has at least 90% (e.g. at least 95%, 98%, or 99%) identity or 100% identity to the sequence of SEQ ID NO:106, wherein the sequence includes at positions numbered with reference to SEQ ID NO:106 Ala at position 14, Ala at position 15, Trp at position 146, Val at position 811, Val at position 812, and Leu at position 813.

In some embodiments, a fusion protein described herein comprises (a) a first polypeptide chain comprising a sequence that has at least 90% (e.g. at least 95%, 98%, or 99%) identity or 100% identity to the sequence of SEQ ID NO:77, wherein the sequence includes at positions numbered with reference to SEQ ID NO:77 Ala at position 14, Ala at position 15, Ser at position 146, Ala at position 148, Glu at position 160, Tyr at position 164, Thr at position 166, Glu at position 167, Trp at position 168, Ala at position 169, Asn at position 170, Val at position 187, Thr at position 193, Glu at position 195, Glu at position 196, and Phe at position 201, and (b) a second polypeptide chain comprising a progranulin variant and a modified Fc polypeptide, wherein the second polypeptide chain comprises a sequence that has at least 90% (e.g. at least 95%, 98%, or 99%) identity or 100% identity to the sequence of SEQ ID NO:107, wherein the sequence includes at positions numbered with reference to SEQ ID NO:107 Ala at position 14, Ala at position 15, Trp at position 146, Val at position 811, Thr at position 812, and Leu at position 813.

In some embodiments, a fusion protein described herein comprises (a) a first polypeptide chain comprising a sequence that has at least 90% (e.g. at least 95%, 98%, or 99%) identity or 100% identity to the sequence of SEQ ID NO:87, wherein the sequence includes at positions numbered with reference to SEQ ID NO:87 Ala at position 14, Ala at position 15, Ser at position 146, Ala at position 148, Leu at position 160, Tyr at position 164, Thr at position 166, Glu at position 167, Trp at position 168, Ser at position 169, Ser at position 170, Val at position 187, Thr at position 193, Glu at position 195, Glu at position 196, and Phe at position 201, and (b) a second polypeptide chain comprising a progranulin variant and a modified Fc polypeptide, wherein the second polypeptide chain comprises a sequence that has at least 90% (e.g. at least 95%, 98%, or 99%) identity or 100% identity to the sequence of SEQ ID NO:103, wherein the sequence includes at positions numbered with reference to SEQ ID NO:103 Ala at position 14, Ala at position 15, Trp at position 146, Pro at position 811, Ile at position 812, and Leu at position 813.

In some embodiments, a fusion protein described herein comprises (a) a first polypeptide chain comprising a sequence that has at least 90% (e.g. at least 95%, 98%, or 99%) identity or 100% identity to the sequence of SEQ ID NO:87, wherein the sequence includes at positions numbered with reference to SEQ ID NO:87 Ala at position 14, Ala at position 15, Ser at position 146, Ala at position 148, Leu at position 160, Tyr at position 164, Thr at position 166, Glu at position 167, Trp at position 168, Ser at position 169, Ser at position 170, Val at position 187, Thr at position 193, Glu at position 195, Glu at position 196, and Phe at position 201, and (b) a second polypeptide chain comprising a progranulin variant and a modified Fc polypeptide, wherein the second polypeptide chain comprises a sequence that has at least 90% (e.g. at least 95%, 98%, or 99%) identity or 100% identity to the sequence of SEQ ID NO:104, wherein the sequence includes at positions numbered with reference to SEQ ID NO:104 Ala at position 14, Ala at position 15, Trp at position 146, Pro at position 811, Phe at position 812, and Leu at position 813.

In some embodiments, a fusion protein described herein comprises (a) a first polypeptide chain comprising a sequence that has at least 90% (e.g. at least 95%, 98%, or 99%) identity or 100% identity to the sequence of SEQ ID NO:87, wherein the sequence includes at positions numbered with reference to SEQ ID NO:87 Ala at position 14, Ala at position 15, Ser at position 146, Ala at position 148, Leu at position 160, Tyr at position 164, Thr at position 166, Glu at position 167, Trp at position 168, Ser at position 169, Ser at position 170, Val at position 187, Thr at position 193, Glu at position 195, Glu at position 196, and Phe at position 201, and (b) a second polypeptide chain comprising a progranulin variant and a modified Fc polypeptide, wherein the second polypeptide chain comprises a sequence that has at least 90% (e.g. at least 95%, 98%, or 99%) identity or 100% identity to the sequence of SEQ ID NO:105, wherein the sequence includes at positions numbered with reference to SEQ ID NO:105 Ala at position 14, Ala at position 15, Trp at position 146, Gln at position 811, Gln at position 812, and Leu at position 813.

In some embodiments, a fusion protein described herein comprises (a) a first polypeptide chain comprising a sequence that has at least 90% (e.g. at least 95%, 98%, or 99%) identity or 100% identity to the sequence of SEQ ID NO:87, wherein the sequence includes at positions numbered with reference to SEQ ID NO:87 Ala at position 14, Ala at position 15, Ser at position 146, Ala at position 148, Leu at position 160, Tyr at position 164, Thr at position 166, Glu at position 167, Trp at position 168, Ser at position 169, Ser at position 170, Val at position 187, Thr at position 193, Glu at position 195, Glu at position 196, and Phe at position 201, and (b) a second polypeptide chain comprising a progranulin variant and a modified Fc polypeptide, wherein the second polypeptide chain comprises a sequence that has at least 90% (e.g. at least 95%, 98%, or 99%) identity or 100% identity to the sequence of SEQ ID NO:106, wherein the sequence includes at positions numbered with reference to SEQ ID NO:106 Ala at position 14, Ala at position 15, Trp at position 146, Val at position 811, Val at position 812, and Leu at position 813.

In some embodiments, a fusion protein described herein comprises (a) a first polypeptide chain comprising a sequence that has at least 90% (e.g. at least 95%, 98%, or 99%) identity or 100% identity to the sequence of SEQ ID NO:87, wherein the sequence includes at positions numbered with reference to SEQ ID NO:87 Ala at position 14, Ala at position 15, Ser at position 146, Ala at position 148, Leu at position 160, Tyr at position 164, Thr at position 166, Glu at position 167, Trp at position 168, Ser at position 169, Ser at position 170, Val at position 187, Thr at position 193, Glu at position 195, Glu at position 196, and Phe at position 201, and (b) a second polypeptide chain comprising a progranulin variant and a modified Fc polypeptide, wherein the second polypeptide chain comprises a sequence that has at least 90% (e.g. at least 95%, 98%, or 99%) identity or 100% identity to the sequence of SEQ ID NO:107, wherein the sequence includes at positions numbered with reference to SEQ ID NO:107 Ala at position 14, Ala at position 15, Trp at position 146, Val at position 811, Thr at position 812, and Leu at position 813.

VIII. Binding Properties

Fusion proteins described herein may have a broad range of binding affinities. For example, in some embodiments, a protein has an affinity for a BBB receptor, e.g., a TfR, ranging anywhere from 1 pM to 10 µM. In some embodiments, the affinity for TfR ranges from 1 nM to 5 µM, or from 10 nM to 1 µM.

Methods for analyzing binding affinity, binding kinetics, and cross-reactivity to analyze binding to a BBB receptor, e.g., TfR, are known in the art. These methods include, but are not limited to, solid-phase binding assays (e.g., ELISA assay), immunoprecipitation, surface plasmon resonance (e.g., Biacore™ (GE Healthcare, Piscataway, N.J.)), kinetic exclusion assays (e.g., KinExA®), flow cytometry, fluorescence-activated cell sorting (FACS), BioLayer interferometry (e.g., Octet® (FortéBio, Inc., Menlo Park, Calif.)), and Western blot analysis. In some embodiments, ELISA is used to determine binding affinity and/or cross-reactivity. Methods for performing ELISA assays are known in the art and are also described in the Example section below. In some embodiments, surface plasmon resonance (SPR) is used to determine binding affinity, binding kinetics, and/or cross-reactivity. In some embodiments, kinetic exclusion assays are used to determine binding affinity, binding kinetics, and/or cross-reactivity. In some embodiments, BioLayer interferometry assays are used to determine binding affinity, binding kinetics, and/or cross-reactivity. evaluation of Effects of Fusion proteins Activity of fusion proteins described herein that comprise a progranulin or a variant thereof, can be assessed using various assays, including assays that measure activity in vitro or in vivo. As described in the Examples, cellular uptake of the fusion proteins described herein may be assayed using bone marrow derived macrophages (BMDMs) and immunostaining with antibodies against human progranulin and human Fc. Cellular effects caused by GRN mutation (e.g., increased cathepsin D activity and elevated mRNA levels of lysosomal genes such as Ctsl, Tmem106b, and Psap) may be evaluated again after the cells are treated with the fusion proteins described herein (Examples 6 and 7). Fluorgenic probes and qPCR techniques may be used in these assays. Finally, pharmacokinetic properties and brain uptake of the fusion proteins described herein may be determined using wild-type and/or transgenic mice, as shown in Examples 9 and 10.

For cellular samples, the assay may include disrupting the cells and breaking open microvesicles. Disruption of cells may be achieved by using freeze-thawing and/or sonication. In some embodiments, a tissue sample is evaluated. A tissue sample can be evaluated using multiple free-thaw cycles, e.g., 2, 3, 4, 5, or more, which are performed before the sonication step to ensure that microvesicles are broken open.

Samples that can be evaluated by the assays described herein include, e.g., brain, liver, kidney, lung, spleen, plasma, serum, cerebrospinal fluid (CSF), and urine. In some embodiments, CSF samples from a patient receiving a fusion protein comprising a progranulin or a variant thereof as described herein may be evaluated.

IX. Bis(Monoacylglycero)Phosphate (Bmp)

Provided herein are methods of monitoring the levels of progranulin or a progranulin variant (e.g., in a sample, in a cell, in a tissue, and/or in a subject), wherein determining the level of progranulin or the progranulin variant comprises measuring the abundance of BMP (e.g., in the sample, cell, tissue, and/or subject).

BMP is a glycerophospholipid that is negatively charged (e.g. at the pH normally present within late endosomes and lysosomes) having the structure depicted in Formula I:

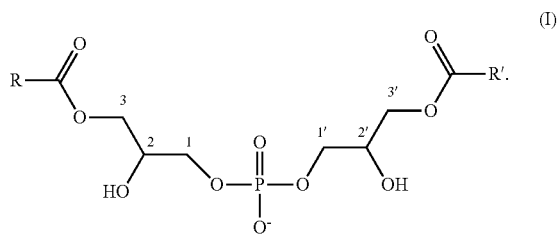

(I)

BMP molecules comprise two fatty acid side chains. R and R' in Formula I represent independently selected saturated or unsaturated aliphatic chains, each of which typically contains 14, 16, 18, 20, or 22 carbon atoms. When a fatty acid side chain is unsaturated, it can contain 1, 2, 3, 4, 5, 6, or more carbon-carbon double bonds. Furthermore, a BMP molecule can contain one or two alkyl ether substituents, wherein the carbonyl oxygen of one or both fatty acid side chains is replaced with two hydrogen atoms. Nomenclature that is used herein to describe a particular BMP species refers to a species having two fatty acid side-chains, wherein the structures of the fatty acid side chains are indicated within parentheses in the BMP format (e.g., BMP(18:1_18:1)). The numerals follow the standard fatty acid notation format of number of "fatty acid carbon atoms:number of double bonds." An "e-" prefix is used to indicate the presence of an alkyl ether substituent wherein the carbonyl oxygen of the fatty acid side chain is replaced with two hydrogen atoms. For example, the "e" in "BMP(16:0e_18:0)" denotes that the side chain having 16 carbon atoms is an alkyl ether substituent.

In some embodiments of methods of the present disclosure, the abundance of a single BMP species is measured. In some embodiments, the abundance of two or more BMP species is measured. In some embodiments, the abundance of at least two, three, four, five, or more of the BMP species in Table 1 is measured. When the abundance of two or more BMP species is measured, any combination of different BMP species can be used.

In some embodiments, the abundance of more than one BMP species can be summed, and the total abundance will be compared to a reference value. For example, the abundance of one or more BMP species (e.g., the BMP species listed in Table 1) can be summed, and the total abundance then compared to a reference value.

TABLE 1

BMP Species

| Name | Total carbon atoms:total unsaturations |
|---|---|
| BMP(14:0_14:0) | BMP(28:0) |
| BMP(14:0_16:0) | BMP(30:0) |
| BMP(14:0_16:1) | BMP(30:1) |
| BMP(14:0_18:0) | BMP(32:0) |
| BMP(14:0_18:1) | BMP(32:1) |
| BMP(14:0_18:2) | BMP(32:2) |
| BMP(14:0_18:3) | BMP(32:3) |
| BMP(14:0_20:1) | BMP(34:1) |
| BMP(14:0_20:2) | BMP(34:2) |
| BMP(14:0_20:3) | BMP(34:3) |
| BMP(14:0_20:4) | BMP(34:4) |
| BMP(14:0_20:5) | BMP(34:5) |
| BMP(14:0_22:4) | BMP(36:4) |
| BMP(14:0_22:5) | BMP(36:5) |
| BMP(14:0_22:6) | BMP(36:6) |
| BMP(16:0_16:0) | BMP(32:0) |
| BMP(16:0_16:1) | BMP(32:1) |
| BMP(16:0_18:0) | BMP(34:0) |
| BMP(16:0_18:1) | BMP(34:1) |
| BMP(16:0_18:2) | BMP(34:2) |
| BMP(16:0_18:3) | BMP(34:3) |
| BMP(16:0_20:1) | BMP(36:1) |
| BMP(16:0_20:2) | BMP(36:2) |
| BMP(16:0_20:3) | BMP(36:3) |
| BMP(16:0_20:4) | BMP(36:4) |
| BMP(16:0_20:5) | BMP(36:5) |
| BMP(16:0_22:4) | BMP(38:4) |
| BMP(16:0_22:5) | BMP(38:5) |
| BMP(16:0_22:6) | BMP(38:6) |
| BMP(16:1_16:1) | BMP(32:2) |
| BMP(16:1_18:0) | BMP(34:1) |
| BMP(16:1_18:1) | BMP(34:2) |
| BMP(16:1_18:2) | BMP(34:3) |
| BMP(16:1_18:3) | BMP(34:4) |
| BMP(16:1_20:1) | BMP(36:2) |
| BMP(16:1_20:2) | BMP(36:3) |
| BMP(16:1_20:3) | BMP(36:4) |
| BMP(16:1_20:4) | BMP(36:5) |
| BMP(16:1_20:5) | BMP(36:6) |
| BMP(16:1_22:4) | BMP(38:5) |
| BMP(16:1_22:5) | BMP(38:6) |
| BMP(16:1_22:6) | BMP(38:7) |
| BMP(16:0e_14:0) | BMP(40:0) |
| BMP(16:0e_16:0) | BMP(32:0) |
| BMP(16:0e_18:0) | BMP(34:0) |
| BMP(16:0e_18:1) | BMP(34:1) |
| BMP(16:0e_18:2) | BMP(34:2) |
| BMP(16:0e_18:3) | BMP(34:3) |
| BMP(16:0e_20:3) | BMP(36:3) |
| BMP(16:0e_20:4) | BMP(36:4) |
| BMP(16:0e_20:5) | BMP(36:5) |
| BMP(16:0e_22:4) | BMP(38:4) |
| BMP(16:0e_22:6) | BMP(38:6) |
| BMP(16:1e_14:0) | BMP(30:1) |
| BMP(16:1e_16:0) | BMP(32:1) |
| BMP(16:1e_18:0) | BMP(34:1) |
| BMP(16:1e_18:1) | BMP(34:2) |
| BMP(16:1e_18:2) | BMP(34:3) |
| BMP(16:1e_18:3) | BMP(34:4) |
| BMP(16:1e_20:3) | BMP(36:4) |
| BMP(16:1e_20:4) | BMP(36:5) |
| BMP(16:1e_20:5) | BMP(36:6) |
| BMP(16:1e_22:4) | BMP(38:5) |
| BMP(16:1e_22:6) | BMP(38:7) |
| BMP(18:0_18:0) | BMP(36:0) |
| BMP(18:0_18:1) | BMP(36:1) |
| BMP(18:0_18:2) | BMP(36:2) |
| BMP(18:0_18:3) | BMP(36:3) |
| BMP(18:0_20:1) | BMP(38:1) |
| BMP(18:0_20:2) | BMP(38:2) |
| BMP(18:0_20:3) | BMP(38:3) |
| BMP(18:0_20:4) | BMP(38:4) |
| BMP(18:0_20:5) | BMP(38:5) |
| BMP(18:0_22:4) | BMP(40:4) |
| BMP(18:0_22:5) | BMP(40:5) |
| BMP(18:0_22:6) | BMP(40:6) |
| BMP(18:1_18:1) | BMP(36:2) |
| BMP(18:1_18:2) | BMP(36:3) |
| BMP(18:1_18:3) | BMP(36:4) |
| BMP(18:1_20:1) | BMP(38:2) |
| BMP(18:1_20:2) | BMP(38:3) |
| BMP(18:1_20:3) | BMP(38:4) |
| BMP(18:1_20:4) | BMP(38:5) |
| BMP(18:1_20:5) | BMP(38:6) |
| BMP(18:1_22:4) | BMP(40:5) |
| BMP(18:1_22:5) | BMP(40:6) |
| BMP(18:1_22:6) | BMP(40:7) |
| BMP(18:2_18:2) | BMP(36:4) |
| BMP(18:2_18:3) | BMP(36:5) |
| BMP(18:2_20:1) | BMP(38:3) |
| BMP(18:2_20:2) | BMP(38:4) |
| BMP(18:2_20:3) | BMP(38:5) |
| BMP(18:2_20:4) | BMP(38:6) |
| BMP(18:2_20:5) | BMP(38:7) |
| BMP(18:2_22:4) | BMP(40:6) |
| BMP(18:2_22:5) | BMP(40:7) |
| BMP(18:2_22:6) | BMP(40:8) |
| BMP(18:3_18:3) | BMP(36:6) |
| BMP(18:3_20:1) | BMP(38:4) |
| BMP(18:3_20:2) | BMP(38:5) |
| BMP(18:3_20:3) | BMP(38:6) |
| BMP(18:3_20:4) | BMP(38:7) |
| BMP(18:3_20:5) | BMP(38:8) |
| BMP(18:3_22:4) | BMP(40:7) |
| BMP(18:3_22:5) | BMP(40:8) |
| BMP(18:3_22:6) | BMP(40:9) |
| BMP(18:0e_14:0) | BMP(32:0) |
| BMP(18:0e_16:0) | BMP(34:0) |
| BMP(18:0e_18:0) | BMP(36:0) |
| BMP(18:0e_18:1) | BMP(36:1) |
| BMP(18:0e_18:2) | BMP(36:2) |
| BMP(18:0e_18:3) | BMP(36:3) |
| BMP(18:0e_20:3) | BMP(38:3) |
| BMP(18:0e_20:4) | BMP(38:4) |
| BMP(18:0e_20:5) | BMP(38:5) |
| BMP(18:0e_22:4) | BMP(40:4) |
| BMP(18:0e_22:6) | BMP(40:6) |
| BMP(18:1e_14:0) | BMP(32:1) |
| BMP(18:1e_16:0) | BMP(34:1) |
| BMP(18:1e_18:0) | BMP(36:1) |
| BMP(18:1e_18:1) | BMP(36:2) |
| BMP(18:1e_18:2) | BMP(36:3) |
| BMP(18:1e_18:3) | BMP(36:4) |
| BMP(18:1e_20:3) | BMP(38:4) |
| BMP(18:1e_20:4) | BMP(38:5) |
| BMP(18:1e_20:5) | BMP(38:6) |
| BMP(18:1e_22:4) | BMP(40:5) |
| BMP(18:1e_22:6) | BMP(40:7) |
| BMP(20:3_20:3) | BMP(40:6) |
| BMP(20:3_20:4) | BMP(40:7) |
| BMP(20:3_20:5) | BMP(40:8) |
| BMP(20:3_22:4) | BMP(42:7) |
| BMP(20:3_22:5) | BMP(42:8) |
| BMP(20:3_22:6) | BMP(42:9) |
| BMP(20:4_20:4) | BMP(40:8) |
| BMP(20:4_20:5) | BMP(40:9) |
| BMP(20:4_22:4) | BMP(42:8) |
| BMP(20:4_22:5) | BMP(42:9) |
| BMP(20:4_22:6) | BMP(42:10) |
| BMP(20:5_20:5) | BMP(40:10) |
| BMP(20:5_22:4) | BMP(42:9) |
| BMP(20:5_22:5) | BMP(42:10) |
| BMP(20:5_22:6) | BMP(42:11) |
| BMP(22:4_22:4) | BMP(44:8) |
| BMP(22:4_22:5) | BMP(44:9) |
| BMP(22:4 22:6) | BMP(44:10) |
| BMP(22:6_22:6) | BMP(44:12) |

In some cases, one or more BMP species may be differentially expressed (e.g., more or less abundant) in one type of sample when compared to another, such as, for example, cell-based samples (e.g., cultured cells) versus tissue-based or blood samples. Accordingly, in some embodiments, the selection of the one or more BMP species (i.e., for the measurement of abundance) depends on the type of sample. In some embodiments, the one or more BMP species comprise BMP(18:1_18:1), e.g., when a sample (e.g., a test sample and/or a reference sample) includes BMDMs. In other embodiments, the one or more BMP species comprise BMP(20:4_20:4), e.g., when a sample comprises tissue (e.g., brain tissue, liver tissue) or plasma, urine, or CSF. In other embodiments, the one or more BMP species comprise BMP(22:6_22:6), e.g., when a sample comprises tissue (e.g., brain tissue, liver tissue) or plasma, urine, or CSF.

In some embodiments, an internal BMP standard (e.g., BMP(14:0_14:0)) is used to measure the abundance of one or more BMP species in a sample and/or determine a reference value (e.g., measure the abundance of one or more BMP species in a reference sample). For example, a known amount of the internal BMP standard can be added to a sample (e.g., a test sample and/or a reference sample) to serve as a calibration point such that the amount of one or more BMP species that are present in the sample can be determined. In some embodiments, a reagent used in the extraction or isolation of BMP from a sample (e.g., methanol) is "spiked" with the internal BMP standard. Typically, the internal BMP standard will be one that does not naturally occur in the subject.

X. Glucosyl Sphingosine (Glcsph)

Provided herein are methods of monitoring the levels of progranulin or a progranulin variant (e.g., in a sample, in a cell, in a tissue, and/or in a subject), wherein determining the level of progranulin or the progranulin variant comprises measuring the abundance of glucosylsphingosine (GlcSph) (e.g., in the sample, cell, tissue, and/or subject).

GlcSph is a lysoglycosphingolipid having the structure depicted in Formula I.

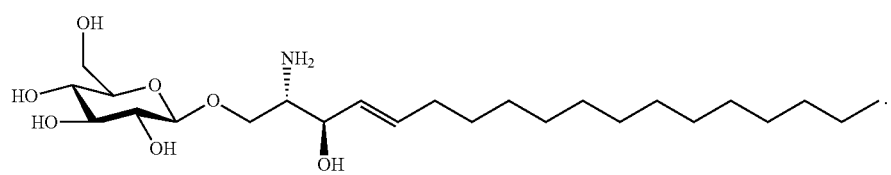

(I)

GlcSph is a substrate of glucocerebrosidase (GCase) and is found to accumulate in cells and tissues of human Gaucher disease patients and mouse models that exhibit reduced GCase activity. The accumulation of GlcSph is implicated in the visceral and neuronal pathologies observed in Gaucher disease.

In some embodiments, the abundance of GlcSph can be compared to a reference value. In some embodiments, a subject having, or at risk of having, a progranulin-associated disorder has an increased GlcSph level compared to the reference value, e.g., the abundance of the GlcSph in the test sample of the subject can be at least about 1.2-fold (e.g., about 1.2-fold, 1.3-fold, 1.4-fold, 1.5-fold, 2-fold, 2.5-fold, 3-fold, 3.5-fold, 4-fold, 4.5-fold, 5-fold, 5.5-fold, 6-fold, 6.5-fold, 7-fold, 7.5-fold, 8-fold, 8.5-fold, 9-fold, 9.5-fold, 10-fold, or more) of the reference value. In some embodiments, the reference value is the GlcSph level in a test sample of the subject having, or at risk of having, a progranulin-associated disorder prior to the subject receiving treatment.

In some embodiments of the methods, the reference value is measured in a reference sample obtained from a reference subject or a population of reference subjects. The reference subject or population of reference subjects can be a healthy control subject or a population of healthy control subjects. The reference subject or population of reference subjects can be a subject or a population of subjects who does not have a progranulin-associated disorder or a decreased level of progranulin. In some embodiments, after the subject having, or at risk of having, a progranulin-associated disorder receives treatment, the GlcSph level in a test sample from the subject can improve over the GlcSph level in a test sample from the subject prior to the subject receiving any treatment. In some embodiments, the improved GlcSph level is closer to the reference value (e.g., the reference value measured in a reference sample obtained from a healthy control subject or a population of healthy control subjects) than the GlcSph level in the subject having, or at risk of having, a progranulin-associated disorder prior to the subject receiving treatment, for example, the improved GlcSph level is within about 20%, 15%, 10%, or 5% of the reference level. In some embodiments, the improved GlcSph level is substantially the same as the reference level.

In some cases, in subjects having, or at risk of having, a progranulin-associated disorder, the increased GlcSph level compared to a reference value can be found in, e.g., whole blood, plasma, a cell, a tissue, serum, cerebrospinal fluid, interstitial fluid, sputum, urine, lymph, or a combination thereof of the subject. In particular embodiments, the increased GlcSph level can be found in the plasma of the subject. In some embodiments of the methods of the disclosure, the test sample taken from the subject having, or at risk of having, a progranulin-associated disorder or one or more reference values can comprise or relate to plasma.

Further, in subjects having, or at risk of having, a progranulin-associated disorder, the increased GlcSph level compared to a reference value can be found in the brain of the subject, for example, in the frontal lobe and/or temporal lobe of the brain. In particular embodiments, the increased GlcSph can be found in one or more regions of the frontal lobe, e.g., superior frontal gyrus, middle frontal gyrus, inferior frontal gyrus, and/or precentral gyrus.

The test sample taken from the subject having, or at risk of having, a progranulin-associated disorder used in the methods described herein can comprise a cell, such as a blood cell, a brain cell, a peripheral blood mononuclear cell (PBMC), a bone marrow-derived macrophage (BMDM), a retinal pigmented epithelial (RPE) cell, an erythrocyte, a leukocyte, a neural cell, a microglial cell, a cerebral cortex cell, a spinal cord cell, a bone marrow cell, a liver cell, a kidney cell, a splenic cell, a lung cell, an eye cell, a chorionic villus cell, a muscle cell, a skin cell, a fibroblast, a heart cell, a lymph node cell, or a combination thereof. In some embodiments, the test sample comprises a blood cell. In some embodiments, the test sample comprises a brain cell.

The test sample taken from the subject having, or at risk of having, a progranulin-associated disorder used in the methods described herein can comprise a tissue, such as brain tissue, cerebral cortex tissue, spinal cord tissue, liver tissue, kidney tissue, muscle tissue, heart tissue, eye tissue, retinal tissue, a lymph node, bone marrow, skin tissue, blood vessel tissue, lung tissue, spleen tissue, valvular tissue, or a combination thereof. In some embodiments, the test sample comprises brain tissue, such as brain tissue from the frontal lobe or temporal lobe of the subject's brain. In particular embodiments, the brain tissue used in the test sample can be from the superior frontal gyrus, middle frontal gyrus, inferior frontal gyrus, and/or precentral gyrus.

The test sample taken from the subject having, or at risk of having, a progranulin-associated disorder can comprise an endosome, a lysosome, an extracellular vesicle, an exosome, a microvesicle, or a combination thereof.

In some embodiments, an internal GlcSph standard is used to measure the abundance of GlcSph in a test sample from a subject having, or at risk of having, a progranulin-associated disorder and/or determine a reference value (e.g., measure the abundance of GlcSph in a reference sample). For example, a known amount of the internal GlcSph standard can be added to a sample (e.g., a test sample and/or a reference sample) to serve as a calibration point such that the amount of GlcSph that is present in the sample can be determined. In some embodiments, a reagent used in the extraction or isolation of GlcSph from a sample (e.g., methanol) is "spiked" with the internal GlcSph standard. Typically, the internal GlcSph standard is be one that does not naturally occur in the subject. In some embodiments, the internal GlcSph is a deuterium-labeled GlcSph, such as GlcSph(d5) used in the Examples.

XI. Monitoring Response to Treatment

In one aspect, the present disclosure provides methods for monitoring progranulin levels or progranulin variant levels in a subject (e.g., a target subject). In another aspects, provided are methods for monitoring a subject's response a progranulin variant or a fusion protein described herein, or pharmaceutical composition or dosing regimen thereof, for treating a disease or disorder (e.g., any described herein).

Typically, the abundance of each of the one or more BMP species and/or GlcSph in a test sample will be compared to one or more reference values (e.g., a corresponding reference value). In some embodiments, a BMP value and/or a GlcSph value is measured before treatment and at one or more time points after treatment. The abundance value taken at a later time point can be compared to the value prior to treatment as well as to a control value, such as that of a healthy or diseased control, to determine how the subject is responding to the therapy. The one or more reference values can be from different cells, tissues, or fluids corresponding to the cell, tissue, or fluid of the test sample.

In some embodiments, the reference value is the abundance of the one or more BMP species that is measured in a reference sample. In some embodiments, the reference value is the abundance of GlcSph that is measured in a reference sample. The reference value can be a measured abundance value (e.g., abundance value measured in the reference sample), or can be derived or extrapolated from a measured abundance value. In some embodiments, the reference value is a range of values, e.g., when the reference values are obtained from a plurality of samples or a population of subjects. Furthermore, the reference value can be presented as a single value (e.g., a measured abundance value, a mean value, or a median value) or a range of values, with or without a standard deviation or standard of error.

When two or more test samples are obtained (e.g., from a subject), the time points at which they are obtained can be separated about 1, 12, 24, or more hours; about 1, 2, 3, 4, 5, 6, 7, or more days; about 1, 2, 3, 4, 5, 6, 7, 8, 9, 10, or more weeks; or even longer. When three or more test samples are obtained, the time intervals between when each test sample is obtained can all be the same, the intervals can all be different, or a combination thereof.

In some embodiments, both the first test sample and the second test sample are obtained from a subject (e.g., a target subject) after the subject has been treated, i.e., the first test sample is obtained from the subject at an earlier time point during treatment than the second test sample. In some embodiments, the first test sample is obtained before the subject has been treated for the disorder associated with a decreased level of progranulin (i.e., a pre-treatment test sample) and the second test sample is obtained after the subject has been treated for the disorder associated with a decreased level of progranulin (i.e., a post-treatment test sample). In some embodiments, more than one (e.g., 1, 2, 3, 4, 5, 6, 7, 8, 9, 10, or more) pre-treatment and/or post-treatment test samples are obtained from the subject. Furthermore, the number of pre-treatment and post-treatment test samples that are obtained need not be the same.

In some embodiments, it may be determined that the subject is not responding to the treatment when the abundance of the BMP species measured is within about 1%, 2%, 3%, 4%, 5%, 6%, 7%, 8%, 9%, 10%, 11%, 12%, 13%, 14%, 15%, 6%1, 7%1, 8%1, 19%, or 20% of the reference value taken in a reference sample from the subject before the subject receiving any treatment.

In some embodiments, it may be determined that the subject is responding to the treatment when the abundance of the BMP species measured is within about 1%, 2%, 3%, 4%, 5%, 6%, 7%, 8%, 9%, 10%, 11%, 12%, 13%, 14%, 15%, 16%, 17%, 18%, 19%, or 20% of the reference value taken in a reference sample from a healthy control subject.

In some embodiments, it may be determined that the subject is not responding to the treatment when the abundance of GlcSph measured is within about 1%, 2%, 3%, 4%, 5%, 6%, 7%, 8%, 9%, 10%, 11%, 12%, 13%, 14%, 15%, 16%, 17%, 18%, 19%, or 20% of the reference value taken in a reference sample from the subject before the subject receiving any treatment.

In some embodiments, it may be determined that the subject is responding to the treatment when the abundance of GlcSph measured is within about 1%, 2%, 3%, 4%, 5%, 6%, 7%, 8%, 9%, 10%, 11%, 12%, 13%, 14%, 15%, 16%, 17%, 18%, 19%, or 20% of the reference value taken in a reference sample from a healthy control subject.

When a subject (e.g., a target subject) is not responding to treatment (e.g., for a disorder associated with a decreased level of progranulin), in some embodiments, the dosage of one or more therapeutic agents (e.g., progranulin) is altered (e.g., increased) and/or the dosing interval is altered (e.g., the time between doses is decreased). In some embodiments, when a subject is not responding to treatment, a different therapeutic agent is selected. In some embodiments, when a subject is not responding to treatment, one or more therapeutic agents is discontinued.

XII. Bmp and Glcsph Detection Techniques

In some embodiments, antibodies can be used to detect and/or measure the abundance of one or more BMP species and/or GlcSph. In some embodiments, BMP species bound to the antibody can be detected such as by microscopy or ELISA. In some embodiments, GlcSph bound to the antibody can be detected such as by microscopy or ELISA.

In other embodiments, mass spectrometry (MS) is used to detect and/or measure the abundance of one or more BMP species and/or GlcSph according to methods of the present disclosure. Mass spectrometry is a technique in which compounds are ionized, and the resulting ions are sorted by their mass-to-charge ratios (abbreviated m/Q, m/q, m/Z, or m/z). A sample (e.g., comprising a BMP molecule and/or a GlcSph molecule), which can be present in gas, liquid, or solid form, is ionized, and the resulting ions are then accelerated through an electric and/or magnetic field, causing them to be separated by their mass-to-charge ratios. The ions ultimately strike an ion detector and a mass spectrogram is generated. The mass-to-charge ratios of the detected ions, together with their relative abundance, can be used to identify the parent compound(s), sometimes by correlating known masses (e.g., of entire or intact molecules) to the masses of the detected ions and/or by recognition of patterns that are detected in the mass spectrogram.

In some embodiments, the one or more BMP species and/or GlcSph can be detected by single MS, which uses a single mass analyzer (e.g., quadrupole). In some embodiments, the one or more BMP species and/or GlcSph can be detected by tandem mass spectrometry (MS/MS), which uses a series of mass analyzers (e.g., three mass analyzers) to perform multiple rounds of mass spectrometry, typically having a molecule fragmentation step in between.

Several methods can be used for fragmentation, including but not limited to collision-induced dissociation (CID), electron capture dissociation (ECD), electron transfer dissociation (ETD), infrared multiphoton dissociation (IRMPD), blackbody infrared radiative dissociation (BIRD), electron-detachment dissociation (EDD), and surface-induced dissociation (SID).

Tandem mass spectrometers can be used to run different types of experiments, including full scans, product ion scans, precursor ion scans, neutral loss scans, and selective (or multiple) reaction monitoring (SRM or MRM) scans. In a full scan experiment, the entire mass range or a portion thereof) of both mass analyzers (e.g., Q1 and Q3) are scanned and the second mass analyzer (e.g., Q2) does not contain any collision gas. This allows all ions contained in a sample to be detected. In a product ion scan experiment, a specific mass-to-charge ratio is selected for the first mass analyzer (e.g., Q1), the second mass analyzer (e.g., Q2) is filled with a collision gas to fragment ions having the selected mass-to-charge ratio, and then the entire mass range (or a portion thereof) of the third mass analyzer (e.g., Q3) is scanned. This allows all fragment ions of a selected precursor ion to be detected. In a precursor ion scan experiment, the entire mass range (or a portion thereof) of the first mass analyzer (e.g., Q1) is scanned, the second mass analyzer (e.g., Q2) is filled with collision gas to fragment ions falling within the scan range, and a specific mass-to-charge ratio is selected for the third mass analyzer (e.g., Q3). By correlating the time between detection of a product ion and the particular mass-to-charge ratio that was selected just prior to its detection, this type of experiment can allow a user to determine which precursor ion(s) may have generated the product ion of interest. In a neutral loss scan experiment, the entire mass range (or a portion thereof) of the first mass analyzer (e.g., Q1) is scanned, the second mass analyzer (e.g., Q2) is filled with collision gas to fragment all ions within the scan range, and the third mass analyzer (e.g., Q3) is scanned across a specified range that corresponds to the fragmentation-induced loss of a single specific mass that has occurred for every potential ion in the precursor scan range. This type of experiment permits the identification of all precursors that have lost a particular chemical group of interest (e.g., a methyl group) in common. In an MRM experiment, one specific mass-to-charge ratio is selected for the first mass analyzer (e.g., Q1), the second mass analyzer (e.g., Q2) is filled with collision gas, and the third mass analyzer (e.g., Q3) is set for another specific mass-to-charge ratio. This type of experiment permits the highly specific detection of molecules that are known to fragment into the products that are selected for in the third mass analyzer. MS and MS/MS methods are described further in Grebe et al. *Clin. Biochem. Rev.* (2011) 32:5-31, hereby incorporated by reference in its entirety for all purposes.

Furthermore, MS and MS/MS techniques can be coupled with liquid chromatography (LC) or gas chromatography (GC) techniques. Such liquid chromatography-mass spectrometry (LC-MS), liquid chromatography-tandem mass spectrometry (LC-MS/MS), gas chromatography-mass spectrometry (GC-MS), and gas chromatography-tandem mass spectrometry (GC-MS/MS) methods allow for enhanced mass resolving and mass determining over what is typically possible with MS or MS/MS alone.

Liquid chromatography refers to a process in which one or more components of a fluid solution are selectively retarded as the fluid uniformly percolates through a column of a finely divided substance, or through capillary passageways. The retardation results from the distribution of the components of the mixture between one or more stationary phases and the bulk fluid (i.e., mobile phase), as the fluid moves relative to the stationary phase(s). High performance liquid chromatography (HPLC), also sometimes known as "high pressure liquid chromatography," is a variant of LC in which the degree of separation is increased by forcing the mobile phase under pressure through a stationary phase, typically a densely packed column.

Furthermore, ultra high performance liquid chromatography (UHPLC), also known as "ultra high pressure liquid chromatography," or "ultra performance liquid chromatography (UPLC)," is a variant of HPLC that is performed using much higher pressures than traditional HPLC techniques.

Gas chromatography refers to a method for separating and/or analyzing compounds that can be vaporized without being decomposed. The mobile phase is a carrier gas that is typically an inert gas (e.g., helium) or an unreactive gas (e.g., nitrogen), and the stationary phase is typically a microscopic liquid or polymer layer positioned on an inert solid support inside glass or metal tubing that serves as the "column." As the gaseous compounds of interest interact with the stationary phase within the column, they are differentially retarded and eluted from the column at different times. The separated compounds can then be introduced into the mass spectrometer.

In some embodiments, antibody-based methods are used to detect and/or measure the abundance of one or more BMP species and/or GlcSph. Non-limiting examples of suitable methods include ELISA, immunofluorescence, and radio-immunoassay (RIA) techniques. Methods for performing ELISA, immunofluorescence, and RIA techniques are known in the art.

Any number of sample types can be used as a test sample and/or reference sample in methods of the present disclosure so long as the sample comprises BMP and/or GlcSph in an amount sufficient for detection such that the abundance can be measured. Non-limiting examples include cells, tissues, blood (e.g., whole blood, plasma, serum), fluids (e.g., cerebrospinal fluid, urine, bronchioalveolar lavage fluid, lymph, semen, breast milk, amniotic fluid), feces, sputum, or any combination thereof. Non-limiting examples of suitable cell types include BMDMs, blood cells (e.g., PBMCs, erythrocytes, leukocytes), neural cells (e.g., brain cells, cerebral cortex cells, spinal cord cells), bone marrow cells, liver cells, kidney cells, splenic cells, lung cells, eye cells (e.g., retinal cells such as RPE cells), chorionic villus cells, muscle cells, skin cells, fibroblasts, heart cells, lymph node cells, or a combination thereof. In some embodiments, the sample comprises a portion of a cell. In some embodiments, the sample is purified from a cell or a tissue. Non-limiting examples of purified samples include endosomes, lysosomes, extracellular vesicles (e.g., exosomes, microvesicles), and combinations thereof.

In some embodiments, the sample (e.g., test sample and/or reference sample) comprises a cell that is a cultured cell. Non-limiting examples include BMDMs and RPE cells. BMDMs can be obtained, for example, by procuring a sample comprising PBMCs and culturing the monocytes contained therein.

Non-limiting examples of suitable tissue sample types include neural tissue (e.g., brain tissue, cerebral cortex tissue, spinal cord tissue), liver tissue, kidney tissue, muscle tissue, heart tissue, eye tissue (e.g., retinal tissue), lymph nodes, bone marrow, skin tissue, blood vessel tissue, lung tissue, spleen tissue, valvular tissue, and a combination thereof. In some embodiments, a test sample and/or a reference sample comprises brain tissue or liver tissue. In some embodiments, a test and/or a reference sample comprises plasma.

XIII. Nucleic Acids, Vectors, and Host Cells

Polypeptide chains contained in the fusion proteins as described herein are typically prepared using recombinant methods. Accordingly, in some aspects, the disclosure provides isolated nucleic acids comprising a nucleic acid sequence encoding any of the progranulin variants, polypeptides, or fusion proteins as described herein, and host cells into which the nucleic acids are introduced that are used to replicate the polypeptide-encoding nucleic acids and/or to express the polypeptides. In some embodiments, the host cell is eukaryotic, e.g., a human cell.

In another aspect, polynucleotides are provided that comprise a nucleotide sequence that encodes the progranulin variants and polypeptide chains described herein. The polynucleotides may be single-stranded or double-stranded. In some embodiments, the polynucleotide is DNA. In particular embodiments, the polynucleotide is cDNA. In some embodiments, the polynucleotide is RNA.

The disclosure provides an isolated nucleic acid comprising a nucleic acid sequence encoding a polypeptide having the sequence of any one of SEQ ID NOS:98-108 and 123-126. Also provided herein is an isolated nucleic acid comprising a nucleic acid sequence encoding a progranulin variant having the sequence of any one of SEQ ID NOS:3-57, 111-121, 127, and 128.

In some embodiments, the polynucleotide is included within a nucleic acid construct. In some embodiments, the construct is a replicable vector. In some embodiments, the vector is selected from a plasmid, a viral vector, a phagemid, a yeast chromosomal vector, and a non-episomal mammalian vector.

In some embodiments, the polynucleotide is operably linked to one or more regulatory nucleotide sequences in an expression construct. In one series of embodiments, the nucleic acid expression constructs are adapted for use as a surface expression library. In some embodiments, the library is adapted for surface expression in yeast. In some embodiments, the library is adapted for surface expression in phage. In another series of embodiments, the nucleic acid expression constructs are adapted for expression of the polypeptide in a system that permits isolation of the polypeptide in milligram or gram quantities. In some embodiments, the system is a mammalian cell expression system. In some embodiments, the system is a yeast cell expression system.

Expression vehicles for production of a recombinant polypeptide include plasmids and other vectors. For instance, suitable vectors include plasmids of the following types: pBR322-derived plasmids, pEMBL-derived plasmids, pEX-derived plasmids, pBTac-derived plasmids, and pUC-derived plasmids for expression in prokaryotic cells, such as E. coli. The pcDNAI/amp, pcDNAI/neo, pRc/CMV, pSV2gpt, pSV2neo, pSV2-dhfr, pTk2, pRSVneo, pMSG, pSVT7, pko-neo, and pHyg-derived vectors are examples of mammalian expression vectors suitable for transfection of eukaryotic cells. Alternatively, derivatives of viruses such as the bovine papilloma virus (BPV-1), or Epstein-Barr virus (pHEBo, pREP-derived, and p205) can be used for transient expression of polypeptides in eukaryotic cells. In some embodiments, it may be desirable to express the recombinant polypeptide by the use of a baculovirus expression system. Examples of such baculovirus expression systems include pVL-derived vectors (such as pVL1392, pVL1393, and pVL941), pAcUW-derived vectors (such as pAcUWI), and pBlueBac-derived vectors. Additional expression systems include adenoviral, adeno-associated virus, and other viral expression systems.

Vectors may be transformed into any suitable host cell. In some embodiments, the host cells, e.g., bacteria or yeast cells, may be adapted for use as a surface expression library. In some cells, the vectors are expressed in host cells to express relatively large quantities of the polypeptide. Such host cells include mammalian cells, yeast cells, insect cells, and prokaryotic cells. In some embodiments, the cells are mammalian cells, such as CHO cell, baby hamster kidney (BHK) cell, NS0 cell, Y0 cell, HEK293 cell, COS cell, Vero cell, or HeLa cell. In particular embodiments, the cells are CHO cells.

A host cell transfected with an expression vector encoding one or more progranulin variants for fusion protein described herein can be cultured under appropriate conditions to allow expression of the one or more polypeptides to occur. The polypeptide(s) may be secreted and isolated from a mixture of cells and medium containing the polypeptide(s). Alternatively, the polypeptide(s) may be retained in the cytoplasm or in a membrane fraction and the cells harvested, lysed, and the polypeptide(s) isolated using a desired method.

XIV. Pharmaceutical Compositions and Kits

In other aspects, pharmaceutical compositions and kits comprising a progranulin variant or fusion protein in accordance with the disclosure are provided.

Pharmaceutical Compositions

Guidance for preparing formulations for use in the disclosure can be found in any number of handbooks for pharmaceutical preparation and formulation that are known to those of skill in the art.

In some embodiments, a pharmaceutical composition comprises a progranulin variant or fusion protein as described herein and further comprises one or more pharmaceutically acceptable carriers and/or excipients. A pharmaceutically acceptable carrier includes any solvents, dispersion media, or coatings that are physiologically compatible and that do not interfere with or otherwise inhibit the activity of the active agent.

The progranulin variant or fusion protein can be formulated for parenteral administration by injection. Typically, a pharmaceutical composition for use in in vivo administration is sterile, e.g., heat sterilization, steam sterilization, sterile filtration, or irradiation.

Dosages and desired drug concentration of pharmaceutical compositions described herein may vary depending on the particular use envisioned.

Kits

In some embodiments, a kit for use in treating a neurodegenerative disease (e.g., FTD, NCL, NPA, NPB, NPC, C9ORF72-associated ALS/FTD, sporadic ALS, AD, Gaucher's disease (e.g., Gaucher's disease types 2 and 3), and Parkinson's disease), atherosclerosis, a disorder associated with TDP-43, and AMD, and a progranulin-associated disorder) comprising a progranulin variant or fusion protein described herein is provided.

In some embodiments, the kit further comprises one or more additional therapeutic agents. For example, in some embodiments, the kit comprises a progranulin variant or fusion protein as described herein and further comprises one or more additional therapeutic agents for use in the treatment of any disease or disorder described herein (e.g., a neurodegenerative disease (e.g., FTD)). In some embodiments, the kit further comprises instructional materials containing directions (i.e., protocols) for the practice of the methods described herein (e.g., instructions for using the kit for administering a fusion protein comprising the progranulin variant). While the instructional materials typically comprise written or printed materials, they are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD-ROM), and the like. Such media may include addresses to internet sites that provide such instructional materials.

XV. Indications

In some embodiments, the progranulin variants and fusion proteins described herein are used to treat a neurodegenerative disease or neurodegenerative diseases. For example, the fusion proteins described herein can be used to treat one or more neurodegenerative diseases selected from the group consisting of AD, primary age-related tauopathy, lewy body dementia, progressive supranuclear palsy (PSP), FTD, FTD with parkinsonism linked to chromosome 17, argyrophilic grain dementia, ALS, ALS/parkinsonism-dementia complex of Guam (ALS-PDC), corticobasal degeneration, chronic traumatic encephalopathy, Creutzfeldt-Jakob disease, dementia pugilistica, diffuse neurofibrillary tangles with calcification, Down's syndrome, familial British dementia, familial Danish dementia, Gerstmann-Straussler-Scheinker disease, globular glial tauopathy, Guadeloupean parkinsonism with dementia, Guadelopean PSP, Hallevorden-Spatz disease, hereditary diffuse leukoencephalopathy with spheroids (HDLS), inclusion-body myositis, multiple system atrophy, myotonic dystrophy, Nasu-Hakola disease, neurofibrillary tangle-predominant dementia, NPC, pallido-ponto-nigral degeneration, Parkinson's disease, Pick's disease, postencephalitic parkinsonism, prion protein cerebral amyloid angiopathy, progressive subcortical gliosis, subacute sclerosing panencephalitis, and tangle only dementia.

A number of neurodegenerative diseases may be caused by or linked to lysosomal storage disorders characterized by the accumulation of undigested or partially digested macromolecules, which ultimately results in cellular and organismal dysfunction as well as clinical abnormalities. Lysosomal storage disorders are defined by the type of accumulated substrate, and may be classified as cholesterol storage disorders, sphingolipidoses, oligosaccharidoses, mucolipidoses, mucopolysaccharidoses, lipoprotein storage disorders, neuronal ceroid lipofuscinoses, and others. In some cases, lysosomal storage disorders also include deficiencies or defects in proteins that result in accumulation of macromolecules, such as proteins necessary for normal post-translational modification of lysosomal enzymes, or proteins important for proper lysosomal trafficking. Examples of neurodegenerative diseases that may be caused by or linked to lysosomal storage disorders include, e.g., FTD, NCL, NPA, NPB, NPC, C9ORF72-associated ALS/FTD, sporadic ALS, AD, Gaucher's disease (e.g., Gaucher's disease types 2 and 3), and Parkinson's disease. In some embodiments, the progranulin variants and fusion proteins described herein are used to treat a neurodegenerative disease caused by or linked to lysosomal storage disorders, including, for example, any of the foregoing neurodegenerative diseases.

Examples of other disorders include atherosclerosis, a disorder associated with TDP-43, and AMD. Such disorders may benefit from administration of the progranulin variants or fusion proteins described herein.

In some embodiments, the progranulin variants and fusion proteins described herein are used to treat FTD. FTD is a progressive neurodegenerative disorder. FTD includes a spectrum of clinically, pathologically, and genetically heterogeneous diseases presenting selective involvement of the frontal and temporal lobes (Gazzina et al., *Eur J Pharmacol.* 817:76-85, 2017). Clinical manifestations of FTD include alterations in behavior and personality, frontal executive deficits, and language dysfunction. Based on the diversity of clinical phenotypes, different presentations have been identified, such as behavioral variants of FTD (bvFTD) and primary progressive aphasia (PPA), which can either be the nonfluent/agrammatic variant PPA (avPPA) or the semantic variant PPA (svPPA). These clinical presentations can also overlap with atypical parkinsonism, such as corticobasal syndrome (CBS), progressive supranuclear palsy (PSP), and ALS (Gazzina et al., *Eur J Pharmacol.* 817:76-85, 2017). FTD is associated with various neuropathological hallmarks, including tau pathology in neurons and astrocytes or cytoplasmic ubiquitin inclusions in neurons. The Trans-activating DNA-binding Protein with a molecular weight of 43 kDa (TDP-43) is the most prominent, ubiquitinated protein pathology accumulating in the majority of cases of FTD as well as in ALS (Petkau and Leavitt, supra). FTD is a significant cause of early-onset dementia with up to 80% of cases presenting between ages 45 and 64. The disease also presents a significant familial component, with about 30-50% of cases reporting family history of the disease (Petkau and Leavitt, supra).

In some embodiments, the progranulin variants and fusion proteins described herein are used to treat a disorder linked to, or associated with, a mutation in GRN. While several genes have been linked to FTD, one of the most frequently mutated genes in FTD is GRN, which maps to human chromosome 17q21 and encodes the cysteine-rich protein progranulin (also known as proepithelin and acrogranin). Recent estimates suggest that GRN mutations account for 5-20% of FTD patients with positive family history and 1-5% of sporadic cases (Rademakers et al., supra). The precise molecular and cellular mechanisms underlying neurodegeneration and disease processes in GRN-associated FTD are unknown, although phenotypic characterization of GRN-knockout mice combined with histological analyses of patients' brain suggests that both inflammation and lysosomal defects are central to the disease (Kao et al., *Nat Rev Neurosci.* 18(6):325-333, 2017). Indeed, massive gliosis is present in cortical regions of patients (Lui et al., *Cell.* 165(4):921-35, 2016) and lipofuscin, a lysosomal pigment denoting lysosomal disorder, has been reported in the eye and cortex of mutated GRN carriers including both presymptomatic individuals and patients (Ward et al., *Sci Transl Med.* 9(385), 2017).

More than seventy GRN disease mutations have been reported and mapped throughout the gene, where they result in confirmed or predicted loss of function (LOF) alleles (Ji et al. *J Med Genet.* 54:145-154, 2017). Most heterozygous mutations linked to FTD cause about 50% reduction in mRNA level primarily as a result of non-sense mRNA decay and a comparable reduction in progranulin protein level (Petkau and Leavitt, supra; Kao et al., supra). Lower levels of progranulin are also found in the blood (serum) and cerebrospinal fluid (CSF) of carriers, including presymptomatic individuals (Finch et al., *Nat Rev Neurosci.* 18(6): 325-333, 2017; Goossens et al., Alzheimers Res Ther. 10(1): 31, 2018; Meeter et al., *Dement Geriatr Cogn Dis Extra.* 6(2):330-340, 2016). Therefore, haplo-insufficiency is believed to be the main disease mechanism in GRN-associated FTD, suggesting that therapeutic approaches that elevate progranulin levels in carriers may delay the age of onset as well as the progression of FTD (Petkau and Leavitt, supra; Kao et al., supra). This notion is supported by human genetic studies indicating that a variant of the gene TMEM106B both enhances the levels of progranulin by 25% and delay the age of onset of GRN-associated FTD by 13 years (Nicholson and Rademakers, *Acta Neuropathol.* 132(5):639-651, 2016).

Homozygous GRN mutations have also been reported, although carriers present a vastly different clinical phenotype known as NCL (Batten disease; incidence 1-2.5 in 100,000 live births; Cotman et al., *Curr Neurol Neurosci Rep.* 13(8):366, 2013), which is a lysosomal storage disorder (Smith et al., *Am J Hum Genet.* 90(6):1102-7, 2012; Almeida et al., *Neurobiol Aging.* 41:200.e1-200.e5, 2016). GRN is in fact one of the 14 ceroid-lipofuscinosis neuronal (CLN) genes reported to be linked to NCL and GRNis also known as CLN11 (Kollmann et al., *Biochim Biophys Acta.* 1832 (11):1866-81, 2013). The progranulin variants or fusion proteins described herein may exhibit anti-inflammatory properties and enhanced lysosomal function, either of which may be beneficial in NCL. In some embodiments, the progranulin variants and fusion proteins described herein can be used to treat NCL.

Patients with Gaucher's disease who carry homozygous mutations in the GBA gene have lower levels of progranulin in their serum (Jian et al., *EBioMedicine* 11:127-137, 2016). Parkinson's disease patients with heterozygous mutations in GBA may also have lower levels of progranulin. In some embodiments, the progranulin variants and fusion proteins described herein can be used to treat Gaucher's disease or Parkinson's disease.

Variants in GRN have been linked to AD (Rademakers et al., supra; Brouwers et al., *Neurology.* 71(9):656-64, 2008; Lee et al., *Neurodegener Dis.* 8(4):216-20, 2011; Viswanathan et al., *Am J Med Genet B Neuropsychiatr Genet.* 150B(5):747-50, 2009) and the TDP-43 pathology is common in the brain of AD patients (Youmans and Wolozin, Exp Neurol. 237(1):90-5, 2012). Progranulin gene delivery has also been shown to decrease amyloid burden in mouse models of AD (van Kampen and Kay, *PLoS One.* 12(8): e0182896, 2017). Thus, in some embodiments, the progranulin variants and fusion proteins described herein can be used to treat AD.

NPA and NPB result from mutations in the gene encoding acid sphingomyelinase (SMPD1). NPC results from mutations in the genes involved in cholesterol transport, i.e., NPC1 and NPC2 (Kolter and Sandhoff, *Annu Rev Cell Dev Biol.* 21:81-103, 2005; Kobayashi et al., *Nat Cell Biol.* 1(2):113-8, 1999). In some embodiments, the progranulin variants and fusion proteins described herein can be used to treat NPA, NPB, and/or NPC.

The vast majority of ALS cases present the TDP-43 pathology, which is also shared with patients harboring GRN mutations (Petkau and Leavitt, *Trends Neurosci.* 37(7):388-98, 2014; Rademakers et al., *Nat Rev Neurol.* 8(8):423-34, 2012). Among all ALS cases, GGGGCC repeat expansions within the C9ORF72 gene are the most common cause of ALS and a significant cause of FTD. The average mutation frequencies reported in North American and European populations are 37% for familial ALS, 6% for sporadic ALS, 21% for familial FTD, and 6% for sporadic FTD patients (Rademakers et al., supra). Additionally, the TMEM106B variant that is protective in GRN-associated FTD is also protective in FTD patients harboring repeat expansions in the C9ORF72 gene (van Blitterswijk et al., *Acta Neuropathol.* 127(3):397-406, 2014). In some embodiments, the progranulin variants and fusion proteins described herein can be used to reduce TDP-43 pathology in C9ORF72-associated ALS/FTD, e.g., by promoting lysosomal function and/or decreasing inflammation.

AMD is a degenerative disease and a major cause of blindness in the developed world. It causes damage to the macula, a small spot near the center of the retina and the part of the eye needed for sharp, central vision. The degenerative changes in the eye and loss of vision may be caused by impaired function of lysosomes and harmful protein accumulations behind the retina (Viiri et al., *PLoS One.* 8(7): e69563, 2013). As the disease progresses, retinal sensory cells in the central vision area are damaged, leading to loss of central vision. In some embodiments, the progranulin variants and fusion proteins described herein can be used to treat AMD.

XVI. Therapeutic Methods

A progranulin variant or fusion protein described herein may be used therapeutically to treat a neurodegenerative disease (e.g., FTD, NCL, NPA, NPB, NPC, C9ORF72-associated ALS/FTD, sporadic ALS, AD, Gaucher's disease (e.g., Gaucher's disease types 2 and 3), and Parkinson's disease), atherosclerosis, a disorder associated with TDP-43, AMD, or a progranulin-associated disorder.

A progranulin variant or fusion protein described herein may be administered to a subject at a therapeutically effective amount or dose. The dosages may be varied according to several factors, including the dose frequency, the chosen route of administration, the formulation of the composition, patient response, the severity of the condition, the subject's weight, and the judgment of the prescribing physician. The dosage can be increased or decreased over time, as required by an individual patient. In some embodiments, a patient initially is given a low dose, which is then increased to an efficacious dosage tolerable to the patient.

In various embodiments, a progranulin variant or fusion protein described herein is administered by any route. In some embodiments, the protein is administered by parenteral delivery. In some embodiments, the protein is administered intravenously. In some embodiments, the protein is administered by intraperitoneal delivery.

XVII. Examples

The present disclosure will be described in greater detail by way of specific examples. The following examples are offered for illustrative purposes only and are not intended to limit the disclosure in any manner. Those of skill in the art will readily recognize a variety of noncritical parameters which can be changed or modified to yield essentially the same results. Efforts have been made to ensure accuracy with respect to numbers used (e.g., amounts, temperatures, etc.), but some experimental error and deviation may be present. The practice of the present disclosure will employ, unless otherwise indicated, conventional methods of protein chemistry, biochemistry, recombinant DNA techniques and pharmacology, within the skill of the art. Such techniques are explained fully in the literature. Additionally, it should be apparent to one of skill in the art that the methods for engineering as applied to certain libraries can also be applied to other libraries described herein.

Example 1. Recombinant Fc Dimer:PGRN Fusion Protein Expression and Purification To express the recombinant Fc dimer:PGRN fusion proteins, constructs were expressed via transient transfection of Glutamine Synthetase (GS) knockout Chinese Hamster Ovary (CHO) K1 cells (Horizon Discovery) using PEIMax (MW 40,000, Linear, Polysciences) at a 1:4 ratio of DNA (μg) to PEI (μL). Cells were initially grown and transfected in BalanCD Transfectory CHO (Irvine Scientific) at 37° C. Post transfection, the cell culture temperature was shifted to 32° C., and the duration of the culture was maintained at 5% $CO_2$ and 80% humidity in an orbital shaker (Infors Multitron). A nutrient feed, BalanCD CHO Feed 4 (Irvine Scientific), was added on day 1 of the culture at 20% of the initial culture volume. After 7 days, protein was harvested by centrifugation, followed by filtration using a 0.22 um PES filter.

For fusion proteins expressed in HEK cells, in Expi293 (Thermo-Fisher), cells were transfected at 2×10⁶ cells/mL density with Expifectamine™ 293/plasmid DNA complex according to manufacturer's instructions (Thermo-Fisher). After transfection, cells were incubated at 37° C. with a humidified atmosphere of 6-8% $CO_2$ in an orbital shaker (Infors HT Multitron). On day one post-transfection, Expifectamine™ transfection enhancer 1 and 2 were added to the culture. Media supernatant was harvested by centrifugation after 96-hour post-transfection. The clarified supernatant was supplemented with EDTA-free protease inhibitor (Roche) and was stored at −80° C.

For recombinant fusion protein purification, clarified media supernatant was loaded on a HiTrap MabSelect Prisma Protein A affinity column (GE Healthcare Life Sciences) and washed with 0.5% (v/v) Triton X-100 in PBS buffer pH 7.4 with 0.5 M NaCl). The fusion protein was eluted in 50 mM citrate buffer with 100 mM NaCl, pH 3.5-3.6. Eluate from the affinity column was either (1) loaded on a HiTrap® desalting column (GE Healthcare Life Sciences) for tandem buffer exchange into a final buffer of 1× PBS or (2) neutralized by addition of arginine-succinate buffer (1 M arginine, 685 mM succinic acid, pH 5.0) to adjust the pH of the eluate. For certain fusion proteins, the eluate from the affinity column was further treated by loading onto a cation exchange column (SP HP, HiTrap™) and washing the column with 200 mM NaCl, pH 5.0. Fusion protein was then eluted from the column by applying a gradient of NaCl solution (200 mM to 500 mM) over 20 column volumes. Fractions containing >95% protein were then pooled together. Ammonium sulfate was added to the pooled fractions to a final concentration of about 1 M, after which the solution was loaded into a hydrophobic interaction column (Butyl HP, HiTrap™). The column was washed with 1 M ammonium sulfate in 0.1 M citrate buffer, pH 6.0, and the protein was eluted by applying a gradient of ammonium sulfate (1 M to 0) over 20 column volumes. Pooled fractions containing >95% protein were combined and dialyzed in 10 mM sodium phosphate buffer containing 6% sucrose. Purified protein in 10 mM sodium phosphate, 6% sucrose, pH 6.5 was obtained. Tables 2 and 3 below show the sequences of exemplary fusion proteins.

Figure 1B:
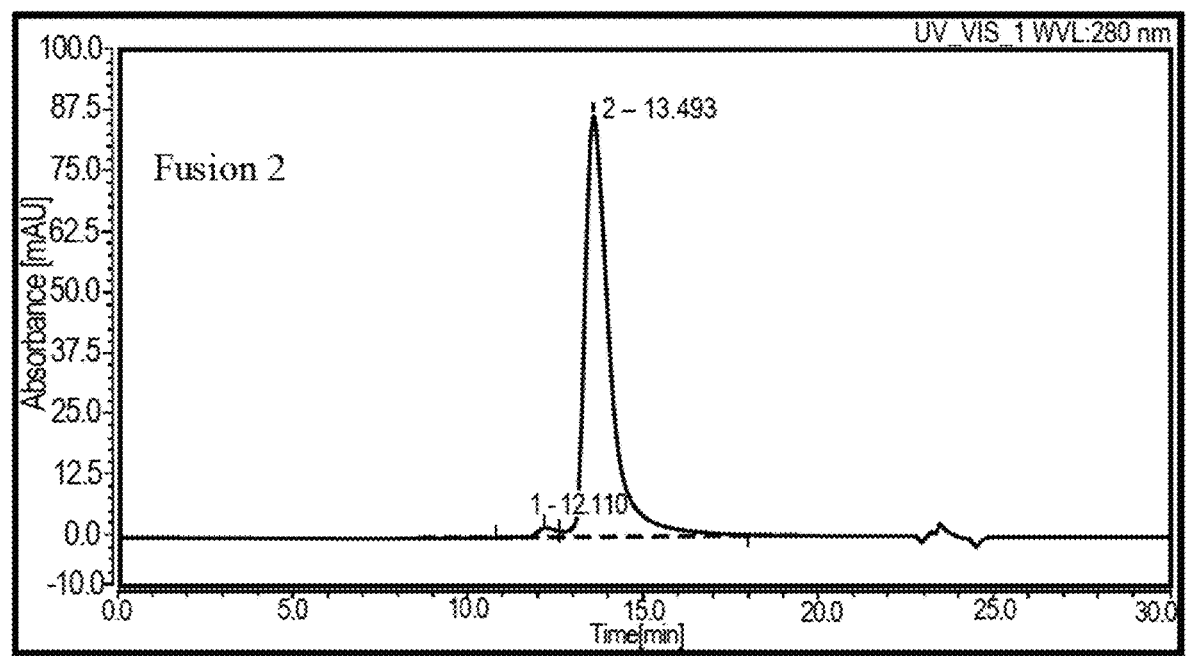

FIGS. 1A and 1B include representative data indicating that the fusion proteins were purified to greater than 98% purity.

TABLE 2

Sequences of Fc Dimer: PGRN Fusion Proteins

| Fc Dimer: PGRN | First Fc Polypeptide | Second Fc Polypeptide-PGRN |
|---|---|---|
| Fusion 1 | SEQ ID NO: 75 | SEQ ID NO: 98 |
| Fusion 2 | SEQ ID NO: 75 | SEQ ID NO: 99 |
| Fusion 3 | SEQ ID NO: 75 | SEQ ID NO: 100 |
| Fusion 4 | SEQ ID NO: 75 | SEQ ID NO: 101 |
| Fusion 5 | SEQ ID NO: 75 | SEQ ID NO: 102 |
| Fusion 6 | SEQ ID NO: 85 | SEQ ID NO: 98 |
| Fusion 7 | SEQ ID NO: 85 | SEQ ID NO: 99 |
| Fusion 8 | SEQ ID NO: 85 | SEQ ID NO: 100 |
| Fusion 9 | SEQ ID NO: 85 | SEQ ID NO: 101 |
| Fusion 10 | SEQ ID NO: 85 | SEQ ID NO: 102 |
| Fusion 11 | SEQ ID NO: 85 | SEQ ID NO: 108 |
| Fusion 32 | SEQ ID NO: 75 | SEQ ID NO: 123 |
| Fusion 34 | SEQ ID NO: 75 | SEQ ID NO: 124 |
| Fusion 36 | SEQ ID NO: 75 | SEQ ID NO: 125 |
| Fusion 37 | SEQ ID NO: 75 | SEQ ID NO: 126 |

TABLE 3

Additional Sequences of Fc Dimer: PGRN Fusion Proteins

| Fc Dimer: PGRN | First Fc Polypeptide | Second Fc Polypeptide-PGRN | | |
|---|---|---|---|---|
| | | Partial hinge + Fc | Linker | PGRN variant |
| Fusion 12 | SEQ ID NO: 85 | SEQ ID NO: 110 | SEQ ID NO: 91 | SEQ ID NO: 111 |
| Fusion 13 | SEQ ID NO: 85 | SEQ ID NO: 110 | SEQ ID NO: 91 | SEQ ID NO: 112 |
| Fusion 14 | SEQ ID NO: 85 | SEQ ID NO: 110 | SEQ ID NO: 91 | SEQ ID NO: 113 |
| Fusion 15 | SEQ ID NO: 85 | SEQ ID NO: 110 | SEQ ID NO: 91 | SEQ ID NO: 114 |
| Fusion 16 | SEQ ID NO: 85 | SEQ ID NO: 110 | SEQ ID NO: 91 | SEQ ID NO: 115 |
| Fusion 17 | SEQ ID NO: 85 | SEQ ID NO: 110 | SEQ ID NO: 91 | SEQ ID NO: 116 |
| Fusion 18 | SEQ ID NO: 85 | SEQ ID NO: 110 | SEQ ID NO: 91 | SEQ ID NO: 117 |
| Fusion 19 | SEQ ID NO: 85 | SEQ ID NO: 110 | SEQ ID NO: 91 | SEQ ID NO: 118 |
| Fusion 20 | SEQ ID NO: 85 | SEQ ID NO: 110 | SEQ ID NO: 91 | SEQ ID NO: 119 |
| Fusion 21 | SEQ ID NO: 85 | SEQ ID NO: 110 | SEQ ID NO: 91 | SEQ ID NO: 120 |
| Fusion 22 | SEQ ID NO: 85 | SEQ ID NO: 110 | SEQ ID NO: 91 | SEQ ID NO: 121 |
| Fusion 23 | SEQ ID NO: 75 | SEQ ID NO: 110 | SEQ ID NO: 91 | SEQ ID NO: 4 |
| Fusion 24 | SEQ ID NO: 75 | SEQ ID NO: 110 | SEQ ID NO: 91 | SEQ ID NO: 5 |
| Fusion 25 | SEQ ID NO: 75 | SEQ ID NO: 110 | SEQ ID NO: 91 | SEQ ID NO: 6 |

TABLE 3-continued

Additional Sequences of Fc Dimer: PGRN Fusion Proteins

| Fc Dimer: PGRN | First Fc Polypeptide | Second Fc Polypeptide-PGRN | | |
|---|---|---|---|---|
| | | Partial hinge + Fc | Linker | PGRN variant |
| Fusion 26 | SEQ ID NO: 75 | SEQ ID NO: 110 | SEQ ID NO: 91 | SEQ ID NO: 7 |
| Fusion 27 | SEQ ID NO: 75 | SEQ ID NO: 110 | SEQ ID NO: 91 | SEQ ID NO: 8 |
| Fusion 28 | SEQ ID NO: 75 | SEQ ID NO: 110 | SEQ ID NO: 91 | SEQ ID NO: 9 |
| Fusion 29 | SEQ ID NO: 75 | SEQ ID NO: 110 | SEQ ID NO: 91 | SEQ ID NO: 10 |
| Fusion 30 | SEQ ID NO: 75 | SEQ ID NO: 110 | SEQ ID NO: 91 | SEQ ID NO: 11 |
| Fusion 31 | SEQ ID NO: 75 | SEQ ID NO: 110 | SEQ ID NO: 91 | SEQ ID NO: 12 |
| Fusion 32 | SEQ ID NO: 75 | SEQ ID NO: 110 | SEQ ID NO: 91 | SEQ ID NO: 13 |
| Fusion 33 | SEQ ID NO: 75 | SEQ ID NO: 110 | SEQ ID NO: 91 | SEQ ID NO: 14 |
| Fusion 34 | SEQ ID NO: 75 | SEQ ID NO: 110 | SEQ ID NO: 91 | SEQ ID NO: 15 |
| Fusion 35 | SEQ ID NO: 75 | SEQ ID NO: 110 | SEQ ID NO: 91 | SEQ ID NO: 16 |
| Fusion 36 | SEQ ID NO: 75 | SEQ ID NO: 110 | SEQ ID NO: 91 | SEQ ID NO: 19 |
| Fusion 37 | SEQ ID NO: 75 | SEQ ID NO: 110 | SEQ ID NO: 91 | SEQ ID NO: 20 |
| Fusion 38 | SEQ ID NO: 75 | SEQ ID NO: 110 | SEQ ID NO: 91 | SEQ ID NO: 21 |
| Fusion 39 | SEQ ID NO: 75 | SEQ ID NO: 110 | SEQ ID NO: 91 | SEQ ID NO: 22 |
| Fusion 40 | SEQ ID NO: 75 | SEQ ID NO: 110 | SEQ ID NO: 91 | SEQ ID NO: 23 |
| Fusion 41 | SEQ ID NO: 75 | SEQ ID NO: 110 | SEQ ID NO: 91 | SEQ ID NO: 24 |
| Fusion 42 | SEQ ID NO: 75 | SEQ ID NO: 110 | SEQ ID NO: 91 | SEQ ID NO: 25 |
| Fusion 43 | SEQ ID NO: 75 | SEQ ID NO: 110 | SEQ ID NO: 91 | SEQ ID NO: 26 |
| Fusion 44 | SEQ ID NO: 75 | SEQ ID NO: 110 | SEQ ID NO: 91 | SEQ ID NO: 30 |
| Fusion 45 | SEQ ID NO: 75 | SEQ ID NO: 110 | SEQ ID NO: 91 | SEQ ID NO: 31 |
| Fusion 46 | SEQ ID NO: 75 | SEQ ID NO: 110 | SEQ ID NO: 91 | SEQ ID NO: 32 |
| Fusion 47 | SEQ ID NO: 75 | SEQ ID NO: 110 | SEQ ID NO: 91 | SEQ ID NO: 33 |
| Fusion 48 | SEQ ID NO: 75 | SEQ ID NO: 110 | SEQ ID NO: 91 | SEQ ID NO: 34 |
| Fusion 49 | SEQ ID NO: 75 | SEQ ID NO: 110 | SEQ ID NO: 91 | SEQ ID NO: 35 |
| Fusion 50 | SEQ ID NO: 75 | SEQ ID NO: 110 | SEQ ID NO: 91 | SEQ ID NO: 36 |
| Fusion 51 | SEQ ID NO: 75 | SEQ ID NO: 110 | SEQ ID NO: 91 | SEQ ID NO: 37 |
| Fusion 52 | SEQ ID NO: 75 | SEQ ID NO: 110 | SEQ ID NO: 91 | SEQ ID NO: 38 |
| Fusion 53 | SEQ ID NO: 75 | SEQ ID NO: 110 | SEQ ID NO: 91 | SEQ ID NO: 39 |
| Fusion 54 | SEQ ID NO: 75 | SEQ ID NO: 110 | SEQ ID NO: 91 | SEQ ID NO: 40 |
| Fusion 55 | SEQ ID NO: 75 | SEQ ID NO: 110 | SEQ ID NO: 91 | SEQ ID NO: 41 |
| Fusion 56 | SEQ ID NO: 75 | SEQ ID NO: 110 | SEQ ID NO: 91 | SEQ ID NO: 42 |
| Fusion 57 | SEQ ID NO: 75 | SEQ ID NO: 110 | SEQ ID NO: 91 | SEQ ID NO: 43 |
| Fusion 58 | SEQ ID NO: 75 | SEQ ID NO: 110 | SEQ ID NO: 91 | SEQ ID NO: 44 |
| Fusion 59 | SEQ ID NO: 75 | SEQ ID NO: 110 | SEQ ID NO: 91 | SEQ ID NO: 45 |
| Fusion 60 | SEQ ID NO: 75 | SEQ ID NO: 110 | SEQ ID NO: 91 | SEQ ID NO: 46 |
| Fusion 61 | SEQ ID NO: 75 | SEQ ID NO: 110 | SEQ ID NO: 91 | SEQ ID NO: 47 |
| Fusion 62 | SEQ ID NO: 75 | SEQ ID NO: 110 | SEQ ID NO: 91 | SEQ ID NO: 48 |
| Fusion 63 | SEQ ID NO: 75 | SEQ ID NO: 110 | SEQ ID NO: 91 | SEQ ID NO: 49 |
| Fusion 64 | SEQ ID NO: 75 | SEQ ID NO: 110 | SEQ ID NO: 91 | SEQ ID NO: 50 |
| Fusion 65 | SEQ ID NO: 75 | SEQ ID NO: 110 | SEQ ID NO: 91 | SEQ ID NO: 51 |
| Fusion 66 | SEQ ID NO: 75 | SEQ ID NO: 110 | SEQ ID NO: 91 | SEQ ID NO: 52 |
| Fusion 67 | SEQ ID NO: 75 | SEQ ID NO: 110 | SEQ ID NO: 91 | SEQ ID NO: 53 |
| Fusion 68 | SEQ ID NO: 75 | SEQ ID NO: 110 | SEQ ID NO: 91 | SEQ ID NO: 54 |
| Fusion 69 | SEQ ID NO: 75 | SEQ ID NO: 110 | SEQ ID NO: 91 | SEQ ID NO: 56 |
| Fusion 70 | SEQ ID NO: 75 | SEQ ID NO: 110 | SEQ ID NO: 91 | SEQ ID NO: 57 |
| Fusion 71 | SEQ ID NO: 75 | SEQ ID NO: 110 | SEQ ID NO: 91 | SEQ ID NO: 127 |
| Fusion 72 | SEQ ID NO: 75 | SEQ ID NO: 110 | SEQ ID NO: 91 | SEQ ID NO: 128 |

Example 2. Top-Down Mass Spectrometry Analysis of C-Terminus Cleavage of Fc Dimer:PGRN Fusion Proteins Intact Fc Dimer:PGRN fusion proteins expressed and purified from CHO cells were measured by peptide-mapping or by top-down mass spectrometry using a Thermo Ultimate 3000 UHPLC coupled to Exactive plus EMR Mass Spectrometer. For comparison, a fusion protein containing wild-type PGRN sequence (Fusion 11) expressed in HEK293 cells or CHO cells was also evaluated.

Top-Down Mass Spectrometry Analysis

Approximately 10 μg of sample in PBS buffer or formulation buffer (10 mM phosphate buffer, pH 6.5, 6% sucrose) was injected for analysis. Liquid chromatography (LC) was performed with a Thermo MabPAC RP column (4 μm, 2.1×50 mm, P/N88648) at a column temperature of 55° C. and using a mobile phase (A) of 0.1 Trifluoroacetic acid (TFA) in $H_2O$ and mobile phase (B) of acetonitrile at a flow rate of 0.3 mL/minute. The gradient started at 20% (B) and ramped up to 70% (B) before returning to 20% (B). Detection was carried out using UV/Vis at 214 nm and 280 nm. The EMR Mass Spectrometer was operated with two All Ion Fragmentation Analysis (AIF) scans.

First AIF setting: scan range 350-5000 m/z. CE: 25. In-source CID 90 ev. Resolution setting: 17,500 and AGC target 3e6, maximum IT: 200 ms. Microscans: 1.

Second AIF setting: scan range 350-5000 m/z. CE: 200. In-source CID 90 ev. Resolution setting: 35,000 and AGC target 1e6, maximum IT: 200 ms. Microscans: 5.

Electrospray ionization (ESI) source conditions: Sheath gas flow rate: 25, Aux Gas rate: 4. Spray voltage 3 kV, capillary temp 325° C., S-lens RF level 125. Aux gas heater temp 300° C. EMR mode on. Trapping gas pressure setting 2.0.

The top-down gas phase reaction induced cleavage of the C-terminus of PGRN between amino acids of aspartic acid (D) and proline (P) (which correspond to position 569 and position 570 of SEQ ID NO:2), which generated intact peptides 7 amino acids in length with sequences corresponding to the distinct C-terminus sequences of the different progranulin variants. The cleaved peptides represented sequential loss from the C terminus. The peptide XIC peaks were extracted using 20 ppm (part per million), and the area under curve (AUC) was used to calculate the percentage of the intact protein against total protein.

Peptide-Mapping Analysis

To prepare the samples, approximately 40 µg of sample in 50 mM bicarbonate (pH 7.8) was incubated with AspN (New England Biolabs, Cat. P8014S) at an enzyme:protein ratio of 1:40 (w/w) for 30 minutes at 37° C. Formic acid (1%) was added to quench the reaction, and the sample was transferred to LCMS vials for analysis. Peptide mapping analyses were performed by liquid chromatography on UHPLC Vanquish (Thermo Scientific, CA, USA) coupled to UV/Vis and Q Exactive Orbitrap electrospray ionization mass spectrometer (Thermo Scientific, CA, USA). For each analysis, 25 µL of sample was injected on a CSH C18 1.7 µm, 2.1×150 mm column (Waters) using a flow rate of 0.20 mL/min at 40° C. under positive ionization mode. Mobile phase A consisted of water with 0.1% formic acid, while mobile phase B consisted of acetonitrile with 0.1% formic acid. The gradient started at 1% (B) and ramped up in three steps from 1% to 10% (B), from 10% to 40% (B), and from 40% to 70% (B) over a 50-minute period before returning to 1% (B). The UV/Vis trace was recorded at wavelengths of 280 and 214 nm, and data was collected using Full MS-ddMS2 acquisition under positive mode. The peak areas were used to calculate the percentages of intact and cleaved peptides.

Table 4 below shows that greater than 95% of Fusion 1 has an intact C-terminus and greater than 80% of Fusion 2 has an intact C-terminus. The presence of clipped fusion protein (e.g., fusion protein missing between 1 and 3 amino acids at the C-terminus) was less than 5% (Fusion 1) and less than 20% (Fusion 2). In Table 4, "-L," "-IL," "-PIL," "-FL," and "-PFL" refers to the terminal amino acids being cleaved from the fusion proteins. Data for additional fusion proteins can be found in Tables 8A and 8B. As a point of reference, about 95% of fusion protein containing wild-type PGRN (Fusion 11) remained intact when expressed in HEK cells, while 7% of Fusion 11 remained intact when expressed in CHO cells.

TABLE 4

| | Fusion 1 (PIL) | | Fusion 2 (PFL) | |
|---|---|---|---|---|
| | Area Counts | % Relative Area | Area Counts | % Relative Area |
| Intact | 50114249 | 95.6 | Intact | 41831754 | 80.3 |
| -L | 2206596 | 4.2 | -L | 9100294 | 17.5 |
| -IL | 12728 | 0.0 | -FL | 529791 | 1.0 |
| -PIL | 76847 | 0.1 | -PFL | 608392 | 1.2 |

Example 3. Thermal Stability and Freeze-Thaw Stability

The thermal stability of fusion proteins was measured by a Prometheus instrument (NanoTemper). Intrinsic fluorescence is used to monitor the protein during temperature ramp-up in order to generate a melting profile ($T_m$, $T_{onset}$). The results for Fusion 1 and Fusion 2 are illustrated in FIG. 2.

Figure 3:
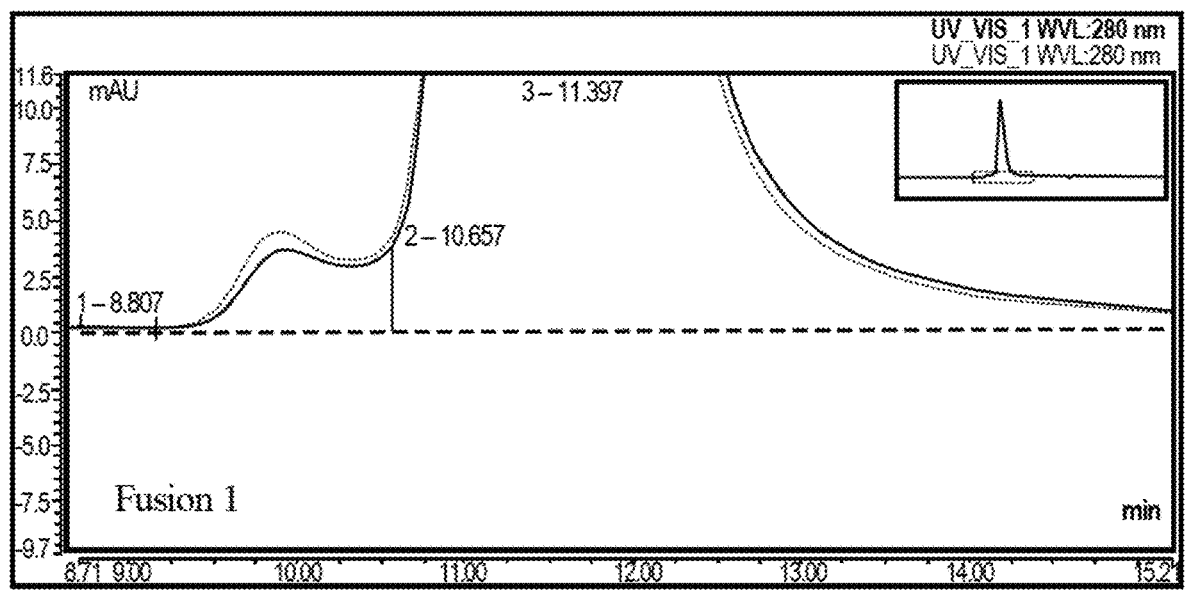
FIG. 3 includes chromatograms illustrating the freeze-thaw stability of exemplary fusion proteins as disclosed herein.
Figure 3:
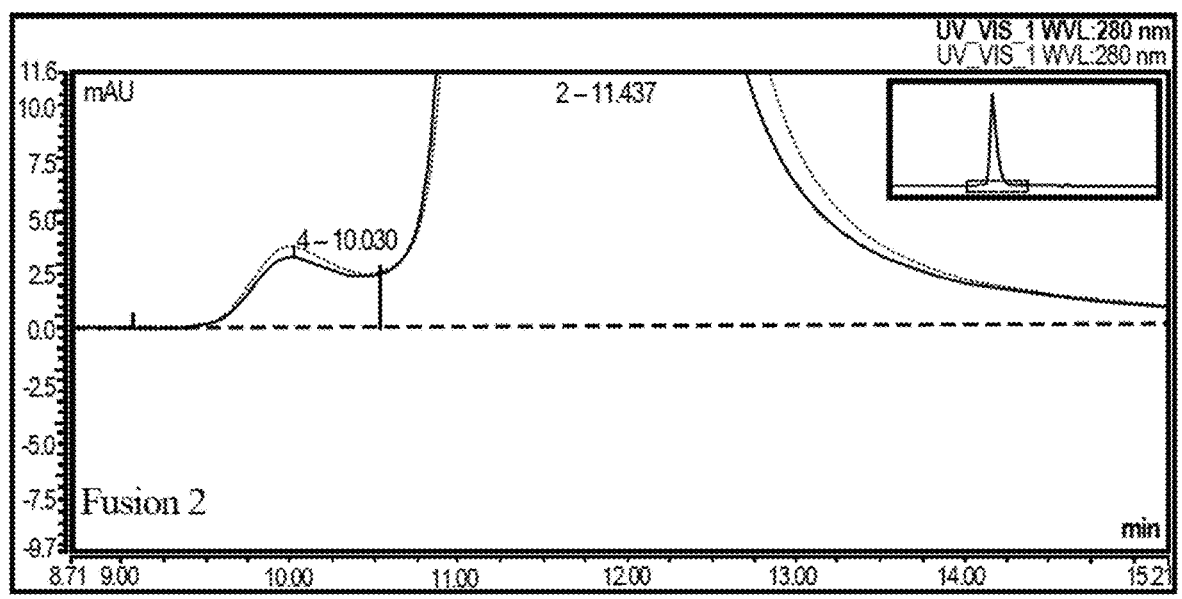
Figure 4:
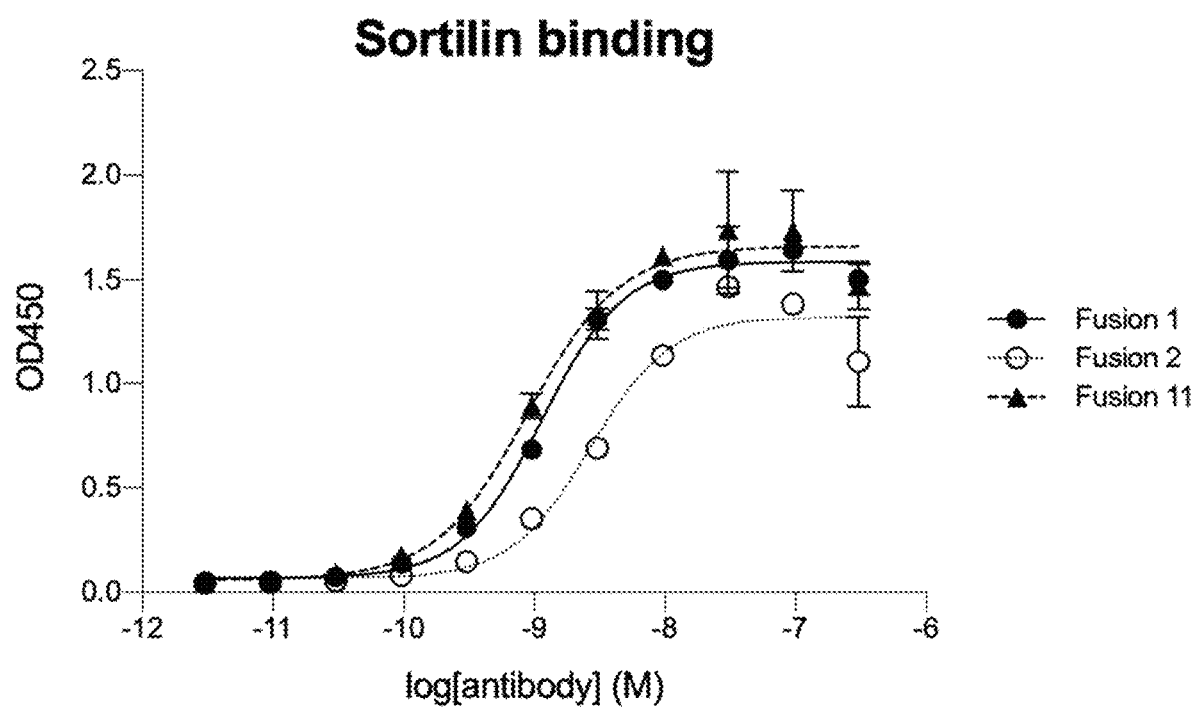
FIG. 4 is a graph illustrating sortilin binding of exemplary fusion proteins disclosed herein.

Fusion proteins were also subjected to freeze-thaw analysis. Briefly, a protein sample was incubated on dry ice for about 10 minutes, after which the sample was transferred to room temperature and incubated for 30 minutes. The freeze-thaw cycle was repeated five times, after which the samples were brought to 4° C. and analyzed using SEC-HPLC (Waters BEH SEC column, 200 Å 1.7 µm, 30 cm, with a mobile phase of 2× PBS with 10% (v/v) ethanol, 0.2 mL/min flow rate). The results for Fusion 1 and Fusion 2 are illustrated in FIG. 3.

The results obtained for Fusion 1 and Fusion 2 (FIGS. 2 and 3) indicate that the two fusion proteins had good thermal stability and good freeze-thaw stability.

Example 4. Recombinant Fc Dimer:PGRN Fusion Protein Binding to Sortilin

All surface plasmon resonance (SPR) experiments were performed on a GE Healthcare Biacore 8K instrument with Series S Sensor Chip CM5 and HBS-EP+ running buffer at 25° C. To measure the binding affinity of the Fc Dimer:PGRN fusion proteins for sortilin, the fusion proteins were captured using a sensor chip that was immobilized with a GE Healthcare Human Antibody Capture Kit (for human sortilin) or a Biacore™ Sensor Chip Protein A (for cynomolgus and mouse sortilin, Cytiva, #29127555). Multi-cycle kinetics were used with a 3-fold concentration series of sortilin analyte ranging from 0.4 nM-100 nM, allowing for 300 seconds of contact time, 600 seconds of dissociation time, and a flow rate of 30 µL/min. A 1:1 kinetics model was used to evaluate the binding kinetics of sortilin binding. The Biacore binding data of Fc dimer:PGRN fusion proteins to sortilin is shown in Tables 5-7 below. Sortilin analyte was sourced as follows: human sortilin (R&D Systems); mouse sortilin (R&D Systems); cynomolgus sortilin (in-house, based on UniProt A0A2K5VHG2).

As illustrated in Table 5, Fusion 1 exhibited stronger affinity for human sortilin relative to Fusion 2. With respect to a fusion protein containing wild-type PGRN (Fusion 11) expressed in HEK cells, Fusion 1 illustrated a smaller loss of binding affinity for human sortilin (approximately 3-fold) than Fusion 2 (approximately 14-fold). The loss of human sortilin binding affinity appears to result from faster off-rate kinetics for both Fusion 1 and Fusion 2 relative to the wild-type PGRN fusion protein. With respect to wild-type PGRN fusion protein (Fusion 11) expressed in HEK cells, Fusion 1 illustrated about the same binding affinity for mouse sortilin and about a 2- to 3-fold weaker binding affinity for cynomolgus sortilin.

TABLE 5

Human sortilin binding

| Fusion Protein | $k_a$ (1/Ms) | $k_d$ (1/s) | $K_D$ (M) | Fold-difference from Fusion 11 (HEK) |
|---|---|---|---|---|
| Fusion 11 (HEK) | 1.08E+05 | 1.66E−03 | 1.53E−08 | 1.0 |
| Fusion 1 (CHO) | 9.59E+04 | 4.66E−03 | 4.85E−08 | 3.2 |
| Fusion 2 (CHO) | 8.50E+04 | 1.82E−02 | 2.14E−07 | 14.0 |

TABLE 6

Mouse sortilin binding

| Fusion Protein | $k_a$ (1/Ms) | $k_d$ (1/s) | $K_D$ (M) |
|---|---|---|---|
| Fusion 11 (HEK) | 3.87 X 10$^4$ | 2.94 X 10$^{-3}$ | 7.61 X 10$^{-8}$ |
| Fusion 1 (CHO) | 2.03 X 10$^5$ | 1.38 X 10$^{-2}$ | 6.38 X 10$^{-8}$ |

TABLE 7

Cynomolgus monkey sortilin binding

| Fusion Protein | $k_a$ (1/Ms) | $k_d$ (1/s) | $K_D$ (M) |
|---|---|---|---|
| Fusion 11 (HEK) | 5.38 X 10⁴ | 1.43 X 10⁻³ | 2.65 X 10⁻⁸ |
| Fusion 1 (CHO) | 4.49 X 10⁴ | 2.96 X 10⁻³ | 6.58 X 10⁻⁸ |

Sortilin binding of additional fusion proteins was analyzed by SPR (described supra) or by a standard colorimetric ELISA assay that measured the binding of Fc dimer:PGRN fusion proteins to immobilized sortilin. For measurement by ELISA, recombinant His-tagged sortilin (R&D Systems, Cat. 3154-ST-050) was immobilized on a Nickel-coated 96-well plate. Fusion proteins containing a mixture of intact and C-terminal cleaved protein ("% intact" in Tables 8A and 8B) were diluted in 3% BSA/TBST and added to the coated wells in serial dilutions. After incubation with the fusion proteins at room temperature for two hours, the wells were washed with TBST. Bound fusion proteins were detected by incubation at room temperature for one hour with an anti-human IgG antibody (goat anti-human IgG HRP antibody, Jackson ImmunoResearch Cat. 109-035-088) diluted in 3% BSA/TBST. After incubation with detection antibody, the wells were washed with TBST and incubated with TMB solution (Surmodics, Cat. TMBW-1000-01) for five minutes. The development reaction was stopped with 450 nM Stop solution (Surmodics, Cat. LSTP-1000-01), and absorbance was measured at 450 nm using a BioTek Synergy Plate Reader (Model Neo2). Results for exemplary fusion proteins are provided in Tables 8A and 8B. All fusion proteins listed in Tables 8A and 8B were expressed from CHO cells except where indicated.

TABLE 8A

| Fusion Protein | QLL replaced with | % Intact (top down MS) | % Intact (peptide mapping) | Sortilin EC50 (nM) (ELISA) | Fold-difference in EC50 |
|---|---|---|---|---|---|
| Fusion 11 (HEK) | — | 95% | — | 2.8 | 1.0 |
| Fusion 11 (CHO) | — | 7% | — | 60 ± 12.7 | 21.0 |
| Fusion 6 | PIL | 98% | — | 13.5 | 4.8 |
| Fusion 7 | PFL | 87% | — | 14.3 | 5.1 |
| Fusion 8 | QQL | 59% | — | 19.1 | 6.8 |
| Fusion 9 | VVL | 39% | — | 18.6 | 6.6 |
| Fusion 10 | VTL | 29% | — | 23.9 | 8.5 |
| Fusion 12 | NIL | 3% | — | 34.4 | 12.3 |
| Fusion 13 | LLL | <1% | — | 56.5 | 20.2 |
| Fusion 14 | PLL | <1% | — | 55 | 19.6 |
| Fusion 15 | PRL | <1% | — | 120 | 42.9 |
| Fusion 16 | YIL | — | 0.6% | >100 | >50 |
| Fusion 17 | VLL | — | 2.5% | >100 | >50 |
| Fusion 18 | VIV | — | 35% | >100 | >50 |
| Fusion 19 | FIL | — | 4.4% | >100 | >50 |
| Fusion 20 | MLL | — | 0.7% | >100 | >50 |
| Fusion 21 | QLLG (SEQ ID NO: 142) | 0% | — | >100 | >50 |
| Fusion 22 | QLLGK (SEQ ID NO: 143) | 0% | — | >100 | >50 |

TABLE 8B

| Fusion Protein | QLL replaced with | % Intact (peptide mapping) | Sortilin $K_D$ (M) (SPR) | Fold-difference in $K_D$ |
|---|---|---|---|---|
| Fusion 11 (HEK) | — | 85.8% | 9.70E−09 | 1.0 |
| Fusion 1 | PIL | 91.0% | 3.27E−08 | 3.4 |
| Fusion 23 | PHL | — | 5.18E−08 | 5.3 |
| Fusion 24 | PKL | 38.0% | 1.10E−08 | 1.1 |
| Fusion 25 | PDL | — | 4.88E−08 | 5.0 |
| Fusion 26 | PEL | 51.4% | 2.98E−08 | 3.1 |
| Fusion 27 | PSL | — | 7.96E−08 | 8.2 |
| Fusion 28 | PTL | — | 5.51E−08 | 5.7 |
| Fusion 29 | PNL | — | 1.04E−07 | 10.7 |
| Fusion 31 | PGL | — | 4.67E−08 | 4.8 |
| Fusion 32 | PPL | 89.70% | 9.30E−09 | 1.0 |
| Fusion 34 | PYL | 77.8% | 2.62E−08 | 2.7 |
| Fusion 35 | PVL | — | 4.57E−08 | 4.7 |
| Fusion 36 | QRL | 64.7% | 1.24E−08 | 1.3 |
| Fusion 37 | QHL | 62.6% | 1.17E−08 | 1.2 |
| Fusion 38 | QKL | 62.7% | 1.57E−08 | 1.6 |
| Fusion 39 | QDL | — | 4.04E−08 | 4.2 |
| Fusion 41 | QNL | 36.5% | 2.68E−08 | 2.8 |
| Fusion 42 | QPL | — | 6.25E−08 | 6.4 |
| Fusion 52 | EFL | 0.00% | 6.84E−09 | 0.7 |
| Fusion 54 | TFL | 0.0% | 1.66E−08 | 1.7 |
| Fusion 60 | RQL | 0.10% | 7.75E−09 | 0.8 |
| Fusion 62 | KQL | 2.4% | 1.91E−08 | 2.0 |
| Fusion 68 | YQL | 0.60% | 8.81E−09 | 0.9 |
| Fusion 70 | QLLLRQLL (SEQ ID NO: 60) | 5.0% | 1.19E−08 | 1.2 |

Fusions 30, 33, 40, 43-51, 53, 55-59, 61, 62-67, 69, 71, and 72 exhibited little to no sortilin binding as measured by SPR.

Fusion 1 and Fusion 2 were also assayed by surface plasmon resonance (SPR) for binding to human TfR. The surface plasmon resonance (SPR) experiments were performed on a GE Healthcare Biacore 8K instrument with Series S Sensor Chip CM5 and HBS-EP+ running buffer at 25° C. To measure the binding affinity of the fusion proteins for hTfR, the sensor chip was immobilized with streptavidin and biotinylated-AviTag-hTfR was captured. Single-cycle kinetics was used with a 3-fold concentration series of fusion protein analyte ranging from 25 nM-2 µM, allowing for 80 seconds of contact time, 180 seconds of dissociation time, and a flow rate of 30 µL/min. A steady-state affinity model was used to demonstrate that the fusion proteins were capable of binding hTfR with an affinity of from about 50 nM to 150 nM.

Example 5. In Vitro Functional Assay

Figure 5:
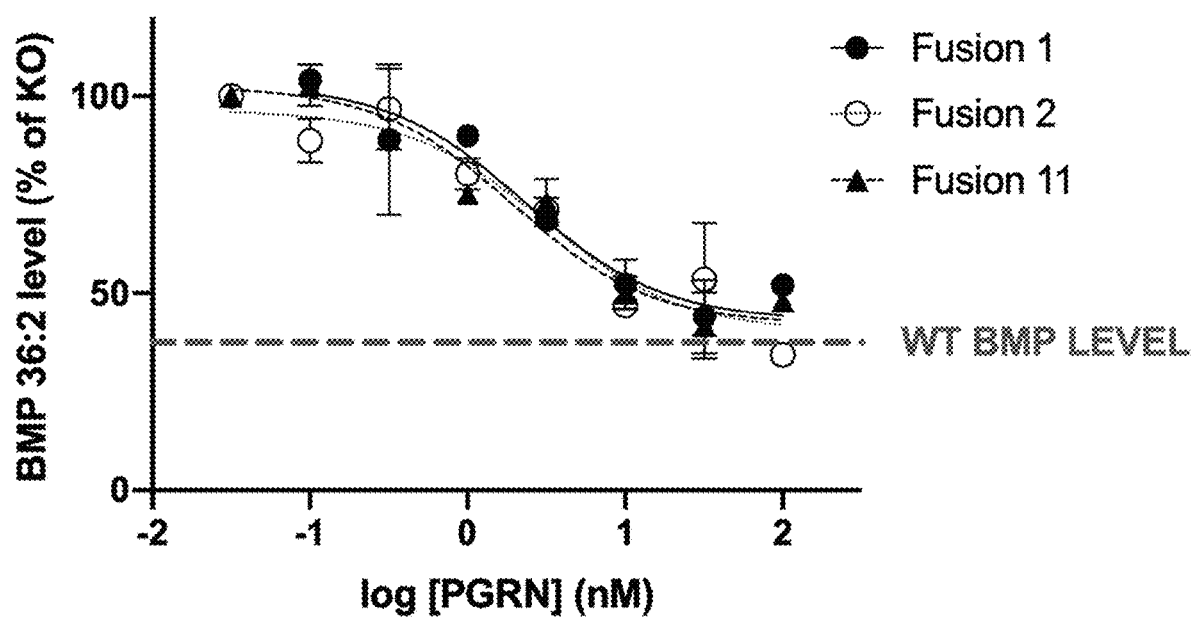
FIG. 5 is a graph illustrating that exemplary fusion proteins as disclosed herein can reduce BMP levels in vitro in cultured cells obtained from bone marrow of GRN KO/hTfR.KI mice.

BMDMs were derived in vitro from bone marrow of GRN KO/hTfR.KI mice (described below) using a similar method as in Trouplin et al. *J. Vis. Exp.* 2013 (81) 50966, but recombinant M-CSF was added directly to the cell growth media to induce differentiation. The BMDMs were treated for 48 hours with semi-log titration of Fusion 11, Fusion 1, and Fusion 2. Cellular lipids were extracted via addition of methanol containing an internal standard mixture and BMP abundance was measured by liquid chromatography-mass spectrometry (LC-MS/MS) on a Q-trap 6500 (SCIEX). GRN KO/hTfR.KI BMDMs had about 2.5-fold increase in BMP 36:2 relative to GRN WT/hTfR.KI BMDMs. Both Fusion 1 and Fusion 2 rescued BMP accumulation in a dose-dependent manner with comparable efficacy (FIG. 5). Relative to a fusion protein containing wild-type PGRN (Fusion 11), Fusion 1 illustrated very similar in vitro potency.

Liquid Chromatography-Mass Spectrometry

BMP analyses were performed by liquid chromatography (Shimadzu Nexera $X_2$ system, Shimadzu Scientific Instrument, Columbia, Md., USA) coupled to electrospray mass spectrometry (Sciex 6500+ QTRAP, Sciex, Framingham, Mass., USA). For each analysis, 5 μL of sample was injected onto a BEH amide 1.7 μm, 2.1×150 mm column (Waters Corporation, Milford, Mass., USA) using a flow rate of 0.40 mL/min. at 55° C. Mobile phase A consisted of water with 10 mM ammonium formate+0.1% formic acid. Mobile phase B consisted of acetonitrile with 0.1% formic acid. The gradient was programmed as follows: 0.0-1.0 min. at 95% B; 1.0-7.0 min. to 50% B; 7.0-7.1 min. to 95% B; and 7.1-12.0 min. at 95% B. Electrospray ionization was performed in the negative-ion mode using the following settings: curtain gas at 25; collision gas was set at medium; ion spray voltage at −4500; temperature at 600; ion source gas 1 at 50; ion source gas 2 at 60; collision energy at −50, CXP at −15; DP at −60; EP at −10; dwell time at 20 ms. Data acquisition was performed using Analyst 1.6.3 (Sciex) in multiple reaction monitoring mode (MRM) with acquisition parameters similar to that described previously (Ullman et al. 2020. *Sci Transl Med* 12(545):eaay1163). BMP species were detected using the MRM transition parameters. BMP species were quantified using BMP(14:0_14:0) as the internal standard. BMP species were identified based on their retention times and MRM properties. Quantification was performed using MultiQuant 3.02 (Sciex) after correction for isotopic overlap. BMP species were normalized to either total protein amount, tissue weight or biofluid volume. Protein concentration was measured using the bicinchoninic acid (BCA) assay (Pierce, Rockford, Ill., USA).

Precursor (Q1) [M-H]⁻ and product ion (Q3) m z transitions were used to measure BMP species. Abbreviations are used herein to refer to species with two side-chains, where the structures of the fatty acid side chains are indicated within parentheses in the BMP format (e.g., BMP(18:1_18:1)). The numerals follow the standard fatty acid notation format of number of fatty acid carbon atoms: number of double bonds. Alternatively the BMP species can be referred to generically according to the total number of carbon atoms: total number of double bonds; species having similar values can be distinguished by their Q1 and Q3 values.

Example 6. Fusion Proteins Cross the BBB and Correct Relevant Pharmacodynamic Endpoints in GRN KO/hTfR.KI Mice Fusion 1 (Table 2) was injected via the tail vein into GRN KO mice (Jackson Laboratory, Stock No. 013175) crossed with hTfR KI mice (GRN KO/hTfR.KI mice) to test its ability to cross the BBB. hTfR KI mice are described in International Patent Publication No. WO2018152285. To generate GRN KO/hTfR.KI mice, in the first round of breeding, GRN heterozygous (GRN HET) mice were crossed to the TfR$^{ms/hu}$ KI homozygous (TfR$^{ms/hu}$.KI HOM) mice to generate GRNHET×TfR$^{ms/hu}$.KI HET progeny. The GRN HET×TfR$^{ms/hu}$.KI HET mice were then crossed to the TfR$^{ms/hu}$.KI HOM mice to get GRN HET×TfR$^{ms/hu}$.KI HOM progeny in this second round. In the third and final round of breeding, GRN HET×TfR$^{ms/hu}$.KI HOM mice were crossed to GRN HET×TfR$^{ms/hu}$.KI HOM mice to generate the final GRN KO×TfR$^{ms/hu}$.KI HOM mice that were used in this study.

2-3 months old GRN KO/hTfR.KI mice were dosed with a single dose of sterile saline (vehicle) or Fusion 1 at 0.5, 1.5, 5, or 15 mg/kg intravenously via the tail vein. Mice were bled by submandibular bleed at 3 days post-dose for plasma isolation. At 7 days post-dose, the mice were sedated with avertine, and a cardiac puncture was performed to collect whole blood for plasma isolation. Animals were transcardially perfused with chilled 1× PBS at a rate of 5 mL/minute for 5-8 minutes, or until the livers were cleared of blood. A 100 mg portion of the liver and the left hemisphere of the brain were collected. Blood samples were centrifuged at 1000×g at 4° C., after which the top plasma layer was removed, snap frozen on dry ice, and stored at or below −80° C. until analysis as described below. All tissue samples were immediately snapped frozen on dry ice and stored at or below −80° C. until analysis as described below.

TABLE 9

Study Design/Experimental Groups

| Molecule | Cell Line | Genotype | Dose (mg/kg) | N/group |
|---|---|---|---|---|
| Saline | N/A | TfR.KI | N/A | 8 |
| Saline | N/A | GRN KO/TfR.KI | N/A | 6 |
| Fusion 1 | CHO | GRN KO/TfR.KI | 0.5 | 6 |
| Fusion 1 | CHO | GRN KO/TfR.KI | 1.5 | 6 |
| Fusion 1 | CHO | GRN KO/TfR.KI | 5 | 6 |
| Fusion 1 | CHO | GRN KO/TfR.KI | 15 | 6 |

To measure fusion protein content in tissue samples, the tissue samples were weighed and homogenized in 10× volume by weight cell lysis buffer (Cell Signaling Technologies; 20 mM Tris-HCl pH 7.5, 150 mM NaCl, 1 mM $Na_2EDTA$, 1 mM EGTA, 1% Triton, 2.5 mM sodium pyrophosphate, 1 mM beta-glycerophosphate, 1 mM $Na_3VO_4$, and 1 μg/mL leupeptin) supplemented with 1× protease inhibitor (Roche) and 1× phosphatase inhibitor (Roche). Samples were homogenized using the TissueLyzer with 3 mm metal beads for 2×3 min at 29 Hz. Following homogenization, samples were spun at maximum speed on the tabletop centrifuge for 20 minutes at 4° C. Supernatant was transferred to new tubes, and a portion of supernatant was analyzed by Fc-PGRN ELISA assay (Fc capture and PGRN detection ELISA) and Fc-Fc ELISA assay (Fc capture and Fc detection ELISA).

BMP analysis on samples was carried out as described in Example 5.

Soluble TREM2 (sTREM2) levels were measured as follows: An MSD GOLD 96w small spot streptavidin plate (MSD L45SA) was prepared for Trem2 assay by coating with 1 μg/mL biotinylated sheep anti-mouse antibody (R&D Systems BAF1729) overnight at 4° C. The next day, the MSD plate was rinsed with tris buffered saline with triton (TBST) and blocked for two hours using 3% bovine serum albumin in TBST, while shaking at 600 rpm. The MSD plate was again rinsed again with TBST, and brain lysates were diluted 5× in blocking solution and added to the MSD plate to incubate for 1 hour at 600 rpm. Following the next TBST rinse, sulfotagged sheep anti-mouse antibody (R&D Systems AF1729) was added to the plate and incubated for 1 hour, again at 600 rpm, and a final rinse was conducted before adding 2× MSD read buffer diluted in water. The plate was then read using the MSD Meso Sector S600. The Trem2 signal was normalized to the protein concentration and plotted with GraphPad Prism.

Figure 6A:
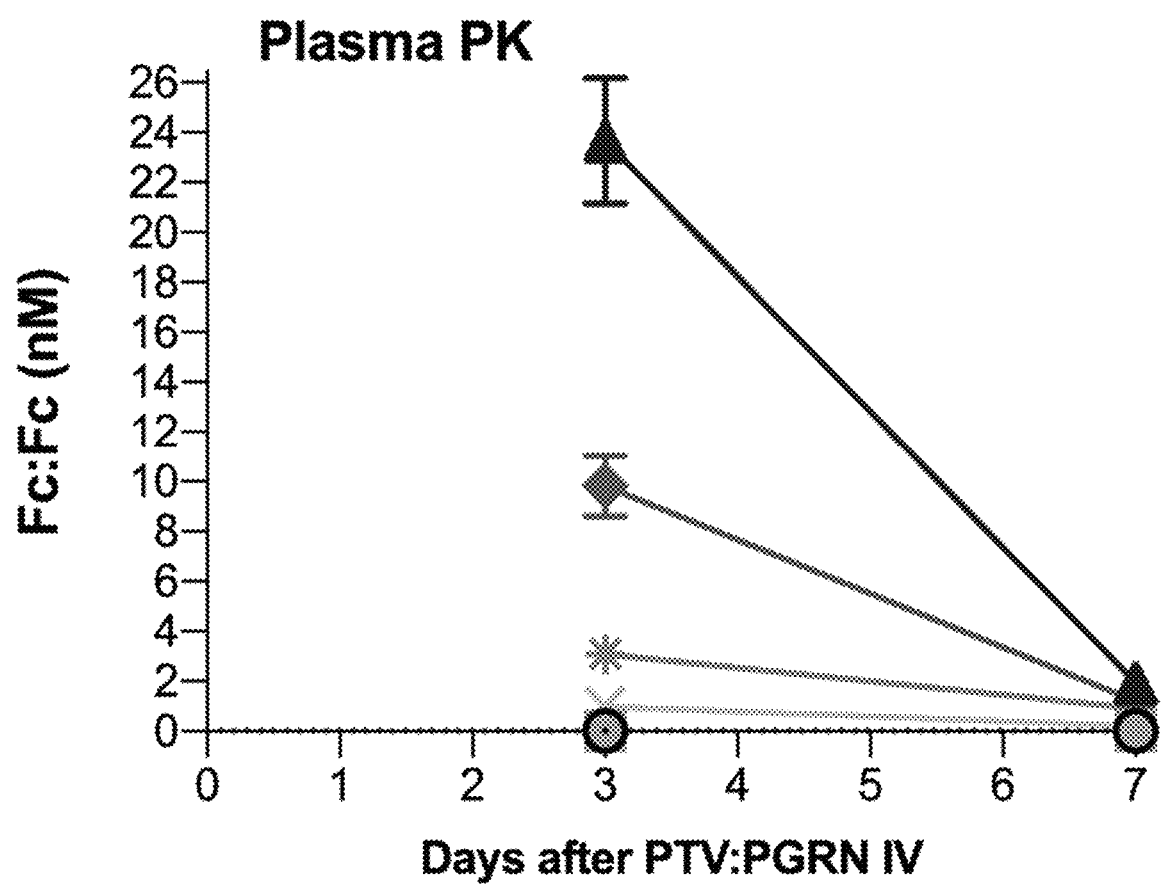
FIGS. 6A-6C show representative plots of protein concentrations of an exemplary fusion protein disclosed herein in plasma (7-day period) and in brain and liver (7 days post-dose) of GRN KO/hTfR.KI mice.
Figure 6B:
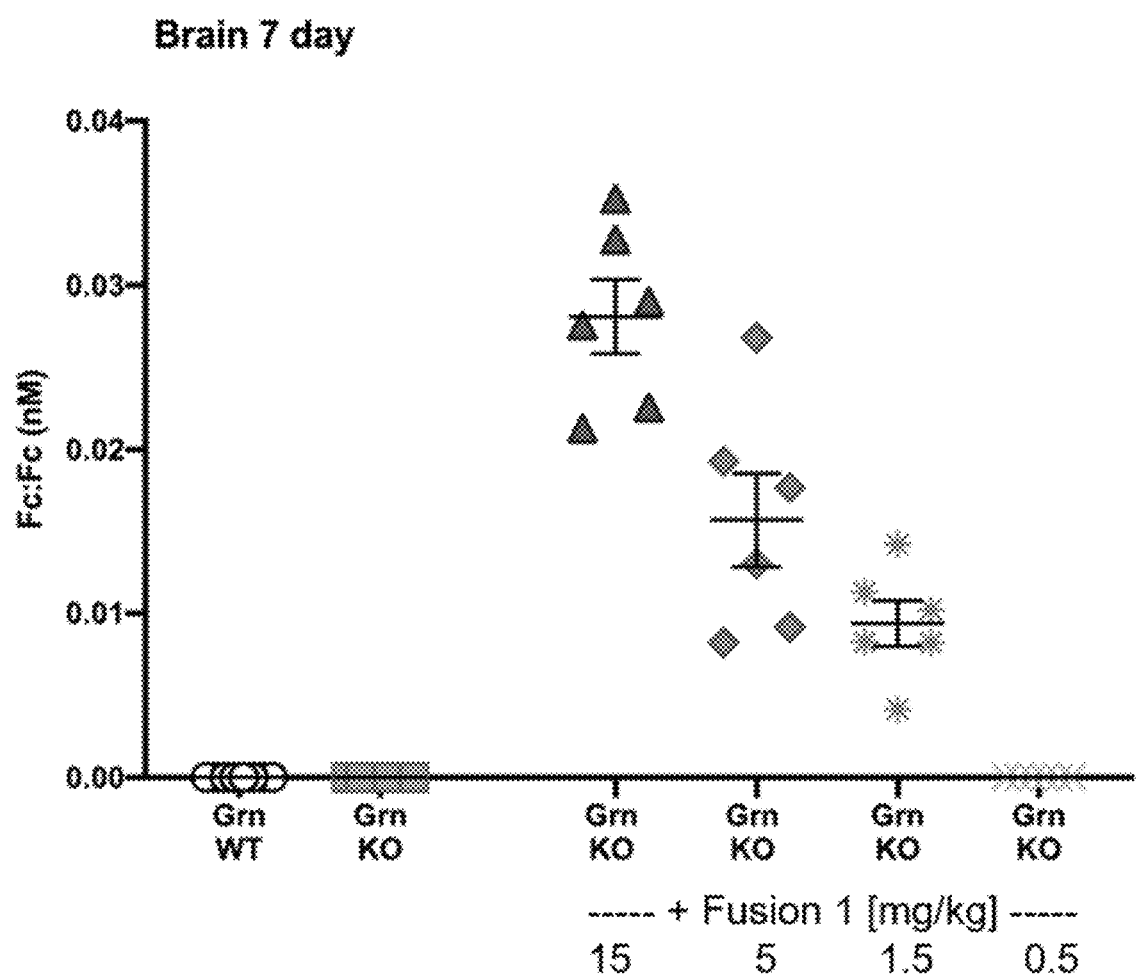
Figure 6C:
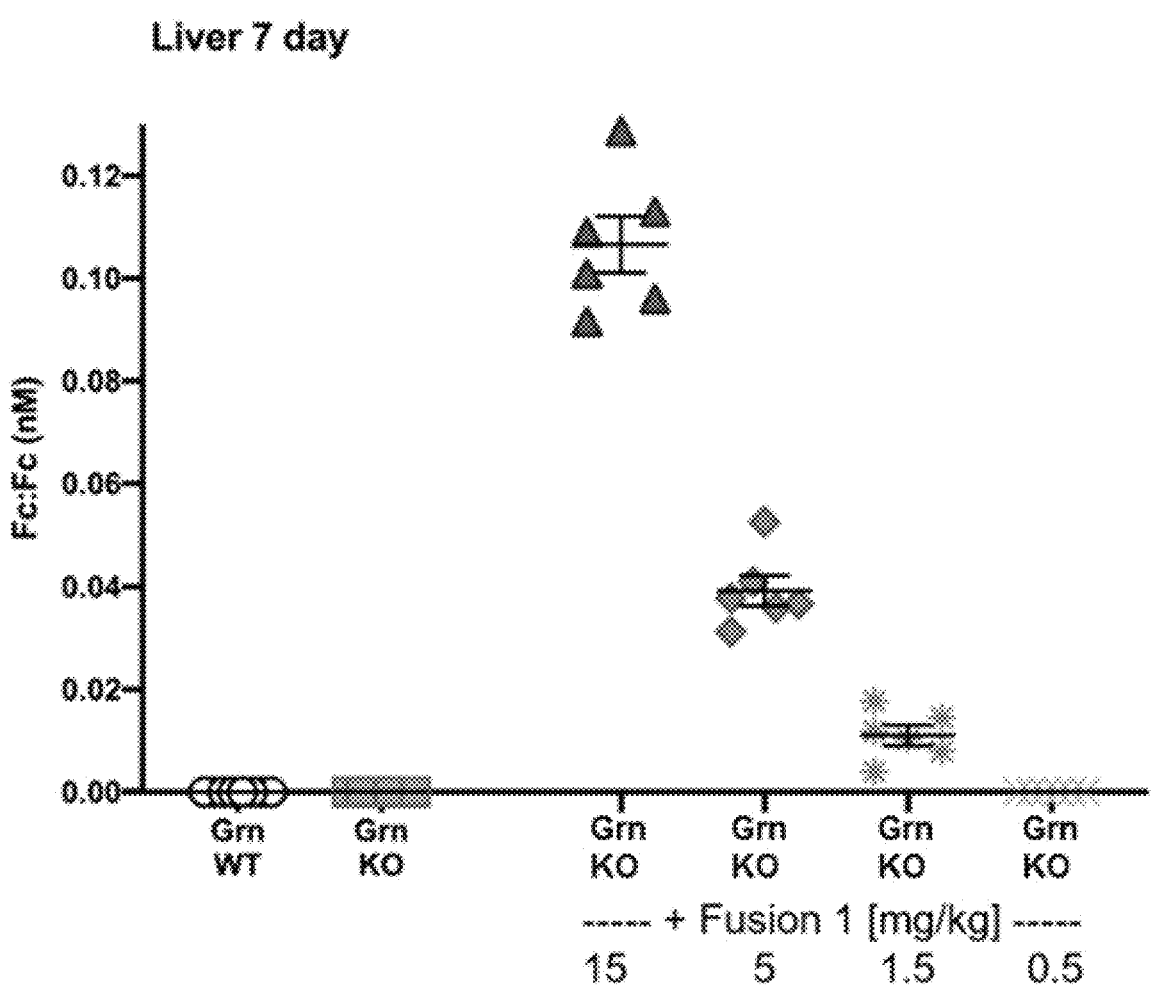

FIGS. 6A-6C illustrate the pharmacokinetics of Fusion 1 in plasma, brain, and liver of GRN KO/hTfR.KI mice. Hollow circles represent the vehicle-treated GRN WT cohort, and squares represent vehicle-treated GRN KO cohort. Fusion protein-treated GRN KO cohorts are represented by triangles (15 mg/kg), diamonds (5 mg/kg), asterisks (1.5 mg/kg) and x-marks (0.5 mg/kg). At all doses, the fusion protein cleared from plasma, brain and liver with less than 0.1 nM of detected protein in tissue and about 1 nM of detected protein in plasma at 7 days post-dose.

Figure 7A:
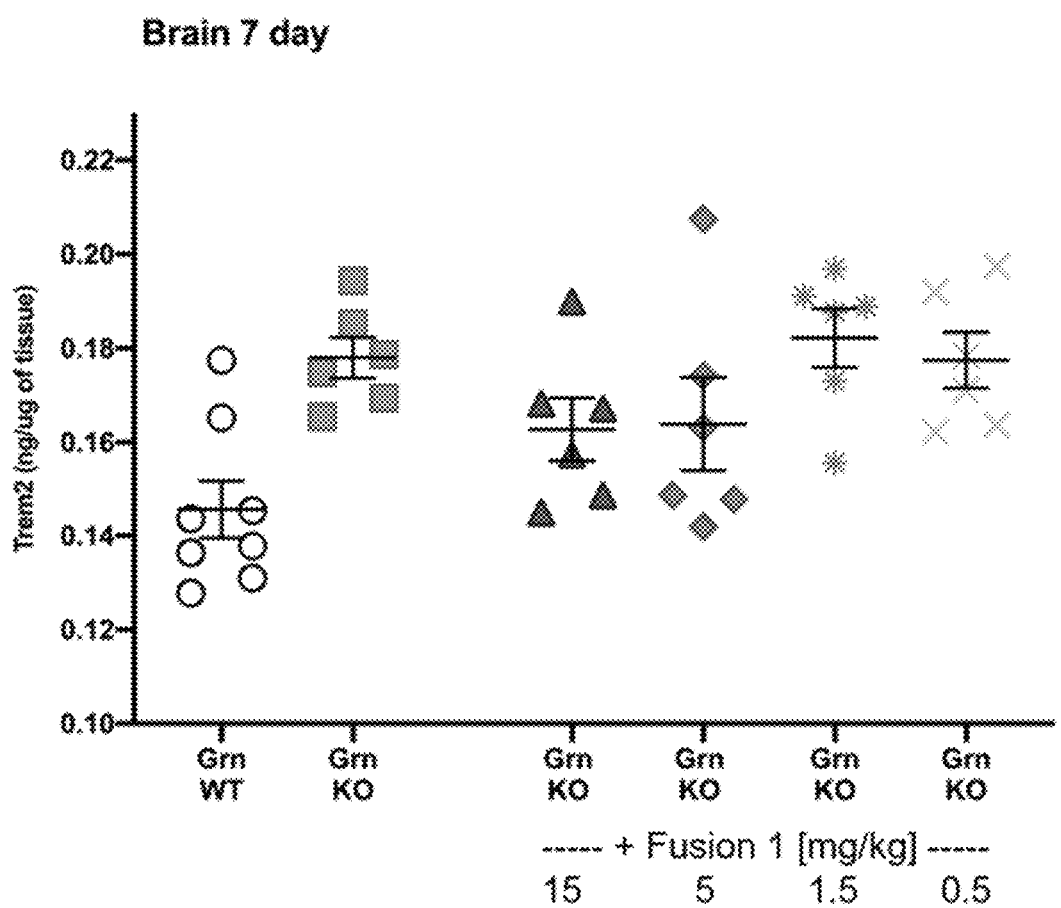
FIGS. 7A and 7B include representative plots of TREM2 levels in brain and liver of GRN KO/hTfR.KI mice at 7 days post-dose after administration of an exemplary fusion protein disclosed herein.
Figure 7B:
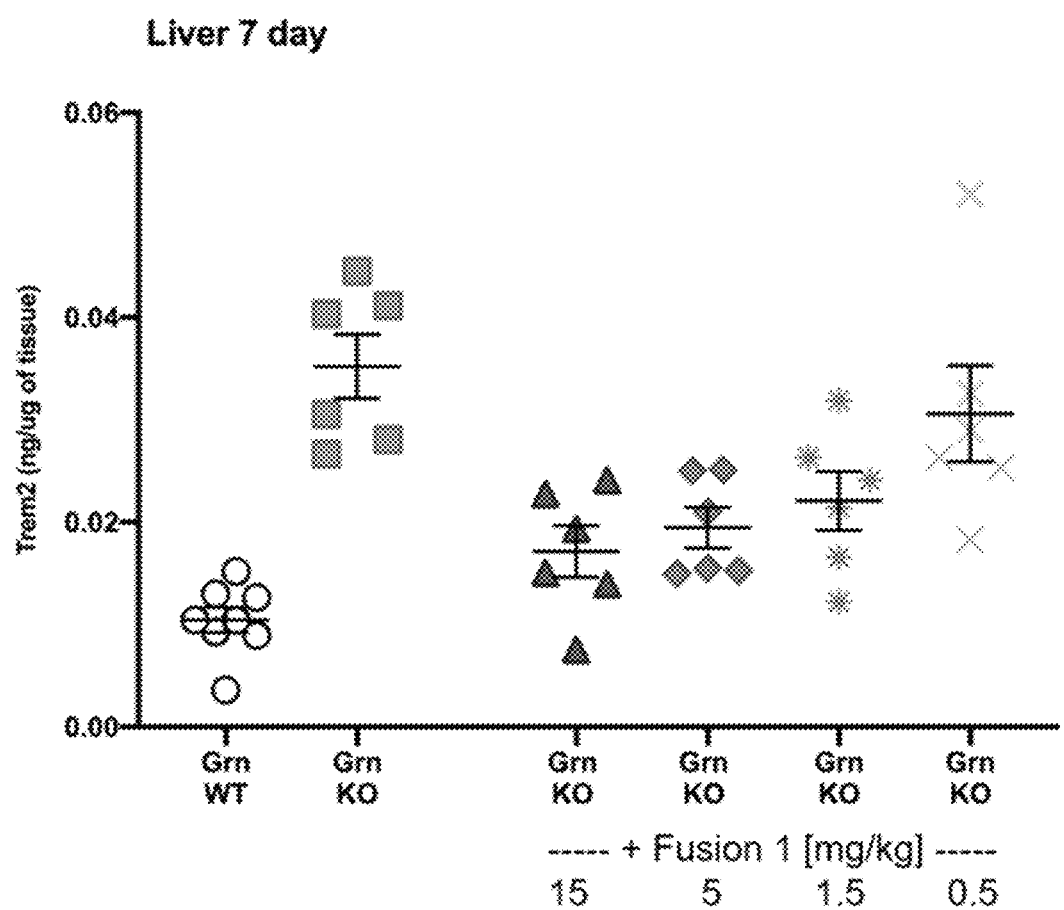

FIGS. 7A and 7B illustrate TREM2 levels in brain and liver tissue of GRN KO/hTfR.KI mice at 7 days post-dose. Hollow circles represent the vehicle-treated GRN WT cohort, and squares represent vehicle-treated GRN KO cohort. Fusion protein-treated GRN KO cohorts are represented by triangles (15 mg/kg), diamonds (5 mg/kg), asterisks (1.5 mg/kg) and x-marks (0.5 mg/kg). Dose levels of 5 mg/kg and 15 mg/kg were able to rescue TREM2 levels in brain, whereas dose levels as low as 1.5 mg/kg were able to rescue TREM2 levels in liver.

Figure 8A:
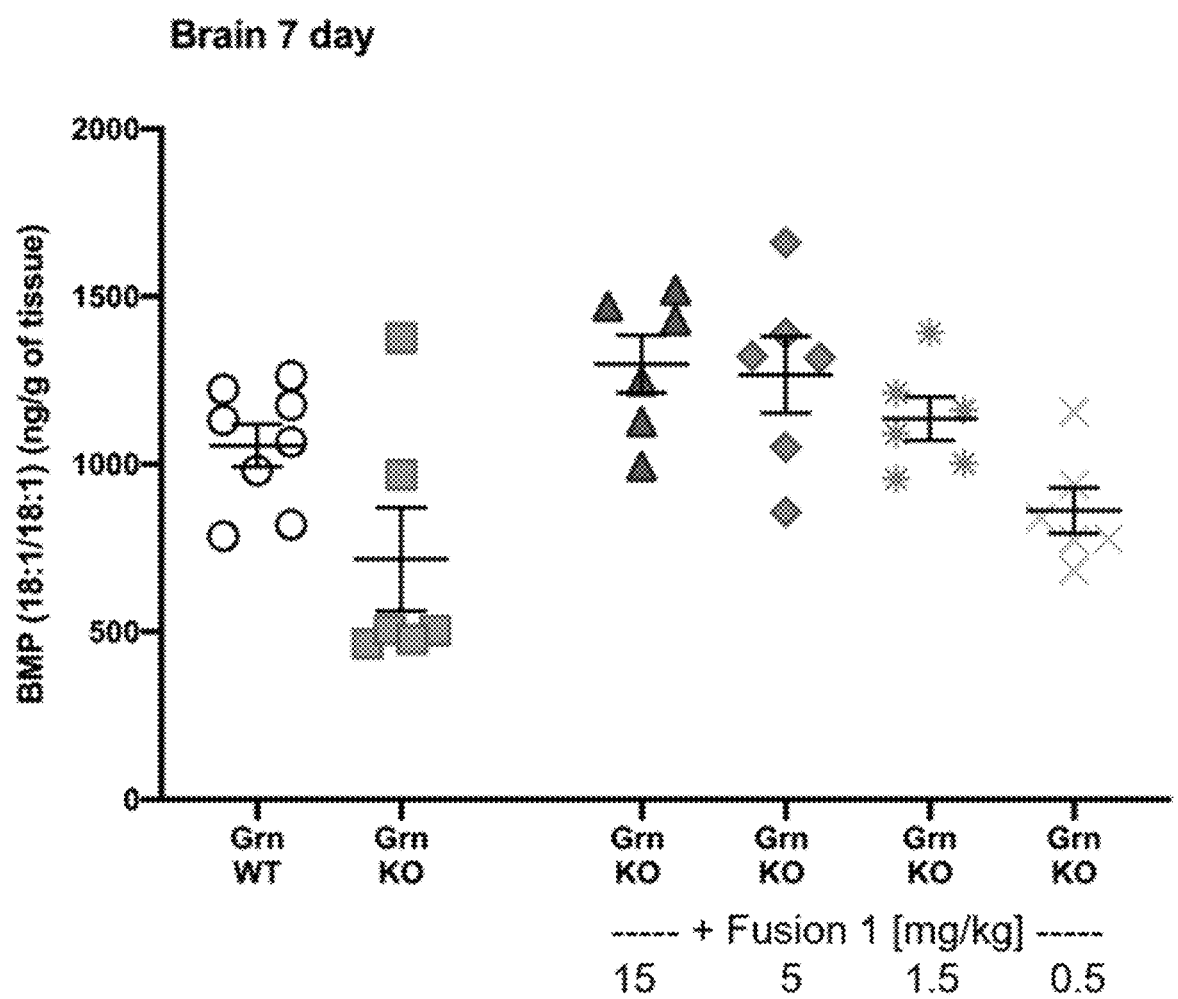
FIGS. 8A and 8B include representative plots of BMP levels in brain and liver of GRN KO/hTfR.KI mice at 7 days post-dose after administration of an exemplary fusion protein disclosed herein.
Figure 8B:
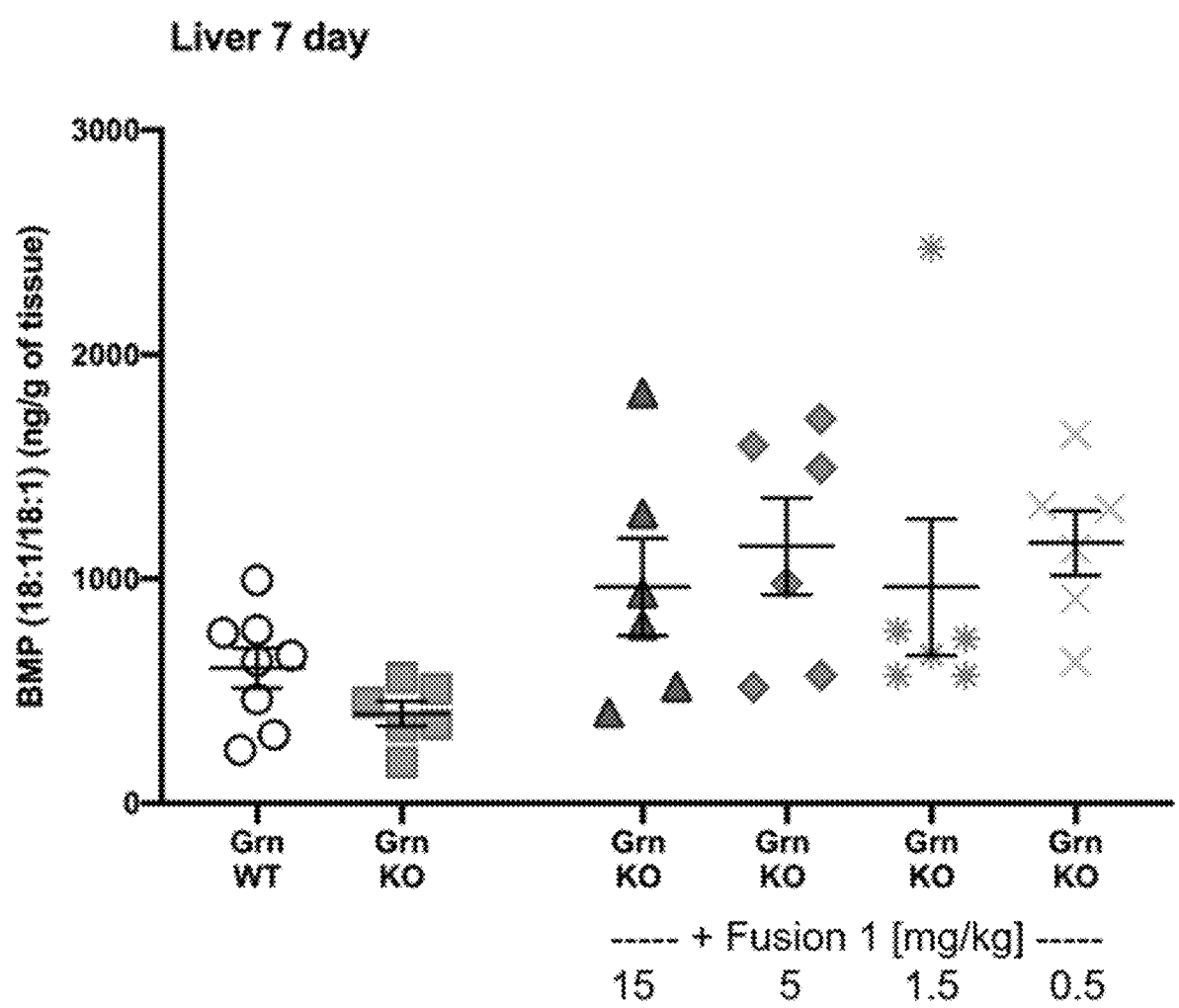

FIGS. 8A and 8B illustrate levels of BMP(18:1/18:1) in brain and liver tissue of GRN KO/hTfR.KI mice at 7 days post-dose. Hollow circles represent the vehicle-treated GRN WT cohort, and squares represent vehicle-treated GRN KO cohort. Fusion protein-treated GRN KO cohorts are represented by triangles (15 mg/kg), diamonds (5 mg/kg), asterisks (1.5 mg/kg) and x-marks (0.5 mg/kg). Dose levels as low as 1.5 mg/kg were able to rescue BMP levels in brain, whereas BMP levels were rescued at all doses in the liver. Similar results were observed for other BMP species, including BMP(20:4/20:4) and BMP(22:6/22:6).

The data in FIGS. 6A-6C, 7A and 7B, and 8A and 8B shows that Fusion 1 is able to cross the BBB in the brain of GRN KO/hTfR.KI mice and correct relevant PD endpoints of granulin deficiency.

Example 7. Rescue of Glucosylsphingosine Levels in Brain Tissue of GRN KO/hTfR.KI Mice Brain Collection & Processing for Lipid Extraction and Glucosylsphingosine Analysis Fusion 1 (as described in Table 2) or a corresponding fusion protein that does not have any TfR-binding ability was injected in a single dose via the tail vein at 5 mg/kg into GRN KO/hTfR.KI mice ("Grn KO" in FIG. 9). The corresponding fusion protein comprises a first polypeptide having the sequence of SEQ ID NO:122 and a second polypeptide having the sequence of SEQ ID NO:108. Both fusion proteins were expressed and purified from CHO cells as described in Example 1. At seven days following administration of the fusion proteins, the mice were sacrificed to examine glucosylsphingosine (GlcSph) levels in brain, liver and plasma. Following anesthetization with a lethal dose of tribromoethanol, mice were cardiac perfused with ice-cold PBS. 18-20 mg of frontal cortex was then collected on ice, weighed, transferred to a 1.5 Safe-Lock Eppendorf tube, along with a 3-mm stainless steel bead, then flash frozen. To prepare brain samples for lipidomic analysis, 400 µL of LCMS-grade methanol with internal standards was added to the samples. Tissues were then homogenized with a Qiagen Tissuelyser for 30 seconds at 25 Hz at 4° C. Samples were then centrifuged for 20 min at 21,000×g at 4° C. Following the spin, the supernatant was transferred to 96-well V-bottom half deep-well plates and stored at −20° C. for 1 hour to further precipitate proteins. Following this incubation, samples were spun for an additional 10 min at 21,000×g at 4° C. 100 µL of the supernatant was transferred to a 96-well plate with glass inserts (Analytical Sales & Services, Ref #27350). The samples were then dried down under nitrogen stream (about 2 hrs) then resuspended in 100 µL acetonitrile/isopropanol/water (92.5/5/2.5, v/v/v) with 5 mM ammonium formate and 0.5% formic acid.

LCMS Assay for Glucosylsphingosine

Glucosylsphingosine (GlcSph) analysis was performed by liquid chromatography (Shimadzu Nexera $X_2$ system, Shimadzu Scientific Instrument, Columbia, Md., USA) coupled to electrospray mass spectrometry (Sciex QTRAP 6500+ Sciex, Framingham, Mass., USA). For each analysis, 10 µL of sample was injected on a HALO HILIC 2.0 µm, 3.0×150 mm column (Advanced Materials Technology, PN 91813-701) using a flow rate of 0.45 mL/min at 45° C. Mobile phase A consisted of 92.5/5/2.5 ACN/IPA/H2O with 5 mM ammonium formate and 0.5% formic Acid. Mobile phase B consisted of 92.5/5/2.5 H2O/IPA/ACN with 5 mM ammonium formate and 0.5% formic Acid. The gradient was programmed as follows: 0.0-3.1 min at 100% B, 3.2 min at 95% B, 5.7 min at 85% B, hold to 7.1 min at 85% B, drop to 0% B at 7.25 min and hold to 8.75 min, and ramp back to 100% at 10.65 min and hold to 11 min. Electrospray ionization was performed in the positive-ion mode applying the following settings: curtain gas at 25; collision gas was set at medium; ion spray voltage at 5500; temperature at 350° C.; ion source Gas 1 at 55; ion source Gas 2 at 60. Data acquisition was performed using Analyst 1.6 (Sciex) in multiple reaction monitoring mode (MRM) with the following parameters: dwell time (msec) and collision energy (CE); entrance potential (EP) at 10; and collision cell exit potential (CXP) at 12.5. Data acquisition parameters were similar to that described previously (Ullman et al. 2020. *Sci Transl Med* 12(545):eaay1163). GlcSph was quantified using the isotope labeled internal standard GlcSph(d5). Quantification was performed using MultiQuant 3.02 (Sciex).

Glucosylsphingosine Brain Result

Figure 9:
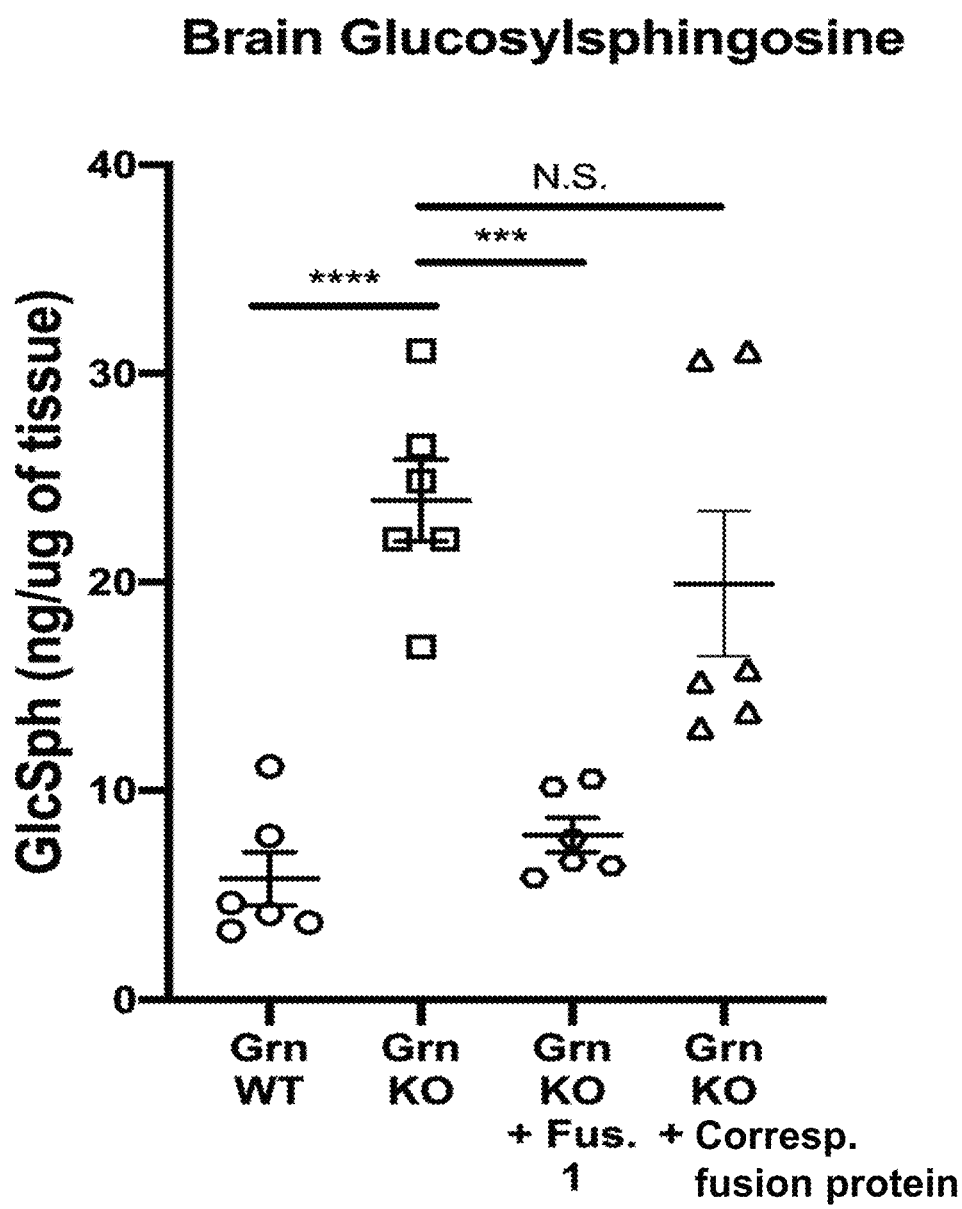
FIG. 9 is a graph illustrating that Fusion 1 as disclosed herein can reduce GlcSph level in the brain of GRN KO/hTfR.KI mice.

GlcSph levels in the brain of GRN KO and GRN WT mice, as well as in GRN KO mice that received an IV administered 5 mg/kg dose of Fusion 1 or the corresponding fusion protein were evaluated (FIG. 9). GRN KO brain GlcSph levels were on average 4.13-fold the value of WT littermates (23.91±1.963 ng/µL vs. 5.782±1.262 ng/µL, respectively, p=<0.0001). In Fusion 1-treated mice, there was an 88% rescue towards GRN WT mice (7.866±0.8237 ng/µL, p=0.0002). Conversely, GRN KO mice treated with the non-CNS targeting corresponding fusion protein only exhibited a 22% return toward WT GlcSph levels (19.92±3.486 ng/µL, p=0.5619).

Figure 10:
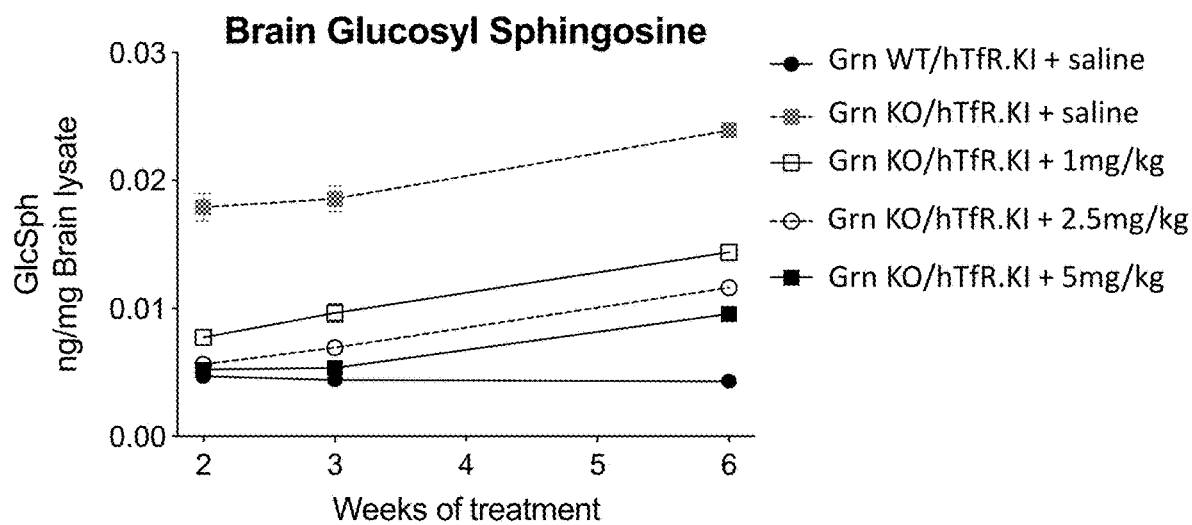
FIG. 10 is a graph illustrating that Fusion 1 as disclosed herein can reduce GlcSph level in the brain of GRN KO/hTfR.KI mice.
Figure 11:
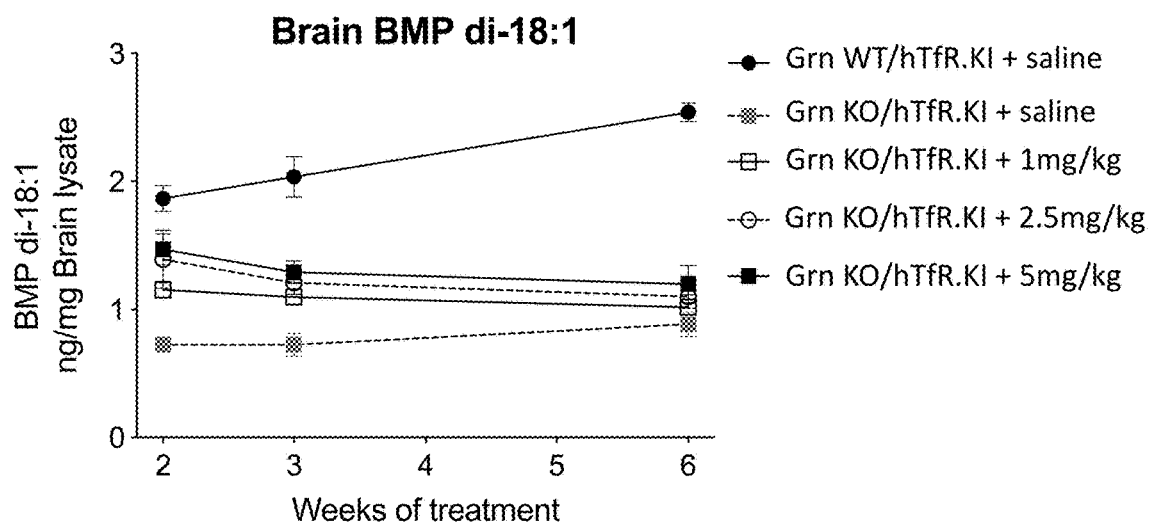
FIG. 11 is a graph illustrating that Fusion 1 as disclosed herein can correct BMP di-18:1 levels in GRN KO/hTfR.KI mice.
Figure 12:
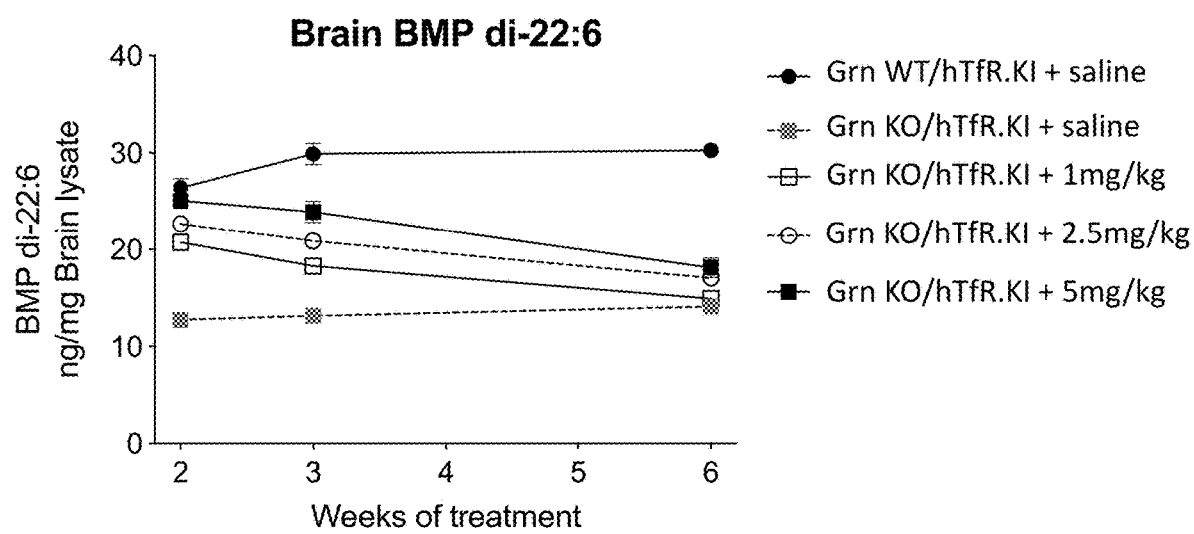
FIG. 12 is a graph illustrating that Fusion 1 as disclosed herein can correct BMP di-22:6 levels in GRN KO/hTfR.KI mice.

Example 8. Durability of BMP and Glucosylsphingosine Correction in GRN KO/hTfR.KI Mice Fusion 1 (as described in Table 2, expressed and purified from CHO cells as described in Example 1) was injected in a single dose via the tail vein into GRN KO/hTfR.KI mice at the following doses: 1 mg/kg, 2.5 mg/kg, and 5 mg/kg. For control, GRN KO/hTfR.KI and GRN wild-type/hTfR.KI mice were injected with saline. At two, three, and six weeks following administration of the fusion protein or saline, cohorts of mice were sacrificed to examine BMP and glucosylphingosine (GlcSph) levels in the brain. Mice were anesthetized and their brain tissues were prepared as described in Example 7. BMP and GlcSph levels were measured as described in Examples 5 and 7, respectively. The results are illustrated in FIGS. 10-12.

Glucosylsphingosine Brain Result

The glucosylsphingosine (GlcSph) levels in GRN KO/hTfR.KI and GRN wild-type/hTfR.KI mice were evaluated. As illustrated in FIG. 10, the GlcSph levels in GRN KO/hTfR.KI was about 4-fold elevated relative to GRN wild-type/hTfR.KI mice. Administration of Fusion 1 at all doses corrected the elevated GlcSph levels in GRN KO/hTfR.KI, with the highest dose administered (5 mg/kg) showing the most improvement of all the fusion protein-treated cohorts. Maximum correction to nearly GRN wild-type levels with a single dose of Fusion 1 was observed at two weeks post-dose, although partial correction was observed out to six weeks post-dose.

BMP Brain Result

As previously reported, the BMP levels in GRN KO/hTfR.KI are impacted by insufficient levels of progranulin. Administration of Fusion 1 the GRN KO/hTfR.KI was able to correct this impact. The levels of representative BMP species are illustrated in FIGS. 11 and 12. Administration of Fusion 1 at all doses corrected the BMP levels in GRN KO/hTfR.KI. At the highest dose administered, maximum correction of BMP levels was observed at two weeks post-dose, with partial correction maintained at three weeks post-dose.

Example 9. Rescue of GCase Activity in GRN KO/hTfR.KI Mice

Fusion 1 (as described in Table 2, expressed and purified from CHO cells as described in Example 1) was injected via the tail vein into GRN KO/hTfR.KI mice at the doses described in Example 8. For control, GRN KO/hTfR.KI and GRN wild-type/hTfR.KI mice were injected with saline. At two, three, and six weeks following administration of the fusion protein or saline, cohorts of mice were sacrificed to examine glucocerebrosidase (GCase) enzyme activity in the brain. Mice were anesthetized and their brain tissues were prepared as described in Example 7. GCase activity was assayed as follows. Brain tissue was lysed in 1% NP-40 in PBS buffer. Total protein levels in the brain lysate samples were measured by BCA assay, and samples were normalized for measurement of GCase activity. Tissue samples were first diluted in GBA activity buffer (phosphate citrate buffer (Sigma-Aldrich cat #P4809) with 0.5% sodium taurocholate and 0.25% Triton X-100) and added to wells of a 96-well plate. 4-MU glucose substrate (Sigma-Aldrich, Cat. M3633-1G) was subsequently added to a final concentration of 1 mM to each sample well. The plate was covered and agitated at 700 RPM for 5 minutes at room temperature before being transferred to a non-$CO_2$ incubator and incubated at 37° C. for three hours. At the end of the incubation period, a stop solution (500 mM glycine, 300 mM NaOH, pH 9.8) was added to the samples to halt the enzymatic reaction, and enzymatic activity was measured in a BioTek plate reader. The results are illustrated in FIG. 13.

Figure 13:
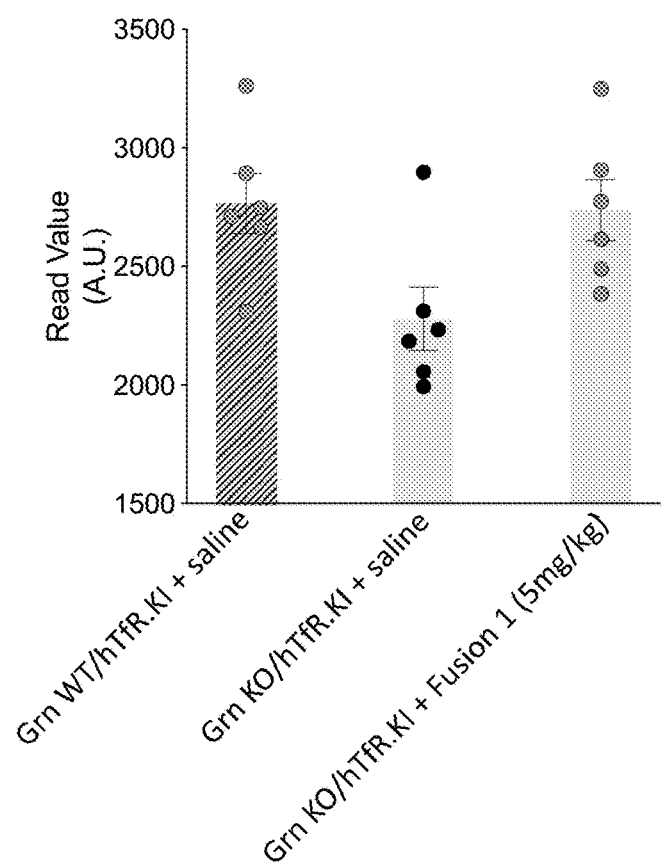
FIG. 13 is a graph illustrating that Fusion 1 as disclosed herein can correct glucocerebrosidase (GCase) activity in the brain of GRN KO/hTfR.KI mice to wild-type levels at two weeks post-dose.

As illustrated in FIG. 13, administration of Fusion 1 corrected GCase activity in the brain of GRN KO/hTfR.KI mice to wild-type levels at two weeks post-dose.

Example 10. Chronic Dosing of Fusion Proteins Rescues Distal Biomarkers in GRN KO/hTfR.KI Mice A study was carried out to determine if chronic dosing with fusion proteins as described herein can rescue distal biomarkers. Fusion proteins were administered by intraperitoneal delivery to 7-month old GRN KO/hTfR.KI mice at 5 mg/kg once per week for eight (8) weeks. For control, GRN KO/hTfR.KI and GRN wild-type/hTfR.KI mice (also referred to as "hTfR.KI mice") were injected with saline. Injections of CD4 were provided to the mice in each cohort starting with initial dose of fusion protein and every two weeks thereafter. Blood samples were obtained by submandibular bleed for plasma isolation at weeks 0, 2, 4, 6, and 8 (post-dose). Twenty-four (24) hours after the eighth and final dose of fusion protein, the cohorts of mice were sacrificed; terminal blood and CSF samples were obtained, and brain and liver tissue were collected and preserved as previously described (Example 6). Quantities of administered fusion proteins were measured in the brain and liver using the Fc:Fc:ELISA described in Example 6. BMP, glucosylphingosine (GlcSph), and Trem2 levels were analyzed in the brain, liver, plasma, and/or CSF. In addition, certain markers of gliosis (CD68, Iba1, GFAP) were analyzed in brain tissue, and neurofilament light chain (Nf-L) levels were analyzed in CSF and plasma samples. BMP, TREM2, and GlcSph levels were measured as described in Examples 5, 6, and 7, respectively. CSF Nf-L levels and brain levels of gliosis markers were measured as described below. Table 10 provides a summary of the experimental design, and the results are illustrated in FIGS. 14-28.

TABLE 10

Study Design/Experimental Groups for Chronic Dosing Study

| Molecule | First Fc Polypeptide | Second Fc Polypeptide-PGRN | Cell Line | Genotype | Dose (mg/kg) |
|---|---|---|---|---|---|
| Saline | — | — | N/A | hTfR.KI | N/A |
| Saline | — | — | N/A | GRN KO/hTfR.KI | N/A |
| Fusion 1 | SEQ ID NO: 75 | SEQ ID NO: 98 | CHO | GRN KO/hTfR.KI | 5 |
| Fusion 11 | SEQ ID NO: 85 | SEQ ID N: 108 | HEK | GRN KO/hTfR.KI | 5 |
| Fc-PGRN (non-TfR binding) | SEQ ID NO: 122 | SEQ ID NO: 108 | CHO | GRN KO/hTfR.KI | 5 |

Methods for CSF and Plasma Analysis of Nf-L

CSF and Plasma Nf-L levels were analyzed as described previously and in line with manufacturer recommendations (Ullman et al. 2020. *Sci Transl Med* 12(545):eaay1163). Briefly, using the Quanterix Simoa Neurofilament Light Advantage (NFL) kit. Briefly, Cerebrospinal fluid was diluted 100× and plasma was diluted 10× in sample diluent (Quanterix 102252) then Simoa detector reagent and bead reagent (Quanterix 103159, 102246) were added and samples were incubated for 30 mins, at 30° C., shaking at 800 rpm. Following this, the sample plate was washed with Simoa Wash Buffer A (Quanterix 103078) on Simoa Microplate Washer according to Quanterix two step protocol, SBG reagent (Quanterix 102250) was added, and samples were again incubated at 30° C., 800 rpm for an additional 10 min. The two-step washer protocol was continued, with the sample beads being twice resuspended in Simoa Wash Buffer B (Quanterix 103079) before final aspiration of buffer. After drying for 10 minutes at RT. sample Nf-L concentrations were measured using the Nf-L analysis protocol on the Quanterix SR-X instrument and interpolated against a calibration curve provided with the Quanterix assay kit.

Assay for Gliosis Markers

Following PBS transcardiac perfusion and post-fixation in 4% PFA, mouse hemibrains were coronally sectioned. Briefly, a multitude of brains (up to 40) were trimmed and mounted in a single gelatin block, then coronally sectioned at a thickness of 40 μm. Gelatin sheets with embedded brain sections were then stored in antigen preservation solution (50% PBS:50% ethlyene glycol+1% PVP) until staining. Sections were stained for gliosis markers GFAP (donkey anti-chicken, Novus NBP1-05198, 1:1000), Iba1 (donkey anti-goat, Novus NB100-1028, 1:1500) & CD68 (donkey anti-rat, BioRad MCA1957, 1:500). Briefly, sections were incubated with rocking at room temperature for 4 hours in blocking buffer (PBS+1% BSA+0.1% fish gelatin+0.5% triton X-100), then transferred to antibody dilution buffer with primary antibodies at concentrations listed above and stored with rocking at 4° C. overnight. Following 3× washes in PBS, samples were then transferred to antibody dilution buffer with secondary antibodies (1:500 dilution) and incubated with rocking at room temperature for 4 hours. Samples were then washed with PBS+DAPI (Invitrogen D1306 1:10, 000) for 20 minutes, then washed twice more with PBS before mounting on 2-×3-inch slides with Prolong Glass hardset mounting media (Life Tech P36984) and allowed to dry overnight at room temperature. Full brain hemispheres were imaged at 20× using a Zeiss Axio Scan.Z1 digital slide scanner. Image analysis was completed using Zeiss Zen Blue 3.2 software. Thalamus ROIs were drawn and a rolling ball thresholding approach was used to determine the area of each gliosis marker relative to total thalamus area. 1-3 sections were analyzed per brain and average percent coverage values were calculated across images.

CNS Cell Type Isolation

To prepare a single cell suspension for sorting CNS cells, brain tissue was dissected and processed into a single cell suspension according to the manufacturers' protocol using the adult brain dissociation kit (Miltenyi Biotec 130-107-677). Cells were Fc blocked (Biolegend #101320, 1:100) and stained for flow cytometric analysis with Fixable Viability Stain BV510 (BD Biosciences #564406, 1:100) to exclude dead cells, CD11b-BV421 (BD Biosciences 562605, 1:100), ACSA2-APC (Miltenyi #130-117-386, 1:100), and Thy1-PE (R&D #FAB7335P, 1:100). Cells were washed with PBS/1% BSA and strained through a 100 m filter before sorting CD11b+ microglia, ACSA2+ astrocytes, and Thy1+ neurons on a FACS Aria III (BD Biosciences) with a 100 m nozzle. Sorted cells were collected directly into MS grade methanol with added internal standards for lipidomic and metabolomic analysis. Cell lysate preparation and LCMS assays for measurement of GAGs, BMPs, gangliosides, GlcCer, and GalCer were performed using methods similar to those described in Example 1.

Results

Figure 14:
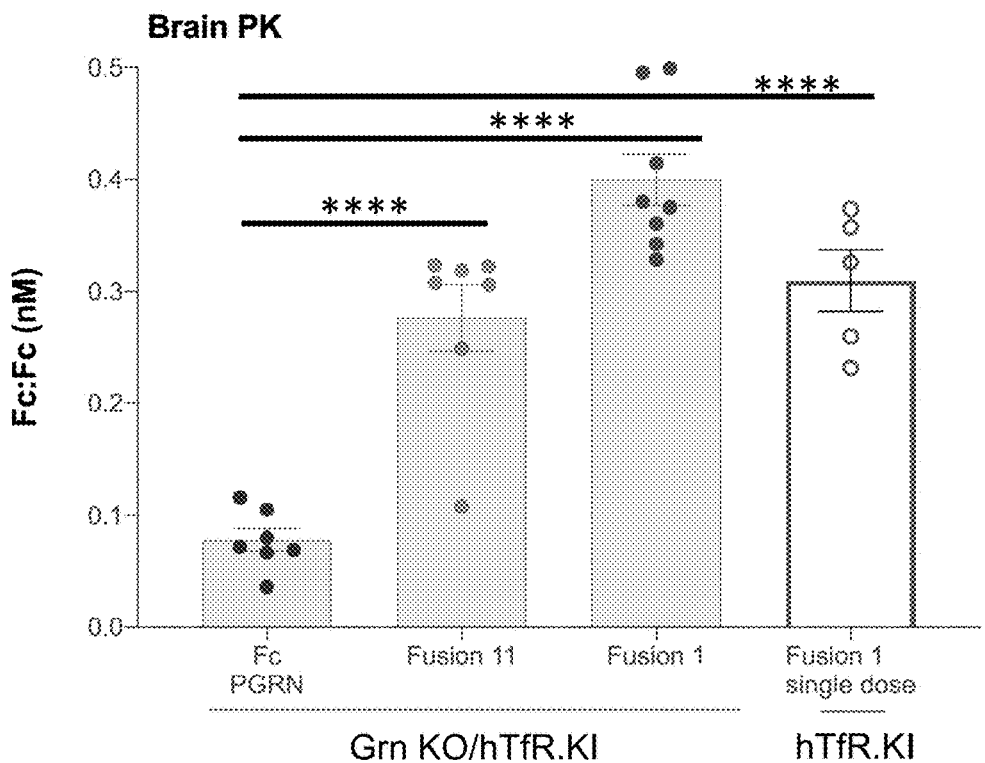
FIG. 14 is a scatter plot illustrating brain protein levels of exemplary fusion proteins disclosed herein in GRN KO/hTfR.KI mice after eight weekly doses. The figure displays mean±SEM and p values: one-way ANOVA with Dunnett multiple comparison test; **** $p<0.0001$.
Figure 15:
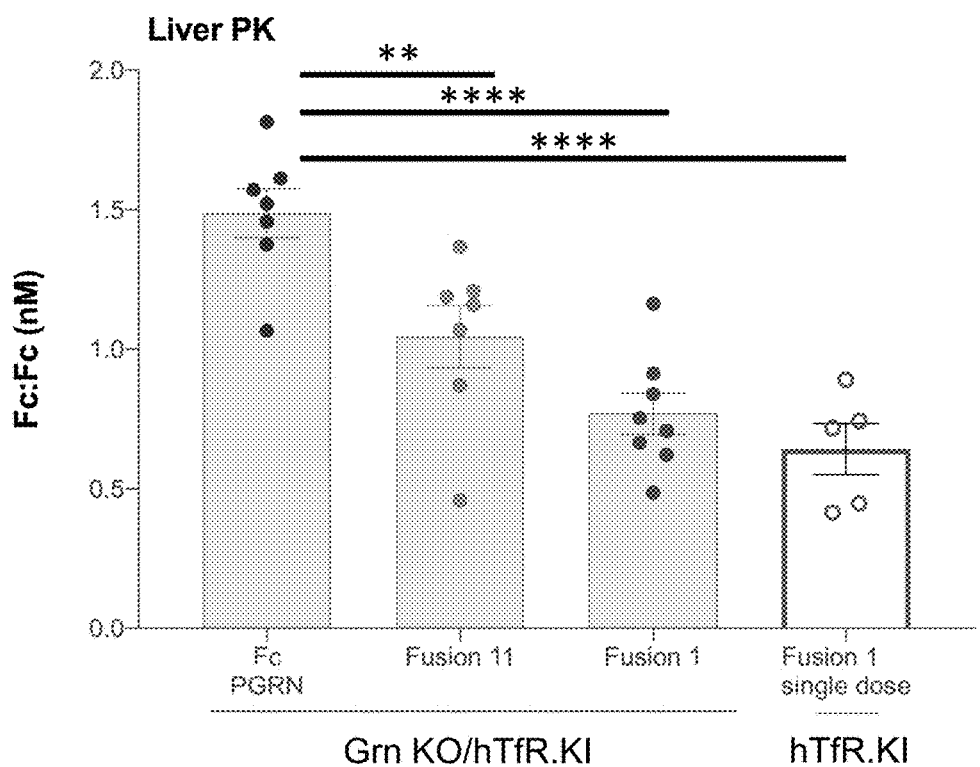
FIG. 15 is a scatter plot illustrating liver protein levels of exemplary fusion proteins disclosed herein in GRN KO/hTfR.KI mice after eight weekly doses. The figure displays mean±SEM and p values: one-way ANOVA with Dunnett multiple comparison test;  $p<0.01$ and ** $p<0.0001$.

FIGS. 14 and 15 provide information about the concentrations of the administered fusion proteins in brain and liver tissues of the treated GRN KO mice cohorts. As illustrated in FIGS. 14 and 15, TfR binding in Fusions 1 and 11 drove a significant increase in the brain uptake of protein relative to the non-TfR binding Fc:PGRN protein. In addition, weekly treatment up to eight (8) weeks with Fusion 1 did not reduce brain uptake of the protein relative to a single intraperitoneal dose of the same. On the other hand, exposure of Fc:PGRN in the liver was greater than that of Fusion 1 and Fusion 11, likely due to lack of TfR-mediated clearance from the periphery.

Figure 16:
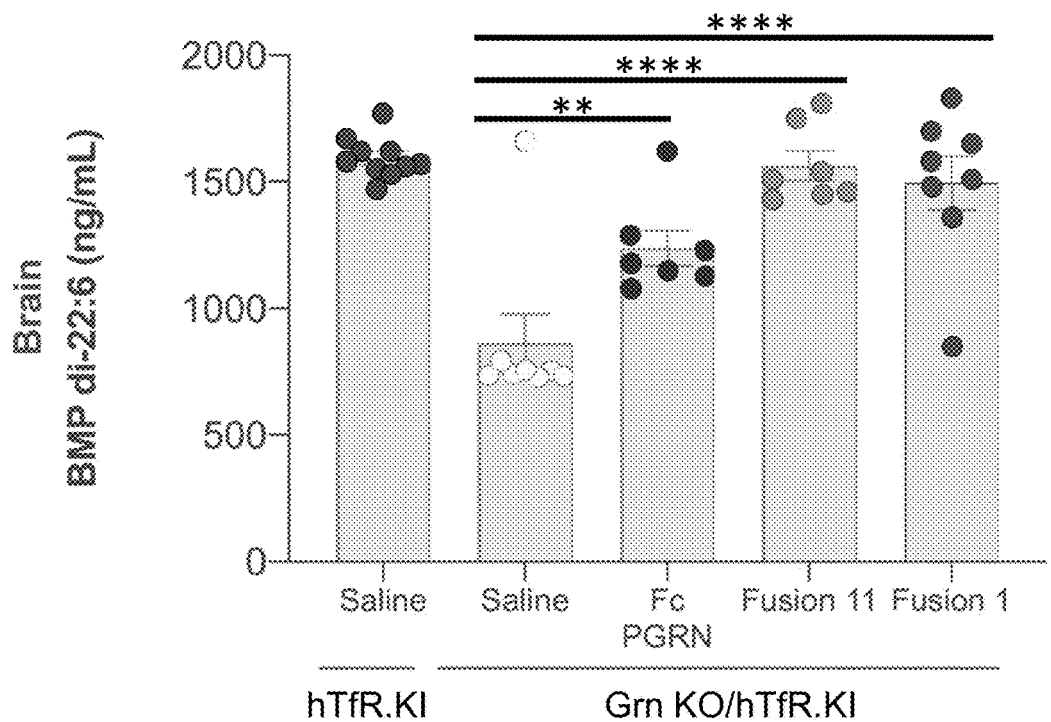
FIG. 16 is a scatter plot illustrating levels of a representative BMP species in the brains of GRN KO/hTfR.KI mice after eight weekly doses of exemplary fusion proteins disclosed herein. The figure displays mean±SEM and p values: one-way ANOVA with Dunnett multiple comparison test;  $p<0.01$ and ** $p<0.0001$.
Figure 17:
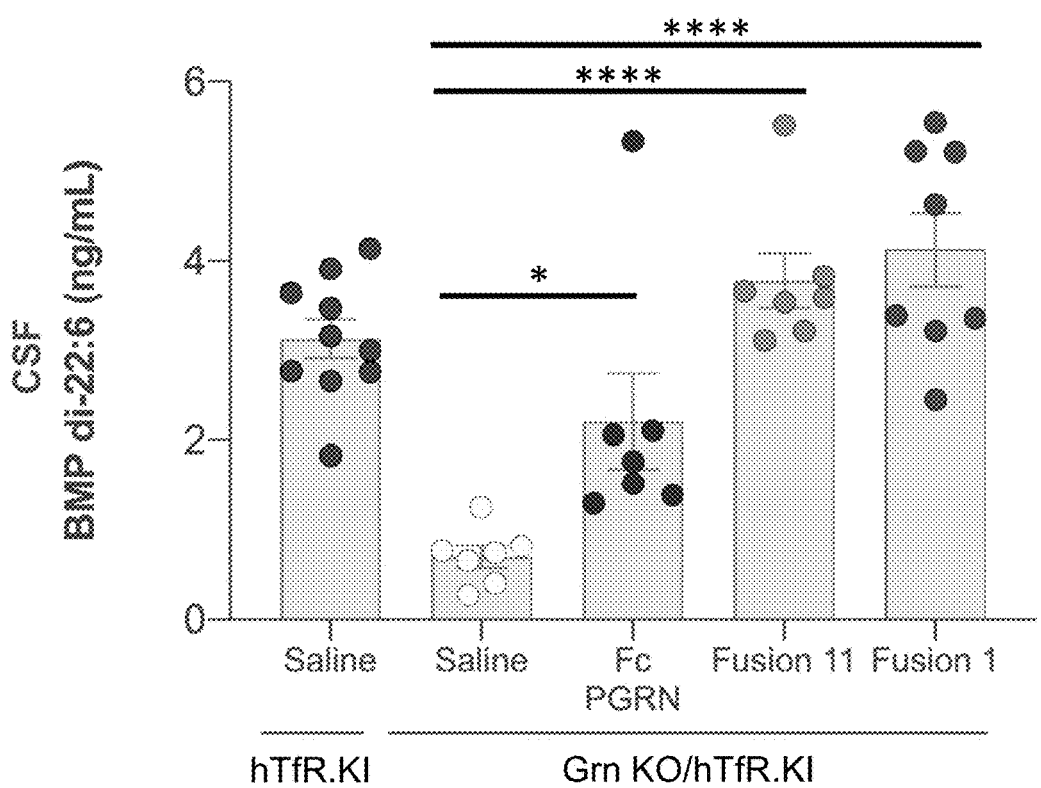
FIG. 17 is a scatter plot illustrating CSF levels of a representative BMP species in GRN KO/hTfR.KI mice after eight weekly doses of exemplary fusion proteins disclosed herein. The figure displays mean±SEM and p values: one-way ANOVA with Dunnett multiple comparison test; * $p<0.05$ and **** $p<0.0001$.
Figure 18:
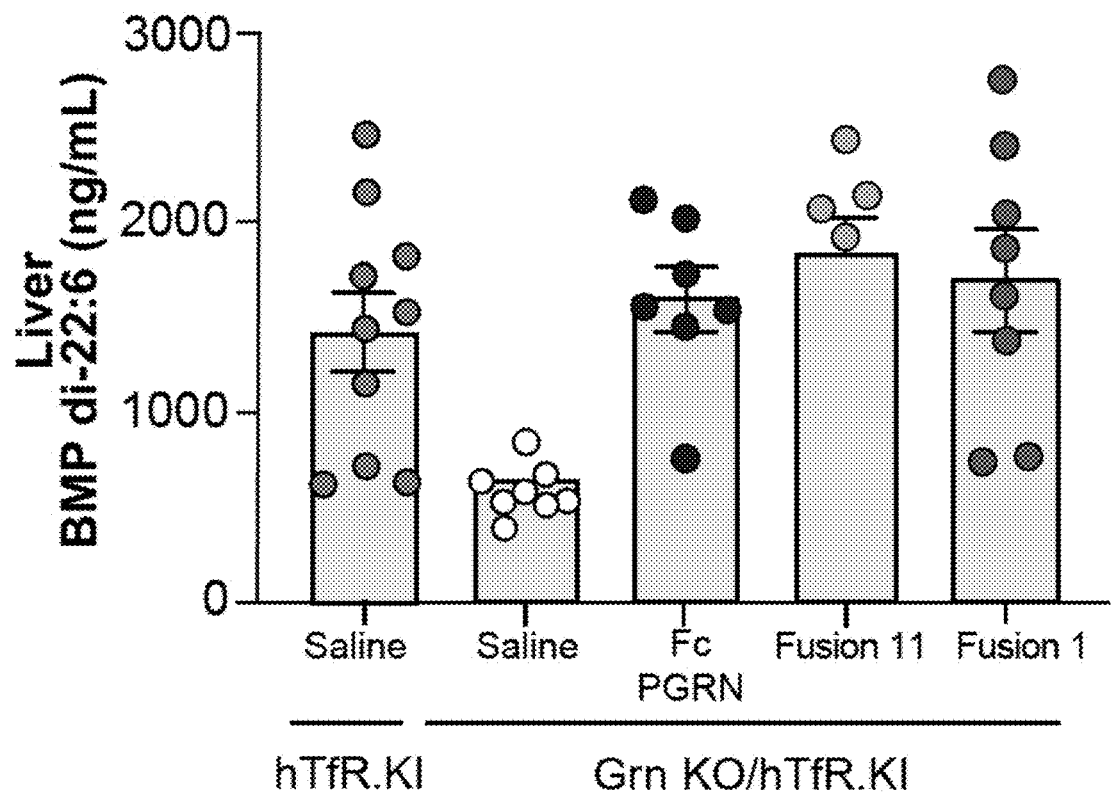
FIG. 18 is a scatter plot illustrating levels of a representative BMP species in the livers of GRN KO/hTfR.KI mice after eight weekly doses of exemplary fusion proteins disclosed herein.
Figure 19:
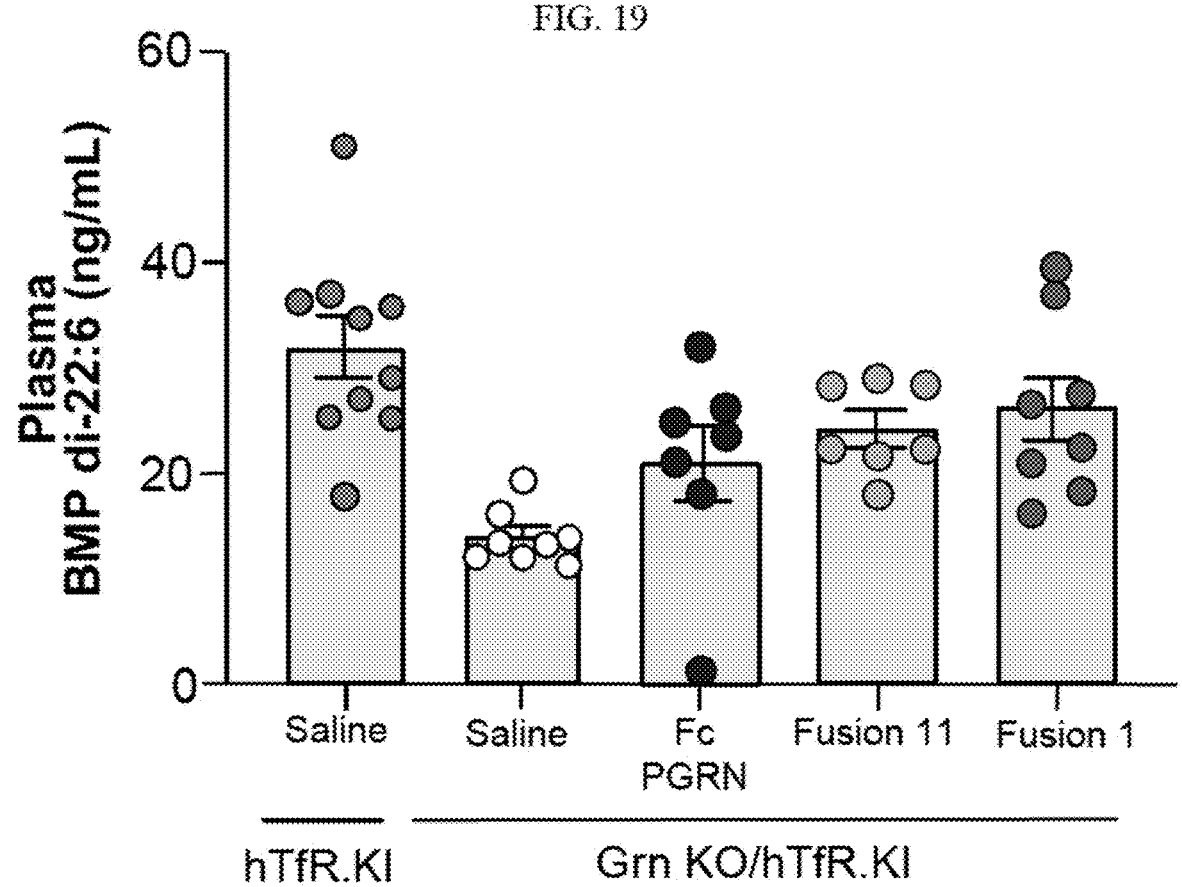
FIG. 19 is a scatter plot illustrating plasma levels of a representative BMP species in GRN KO/hTfR.KI mice after eight weekly doses of exemplary fusion proteins disclosed herein.

FIGS. 16-19 provide information about the levels of an exemplary BMP (di-22:6) in the brain, CSF, liver, and plasma of the treated GRN KO mice cohorts. As illustrated in FIGS. 16 and 17, weekly administration of both Fusion 1 and Fusion 11 up to eight (8) weeks improved rescue of BMP levels in CNS compartments (brain, CSF) relative to vehicle treatment or treatment with Fc:PGRN. In the periphery (liver, plasma), administration of Fc:PGRN, Fusion 1, and Fusion 11 rescued BMP levels with equivalent effect.

Figure 20:
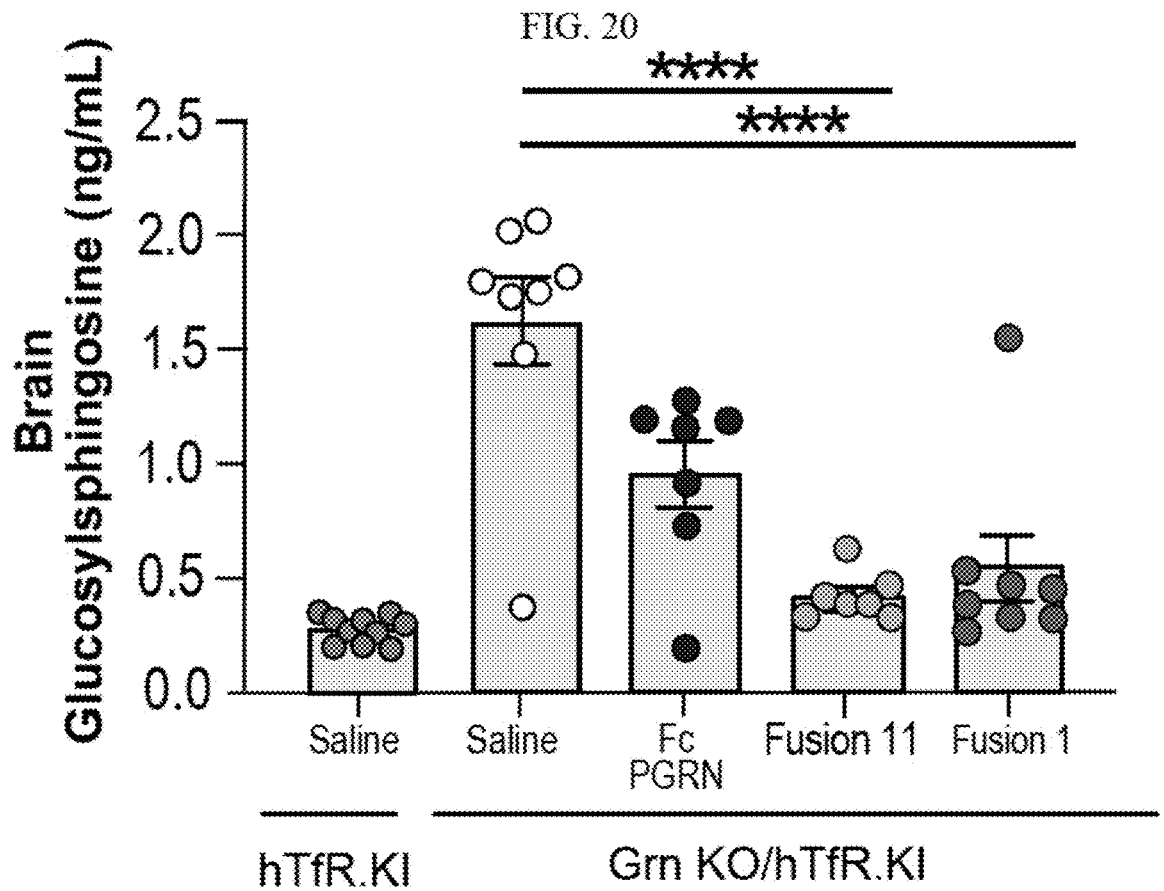
FIG. 20 is a scatter plot illustrating brain glucosylsphingosine (GlcSph) levels in GRN KO/hTfR.KI mice after eight weekly doses of exemplary fusion proteins disclosed herein. The figure displays mean±SEM and p values: one-way ANOVA with Dunnett multiple comparison test; **** $p<0.0001$.
Figure 21:
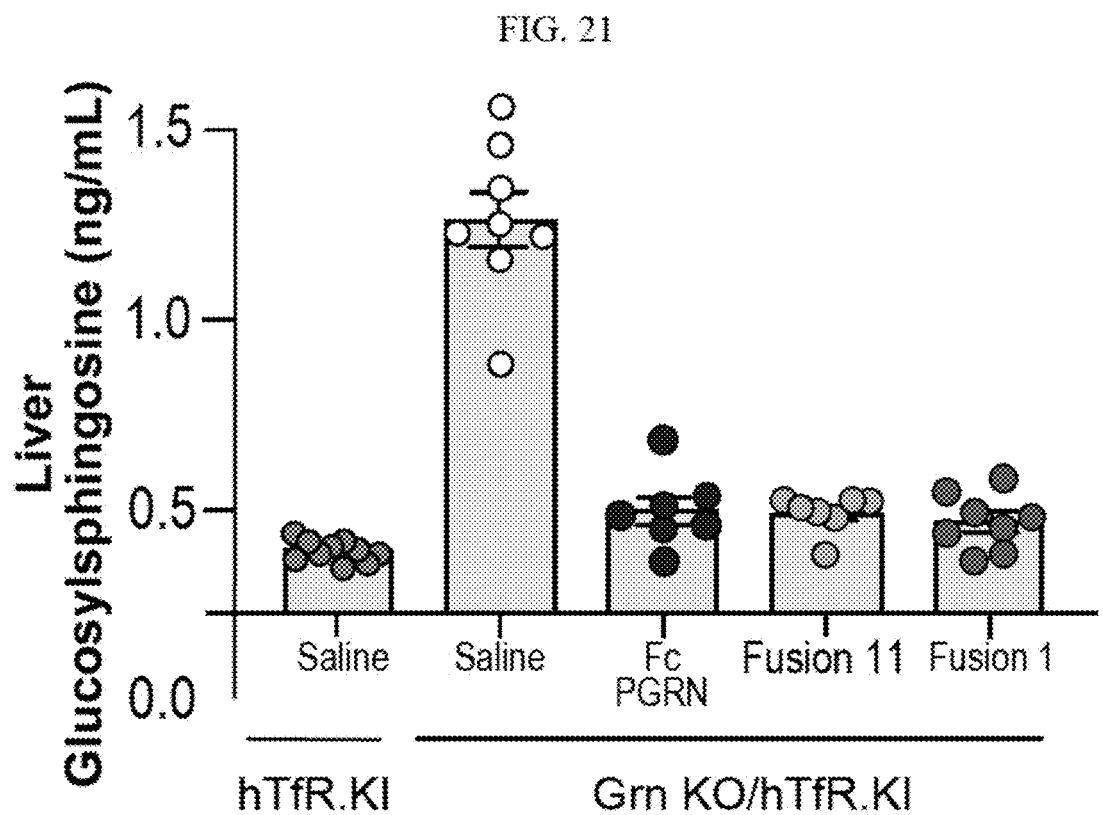
FIG. 21 is a scatter plot illustrating liver glucosylsphingosine (GlcSph) levels in GRN KO/hTfR.KI mice after eight weekly doses of exemplary fusion proteins disclosed herein.

FIGS. 20 and 21 provide information about the GlcSph levels in brain and liver tissues of the treated GRN KO mice cohorts. As illustrated in FIG. 20, weekly administration of Fusions 1 and 11 up to eight (8) weeks rescued GlcSph levels in the brain in a statistically significant manner relative to vehicle treatment and treatment with Fc:PGRN. In the periphery (FIG. 21), weekly administration of Fc:PGRN, Fusion 1, and Fusion 11 rescued GlcSph levels with equivalent effect.

Figure 22:
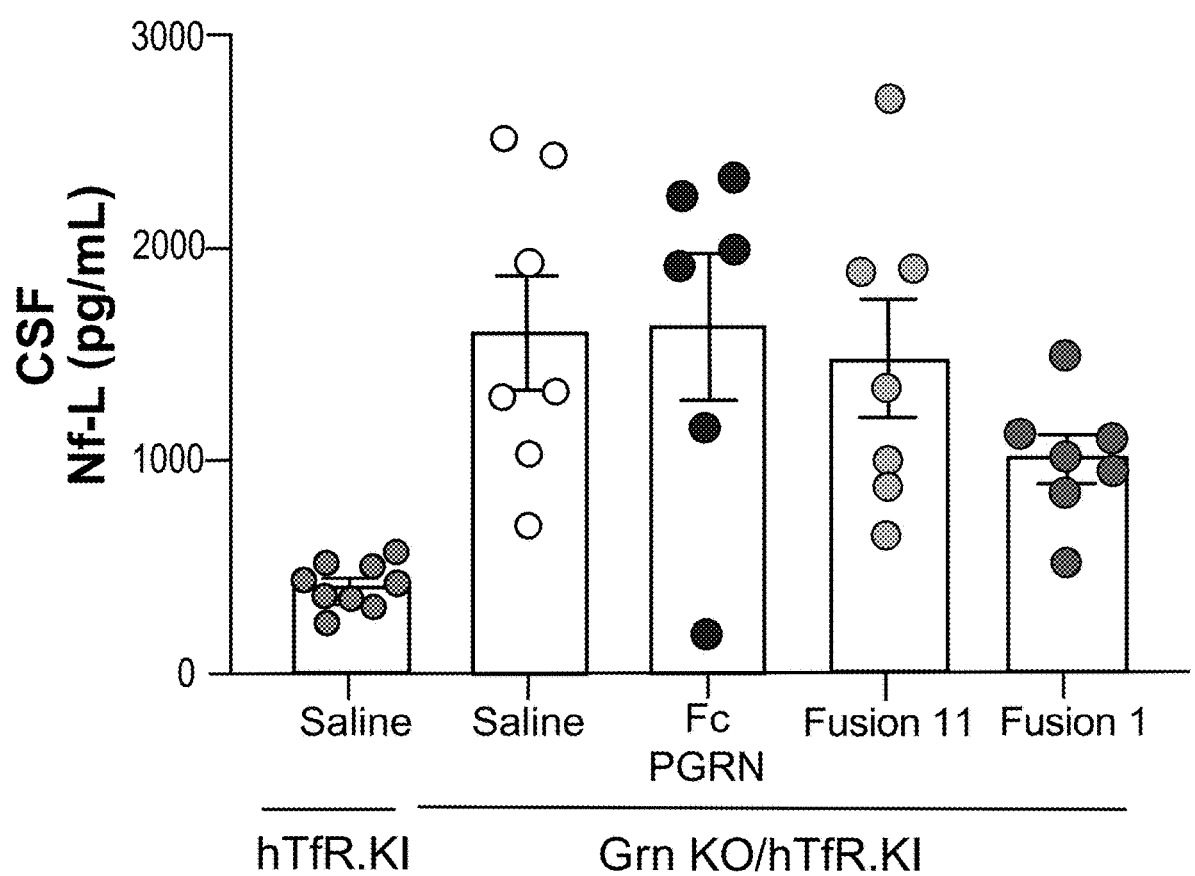
FIG. 22 is a scatter plot illustrating CSF neurofilament (Nf-L) levels in GRN KO/hTfR.KI mice after eight weekly doses of exemplary fusion proteins disclosed herein.

FIG. 22 provides information about CSF Nf-L levels in the treated GRN KO mice cohorts. As illustrated in FIG. 22, a trend in reduction of CSF Nf-L was observed following eight (8) weeks of weekly administration of Fusion 1 in GRN KO mice. In contrast, CSF Nf-L did not appear to be corrected by weekly treatment with Fc:PGRN or Fusion 11.

Figure 23:
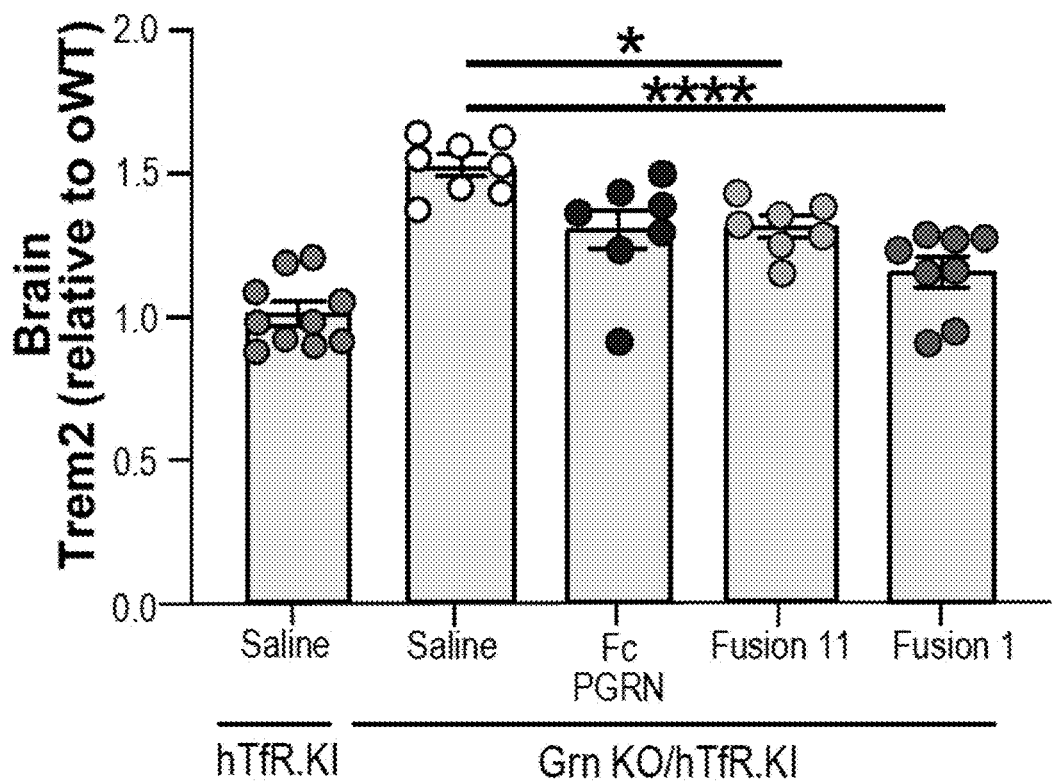
FIG. 23 is a scatter plot illustrating relative brain Trem2 levels in GRN KO/hTfR.KI mice after eight weekly doses of exemplary fusion proteins disclosed herein. The figure displays mean±SEM and p values: one-way ANOVA with Dunnett multiple comparison test; * p<0.05 and **** p<0.0001.

FIG. 23 provides information about relative TREM2 levels in the brains of the treated GRN KO mice cohorts. As illustrated in FIG. 23, weekly administration of Fusion 1 up to eight (8) weeks reduced TREM2 levels in brain tissue in a statistically significant manner relative to vehicle treatment. Weekly administration of Fusion 11 also reduced TREM2 levels in the brains of GRN KO mice, but the effect was not as great as that observed with weekly administration of Fusion 1.

Figure 24:
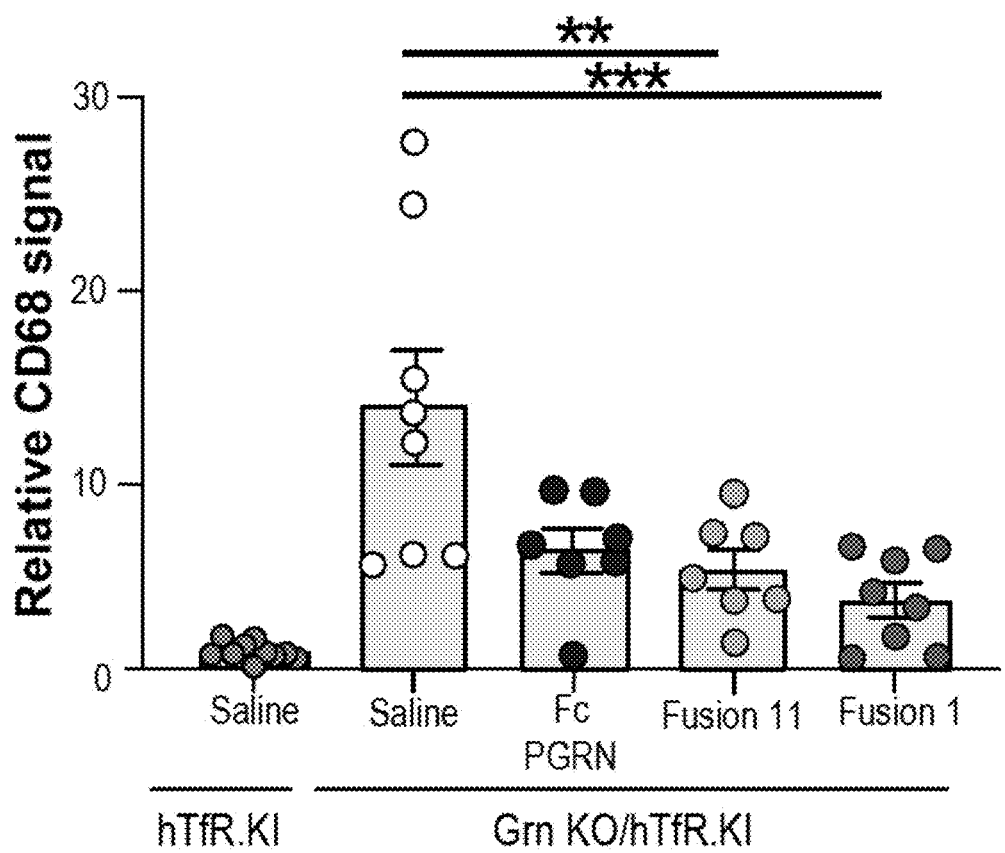
FIG. 24 is a scatter plot illustrating relative brain CD68 levels in GRN KO/hTfR.KI mice after eight weekly doses of exemplary fusion proteins disclosed herein. The figure displays mean±SEM and p values: one-way ANOVA with Dunnett multiple comparison test; p<0.01 and * p<0.001.
Figure 25:
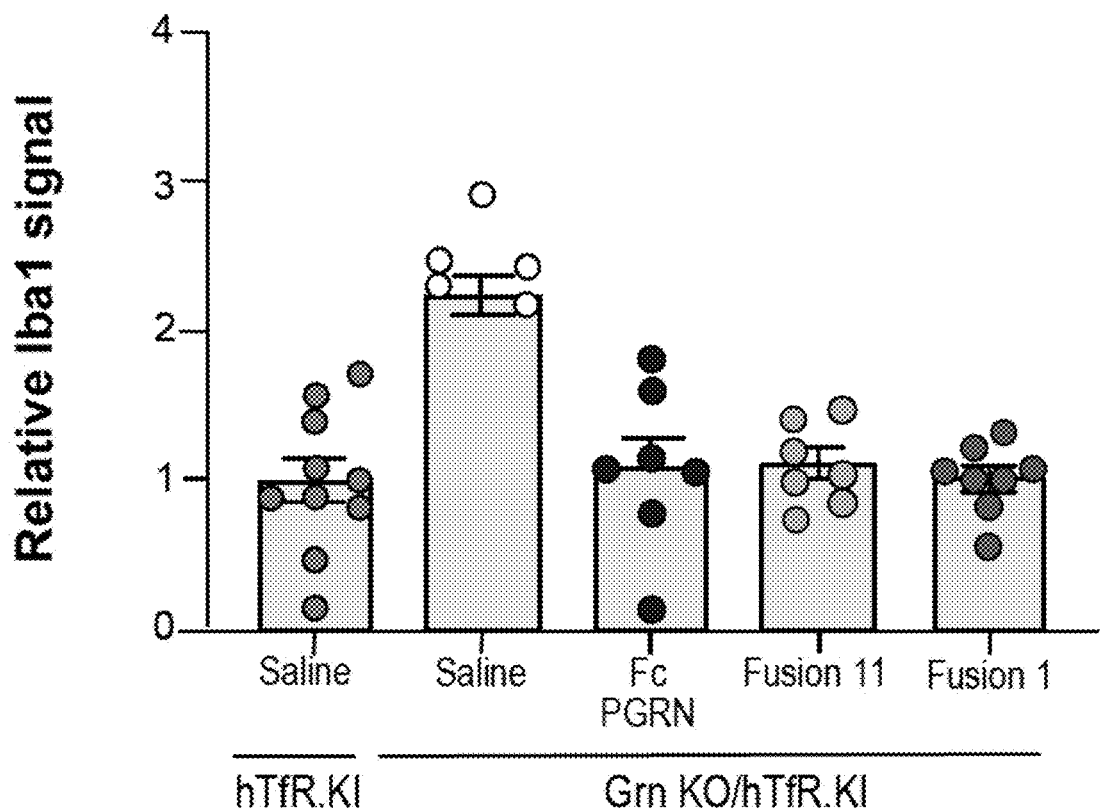
FIG. 25 is a scatter plot illustrating relative brain Iba1 levels in GRN KO/hTfR.KI mice after eight weekly doses of exemplary fusion proteins disclosed herein.
Figure 26:
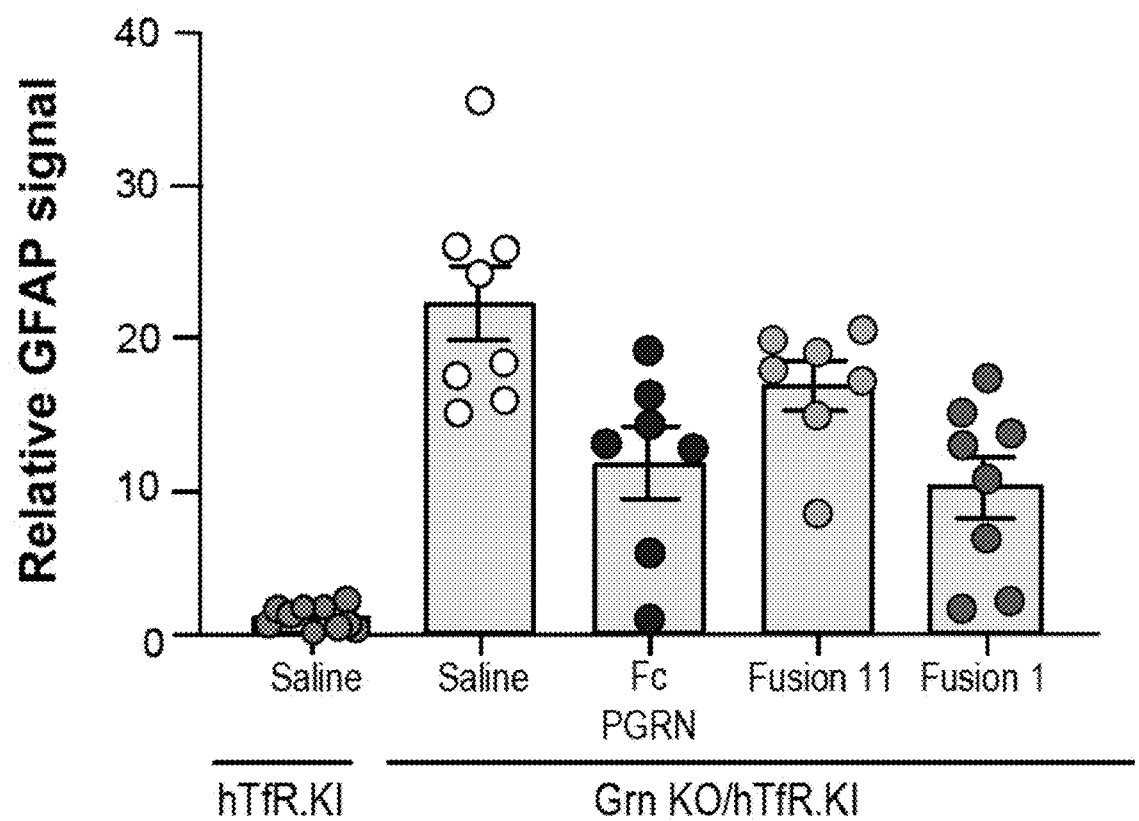
FIG. 26 is a scatter plot illustrating relative brain GFAP levels in GRN KO/hTfR.KI mice after eight weekly doses of exemplary fusion proteins disclosed herein.

FIGS. 24-26 provide information about gliosis markers in the brain (thalamus) of the treated GRN KO mice cohorts. As illustrated in FIGS. 24-26, weekly administration of Fc:PGRN, Fusion 1, and Fusion 11 up to eight (8) weeks reduced levels of CD68, Iba1, and GFAP in the brains of GRN KO mice relative to vehicle treatment.

Figure 27:
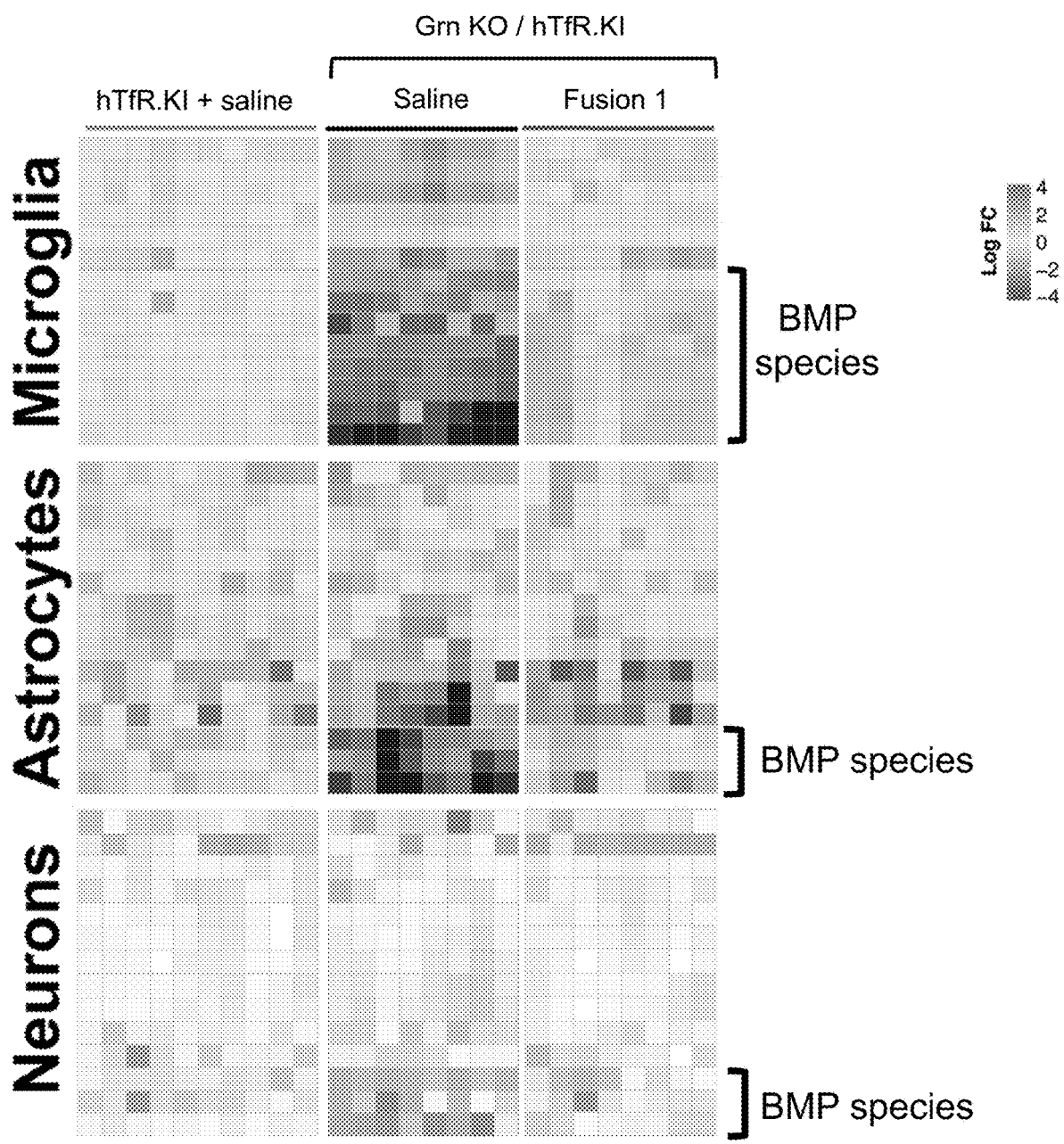
FIG. 27 is a heat map illustrating relative changes in BMP species and lipids in GRN KO/hTfR.KI mice after eight weekly doses of exemplary fusion proteins disclosed herein.
Figure 28:
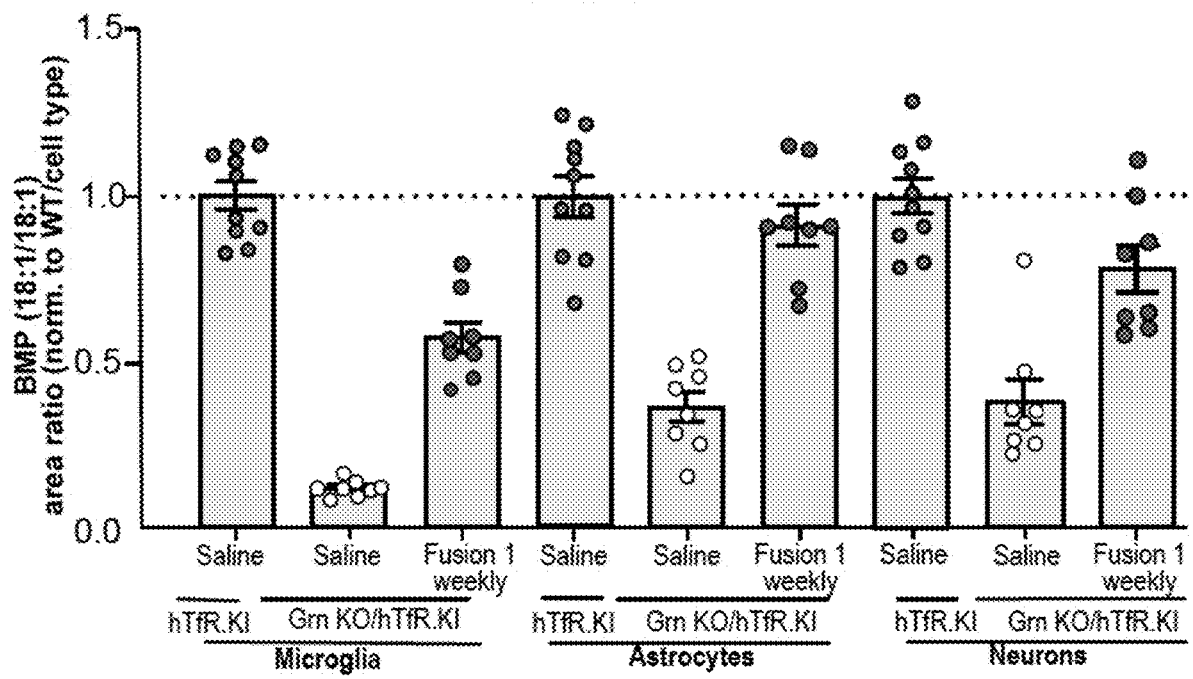
FIGS. 28-30 provide scatter plots illustrating levels of representative BMP species in neurons, astrocytes, and microglial cells of GRN KO/hTfR.KI mice after eight weekly doses of an exemplary fusion protein disclosed herein.
Figure 29:
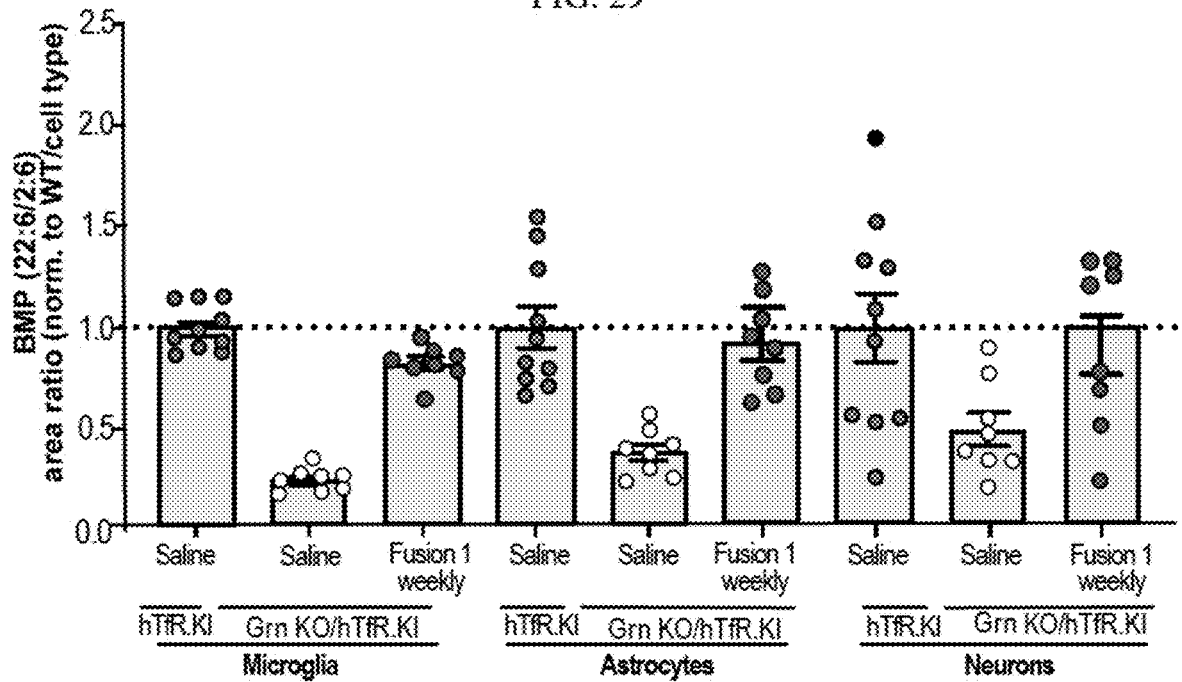
Figure 30:
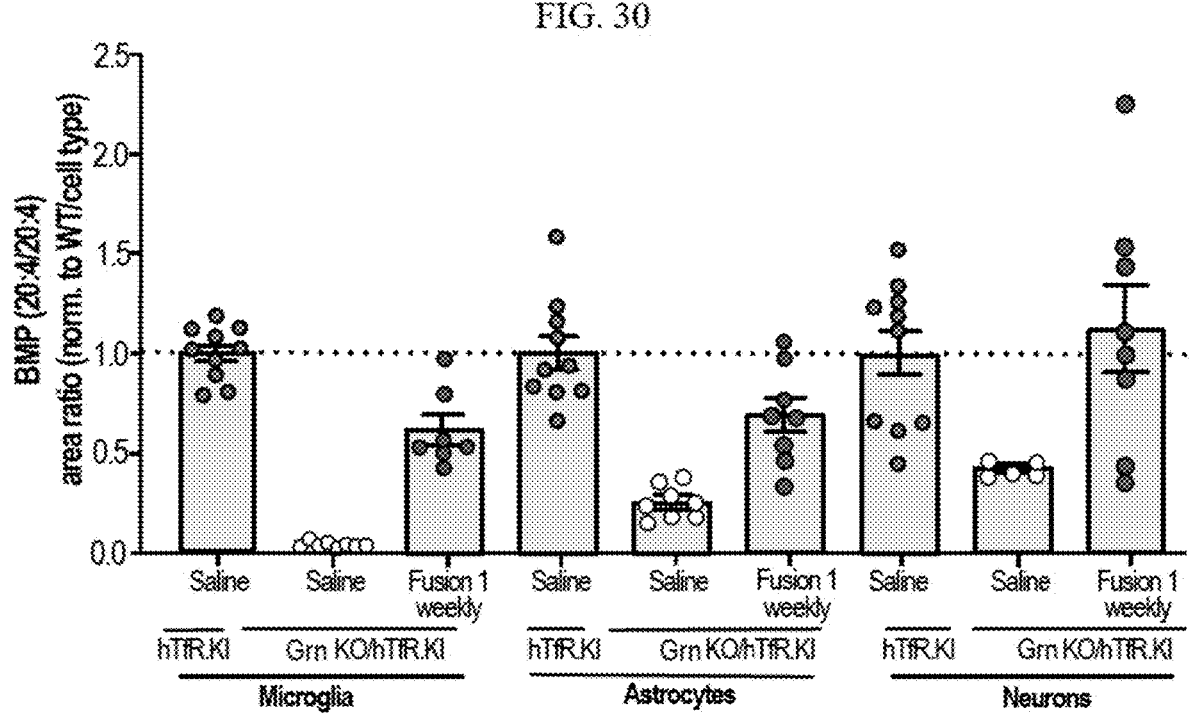

FIG. 27 is a heat map of BMP and certain lipids in the neurons, astrocytes, and microglial cells sorted from the brain tissues of the treated GRN KO mice cohorts. As illustrated in FIG. 27, weekly administration of Fusion 1 up to eight (8) weeks rescued BMP phenotypes across microglia, astrocytes and neurons. The rescue was most pronounced in microglial cells, although correction was also observed in astrocytes and neurons to a lesser extent. FIGS. 28-30 illustrate the trends in correction of certain BMP species (BMP 18:1/18:1, BMP 22:6/22:6, and BMP 20:4/20:4) upon administration of Fusion 1 in the sorted populations of neurons, astrocytes, and microglial cells of the treated GRN KO (relative to CNS cells of vehicle-treated GRN wild-type (hTfR.KI) cohorts).

It is understood that the examples and embodiments described herein are for illustrative purposes only and that various modifications or changes in light thereof will be suggested to persons skilled in the art and are to be included within the spirit and purview of this application and scope of the appended claims. The sequences of the sequence accession numbers cited herein are hereby incorporated by reference.

INFORMAL SEQUENCE LISTING

| SEQ ID NO: | Sequence | Description |
|---|---|---|
| 1 | MWTLVSWVALTAGLVAGTRCPDGQFCPVACCLDPGGASYSCCRPLLDKWPTTLSRHLGGPCQVDAHCSA GHSCIFTVSGTSSCCPFPEAVACGDGHHCCPRGFHCSADGRSCFQRSGNNSVGAIQCPDSQFECPDFSTCCV MVDGSWGCCPMPQASCCEDRVHCCPHGAFCDLVHTRCITPTGTHPLAKKLPAQRTNRAVALSSSVMCPD ARSRCPDGSTCCELPSGKYGCCPMPNATCCSDHLHCCPQDTVCDLIQSKCLSKENATTDLLTKLPAHTVGD VKCDMEVSCPDGYTCCRLQSGAWGCCPFTQAVCCEDHIHCCPAGFTCDTQKGTCEQGPHQVPWMEKAP | Progranulin (PGRN) polypeptide containing the signal peptide |

INFORMAL SEQUENCE LISTING

| SEQ ID NO: | Sequence | Description |
|---|---|---|
|  | AHLSLPDPQALKRDVPCDNVSSCPSSDTCCQLTSGEWGCCPIPEAVCCSDHQHCCPQGYTCVAEGQCQRG SEIVAGLEKMPARRASLSHPRDIGCDQHTSCPVGQTCCPSLGGSWACCQLPHAVCCEDRQHCCPAGYTCN VKARSCEKEVVSAQPATFLARSPHVGVKDVECGEGHFCHDNQTCCRDNRQGWACCPYRQGVCCADRRH CCPAGFRCAARGTKCLRREAPRWDAPLRDPALRQLL | (amino acids 1-17) |
| 2 | TRCPDGQFCPVACCLDPGGASYSCCRPLLDKWPTTLSRHLGGPCQVDAHCSAGHSCIFTVSGTSSCCPFPE AVACGDGHHCCPRGFHCSADGRSCFQRSGNNSVGAIQCPDSQFECPDFSTCCVMVDGSWGCCPMPQASC CEDRVHCCPHGAFCDLVHTRCITPTGTHPLAKKLPAQRTNRAVALSSSVMCPDARSRCPDGSTCCELPSGK YGCCPMPNATCCSDHLHCCPQDTVCDLIQSKCLSKENATTDLLTKLPAHTVGDVKCDMEVSCPDGYTCCR LQSGAWGCCPFTQAVCCEDHIHCCPAGFTCDTQKGTCEQGPHQVPWMEKAPAHLSLPDPQALKRDVPCD NVSSCPSSDTCCQLTSGEWGCCPIPEAVCCSDHQHCCPQGYTCVAEGQCQRGSEIVAGLEKMPARRASLSH PRDIGCDQHTSCPVGQTCCPSLGGSWACCQLPHAVCCEDRQHCCPAGYTCNVKARSCEKEVVSAQPATFL ARSPHVGVKDVECGEGHFCHDNQTCCRDNRQGWACCPYRQGVCCADRRHCCPAGFRCAARGTKCLRRE APRWDAPLRDPALRQLL | mature PRGN |
| 3 | TRCPDGQFCPVACCLDPGGASYSCCRPLLDKWPTTLSRHLGGPCQVDAHCSAGHSCIFTVSGTSSCCPFPE AVACGDGHHCCPRGFHCSADGRSCFQRSGNNSVGAIQCPDSQFECPDFSTCCVMVDGSWGCCPMPQASC CEDRVHCCPHGAFCDLVHTRCITPTGTHPLAKKLPAQRTNRAVALSSSVMCPDARSRCPDGSTCCELPSGK YGCCPMPNATCCSDHLHCCPQDTVCDLIQSKCLSKENATTDLLTKLPAHTVGDVKCDMEVSCPDGYTCCR LQSGAWGCCPFTQAVCCEDHIHCCPAGFTCDTQKGTCEQGPHQVPWMEKAPAHLSLPDPQALKRDVPCD NVSSCPSSDTCCQLTSGEWGCCPIPEAVCCSDHQHCCPQGYTCVAEGQCQRGSEIVAGLEKMPARRASLSH PRDIGCDQHTSCPVGQTCCPSLGGSWACCQLPHAVCCEDRQHCCPAGYTCNVKARSCEKEVVSAQPATFL ARSPHVGVKDVECGEGHFCHDNQTCCRDNRQGWACCPYRQGVCCADRRHCCPAGFRCAARGTKCLRRE APRWDAPLRDPALRX$_1$X$_2$X$_3$,wherein each of X$_1$, X$_2$, and X$_3$ is independently an amino acid, and X$_1$X$_2$X$_3$ together is not QLL | PGRN variant-1 |
| 4 | TRCPDGQFCPVACCLDPGGASYSCCRPLLDKWPTTLSRHLGGPCQVDAHCSAGHSCIFTVSGTSSCCPFPE AVACGDGHHCCPRGFHCSADGRSCFQRSGNNSVGAIQCPDSQFECPDFSTCCVMVDGSWGCCPMPQASC CEDRVHCCPHGAFCDLVHTRCITPTGTHPLAKKLPAQRTNRAVALSSSVMCPDARSRCPDGSTCCELPSGK YGCCPMPNATCCSDHLHCCPQDTVCDLIQSKCLSKENATTDLLTKLPAHTVGDVKCDMEVSCPDGYTCCR LQSGAWGCCPFTQAVCCEDHIHCCPAGFTCDTQKGTCEQGPHQVPWMEKAPAHLSLPDPQALKRDVPCD NVSSCPSSDTCCQLTSGEWGCCPIPEAVCCSDHQHCCPQGYTCVAEGQCQRGSEIVAGLEKMPARRASLSH PRDIGCDQHTSCPVGQTCCPSLGGSWACCQLPHAVCCEDRQHCCPAGYTCNVKARSCEKEVVSAQPATFL ARSPHVGVKDVECGEGHFCHDNQTCCRDNRQGWACCPYRQGVCCADRRHCCPAGFRCAARGTKCLRRE APRWDAPLRDPALRPHL | PGRN variant-2 |
| 5 | TRCPDGQFCPVACCLDPGGASYSCCRPLLDKWPTTLSRHLGGPCQVDAHCSAGHSCIFTVSGTSSCCPFPE AVACGDGHHCCPRGFHCSADGRSCFQRSGNNSVGAIQCPDSQFECPDFSTCCVMVDGSWGCCPMPQASC CEDRVHCCPHGAFCDLVHTRCITPTGTHPLAKKLPAQRTNRAVALSSSVMCPDARSRCPDGSTCCELPSGK YGCCPMPNATCCSDHLHCCPQDTVCDLIQSKCLSKENATTDLLTKLPAHTVGDVKCDMEVSCPDGYTCCR LQSGAWGCCPFTQAVCCEDHIHCCPAGFTCDTQKGTCEQGPHQVPWMEKAPAHLSLPDPQALKRDVPCD NVSSCPSSDTCCQLTSGEWGCCPIPEAVCCSDHQHCCPQGYTCVAEGQCQRGSEIVAGLEKMPARRASLSH PRDIGCDQHTSCPVGQTCCPSLGGSWACCQLPHAVCCEDRQHCCPAGYTCNVKARSCEKEVVSAQPATFL ARSPHVGVKDVECGEGHFCHDNQTCCRDNRQGWACCPYRQGVCCADRRHCCPAGFRCAARGTKCLRRE APRWDAPLRDPALRPKL | PGRN variant-3 |
| 6 | TRCPDGQFCPVACCLDPGGASYSCCRPLLDKWPTTLSRHLGGPCQVDAHCSAGHSCIFTVSGTSSCCPFPE AVACGDGHHCCPRGFHCSADGRSCFQRSGNNSVGAIQCPDSQFECPDFSTCCVMVDGSWGCCPMPQASC CEDRVHCCPHGAFCDLVHTRCITPTGTHPLAKKLPAQRTNRAVALSSSVMCPDARSRCPDGSTCCELPSGK YGCCPMPNATCCSDHLHCCPQDTVCDLIQSKCLSKENATTDLLTKLPAHTVGDVKCDMEVSCPDGYTCCR LQSGAWGCCPFTQAVCCEDHIHCCPAGFTCDTQKGTCEQGPHQVPWMEKAPAHLSLPDPQALKRDVPCD NVSSCPSSDTCCQLTSGEWGCCPIPEAVCCSDHQHCCPQGYTCVAEGQCQRGSEIVAGLEKMPARRASLSH PRDIGCDQHTSCPVGQTCCPSLGGSWACCQLPHAVCCEDRQHCCPAGYTCNVKARSCEKEVVSAQPATFL ARSPHVGVKDVECGEGHFCHDNQTCCRDNRQGWACCPYRQGVCCADRRHCCPAGFRCAARGTKCLRRE APRWDAPLRDPALRPDL | PGRN variant-4 |
| 7 | TRCPDGQFCPVACCLDPGGASYSCCRPLLDKWPTTLSRHLGGPCQVDAHCSAGHSCIFTVSGTSSCCPFPE AVACGDGHHCCPRGFHCSADGRSCFQRSGNNSVGAIQCPDSQFECPDFSTCCVMVDGSWGCCPMPQASC CEDRVHCCPHGAFCDLVHTRCITPTGTHPLAKKLPAQRTNRAVALSSSVMCPDARSRCPDGSTCCELPSGK YGCCPMPNATCCSDHLHCCPQDTVCDLIQSKCLSKENATTDLLTKLPAHTVGDVKCDMEVSCPDGYTCCR LQSGAWGCCPFTQAVCCEDHIHCCPAGFTCDTQKGTCEQGPHQVPWMEKAPAHLSLPDPQALKRDVPCD NVSSCPSSDTCCQLTSGEWGCCPIPEAVCCSDHQHCCPQGYTCVAEGQCQRGSEIVAGLEKMPARRASLSH PRDIGCDQHTSCPVGQTCCPSLGGSWACCQLPHAVCCEDRQHCCPAGYTCNVKARSCEKEVVSAQPATFL ARSPHVGVKDVECGEGHFCHDNQTCCRDNRQGWACCPYRQGVCCADRRHCCPAGFRCAARGTKCLRRE APRWDAPLRDPALRPEL | PGRN variant-5 |
| 8 | TRCPDGQFCPVACCLDPGGASYSCCRPLLDKWPTTLSRHLGGPCQVDAHCSAGHSCIFTVSGTSSCCPFPE AVACGDGHHCCPRGFHCSADGRSCFQRSGNNSVGAIQCPDSQFECPDFSTCCVMVDGSWGCCPMPQASC CEDRVHCCPHGAFCDLVHTRCITPTGTHPLAKKLPAQRTNRAVALSSSVMCPDARSRCPDGSTCCELPSGK YGCCPMPNATCCSDHLHCCPQDTVCDLIQSKCLSKENATTDLLTKLPAHTVGDVKCDMEVSCPDGYTCCR LQSGAWGCCPFTQAVCCEDHIHCCPAGFTCDTQKGTCEQGPHQVPWMEKAPAHLSLPDPQALKRDVPCD NVSSCPSSDTCCQLTSGEWGCCPIPEAVCCSDHQHCCPQGYTCVAEGQCQRGSEIVAGLEKMPARRASLSH PRDIGCDQHTSCPVGQTCCPSLGGSWACCQLPHAVCCEDRQHCCPAGYTCNVKARSCEKEVVSAQPATFL | PGRN variant-6 |

INFORMAL SEQUENCE LISTING

| SEQ ID NO: | Sequence | Description |
|---|---|---|
| | ARSPHVGVKDVECGEGHFCHDNQTCCRDNRQGWACCPYRQGVCCADRRHCCPAGFRCAARGTKCLRRE<br>APRWDAPLRDPALRPSL | |
| 9 | TRCPDGQFCPVACCLDPGGASYSCCRPLLDKWPTTLSRHLGGPCQVDAHCSAGHSCIFTVSGTSSCCPFPE<br>AVACGDGHHCCPRGFHCSADGRSCFQRSGNNSVGAIQCPDSQFECPDFSTCCVMVDGSWGCCPMPQASC<br>CEDRVHCCPHGAFCDLVHTRCITPTGTHPLAKKLPAQRTNRAVALSSSVMCPDARSRCPDGSTCCELPSGK<br>YGCCPMPNATCCSDHLHCCPQDTVCDLIQSKCLSKENATTDLLTKLPAHTVGDVKCDMEVSCPDGYTCCR<br>LQSGAWGCCPFTQAVCCEDHIHCCPAGFTCDTQKGTCEQGPHQVPWMEKAPAHLSLPDPQALKRDVPCD<br>NVSSCPSSDTCCQLTSGEWGCCPIPEAVCCSDHQHCCPQGYTCVAEGQCQRGSEIVAGLEKMPARRASLSH<br>PRDIGCDQHTSCPVGQTCCPSLGGSWACCQLPHAVCCEDRQHCCPAGYTCNVKARSCEKEVVSAQPATFL<br>ARSPHVGVKDVECGEGHFCHDNQTCCRDNRQGWACCPYRQGVCCADRRHCCPAGFRCAARGTKCLRRE<br>APRWDAPLRDPALRPTL | PGRN variant-7 |
| 10 | TRCPDGQFCPVACCLDPGGASYSCCRPLLDKWPTTLSRHLGGPCQVDAHCSAGHSCIFTVSGTSSCCPFPE<br>AVACGDGHHCCPRGFHCSADGRSCFQRSGNNSVGAIQCPDSQFECPDFSTCCVMVDGSWGCCPMPQASC<br>CEDRVHCCPHGAFCDLVHTRCITPTGTHPLAKKLPAQRTNRAVALSSSVMCPDARSRCPDGSTCCELPSGK<br>YGCCPMPNATCCSDHLHCCPQDTVCDLIQSKCLSKENATTDLLTKLPAHTVGDVKCDMEVSCPDGYTCCR<br>LQSGAWGCCPFTQAVCCEDHIHCCPAGFTCDTQKGTCEQGPHQVPWMEKAPAHLSLPDPQALKRDVPCD<br>NVSSCPSSDTCCQLTSGEWGCCPIPEAVCCSDHQHCCPQGYTCVAEGQCQRGSEIVAGLEKMPARRASLSH<br>PRDIGCDQHTSCPVGQTCCPSLGGSWACCQLPHAVCCEDRQHCCPAGYTCNVKARSCEKEVVSAQPATFL<br>ARSPHVGVKDVECGEGHFCHDNQTCCRDNRQGWACCPYRQGVCCADRRHCCPAGFRCAARGTKCLRRE<br>APRWDAPLRDPALRPNL | PGRN variant-8 |
| 11 | TRCPDGQFCPVACCLDPGGASYSCCRPLLDKWPTTLSRHLGGPCQVDAHCSAGHSCIFTVSGTSSCCPFPE<br>AVACGDGHHCCPRGFHCSADGRSCFQRSGNNSVGAIQCPDSQFECPDFSTCCVMVDGSWGCCPMPQASC<br>CEDRVHCCPHGAFCDLVHTRCITPTGTHPLAKKLPAQRTNRAVALSSSVMCPDARSRCPDGSTCCELPSGK<br>YGCCPMPNATCCSDHLHCCPQDTVCDLIQSKCLSKENATTDLLTKLPAHTVGDVKCDMEVSCPDGYTCCR<br>LQSGAWGCCPFTQAVCCEDHIHCCPAGFTCDTQKGTCEQGPHQVPWMEKAPAHLSLPDPQALKRDVPCD<br>NVSSCPSSDTCCQLTSGEWGCCPIPEAVCCSDHQHCCPQGYTCVAEGQCQRGSEIVAGLEKMPARRASLSH<br>PRDIGCDQHTSCPVGQTCCPSLGGSWACCQLPHAVCCEDRQHCCPAGYTCNVKARSCEKEVVSAQPATFL<br>ARSPHVGVKDVECGEGHFCHDNQTCCRDNRQGWACCPYRQGVCCADRRHCCPAGFRCAARGTKCLRRE<br>APRWDAPLRDPALRPQL | PGRN variant-9 |
| 12 | TRCPDGQFCPVACCLDPGGASYSCCRPLLDKWPTTLSRHLGGPCQVDAHCSAGHSCIFTVSGTSSCCPFPE<br>AVACGDGHHCCPRGFHCSADGRSCFQRSGNNSVGAIQCPDSQFECPDFSTCCVMVDGSWGCCPMPQASC<br>CEDRVHCCPHGAFCDLVHTRCITPTGTHPLAKKLPAQRTNRAVALSSSVMCPDARSRCPDGSTCCELPSGK<br>YGCCPMPNATCCSDHLHCCPQDTVCDLIQSKCLSKENATTDLLTKLPAHTVGDVKCDMEVSCPDGYTCCR<br>LQSGAWGCCPFTQAVCCEDHIHCCPAGFTCDTQKGTCEQGPHQVPWMEKAPAHLSLPDPQALKRDVPCD<br>NVSSCPSSDTCCQLTSGEWGCCPIPEAVCCSDHQHCCPQGYTCVAEGQCQRGSEIVAGLEKMPARRASLSH<br>PRDIGCDQHTSCPVGQTCCPSLGGSWACCQLPHAVCCEDRQHCCPAGYTCNVKARSCEKEVVSAQPATFL<br>ARSPHVGVKDVECGEGHFCHDNQTCCRDNRQGWACCPYRQGVCCADRRHCCPAGFRCAARGTKCLRRE<br>APRWDAPLRDPALRPGL | PGRN variant-10 |
| 13 | TRCPDGQFCPVACCLDPGGASYSCCRPLLDKWPTTLSRHLGGPCQVDAHCSAGHSCIFTVSGTSSCCPFPE<br>AVACGDGHHCCPRGFHCSADGRSCFQRSGNNSVGAIQCPDSQFECPDFSTCCVMVDGSWGCCPMPQASC<br>CEDRVHCCPHGAFCDLVHTRCITPTGTHPLAKKLPAQRTNRAVALSSSVMCPDARSRCPDGSTCCELPSGK<br>YGCCPMPNATCCSDHLHCCPQDTVCDLIQSKCLSKENATTDLLTKLPAHTVGDVKCDMEVSCPDGYTCCR<br>LQSGAWGCCPFTQAVCCEDHIHCCPAGFTCDTQKGTCEQGPHQVPWMEKAPAHLSLPDPQALKRDVPCD<br>NVSSCPSSDTCCQLTSGEWGCCPIPEAVCCSDHQHCCPQGYTCVAEGQCQRGSEIVAGLEKMPARRASLSH<br>PRDIGCDQHTSCPVGQTCCPSLGGSWACCQLPHAVCCEDRQHCCPAGYTCNVKARSCEKEVVSAQPATFL<br>ARSPHVGVKDVECGEGHFCHDNQTCCRDNRQGWACCPYRQGVCCADRRHCCPAGFRCAARGTKCLRRE<br>APRWDAPLRDPALRPPL | PGRN variant-11 |
| 14 | TRCPDGQFCPVACCLDPGGASYSCCRPLLDKWPTTLSRHLGGPCQVDAHCSAGHSCIFTVSGTSSCCPFPE<br>CPRGFHCSADGRSCFQRSGNNSVGAIQCPDSQFECPDFSTCCVMVDGSWGCCPMPQASC<br>CEDRVHCCPHGAFCDLVHTRCITPTGTHPLAKKLPAQRTNRAVALSSSVMCPDARSRCPDGSTCCELPSGK<br>YGCCPMPNATCCSDHLHCCPQDTVCDLIQSKCLSKENATTDLLTKLPAHTVGDVKCDMEVSCPDGYTCCR<br>LQSGAWGCCPFTQAVCCEDHIHCCPAGFTCDTQKGTCEQGPHQVPWMEKAPAHLSLPDPQALKRDVPCD<br>NVSSCPSSDTCCQLTSGEWGCCPIPEAVCCSDHQHCCPQGYTCVAEGQCQRGSEIVAGLEKMPARRASLSH<br>PRDIGCDQHTSCPVGQTCCPSLGGSWACCQLPHAVCCEDRQHCCPAGYTCNVKARSCEKEVVSAQPATFL<br>ARSPHVGVKDVECGEGHFCHDNQTCCRDNRQGWACCPYRQGVCCADRRHCCPAGFRCAARGTKCLRRE<br>APRWDAPLRDPALRPAL | PGRN variant-12 |
| 15 | TRCPDGQFCPVACCLDPGGASYSCCRPLLDKWPTTLSRHLGGPCQVDAHCSAGHSCIFTVSGTSSCCPFPE<br>AVACGDGHHCCPRGFHCSADGRSCFQRSGNNSVGAIQCPDSQFECPDFSTCCVMVDGSWGCCPMPQASC<br>CEDRVHCCPHGAFCDLVHTRCITPTGTHPLAKKLPAQRTNRAVALSSSVMCPDARSRCPDGSTCCELPSGK<br>YGCCPMPNATCCSDHLHCCPQDTVCDLIQSKCLSKENATTDLLTKLPAHTVGDVKCDMEVSCPDGYTCCR<br>LQSGAWGCCPFTQAVCCEDHIHCCPAGFTCDTQKGTCEQGPHQVPWMEKAPAHLSLPDPQALKRDVPCD<br>NVSSCPSSDTCCQLTSGEWGCCPIPEAVCCSDHQHCCPQGYTCVAEGQCQRGSEIVAGLEKMPARRASLSH<br>PRDIGCDQHTSCPVGQTCCPSLGGSWACCQLPHAVCCEDRQHCCPAGYTCNVKARSCEKEVVSAQPATFL<br>ARSPHVGVKDVECGEGHFCHDNQTCCRDNRQGWACCPYRQGVCCADRRHCCPAGFRCAARGTKCLRRE<br>APRWDAPLRDPALRPYL | PGRN variant-13 |

INFORMAL SEQUENCE LISTING

| SEQ ID NO: | Sequence | Description |
|---|---|---|
| 16 | TRCPDGQFCPVACCLDPGGASYSCCRPLLDKWPTTLSRHLGGPCQVDAHCSAGHSCIFTVSGTSSCCPFPE<br>AVACGDGHHCCPRGFHCSADGRSCFQRSGNNSVGAIQCPDSQFECPDFSTCCVMVDGSWGCCPMPQASC<br>CEDRVHCCPHGAFCDLVHTRCITPTGTHPLAKKLPAQRTNRAVALSSSVMCPDARSRCPDGSTCCELPSGK<br>YGCCPMPNATCCSDHLHCCPQDTVCDLIQSKCLSKENATTDLLTKLPAHTVGDVKCDMEVSCPDGYTCCR<br>LQSGAWGCCPFTQAVCCEDHIHCCPAGFTCDTQKGTCEQGPHQVPWMEKAPAHLSLPDPQALKRDVPCD<br>NVSSCPSSDTCCQLTSGEWGCCPIPEAVCCSDHQHCCPQGYTCVAEGQCQRGSEIVAGLEKMPARRASLSH<br>PRDIGCDQHTSCPVGQTCCPSLGGSWACCQLPHAVCCEDRQHCCPAGYTCNVKARSCEKEVVSAQPATFL<br>ARSPHVGVKDVECGEGHFCHDNQTCCRDNRQGWACCPYRQGVCCADRRHCCPAGFRCAARGTKCLRRE<br>APRWDAPLRDPALRPVL | PGRN variant-14 |
| 17 | TRCPDGQFCPVACCLDPGGASYSCCRPLLDKWPTTLSRHLGGPCQVDAHCSAGHSCIFTVSGTSSCCPFPE<br>AVACGDGHHCCPRGFHCSADGRSCFQRSGNNSVGAIQCPDSQFECPDFSTCCVMVDGSWGCCPMPQASC<br>CEDRVHCCPHGAFCDLVHTRCITPTGTHPLAKKLPAQRTNRAVALSSSVMCPDARSRCPDGSTCCELPSGK<br>YGCCPMPNATCCSDHLHCCPQDTVCDLIQSKCLSKENATTDLLTKLPAHTVGDVKCDMEVSCPDGYTCCR<br>LQSGAWGCCPFTQAVCCEDHIHCCPAGFTCDTQKGTCEQGPHQVPWMEKAPAHLSLPDPQALKRDVPCD<br>NVSSCPSSDTCCQLTSGEWGCCPIPEAVCCSDHQHCCPQGYTCVAEGQCQRGSEIVAGLEKMPARRASLSH<br>PRDIGCDQHTSCPVGQTCCPSLGGSWACCQLPHAVCCEDRQHCCPAGYTCNVKARSCEKEVVSAQPATFL<br>ARSPHVGVKDVECGEGHFCHDNQTCCRDNRQGWACCPYRQGVCCADRRHCCPAGFRCAARGTKCLRRE<br>APRWDAPLRDPALRPIL | PGRN variant-15 |
| 18 | TRCPDGQFCPVACCLDPGGASYSCCRPLLDKWPTTLSRHLGGPCQVDAHCSAGHSCIFTVSGTSSCCPFPE<br>AVACGDGHHCCPRGFHCSADGRSCFQRSGNNSVGAIQCPDSQFECPDFSTCCVMVDGSWGCCPMPQASC<br>CEDRVHCCPHGAFCDLVHTRCITPTGTHPLAKKLPAQRTNRAVALSSSVMCPDARSRCPDGSTCCELPSGK<br>YGCCPMPNATCCSDHLHCCPQDTVCDLIQSKCLSKENATTDLLTKLPAHTVGDVKCDMEVSCPDGYTCCR<br>LQSGAWGCCPFTQAVCCEDHIHCCPAGFTCDTQKGTCEQGPHQVPWMEKAPAHLSLPDPQALKRDVPCD<br>NVSSCPSSDTCCQLTSGEWGCCPIPEAVCCSDHQHCCPQGYTCVAEGQCQRGSEIVAGLEKMPARRASLSH<br>PRDIGCDQHTSCPVGQTCCPSLGGSWACCQLPHAVCCEDRQHCCPAGYTCNVKARSCEKEVVSAQPATFL<br>ARSPHVGVKDVECGEGHFCHDNQTCCRDNRQGWACCPYRQGVCCADRRHCCPAGFRCAARGTKCLRRE<br>APRWDAPLRDPALRPFL | PGRN variant-16 |
| 19 | TRCPDGQFCPVACCLDPGGASYSCCRPLLDKWPTTLSRHLGGPCQVDAHCSAGHSCIFTVSGTSSCCPFPE<br>AVACGDGHHCCPRGFHCSADGRSCFQRSGNNSVGAIQCPDSQFECPDFSTCCVMVDGSWGCCPMPQASC<br>CEDRVHCCPHGAFCDLVHTRCITPTGTHPLAKKLPAQRTNRAVALSSSVMCPDARSRCPDGSTCCELPSGK<br>YGCCPMPNATCCSDHLHCCPQDTVCDLIQSKCLSKENATTDLLTKLPAHTVGDVKCDMEVSCPDGYTCCR<br>LQSGAWGCCPFTQAVCCEDHIHCCPAGFTCDTQKGTCEQGPHQVPWMEKAPAHLSLPDPQALKRDVPCD<br>NVSSCPSSDTCCQLTSGEWGCCPIPEAVCCSDHQHCCPQGYTCVAEGQCQRGSEIVAGLEKMPARRASLSH<br>PRDIGCDQHTSCPVGQTCCPSLGGSWACCQLPHAVCCEDRQHCCPAGYTCNVKARSCEKEVVSAQPATFL<br>ARSPHVGVKDVECGEGHFCHDNQTCCRDNRQGWACCPYRQGVCCADRRHCCPAGFRCAARGTKCLRRE<br>APRWDAPLRDPALRQRL | PGRN variant-17 |
| 20 | TRCPDGQFCPVACCLDPGGASYSCCRPLLDKWPTTLSRHLGGPCQVDAHCSAGHSCIFTVSGTSSCCPFPE<br>AVACGDGHHCCPRGFHCSADGRSCFQRSGNNSVGAIQCPDSQFECPDFSTCCVMVDGSWGCCPMPQASC<br>CEDRVHCCPHGAFCDLVHTRCITPTGTHPLAKKLPAQRTNRAVALSSSVMCPDARSRCPDGSTCCELPSGK<br>YGCCPMPNATCCSDHLHCCPQDTVCDLIQSKCLSKENATTDLLTKLPAHTVGDVKCDMEVSCPDGYTCCR<br>LQSGAWGCCPFTQAVCCEDHIHCCPAGFTCDTQKGTCEQGPHQVPWMEKAPAHLSLPDPQALKRDVPCD<br>NVSSCPSSDTCCQLTSGEWGCCPIPEAVCCSDHQHCCPQGYTCVAEGQCQRGSEIVAGLEKMPARRASLSH<br>PRDIGCDQHTSCPVGQTCCPSLGGSWACCQLPHAVCCEDRQHCCPAGYTCNVKARSCEKEVVSAQPATFL<br>ARSPHVGVKDVECGEGHFCHDNQTCCRDNRQGWACCPYRQGVCCADRRHCCPAGFRCAARGTKCLRRE<br>APRWDAPLRDPALRQHL | PGRN variant-18 |
| 21 | TRCPDGQFCPVACCLDPGGASYSCCRPLLDKWPTTLSRHLGGPCQVDAHCSAGHSCIFTVSGTSSCCPFPE<br>AVACGDGHHCCPRGFHCSADGRSCFQRSGNNSVGAIQCPDSQFECPDFSTCCVMVDGSWGCCPMPQASC<br>CEDRVHCCPHGAFCDLVHTRCITPTGTHPLAKKLPAQRTNRAVALSSSVMCPDARSRCPDGSTCCELPSGK<br>YGCCPMPNATCCSDHLHCCPQDTVCDLIQSKCLSKENATTDLLTKLPAHTVGDVKCDMEVSCPDGYTCCR<br>LQSGAWGCCPFTQAVCCEDHIHCCPAGFTCDTQKGTCEQGPHQVPWMEKAPAHLSLPDPQALKRDVPCD<br>NVSSCPSSDTCCQLTSGEWGCCPIPEAVCCSDHQHCCPQGYTCVAEGQCQRGSEIVAGLEKMPARRASLSH<br>PRDIGCDQHTSCPVGQTCCPSLGGSWACCQLPHAVCCEDRQHCCPAGYTCNVKARSCEKEVVSAQPATFL<br>ARSPHVGVKDVECGEGHFCHDNQTCCRDNRQGWACCPYRQGVCCADRRHCCPAGFRCAARGTKCLRRE<br>APRWDAPLRDPALRQKL | PGRN variant-19 |
| 22 | TRCPDGQFCPVACCLDPGGASYSCCRPLLDKWPTTLSRHLGGPCQVDAHCSAGHSCIFTVSGTSSCCPFPE<br>AVACGDGHHCCPRGFHCSADGRSCFQRSGNNSVGAIQCPDSQFECPDFSTCCVMVDGSWGCCPMPQASC<br>CEDRVHCCPHGAFCDLVHTRCITPTGTHPLAKKLPAQRTNRAVALSSSVMCPDARSRCPDGSTCCELPSGK<br>YGCCPMPNATCCSDHLHCCPQDTVCDLIQSKCLSKENATTDLLTKLPAHTVGDVKCDMEVSCPDGYTCCR<br>LQSGAWGCCPFTQAVCCEDHIHCCPAGFTCDTQKGTCEQGPHQVPWMEKAPAHLSLPDPQALKRDVPCD<br>NVSSCPSSDTCCQLTSGEWGCCPIPEAVCCSDHQHCCPQGYTCVAEGQCQRGSEIVAGLEKMPARRASLSH<br>PRDIGCDQHTSCPVGQTCCPSLGGSWACCQLPHAVCCEDRQHCCPAGYTCNVKARSCEKEVVSAQPATFL<br>ARSPHVGVKDVECGEGHFCHDNQTCCRDNRQGWACCPYRQGVCCADRRHCCPAGFRCAARGTKCLRRE<br>APRWDAPLRDPALRQDL | PGRN variant-20 |
| 23 | TRCPDGQFCPVACCLDPGGASYSCCRPLLDKWPTTLSRHLGGPCQVDAHCSAGHSCIFTVSGTSSCCPFPE<br>AVACGDGHHCCPRGFHCSADGRSCFQRSGNNSVGAIQCPDSQFECPDFSTCCVMVDGSWGCCPMPQASC<br>CEDRVHCCPHGAFCDLVHTRCITPTGTHPLAKKLPAQRTNRAVALSSSVMCPDARSRCPDGSTCCELPSGK | PGRN variant-21 |

| INFORMAL SEQUENCE LISTING | | |
|---|---|---|
| SEQ ID NO: | Sequence | Description |
| | YGCCPMPNATCCSDHLHCCPQDTVCDLIQSKCLSKENATTDLLTKLPAHTVGDVKCDMEVSCPDGYTCCR LQSGAWGCCPFTQAVCCEDHIHCCPAGFTCDTQKGTCEQGPHQVPWMEKAPAHLSLPDPQALKRDVPCD NVSSCPSSDTCCQLTSGEWGCCPIPEAVCCSDHQHCCPQGYTCVAEGQCQRGSEIVAGLEKMPARRASLSH PRDIGCDQHTSCPVGQTCCPSLGGSWACCQLPHAVCCEDRQHCCPAGYTCNVKARSCEKEVVSAQPATFL ARSPHVGVKDVECGEGHFCHDNQTCCRDNRQGWACCPYRQGVCCADRRHCCPAGFRCAARGTKCLRRE APRWDAPLRDPALRQEL | |
| 24 | TRCPDGQFCPVACCLDPGGASYSCCRPLLDKWPTTLSRHLGGPCQVDAHCSAGHSCIFTVSGTSSCCPFPE AVACGDGHHCCPRGFHCSADGRSCFQRSGNNSVGAIQCPDSQFECPDFSTCCVMVDGSWGCCPMPQASC CEDRVHCCPHGAFCDLVHTRCITPTGTHPLAKKLPAQRTNRAVALSSSVMCPDARSRCPDGSTCCELPSGK YGCCPMPNATCCSDHLHCCPQDTVCDLIQSKCLSKENATTDLLTKLPAHTVGDVKCDMEVSCPDGYTCCR LQSGAWGCCPFTQAVCCEDHIHCCPAGFTCDTQKGTCEQGPHQVPWMEKAPAHLSLPDPQALKRDVPCD NVSSCPSSDTCCQLTSGEWGCCPIPEAVCCSDHQHCCPQGYTCVAEGQCQRGSEIVAGLEKMPARRASLSH PRDIGCDQHTSCPVGQTCCPSLGGSWACCQLPHAVCCEDRQHCCPAGYTCNVKARSCEKEVVSAQPATFL ARSPHVGVKDVECGEGHFCHDNQTCCRDNRQGWACCPYRQGVCCADRRHCCPAGFRCAARGTKCLRRE APRWDAPLRDPALRQNL | PGRN variant-22 |
| 25 | TRCPDGQFCPVACCLDPGGASYSCCRPLLDKWPTTLSRHLGGPCQVDAHCSAGHSCIFTVSGTSSCCPFPE AVACGDGHHCCPRGFHCSADGRSCFQRSGNNSVGAIQCPDSQFECPDFSTCCVMVDGSWGCCPMPQASC CEDRVHCCPHGAFCDLVHTRCITPTGTHPLAKKLPAQRTNRAVALSSSVMCPDARSRCPDGSTCCELPSGK YGCCPMPNATCCSDHLHCCPQDTVCDLIQSKCLSKENATTDLLTKLPAHTVGDVKCDMEVSCPDGYTCCR LQSGAWGCCPFTQAVCCEDHIHCCPAGFTCDTQKGTCEQGPHQVPWMEKAPAHLSLPDPQALKRDVPCD NVSSCPSSDTCCQLTSGEWGCCPIPEAVCCSDHQHCCPQGYTCVAEGQCQRGSEIVAGLEKMPARRASLSH PRDIGCDQHTSCPVGQTCCPSLGGSWACCQLPHAVCCEDRQHCCPAGYTCNVKARSCEKEVVSAQPATFL ARSPHVGVKDVECGEGHFCHDNQTCCRDNRQGWACCPYRQGVCCADRRHCCPAGFRCAARGTKCLRRE APRWDAPLRDPALRQPL | PGRN variant-23 |
| 26 | TRCPDGQFCPVACCLDPGGASYSCCRPLLDKWPTTLSRHLGGPCQVDAHCSAGHSCIFTVSGTSSCCPFPE AVACGDGHHCCPRGFHCSADGRSCFQRSGNNSVGAIQCPDSQFECPDFSTCCVMVDGSWGCCPMPQASC CEDRVHCCPHGAFCDLVHTRCITPTGTHPLAKKLPAQRTNRAVALSSSVMCPDARSRCPDGSTCCELPSGK YGCCPMPNATCCSDHLHCCPQDTVCDLIQSKCLSKENATTDLLTKLPAHTVGDVKCDMEVSCPDGYTCCR LQSGAWGCCPFTQAVCCEDHIHCCPAGFTCDTQKGTCEQGPHQVPWMEKAPAHLSLPDPQALKRDVPCD NVSSCPSSDTCCQLTSGEWGCCPIPEAVCCSDHQHCCPQGYTCVAEGQCQRGSEIVAGLEKMPARRASLSH PRDIGCDQHTSCPVGQTCCPSLGGSWACCQLPHAVCCEDRQHCCPAGYTCNVKARSCEKEVVSAQPATFL ARSPHVGVKDVECGEGHFCHDNQTCCRDNRQGWACCPYRQGVCCADRRHCCPAGFRCAARGTKCLRRE APRWDAPLRDPALRQYL | PGRN variant-24 |
| 27 | TRCPDGQFCPVACCLDPGGASYSCCRPLLDKWPTTLSRHLGGPCQVDAHCSAGHSCIFTVSGTSSCCPFPE AVACGDGHHCCPRGFHCSADGRSCFQRSGNNSVGAIQCPDSQFECPDFSTCCVMVDGSWGCCPMPQASC CEDRVHCCPHGAFCDLVHTRCITPTGTHPLAKKLPAQRTNRAVALSSSVMCPDARSRCPDGSTCCELPSGK YGCCPMPNATCCSDHLHCCPQDTVCDLIQSKCLSKENATTDLLTKLPAHTVGDVKCDMEVSCPDGYTCCR LQSGAWGCCPFTQAVCCEDHIHCCPAGFTCDTQKGTCEQGPHQVPWMEKAPAHLSLPDPQALKRDVPCD NVSSCPSSDTCCQLTSGEWGCCPIPEAVCCSDHQHCCPQGYTCVAEGQCQRGSEIVAGLEKMPARRASLSH PRDIGCDQHTSCPVGQTCCPSLGGSWACCQLPHAVCCEDRQHCCPAGYTCNVKARSCEKEVVSAQPATFL ARSPHVGVKDVECGEGHFCHDNQTCCRDNRQGWACCPYRQGVCCADRRHCCPAGFRCAARGTKCLRRE APRWDAPLRDPALRQQL | PGRN variant-25 |
| 28 | TRCPDGQFCPVACCLDPGGASYSCCRPLLDKWPTTLSRHLGGPCQVDAHCSAGHSCIFTVSGTSSCCPFPE AVACGDGHHCCPRGFHCSADGRSCFQRSGNNSVGAIQCPDSQFECPDFSTCCVMVDGSWGCCPMPQASC CEDRVHCCPHGAFCDLVHTRCITPTGTHPLAKKLPAQRTNRAVALSSSVMCPDARSRCPDGSTCCELPSGK YGCCPMPNATCCSDHLHCCPQDTVCDLIQSKCLSKENATTDLLTKLPAHTVGDVKCDMEVSCPDGYTCCR LQSGAWGCCPFTQAVCCEDHIHCCPAGFTCDTQKGTCEQGPHQVPWMEKAPAHLSLPDPQALKRDVPCD NVSSCPSSDTCCQLTSGEWGCCPIPEAVCCSDHQHCCPQGYTCVAEGQCQRGSEIVAGLEKMPARRASLSH PRDIGCDQHTSCPVGQTCCPSLGGSWACCQLPHAVCCEDRQHCCPAGYTCNVKARSCEKEVVSAQPATFL ARSPHVGVKDVECGEGHFCHDNQTCCRDNRQGWACCPYRQGVCCADRRHCCPAGFRCAARGTKCLRRE APRWDAPLRDPALRVVL | PGRN variant-26 |
| 29 | TRCPDGQFCPVACCLDPGGASYSCCRPLLDKWPTTLSRHLGGPCQVDAHCSAGHSCIFTVSGTSSCCPFPE AVACGDGHHCCPRGFHCSADGRSCFQRSGNNSVGAIQCPDSQFECPDFSTCCVMVDGSWGCCPMPQASC CEDRVHCCPHGAFCDLVHTRCITPTGTHPLAKKLPAQRTNRAVALSSSVMCPDARSRCPDGSTCCELPSGK YGCCPMPNATCCSDHLHCCPQDTVCDLIQSKCLSKENATTDLLTKLPAHTVGDVKCDMEVSCPDGYTCCR LQSGAWGCCPFTQAVCCEDHIHCCPAGFTCDTQKGTCEQGPHQVPWMEKAPAHLSLPDPQALKRDVPCD NVSSCPSSDTCCQLTSGEWGCCPIPEAVCCSDHQHCCPQGYTCVAEGQCQRGSEIVAGLEKMPARRASLSH PRDIGCDQHTSCPVGQTCCPSLGGSWACCQLPHAVCCEDRQHCCPAGYTCNVKARSCEKEVVSAQPATFL ARSPHVGVKDVECGEGHFCHDNQTCCRDNRQGWACCPYRQGVCCADRRHCCPAGFRCAARGTKCLRRE APRWDAPLRDPALRVTL | PGRN variant-27 |
| 30 | TRCPDGQFCPVACCLDPGGASYSCCRPLLDKWPTTLSRHLGGPCQVDAHCSAGHSCIFTVSGTSSCCPFPE AVACGDGHHCCPRGFHCSADGRSCFQRSGNNSVGAIQCPDSQFECPDFSTCCVMVDGSWGCCPMPQASC CEDRVHCCPHGAFCDLVHTRCITPTGTHPLAKKLPAQRTNRAVALSSSVMCPDARSRCPDGSTCCELPSGK YGCCPMPNATCCSDHLHCCPQDTVCDLIQSKCLSKENATTDLLTKLPAHTVGDVKCDMEVSCPDGYTCCR LQSGAWGCCPFTQAVCCEDHIHCCPAGFTCDTQKGTCEQGPHQVPWMEKAPAHLSLPDPQALKRDVPCD NVSSCPSSDTCCQLTSGEWGCCPIPEAVCCSDHQHCCPQGYTCVAEGQCQRGSEIVAGLEKMPARRASLSH | PGRN variant-28 |

| SEQ ID NO: | Sequence | Description |
|---|---|---|
| | PRDIGCDQHTSCPVGQTCCPSLGGSWACCQLPHAVCCEDRQHCCPAGYTCNVKARSCEKEVVSAQPATFL ARSPHVGVKDVECGEGHFCHDNQTCCRDNRQGWACCPYRQGVCCADRRHCCPAGFRCAARGTKCLRRE APRWDAPLRDPALRRIL | |
| 31 | TRCPDGQFCPVACCLDPGGASYSCCRPLLDKWPTTLSRHLGGPCQVDAHCSAGHSCIFTVSGTSSCCPFPE AVACGDGHHCCPRGFHCSADGRSCFQRSGNNSVGAIQCPDSQFECPDFSTCCVMVDGSWGCCPMPQASC CEDRVHCCPHGAFCDLVHTRCITPTGTHPLAKKLPAQRTNRAVALSSSVMCPDARSRCPDGSTCCELPSGK YGCCPMPNATCCSDHLHCCPQDTVCDLIQSKCLSKENATTDLLTKLPAHTVGDVKCDMEVSCPDGYTCCR LQSGAWGCCPFTQAVCCEDHIHCCPAGFTCDTQKGTCEQGPHQVPWMEKAPAHLSLPDPQALKRDVPCD NVSSCPSSDTCCQLTSGEWGCCPIPEAVCCSDHQHCCPQGYTCVAEGQCQRGSEIVAGLEKMPARRASLSH PRDIGCDQHTSCPVGQTCCPSLGGSWACCQLPHAVCCEDRQHCCPAGYTCNVKARSCEKEVVSAQPATFL ARSPHVGVKDVECGEGHFCHDNQTCCRDNRQGWACCPYRQGVCCADRRHCCPAGFRCAARGTKCLRRE APRWDAPLRDPALRHIL | PGRN variant-29 |
| 32 | TRCPDGQFCPVACCLDPGGASYSCCRPLLDKWPTTLSRHLGGPCQVDAHCSAGHSCIFTVSGTSSCCPFPE AVACGDGHHCCPRGFHCSADGRSCFQRSGNNSVGAIQCPDSQFECPDFSTCCVMVDGSWGCCPMPQASC CEDRVHCCPHGAFCDLVHTRCITPTGTHPLAKKLPAQRTNRAVALSSSVMCPDARSRCPDGSTCCELPSGK YGCCPMPNATCCSDHLHCCPQDTVCDLIQSKCLSKENATTDLLTKLPAHTVGDVKCDMEVSCPDGYTCCR LQSGAWGCCPFTQAVCCEDHIHCCPAGFTCDTQKGTCEQGPHQVPWMEKAPAHLSLPDPQALKRDVPCD NVSSCPSSDTCCQLTSGEWGCCPIPEAVCCSDHQHCCPQGYTCVAEGQCQRGSEIVAGLEKMPARRASLSH PRDIGCDQHTSCPVGQTCCPSLGGSWACCQLPHAVCCEDRQHCCPAGYTCNVKARSCEKEVVSAQPATFL ARSPHVGVKDVECGEGHFCHDNQTCCRDNRQGWACCPYRQGVCCADRRHCCPAGFRCAARGTKCLRRE APRWDAPLRDPALRKIL | PGRN variant-30 |
| 33 | TRCPDGQFCPVACCLDPGGASYSCCRPLLDKWPTTLSRHLGGPCQVDAHCSAGHSCIFTVSGTSSCCPFPE AVACGDGHHCCPRGFHCSADGRSCFQRSGNNSVGAIQCPDSQFECPDFSTCCVMVDGSWGCCPMPQASC CEDRVHCCPHGAFCDLVHTRCITPTGTHPLAKKLPAQRTNRAVALSSSVMCPDARSRCPDGSTCCELPSGK YGCCPMPNATCCSDHLHCCPQDTVCDLIQSKCLSKENATTDLLTKLPAHTVGDVKCDMEVSCPDGYTCCR LQSGAWGCCPFTQAVCCEDHIHCCPAGFTCDTQKGTCEQGPHQVPWMEKAPAHLSLPDPQALKRDVPCD NVSSCPSSDTCCQLTSGEWGCCPIPEAVCCSDHQHCCPQGYTCVAEGQCQRGSEIVAGLEKMPARRASLSH PRDIGCDQHTSCPVGQTCCPSLGGSWACCQLPHAVCCEDRQHCCPAGYTCNVKARSCEKEVVSAQPATFL ARSPHVGVKDVECGEGHFCHDNQTCCRDNRQGWACCPYRQGVCCADRRHCCPAGFRCAARGTKCLRRE APRWDAPLRDPALREIL | PGRN variant-31 |
| 34 | TRCPDGQFCPVACCLDPGGASYSCCRPLLDKWPTTLSRHLGGPCQVDAHCSAGHSCIFTVSGTSSCCPFPE AVACGDGHHCCPRGFHCSADGRSCFQRSGNNSVGAIQCPDSQFECPDFSTCCVMVDGSWGCCPMPQASC CEDRVHCCPHGAFCDLVHTRCITPTGTHPLAKKLPAQRTNRAVALSSSVMCPDARSRCPDGSTCCELPSGK YGCCPMPNATCCSDHLHCCPQDTVCDLIQSKCLSKENATTDLLTKLPAHTVGDVKCDMEVSCPDGYTCCR LQSGAWGCCPFTQAVCCEDHIHCCPAGFTCDTQKGTCEQGPHQVPWMEKAPAHLSLPDPQALKRDVPCD NVSSCPSSDTCCQLTSGEWGCCPIPEAVCCSDHQHCCPQGYTCVAEGQCQRGSEIVAGLEKMPARRASLSH PRDIGCDQHTSCPVGQTCCPSLGGSWACCQLPHAVCCEDRQHCCPAGYTCNVKARSCEKEVVSAQPATFL ARSPHVGVKDVECGEGHFCHDNQTCCRDNRQGWACCPYRQGVCCADRRHCCPAGFRCAARGTKCLRRE APRWDAPLRDPALRRFL | PGRN variant-32 |
| 35 | TRCPDGQFCPVACCLDPGGASYSCCRPLLDKWPTTLSRHLGGPCQVDAHCSAGHSCIFTVSGTSSCCPFPE AVACGDGHHCCPRGFHCSADGRSCFQRSGNNSVGAIQCPDSQFECPDFSTCCVMVDGSWGCCPMPQASC CEDRVHCCPHGAFCDLVHTRCITPTGTHPLAKKLPAQRTNRAVALSSSVMCPDARSRCPDGSTCCELPSGK YGCCPMPNATCCSDHLHCCPQDTVCDLIQSKCLSKENATTDLLTKLPAHTVGDVKCDMEVSCPDGYTCCR LQSGAWGCCPFTQAVCCEDHIHCCPAGFTCDTQKGTCEQGPHQVPWMEKAPAHLSLPDPQALKRDVPCD NVSSCPSSDTCCQLTSGEWGCCPIPEAVCCSDHQHCCPQGYTCVAEGQCQRGSEIVAGLEKMPARRASLSH PRDIGCDQHTSCPVGQTCCPSLGGSWACCQLPHAVCCEDRQHCCPAGYTCNVKARSCEKEVVSAQPATFL ARSPHVGVKDVECGEGHFCHDNQTCCRDNRQGWACCPYRQGVCCADRRHCCPAGFRCAARGTKCLRRE APRWDAPLRDPALRHFL | PGRN variant-33 |
| 36 | TRCPDGQFCPVACCLDPGGASYSCCRPLLDKWPTTLSRHLGGPCQVDAHCSAGHSCIFTVSGTSSCCPFPE AVACGDGHHCCPRGFHCSADGRSCFQRSGNNSVGAIQCPDSQFECPDFSTCCVMVDGSWGCCPMPQASC CEDRVHCCPHGAFCDLVHTRCITPTGTHPLAKKLPAQRTNRAVALSSSVMCPDARSRCPDGSTCCELPSGK YGCCPMPNATCCSDHLHCCPQDTVCDLIQSKCLSKENATTDLLTKLPAHTVGDVKCDMEVSCPDGYTCCR LQSGAWGCCPFTQAVCCEDHIHCCPAGFTCDTQKGTCEQGPHQVPWMEKAPAHLSLPDPQALKRDVPCD NVSSCPSSDTCCQLTSGEWGCCPIPEAVCCSDHQHCCPQGYTCVAEGQCQRGSEIVAGLEKMPARRASLSH PRDIGCDQHTSCPVGQTCCPSLGGSWACCQLPHAVCCEDRQHCCPAGYTCNVKARSCEKEVVSAQPATFL ARSPHVGVKDVECGEGHFCHDNQTCCRDNRQGWACCPYRQGVCCADRRHCCPAGFRCAARGTKCLRRE APRWDAPLRDPALRKFL | PGRN variant-34 |
| 37 | TRCPDGQFCPVACCLDPGGASYSCCRPLLDKWPTTLSRHLGGPCQVDAHCSAGHSCIFTVSGTSSCCPFPE AVACGDGHHCCPRGFHCSADGRSCFQRSGNNSVGAIQCPDSQFECPDFSTCCVMVDGSWGCCPMPQASC CEDRVHCCPHGAFCDLVHTRCITPTGTHPLAKKLPAQRTNRAVALSSSVMCPDARSRCPDGSTCCELPSGK YGCCPMPNATCCSDHLHCCPQDTVCDLIQSKCLSKENATTDLLTKLPAHTVGDVKCDMEVSCPDGYTCCR LQSGAWGCCPFTQAVCCEDHIHCCPAGFTCDTQKGTCEQGPHQVPWMEKAPAHLSLPDPQALKRDVPCD NVSSCPSSDTCCQLTSGEWGCCPIPEAVCCSDHQHCCPQGYTCVAEGQCQRGSEIVAGLEKMPARRASLSH PRDIGCDQHTSCPVGQTCCPSLGGSWACCQLPHAVCCEDRQHCCPAGYTCNVKARSCEKEVVSAQPATFL ARSPHVGVKDVECGEGHFCHDNQTCCRDNRQGWACCPYRQGVCCADRRHCCPAGFRCAARGTKCLRRE APRWDAPLRDPALRDFL | PGRN variant-35 |

-continued

INFORMAL SEQUENCE LISTING

| SEQ ID NO: | Sequence | Description |
|---|---|---|
| 38 | TRCPDGQFCPVACCLDPGGASYSCCRPLLDKWPTTLSRHLGGPCQVDAHCSAGHSCIFTVSGTSSCCPFPE AVACGDGHHCCPRGFHCSADGRSCFQRSGNNSVGAIQCPDSQFECPDFSTCCVMVDGSWGCCPMPQASC CEDRVHCCPHGAFCDLVHTRCITPTGTHPLAKKLPAQRTNRAVALSSSVMCPDARSRCPDGSTCCELPSGK YGCCPMPNATCCSDHLHCCPQDTVCDLIQSKCLSKENATTDLLTKLPAHTVGDVKCDMEVSCPDGYTCCR LQSGAWGCCPFTQAVCCEDHIHCCPAGFTCDTQKGTCEQGPHQVPWMEKAPAHLSLPDPQALKRDVPCD NVSSCPSSDTCCQLTSGEWGCCPIPEAVCCSDHQHCCPQGYTCVAEGQCQRGSEIVAGLEKMPARRASLSH PRDIGCDQHTSCPVGQTCCPSLGGSWACCQLPHAVCCEDRQHCCPAGYTCNVKARSCEKEVVSAQPATFL ARSPHVGVKDVECGEGHFCHDNQTCCRDNRQGWACCPYRQGVCCADRRHCCPAGFRCAARGTKCLRRE APRWDAPLRDPALREFL | PGRN variant-36 |
| 39 | TRCPDGQFCPVACCLDPGGASYSCCRPLLDKWPTTLSRHLGGPCQVDAHCSAGHSCIFTVSGTSSCCPFPE AVACGDGHHCCPRGFHCSADGRSCFQRSGNNSVGAIQCPDSQFECPDFSTCCVMVDGSWGCCPMPQASC CEDRVHCCPHGAFCDLVHTRCITPTGTHPLAKKLPAQRTNRAVALSSSVMCPDARSRCPDGSTCCELPSGK YGCCPMPNATCCSDHLHCCPQDTVCDLIQSKCLSKENATTDLLTKLPAHTVGDVKCDMEVSCPDGYTCCR LQSGAWGCCPFTQAVCCEDHIHCCPAGFTCDTQKGTCEQGPHQVPWMEKAPAHLSLPDPQALKRDVPCD NVSSCPSSDTCCQLTSGEWGCCPIPEAVCCSDHQHCCPQGYTCVAEGQCQRGSEIVAGLEKMPARRASLSH PRDIGCDQHTSCPVGQTCCPSLGGSWACCQLPHAVCCEDRQHCCPAGYTCNVKARSCEKEVVSAQPATFL ARSPHVGVKDVECGEGHFCHDNQTCCRDNRQGWACCPYRQGVCCADRRHCCPAGFRCAARGTKCLRRE APRWDAPLRDPALRSFL | PGRN variant-37 |
| 40 | TRCPDGQFCPVACCLDPGGASYSCCRPLLDKWPTTLSRHLGGPCQVDAHCSAGHSCIFTVSGTSSCCPFPE AVACGDGHHCCPRGFHCSADGRSCFQRSGNNSVGAIQCPDSQFECPDFSTCCVMVDGSWGCCPMPQASC CEDRVHCCPHGAFCDLVHTRCITPTGTHPLAKKLPAQRTNRAVALSSSVMCPDARSRCPDGSTCCELPSGK YGCCPMPNATCCSDHLHCCPQDTVCDLIQSKCLSKENATTDLLTKLPAHTVGDVKCDMEVSCPDGYTCCR LQSGAWGCCPFTQAVCCEDHIHCCPAGFTCDTQKGTCEQGPHQVPWMEKAPAHLSLPDPQALKRDVPCD NVSSCPSSDTCCQLTSGEWGCCPIPEAVCCSDHQHCCPQGYTCVAEGQCQRGSEIVAGLEKMPARRASLSH PRDIGCDQHTSCPVGQTCCPSLGGSWACCQLPHAVCCEDRQHCCPAGYTCNVKARSCEKEVVSAQPATFL ARSPHVGVKDVECGEGHFCHDNQTCCRDNRQGWACCPYRQGVCCADRRHCCPAGFRCAARGTKCLRRE APRWDAPLRDPALRTFL | PGRN variant-38 |
| 41 | TRCPDGQFCPVACCLDPGGASYSCCRPLLDKWPTTLSRHLGGPCQVDAHCSAGHSCIFTVSGTSSCCPFPE AVACGDGHHCCPRGFHCSADGRSCFQRSGNNSVGAIQCPDSQFECPDFSTCCVMVDGSWGCCPMPQASC CEDRVHCCPHGAFCDLVHTRCITPTGTHPLAKKLPAQRTNRAVALSSSVMCPDARSRCPDGSTCCELPSGK YGCCPMPNATCCSDHLHCCPQDTVCDLIQSKCLSKENATTDLLTKLPAHTVGDVKCDMEVSCPDGYTCCR LQSGAWGCCPFTQAVCCEDHIHCCPAGFTCDTQKGTCEQGPHQVPWMEKAPAHLSLPDPQALKRDVPCD NVSSCPSSDTCCQLTSGEWGCCPIPEAVCCSDHQHCCPQGYTCVAEGQCQRGSEIVAGLEKMPARRASLSH PRDIGCDQHTSCPVGQTCCPSLGGSWACCQLPHAVCCEDRQHCCPAGYTCNVKARSCEKEVVSAQPATFL ARSPHVGVKDVECGEGHFCHDNQTCCRDNRQGWACCPYRQGVCCADRRHCCPAGFRCAARGTKCLRRE APRWDAPLRDPALRNFL | PGRN variant-39 |
| 42 | TRCPDGQFCPVACCLDPGGASYSCCRPLLDKWPTTLSRHLGGPCQVDAHCSAGHSCIFTVSGTSSCCPFPE AVACGDGHHCCPRGFHCSADGRSCFQRSGNNSVGAIQCPDSQFECPDFSTCCVMVDGSWGCCPMPQASC CEDRVHCCPHGAFCDLVHTRCITPTGTHPLAKKLPAQRTNRAVALSSSVMCPDARSRCPDGSTCCELPSGK YGCCPMPNATCCSDHLHCCPQDTVCDLIQSKCLSKENATTDLLTKLPAHTVGDVKCDMEVSCPDGYTCCR LQSGAWGCCPFTQAVCCEDHIHCCPAGFTCDTQKGTCEQGPHQVPWMEKAPAHLSLPDPQALKRDVPCD NVSSCPSSDTCCQLTSGEWGCCPIPEAVCCSDHQHCCPQGYTCVAEGQCQRGSEIVAGLEKMPARRASLSH PRDIGCDQHTSCPVGQTCCPSLGGSWACCQLPHAVCCEDRQHCCPAGYTCNVKARSCEKEVVSAQPATFL ARSPHVGVKDVECGEGHFCHDNQTCCRDNRQGWACCPYRQGVCCADRRHCCPAGFRCAARGTKCLRRE APRWDAPLRDPALRQFL | PGRN variant-40 |
| 43 | TRCPDGQFCPVACCLDPGGASYSCCRPLLDKWPTTLSRHLGGPCQVDAHCSAGHSCIFTVSGTSSCCPFPE AVACGDGHHCCPRGFHCSADGRSCFQRSGNNSVGAIQCPDSQFECPDFSTCCVMVDGSWGCCPMPQASC CEDRVHCCPHGAFCDLVHTRCITPTGTHPLAKKLPAQRTNRAVALSSSVMCPDARSRCPDGSTCCELPSGK YGCCPMPNATCCSDHLHCCPQDTVCDLIQSKCLSKENATTDLLTKLPAHTVGDVKCDMEVSCPDGYTCCR LQSGAWGCCPFTQAVCCEDHIHCCPAGFTCDTQKGTCEQGPHQVPWMEKAPAHLSLPDPQALKRDVPCD NVSSCPSSDTCCQLTSGEWGCCPIPEAVCCSDHQHCCPQGYTCVAEGQCQRGSEIVAGLEKMPARRASLSH PRDIGCDQHTSCPVGQTCCPSLGGSWACCQLPHAVCCEDRQHCCPAGYTCNVKARSCEKEVVSAQPATFL ARSPHVGVKDVECGEGHFCHDNQTCCRDNRQGWACCPYRQGVCCADRRHCCPAGFRCAARGTKCLRRE APRWDAPLRDPALRLFL | PGRN variant-41 |
| 44 | TRCPDGQFCPVACCLDPGGASYSCCRPLLDKWPTTLSRHLGGPCQVDAHCSAGHSCIFTVSGTSSCCPFPE AVACGDGHHCCPRGFHCSADGRSCFQRSGNNSVGAIQCPDSQFECPDFSTCCVMVDGSWGCCPMPQASC CEDRVHCCPHGAFCDLVHTRCITPTGTHPLAKKLPAQRTNRAVALSSSVMCPDARSRCPDGSTCCELPSGK YGCCPMPNATCCSDHLHCCPQDTVCDLIQSKCLSKENATTDLLTKLPAHTVGDVKCDMEVSCPDGYTCCR LQSGAWGCCPFTQAVCCEDHIHCCPAGFTCDTQKGTCEQGPHQVPWMEKAPAHLSLPDPQALKRDVPCD NVSSCPSSDTCCQLTSGEWGCCPIPEAVCCSDHQHCCPQGYTCVAEGQCQRGSEIVAGLEKMPARRASLSH PRDIGCDQHTSCPVGQTCCPSLGGSWACCQLPHAVCCEDRQHCCPAGYTCNVKARSCEKEVVSAQPATFL ARSPHVGVKDVECGEGHFCHDNQTCCRDNRQGWACCPYRQGVCCADRRHCCPAGFRCAARGTKCLRRE APRWDAPLRDPALRFFL | PGRN variant-42 |
| 45 | TRCPDGQFCPVACCLDPGGASYSCCRPLLDKWPTTLSRHLGGPCQVDAHCSAGHSCIFTVSGTSSCCPFPE AVACGDGHHCCPRGFHCSADGRSCFQRSGNNSVGAIQCPDSQFECPDFSTCCVMVDGSWGCCPMPQASC | PGRN variant-43 |

-continued

INFORMAL SEQUENCE LISTING

| SEQ ID NO: | Sequence | Description |
|---|---|---|
|  | CEDRVHCCPHGAFCDLVHTRCITPTGTHPLAKKLPAQRTNRAVALSSSVMCPDARSRCPDGSTCCELPSGK YGCCPMPNATCCSDHLHCCPQDTVCDLIQSKCLSKENATTDLLTKLPAHTVGDVKCDMEVSCPDGYTCCR LQSGAWGCCPFTQAVCCEDHIHCCPAGFTCDTQKGTCEQGPHQVPWMEKAPAHLSLPDPQALKRDVPCD NVSSCPSSDTCCQLTSGEWGCCPIPEAVCCSDHQHCCPQGYTCVAEGQCQRGSEIVAGLEKMPARRASLSH PRDIGCDQHTSCPVGQTCCPSLGGSWACCQLPHAVCCEDRQHCCPAGYTCNVKARSCEKEVVSAQPATFL ARSPHVGVKDVECGEGHFCHDNQTCCRDNRQGWACCPYRQGVCCADRRHCCPAGFRCAARGTKCLRRE APRWDAPLRDPALRYFL |  |
| 46 | TRCPDGQFCPVACCLDPGGASYSCCRPLLDKWPTTLSRHLGGPCQVDAHCSAGHSCIFTVSGTSSCCPFPE AVACGDGHHCCPRGFHCSADGRSCFQRSGNNSVGAIQCPDSQFECPDFSTCCVMVDGSWGCCPMPQASC CEDRVHCCPHGAFCDLVHTRCITPTGTHPLAKKLPAQRTNRAVALSSSVMCPDARSRCPDGSTCCELPSGK YGCCPMPNATCCSDHLHCCPQDTVCDLIQSKCLSKENATTDLLTKLPAHTVGDVKCDMEVSCPDGYTCCR LQSGAWGCCPFTQAVCCEDHIHCCPAGFTCDTQKGTCEQGPHQVPWMEKAPAHLSLPDPQALKRDVPCD NVSSCPSSDTCCQLTSGEWGCCPIPEAVCCSDHQHCCPQGYTCVAEGQCQRGSEIVAGLEKMPARRASLSH PRDIGCDQHTSCPVGQTCCPSLGGSWACCQLPHAVCCEDRQHCCPAGYTCNVKARSCEKEVVSAQPATFL ARSPHVGVKDVECGEGHFCHDNQTCCRDNRQGWACCPYRQGVCCADRRHCCPAGFRCAARGTKCLRRE APRWDAPLRDPALRRQL | PGRN variant-44 |
| 47 | TRCPDGQFCPVACCLDPGGASYSCCRPLLDKWPTTLSRHLGGPCQVDAHCSAGHSCIFTVSGTSSCCPFPE AVACGDGHHCCPRGFHCSADGRSCFQRSGNNSVGAIQCPDSQFECPDFSTCCVMVDGSWGCCPMPQASC CEDRVHCCPHGAFCDLVHTRCITPTGTHPLAKKLPAQRTNRAVALSSSVMCPDARSRCPDGSTCCELPSGK YGCCPMPNATCCSDHLHCCPQDTVCDLIQSKCLSKENATTDLLTKLPAHTVGDVKCDMEVSCPDGYTCCR LQSGAWGCCPFTQAVCCEDHIHCCPAGFTCDTQKGTCEQGPHQVPWMEKAPAHLSLPDPQALKRDVPCD NVSSCPSSDTCCQLTSGEWGCCPIPEAVCCSDHQHCCPQGYTCVAEGQCQRGSEIVAGLEKMPARRASLSH PRDIGCDQHTSCPVGQTCCPSLGGSWACCQLPHAVCCEDRQHCCPAGYTCNVKARSCEKEVVSAQPATFL ARSPHVGVKDVECGEGHFCHDNQTCCRDNRQGWACCPYRQGVCCADRRHCCPAGFRCAARGTKCLRRE APRWDAPLRDPALRHQL | PGRN variant-45 |
| 48 | TRCPDGQFCPVACCLDPGGASYSCCRPLLDKWPTTLSRHLGGPCQVDAHCSAGHSCIFTVSGTSSCCPFPE AVACGDGHHCCPRGFHCSADGRSCFQRSGNNSVGAIQCPDSQFECPDFSTCCVMVDGSWGCCPMPQASC CEDRVHCCPHGAFCDLVHTRCITPTGTHPLAKKLPAQRTNRAVALSSSVMCPDARSRCPDGSTCCELPSGK YGCCPMPNATCCSDHLHCCPQDTVCDLIQSKCLSKENATTDLLTKLPAHTVGDVKCDMEVSCPDGYTCCR LQSGAWGCCPFTQAVCCEDHIHCCPAGFTCDTQKGTCEQGPHQVPWMEKAPAHLSLPDPQALKRDVPCD NVSSCPSSDTCCQLTSGEWGCCPIPEAVCCSDHQHCCPQGYTCVAEGQCQRGSEIVAGLEKMPARRASLSH PRDIGCDQHTSCPVGQTCCPSLGGSWACCQLPHAVCCEDRQHCCPAGYTCNVKARSCEKEVVSAQPATFL ARSPHVGVKDVECGEGHFCHDNQTCCRDNRQGWACCPYRQGVCCADRRHCCPAGFRCAARGTKCLRRE APRWDAPLRDPALRKQL | PGRN variant-46 |
| 49 | TRCPDGQFCPVACCLDPGGASYSCCRPLLDKWPTTLSRHLGGPCQVDAHCSAGHSCIFTVSGTSSCCPFPE AVACGDGHHCCPRGFHCSADGRSCFQRSGNNSVGAIQCPDSQFECPDFSTCCVMVDGSWGCCPMPQASC CEDRVHCCPHGAFCDLVHTRCITPTGTHPLAKKLPAQRTNRAVALSSSVMCPDARSRCPDGSTCCELPSGK YGCCPMPNATCCSDHLHCCPQDTVCDLIQSKCLSKENATTDLLTKLPAHTVGDVKCDMEVSCPDGYTCCR LQSGAWGCCPFTQAVCCEDHIHCCPAGFTCDTQKGTCEQGPHQVPWMEKAPAHLSLPDPQALKRDVPCD NVSSCPSSDTCCQLTSGEWGCCPIPEAVCCSDHQHCCPQGYTCVAEGQCQRGSEIVAGLEKMPARRASLSH PRDIGCDQHTSCPVGQTCCPSLGGSWACCQLPHAVCCEDRQHCCPAGYTCNVKARSCEKEVVSAQPATFL ARSPHVGVKDVECGEGHFCHDNQTCCRDNRQGWACCPYRQGVCCADRRHCCPAGFRCAARGTKCLRRE APRWDAPLRDPALRDQL | PGRN variant-47 |
| 50 | TRCPDGQFCPVACCLDPGGASYSCCRPLLDKWPTTLSRHLGGPCQVDAHCSAGHSCIFTVSGTSSCCPFPE AVACGDGHHCCPRGFHCSADGRSCFQRSGNNSVGAIQCPDSQFECPDFSTCCVMVDGSWGCCPMPQASC CEDRVHCCPHGAFCDLVHTRCITPTGTHPLAKKLPAQRTNRAVALSSSVMCPDARSRCPDGSTCCELPSGK YGCCPMPNATCCSDHLHCCPQDTVCDLIQSKCLSKENATTDLLTKLPAHTVGDVKCDMEVSCPDGYTCCR LQSGAWGCCPFTQAVCCEDHIHCCPAGFTCDTQKGTCEQGPHQVPWMEKAPAHLSLPDPQALKRDVPCD NVSSCPSSDTCCQLTSGEWGCCPIPEAVCCSDHQHCCPQGYTCVAEGQCQRGSEIVAGLEKMPARRASLSH PRDIGCDQHTSCPVGQTCCPSLGGSWACCQLPHAVCCEDRQHCCPAGYTCNVKARSCEKEVVSAQPATFL ARSPHVGVKDVECGEGHFCHDNQTCCRDNRQGWACCPYRQGVCCADRRHCCPAGFRCAARGTKCLRRE APRWDAPLRDPALREQL | PGRN variant-48 |
| 51 | TRCPDGQFCPVACCLDPGGASYSCCRPLLDKWPTTLSRHLGGPCQVDAHCSAGHSCIFTVSGTSSCCPFPE AVACGDGHHCCPRGFHCSADGRSCFQRSGNNSVGAIQCPDSQFECPDFSTCCVMVDGSWGCCPMPQASC CEDRVHCCPHGAFCDLVHTRCITPTGTHPLAKKLPAQRTNRAVALSSSVMCPDARSRCPDGSTCCELPSGK YGCCPMPNATCCSDHLHCCPQDTVCDLIQSKCLSKENATTDLLTKLPAHTVGDVKCDMEVSCPDGYTCCR LQSGAWGCCPFTQAVCCEDHIHCCPAGFTCDTQKGTCEQGPHQVPWMEKAPAHLSLPDPQALKRDVPCD NVSSCPSSDTCCQLTSGEWGCCPIPEAVCCSDHQHCCPQGYTCVAEGQCQRGSEIVAGLEKMPARRASLSH PRDIGCDQHTSCPVGQTCCPSLGGSWACCQLPHAVCCEDRQHCCPAGYTCNVKARSCEKEVVSAQPATFL ARSPHVGVKDVECGEGHFCHDNQTCCRDNRQGWACCPYRQGVCCADRRHCCPAGFRCAARGTKCLRRE APRWDAPLRDPALRNQL | PGRN variant-49 |
| 52 | TRCPDGQFCPVACCLDPGGASYSCCRPLLDKWPTTLSRHLGGPCQVDAHCSAGHSCIFTVSGTSSCCPFPE AVACGDGHHCCPRGFHCSADGRSCFQRSGNNSVGAIQCPDSQFECPDFSTCCVMVDGSWGCCPMPQASC CEDRVHCCPHGAFCDLVHTRCITPTGTHPLAKKLPAQRTNRAVALSSSVMCPDARSRCPDGSTCCELPSGK YGCCPMPNATCCSDHLHCCPQDTVCDLIQSKCLSKENATTDLLTKLPAHTVGDVKCDMEVSCPDGYTCCR LQSGAWGCCPFTQAVCCEDHIHCCPAGFTCDTQKGTCEQGPHQVPWMEKAPAHLSLPDPQALKRDVPCD | PGRN variant-50 |

| SEQ ID NO: | Sequence | Description |
|---|---|---|
|  | NVSSCPSSDTCCQLTSGEWGCCPIPEAVCCSDHQHCCPQGYTCVAEGQCQRGSEIVAGLEKMPARRASLSH PRDIGCDQHTSCPVGQTCCPSLGGSWACCQLPHAVCCEDRQHCCPAGYTCNVKARSCEKEVVSAQPATFL ARSPHVGVKDVECGEGHFCHDNQTCCRDNRQGWACCPYRQGVCCADRRHCCPAGFRCAARGTKCLRRE APRWDAPLRDPALRLQL |  |
| 53 | TRCPDGQFCPVACCLDPGGASYSCCRPLLDKWPTTLSRHLGGPCQVDAHCSAGHSCIFTVSGTSSCCPFPE AVACGDGHHCCPRGFHCSADGRSCFQRSGNNSVGAIQCPDSQFECPDFSTCCVMVDGSWGCCPMPQASC CEDRVHCCPHGAFCDLVHTRCITPTGTHPLAKKLPAQRTNRAVALSSSVMCPDARSRCPDGSTCCELPSGK YGCCPMPNATCCSDHLHCCPQDTVCDLIQSKCLSKENATTDLLTKLPAHTVGDVKCDMEVSCPDGYTCCR LQSGAWGCCPFTQAVCCEDHIHCCPAGFTCDTQKGTCEQGPHQVPWMEKAPAHLSLPDPQALKRDVPCD NVSSCPSSDTCCQLTSGEWGCCPIPEAVCCSDHQHCCPQGYTCVAEGQCQRGSEIVAGLEKMPARRASLSH PRDIGCDQHTSCPVGQTCCPSLGGSWACCQLPHAVCCEDRQHCCPAGYTCNVKARSCEKEVVSAQPATFL ARSPHVGVKDVECGEGHFCHDNQTCCRDNRQGWACCPYRQGVCCADRRHCCPAGFRCAARGTKCLRRE APRWDAPLRDPALRFQL | PGRN variant-51 |
| 54 | TRCPDGQFCPVACCLDPGGASYSCCRPLLDKWPTTLSRHLGGPCQVDAHCSAGHSCIFTVSGTSSCCPFPE AVACGDGHHCCPRGFHCSADGRSCFQRSGNNSVGAIQCPDSQFECPDFSTCCVMVDGSWGCCPMPQASC CEDRVHCCPHGAFCDLVHTRCITPTGTHPLAKKLPAQRTNRAVALSSSVMCPDARSRCPDGSTCCELPSGK YGCCPMPNATCCSDHLHCCPQDTVCDLIQSKCLSKENATTDLLTKLPAHTVGDVKCDMEVSCPDGYTCCR LQSGAWGCCPFTQAVCCEDHIHCCPAGFTCDTQKGTCEQGPHQVPWMEKAPAHLSLPDPQALKRDVPCD NVSSCPSSDTCCQLTSGEWGCCPIPEAVCCSDHQHCCPQGYTCVAEGQCQRGSEIVAGLEKMPARRASLSH PRDIGCDQHTSCPVGQTCCPSLGGSWACCQLPHAVCCEDRQHCCPAGYTCNVKARSCEKEVVSAQPATFL ARSPHVGVKDVECGEGHFCHDNQTCCRDNRQGWACCPYRQGVCCADRRHCCPAGFRCAARGTKCLRRE APRWDAPLRDPALRYQL | PGRN variant-52 |
| 55 | TRCPDGQFCPVACCLDPGGASYSCCRPLLDKWPTTLSRHLGGPCQVDAHCSAGHSCIFTVSGTSSCCPFPE AVACGDGHHCCPRGFHCSADGRSCFQRSGNNSVGAIQCPDSQFECPDFSTCCVMVDGSWGCCPMPQASC CEDRVHCCPHGAFCDLVHTRCITPTGTHPLAKKLPAQRTNRAVALSSSVMCPDARSRCPDGSTCCELPSGK YGCCPMPNATCCSDHLHCCPQDTVCDLIQSKCLSKENATTDLLTKLPAHTVGDVKCDMEVSCPDGYTCCR LQSGAWGCCPFTQAVCCEDHIHCCPAGFTCDTQKGTCEQGPHQVPWMEKAPAHLSLPDPQALKRDVPCD NVSSCPSSDTCCQLTSGEWGCCPIPEAVCCSDHQHCCPQGYTCVAEGQCQRGSEIVAGLEKMPARRASLSH PRDIGCDQHTSCPVGQTCCPSLGGSWACCQLPHAVCCEDRQHCCPAGYTCNVKARSCEKEVVSAQPATFL ARSPHVGVKDVECGEGHFCHDNQTCCRDNRQGWACCPYRQGVCCADRRHCCPAGFRCAARGTKCLRRE APRWDAPLRDPALRQLLY$_1$Y$_2$QLL, wherein Y$_1$ is L or absent, and Y$_2$ is R or absent | PGRN variant-53 |
| 56 | TRCPDGQFCPVACCLDPGGASYSCCRPLLDKWPTTLSRHLGGPCQVDAHCSAGHSCIFTVSGTSSCCPFPE AVACGDGHHCCPRGFHCSADGRSCFQRSGNNSVGAIQCPDSQFECPDFSTCCVMVDGSWGCCPMPQASC CEDRVHCCPHGAFCDLVHTRCITPTGTHPLAKKLPAQRTNRAVALSSSVMCPDARSRCPDGSTCCELPSGK YGCCPMPNATCCSDHLHCCPQDTVCDLIQSKCLSKENATTDLLTKLPAHTVGDVKCDMEVSCPDGYTCCR LQSGAWGCCPFTQAVCCEDHIHCCPAGFTCDTQKGTCEQGPHQVPWMEKAPAHLSLPDPQALKRDVPCD NVSSCPSSDTCCQLTSGEWGCCPIPEAVCCSDHQHCCPQGYTCVAEGQCQRGSEIVAGLEKMPARRASLSH PRDIGCDQHTSCPVGQTCCPSLGGSWACCQLPHAVCCEDRQHCCPAGYTCNVKARSCEKEVVSAQPATFL ARSPHVGVKDVECGEGHFCHDNQTCCRDNRQGWACCPYRQGVCCADRRHCCPAGFRCAARGTKCLRRE APRWDAPLRDPALRQLLQLL | PGRN variant-54 |
| 57 | TRCPDGQFCPVACCLDPGGASYSCCRPLLDKWPTTLSRHLGGPCQVDAHCSAGHSCIFTVSGTSSCCPFPE AVACGDGHHCCPRGFHCSADGRSCFQRSGNNSVGAIQCPDSQFECPDFSTCCVMVDGSWGCCPMPQASC CEDRVHCCPHGAFCDLVHTRCITPTGTHPLAKKLPAQRTNRAVALSSSVMCPDARSRCPDGSTCCELPSGK YGCCPMPNATCCSDHLHCCPQDTVCDLIQSKCLSKENATTDLLTKLPAHTVGDVKCDMEVSCPDGYTCCR LQSGAWGCCPFTQAVCCEDHIHCCPAGFTCDTQKGTCEQGPHQVPWMEKAPAHLSLPDPQALKRDVPCD NVSSCPSSDTCCQLTSGEWGCCPIPEAVCCSDHQHCCPQGYTCVAEGQCQRGSEIVAGLEKMPARRASLSH PRDIGCDQHTSCPVGQTCCPSLGGSWACCQLPHAVCCEDRQHCCPAGYTCNVKARSCEKEVVSAQPATFL ARSPHVGVKDVECGEGHFCHDNQTCCRDNRQGWACCPYRQGVCCADRRHCCPAGFRCAARGTKCLRRE APRWDAPLRDPALRQLLLRQLL | PGRN variant-55 |
| 58 | LRQLL |  |
| 59 | QLLQLL |  |
| 60 | QLLLRQLL |  |
| 61 | APELLGGPSVFLFPPKPKDTLMISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYTLPPSRDELTKNQVSLTCLVK GFYPSDIAVEWESNGQPENNYKTTPPVLDSDGSFFLYSKLTVDKSRWQQGNVFSCSVMHEALHNHYTQKS LSLSPGK | Wild-type human Fc sequence positions 231-447 EU index numbering |
| 62 | APELLGGPSVFLFPPKPKDTLMISRTPEVTCVVVDVSHEDPEVKFNWYVDGVEVHNAKTKPREEQYNSTY RVVSVLTVLHQDWLNGKEYKCKVSNKALPAPIEKTISKAK | CH2 domain sequence positions 231-340 EU index numbering |

-continued

INFORMAL SEQUENCE LISTING

| SEQ ID NO: | Sequence | Description |
|---|---|---|
| 63 | GQPREPQVYTLPPSRDELTKNQVSLTCLVKGFYPSDIAVEWESNGQPENNYKTTPPVLDSDGSFFLYSKLT VDKSRWQQGNVFSCSVMHEALHNHYTQKSLSLSPGK | CH3 domain sequence Positions 341-447 EU index numbering |
| 64 | APELLGGPSVFLFPPKPKDTLMISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYTLPPSRDELTKNQVSLWCLVK GFYPSDIAVEWESNGQPENNYKTTPPVLDSDGSFFLYSKLTVDKSRWQQGNVFSCSVMHEALHNHYTQKS LSLSPGK | Fc sequence with knob mutation |
| 65 | APEAAGGPSVFLFPPKPKDTLMISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYTLPPSRDELTKNQVSLWCLVK GFYPSDIAVEWESNGQPENNYKTTPPVLDSDGSFFLYSKLTVDKSRWQQGNVFSCSVMHEALHNHYTQKS LSLSPGK | Fc sequence with knob and LALA mutations |
| 66 | APELLGGPSVFLFPPKPKDTLMISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYTLPPSRDELTKNQVSLSCAVK GFYPSDIAVEWESNGQPENNYKTTPPVLDSDGSFFLYSKLTVDKSRWQQGNVFSCSVMHEALHNHYTQKS LSLSPGK | Fc sequence with hole mutations |
| 67 | APEAAGGPSVFLFPPKPKDTLMISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYTLPPSRDELTKNQVSLSCAVK GFYPSDIAVEWESNGQPENNYKTTPPVLDSDGSFFLYSKLTVDKSRWQQGNVFSCSVMHEALHNHYTQKS LSLSPGK | Fc sequence with hole and LALA mutations |
| 68 | APELLGGPSVFLFPPKPKDTLMISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYTLPPSRDELTKNQVSLTCLVK GFYPSDIAVEWESYGTEWANYKTTPPVLDSDGSFFLYSKLTVTKEEWQQGFVFSCSVMHEALHNHYTQKS LSLSPGK | Clone CH3C.35.23.2 |
| 69 | APELLGGPSVFLFPPKPKDTLMISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYTLPPSRDELTKNQVSLWCLVK GFYPSDIAVEWESYGTEWANYKTTPPVLDSDGSFFLYSKLTVTKEEWQQGFVFSCSVMHEALHNHYTQKS LSLSPGK | Clone CH3C.35.23.2 with knob mutation |
| 70 | APEAAGGPSVFLFPPKPKDTLMISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYTLPPSRDELTKNQVSLWCLVK GFYPSDIAVEWESYGTEWANYKTTPPVLDSDGSFFLYSKLTVTKEEWQQGFVFSCSVMHEALHNHYTQKS LSLSPGK | Clone CH3C.35.23.2 with knob and LALA mutations |
| 71 | APELLGGPSVFLFPPKPKDTLMISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYTLPPSRDELTKNQVSLSCAVK GFYPSDIAVEWESYGTEWANYKTTPPVLDSDGSFFLYSKLTVTKEEWQQGFVFSCSVMHEALHNHYTQKS LSLSPGK | Clone CH3C.35.23.2 with hole mutations |
| 72 | APEAAGGPSVFLFPPKPKDTLMISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYTLPPSRDELTKNQVSLSCAVK GFYPSDIAVEWESYGTEWANYKTTPPVLDSDGSFFLYSKLIVTKEEWQQGFVFSCSVMHEALHNHYTQKS LSLSPGK | Clone CH3C.35.23.2 with hole and LALA mutations |
| 73 | DKTHTCPPCPAPELLGGPSVFLFPPKPKDTLMISRTPEVTCVVVDVSHEDPEVKFNWYVDGVEVHNAKTKP REEQYNSTYRVVSVLTVLHQDWLNGKEYKCKVSNKALPAPIEKTISKAKGQPREPQVYTLPPSRDELTKN QVSLTCLVKGFYPSDIAVEWESYGTEWANYKTTPPVLDSDGSFFLYSKLTVTKEEWQQGFVFSCSVMHEA LHNHYTQKSLSLSPGK | Partial hinge-Clone CH3C.35.23.2 |
| 74 | DKTHTCPPCPAPELLGGPSVFLFPPKPKDTLMISRTPEVTCVVVDVSHEDPEVKFNWYVDGVEVHNAKTKP REEQYNSTYRVVSVLTVLHQDWLNGKEYKCKVSNKALPAPIEKTISKAKGQPREPQVYTLPPSRDELTKN QVSLWCLVKGFYPSDIAVEWESYGTEWANYKTTPPVLDSDGSFFLYSKLTVTKEEWQQGFVFSCSVMHE ALHNHYTQKSLSLSPGK | Partial hinge-Clone CH3C.35.23.2 with knob mutation |
| 75 | DKTHTCPPCPAPEAAGGPSVFLFPPKPKDTLMISRTPEVTCVVVDVSHEDPEVKFNWYVDGVEVHNAKTK PREEQYNSTYRVVSVLTVLHQDWLNGKEYKCKVSNKALPAPIEKTISKAKGQPREPQVYTLPPSRDELTKN QVSLWCLVKGFYPSDIAVEWESYGTEWANYKTTPPVLDSDGSFFLYSKLTVTKEEWQQGFVFSCSVMHE ALHNHYTQKSLSLSPGK | Partial hinge-Clone CH3C.35.23.2. with knob and LALA mutations |
| 76 | DKTHTCPPCPAPELLGGPSVFLFPPKPKDTLMISRTPEVTCVVVDVSHEDPEVKFNWYVDGVEVHNAKTKP REEQYNSTYRVVSVLTVLHQDWLNGKEYKCKVSNKALPAPIEKTISKAKGQPREPQVYTLPPSRDELTKN QVSLSCAVKGFYPSDIAVEWESYGTEWANYKTTPPVLDSDGSFFLVSKLTVTKEEWQQGFVFSCSVMHEA LHNHYTQKSLSLSPGK | Partial hinge-Clone CH3C.35.23.2 with hole mutations |

| SEQ ID NO: | Sequence | Description |
|---|---|---|
| 77 | DKTHTCPPCPAPEAAGGPSVFLFPPKPKDTLMISRTPEVTCVVVDVSHEDPEVKFNWYVDGVEVHNAKTK PREEQYNSTYRVVSVLTVLHQDWLNGKEYKCKVSNKALPAPIEKTISKAKGQPREPQVYTLPPSRDELTKN QVSLSCAVKGFYPSDIAVEWESYGTEWANYKTTPPVLDSDGSFFLVSKLTVTKEEWQQGFVFSCSVMHEA LHNHYTQKSLSLSPGK | Partial hinge-Clone CH3C.35.23.2. with hole and LALA mutations |
| 78 | APELLGGPSVFLFPPKPKDTLMISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYTLPPSRDELTKNQVSLTCLVK GFYPSDIAVLWESYGTEWSSYKTTPPVLDSDGSFFLYSKLTVTKEEWQQGFVFSCSVMHEALHNHYTQKS LSLSPGK | Clone CH3C.35.21.17 |
| 79 | APELLGGPSVFLFPPKPKDTLMISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYTLPPSRDELTKNQVSLWCLVK GFYPSDIAVLWESYGTEWSSYKTTPPVLDSDGSFFLYSKLIVTKEEWQQGFVFSCSVMHEALHNHYTQKS LSLSPGK | Clone CH3C.35.21.17 with knob mutation |
| 80 | APEAAGGPSVFLFPPKPKDTLMISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYTLPPSRDELTKNQVSLWCLVK GFYPSDIAVLWESYGTEWSSYKTTPPVLDSDGSFFLYSKLIVTKEEWQQGFVFSCSVMHEALHNHYTQKS LSLSPGK | Clone CH3C.35.21.17 with knob and LALA mutations |
| 81 | APELLGGPSVFLFPPKPKDTLMISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYTLPPSRDELTKNQVSLSCAVK GFYPSDIAVLWESYGTEWSSYKTTPPVLDSDGSFFLVSKLIVTKEEWQQGFVFSCSVMHEALHNHYTQKS LSLSPGK | Clone CH3C.35.21.17 with hole mutations |
| 82 | APEAAGGPSVFLFPPKPKDTLMISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYTLPPSRDELTKNQVSLSCAVK GFYPSDIAVLWESYGTEWSSYKTTPPVLDSDGSFFLYSKLIVTKEEWQQGFVFSCSVMHEALHNHYTQKS LSLSPGK | Clone CH3C.35.21.17 with hole and LALA mutations |
| 83 | DKTHTCPPCPAPELLGGPSVFLFPPKPKDTLMISRTPEVTCVVVDVSHEDPEVKFNWYVDGVEVHNAKTKP REEQYNSTYRVVSVLTVLHQDWLNGKEYKCKVSNKALPAPIEKTISKAKGQPREPQVYTLPPSRDELTKN QVSLTCLVKGFYPSDIAVLWESYGTEWSSYKTTPPVLDSDGSFFLYSKLTVTKEEWQQGFVFSCSVMHEAL HNHYTQKSLSLSPGK | Partial hinge-Clone CH3C.35.21.17 |
| 84 | DKTHTCPPCPAPELLGGPSVFLFPPKPKDTLMISRTPEVTCVVVDVSHEDPEVKFNWYVDGVEVHNAKTKP REEQYNSTYRVVSVLTVLHQDWLNGKEYKCKVSNKALPAPIEKTISKAKGQPREPQVYTLPPSRDELTKN QVSLWCLVKGFYPSDIAVLWESYGTEWSSYKTTPPVLDSDGSFFLYSKLTVTKEEWQQGFVFSCSVMHEA LHNHYTQKSLSLSPGK | Partial hinge-Clone CH3C.35.21.17 with knob mutation |
| 85 | DKTHTCPPCPAPEAAGGPSVFLFPPKPKDTLMISRTPEVTCVVVDVSHEDPEVKFNWYVDGVEVHNAKTK PREEQYNSTYRVVSVLTVLHQDWLNGKEYKCKVSNKALPAPIEKTISKAKGQPREPQVYTLPPSRDELTKN QVSLWCLVKGFYPSDIAVLWESYGTEWSSYKTTPPVLDSDGSFFLYSKLTVTKEEWQQGFVFSCSVMHEA LHNHYTQKSLSLSPGK | Partial hinge-Clone CH3C.35.21.17 with knob and LALA mutations |
| 86 | DKTHTCPPCPAPELLGGPSVFLFPPKPKDTLMISRTPEVTCVVVDVSHEDPEVKFNWYVDGVEVHNAKTKP REEQYNSTYRVVSVLTVLHQDWLNGKEYKCKVSNKALPAPIEKTISKAKGQPREPQVYTLPPSRDELTKN QVSLSCAVKGFYPSDIAVLWESYGTEWSSYKTTPPVLDSDGSFFLVSKLTVTKEEWQQGFVFSCSVMHEA LHNHYTQKSLSLSPGK | Partial hinge-Clone CH3C.35.21.17 with hole mutations |
| 87 | DKTHTCPPCPAPEAAGGPSVFLFPPKPKDTLMISRTPEVTCVVVDVSHEDPEVKFNWYVDGVEVHNAKTK PREEQYNSTYRVVSVLTVLHQDWLNGKEYKCKVSNKALPAPIEKTISKAKGQPREPQVYTLPPSRDELTKN QVSLSCAVKGFYPSDIAVLWESYGTEWSSYKTTPPVLDSDGSFFLVSKLTVIKEEWQQGFVFSCSVMHEA LHNHYTQKSLSLSPGK | Partial hinge-Clone CH3C.35.21.17 with hole and LALA mutations |
| 88 | EPKSCDKTHTCPPCP | Human IgG1 hinge amino acid sequence |
| 89 | DKTHTCPPCP | Portion of human IgG1 hinge sequence (Partial hinge) |
| 90 | GGGGS | Polypeptide linker |
| 91 | GGGGSGGGGS | Polypeptide linker |

| SEQ ID NO: | Sequence | Description |
|---|---|---|
| 92 | GGSG | Polypeptide linker |
| 93 | SGGG | Polypeptide linker |
| 94 | KESGSVSSEQLAQFRSLD | Polypeptide linker |
| 95 | EGKSSGSGSESKST | Polypeptide linker |
| 96 | GSAGSAAGSGEF | Polypeptide linker |
| 97 | AEAAAKA | Polypeptide linker |
| 98 | DKTHTCPPCPAPEAAGGPSVFLFPPKPKDTLMISRTPEVTCVVVDVSHEDPEVKFNWYVDGVEVHNAKTK PREEQYNSTYRVVSVLTVLHQDWLNGKEYKCKVSNKALPAPIEKTISKAKGQPREPQVYTLPPSRDELTKN QVSLSCAVKGFYPSDIAVEWESNGQPENNYKTTPPVLDSDGSFFLVSKLTVDKSRWQQGNVFSCSVMHEA LHNHYTQKSLSLSPGKGGGGSGGGGSTRCPDGQFCPVACCLDPGGASYSCCRPLLDKWPTTLSRHLGGPC QVDAHCSAGHSCIFTVSGTSSCCPFPEAVACGDGHHCCPRGFHCSADGRSCFQRSGNNSVGAIQCPDSQFE CPDFSTCCVMVDGSWGCCPMPQASCCEDRVHCCPHGAFCDLVHTRCITPTGTHPLAKKLPAQRTNRAVA LSSSVMCPDARSRCPDGSTCCELPSGKYGCCPMPNATCCSDHLHCCPQDTVCDLIQSKCLSKENATTDLLT KLPAHTVGDVKCDMEVSCPDGYTCCRLQSGAWGCCPFTQAVCCEDHIHCCPAGFTCDTQKGTCEQGPHQ VPWMEKAPAHLSLPDPQALKRDVPCDNVSSCPSSDTCCQLTSGEWGCCPIPEAVCCSDHQHCCPQGYTCV AEGQCQRGSEIVAGLEKMPARRASLSHPRDIGCDQHTSCPVGQTCCPSLGGSWACCQLPHAVCCEDRQHC CPAGYTCNVKARSCEKEVVSAQPATFLARSPHVGVKDVECGEGHFCHDNQTCCRDNRQGWACCPYRQG VCCADRRHCCPAGFRCAARGTKCLRREAPRWDAPLRDPALRPIL | Partial hinge-Fc polypeptide with hole and LALA mutations-$(G_4S)_2$- PGRN(PIL) |
| 99 | DKTHTCPPCPAPEAAGGPSVFLFPPKPKDTLMISRTPEVTCVVVDVSHEDPEVKFNWYVDGVEVHNAKTK PREEQYNSTYRVVSVLTVLHQDWLNGKEYKCKVSNKALPAPIEKTISKAKGQPREPQVYTLPPSRDELTKN QVSLSCAVKGFYPSDIAVEWESNGQPENNYKTTPPVLDSDGSFFLVSKLTVDKSRWQQGNVFSCSVMHEA LHNHYTQKSLSLSPGKGGGGSGGGGSTRCPDGQFCPVACCLDPGGASYSCCRPLLDKWPTTLSRHLGGPC QVDAHCSAGHSCIFTVSGTSSCCPFPEAVACGDGHHCCPRGFHCSADGRSCFQRSGNNSVGAIQCPDSQFE CPDFSTCCVMVDGSWGCCPMPQASCCEDRVHCCPHGAFCDLVHTRCITPTGTHPLAKKLPAQRTNRAVA LSSSVMCPDARSRCPDGSTCCELPSGKYGCCPMPNATCCSDHLHCCPQDTVCDLIQSKCLSKENATTDLLT KLPAHTVGDVKCDMEVSCPDGYTCCRLQSGAWGCCPFTQAVCCEDHIHCCPAGFTCDTQKGTCEQGPHQ VPWMEKAPAHLSLPDPQALKRDVPCDNVSSCPSSDTCCQLTSGEWGCCPIPEAVCCSDHQHCCPQGYTCV AEGQCQRGSEIVAGLEKMPARRASLSHPRDIGCDQHTSCPVGQTCCPSLGGSWACCQLPHAVCCEDRQHC CPAGYTCNVKARSCEKEVVSAQPATFLARSPHVGVKDVECGEGHFCHDNQTCCRDNRQGWACCPYRQG VCCADRRHCCPAGFRCAARGTKCLRREAPRWDAPLRDPALRPFL | Partial hinge-Fc polypeptide with hole and LALA mutations-$(G_4S)_2$- PGRN(PFL) |
| 100 | DKTHTCPPCPAPEAAGGPSVFLFPPKPKDTLMISRTPEVTCVVVDVSHEDPEVKFNWYVDGVEVHNAKTK PREEQYNSTYRVVSVLTVLHQDWLNGKEYKCKVSNKALPAPIEKTISKAKGQPREPQVYTLPPSRDELTKN QVSLSCAVKGFYPSDIAVEWESNGQPENNYKTTPPVLDSDGSFFLVSKLTVDKSRWQQGNVFSCSVMHEA LHNHYTQKSLSLSPGKGGGGSGGGGSTRCPDGQFCPVACCLDPGGASYSCCRPLLDKWPTTLSRHLGGPC QVDAHCSAGHSCIFTVSGTSSCCPFPEAVACGDGHHCCPRGFHCSADGRSCFQRSGNNSVGAIQCPDSQFE CPDFSTCCVMVDGSWGCCPMPQASCCEDRVHCCPHGAFCDLVHTRCITPTGTHPLAKKLPAQRTNRAVA LSSSVMCPDARSRCPDGSTCCELPSGKYGCCPMPNATCCSDHLHCCPQDTVCDLIQSKCLSKENATTDLLT KLPAHTVGDVKCDMEVSCPDGYTCCRLQSGAWGCCPFTQAVCCEDHIHCCPAGFTCDTQKGTCEQGPHQ VPWMEKAPAHLSLPDPQALKRDVPCDNVSSCPSSDTCCQLTSGEWGCCPIPEAVCCSDHQHCCPQGYTCV AEGQCQRGSEIVAGLEKMPARRASLSHPRDIGCDQHTSCPVGQTCCPSLGGSWACCQLPHAVCCEDRQHC CPAGYTCNVKARSCEKEVVSAQPATFLARSPHVGVKDVECGEGHFCHDNQTCCRDNRQGWACCPYRQG VCCADRRHCCPAGFRCAARGTKCLRREAPRWDAPLRDPALRQQL | Partial hinge-Fc polypeptide with hole and LALA mutations-$(G_4S)_2$- PGRN(QQL) |
| 101 | DKTHTCPPCPAPEAAGGPSVFLFPPKPKDTLMISRTPEVTCVVVDVSHEDPEVKFNWYVDGVEVHNAKTK PREEQYNSTYRVVSVLTVLHQDWLNGKEYKCKVSNKALPAPIEKTISKAKGQPREPQVYTLPPSRDELTKN QVSLSCAVKGFYPSDIAVEWESNGQPENNYKTTPPVLDSDGSFFLVSKLTVDKSRWQQGNVFSCSVMHEA LHNHYTQKSLSLSPGKGGGGSGGGGSTRCPDGQFCPVACCLDPGGASYSCCRPLLDKWPTTLSRHLGGPC QVDAHCSAGHSCIFTVSGTSSCCPFPEAVACGDGHHCCPRGFHCSADGRSCFQRSGNNSVGAIQCPDSQFE CPDFSTCCVMVDGSWGCCPMPQASCCEDRVHCCPHGAFCDLVHTRCITPTGTHPLAKKLPAQRTNRAVA LSSSVMCPDARSRCPDGSTCCELPSGKYGCCPMPNATCCSDHLHCCPQDTVCDLIQSKCLSKENATTDLLT KLPAHTVGDVKCDMEVSCPDGYTCCRLQSGAWGCCPFTQAVCCEDHIHCCPAGFTCDTQKGTCEQGPHQ VPWMEKAPAHLSLPDPQALKRDVPCDNVSSCPSSDTCCQLTSGEWGCCPIPEAVCCSDHQHCCPQGYTCV AEGQCQRGSEIVAGLEKMPARRASLSHPRDIGCDQHTSCPVGQTCCPSLGGSWACCQLPHAVCCEDRQHC CPAGYTCNVKARSCEKEVVSAQPATFLARSPHVGVKDVECGEGHFCHDNQTCCRDNRQGWACCPYRQG VCCADRRHCCPAGFRCAARGTKCLRREAPRWDAPLRDPALRVVL | Partial hinge-Fc polypeptide with hole and LALA mutations-$(G_4S)_2$- PGRN(VVL) |
| 102 | DKTHTCPPCPAPEAAGGPSVFLFPPKPKDTLMISRTPEVTCVVVDVSHEDPEVKFNWYVDGVEVHNAKTK PREEQYNSTYRVVSVLTVLHQDWLNGKEYKCKVSNKALPAPIEKTISKAKGQPREPQVYTLPPSRDELTKN QVSLSCAVKGFYPSDIAVEWESNGQPENNYKTTPPVLDSDGSFFLVSKLTVDKSRWQQGNVFSCSVMHEA LHNHYTQKSLSLSPGKGGGGSGGGGSTRCPDGQFCPVACCLDPGGASYSCCRPLLDKWPTTLSRHLGGPC QVDAHCSAGHSCIFTVSGTSSCCPFPEAVACGDGHHCCPRGFHCSADGRSCFQRSGNNSVGAIQCPDSQFE CPDFSTCCVMVDGSWGCCPMPQASCCEDRVHCCPHGAFCDLVHTRCITPTGTHPLAKKLPAQRTNRAVA LSSSVMCPDARSRCPDGSTCCELPSGKYGCCPMPNATCCSDHLHCCPQDTVCDLIQSKCLSKENATTDLLT KLPAHTVGDVKCDMEVSCPDGYTCCRLQSGAWGCCPFTQAVCCEDHIHCCPAGFTCDTQKGTCEQGPHQ | Partialhinge-Fc polypeptide with hole and LALA mutations-$(G_4S)_2$- PGRN(VTL) |

| SEQ ID NO: | Sequence | Description |
|---|---|---|
|  | VPWMEKAPAHLSLPDPQALKRDVPCDNVSSCPSSDTCCQLTSGEWGCCPIPEAVCCSDHQHCCPQGYTCV AEGQCQRGSEIVAGLEKMPARRASLSHPRDIGCDQHTSCPVGQTCCPSLGGSWACCQLPHAVCCEDRQHC CPAGYTCNVKARSCEKEVVSAQPATFLARSPHVGKDVECGEGHFCHDNQTCCRDNRQGWACCPYRQG VCCADRRHCCPAGFRCAARGTKCLRREAPRWDAPLRDPALRVTL |  |
| 103 | DKTHTCPPCPAPEAAGGPSVFLFPPKPKDTLMISRTPEVTCVVVDVSHEDPEVKFNWYVDGVEVHNAKTK PREEQYNSTYRVVSVLTVLHQDWLNGKEYKCKVSNKALPAPIEKTISKAKGQPREPQVYTLPPSRDELTKN QVSLWCLVKGFYPSDIAVEWESNGQPENNYKTTPPVLDSDGSFFLYSKLTVDKSRWQQGNVFSCSVMHE ALHNHYTQKSLSLSPGKGGGGSGGGGSTRCPDGQFCPVACCLDPGGASYSCCRPLLDKWPTTLSRHLGGP CQVDAHCSAGHSCIFTVSGTSSCCPFFPEAVACGDGHHCCPRGFHCSADGRSCFQRSGNNSVGAIQCPDSQF ECPDFSTCCVMVDGSWGCCPMPQASCCEDRVHCCPHGAFCDLVHTRCITPTGTHPLAKKLPAQRTNRAV ALSSSVMCPDARSRCPDGSTCCELPSGKYGCCPMPNATCCSDHLHCCPQDTVCDLIQSKCLSKENATTDLL TKLPAHTVGDVKCDMEVSCPDGYTCCRLQSGAWGCCPFTQAVCCEDHIHCCPAGFTCDTQKGTCEQGPH QVPWMEKAPAHLSLPDPQALKRDVPCDNVSSCPSSDTCCQLTSGEWGCCPIPEAVCCSDHQHCCPQGYTC VAEGQCQRGSEIVAGLEKMPARRASLSHPRDIGCDQHTSCPVGQTCCPSLGGSWACCQLPHAVCCEDRQH CCPAGYTCNVKARSCEKEVVSAQPATFLARSPHVGKDVECGEGHFCHDNQTCCRDNRQGWACCPYRQ GVCCADRRHCCPAGFRCAARGTKCLRREAPRWDAPLRDPALRPIL | Partial hinge-Fc polypeptide with knob and LALA mutations-$(G_4S)_2$-PGRN(PIL) |
| 104 | DKTHTCPPCPAPEAAGGPSVFLFPPKPKDTLMISRTPEVTCVVVDVSHEDPEVKFNWYVDGVEVHNAKTK PREEQYNSTYRVVSVLTVLHQDWLNGKEYKCKVSNKALPAPIEKTISKAKGQPREPQVYTLPPSRDELTKN QVSLWCLVKGFYPSDIAVEWESNGQPENNYKTTPPVLDSDGSFFLYSKLTVDKSRWQQGNVFSCSVMHE ALHNHYTQKSLSLSPGKGGGGSGGGGSTRCPDGQFCPVACCLDPGGASYSCCRPLLDKWPTTLSRHLGGP CQVDAHCSAGHSCIFTVSGTSSCCPFFPEAVACGDGHHCCPRGFHCSADGRSCFQRSGNNSVGAIQCPDSQF ECPDFSTCCVMVDGSWGCCPMPQASCCEDRVHCCPHGAFCDLVHTRCITPTGTHPLAKKLPAQRTNRAV ALSSSVMCPDARSRCPDGSTCCELPSGKYGCCPMPNATCCSDHLHCCPQDTVCDLIQSKCLSKENATTDLL TKLPAHTVGDVKCDMEVSCPDGYTCCRLQSGAWGCCPFTQAVCCEDHIHCCPAGFTCDTQKGTCEQGPH QVPWMEKAPAHLSLPDPQALKRDVPCDNVSSCPSSDTCCQLTSGEWGCCPIPEAVCCSDHQHCCPQGYTC VAEGQCQRGSEIVAGLEKMPARRASLSHPRDIGCDQHTSCPVGQTCCPSLGGSWACCQLPHAVCCEDRQH CCPAGYTCNVKARSCEKEVVSAQPATFLARSPHVGKDVECGEGHFCHDNQTCCRDNRQGWACCPYRQ GVCCADRRHCCPAGFRCAARGTKCLRREAPRWDAPLRDPALRPFL | Partial hinge-Fc polypeptide with knob and LALA mutations-$(G_4S)_2$-PGRN(PFL) |
| 105 | DKTHTCPPCPAPEAAGGPSVFLFPPKPKDTLMISRTPEVTCVVVDVSHEDPEVKFNWYVDGVEVHNAKTK PREEQYNSTYRVVSVLTVLHQDWLNGKEYKCKVSNKALPAPIEKTISKAKGQPREPQVYTLPPSRDELTKN QVSLWCLVKGFYPSDIAVEWESNGQPENNYKTTPPVLDSDGSFFLYSKLTVDKSRWQQGNVFSCSVMHE ALHNHYTQKSLSLSPGKGGGGSGGGGSTRCPDGQFCPVACCLDPGGASYSCCRPLLDKWPTTLSRHLGGP CQVDAHCSAGHSCIFTVSGTSSCCPFFPEAVACGDGHHCCPRGFHCSADGRSCFQRSGNNSVGAIQCPDSQF ECPDFSTCCVMVDGSWGCCPMPQASCCEDRVHCCPHGAFCDLVHTRCITPTGTHPLAKKLPAQRTNRAV ALSSSVMCPDARSRCPDGSTCCELPSGKYGCCPMPNATCCSDHLHCCPQDTVCDLIQSKCLSKENATTDLL TKLPAHTVGDVKCDMEVSCPDGYTCCRLQSGAWGCCPFTQAVCCEDHIHCCPAGFTCDTQKGTCEQGPH QVPWMEKAPAHLSLPDPQALKRDVPCDNVSSCPSSDTCCQLTSGEWGCCPIPEAVCCSDHQHCCPQGYTC VAEGQCQRGSEIVAGLEKMPARRASLSHPRDIGCDQHTSCPVGQTCCPSLGGSWACCQLPHAVCCEDRQH CCPAGYTCNVKARSCEKEVVSAQPATFLARSPHVGKDVECGEGHFCHDNQTCCRDNRQGWACCPYRQ GVCCADRRHCCPAGFRCAARGTKCLRREAPRWDAPLRDPALRQQL | Partial hinge-Fc polypeptide with knob and LALA mutations-$(G_4S)_2$-PGRN(QQL) |
| 106 | DKTHTCPPCPAPEAAGGPSVFLFPPKPKDTLMISRTPEVTCVVVDVSHEDPEVKFNWYVDGVEVHNAKTK PREEQYNSTYRVVSVLTVLHQDWLNGKEYKCKVSNKALPAPIEKTISKAKGQPREPQVYTLPPSRDELTKN QVSLWCLVKGFYPSDIAVEWESNGQPENNYKTTPPVLDSDGSFFLYSKLTVDKSRWQQGNVFSCSVMHE ALHNHYTQKSLSLSPGKGGGGSGGGGSTRCPDGQFCPVACCLDPGGASYSCCRPLLDKWPTTLSRHLGGP CQVDAHCSAGHSCIFTVSGTSSCCPFFPEAVACGDGHHCCPRGFHCSADGRSCFQRSGNNSVGAIQCPDSQF ECPDFSTCCVMVDGSWGCCPMPQASCCEDRVHCCPHGAFCDLVHTRCITPTGTHPLAKKLPAQRTNRAV ALSSSVMCPDARSRCPDGSTCCELPSGKYGCCPMPNATCCSDHLHCCPQDTVCDLIQSKCLSKENATTDLL TKLPAHTVGDVKCDMEVSCPDGYTCCRLQSGAWGCCPFTQAVCCEDHIHCCPAGFTCDTQKGTCEQGPH QVPWMEKAPAHLSLPDPQALKRDVPCDNVSSCPSSDTCCQLTSGEWGCCPIPEAVCCSDHQHCCPQGYTC VAEGQCQRGSEIVAGLEKMPARRASLSHPRDIGCDQHTSCPVGQTCCPSLGGSWACCQLPHAVCCEDRQH CCPAGYTCNVKARSCEKEVVSAQPATFLARSPHVGKDVECGEGHFCHDNQTCCRDNRQGWACCPYRQ GVCCADRRHCCPAGFRCAARGTKCLRREAPRWDAPLRDPALRVVL | Partial hinge-Fc polypeptide with knob and LALA mutations-$(G_4S)_2$-PGRN(VVL) |
| 107 | DKTHTCPPCPAPEAAGGPSVFLFPPKPKDTLMISRTPEVTCVVVDVSHEDPEVKFNWYVDGVEVHNAKTK PREEQYNSTYRVVSVLTVLHQDWLNGKEYKCKVSNKALPAPIEKTISKAKGQPREPQVYTLPPSRDELTKN QVSLWCLVKGFYPSDIAVEWESNGQPENNYKTTPPVLDSDGSFFLYSKLTVDKSRWQQGNVFSCSVMHE ALHNHYTQKSLSLSPGKGGGGSGGGGSTRCPDGQFCPVACCLDPGGASYSCCRPLLDKWPTTLSRHLGGP CQVDAHCSAGHSCIFTVSGTSSCCPFFPEAVACGDGHHCCPRGFHCSADGRSCFQRSGNNSVGAIQCPDSQF ECPDFSTCCVMVDGSWGCCPMPQASCCEDRVHCCPHGAFCDLVHTRCITPTGTHPLAKKLPAQRTNRAV ALSSSVMCPDARSRCPDGSTCCELPSGKYGCCPMPNATCCSDHLHCCPQDTVCDLIQSKCLSKENATTDLL TKLPAHTVGDVKCDMEVSCPDGYTCCRLQSGAWGCCPFTQAVCCEDHIHCCPAGFTCDTQKGTCEQGPH QVPWMEKAPAHLSLPDPQALKRDVPCDNVSSCPSSDTCCQLTSGEWGCCPIPEAVCCSDHQHCCPQGYTC VAEGQCQRGSEIVAGLEKMPARRASLSHPRDIGCDQHTSCPVGQTCCPSLGGSWACCQLPHAVCCEDRQH CCPAGYTCNVKARSCEKEVVSAQPATFLARSPHVGKDVECGEGHFCHDNQTCCRDNRQGWACCPYRQ GVCCADRRHCCPAGFRCAARGTKCLRREAPRWDAPLRDPALRVTL | Partiai hinge-Fc polypeptide with knob and LALA mutations-$(G_4S)_2$-PGRN(VTL) |
| 108 | DKTHTCPPCPAPEAAGGPSVFLFPPKPKDTLMISRTPEVTCVVVDVSHEDPEVKFNWYVDGVEVHNAKTK PREEQYNSTYRVVSVLTVLHQDWLNGKEYKCKVSNKALPAPIEKTISKAKGQPREPQVYTLPPSRDELTKN QVSLSCAVKGFYPSDIAVEWESNGQPENNYKTTPPVLDSDGSFFLVSKLTVDKSRWQQGNVFSCSVMHEA | Partial hinge-Fc polypeptide with hole and LALA |

| SEQ ID NO: | Sequence | Description |
|---|---|---|
| | LHNHYTQKSLSLSPGKGGGGSGGGGSTRCPDGQFCPVACCLDPGGASYSCCRPLLDKWPTTLSRHLGGPC QVDAHCSAGHSCIFTVSGTSSCCPFPEAVACGDGHHCCPRGFHCSADGRSCFQRSGNNSVGAIQCPDSQFE CPDFSTCCVMVDGSWGCCPMPQASCCEDRVHCCPHGAFCDLVHTRCITPTGTHPLAKKLPAQRTNRAVA LSSSVMCPDARSRCPDGSTCCELPSGKYGCCPMPNATCCSDHLHCCPQDTVCDLIQSKCLSKENATTDLLT KLPAHTVGDVKCDMEVSCPDGYTCCRLQSGAWGCCPFTQAVCCEDHIHCCPAGFTCDTQKGTCEQGPHQ VPWMEKAPAHLSLPDPQALKRDVPCDNVSSCPSSDTCCQLTSGEWGCCPIPEAVCCSDHQHCCPQGYTCV AEGQCQRGSEIVAGLEKMPARRASLSHPRDIGCDQHTSCPVGQTCCPSLGGSWACCQLPHAVCCEDRQHC CPAGYTCNVKARSCEKEVVSAQPATFLARSPHVGVKDVECGEGHFCHDNQTCCRDNRQGWACCPYRQG VCCADRRHCCPAGFRCAARGTKCLRREAPRWDAPLRDPALRQLL | mutations-(G$_4$S)$_2$-PGRN |
| 109 | MMDQARSAFSNLFGGEPLSYTRFSLARQVDGDNSHVEMKLAVDEEENADNNTKANVTKPKRCSGSICYG TIAVIVFFLIGFMIGYLGYCKGVEPKTECERLAGTESPVREEPGEDFPAARRLYWDDLKRKLSEKLDSTDFT GTIKLLNENSYVPREAGSQKDENLALYVENQFREFKLSKVWRDQHFVKIQVKDSAQNSVIIVDKNGRLVY LVENPGGYVAYSKAATVTGKLVHANFGTKKDFEDLYTPVNGSIVIVRAGKITFAEKVANAESLNAIGVLIY MDQTKFPIVNAELSFFGHAHLGTGDPYTPGFPSFNHTQFPPSRSSGLPNIPVQTISRAAAEKLFGNMEGDCPS DWKTDSTCRMVTSESKNVKLTVSNVLKEIKILNIFGVIKGFVEPDHYVVGAQRDAWGPGAAKSGVGTAL LLKLAQMFSDMVLKDGFQPSRSIIFASWSAGDFGSVGATEWLEGYLSSLHLKAFTYINLDKAVLGTSNFKV SASPLLYTLIEKTMQNVKHPVTGQFLYQDSNWASKVEKLTLDNAAFPPLAYSGIPAVSFCFCEDTDYPYLG TTMDTYKELIERIPELNKVARAAAEVAGQFVIKLTHDVELNLDYERYNSQLLSFVRDLNQYRADIKEMGLS LQWLYSARGDFFRATSRLTTDFGNAEKTDRFVMKKLNDRVMRVEYHFLSPYVSPKESPFRHVFWGSGSH TLPALLENLKLRKQNNGAFNETLFRNQLALATWTIQGAANALSGDVWDIDNEF | Human transferrin receptor protein 1 (TFR1) |
| 110 | DKTHTCPPCPAPEAAGGPSVFLFPPKPKDTLMISRTPEVTCVVVDVSHEDPEVKFNWYVDGVEVHNAKTK PREEQYNSTYRVVSVLTVLHQDWLNGKEYKCKVSNKALPAPIEKTISKAKGQPREPQVYTLPPSRDELTKN QVSLSCAVKGFYPSDIAVEWESNGQPENNYKTTPPVLDSDGSFFLVSKLTVDKSRWQQGNVFSCSVMHEA LHNHYTQKSLSLSPGK | Partial hinge-Fc sequence with hole and LALA mutations |
| 111 | TRCPDGQFCPVACCLDPGGASYSCCRPLLDKWPTTLSRHLGGPCQVDAHCSAGHSCIFTVSGTSSCCPFPE AVACGDGHHCCPRGFHCSADGRSCFQRSGNNSVGAIQCPDSQFECPDFSTCCVMVDGSWGCCPMPQASC CEDRVHCCPHGAFCDLVHTRCITPTGTHPLAKKLPAQRTNRAVALSSSVMCPDARSRCPDGSTCCELPSGK YGCCPMPNATCCSDHLHCCPQDTVCDLIQSKCLSKENATTDLLTKLPAHTVGDVKCDMEVSCPDGYTCCR LQSGAWGCCPFTQAVCCEDHIHCCPAGFTCDTQKGTCEQGPHQVPWMEKAPAHLSLPDPQALKRDVPCD NVSSCPSSDTCCQLTSGEWGCCPIPEAVCCSDHQHCCPQGYTCVAEGQCQRGSEIVAGLEKMPARRASLSH PRDIGCDQHTSCPVGQTCCPSLGGSWACCQLPHAVCCEDRQHCCPAGYTCNVKARSCEKEVVSAQPATFL ARSPHVGVKDVECGEGHFCHDNQTCCRDNRQGWACCPYRQGVCCADRRHCCPAGFRCAARGTKCLRRE APRWDAPLRDPALRNIL | PGRN variant-56 |
| 112 | TRCPDGQFCPVACCLDPGGASYSCCRPLLDKWPTTLSRHLGGPCQVDAHCSAGHSCIFTVSGTSSCCPFPE AVACGDGHHCCPRGFHCSADGRSCFQRSGNNSVGAIQCPDSQFECPDFSTCCVMVDGSWGCCPMPQASC CEDRVHCCPHGAFCDLVHTRCITPTGTHPLAKKLPAQRTNRAVALSSSVMCPDARSRCPDGSTCCELPSGK YGCCPMPNATCCSDHLHCCPQDTVCDLIQSKCLSKENATTDLLTKLPAHTVGDVKCDMEVSCPDGYTCCR LQSGAWGCCPFTQAVCCEDHIHCCPAGFTCDTQKGTCEQGPHQVPWMEKAPAHLSLPDPQALKRDVPCD NVSSCPSSDTCCQLTSGEWGCCPIPEAVCCSDHQHCCPQGYTCVAEGQCQRGSEIVAGLEKMPARRASLSH PRDIGCDQHTSCPVGQTCCPSLGGSWACCQLPHAVCCEDRQHCCPAGYTCNVKARSCEKEVVSAQPATFL ARSPHVGVKDVECGEGHFCHDNQTCCRDNRQGWACCPYRQGVCCADRRHCCPAGFRCAARGTKCLRRE APRWDAPLRDPALRLLL | PGRN variant-57 |
| 113 | TRCPDGQFCPVACCLDPGGASYSCCRPLLDKWPTTLSRHLGGPCQVDAHCSAGHSCIFTVSGTSSCCPFPE AVACGDGHHCCPRGFHCSADGRSCFQRSGNNSVGAIQCPDSQFECPDFSTCCVMVDGSWGCCPMPQASC CEDRVHCCPHGAFCDLVHTRCITPTGTHPLAKKLPAQRTNRAVALSSSVMCPDARSRCPDGSTCCELPSGK YGCCPMPNATCCSDHLHCCPQDTVCDLIQSKCLSKENATTDLLTKLPAHTVGDVKCDMEVSCPDGYTCCR LQSGAWGCCPFTQAVCCEDHIHCCPAGFTCDTQKGTCEQGPHQVPWMEKAPAHLSLPDPQALKRDVPCD NVSSCPSSDTCCQLTSGEWGCCPIPEAVCCSDHQHCCPQGYTCVAEGQCQRGSEIVAGLEKMPARRASLSH PRDIGCDQHTSCPVGQTCCPSLGGSWACCQLPHAVCCEDRQHCCPAGYTCNVKARSCEKEVVSAQPATFL ARSPHVGVKDVECGEGHFCHDNQTCCRDNRQGWACCPYRQGVCCADRRHCCPAGFRCAARGTKCLRRE APRWDAPLRDPALRPLL | PGRN variant-58 |
| 114 | TRCPDGQFCPVACCLDPGGASYSCCRPLLDKWPTTLSRHLGGPCQVDAHCSAGHSCIFTVSGTSSCCPFPE AVACGDGHHCCPRGFHCSADGRSCFQRSGNNSVGAIQCPDSQFECPDFSTCCVMVDGSWGCCPMPQASC CEDRVHCCPHGAFCDLVHTRCITPTGTHPLAKKLPAQRTNRAVALSSSVMCPDARSRCPDGSTCCELPSGK YGCCPMPNATCCSDHLHCCPQDTVCDLIQSKCLSKENATTDLLTKLPAHTVGDVKCDMEVSCPDGYTCCR LQSGAWGCCPFTQAVCCEDHIHCCPAGFTCDTQKGTCEQGPHQVPWMEKAPAHLSLPDPQALKRDVPCD NVSSCPSSDTCCQLTSGEWGCCPIPEAVCCSDHQHCCPQGYTCVAEGQCQRGSEIVAGLEKMPARRASLSH PRDIGCDQHTSCPVGQTCCPSLGGSWACCQLPHAVCCEDRQHCCPAGYTCNVKARSCEKEVVSAQPATFL ARSPHVGVKDVECGEGHFCHDNQTCCRDNRQGWACCPYRQGVCCADRRHCCPAGFRCAARGTKCLRRE APRWDAPLRDPALRPRL | PGRN variant-59 |
| 115 | TRCPDGQFCPVACCLDPGGASYSCCRPLLDKWPTTLSRHLGGPCQVDAHCSAGHSCIFTVSGTSSCCPFPE AVACGDGHHCCPRGFHCSADGRSCFQRSGNNSVGAIQCPDSQFECPDFSTCCVMVDGSWGCCPMPQASC CEDRVHCCPHGAFCDLVHTRCITPTGTHPLAKKLPAQRTNRAVALSSSVMCPDARSRCPDGSTCCELPSGK YGCCPMPNATCCSDHLHCCPQDTVCDLIQSKCLSKENATTDLLTKLPAHTVGDVKCDMEVSCPDGYTCCR LQSGAWGCCPFTQAVCCEDHIHCCPAGFTCDTQKGTCEQGPHQVPWMEKAPAHLSLPDPQALKRDVPCD NVSSCPSSDTCCQLTSGEWGCCPIPEAVCCSDHQHCCPQGYTCVAEGQCQRGSEIVAGLEKMPARRASLSH | PGRN variant-60 |

-continued

INFORMAL SEQUENCE LISTING

| SEQ ID NO: | Sequence | Description |
|---|---|---|
|  | PRDIGCDQHTSCPVGQTCCPSLGGSWACCQLPHAVCCEDRQHCCPAGYTCNVKARSCEKEVVSAQPATFL ARSPHVGVKDVECGEGHFCHDNQTCCRDNRQGWACCPYRQGVCCADRRHCCPAGFRCAARGTKCLRRE APRWDAPLRDPALRYIL |  |
| 116 | TRCPDGQFCPVACCLDPGGASYSCCRPLLDKWPTTLSRHLGGPCQVDAHCSAGHSCIFTVSGTSSCCPFPE AVACGDGHHCCPRGFHCSADGRSCFQRSGNNSVGAIQCPDSQFECPDFSTCCVMVDGSWGCCPMPQASC CEDRVHCCPHGAFCDLVHTRCITPTGTHPLAKKLPAQRTNRAVALSSSVMCPDARSRCPDGSTCCELPSGK YGCCPMPNATCCSDHLHCCPQDTVCDLIQSKCLSKENATTDLLTKLPAHTVGDVKCDMEVSCPDGYTCCR LQSGAWGCCPFTQAVCCEDHIHCCPAGFTCDTQKGTCEQGPHQVPWMEKAPAHLSLPDPQALKRDVPCD NVSSCPSSDTCCQLTSGEWGCCPIPEAVCCSDHQHCCPQGYTCVAEGQCQRGSEIVAGLEKMPARRASLSH PRDIGCDQHTSCPVGQTCCPSLGGSWACCQLPHAVCCEDRQHCCPAGYTCNVKARSCEKEVVSAQPATFL ARSPHVGVKDVECGEGHFCHDNQTCCRDNRQGWACCPYRQGVCCADRRHCCPAGFRCAARGTKCLRRE APRWDAPLRDPALRVLL | PGRN variant-61 |
| 117 | TRCPDGQFCPVACCLDPGGASYSCCRPLLDKWPTTLSRHLGGPCQVDAHCSAGHSCIFTVSGTSSCCPFPE AVACGDGHHCCPRGFHCSADGRSCFQRSGNNSVGAIQCPDSQFECPDFSTCCVMVDGSWGCCPMPQASC CEDRVHCCPHGAFCDLVHTRCITPTGTHPLAKKLPAQRTNRAVALSSSVMCPDARSRCPDGSTCCELPSGK YGCCPMPNATCCSDHLHCCPQDTVCDLIQSKCLSKENATTDLLTKLPAHTVGDVKCDMEVSCPDGYTCCR LQSGAWGCCPFTQAVCCEDHIHCCPAGFTCDTQKGTCEQGPHQVPWMEKAPAHLSLPDPQALKRDVPCD NVSSCPSSDTCCQLTSGEWGCCPIPEAVCCSDHQHCCPQGYTCVAEGQCQRGSEIVAGLEKMPARRASLSH PRDIGCDQHTSCPVGQTCCPSLGGSWACCQLPHAVCCEDRQHCCPAGYTCNVKARSCEKEVVSAQPATFL ARSPHVGVKDVECGEGHFCHDNQTCCRDNRQGWACCPYRQGVCCADRRHCCPAGFRCAARGTKCLRRE APRWDAPLRDPALRVIV | PGRN variant-62 |
| 118 | TRCPDGQFCPVACCLDPGGASYSCCRPLLDKWPTTLSRHLGGPCQVDAHCSAGHSCIFTVSGTSSCCPFPE AVACGDGHHCCPRGFHCSADGRSCFQRSGNNSVGAIQCPDSQFECPDFSTCCVMVDGSWGCCPMPQASC CEDRVHCCPHGAFCDLVHTRCITPTGTHPLAKKLPAQRTNRAVALSSSVMCPDARSRCPDGSTCCELPSGK YGCCPMPNATCCSDHLHCCPQDTVCDLIQSKCLSKENATTDLLTKLPAHTVGDVKCDMEVSCPDGYTCCR LQSGAWGCCPFTQAVCCEDHIHCCPAGFTCDTQKGTCEQGPHQVPWMEKAPAHLSLPDPQALKRDVPCD NVSSCPSSDTCCQLTSGEWGCCPIPEAVCCSDHQHCCPQGYTCVAEGQCQRGSEIVAGLEKMPARRASLSH PRDIGCDQHTSCPVGQTCCPSLGGSWACCQLPHAVCCEDRQHCCPAGYTCNVKARSCEKEVVSAQPATFL ARSPHVGVKDVECGEGHFCHDNQTCCRDNRQGWACCPYRQGVCCADRRHCCPAGFRCAARGTKCLRRE APRWDAPLRDPALRFIL | PGRN variant-63 |
| 119 | TRCPDGQFCPVACCLDPGGASYSCCRPLLDKWPTTLSRHLGGPCQVDAHCSAGHSCIFTVSGTSSCCPFPE AVACGDGHHCCPRGFHCSADGRSCFQRSGNNSVGAIQCPDSQFECPDFSTCCVMVDGSWGCCPMPQASC CEDRVHCCPHGAFCDLVHTRCITPTGTHPLAKKLPAQRTNRAVALSSSVMCPDARSRCPDGSTCCELPSGK YGCCPMPNATCCSDHLHCCPQDTVCDLIQSKCLSKENATTDLLTKLPAHTVGDVKCDMEVSCPDGYTCCR LQSGAWGCCPFTQAVCCEDHIHCCPAGFTCDTQKGTCEQGPHQVPWMEKAPAHLSLPDPQALKRDVPCD NVSSCPSSDTCCQLTSGEWGCCPIPEAVCCSDHQHCCPQGYTCVAEGQCQRGSEIVAGLEKMPARRASLSH PRDIGCDQHTSCPVGQTCCPSLGGSWACCQLPHAVCCEDRQHCCPAGYTCNVKARSCEKEVVSAQPATFL ARSPHVGVKDVECGEGHFCHDNQTCCRDNRQGWACCPYRQGVCCADRRHCCPAGFRCAARGTKCLRRE APRWDAPLRDPALRMLL | PGRN variant-64 |
| 120 | TRCPDGQFCPVACCLDPGGASYSCCRPLLDKWPTTLSRHLGGPCQVDAHCSAGHSCIFTVSGTSSCCPFPE AVACGDGHHCCPRGFHCSADGRSCFQRSGNNSVGAIQCPDSQFECPDFSTCCVMVDGSWGCCPMPQASC CEDRVHCCPHGAFCDLVHTRCITPTGTHPLAKKLPAQRTNRAVALSSSVMCPDARSRCPDGSTCCELPSGK YGCCPMPNATCCSDHLHCCPQDTVCDLIQSKCLSKENATTDLLTKLPAHTVGDVKCDMEVSCPDGYTCCR LQSGAWGCCPFTQAVCCEDHIHCCPAGFTCDTQKGTCEQGPHQVPWMEKAPAHLSLPDPQALKRDVPCD NVSSCPSSDTCCQLTSGEWGCCPIPEAVCCSDHQHCCPQGYTCVAEGQCQRGSEIVAGLEKMPARRASLSH PRDIGCDQHTSCPVGQTCCPSLGGSWACCQLPHAVCCEDRQHCCPAGYTCNVKARSCEKEVVSAQPATFL ARSPHVGVKDVECGEGHFCHDNQTCCRDNRQGWACCPYRQGVCCADRRHCCPAGFRCAARGTKCLRRE APRWDAPLRDPALRQLLG | PGRN variant-65 |
| 121 | TRCPDGQFCPVACCLDPGGASYSCCRPLLDKWPTTLSRHLGGPCQVDAHCSAGHSCIFTVSGTSSCCPFPE AVACGDGHHCCPRGFHCSADGRSCFQRSGNNSVGAIQCPDSQFECPDFSTCCVMVDGSWGCCPMPQASC CEDRVHCCPHGAFCDLVHTRCITPTGTHPLAKKLPAQRTNRAVALSSSVMCPDARSRCPDGSTCCELPSGK YGCCPMPNATCCSDHLHCCPQDTVCDLIQSKCLSKENATTDLLTKLPAHTVGDVKCDMEVSCPDGYTCCR LQSGAWGCCPFTQAVCCEDHIHCCPAGFTCDTQKGTCEQGPHQVPWMEKAPAHLSLPDPQALKRDVPCD NVSSCPSSDTCCQLTSGEWGCCPIPEAVCCSDHQHCCPQGYTCVAEGQCQRGSEIVAGLEKMPARRASLSH PRDIGCDQHTSCPVGQTCCPSLGGSWACCQLPHAVCCEDRQHCCPAGYTCNVKARSCEKEVVSAQPATFL ARSPHVGVKDVECGEGHFCHDNQTCCRDNRQGWACCPYRQGVCCADRRHCCPAGFRCAARGTKCLRRE APRWDAPLRDPALRQLLGK | PGRN variant-66 |
| 122 | DKTHTCPPCPAPEAAGGPSVFLFPPKPKDTLMISRTPEVTCVVVDVSHEDPEVKFNWYVDGVEVHNAKTK PREEQYNSTYRVVSVLTVLHQDWLNGKEYKCKVSNKALPAPIEKTISKAKGQPREPQVYTLPPSRDELTKN QVSLWCLVKGFYPSDIAVEWESNGQPENNYKTTPPVLDSDGSFFLYSKLTVDKSRWQQGNVFSCSVMHE ALHNHYTQKSLSLSPGK | Partial hinge-Fc sequence with knob and LALA mutations |
| 123 | DKTHTCPPCPAPEAAGGPSVFLFPPKPKDTLMISRTPEVTCVVVDVSHEDPEVKFNWYVDGVEVHNAKTK PREEQYNSTYRVVSVLTVLHQDWLNGKEYKCKVSNKALPAPIEKTISKAKGQPREPQVYTLPPSRDELTKN QVSLSCAVKGFYPSDIAVEWESNGQPENNYKTTPPVLDSDGSFFLVSKLTVDKSRWQQGNVFSCSVMHEA LHNHYTQKSLSLSPGKGGGGSGGGGSTRCPDGQFCPVACCLDPGGASYSCCRPLLDKWPTTLSRHLGGPC | Partial hinge-Fc polypeptide with hole and LALA mutations-(G$_4$S)$_2$- |

-continued

INFORMAL SEQUENCE LISTING

| SEQ ID NO: | Sequence | Description |
|---|---|---|
| | QVDAHCSAGHSCIFTVSGTSSCCPFPEAVACGDGHHCCPRGFHCSADGRSCFQRSGNNSVGAIQCPDSQFE CPDFSTCCVMVDGSWGCCPMPQASCCEDRVHCCPHGAFCDLVHTRCITPTGTHPLAKKLPAQRTNRAVA LSSSVMCPDARSRCPDGSTCCELPSGKYGCCPMPNATCCSDHLHCCPQDTVCDLIQSKCLSKENATTDLLT KLPAHTVGDVKCDMEVSCPDGYTCCRLQSGAWGCCPFTQAVCCEDHIHCCPAGFTCDTQKGTCEQGPHQ VPWMEKAPAHLSLPDPQALKRDVPCDNVSSCPSSDTCCQLTSGEWGCCPIPEAVCCSDHQHCCPQGYTCV AEGQCQRGSEIVAGLEKMPARRASLSHPRDIGCDQHTSCPVGQTCCPSLGGSWACCQLPHAVCCEDRQHC CPAGYTCNVKARSCEKEVVSAQPATFLARSPHVGVKDVECGEGHFCHDNQTCCRDNRQGWACCPYRQG VCCADRRHCCPAGFRCAARGTKCLRREAPRWDAPLRDPALRPPL | PGRN(PPL) |
| 124 | DKTHTCPPCPAPEAAGGPSVFLFPPKPKDTLMISRTPEVTCVVVDVSHEDPEVKFNWYVDGVEVHNAKTK PREEQYNSTYRVVSVLTVLHQDWLNGKEYKCKVSNKALPAPIEKTISKAKGQPREPQVYTLPPSRDELTKN QVSLSCAVKGFYPSDIAVEWESNGQPENNYKTTPPVLDSDGSFFLVSKLTVDKSRWQQGNVFSCSVMHEA LHNHYTQKSLSLSPGKGGGGSGGGGSTRCPDGQFCPVACCLDPGGASYSCCRPLLDKWPTTLSRHLGGPC QVDAHCSAGHSCIFTVSGTSSCCPFPEAVACGDGHHCCPRGFHCSADGRSCFQRSGNNSVGAIQCPDSQFE CPDFSTCCVMVDGSWGCCPMPQASCCEDRVHCCPHGAFCDLVHTRCITPTGTHPLAKKLPAQRTNRAVA LSSSVMCPDARSRCPDGSTCCELPSGKYGCCPMPNATCCSDHLHCCPQDTVCDLIQSKCLSKENATTDLLT KLPAHTVGDVKCDMEVSCPDGYTCCRLQSGAWGCCPFTQAVCCEDHIHCCPAGFTCDTQKGTCEQGPHQ VPWMEKAPAHLSLPDPQALKRDVPCDNVSSCPSSDTCCQLTSGEWGCCPIPEAVCCSDHQHCCPQGYTCV AEGQCQRGSEIVAGLEKMPARRASLSHPRDIGCDQHTSCPVGQTCCPSLGGSWACCQLPHAVCCEDRQHC CPAGYTCNVKARSCEKEVVSAQPATFLARSPHVGVKDVECGEGHFCHDNQTCCRDNRQGWACCPYRQG VCCADRRHCCPAGFRCAARGTKCLRREAPRWDAPLRDPALRPYL | Partial hinge-Fc polypeptide with hole and LALA mutations-(G$_4$S)$_2$-PGRN(PYL) |
| 125 | DKTHTCPPCPAPEAAGGPSVFLFPPKPKDTLMISRTPEVTCVVVDVSHEDPEVKFNWYVDGVEVHNAKTK PREEQYNSTYRVVSVLTVLHQDWLNGKEYKCKVSNKALPAPIEKTISKAKGQPREPQVYTLPPSRDELTKN QVSLSCAVKGFYPSDIAVEWESNGQPENNYKTTPPVLDSDGSFFLVSKLTVDKSRWQQGNVFSCSVMHEA LHNHYTQKSLSLSPGKGGGGSGGGGSTRCPDGQFCPVACCLDPGGASYSCCRPLLDKWPTTLSRHLGGPC QVDAHCSAGHSCIFTVSGTSSCCPFPEAVACGDGHHCCPRGFHCSADGRSCFQRSGNNSVGAIQCPDSQFE CPDFSTCCVMVDGSWGCCPMPQASCCEDRVHCCPHGAFCDLVHTRCITPTGTHPLAKKLPAQRTNRAVA LSSSVMCPDARSRCPDGSTCCELPSGKYGCCPMPNATCCSDHLHCCPQDTVCDLIQSKCLSKENATTDLLT KLPAHTVGDVKCDMEVSCPDGYTCCRLQSGAWGCCPFTQAVCCEDHIHCCPAGFTCDTQKGTCEQGPHQ VPWMEKAPAHLSLPDPQALKRDVPCDNVSSCPSSDTCCQLTSGEWGCCPIPEAVCCSDHQHCCPQGYTCV AEGQCQRGSEIVAGLEKMPARRASLSHPRDIGCDQHTSCPVGQTCCPSLGGSWACCQLPHAVCCEDRQHC CPAGYTCNVKARSCEKEVVSAQPATFLARSPHVGVKDVECGEGHFCHDNQTCCRDNRQGWACCPYRQG VCCADRRHCCPAGFRCAARGTKCLRREAPRWDAPLRDPALRQRL | Partial hinge-Fc polypeptide with hole and LALA mutations-(G$_4$S)$_2$-PGRN(QRL) |
| 126 | DKTHTCPPCPAPEAAGGPSVFLFPPKPKDTLMISRTPEVTCVVVDVSHEDPEVKFNWYVDGVEVHNAKTK PREEQYNSTYRVVSVLTVLHQDWLNGKEYKCKVSNKALPAPIEKTISKAKGQPREPQVYTLPPSRDELTKN QVSLSCAVKGFYPSDIAVEWESNGQPENNYKTTPPVLDSDGSFFLVSKLTVDKSRWQQGNVFSCSVMHEA LHNHYTQKSLSLSPGKGGGGSGGGGSTRCPDGQFCPVACCLDPGGASYSCCRPLLDKWPTTLSRHLGGPC QVDAHCSAGHSCIFTVSGTSSCCPFPEAVACGDGHHCCPRGFHCSADGRSCFQRSGNNSVGAIQCPDSQFE CPDFSTCCVMVDGSWGCCPMPQASCCEDRVHCCPHGAFCDLVHTRCITPTGTHPLAKKLPAQRTNRAVA LSSSVMCPDARSRCPDGSTCCELPSGKYGCCPMPNATCCSDHLHCCPQDTVCDLIQSKCLSKENATTDLLT KLPAHTVGDVKCDMEVSCPDGYTCCRLQSGAWGCCPFTQAVCCEDHIHCCPAGFTCDTQKGTCEQGPHQ VPWMEKAPAHLSLPDPQALKRDVPCDNVSSCPSSDTCCQLTSGEWGCCPIPEAVCCSDHQHCCPQGYTCV AEGQCQRGSEIVAGLEKMPARRASLSHPRDIGCDQHTSCPVGQTCCPSLGGSWACCQLPHAVCCEDRQHC CPAGYTCNVKARSCEKEVVSAQPATFLARSPHVGVKDVECGEGHFCHDNQTCCRDNRQGWACCPYRQG VCCADRRHCCPAGFRCAARGTKCLRREAPRWDAPLRDPALRQHL | Partial hinge-Fc polypeptide with hole and LALA mutations-(G$_4$S)$_2$-PGRN(QHL) |
| 127 | TRCPDGQFCPVACCLDPGGASYSCCRPLLDKWPTTLSRHLGGPCQVDAHCSAGHSCIFTVSGTSSCCPFPE AVACGDGHHCCPRGFHCSADGRSCFQRSGNNSVGAIQCPDSQFECPDFSTCCVMVDGSWGCCPMPQASC CEDRVHCCPHGAFCDLVHTRCITPTGTHPLAKKLPAQRTNRAVALSSSVMCPDARSRCPDGSTCCELPSGK YGCCPMPNATCCSDHLHCCPQDTVCDLIQSKCLSKENATTDLLTKLPAHTVGDVKCDMEVSCPDGYTCCR LQSGAWGCCPFTQAVCCEDHIHCCPAGFTCDTQKGTCEQGPHQVPWMEKAPAHLSLPDPQALKRDVPCD NVSSCPSSDTCCQLTSGEWGCCPIPEAVCCSDHQHCCPQGYTCVAEGQCQRGSEIVAGLEKMPARRASLSH PRDIGCDQHTSCPVGQTCCPSLGGSWACCQLPHAVCCEDRQHCCPAGYTCNVKARSCEKEVVSAQPATFL ARSPHVGVKDVECGEGHFCHDNQTCCRDNRQGWACCPYRQGVCCADRRHCCPAGFRCAARGTKCLRRE APRWDAPLRDPALRQLY | PGRN variant-67 |
| 128 | TRCPDGQFCPVACCLDPGGASYSCCRPLLDKWPTTLSRHLGGPCQVDAHCSAGHSCIFTVSGTSSCCPFPE AVACGDGHHCCPRGFHCSADGRSCFQRSGNNSVGAIQCPDSQFECPDFSTCCVMVDGSWGCCPMPQASC CEDRVHCCPHGAFCDLVHTRCITPTGTHPLAKKLPAQRTNRAVALSSSVMCPDARSRCPDGSTCCELPSGK YGCCPMPNATCCSDHLHCCPQDTVCDLIQSKCLSKENATTDLLTKLPAHTVGDVKCDMEVSCPDGYTCCR LQSGAWGCCPFTQAVCCEDHIHCCPAGFTCDTQKGTCEQGPHQVPWMEKAPAHLSLPDPQALKRDVPCD NVSSCPSSDTCCQLTSGEWGCCPIPEAVCCSDHQHCCPQGYTCVAEGQCQRGSEIVAGLEKMPARRASLSH PRDIGCDQHTSCPVGQTCCPSLGGSWACCQLPHAVCCEDRQHCCPAGYTCNVKARSCEKEVVSAQPATFL ARSPHVGVKDVECGEGHFCHDNQTCCRDNRQGWACCPYRQGVCCADRRHCCPAGFRCAARGTKCLRRE APRWDAPLRDPALRQLP | PGRN variant-68 |
| 129 | APEAAGGPSVFLFPPKPKDTLMISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYTLPPSRDELTKNQVSLWCLVK GFYPSDIAVEWESYGTEWANYKTTPPVLDSDGSFFLYSKLIVTKEEWQQGFVFSCSVMHEALHNHYTQKS LSLSPG | Clone CH3C.35.23.2 with knob and LALA mutations, truncated |

| SEQ ID NO: | Sequence | Description |
|---|---|---|
| 130 | DKTHTCPPCPAPEAAGGPSVFLFPPKPKDTLMISRTPEVTCVVVDVSHEDPEVKFNWYVDGVEVHNAKTK PREEQYNSTYRVVSVLTVLHQDWLNGKEYKCKVSNKALPAPIEKTISKAKGQPREPQVYTLPPSRDELTKN QVSLWCLVKGFYPSDIAVEWESYGTEWANYKTTPPVLDSDGSFFLYSKLIVTKEEWQQGFVFSCSVMHE ALHNHYTQKSLSLSPG | Partial hinge-Clone CH3C.35.23.2 with knoband LALA mutations, truncated |
| 131 | APEAAGGPSVFLFPPKPKDTLMISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYTLPPSRDELTKNQVSLWCLVK GFYPSDIAVLWESYGTEWSSYKTTPPVLDSDGSFFLYSKLTVTKEEWQQGFVFSCSVMHEALHNHYTQKS LSLSPG | Clone CH3C.35.21.17 with knob and LALA mutations, truncated |
| 132 | DKTHTCPPCPAPEAAGGPSVFLFPPKPKDTLMISRTPEVTCVVVDVSHEDPEVKFNWYVDGVEVHNAKTK PREEQYNSTYRVVSVLTVLHQDWLNGKEYKCKVSNKALPAPIEKTISKAKGQPREPQVYTLPPSRDELTKN QVSLWCLVKGFYPSDIAVLWESYGTEWSSYKTTPPVLDSDGSFFLYSKLTVIKEEWQQGFVFSCSVMHEA LHNHYTQKSLSLSPG | Partial hinge-Clone CH3C.35.21.17 with knob and LALA mutations, truncated |

What is claimed is:

1. A fusion protein comprising:
   (a) a progranulin variant comprising an amino acid sequence having at least 90% identity to SEQ ID NO:2 and an amino acid sequence defined by $X_1X_2X_3$ at the positions corresponding to residues 574 to 576 of SEQ ID NO:2, wherein $X_1X_2X_3$ is selected from the group consisting of: PIL, PFL, PPL, PYL, QRL, and QHL;
   (b) a first Fc polypeptide that is linked to the progranulin variant of (a); and
   (c) a second Fc polypeptide that forms an Fc polypeptide dimer with the first Fc polypeptide.

2. The fusion protein of claim 1, wherein the first Fc polypeptide or the second Fc polypeptide specifically binds to a transferrin receptor.

3. The fusion protein of claim 1, wherein the first Fc polypeptide is linked to the progranulin variant by a polypeptide linker comprising $G_4S$ (SEQ ID NO:90) or $(G_4S)_2$ (SEQ ID NO:91).

4. The fusion protein of claim 1, wherein the C-terminus of the first Fc polypeptide is linked to the N-terminus of the progranulin variant.

5. The fusion protein of claim 1, wherein:
   (i) the first Fc polypeptide comprises a W at position 366 and the second Fc polypeptide comprises an S at position 366, an A at position 368, and a V at position 407, according to EU numbering; or
   (ii) the first Fc polypeptide comprises an S at position 366, an A at position 368, and a V at position 407 and the second Fc polypeptide comprises a W at position 366, according to EU numbering.

6. The fusion protein of claim 1, wherein the first Fc polypeptide and/or the second Fc polypeptide independently comprises an A at position 234 and an A at position 235, according to EU numbering.

7. The fusion protein of claim 1, wherein the second Fc polypeptide comprises a sequence selected from the group consisting of SEQ ID NOS:70, 75, 80, 85, and 129-132.

8. The fusion protein of claim 1, wherein $X_1X_2X_3$ is PIL.

9. The fusion protein of claim 1, wherein the progranulin variant comprises the sequence of any one of SEQ ID NOS: 13, 15, and 17-20.

10. The fusion protein of claim 1, wherein the first Fc polypeptide linked to the progranulin variant comprises the sequence of SEQ ID NO:98, and the second Fc polypeptide comprises the sequence of SEQ ID NO:75 or 130.

11. The fusion protein of claim 1, wherein the first Fc polypeptide linked to the progranulin variant comprises the sequence of SEQ ID NO:99, and the second Fc polypeptide the sequence of SEQ ID NO:75 or 130.

12. The fusion protein of claim 1, wherein the first Fc polypeptide linked to the progranulin variant comprises the sequence of SEQ ID NO:126, and the second Fc polypeptide comprises the sequence of SEQ ID NO:75 or 130.

13. The fusion protein of claim 1, wherein the first Fc polypeptide linked to the progranulin variant comprises the sequence of SEQ ID NO:98, and the second Fc polypeptide comprises the sequence of SEQ ID NO:85 or 132.

14. The fusion protein of claim 1, wherein the first Fc polypeptide linked to the progranulin variant comprises the sequence of SEQ ID NO:99, and the second Fc polypeptide the sequence of SEQ ID NO:85 or 132.

15. A pharmaceutical composition comprising the fusion protein of claim 1 and a pharmaceutically acceptable carrier.

16. A pharmaceutical composition comprising the fusion protein of claim 1 and a pharmaceutically acceptable carrier.

17. The pharmaceutical composition of claim 16, wherein more than 50% of the fusion protein in the pharmaceutical composition comprises an intact C-terminus in the progranulin variant of the fusion protein.

18. The pharmaceutical composition of claim 16, wherein the $K_D$ value for sortilin binding of the fusion protein is less than about 100 nM.

19. The pharmaceutical composition of claim 16, wherein the EC50 value for sortilin binding of the fusion protein is less than about 25 nM.

20. A method of treating a subject having a neurodegenerative disease, atherosclerosis, a disorder associated with TDP-43, age-related macular degeneration (AMD), or a progranulin-associated disorder, the method comprising administering the fusion protein of claim 1 to the subject.

21. The method of claim 20, wherein the subject has a neurodegenerative disease selected from the group consisting of frontotemporal dementia (FTD), neuronal ceroid lipofuscinosis (NCL), Niemann-Pick disease type A (NPA), Niemann-Pick disease type B (NPB), Niemann-Pick disease type C (NPC), C9ORF72-associated amyotrophic lateral sclerosis (ALS)/FTD, sporadic ALS, Alzheimer's disease (AD), Gaucher's disease, and Parkinson's disease.

22. One or more polynucleotides comprising one or more nucleic acid sequences encoding the polypeptides (b) and (c) of the fusion protein of claim 1.

23. One or more vectors comprising the one or more polynucleotides of claim 22.

24. A host cell comprising the one or more vectors of claim 23.

25. A method for producing a fusion protein, comprising culturing the host cell of claim 24 under conditions in which the polypeptides encoded by the one or more vectors are expressed.

26. A host cell comprising the one or more polynucleotides of claim 22.

27. A method for producing a fusion protein, comprising culturing the host cell of claim 26 under conditions in which the polypeptides encoded by the one or more polynucleotides are expressed.

28. A fusion protein comprising:
(a) a progranulin variant comprising an amino acid sequence having at least 90% identity to SEQ ID NO:2 and an amino acid sequence defined by $X_1X_2X_3$ at the positions corresponding to amino acid residues 574 to 576 of SEQ ID NO:2, wherein $X_1X_2X_3$ is PIL;
(b) a first Fc polypeptide that is linked to the progranulin variant of (a); and
(c) a second Fc polypeptide that forms an Fc polypeptide dimer with the first Fc polypeptide;
wherein the first Fc polypeptide or the second Fc polypeptide specifically binds to a transferrin receptor.

29. The fusion protein of claim 28, wherein the first Fc polypeptide is linked to the progranulin variant by a polypeptide linker comprising G4S (SEQ ID NO:90) or (G45)2 (SEQ ID NO:91).

30. The fusion protein of claim 28, wherein the C-terminus of the first Fc polypeptide is linked to the N-terminus of the progranulin variant.

31. The fusion protein of claim 28, wherein:
(i) the first Fc polypeptide comprises a W at position 366 and the second Fc polypeptide comprises an S at position 366, an A at position 368, and a V at position 407, according to EU numbering; or
(ii) the first Fc polypeptide comprises an S at position 366, an A at position 368, and a V at position 407 and the second Fc polypeptide comprises a W at position 366, according to EU numbering.

32. The fusion protein of claim 28, wherein the first Fc polypeptide and/or the second Fc polypeptide independently comprises an A at position 234 and an A at position 235, according to EU numbering.

33. One or more polynucleotides comprising one or more nucleic acid sequences encoding the polypeptides (b) and (c) of the fusion protein of claim 28.

34. One or more vectors comprising the one or more polynucleotides of claim 33.

35. A host cell comprising the one or more vectors of claim 34.

36. A method for producing a fusion protein, comprising culturing the host cell of claim 35 under conditions in which the polypeptides encoded by the one or more vectors are expressed.

37. A host cell comprising the one or more polynucleotides of claim 33.

38. A method for producing a fusion protein, comprising culturing the host cell of claim 37 under conditions in which the polypeptides encoded by the one or more polynucleotides are expressed.

39. A protein comprising:
(a) a fusion polypeptide comprising a progranulin variant linked to a first Fc polypeptide, wherein the fusion polypeptide sequence comprises SEQ ID NO:98; and
(b) a second Fc polypeptide comprising a sequence that is at least 95% identical to SEQ ID NO:75.

40. The protein of claim 39, wherein the second Fc polypeptide comprises a sequence that is SEQ ID NO:75.

41. A pharmaceutical composition comprising the protein of claim 40 and a pharmaceutically acceptable carrier.

42. The protein of claim 39, wherein the second Fc polypeptide comprises a sequence that is SEQ ID NO:130.

43. A pharmaceutical composition comprising the protein of claim 42 and a pharmaceutically acceptable carrier.

44. A pharmaceutical composition comprising the protein of claim 39 and a pharmaceutically acceptable carrier.

45. A protein comprising:
(a) a fusion polypeptide comprising a progranulin variant linked to a first Fc polypeptide, wherein the fusion polypeptide sequence comprises SEQ ID NO:98; and
(b) a second Fc polypeptide comprising a sequence that is at least 95% identical to SEQ ID NO:85.

46. A pharmaceutical composition comprising the protein of claim 45 and a pharmaceutically acceptable carrier.

47. The protein of claim 45, wherein the second Fc polypeptide comprises a sequence that is SEQ ID NO:85.

48. A pharmaceutical composition comprising the protein of claim 47 and a pharmaceutically acceptable carrier.

49. The protein of claim 45, wherein the second Fc polypeptide comprises a sequence that is SEQ ID NO:132.

50. A pharmaceutical composition comprising the protein of claim 49 and a pharmaceutically acceptable carrier.

* * * * *